United States Patent
Albrecht et al.

(10) Patent No.: US 10,526,287 B2
(45) Date of Patent: Jan. 7, 2020

(54) LSD1 INHIBITORS AND USES THEREOF

(71) Applicant: Constellation Pharmaceuticals, Inc., Cambridge, MA (US)

(72) Inventors: Brian K. Albrecht, Cambridge, MA (US); James Edmund Audia, Cambridge, MA (US); Alexandre Côté, Cambridge, MA (US); Martin Duplessis, Somerville, MA (US); Victor S. Gehling, Somerville, MA (US); Jean-Christophe Harmange, Andover, MA (US); Rishi G. Vaswani, Lexington, MA (US)

(73) Assignee: Constellation Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/567,978

(22) PCT Filed: Apr. 22, 2016

(86) PCT No.: PCT/US2016/028864
§ 371 (c)(1),
(2) Date: Oct. 20, 2017

(87) PCT Pub. No.: WO2016/172496
PCT Pub. Date: Oct. 27, 2016

(65) Prior Publication Data
US 2018/0290976 A1 Oct. 11, 2018

Related U.S. Application Data

(60) Provisional application No. 62/151,706, filed on Apr. 23, 2015.

(51) Int. Cl.
| | | |
|---|---|---|
| *C07D 211/22* | (2006.01) | |
| *C07D 211/26* | (2006.01) | |
| *C07D 309/20* | (2006.01) | |
| *C07D 215/44* | (2006.01) | |
| *C07D 317/28* | (2006.01) | |

(Continued)

(52) U.S. Cl.
CPC ............ *C07D 211/26* (2013.01); *A61P 35/00* (2018.01); *C07C 211/09* (2013.01); *C07C 211/36* (2013.01); *C07C 211/40* (2013.01); *C07C 215/14* (2013.01); *C07C 215/42* (2013.01); *C07C 215/44* (2013.01); *C07C 217/08* (2013.01); *C07C 229/10* (2013.01); *C07C 229/38* (2013.01); *C07C 229/46* (2013.01); *C07C 233/41* (2013.01); *C07C 237/06* (2013.01); *C07C 255/24* (2013.01); *C07C 255/30* (2013.01); *C07C 255/58* (2013.01); *C07D 205/12* (2013.01); *C07D 207/32* (2013.01); *C07D 211/22* (2013.01); *C07D 211/36* (2013.01); *C07D 211/58* (2013.01); *C07D 211/76* (2013.01); *C07D 213/38* (2013.01); *C07D 213/64* (2013.01); *C07D 213/69* (2013.01); *C07D 213/73* (2013.01); *C07D 215/44* (2013.01); *C07D 239/30* (2013.01); *C07D 263/32* (2013.01); *C07D 295/195* (2013.01); *C07D 305/06* (2013.01); *C07D 309/20* (2013.01); *C07D 317/28* (2013.01); *C07D 401/04* (2013.01); *C07D 401/06* (2013.01); *C07D 403/04* (2013.01); *C07D 403/06* (2013.01); *C07D 403/10* (2013.01); *C07D 405/04* (2013.01); *C07D 417/06* (2013.01); *C07B 2200/07* (2013.01); *C07C 2601/02* (2017.05);

(Continued)

(58) Field of Classification Search
CPC .................................................. C07D 211/26
See application file for complete search history.

(56) References Cited

U.S. PATENT DOCUMENTS

| | | |
|---|---|---|
| 4,639,273 A | 1/1987 | Gilmore et al. |
| 5,188,927 A | 2/1993 | Okada et al. |

(Continued)

FOREIGN PATENT DOCUMENTS

| | | |
|---|---|---|
| AU | 2005266890 A1 | 2/2006 |
| CN | 102947285 A | 2/2013 |

(Continued)

OTHER PUBLICATIONS

Alford et al., Organic Letters, (2012) VOI. 14. No. 23, pp. 6020-6023.*

(Continued)

*Primary Examiner* — Paul V Ward
(74) *Attorney, Agent, or Firm* — McCarter & English, LLP; Steven G. Davis; Michael J. DeGrazia

(57) ABSTRACT

Provided are novel compounds of Formula (I):

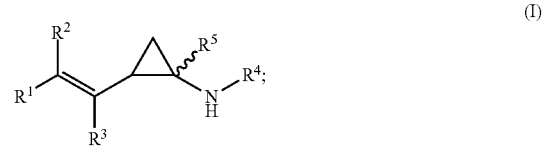

(I)

and pharmaceutically acceptable salts thereof, which are useful for treating a variety of diseases, disorders or conditions, associated with LSD1. Also provided are pharmaceutical compositions comprising the novel compounds of Formula (I), pharmaceutically acceptable salts thereof, and methods for their use in treating one or more diseases, disorders or conditions, associated with LSD1.

22 Claims, No Drawings

(51) Int. Cl.

| | | |
|---|---|---|
| *C07D 401/04* | (2006.01) | |
| *C07D 401/06* | (2006.01) | |
| *C07D 403/04* | (2006.01) | |
| *C07D 403/06* | (2006.01) | |
| *C07D 403/10* | (2006.01) | |
| *C07D 405/04* | (2006.01) | |
| *C07D 239/30* | (2006.01) | |
| *C07C 215/44* | (2006.01) | |
| *C07D 417/06* | (2006.01) | |
| *C07D 263/32* | (2006.01) | |
| *C07D 205/12* | (2006.01) | |
| *C07D 207/32* | (2006.01) | |
| *C07D 211/36* | (2006.01) | |
| *C07D 213/64* | (2006.01) | |
| *C07D 305/06* | (2006.01) | |
| *C07C 255/58* | (2006.01) | |
| *C07C 211/09* | (2006.01) | |
| *C07C 211/36* | (2006.01) | |
| *C07C 211/40* | (2006.01) | |
| *C07C 215/14* | (2006.01) | |
| *C07C 217/08* | (2006.01) | |
| *C07C 229/10* | (2006.01) | |
| *C07C 229/38* | (2006.01) | |
| *C07C 229/46* | (2006.01) | |
| *C07C 233/41* | (2006.01) | |
| *C07C 237/06* | (2006.01) | |
| *C07C 255/24* | (2006.01) | |
| *C07C 215/42* | (2006.01) | |
| *C07C 255/30* | (2006.01) | |
| *C07D 211/58* | (2006.01) | |
| *C07D 211/76* | (2006.01) | |
| *C07D 213/38* | (2006.01) | |
| *C07D 213/69* | (2006.01) | |
| *C07D 213/73* | (2006.01) | |
| *C07D 295/195* | (2006.01) | |
| *A61P 35/00* | (2006.01) | |

(52) U.S. Cl.
CPC ...... *C07C 2601/04* (2017.05); *C07C 2601/14* (2017.05); *C07C 2602/44* (2017.05)

(56) References Cited

U.S. PATENT DOCUMENTS

| | | |
|---|---|---|
| 5,344,467 A | 9/1994 | Huang et al. |
| 5,424,293 A | 6/1995 | Zoller et al. |
| 5,554,594 A | 9/1996 | Zoller et al. |
| 6,518,444 B1 | 2/2003 | McConville et al. |
| 7,135,437 B2 | 11/2006 | Pallas et al. |
| 7,172,703 B2 | 2/2007 | Javora et al. |
| 7,285,607 B2 | 10/2007 | Blann et al. |
| 7,507,485 B2 | 3/2009 | Oh et al. |
| 7,678,281 B2 | 3/2010 | Javora et al. |
| 8,877,832 B2 | 11/2014 | Ito et al. |
| 8,992,932 B2 | 3/2015 | Lerchen et al. |
| 9,315,488 B2 | 4/2016 | Ding et al. |
| 2003/0096708 A1 | 5/2003 | Agbaje et al. |
| 2004/0034015 A1 | 2/2004 | Robichaud et al. |
| 2004/0043983 A1 | 3/2004 | Li |
| 2004/0043985 A1 | 3/2004 | Hicks et al. |
| 2004/0127482 A1 | 7/2004 | Robichaud et al. |
| 2007/0027178 A1 | 2/2007 | Lee |
| 2007/0049613 A1 | 3/2007 | Chen et al. |
| 2007/0138101 A1 | 6/2007 | Javora et al. |
| 2010/0055169 A1 | 3/2010 | Dande et al. |
| 2012/0190770 A1 | 7/2012 | Ito et al. |
| 2015/0057326 A1 | 2/2015 | Wu |
| 2015/0069342 A1 | 3/2015 | Lee et al. |
| 2015/0069344 A1 | 3/2015 | Kim et al. |
| 2015/0069347 A1 | 3/2015 | Kim et al. |
| 2015/0069355 A1 | 3/2015 | Hwang et al. |
| 2015/0221878 A1 | 8/2015 | Rai et al. |
| 2015/0239918 A1 | 8/2015 | Johnson et al. |

FOREIGN PATENT DOCUMENTS

| | | |
|---|---|---|
| DE | 10302781 A1 | 9/2003 |
| DE | 102012001247 A1 | 7/2012 |
| EP | 461670 A1 | 12/1991 |
| EP | 580008 A2 | 1/1994 |
| EP | 584694 A1 | 3/1994 |
| EP | 678786 A1 | 10/1995 |
| EP | 2433940 A1 | 3/2012 |
| JP | 2003-064035 A | 3/2003 |
| JP | 2004-189893 A | 7/2004 |
| JP | 2008-207466 A | 9/2008 |
| JP | 2010-126651 A | 6/2010 |
| JP | 47-89966 B2 | 10/2011 |
| JP | 2012-077108 A | 4/2012 |
| JP | 2014-232188 A | 12/2014 |
| JP | 2015-030699 A | 2/2015 |
| WO | 1987/07637 A2 | 12/1987 |
| WO | 1992/17456 A1 | 10/1992 |
| WO | 1992/20762 A1 | 11/1992 |
| WO | 1992/20765 A1 | 11/1992 |
| WO | 1993/16684 A1 | 9/1993 |
| WO | 1997/01545 A1 | 1/1997 |
| WO | 1997/29825 A1 | 8/1997 |
| WO | 2000/069828 A1 | 11/2000 |
| WO | 2001/010822 A1 | 2/2001 |
| WO | 2001/089302 A2 | 11/2001 |
| WO | 2002/000623 A2 | 1/2002 |
| WO | 2002/021924 A2 | 3/2002 |
| WO | 2002/096199 A2 | 12/2002 |
| WO | 2002/102153 A2 | 12/2002 |
| WO | 2003/003008 A1 | 1/2003 |
| WO | 2004/018436 A2 | 3/2004 |
| WO | 2004/019681 A2 | 3/2004 |
| WO | 2004/052862 A1 | 6/2004 |
| WO | 2004/078686 A1 | 9/2004 |
| WO | 2005/040135 A1 | 5/2005 |
| WO | 2005/105734 A1 | 11/2005 |
| WO | 2005/118543 A1 | 12/2005 |
| WO | 2005/123884 A2 | 12/2005 |
| WO | 2006/024783 A1 | 3/2006 |
| WO | 2006/032926 A2 | 3/2006 |
| WO | 2006/037335 A2 | 4/2006 |
| WO | 2006/038594 A1 | 4/2006 |
| WO | 2007/033002 A1 | 3/2007 |
| WO | 2007/044100 A1 | 4/2007 |
| WO | 2007/071396 A2 | 6/2007 |
| WO | 2007/116011 A2 | 10/2007 |
| WO | 2008/104994 A2 | 9/2008 |
| WO | 2009/067797 A1 | 6/2009 |
| WO | 2009/087225 A2 | 7/2009 |
| WO | 2009/105782 A1 | 8/2009 |
| WO | 2009/121486 A1 | 10/2009 |
| WO | 2010/007317 A1 | 1/2010 |
| WO | 2010/129687 A1 | 11/2010 |
| WO | 2010/148422 A1 | 12/2010 |
| WO | 2010/148652 A1 | 12/2010 |
| WO | 2011/039403 A1 | 4/2011 |
| WO | 2012/016188 A2 | 2/2012 |
| WO | 2012/020215 A1 | 2/2012 |
| WO | 2012/146338 A1 | 11/2012 |
| WO | 2012/178123 A1 | 12/2012 |
| WO | 2012/178124 A1 | 12/2012 |
| WO | 2012/178125 A1 | 12/2012 |
| WO | 2013/005057 A1 | 1/2013 |
| WO | 2013/014207 A1 | 1/2013 |
| WO | 2013/045516 A1 | 4/2013 |
| WO | 2013/049686 A1 | 4/2013 |
| WO | 2013/057320 A1 | 4/2013 |
| WO | 2013/068075 A1 | 5/2013 |
| WO | 2013/168103 A1 | 11/2013 |
| WO | 2014/045031 A1 | 3/2014 |
| WO | 2014/052896 A1 | 4/2014 |
| WO | 2014/057095 A1 | 4/2014 |

(56) References Cited

FOREIGN PATENT DOCUMENTS

| WO | 2014/065083 A1 | 5/2014 |
|---|---|---|
| WO | 2014/068893 A1 | 5/2014 |
| WO | 2014/157267 A1 | 10/2014 |
| WO | 2014/210564 A1 | 12/2014 |
| WO | 2015/014986 A1 | 2/2015 |
| WO | 2015/024120 A1 | 2/2015 |
| WO | 2015/126357 A1 | 8/2015 |
| WO | 2015/133247 A1 | 9/2015 |

OTHER PUBLICATIONS

McMahon et al. (2000).*
Pinedo et al. (2000).*
Neidle et al. (2008): Cancer Drug Design and Discovery Neidle, Stephen, ed. (Elsevier/Academic Press, 2008).*
Alford et al., Expanding the scope of donor/acceptor carbenes to N-phthalimido donor groups: diastereoselective synthesis of 1-cyclopropane a-amino acids. Org Lett. Dec. 7, 2012;14(23):6020-3.
Bennani-Baiti et al., Human Pathology 2012, 43, 1300-1307.
Cai et al., Cancer Cell, 20, 457-471, Oct. 18, 2011.
Haymai et al., Int. J. Cancer, 128, 574-594 (2011).
Konovolav et a., Journal of Ovarian Research 2013, 6, 75.
Lian et al., FASEB J. vol. 27, No. 1_supplement, Apr. 2013 (abstract only).
Liang et al., mBio, Jan./Feb. 2013, vol. 4, Issue 1, e00558-12.
Northcott, et al., (2014) Nature 511, 428-434.
Pajtler et al., (2013) Acta Neuropathol. Commun. 1, 19-31.
Sakane et al., PLOS Pathogens, Aug. 2011, vol. 7, Issue 8, e1002184.
Willmann et al., Int. J. Cancer. 131; 2704-2709; (2012).
Yokoyama et al., Molecular and Cell Biology, vol. 28, No. 12, 3995-4003, Jun. 2008.
Yu et al., Biochemical and Biophysical Research Communications 437, 2013, 192-198.
Zhang et al., Cell Reports 5, 1-13, Oct. 31, 2013.

* cited by examiner

LSD1 INHIBITORS AND USES THEREOF

RELATED APPLICATIONS

This application is a § 371 national stage filing of International Application No. PCT/US2016/028864, filed Apr. 22, 2016, which claims the benefit of U.S. Provisional Application No. 62/151,706, filed Apr. 23, 2015. The entire contents of each of the aforementioned applications are incorporated herein by reference.

BACKGROUND OF THE INVENTION

Lysine-specific demethylase (LSD1) also known as lysine (K)-specific demethylase 1A (LSD1) is a protein in humans that in encoded by the KDM1A gene and specifically demethylates mono- or dimethylated dimethylated histone H3 lysine4 (H3K4) and H3 lysine 9 (H3K9) via a redox process. Biochimica et Biophysica Acta 1829 (2013) 981-986. LSD1 has been found to possess oncogenic properties in several cancers ranging from prostate (Cancer Res., 66 (2006), pp. 11341-11347) bladder (Mol. Carcinog., 50 (2011), pp. 931-944) neuroblastomas, (Cancer Res., 69 (2009), pp. 2065-2071) lung cancers, (PLoS One, 7 (2012), p. e35065) sarcomas and hepato-carcinomas (Tumour Biol. (2012). LSD1 pharmacological inhibitors have been shown e.g., to treat leukemias (Nat. Med., 18 (2012), pp. 605-611) and also solid tumors (Tumour Biol. (2012)).

SUMMARY OF THE INVENTION

Disclosed are compounds and pharmaceutical compositions thereof that modulate the activity of LSD1 (See e.g., Table 5). Such compounds include those of structural Formula

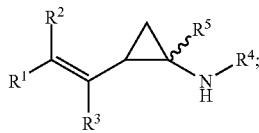

or a pharmaceutically acceptable salt thereof, wherein each of $R^1$, $R^2$, $R^3$, $R^4$, and $R^5$ are defined and described herein.

Compounds described herein, and pharmaceutically acceptable compositions thereof, are useful for treating a variety of diseases, disorders or conditions, associated with LSD1. Such diseases, disorders, or conditions include those described herein.

Compounds described herein are also useful for the study of LSD1 in biological and pathological phenomena; the study of intracellular signal transduction pathways mediated by LSD1 and the comparative evaluation of new LSD1 modulators.

DETAILED DESCRIPTION OF CERTAIN EMBODIMENTS

1. General Description of Compounds of the Invention

In certain embodiments, the present disclosure provides a compound of Formula I:

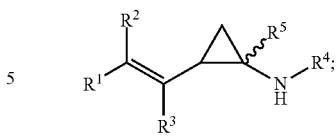

or a pharmaceutically acceptable salt thereof, wherein
$R^1$ is selected from carbocyclyl, heterocyclyl, aryl and heteroaryl, each of which being optionally substituted with up to 4 independently selected substituents;
each of $R^2$ and $R^3$ is independently selected from hydrogen, halo, —CN and optionally substituted $C_1$-$C_8$ alkyl;
$R^4$ is selected from hydrogen, optionally substituted carbocyclyl, optionally substituted heterocyclyl, and —C($R^6$)($R^7$)($R^8$);
each $R^5$ is independently selected from hydrogen and optionally substituted $C_1$-$C_4$ alkyl;
$R^6$ is selected from hydrogen and —$C_1$-$C_4$
$R^7$ is selected from hydrogen, halo, —CN, and optionally substituted $C_1$-$C_8$ alkyl; and
$R^8$ is selected from hydrogen, halo, —$C_1$-$C_4$ alkyl, —($C_0$-$C_4$ alkylene)-carbocyclyl, —($C_0$-$C_4$ alkylene)-heterocyclyl, —($C_0$-$C_4$ alkylene)-aryl, and —($C_0$-$C_4$ alkylene)-heteroaryl, wherein any carbocyclyl, heterocyclyl, aryl, heteroaryl, or alkyl portion of $R^8$ is optionally substituted;
provided that the compound is other than

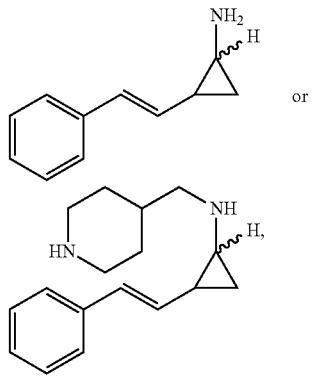

or a pharmaceutically acceptable salt thereof.

2. Compounds and Definitions

The terms "halo" and "halogen" as used herein refer to an atom selected from fluorine (fluoro, —F), chlorine (chloro, —Cl), bromine (bromo, —Br), and iodine (iodo, —I).

The term "alkyl" used alone or as part of a larger moiety, such as "alkoxy", "haloalkyl", "aralkyl", "heteroaralkyl" and the like, means saturated straight-chain or branched monovalent hydrocarbon radical. Unless otherwise specified, an alkyl group typically has 1-6 carbon atoms, i.e., ($C_1$-$C_6$)alkyl. As used herein, a "($C_1$-$C_6$)alkyl" group is means a radical having from 1 to 6 carbon atoms in a linear or branched arrangement.

The term "haloalkyl" includes mono, poly, and perhaloalkyl groups where the halogens are independently selected from fluorine, chlorine, bromine, and iodine.

"Alkoxy" means an alkyl radical attached through an oxygen linking atom, represented by —O-alkyl. For example, "($C_1$-$C_4$)alkoxy" includes methoxy, ethoxy, propoxy, and butoxy.

The term "aryl" used alone or as part of a larger moiety as in "aralkyl", "aralkoxy", or "aryloxyalkyl", refers to an aromatic carbocyclic ring system having, unless otherwise specified, a total of 6 to 14 ring members. The term "aryl" may be used interchangeably with the term "aryl ring", "aryl group", "aryl moiety," or "aryl radical". In certain embodiments of the present disclosure, "aryl" refers to an aromatic ring system which includes, but is not limited to, phenyl (abbreviated as "Ph"), naphthyl and the like. It will be understood that when specified, optional substituents on an aryl group (e.g., in the case of an optionally substituted aryl or aryl which is optionally substituted) may be present on any substitutable position, i.e., any ring carbon substituted with hydrogen.

The term "carbocyclyl" (also referred to herein as "carbocycle" or "cycloaliphatic", as used herein, means a monocyclic, bicyclic (e.g., a bridged or spiro bicyclic ring), polycyclic (e.g., tricyclic), or fused hydrocarbon ring system that is completely saturated or that contains one or more units of unsaturation, but where there is no aromatic ring. Cycloalkyl is a completely satureard carbocycle. Monocyclic carbocyclyl groups include, without limitation, cyclopropyl, cyclobutyl, cyclopentyl, cyclopentenyl, cyclohexyl, cyclohexenyl, cycloheptyl, cycloheptenyl, and cyclooctyl. Bridged bicyclic carbocyclyl groups include, without limitation, bicyclo[3.2.1]octane, bicyclo[2.2.1]heptane, hicyclo[3.1.0]hexane, and the like. Spiro bicyclic carbocyclyl groups include, e.g., spiro[3.6]decane, spiro[4.5]decane, and the like. Fused carbocyclyl rings include, e.g., decahydronaphthalene, octahydropentalene, and the like. It will be understood that when specified, optional substituents on a carbocyclyl (e.g., in the case of an optionally substituted carbocyclyl or carbocyclyl which is optionally substituted) may be present on any substitutable position and, include, e.g., the position at which the carbocyclyl group is attached.

The term "heteroaryl" used alone or as part of a larger moiety as in "heteroarylalkyl", "heteroarylalkoxy", or "theteroarylaminoalkyl", refers to a 5-10-membered aromatic radical containing 1-4 heteroatoms selected from N, quaternary ammonium cation, O, and S, and includes, for example, thienyl, (uranyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl" may be used interchangeably with the terms "heteroaryl ring", "heteroaryl group", or "heteroaromatic". The terms "heteroaryl" and "heteroar-", as used herein, also include groups in which a heteroaromatic ring is fused to one or more aryl rings, where the radical or point of attachment is on the heteroaromatic ring. Nonlimiting examples include indolyl, indazolyl, benzimidazolyl, henzthiazolyl, quinolyl, quinazolinyl, and quinoxalinyl. It will be understood that when specified, optional substituents on a heteroaryl group may be present on any substitutable position (carbon and nitrogen).

The term "heterocyclyl" means a 3-12 membered (e.g., a 4-, 5-, 6- and 7-membered) saturated or partially unsaturated heterocyclic ring containing 1 to 4 heteroatoms independently selected from N, O, and S. It can be mononcyclic, bicyclic (e.g., a bridged, fused, or spiro bicyclic ring), or tricyclic. The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, 1-azaspiro[4.5]decane, and tetrahydropyrimidinyl. A heterocyclyl group may be mono- or bicyclic. The term "heterocyclyl" also includes, e.g., unsaturated heterocyclic radicals fused to another unsaturated heterocyclic radical or aryl or heteroaryl ring, such as for example, tetrahydronaphthyridine, indolinone, dihydropyrrolotriazole, imidazopyrimidine, quinolinone, dioxaspirodecane. It will also be understood that when specified, optional substituents on a heterocyclyl group may be present on any substitutable position and, include, e.g., the position at which the heterocyclyl is attached (e.g., in the case of an optionally substituted heterocyclyl or heterocyclyl which is optionally substituted).

The term "spiro" refers to rings that shares one ring atom (e.g., carbon).

The term "fused" refers to rings that share two adjacent ring ring atoms with one another.

The term "bridged" refers to rings that share at least three ring atoms with one another.

As described herein, compounds herein may contain "optionally substituted" moieties. Unless otherwise indicated, an "optionally substituted" group may have a suitable substituent that results in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein. In one embodiment, suitable substituents for an optionally substituted alkyl, carbocyclyl, heterocyclyl, aryl group and heteroaryl group are those which do not substantially diminish the LSD1 activity of the compound. Examples include halogen, =O, —CN, —OR$^c$, —NR$^a$R$^b$, —S(O)$_i$R$^c$, —NR$^d$S(O)$_2$R$^c$, —S(O)$_2$NR$^e$R$^f$, —C(=O)OR$^c$, —OC(=O)R$^c$, —OC(=O)R$^c$, —OC(=S)OR$^c$, —C(=S) OR$^c$, —O(C=S)R$^c$, —C(=O)NR$^e$R$^f$, —NR$^d$C(=O)R$^c$, —C(=S)NR$^e$R$^f$, —NR$^d$C(=S)R$^c$, —NR$^d$(C=O)OR$^c$, —O(C=O)NR$^e$R$^f$, —NR$^d$(C=S)OR$^c$, —O(C=S)NR$^e$R$^f$, —NR$^d$(C=O)NR$^e$R$^f$, —NR$^d$(C=S)NR$^e$R$^f$, —C(=S)R$^c$, —C(=O)R$^c$, (C$_1$-C$_6$)alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl and —(CH$_2$)$_{1-4}$-heteroaryl, wherein each of the (C$_1$-C$_6$)alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl and —(CH$_2$)$_{1-4}$-heteroaryl are optionally substituted with halogen, OR$^c$, —NO$_2$, —CN, —NR$^d$C(=O)R$^c$, —S(O)$_i$R$^c$, —C(=O)OR$^c$, —C(=O) NR$^e$R$^f$, —C(=O)R$^c$, (C$_1$-C$_3$)alkyl, halo(C$_1$-C$_3$)alkyl, (C$_1$-C$_3$)alkoxy(C$_1$-C$_3$)alkyl, (C$_1$-C$_3$)alkoxy, and halo(C$_1$-C$_3$) alkoxy; wherein R$^a$ and R$^b$ are each independently selected from —H and (C$_1$-C$_6$)alkyl optionally substituted with 1 to 3 substituents independently selected from halogen, hydroxy, COOH, —NR$^g$R$^h$, and (C$_1$-C$_3$)alkoxy; R$^c$ is —H or (C$_1$-C$_6$)alkyl optionally substituted with 1 to 3 substituents independently selected from halogen, —NR$^g$R$^h$, hydroxyl, and (C$_1$-C$_3$)alkoxy; R$^d$ is —H or (C$_1$-C$_6$)alkyl optionally substituted with 1 to 3 substituents independently selected from halogen, —NR$^g$R$^h$, hydroxyl, and (C$_1$-C$_3$) alkoxy; R$^e$ and R$^f$ are each independently selected from —H and (C$_1$-C$_6$)alkyl optionally substituted with 1 to 3 substituents independently selected from halogen, —NR$^g$R$^h$, hydroxyl, and (C$_1$-C$_3$)alkoxy; or R$^e$ and R$^f$, together with the nitrogen to which they are attached, form a 3-8 membered ring optionally substituted with 1 to 3 substituents independently selected from halogen, —NR$^g$R$^h$, —CN, (C$_1$-C$_6$) alkyl, halo(C$_1$-C$_6$)alkyl, (C$_1$-C$_3$)alkoxy, halo(C$_1$-C$_3$)alkoxy, and (C$_1$-C$_3$)alkoxy(C$_1$-C$_6$)alkyl; R$^g$ and R$^h$ are each independently selected from —H, (C$_1$-C$_6$)alkyl, halo(C$_1$-C$_6$) alkyl, hydroxy(C$_1$-C$_6$)alkyl, and (C$_1$-C$_3$)alkoxy(C$_1$-C$_6$) alkyl; and i is 0, 1 or 2. In another embodiment, suitables substituents are selected from halo, =O, —CN, —S(O)$_i$R$^c$; —NR$^c$R$^b$, aryl(C$_1$-C$_3$)alkyl- wherein the aryl portion is optionally substituted with C(=O)R$^e$ or —C(=O)NR$^e$R$^f$, and (C$_1$-C$_6$)alkyl optionally substituted with —CN, halo, OR$^e$, —C(=O)NR$^e$R$^f$, —C(=O)OR$^e$, (C$_1$-C$_3$)alkoxy, and —C(=O)R$^e$. In one alternative, i is 2; R$^a$ is —H; R$^b$ is —H or (C$_1$-C$_4$)alkyl; R$^c$ is —H or (C$_1$-C$_4$)alkyl; R$^e$ is —H or (C$_1$-C$_4$)alkyl; and R$^f$ is —H or (C$_1$-C$_4$)alkyl.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. "Geometric isomer" are stereoisomers that differ in the orientation of substituent atoms in relationship to a carbon-carbon double bond, to a carbocyclyl ring, or to a bridged bicyclic system. The symbol "*" in a structural formula represents the presence of a chiral carbon center. "R" and "S" represent the configuration of substituents around one or more chiral carbon atoms. A wavy line " ~~~ " in a structural formula denotes a position at which the stereochemistry is not defined or at which a mixture of stereoisomers exits. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. When a disclosed compound is named or depicted by structure without indicating a particular geometric isomer form, it is to be understood that the name or structure encompasses one geometric isomer free of other geometric isomers, mixtures of geometric isomers, or all geometric isomers.

"Racemate" or "racemic mixture" means a compound of equimolar quantities of two enantiomers, wherein such mixtures exhibit no optical activity, i.e., they do not rotate the plane of polarized light.

The compounds of the invention may be prepared as individual enantiomers by either enantio-specific synthesis or resolved from an enantiomerically enriched mixture. Conventional resolution techniques include forming the salt of a free base of each isomer of an enantiomeric pair using an optically active acid (followed by fractional crystallization and regeneration of the free base), forming the salt of the acid form of each enantiomer of an enantiomeric pair using an optically active amine (followed by fractional crystallization and regeneration of the free acid), forming an ester or amide of each of the enantiomers of an enantiomeric pair using an optically pure acid, amine or alcohol (followed by chromatographic separation and removal of the chiral auxiliary), or resolving an enantiomeric mixture of either a starting material or a final product using various well known chromatographic methods.

In some cases (such as in compound 127), when a compound is drawn as a single stereoisomer, but notes as being "racemic", it means that the depicted stereoisomer is present in equimolar amount relative to the other stereoisomer.

In some cases (such as in compound 249), when a compound is drawn as a single stereoisomer, but named as being one enantiomer or the other (e.g., "1R,2S or 1S,2R"), it means that either single stereoisomer is present with a stereochemical purity of at least at least 85%, at least 90%, at least 95%, at least 97%, at least 98% or at least 99% by weight, i.e., the percent by weight relative to the other enantiomer of the compound.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and e.g, the compound has at least two chiral centers, it is to be understood that the name or structure encompasses one stereoisomer free of other stereoisomers, mixtures of stereoisomers, and mixtures of stereoisomers in which one or more stereoisomers is enriched relative to the other stereoisomer(s). For example, the name or structure may encompass one stereoisomer free of other diastereomers, mixtures of stereoisomers, and mixtures of stereoisomers in which one or more diastereomers is enriched relative to the other diastereomer(s).

The compounds described herein may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include e.g., ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, benzoates and salts with amino acids such as glutamic acid.

3. Description of Exemplary Compounds

In a first embodiment, the present disclosure provides a compound of Formula I:

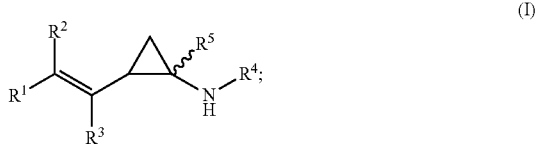

(I)

or a pharmaceutically acceptable salt thereof, wherein the variables are as described above.

In a second embodiment, $R^7$ in Formula I is hydrogen, wherein the remaining variables are as described in Formula I.

In a third embodiment, $R^1$ in Formula I is selected from carbocyclyl, heterocyclyl, aryl and heteroaryl, each of which being optionally substituted with up to 3 substituents independently selected from $R^X$; each of $R^2$ and $R^3$ is independently selected from hydrogen, halo, and $C_1$-$C_4$ alkyl; each $R^5$ is independently selected from hydrogen and $C_1$-$C_4$ alkyl; $R^6$ is hydrogen; $R^8$ is selected from —($C_0$-$C_4$ alkylene)-carbocyclyl, —($C_0$-$C_4$ alkylene)-heterocyclyl, —($C_0$-$C_4$ alkylene)-aryl, and —($C_0$-$C_4$ alkylene)-heteroaryl, wherein said carbocyclyl, heterocyclyl, aryl, and heteroaryl are each optionally substituted with up to 3 substituents independently selected from $R^Y$; $R^X$ and $R^Y$ are each independently selected from halogen, —CN, —$NR^aR^b$, —$S(O)_iR^c$, —$NR^dS(O)_2R^c$, —$S(O)_2NR^eR^f$, —C(=O)$OR^c$, —OC(=O) $OR^c$, —OC(=O)$R^c$, —OC(=S)$OR^c$, —C(=S)$OR^c$, —O(C=S)$R^c$, —C(=O)$NR^eR^f$, —$NR^dC$(=O)$R^c$, —C(=S)$NR^eR^f$, —$NR^dC$(=S)$R^c$, —$NR^d$(C=O)$OR^c$, —O(C=O)$NR^eR^f$, —$NR^d$(C=S)$OR^c$, —O(C=S)$NR^eR^f$, —$NR^d$(C=O)$NR^eR^f$, —$NR^d$(C=S)$NR^eR^f$, —C(=S)$R^c$, —C(=O)$R^c$, $(C_1$-$C_6)$alkyl, cycloalkyl, —$(CH_2)_{1-4}$-cycloalkyl, heterocyclyl, —$(CH_2)_{1-4}$-heterocyclyl, aryl, —$(CH_2)_{1-4}$-aryl, heteroaryl and —$(CH_2)_{1-4}$-heteroaryl, wherein each of the $(C_1$-$C_6)$alkyl, cycloalkyl, —$(CH_2)_{1-4}$-cycloalkyl, heterocyclyl, —$(CH_2)_{1-4}$-heterocyclyl, aryl, —$(CH_2)_{1-4}$-aryl, heteroaryl and —$(CH_2)_{1-4}$-heteroaryl are optionally substituted with halogen, $OR^c$, —$NO_2$, —CN, —$NR^dC$(=O)$R^c$, —$NR^gR^h$, —$S(O)_iR^c$, —C(=O)$OR^c$, —C(=O)$NR^eR^f$, —C(=O)$OR^c$, $(C_1$-$C_3)$alkyl, halo$(C_1$-$C_3)$ alkyl, $(C_1$-$C_3)$alkoxy$(C_1$-$C_3)$alkyl, $(C_1$-$C_3)$alkoxy, and halo $(C_1$-$C_3)$alkoxy; or two $R^X$ bonded to the same carbon atom or two $R^Y$ bonded to the same carbon atom are taken together to form =O; where $R^a$ and $R^b$ are each independently selected from —H and $(C_1$-$C_6)$alkyl optionally substituted with 1 to 3 substituents independently selected from halogen, hydroxy, COOH, —$NR^gR^h$, and $(C_1$-$C_3)$alkoxy; $R^c$ is —H or $(C_1$-$C_6)$alkyl optionally substituted with 1 to 3 substituents independently selected from halogen, —$NR^gR^h$, hydroxyl, and $(C_1$-$C_3)$alkoxy; $R^d$ is —H or $(C_1$-$C_6)$alkyl optionally substituted with 1 to 3 substituents independently selected from halogen, —$NR^gR^h$, hydroxyl, and $(C_1$-$C_3)$alkoxy; $R^e$ and $R^f$ are each independently selected from —H and $(C_1$-$C_6)$alkyl optionally substituted with 1 to 3 substituents independently selected from halogen, —$NR^gR^h$, hydroxyl, and $(C_1$-$C_3)$alkoxy; or $R^e$ and $R^f$, together with the nitrogen to which they are attached, form a 3-8 membered ring optionally substituted with 1 to 3 substituents independently selected from halogen, —$NR^gR^h$, —CN, $(C_1$-$C_6)$alkyl, halo$(C_1$-$C_6)$alkyl, $(C_1$-$C_3)$ alkoxy, halo$(C_1$-$C_3)$alkoxy, and $(C_1$-$C_3)$alkoxy$(C_1$-$C_6)$alkyl; $R^g$ and $R^h$ are each independently selected from —H, $(C_1$-$C_6)$alkyl, halo$(C_1$-$C_6)$alkyl, hydroxy$(C_1$-$C_6)$alkyl, and $(C_1$-$C_3)$alkoxy$(C_1$-$C_6)$alkyl; and i is 0, 1 or 2, wherein the remaining variables are as described in Formula I or the second embodiment.

In a fourth embodiment, $R^1$ in Formula I is aryl, heteroaryl, or heterocyclyl, each being optionally substituted with up to 3 substituents independently selected from $R^X$, wherein the remaining variables are as described in Formula I or the first, second or third embodiment.

In a fifth embodiment, $R^1$ in Formula I is phenyl, pyridinyl, pyrazolyl, imidazolyl, or pyrimidinyl, each being optionally substituted with up to 3 substituents independently selected from $R^X$, wherein the remaining variables are as described in Formula I or the first, second, third, or fourth embodiment.

In a sixth embodiment, $R^X$ and $R^Y$ in the third, fourth, or fifth embodiment are each independently selected from halogen, halo$(C_1$-$C_4)$alkyl, $(C_1$-$C_4)$alkoxy, halo$(C_1$-$C_4)$ alkoxy, hydroxy$(C_1$-$C_4)$alkyl, cyano$(C_1$-$C_4)$alkyl, hydroxy $(C_1$-$C_4)$alkoxy, $(C_1$-$C_4)$alkoxy$(C_1$-$C_4)$alkyl, halo$(C_1$-$C_4)$ alkoxy$(C_1$-$C_4)$alkyl, —$(CH_2)_{1-4}$-aryl, —$(CH_2)_{1-4}$-aryl-COOH, —$(CH_2)_{1-4}$-aryl-C(=O)$NR^eR^f$, —$NR^d$(C=O) $OR^c$, —CN, —C(=O)$NR^eR^f$, —$NR^aR^b$, and $(C_1$-$C_4)$alkyl optionally substituted with —C(=O)$NR^eR^f$, —C(=O)$OR^c$, or —$S(O)_iR^c$; or two $R^X$ bonded to the same carbon atom or two $R^Y$ bonded to the same carbon atom are taken together to form =O, wherein the remaining variables are as described in Formula I.

In a seventh embodiment, $R^X$ in the third, fourth, fifth, or sixth embodiment is selected from halogen, halo$(C_1$-$C_4)$ alkyl, $(C_1$-$C_4)$alkoxy, halo$(C_1$-$C_4)$alkoxy, hydroxy$(C_1$-$C_4)$ alkyl, —CN, —C(=O)$NR^eR^f$, —$NR^aR^b$, and $(C_1$-$C_4)$alkyl optionally substituted with —C(=O)$NR^eR^f$; or two $R^X$ bonded to the same carbon atom are taken together to form =O, wherein the remaining variables are as described in Formula I. Alternatively, $R^X$ is halogen, —CN, —C(=O) $NR^eR^f$, or $(C_1$-$C_4)$alkyl; or two $R^X$ on the same carbon atom are taken together to form =O, wherein the remaining variables are as described in Formula I. In another alternative, $R^X$ is halogen, —CN, $(C_1$-$C_4)$alkyl, —C(=O)$NH_2$, or —C(=O)$NH(C_1$-$C_3)$alkyl; or two $R^X$ on the same carbon atom are taken together to form =O, wherein the remaining variables are as described in Formula I.

In an eighth embodiment, $R^1$ in Formula I is selected from unsubstituted phenyl, 2-fluorophenyl, pyridin-3-yl, 1-methyl-1H-pyrazol-4-yl, 1-methyl-1H-imidazol-4-yl, 1-methyl-6-oxopyridin-3-yl, 1-methyl-6-oxopyridin-4-yl, 4-cyanophenyl, pyrimidin-5-yl, 4-aminocarbonylphenyl, and 4-methylaminocarbonylphenyl, wherein the remaining variables are as described in Formula I or the, first, second, third, fourth, fifth, sixth, or seventh embodiment.

In a ninth embodiment, $R^1$ in Formula I is selected from unsubstituted phenyl, 2-fluorophenyl and pyridin-3-yl, wherein the remaining variables are as described in Formula I or the, first, second, third, fourth, fifth, sixth, seventh, or eighth embodiment.

In a tenth embodiment, $R^2$ in Formula I is hydrogen, wherein the remaining variables are as described in Formula I or the second, third, fourth, fifth, sixth, seventh, eighth, or ninth embodiment.

In an eleventh embodiment, $R^3$ in Formula I is selected from hydrogen, halo and $C_1$-$C_4$ alkyl, wherein the remaining variables are as described in Formula I or the second, third, fourth, fifth, sixth, seventh, eighth, ninth, or tenth embodiment. Alternatively, $R^3$ in Formula I is selected from hydrogen, fluoro, —$CH_3$ and —$CH_2CH_3$, wherein the remaining variables are as described in Formula I or the second, third, fourth, fifth, sixth, seventh, eighth, ninth, or tenth embodiment. In another alternative, $R^3$ in Formula I is selected from hydrogen and —$CH_3$, wherein the remaining variables are as described in Formula I or the second, third, fourth, fifth, sixth, seventh, eighth, ninth, or tenth embodiment.

In a twelfth embodiment, $R^4$ in Formula I is hydrogen, —$CH_2$-piperidinyl, —$CH_2$-pyridinyl, —$CH_2$-cyclopropyl, piperidinyl, 1-azaspiro[4.5]decane-8-yl or bicyclo[3.2.1]octan-8-amine-3-yl, or cyclohexyl, wherein each of said piperidinyl, pyridinyl, cyclopropyl, and cyclohexyl, is optionally substituted with up to 3 substituents independently selected from $R^Y$, wherein the remaining variables are as described in Formula I or the second, third, fourth, fifth, sixth, seventh, eighth, ninth, tenth, or eleventh embodiment.

In a thirteenth embodiment, $R^Y$ in the third, sixth or twelfth embodiment is selected from halogen, halo($C_1$-$C_4$) alkyl, ($C_1$-$C_4$)alkoxy, halo($C_1$-$C_4$)alkoxy, cyano($C_1$-$C_4$) alkyl, hydroxy($C_1$-$C_4$)alkyl, hydroxy($C_1$-$C_4$)alkoxy, ($C_1$-$C_4$) alkoxy($C_1$-$C_4$)alkyl, halo($C_1$-$C_4$)alkoxy($C_1$-$C_4$)alkyl, —$(CH_2)_{1-4}$-aryl, —$(CH_2)_{1-4}$-aryl-COOH, —$(CH_2)_{1-4}$-aryl—C(=O)NR$^e$R$^f$, —NR$^a$R$^b$, —NR$^d$C(=O)OR$^c$, —C(=O)NR$^e$R$^f$, and ($C_1$-$C_6$)alkyl optionally substituted with —C(=O)OR$^c$, —C(=O)NR$^e$R$^f$, or —S(O)$_i$R$^c$; or two $R^Y$ on the same carbon atom are taken together to form =O, wherein the remaining variables are as described in Formula I or the second, third, fourth, fifth, sixth, seventh, eighth, ninth, tenth, eleventh, or twelfth embodiment. Alternatively, $R^Y$ in the third, sixth, or twelfth embodiment is selected from —$NH_2$, —NH($C_1$-$C_4$)alkyl, ($C_1$-$C_4$)alkoxy($C_1$-$C_4$)alkyl, cyano($C_1$-$C_4$)alkyl, —$(CH_2)_{1-4}$-aryl, —NR$^d$C(=O)OR$^c$, —$(CH_2)_{1-4}$-arylCOOH, —$(CH_2)_{1-4}$-aryl-C(=O)NR$^e$R$^f$, hydroxy($C_1$-$C_6$)alkyl, —C(=O)NR$^e$R$^f$, —NR$^a$R$^b$, and ($C_1$-$C_6$)alkyl optionally substituted with —S(O)$_2$R$^c$, —C(=O) OR$^c$, or —C(=O)NR$^e$R$^f$, where R$^a$ is ($C_1$-$C_6$)alkyl optionally substituted with COOH; R$^b$ is —H; R$^e$ is —H or ($C_1$-$C_6$)alkyl; R$^f$ is —H or ($C_1$-$C_6$)alkyl; and R$^c$ is —H or ($C_1$-$C_6$)alkyl optionally substituted with COOH, wherein the remaining variables are as described in Formula I or the second, third, fourth, fifth, sixth, seventh, eighth, ninth, tenth, eleventh, or twelfth embodiment.

In a fourteenth embodiment, $R^4$ in Formula I is selected from hydrogen, 1-((2-ethylsulfonyl)ethyl)piperidin-4-ylmethyl, 1-(2-cyanoethyl)piperidin-4-ylmethyl, 1-(2-hydroxy-2,2-dimethylethyl)piperidin-4-ylmethyl, 1-(3-carboxy-2,2-dimethylpropyl)piperidin-4-ylmethyl, 1-(3-carboxy-3,3-dimethylpropyl)piperidin-4-ylmethyl, 1-(4-aminocarbonylbenzyl)piperidin-4-ylmethyl, 1-(4-carboxybenzyl)piperidin-4-ylmethyl, 1-(4-dimethylaminocarbonylbenzyl)piperidin-4-ylmethyl, 1-(aminocarbonylethyl)piperidin-4-ylmethyl, 1-(carboxyethyl)piperidin-4-ylmethyl, 1-(carboxymethyl)piperidin-4-ylmethyl, 1-(dimethylaminoethyl)piperidin-4-ylmethyl, 1-(methoxyethyl)piperidin-4-ylmethyl, 1-benzylpiperidin-4-ylmethyl, 2-aminopyridin-3-ylmethyl, 4-amino-4-methylcyclohexyl, 4-aminocyclohexyl, 4-carbboxypropylaminocyclhexyl, 4-carboxyethylaminocyclohexyl, 4-ethylaminocyclohexyl, 4-fluoropiperidin-4-ylmethyl, 8-aminobicyclo[3.2.1]octan-3-yl, azaspiro[4.5]decan-8-yl, cyclopropylmethyl, piperidin-4-yl, and piperidin-4-ylmethyl, wherein the remaining variables are as described in Formula I or the second, third, fourth, fifth, sixth, seventh, eighth, ninth, tenth, eleventh, twelfth, or thirteenth embodiment. Alternatively, $R^4$ in Formula I is selected from hydrogen 1-(4-carboxybenzyl)piperidin-4-ylmethyl, piperidin-4-ylmethyl, 1-(carboxyethyl)piperidin-4-ylmethyl, 1-benzylpiperidin-4-ylmethyl, 4-fluoropiperidin-4-ylmethyl, 4-aminocyclohexyl, 1-(carboxymethyl)piperidin-4-ylmethyl, 1-((2-ethylsulfonyl)ethyl)piperidin-4-ylmethyl, 2-aminopyridin-3-ylmethyl, 1-(2-hydroxy-2,2-dimethylethyl)piperidin-4-ylmethyl, cyclopropylmethyl, piperidin-4-ylmethyl, piperidin-4-yl, and 4-carboxyethylaminocyclohexyl, wherein the remaining variables are as described in Formula I or the second, third, fourth, fifth, sixth, seventh, eighth, ninth, tenth, eleventh, or twelfth, or thirteenth embodiment.

Specific examples of compounds are provided in the EXEMPLIFICATION section and are included as part of a fourteenth embodiment herein. Pharmaceutically acceptable salts as well as the neutral forms of the compounds in the EXEMPLIFICATION are also included.

4. Uses, Formulation and Administration

Pharmaceutically Acceptable Compositions

According to another embodiment, this disclosure provides a composition comprising a compound described herein or a pharmaceutically acceptable derivative thereof and a pharmaceutically acceptable carrier, adjuvant, or vehicle. The amount of compound in compositions is such that is effective to measurably modulate LSD1, or a mutant thereof in a biological sample or in a patient.

In certain embodiments, a composition described herein is formulated for administration to a patient in need of such composition. In some embodiments, a composition described herein is formulated for oral administration to a patient.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable compositions described herein may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Pharmaceutically acceptable compositions described herein may also be prepared in injectable form. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Pharmaceutically acceptable compositions described herein may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

The amount of compounds described herein that may be combined with the carrier materials to produce a composition in a single dosage form will vary depending upon the host treated and the particular mode of administration. In some embodiments, provided compositions should be formulated so that a dosage of between 0.01-100 mg/kg body weight/day of the inhibitor, such as e.g., 0.1-100 mg/kg body weight/day, can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the composition.

Uses of Compounds and Pharmaceutically Acceptable Compositions

In some embodiments, compounds and compositions described herein are useful in treating diseases and/or disorders associated with overexpression of LSD1 and/or expression of a mutant form of LSD1, such as those mutant forms that alter LSD1 substrate activity.

In some embodiments, compounds and compositions described herein are useful in treating diseases and/or disorders associated with cellular proliferation. In some embodiments, compounds and compositions described herein are useful in treating diseases and/or disorders associated with misregulation of cell cycle or DNA repair. In some embodiments, compounds and compositions described herein are useful in treating cancer. Exemplary types of cancer include breast cancer, prostate cancer, colon cancer, renal cell carcinoma, glioblastoma multiforme cancer, bladder cancer, melanoma, bronchial cancer, lymphoma and liver cancer.

In some embodiments, the present disclosure provides a method of reducing the activity of LSD1 in a subject comprising the step of administering a compound of Formula I, or a composition comprising any of the compounds herein. In some embodiments, the present disclosure provides a method of reducing the activity of wide-type LSD1 in a subject comprising the step of administering a compound of Formula I, or a composition comprising any of the foregoing. In some embodiments, the present disclosure provides a method of reducing the activity of a mutant form of LSD1 in a subject comprising the step of administering a compound of Formula I, or a composition comprising any of the foregoing.

In some embodiments, the present disclosure provides a method of treating a disease or condition related to cancer including e.g., tumors such as skin, breast, brain, cervical carcinomas, testicular carcinomas, etc. In one aspect, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas.

In some embodiments, the present disclosure provides a method of treating a disease or condition selected from one or more of the following, Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angio sarcoma, hepatocellular adenoma, hemangioma; Bone: osteogenic sarcoma (osteosarcoma), fibro sarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibro sarcoma, melanoma), vagina (clear cell carcinoma, squamous cell carcinoma, botryoid sarcoma (embryonal rhabdomyo sarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

In one embodiment, the present disclosure provides a method of treating a disease or condition seleted from CML, T-ALL, neuroblastoma, breast cancer, prostate cancer, herpes simplex virus reactivation, and HIV infection comprising the step of administering to a subject in need thereof a compound of Formula I, or a pharmaceutically acceptable salt thereof. In one alternative, the disease or condition is selected from CML, T-ALL, and neuroblastoma.

Certain exemplary provided compounds, e.g., having structural formula I are set forth in the EXEMPLIFICATION section below. In some embodiments, a provided compound is one or more compounds selected from those exemplified in the EXEMPLIFICATION section below, or a pharmaceutically acceptable salt thereof.

EXEMPLIFICATION

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples that follow and the references to the scientific and patent literature cited herein. It should further be appreciated that the contents of those cited references are incorporated herein by reference to help illustrate the state of the art.

General Synthetic Scheme:

As depicted in the Examples below, in certain exemplary embodiments, compounds are prepared according to the following general procedures. It will be appreciated that, although the synthetic methods and Schemes depict the synthesis of certain compounds of the present invention, the following methods and other methods known to one of ordinary skill in the art can be applied to all compounds and subclasses and species of each of these compounds, as described herein.

It will be appreciated that for compound preparations described herein, when reverse phase HPLC is used to purify a compound, a compound may exist as an acid addition salt. In some embodiments, a compound may exist as a formic acid or mono-, di-, or tri-trifluoroacetic acid salt.

It will further be appreciated that the present disclosure contemplates individual compounds described herein. Where individual compounds exemplified are isolated and/or characterized as a salt, for example, as a trifluoroacetic acid salt, the present disclosure contemplates a free base of the salt, as well as other pharmaceutically acceptable salts of the free base.

Unless otherwise noted, all solvents, chemicals, and reagents were obtained commercially and used without purification. The $^1$H NMR spectra were obtained in CDCl$_3$, d$_6$-DMSO, CD$_3$OD, or d$_6$-acetone at 25° C. at 300 MHz on an OXFORD (Varian) with chemical shift (δ, ppm) reported relative to TMS as an internal standard. HPLC-MS chromatograms and spectra were obtained with Shimadzu LC-MS-2020 system. Chiral analysis and purification were obtained with Yilite P270.

PREPARATION OF INTERMEDIATES

Intermediate A: tert-butyl 4-((4-formylpiperidin-1-yl)methyl)benzoate

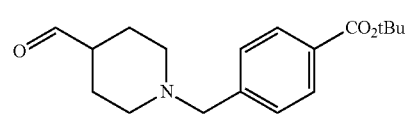 [SMILES: CC(C)(C)OC(=O)c1ccc(CN2CCC(C=O)CC2)cc1]

Tert-butyl 4-((4-formylpiperidin-1-yl)methyl)benzoate was synthesized according to the method highlighted in Johnson, Neil W.; Kasparec, Jiri; Miller, William Henry; Rouse, Meagan B.; Suarez, Dominic; Tian, Xinrong; Cyclopropylamines as LSD1 Inhibitors; U.S. Pat. No. 8,853,408, Oct. 7, 2014.

Intermediate B: tert-butyl 2-(4-formylpiperidin-1-yl)acetate

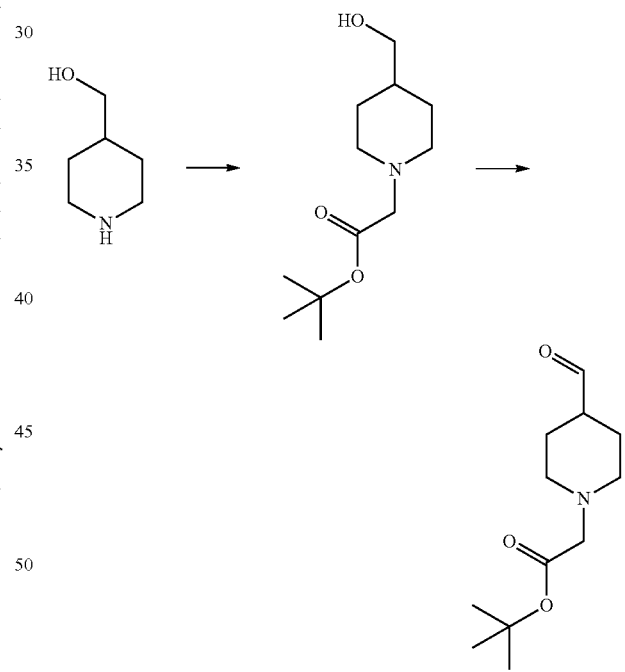

Step 1

To piperidin-4-ylmethanol (1 g, 8.68 mmol) and tert-butyl 2-bromoacetate (1.69 g, 8.68 mmol) were dissolved in acetonitrile (9 mL). Potassium carbonate (1.79 g, 13.0 mmol) was added and reaction mixture was stirred at 25° C. for 16 hours. The reaction mixture was filtered and the filtrate was evaporated under reduced pressure. The crude residue was dried under high vacuum to afford tert-butyl 2-(4-(hydroxymethyl)piperidin-1-yl)acetate (2.11 g, 9.20 mmol) in quantitative yield. LCMS (ESI+): 230.0 (M+H)

Step 2

Oxalyl chloride (1.09 mL, 12.8 mmol) was dissolved in DCM (24 mL), cooled to −78° C. Dimethyl sulfoxide (1.07 mL, 18.4 mmol) mixed with DCM (0.1 mL) was added dropwise to the cold reaction mixture. The reaction mixture was stirred 15 minutes. tert-Butyl 2-(4-(hydroxymethyl)piperidin-1-yl)acetate (2.11 g, 9.20 mmol) in solution in DCM (3 mL) was added dropwise to the −78° C. reaction mixture. The mixture was stirred for 30 minutes. Triethylamine (6.40 mL, 46.0 mmol) was added and the mixture was warmed to room temperature. The reaction mixture was stirred for 1 hour. The reaction mixture was quenched with NH$_4$Cl (saturated aqueous) and extracted with Ethyl acetate. The organic phase was washed with brine, dried with sodium sulfate, filtered, and evaporated under reduced pressure. The crude tert-butyl 2-(4-formylpiperidin-1-yl)acetate (1.27 g, 5.58 mmol) was carried to next step without further purification (61% yield). LCMS (ESI+): 228 (M+H)/246 (M+H$_2$O+H)

Intermediate C: Racemic 2-((E)-styryl)cyclopropanamine Hydrochloride

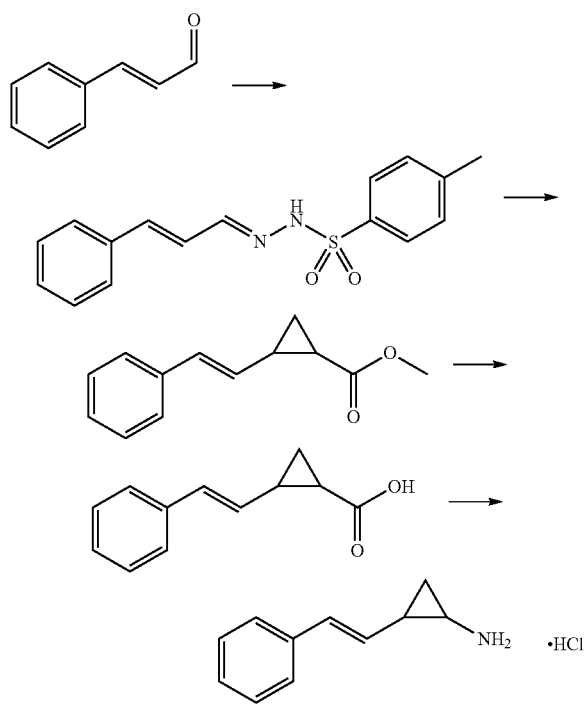

Step 1: (E)-4-methyl-N'-((E)-3-phenylallylidene)benzenesulfonohydrazide

A round bottom flask was charged with cinnamaldehyde (12.7 g, 96.0 mmol), a stirbar, and methanol (100 mL) before the addition of 4-methylbenzenesulfonohydrazide (14.0 g, 75.6 mmol). Stirred at room temperature for 15 minutes. Reaction complete. The white solid material is filtered on a paper filter under suction, washed with hexanes, dried under suction and collected to afford (E)-4-methyl-N'-((E)-3-phenylallylidene)benzenesulfonohydrazide (27.6 g, 91.8 mmol) in 96% yield. LCMS (ESI+): 301 (M+H)

Step 2: (E)-methyl 2-styrylcyclopropanecarboxylate

A round bottom flask was charged with (E)-4-methyl-N'-((E)-3-phenylallylidene)benzenesulfonohydrazide (2.98 g, 9.92 mmol), a stirbar, and 1,4-dioxane (60 mL, 0.1 M) before the addition of potassium carbonate (2.04 g, 14.8 mmol) and methyl acrylate (8.97 mL, 99.1 mmol). The reaction mixture was stirred at 110° C. for 16 hours. The reaction mixture was cooled, evaporated under reduced pressure, diluted with MTBE, and filtered under suction on a 5 cm pad of celite. The organics were evaporated under reduced pressure. The crude residue was purified by column chromatography (silica 24 g, 5% to 50% to Ethyl acetate in hexanes) to afford racemic (E)-methyl 2-styrylcyclopropanecarboxylate (1.02 g, 5.04 mmol) in 50% yield. LCMS (ESI+): 203.1 (M+H)

Step 3: racemic-(Z)-2-(1-fluoro-2-phenylvinyl)cyclopropanecarboxylic Acid (E)-methyl 2-styrylcyclopropanecarboxylate (1.02 g, 5.04 mmol) was dissolved in THF:Methanol (10 mL: 5 mL), and Sodium hydroxide, 6M aqueous (2.09 mL, 12.6 mmol) was added to the mixture. The mixture was stirred at 50° C. for 1 hour. The reaction mixture was acidified to pH 2 using Hydrochloric acid (2M aqueous). The reaction mixture was partitioned between brine and Ethyl acetate. The organic layer was isolated, washed with brine, dried with Na$_2$SO$_4$, filtered, and evaporated under reduced pressure to afford racemic-(Z)-2-(1-fluoro-2-phenylvinyl)cyclopropanecarboxylic acid as a cis/trans mixture (820 mg, 86% yield). LCMS (ESI+): 189 (M+H)

Step 4

(E)-2-styrylcyclopropanecarboxylic acid (820 mg, 4.35 mmol) was dissolved in THF (20 mls) mixed with Triethylamine (1.21 mL, 8.70 mmol), and the solution was then cooled to 0° C. The solution was mixed with ethyl carbonochloridate (ethyl chloroformate) (589 mg, 5.43 mmol), and the reaction mixture was stirred at 0° C. for 0.5 hour. A solution of sodium azide (1.41 g, 21.7 mmol) in 10 ml of water was added and the reaction mixture was stirred at 0° C. for one hour. The reaction mixture was diluted with water and extracted with Ethyl acetate. The combined extracts were washed with brine, dried with sodium sulphate and evaporated under reduced pressure. The residue was taken up in benzene (6 mL), and the solution was heated to 100° C. for 2 hours. Potassium trimethylsilanolate (836 mg, 6.52 mmol) was added to the reaction mixture and stirred for 1.5 hour. The mixture was quenched with ammonium chloride (saturated aqueous) and stirred vigorously for one hour. The aqueous layer was basified with potassium carbonate (2M aqueous). The aqueous phase was extracted twice with DCM (2×50 mL) and the combined organic extracts were washed with brine, dried with sodium sulfate and evaporated under reduced pressure. The residue was redissolved in DCM and Hydrochloric acid (4M in 1,4-dioxane, 1.1 mL, 4.4 mmol) was added dropwise, after which a solid crashed out of solution. The volatiles were evaporated under reduced pressure, and the residue was placed under high vacuum for two hours to afford racemic 2-((E)-styryl)cyclopropanamine hydrochloride (378 mg, 1.93 mmol) as a single diastereomer in 44% yield. LCMS (ESI+): 160 (M+H)/143 (M−NH$_2$)+.

3-((4-oxopiperidin-1-yl)methyl)pyridin-2(1H)-one

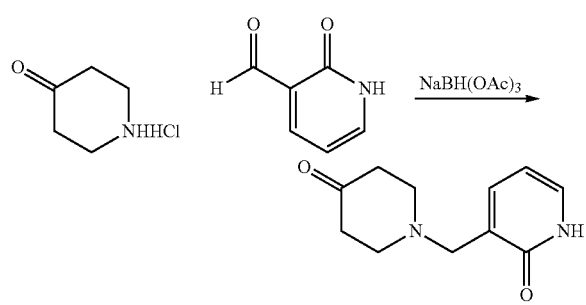

To a round bottomed flask was added piperidin-4-one hydrochloride (225 mg, 1.65 mmol), DCM, and 2-oxo-1,2-dihydropyridine-3-carbaldehyde (135 mg, 1.10 mmol). The solution was stirred at room temperature for 5 min before addition of sodium triacetoxyborohydride (347 mg, 1.64 mmol). The reaction was stirred at room temperature for 1 h before diluting with MeOH. The solution was stirred overnight and then concentrated. The crude residue was purified via Biotage to afford 3-((4-oxopiperidin-1-yl)methyl)pyridin-2(1H)-one (133 mg). LCMS: 207 (M+H).

tert-butyl 4-((4-oxopiperidin-1-yl)methyl)benzoate

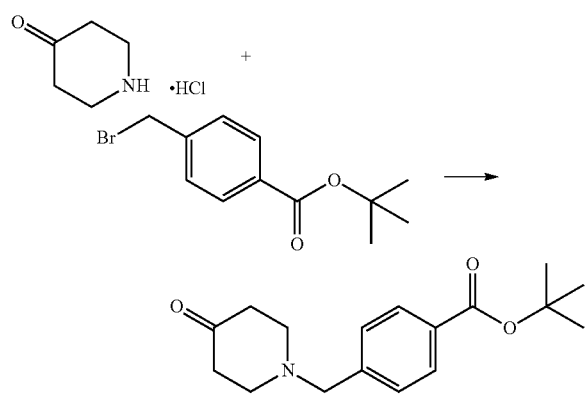

To piperidin-4-one hydrochloride (2 g, 14.7 mmol) and tert-butyl 4-(bromomethyl)benzoate (3.98 g, 14.7 mmol) were dissolved in 9 mL of ACN. Potassium carbonate (3.04 g, 22.0 mmol) was added and reaction mixture was stirred at 25° C. for 16 hours. The volatiles were evaporated and the crude residue was purified on a 24 g silica column with EtOAc to 20% methanol in EtOAc to afford tert-butyl 4-((4-oxopiperidin-1-yl)methyl)benzoate (435 mg, 1.50 mmol) in 36% yield. LCMS (ESI+): 290.1 (M+H)/308.2 (M+H$_2$O+H).

N-methyl-4((4-oxopiperidin-1-yl)methyl)benzamide

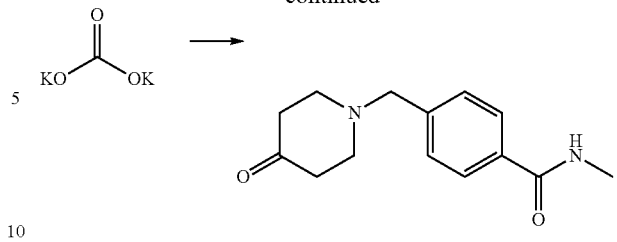

Piperidin-4-one hydrochloride (250 mg, 1.84 mmol) and 4-(chloromethyl)-N-methylbenzamide (337 mg, 1.84 mmol) were dissolved in tetrahydrofuran (10 mL), and potassium carbonate (939 mg, 6.80 mmol) was added followed by potassium iodide (76.3 mg, 460 μmol). The reaction mixture was heated to 65° C. for 24 hours. The reaction mixture was evaporated and impregnated on silica gel. The compound was purified by silica gel chromatography (24 gram column, methanol:ethyl acetate gradient) to afford N-methyl-4-((4-oxopiperidin-1-yl)methyl)benzamide (104 mg, 422 μmol) in 23% yield. LCMS (ESI+): 265.1 (M+H$_2$O+H).

4-((4-oxopiperidin-1-yl)methyl)benzamide

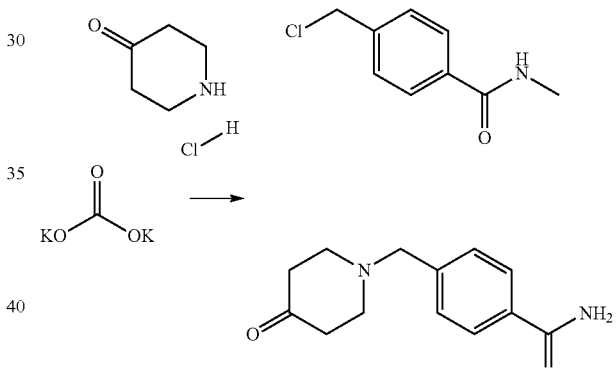

Piperidin-4-one hydrochloride (250 mg, 1.84 mmol) and 4-(chloromethyl)benzamide (312 mg, 1.84 mmol) were dissolved in tetrahydrofuran (10 mL), and potassium carbonate (939 mg, 6.80 mmol) was added followed by potassium iodide (76.3 mg, 460 μmol). The reaction mixture was heated to 65° C. for 24 hours. The reaction mixture was evaporated and impregnated on silica gel. The compound was purified by silica gel chromatography (methanol:ethyl acetate gradient) to afford 4-((4-oxopiperidin-1-yl)methyl)benzamide (137 mg, 589 μmol) in 32% yield. LCMS (ESI+): 251.1 (M+H2O+H)

3-(4-formylpiperidin-1-yl)propanenitrile

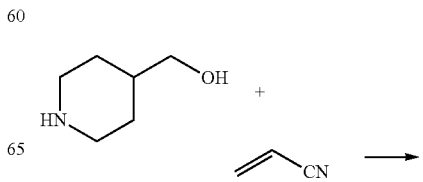

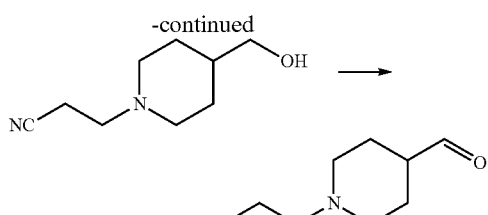

Step 1: 3-(4-(hydroxymethyl)piperidin-1-yl)propanenitrile

Piperidin-4-ylmethanol (750 mg, 6.51 mmol) and acrylonitrile (345 mg, 6.51 mmol) were dissolved in methanol (30 mL). Diisopropylethylamine (2.3 mL, 13 mmol) was added and reaction mixture was stirred at 25° C. for 16 hours. The volatiles were evaporated to afford 3-(4-(hydroxymethyl)piperidin-1-yl)propanenitrile (920 mg, 5.46 mmol), 84% yield. LCMS (ESI+): 169.0 (M+H).

Step 2: 3-(4-formylpiperidin-1-yl)propanenitrile

Oxalyl chloride (168 mg, 1.33 mmol) was dissolved in methylene chloride (5 mL), cooled to −78° C. Dimethyl sulfoxide (111 μL, 1.90 mmol) mixed with methylene chloride (100 μL) was added dropwise to the cold reaction mixture. 3-(4-(hydroxymethyl)piperidin-1-yl)propanenitrile (168 mg, 1 mmol) dissolved in methylene chloride (3 mL) was added, cooled to −78° C. and stirred for 45 minutes. Triethylamine (695 μL) was added to the reaction mixture, and warmed to room temperature over 2 hours. After completion (disappearance of starting material by HPLC-MS), the reaction mixture was quenched with ammonium chloride (aq.) and extracted with EtOAc. The organic phase was washed with brine, dried with $Na_2SO_4$, filtered, and evaporated to afford 3-(4-formylpiperidin-1-yl)propanenitrile (145 mg) in 87% yield. LCMS (ESI+): 167 (M+H), 185 (M+$H_2O$+H).

tert-butyl 2,2-dimethyl-3-((4-oxocyclohexyl)amino)propanoate

To a round bottomed flask was added tert-butyl 3-amino-2,2-dimethylpropanoate (11.46 g, 64.2 mmol), cyclohexane-1,4-dione (29.3 g, 261 mmol), and DCM (300 mL). The solution was stirred at room temperature for 5 min before addition of sodium triacetoxyborohydride (20.8 g, 98.1 mmol). The solution was stirred at room temperature for 1 h before diluting with water. The pH of the aqueous layer was adjusted to pH=10 with potassium carbonate solution. The layers were separated and the aqueous was extracted with DCM. The combined organics layer was dried over $Na_2SO_4$, filtered, and concentrated. The crude residue was purified via Biotage (100 g, 10% EtOAc/hex to 40% EtOAc/hex) to afford tert-butyl 2,2-dimethyl-3-((4-oxocyclohexyl)amino)propanoate (10.34 g, 38.4 mmol). LCMS: 270 (M+H).

Using the appropriate starting materials and modifications the following intermediates were synthesized using the procedures described for the synthesis of tert-butyl 2,2-dimethyl-3-((4-oxocyclohexyeamino)propanoate.

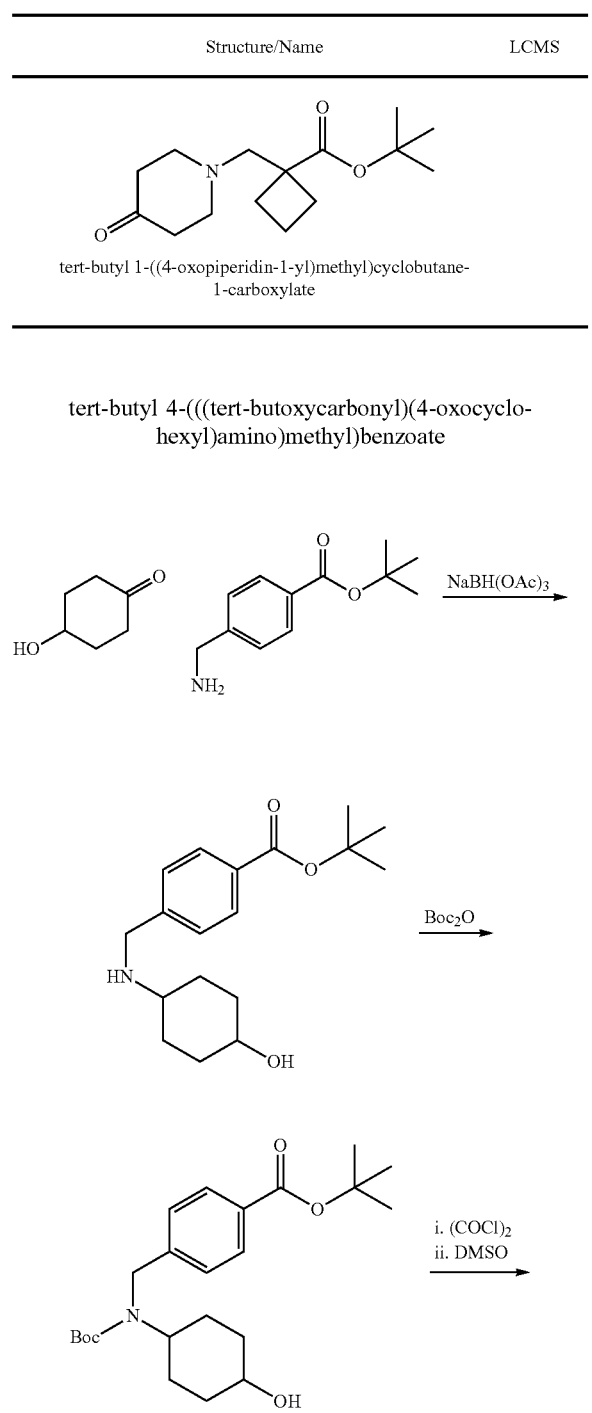

| Structure/Name | LCMS |
|---|---|
| tert-butyl 1-((4-oxopiperidin-1-yl)methyl)cyclobutane-1-carboxylate | | tert-butyl 4-(((tert-butoxycarbonyl)(4-oxocyclohexyl)amino)methyl)benzoate

Step 1: tert-butyl 4-(((4-hydroxycyclohexyl)amino)methyl)benzoate

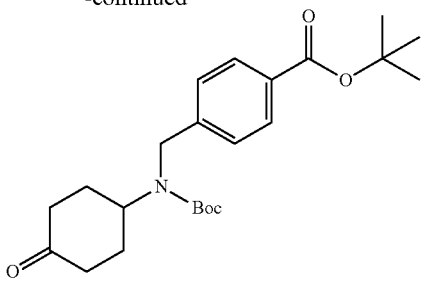

4-hydroxycyclohexanone (1.25 g, 11.00 mmol) and tert-butyl 4-(aminomethyl)benzoate (2.3 g, 11.0 mmol) was dissolved in 1,2-dichloroethane (50 mL) was added sodium (triacetoxy)borohydride (2.33 g, 11.0 mmol). After 30 min, potassium carbonate (1M aqueous) was added, followed by methylene chloride. The organic phase was isolated, washed with brine and evaporated under pressure to afford residue tert-butyl 4-(((4-hydroxycyclohexyeamino)methyl)benzoate (3.35 g, 10.9 mmol) was obtained in quantitative yield. LCMS (ESI+): 306.2 (M+H).

Step 2: tert-butyl 4-(((tert-butoxycarbonyl)(4-hydroxycyclohexyl)amino)methyl)benzoate tert-butyl 4-(((4-hydroxycyclohexyl)amino)methyl)benzoate (3.35 g, 10.9 mmol) was dissolved in tetrahydrofuran (100 mL), triethylamine (2.25 mL, 16.3 mmol) was added, followed by di-tert-butyl dicarbonate (2.59 g, 11.9 mmol). The reaction mixture was stirred for 16 hours at room temperature. The volatiles were evaporated under reduced pressure and the crude residue was purified on silica gel (5% to 50% EtOAc:Hexanes). The pure fractions were evaporated to afford tert-butyl 4-(((tert-butoxycarbonyl)(4-hydroxycyclohexyl)amino)methyl)benzoate (4.11 g, 10.1 mmol) in 93% yield. LCMS (ESI+): 428.2 (M+Na).

Step 3: tert-butyl 4-(((tert-butoxycarbonyl)(4-oxocyclohexyl)amino)methyl)benzoate Oxalyl chloride (1.91 g, 15.1 mmol) was dissolved in methylene chloride (60 mL) and the mixture was cooled to −78° C. Dimethyl sulfoxide (1.42 mL, 20.2 mmol) mixed with methylene chloride (100 µL) was added dropwise to the cold reaction mixture and stirred 5 minutes. Tert-butyl 4-(((tert-butoxycarbonyl)(4-hydroxycyclohexyl)amino) methyl)benzoate (4.11 g, 10.1 mmol) in solution in methylene chloride (15 mL) was added to the −78° C. reaction mixture and stirred for 30 minutes. Triethylamine (7.01 mL, 50.4 mmol) was added and the reaction mixture was warmed to 25° C. over 2 hours. The reaction mixture was diluted with ammonium chloride (aq.) and extracted with EtOAc. The organic layer was washed with brine, dried with sodium sulfate, filtered, and evaporated to afford tert-butyl 4-(((tert-butoxycarbonyl)(4-oxocyclohexyl)amino)methyl)benzoate (4.40 g, 10.9 mmol) in quantitative yield. LCMS (ESI+): 426.2 (M+Na).

2-((E)-1-phenylprop-1-en-2-yl)cyclopropanamine Hydrochloride Salt (Racemic)

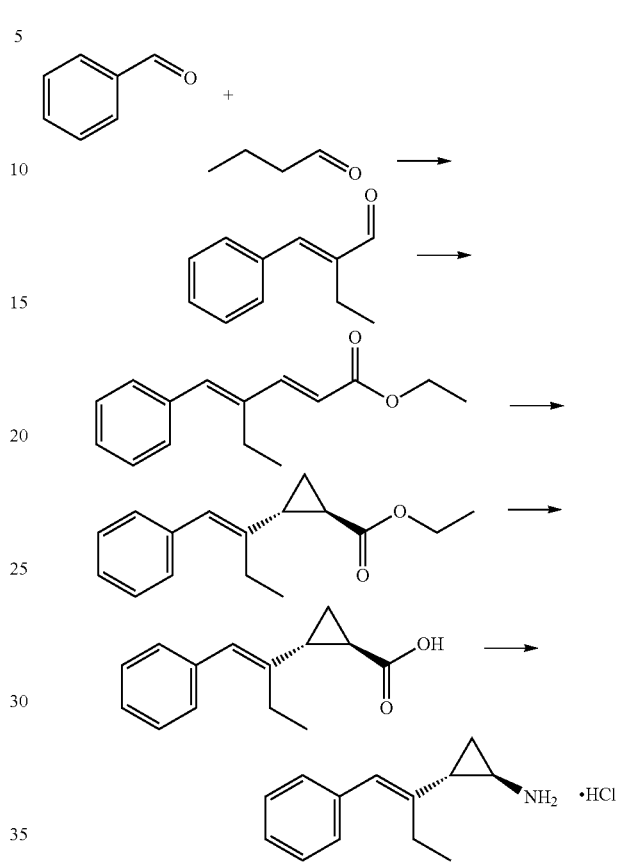

Step 1: (E)-2-benzylidenebutanal

To a solution of benzaldehyde (100 ml, 980 mmol, 1.00 eq) in methanol (750.00 mL) was added sodium hydroxide (2.5 M aq., 79.16 mL, 1.00 eq). Butanal (18.55 g, 257.26 mmol, 1.30 eq) was added dropwise at 0° C. The reaction mixture was stirred at 25° C. for 2 hr. The reaction mixture was evaporated to a volume of 200 mL. Water (1000 mL) was added and the mixture was extracted with MTBE (3×400 mL). The organic layer was washed with brine, dried with Na$_2$SO$_4$, filtered on a pad of celite (top) and silica (bottom) under suction. After evaporation of the volatiles, the crude residue was partitioned between methylene chloride and water/brine (500 mL/500 mL) mixture. The organic phase was isolated, dried with anhydrous sodium sulfate, filtered, and evaporated under reduced pressure to afford (E)-2-benzylidenebutanal (151 g, 942 mmol) in 96% yield. $^1$H NMR (400 MHz, CDCl3) δ 9.56 (s, 1H), 7.57-7.49 (m, 2H), 7.49-7.36 (m, 3H), 7.22 (s, 1H), 2.60-2.55 (q, J=7.5 Hz, 2H), 1.20-1.10 (m, 3H).

Step 2: (2E,4E)-ethyl 4-benzylidenehex-2-enoate

Under a nitrogen atmosphere, a potassium tert-butoxide solution (1M in tetrahydrofuran, 173 mL, 173 mmol) was dissolved in tetrahydrofuran (800 mL), cooled to 0° C. and ethyl 2-(diethoxyphosphoryl)acetate (25.3 ml, 40.5 g, 181 mmol) was added dropwise to the reaction mixture over 10 minutes under vigorous stirring. The reaction mixture was stirred while warming to 25° C. for 30 minutes. After cooling 0° C., (E)-2-benzylidenebutanal (27.8 g, 173 mmol) in solution in tetrahydrofuran (100 mL) was added to the reaction mixture, and the reaction mixture was stirred at 25° C. for 16 hours. The reaction mixture was evaporated to a volume of 200 mL. The reaction mixture was quenched with water (400 mL) and extracted with EtOAc (2×350 mL). The organic layer was washed with brine, dried with sodium sulfate and filtered on a pad of silica (5 cm). The solvent was evaporated under reduced pressure to give (2E,4E)-ethyl 4-benzylidenehex-2-enoate (33.1 g, 143 mmol) in 83% yield. $^1$H NMR (400 MHz, DMSO-d6) δ 7.26-7.49 (m, 6H), 6.97 (s, 1H), 6.04 (d, J=15.87 Hz, 1H), 4.16 (q, J=7.08 Hz, 2H), 2.42-2.52 (m, 2H), 1.24 (t, J=7.08 Hz, 3H), 1.12 (t, J=7.57 Hz, 3H). LCMS (ESI+): 231 (M+H).

Step 3: (trans)-ethyl 2-(E)-1-phenylbut-1-en-2-yl) cyclopropanecarboxylate

Under a nitrogen atmosphere, sodium hydride (60% in oil, 5.23 g, 131 mmol) was dissolved in DMSO (350 mL). The mixture was stirred for 15 minutes at 25° C. Trimethylsulfoxonium iodide (29.2 g, 133 mmol) was added, reaction mixture was stirred 45 minutes at 25° C. (hydrogen gas evolution!). (2E,4E)-ethyl 4-benzylidenehex-2-enoate (25.0 g, 108 mmol) dissolved in DMSO (25 mL) was added over 1 minute. The reaction mixture was stirred at 40° C. for 16 hours. The reaction mixture was cooled to 20° C. in a water batch and quenched with saturated aqueous ammonium chloride (250 mL) and brine (50 mL). After stirring for 10 minutes, the mixture was extracted with hexanes (2×300 mL). The organic layers were combined, dried with sodium sulfate, filtered and evaporated under reduced pressure to afford (trans)-ethyl 2-((E)-1-phenylbut-1-en-2-yl)cyclopropanecarboxylate (19.0 g, 77.7 mmol) which was used in the subsequent step without further purification. $^1$H NMR (400 MHz, DMSO-d6) δ 7.28-7.36 (m, 2H), 7.14-7.24 (m, 3H), 6.24 (s, 1H), 4.10 (q, J=7.08 Hz, 2H), 2.11-2.29 (m, 2H), 1.93-2.02 (m, 1H), 1.74 (td, J=4.76, 8.30 Hz, 1H), 1.23-1.32 (m, 2H), 1.20 (t, J=7.50 Hz, 3H), 1.05-1.09 (m, 3H) 20/20 LCMS (ESI+): 245.1 (M+H).

Step 4: (trans)-2-((E)-1-phenylbut-1-en-2-yl)cyclopropane-1-carboxylic Acid

Crude ethyl 2-((E)-1-phenylbut-1-en-2-yl)cyclopropanecarboxylate (19.0 g, 77.7 mmol) was dissolved in a tetrahydrofuran:methanol mixture (100 mL:50 mL). Sodium hydroxide (6M aqueous, 65.3 mL, 392 mmol) was added and the mixture was stirred at 50° C. for 3 hours. The reaction mixture was concentrated under reduced pressure to a volume of 100 mL partitioned between hexanes (200 mL) and a 1:1:10 $K_2CO_3$ (aq.):NaHCO$_3$ (aq.sat):water mixture (250 mL). The aqueous phase was isolated, cooled to 0° C. and acidified to pH=2 with 2M hydrochloric acid. The resulting suspension was extracted with EtOAc (2×250 mL). The organic phase was washed with brine, dried with $Na_2SO_4$, filtered, evaporated under reduced pressure. The crude residue was purified by column chromatography (25:75 EtOAc:hexanes to 100% EtOAc). Pure fractions were pooled, and evaporated under reduced pressure to afford racemic (trans)-2-((E)-1-phenylbut-1-en-2-yl)cyclopropane-1-carboxylic acid (10.0 g, 46.2 mmol) in 43% yield over 2 steps. 1H NMR (400 MHz, DMSO-d6) δ 12.21 (s, 1H), 7.27-7.37 (m, 2H), 7.14-7.24 (m, 3H), 6.23 (s, 1H), 2.11-2.32 (m, 2H), 1.88-1.97 (m, 1H), 1.55-1.66 (m, 1H), 1.14-1.29 (m, 2H), 1.06-1.12 (m, 3H). LCMS (ESI+): 171.1 (M−CO2+H).

Step 5: (trans)-2-((E)-1-phenylbut-1-en-2-yl)cyclopropanamine Hydrochloride (Racemic)

Racemic (trans)-2-((E)-1-phenylbut-1-en-2-yl)cyclopropane-1-carboxylic acid acid (9.8 g, 45.3 mmol) was dissolved in tetrahydrofuran (230 mL) mixed with triethylamine (15.7 mL, 113 mmol), and the solution was then cooled to 0° C. The solution was mixed with ethyl chloroformate (5.89 g, 54.3 mmol), and the reaction mixture was stirred at 0° C. for 0.5 hour. A solution of sodium azide (9.68 g, 149 mmol) in 200 ml of water was added and the reaction mixture was stirred at 0° C. for one hour. The reaction mixture was diluted with water and extracted with EtOAc (250 mL). The combined extracts were washed with brine, dried with sodium sulfate and evaporated to a volume of 50 mL. Toluene (50 mL) was added to the crude residue and the solution was evaporated to a volume of approximately 25 mL under reduced pressure. In a 3-neck 1 L-flask fitted with an outlet, a condenser, and an addition funnel, all under a nitrogen atmosphere, toluene (100 mL) was heated to 90° C. The solution in toluene was transferred to the addition funnel. The acyl azide solution was added slowly over 30 minutes to the 90° C. toluene solution. The reaction mixture was heated for 90 minutes after completion of the addition. Potassium trimethylsilanolate (7.54 g, 58.8 mmol) was added to the mixture cooled to 25° C. Stirred for 1.5 hour. Hydrochloric acid (3M aqueous) was added (400 mL), and the layers were separated (three layers, hexanes, an orange semi-solid, and aqueous). The organic layer was extracted twice with hydrogen chloride (3M aqueous) (2×200 mL), and the aqueous extracts were combined, along with the orange semi-solid. The aqueous layer was cooled to 0° C. and basified to pH 12-13 using sodium hydroxide (6M), at which point the mixture becomes cloudy. The aqueous layer was extracted with MTBE (4×200 mL). The organic extracts were washed with brine, dried with sodium sulfate, filtered and evaporated under reduced pressure. The crude oil was redissolved in MTBE (50 ml), cooled to 0° C., added hydrogen chloride (48 mL, 2M in Et$_2$O). The solid was filtered on a paper filter under suction and the solid cake was washed with ice-cold MTBE. The solid was dried under a stream of nitrogen, collected and dried under high vacuum for 24 hours to afford (trans)-2-(E)-1-phenylbut-1-en-2-yl) cyclopropanamine hydrochloride (5.50 g, 24.5 mmol) in 54% yield. $^1$H NMR (400 MHz, DMSO-d6) δ 8.54 (hr. s., 3H), 7.27-7.46 (m, 2H), 7.11-7.24 (m, 3H), 6.16 (s, 1H), 2.59 (br. s., 1H), 2.12-2.34 (m, 2H), 1.87-1.99 (m, 1H), 1.01-1.24 (m, 5H). LCMS (ESI+): 171 (M−NH2)+/188 (M+H).

Synthesis of intermediate (trans)-2-((E)-1-(4-iodophenyl)prop-1-en-2-yl)cyclopropanamine(racemic)

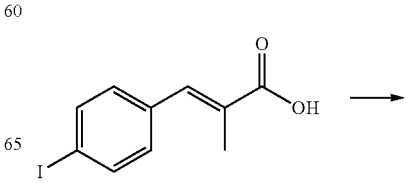

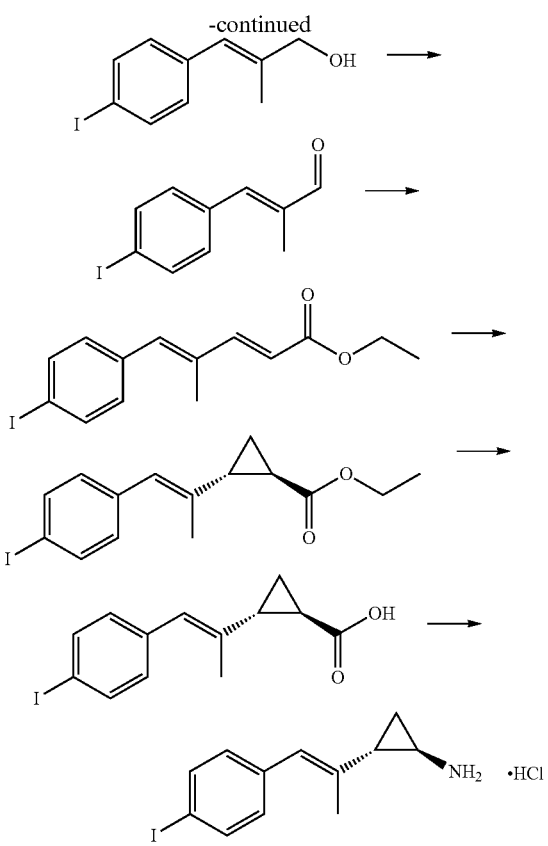

Step 1: (E)-3-(4-iodophenyl)-2-methylprop-2-en-1-ol (E)-3-(4-iodophenyl)-2-methylacrylic acid (12.2 g, 42.2 mmol) was dissolved in tetrahydrofuran (200 mL) and triethylamine (11.7 mL, 84.6 mmol) was added. The reaction mixture was cooled to 0° C. Isobutyl chloroformate (6.57 mL, 50.7 mmol) was added, and stirred for 45 minutes. Sodium borohydride (3.97 g, 105 mmol) was added to the reaction mixture and methanol (3 mL) was added. The reaction mixture was stirred for one hour while warming to 25° C. The reaction mixture was acidified to pH=2 with hydrochloric acid (2M aqueous). The reaction mixture was extracted with ethyl acetate (3×100 mL). The combined organic extracts were washed with brine, with sodium sulfate, filtered and evaporated to afford (E)-3-(4-iodophenyl)-2-methylprop-2-en-1-ol (6.25 g, 22.8 mmol) in 54% yield.

Step 2: (E)-3-(4-iodophenyl)-2-methylacrylaldehyde

Oxalyl chloride (2.58 mL, 30.6 mmol) was dissolved in methylene chloride (60 mL) and the mixture was cooled to −78° C. Dimethyl sulfoxide (3.21 mL, 45.4 mmol) was added dropwise, and the reaction mixture was stirred for 20 minutes. (E)-3-(4-iodophenyl)-2-methylprop-2-en-1-ol (6.24 g, 22.7 mmol) dissolved in methylene chloride (30 mL) was added at −78° C. The reaction mixture was stirred for 30 minutes. Triethylamine (12.6 mL, 90.8 mmol) was added and the reaction mixture was stirred for 1.5 hour while gradually increasing the reaction temperature to 25° C. The reaction mixture was quenched with Ammonium chloride (aq.) and extracted with EtOAc. Washed with brine, dried with Na$_2$SO$_4$, filtered, and evaporated to afford (E)-3-(4-iodophenyl)-2-methylacrylaldehyde (6.20 g, 22.7 mmol) in 74% yield. LCMS (ESI+): 273.5 (M+H).

Step 3: (2E,4E)-ethyl 5-(4-iodophenyl)-4-methyl-penta-2,4-dienoate

Ethyl 2-(diethoxyphosphoryl)acetate (5.58 g, 24.9 mmol) was dissolved in tetrahydrofuran (45 mL) and cooled to 0° C. Potassium tert-butoxide (1M in tetrahydrofuran, 24.9 mL, 24.9 mmol) was added to the reaction mixture and stirred vigorously for 15 minutes. (E)-3-(4-iodophenyl)-2-methyl-acrylaldehyde (6.2 g, 22.7 mmol) dissolved in tetrahydrofuran (12 mL) was added. The reaction mixture was quenched with NaHCO$_3$ (aq., sat.) and extracted with EtOAc. The organic phase was washed with brine and dried with Na$_2$SO$_4$. The solvent was evaporated under reduced pressure and the residue was purified by column chromatography on silica gel (120 g column, 0 to 15% EtOAc in hexanes) to give (2E,4E)-ethyl 5-(4-iodophenyl)-4-methyl-penta-2,4-dienoate (6.15 g, 17.9 mmol) in 79% yield over 2 steps. LCMS (ESI+): 343.0 (M+H).

Step 4: ethyl (trans)-2-(E)-1-(4-iodophenyl)prop-1-en-2-yl)cyclopropane-1-carboxylate A round-bottomed flask with sodium hydride (60% dispersion in oil, 820 mg, 20.5 mmol) was put under nitrogen atmosphere, DMSO (100 mL) was added, and stirred 15 minutes at 25° C. Trimethylsulfoxonium iodide (6.15 g, 21.4 mmol) was added and stirred 45 minutes at 25° C. (2E,4E)-ethyl 5-(4-iodophenyl)-4-methylpenta-2,4-dienoate (6.15 g, 17.9 mmol) in DMSO (25 mL) was added. The reaction mixture was stirred at 40° C. for 16 hours. The reaction mixture was quenched with sat. aq. ammonium chloride (150 mL) and brine (25 mL) with a water bath present to act as a heat sink. The reaction mixture was extracted with hexanes (100 mL). The organic phase was evaporated under reduced pressure to afford ethyl (trans)-2-((E)-1-(4-iodophenyl)prop-1-en-2-yl)cyclopropane-1-carboxylate (535 mg, 1.50 mmol) in 62% yield. LCMS (ESI+): 357.0 (M+H).

Step 5: (trans)-2-(E)-1-(4-iodophenyl)prop-1-en-2-yl)cyclopropane-1-carboxylic acid Ethyl (trans)-2-((E)-1-(4-iodophenyl)prop-1-en-2-yl)cyclopropane-1-carboxylate (4.61 g, 12.9 mmol) was dissolved in tetrahydrofuran (50 mL) and methanol (10 mL), Sodium hydroxide (8.60 mL, 51.6 mmol) was added. The reaction mixture was heated to 40° C. and stirred for 6 hours. After cooling to 0° C., the reaction mixture was acidified to pH=2 with hydrochloric acid (2M aqueous). The reaction mixture was extracted with ethyl acetate (3×100 mL). The combined organic extracts were washed with brine, dried with sodium sulfate and evaporated under reduced pressure to afford (trans)-2-((E)-1-(4-iodophenyl)prop-1-en-2-yl)cyclopropane-1-carboxylic acid (3.91 g, 11.9 mmol) in 92% yield. LCMS (ESI+): 314.2 (M+H).

Step 6: (trans)-2-((E)-1-(4-iodophenyl)prop-1-en-2-yl)cyclopropanamine Hydrochloride (Racemic)

(trans)-2-((E)-1-(4-iodophenyl)prop-1-en-2-yl)cyclopropane-1-carboxylic acid (3.91 g, 11.9 mmol) was dissolved in tetrahydrofuran (120 mL), mixed with triethylamine (4.13 mL, 29.7 mmol), and the solution was cooled to 0° C. The solution was mixed with ethyl chloroformate (1.60 g, 14.8 mmol), and the reaction mixture was stirred at 0° C. for 0.5 hour. A solution of sodium azide (3.86 g, 59.5 mmol) in water (60 mL) was added and the reaction mixture was stirred at 0° C. for one hour. The reaction mixture was diluted with water and extracted with EtOAc. The combined extracts were washed with brine, dried with sodium sulphate and evaporated. The residue was taken up in toluene (15 mL) and the solution was heated to reflux for 2 hours. Potassium trimethylsilanolate (2.28 g, 17.8 mmol) was added to the mixture cooled at room temperature and stirred for 1.5 hour. Hydrochloric acid (2M aqueous) was added (50 mL) and the reaction mixture was stirred for 15 minutes. The precipitate was filtered under suction on a Buchner funnel and washed with MTBE. The solid was collected and dried under vacuum to afford (trans)-2-(E)-1-(4-iodophenyl)prop-1-en-2-yl)cyclopropanamine hydrochloride (1.35 g, 4.02 mmol) in 34% yield. LCMS (ESI+): 300.1 (M+H)/283.0 [(M−NH$_2$)+].

tert-butyl 4-(((trans)-2-((E)-1-(4-iodophenyl)prop-1-en-2-yl)cyclopropyl)amino)piperidine-1-carboxylate (Racemic)

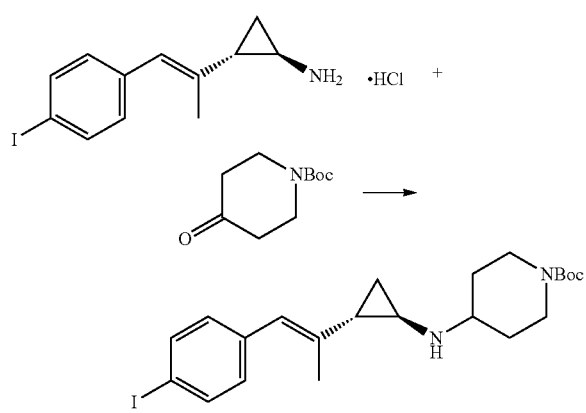

To (trans)-2-((E)-1-(4-iodophenyl)prop-1-en-2-yl)cyclopropanamine hydrochloride (500 mg, 1.48 mmol) and tert-butyl 4-oxopiperidine-1-carboxylate (294 mg, 1.48 mmol) in 1,2-dichloroethane (4 mL) was added sodium (triacetoxy)borohydride (627 mg, 2.96 mmol). After 30 min, methylene chloride and potassium carbonate (1M aqueous) were added to the reaction mixture. The organic phase was isolated, evaporated and the crude residue purified by silica gel column chromatography (40 g, 0% to 10% methanol in EtOAc) to afford tert-butyl 4-(((trans)-2-((E)-1-(4-iodophenyl)prop-1-en-2-yl)cyclopropyl)amino)piperidine-1-carboxylate (535 mg, 1.10 mmol) in 75% yield. LCMS (ESI+): 483.1 (M+H).

1-ethyl-2-((E)-1-phenylprop-1-en-2-yl)cyclopropanamine

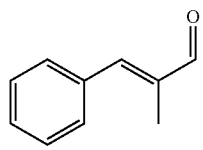

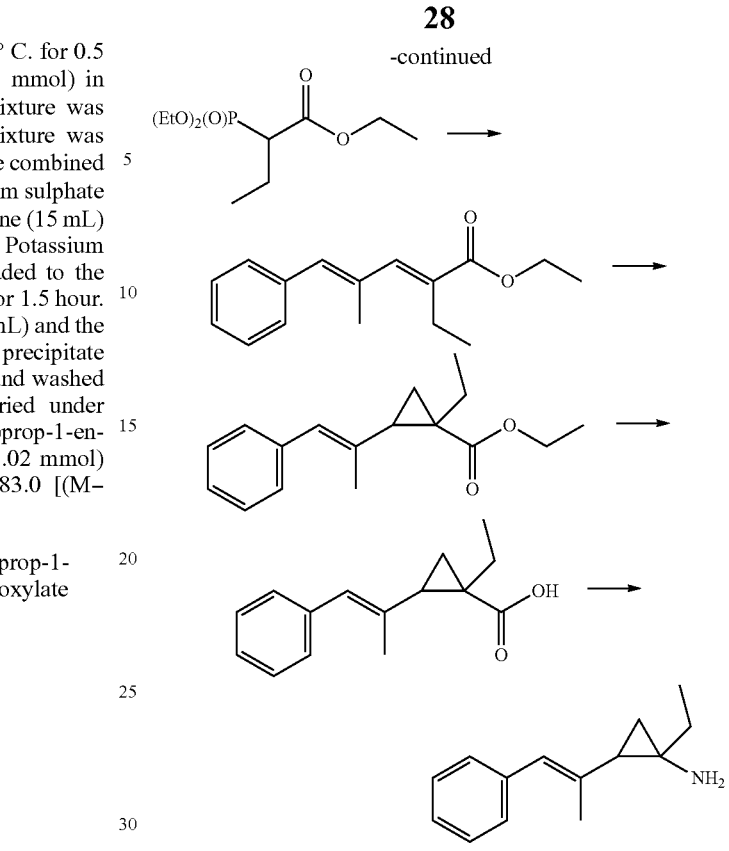

Step 1: (2E,4E)-ethyl 2-ethyl-4-methyl-5-phenylpenta-2,4-dienoate

To a solution of sodium hydride (60% dispersion in mineral oil, 351 mg, 8.82 mmol) in tetrahydrofuran (12 mL) at 0° C., triethyl phosphonoacetate (2.12 g, 8.40 mmol) was added dropwise. The mixture was stirred at 0° C. for 20 minutes. Then, trans-alpha-methylcinnamaldehyde (1.35 g, 9.24 mmol) was added dropwise at 0° C. The reaction was stirred at room temperature for 12 hours and quenched with brine. The solution was concentrated to ⅓ of the original volume under reduced pressure. The aqueous layer was extracted with methylene chloride and the combined organic layers were dried over Na$_2$SO$_4$. The solvent was evaporated under reduced pressure and the residue was purified by column chromatography on silica gel to give (2E,4E)-ethyl 2-ethyl-4-methyl-5-phenylpenta-2,4-dienoate (1.77 g, 7.24 mmol) in quantitative yield. LCMS (ESI+): 245.6 (M+H)

Step 2: ethyl (E)-1-ethyl-2-(1-phenylprop-1-en-2-yl)cyclopropane-1-carboxylate

Sodium hydride (60% dispersion in oil, 361 mg, 9.05 mmol) in a round bottomed flask was put under nitrogen atmosphere, dimethyl sulfoxide (24 mL) was added, and the mixture was stirred 15 minutes at 25° C. Trimethylsulfoxonium iodide (2.07 g, 9.41 mmol) was added, stirred 45 minutes at 25° C. (2E,4E)-ethyl 2-ethyl-4-methyl-5-phenylpenta-2,4-dienoate (1.77 g, 7.24 mmol) in dimethyl sulfoxide (12 mL) was added. The reaction mixture was stirred at 40° C. for 36 hours. The reaction mixture was cooled to 20° C. in a water bach and quenched with saturated aqueous ammonium chloride (250 mL) and brine (50 mL). After stirring for 10 minutes, the mixture was extracted with hexanes (2×300 mL). The organic layers were combined, dried with sodium sulfate, filtered and evaporated under reduced pressure to afford ethyl (E)-1-ethyl-2-(1-phenyl-prop-1-en-2-yl)cyclopropane-1-carboxylate (1.01 g, 3.90 mmol) in 54% yield.

Step 3: 1-ethyl-2-((E)-1-phenylprop-1-en-2-yl)cyclopropanecarboxylic Acid

Ethyl (E)-1-ethyl-2-(1-phenylprop-1-en-2-yl)cyclopropane-1-carboxylate (1.0 g, 4.09 mmol) was dissolved in tetrahydrofuran (40 mL) and methanol (10 mL). Sodium hydroxide was added (6M aq., 6 mL, 36 mmol) and the reaction mixture was stirred for 3 hours at 50° C. The reaction mixture was acidified to pH 5 using hydrochloric acid (1M aqueous). Reaction mixture was partitioned between brine and EtOAc. The organic layer was washed with brine, dried with sodium sulfate, filtered and evaporated under reduced pressure. The crude residue was purified by silica gel column chromatography (Hexanes:EtOAc). The pure fractions were evaporated to afford 1-ethyl-2-((E)-1-phenylprop-1-en-2-yl)cyclopropanecarboxylic acid (810 mg, 3.51 mmol) in 86% yield. LCMS (ESI+): 231.1 (M+H).

Step 4: 1-ethyl-2-(E)-1-phenylprop-1-en-2-yl)cyclopropanamine 1-ethyl-2-((E)-1-phenylprop-1-en-2-yl)cyclopropanecarboxylic acid (810 mg, 3.51 mmol) was dissolved in tetrahydrofuran (85 mL) mixed with triethylamine (1.22 mL, 8.77 mmol), and the solution was then cooled to 0° C. The solution was mixed with ethyl chloroformate (513 mg, 4.73 mmol), and the reaction mixture was stirred at 0° C. for 0.5 hour. A solution of sodium azide (1.13 g, 17.5 mmol) in water (40 mL) was added and the reaction mixture was stirred at 0° C. for one hour. The reaction mixture was diluted with water and extracted with EtOAc. The combined extracts were washed with brine, dried with sodium sulphate and evaporated under reduced pressure. The residue was taken up in benzene (5 mL), and the solution was heated to reflux for 2 hours. Potassium trimethylsilanolate (900 mg, 7.02 mmol) was added to the mixture cooled at 25° C. and stirred for 1.5 hour. Hydrochloric acid (2M aqueous, 40 mL, 80 mmol) was added to the reaction mixture and stirred. The volume of organics was increased to 200 mL with MTBE. Hydrochloric acid (2M aqueous) was added (100 mL), and the layers were separated. The organic layer was extracted twice with hydrochloric acid (2M aq.) (2×100 mL), and the aqueous extracts were combined. The aqueous layer was basified to pH 10-11 using sodium hydroxide (6M), at which point the mixture becomes cloudy. The aqueous layer was extracted with methylene chloride (2×200 mL). The organic extracts were washed with brine, dried with sodium sulfate, filtered and evaporated under reduced pressure to afford racemic 1-ethyl-2-((E)-1-phenylprop-1-en-2-yl)cyclopropanamine (495 mg, 2.45 mmol) in 70% yield. LCMS (ESI+): 202.2 (M+H), 185.1 [(M−NH2)+].

Synthesis of racemic 2-((E)-4-methoxy-1-phenyl-but-1-en-2-yl)cyclopropanamine Hydrochloride

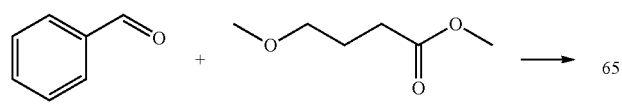

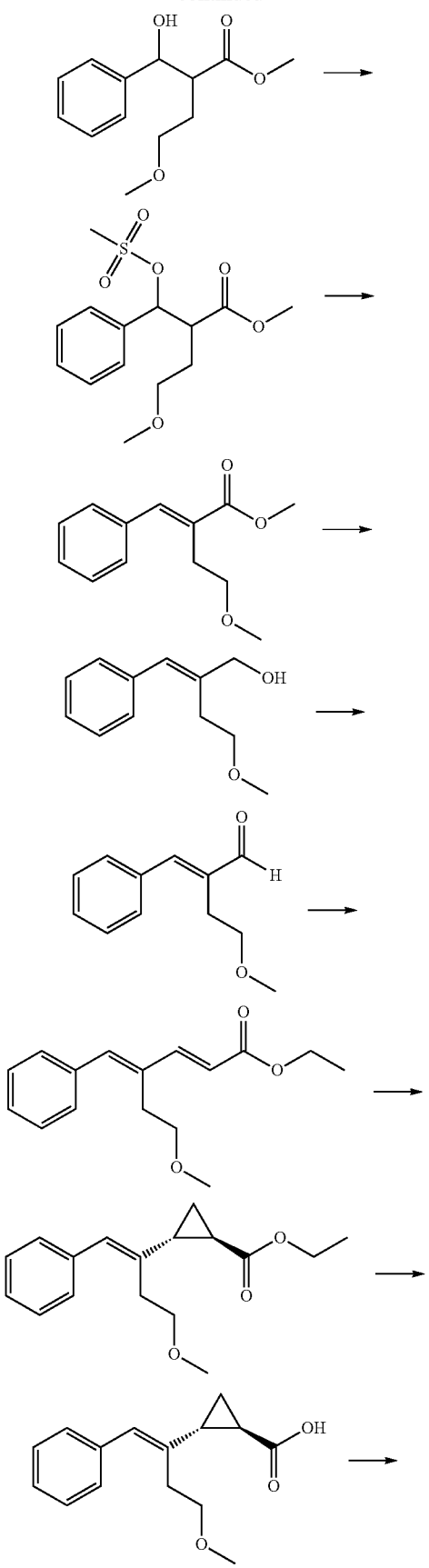

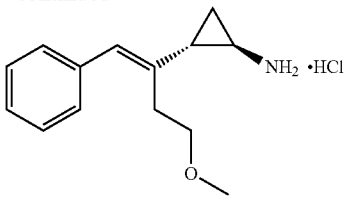

Step 1: methyl 2-(hydroxy(phenyl)methyl)-4-methoxybutanoate

Lithium diisopropylamide was prepared by addition of n-butyllithium (2.5 M in hexanes, 11.7 mL, 58.8 mmol) to diisopropylamine (9.7 mL, 70.6 mmol) in dry tetrahydrofuran (100 mL) at −78° C. Stirring was continued for 15 min at −78° C. before methyl 4-methoxyhutanoate (6.84 g, 51.8 mmol) was added to the reaction mixture. Stirring was continued for 20 min at −78° C. and benzaldehyde (5 g, 47.1 mmol) in tetrahydrofuran (20 mL) was added, and the reaction mixture allowed to warm slowly to room temperature. Stirring was continued for 2 hours, water (50 mL) was added under stirring and the mixture was extracted with ether (3×50 mL). The combined organic extracts were washed with brine, dried with sodium sulfate, filtered and evaporated under reduced pressure to afford methyl 2-(hydroxy(phenyl)methyl)-4-methoxybutanoate (10.7 g, 44.9 mmol) in 95% yield. LCMS (ESI+): 261.1 (M+Na).

Step 2: methyl 4-methoxy-2-(((methylsulfonyl)oxy)(phenyl)methyl)butanoate

Methyl 2-(hydroxy(phenyl)methyl)-4-methoxybutanoate (10.7 g, 45 mmol) was dissolved in methylene chloride (150 mL), triethylamine (12.5 mL, 90.0 mmol) was added, cooled to 0° C., then methanesulfonyl chloride (4.00 mL, 51.7 mmol) was added dropwise. The reaction mixture was gradually warmed to room temperature, and stirred for 16 hours. The reaction mixture was quenched with NaHCO₃ (saturated aq.), the organic phase was isolated, dried with sodium sulfate, filtered, evaporated to afford methyl 4-methoxy-2-(((methylsulfonyl)oxy)(phenyl)methyl)butanoate (14.2 g, 44.8 mmol) in quantitative yield. LCMS (ESI+): 339.1 (M+Na).

Step 3: (E)-methyl 2-benzylidene-4-methoxybutanoate

Methyl 4-methoxy-2-(((methylsulfonyl)oxy)(phenyl)methyl)butanoate (14 g, 44.2 mmol) was dissolved in toluene (90 mL), 1,8-Diazabicycloundec-7-ene (6.60 mL, 44.2 mmol) was added, and the reaction mixture was heated to reflux for 72 hours. The volatiles were evaporated and the crude residue was purified by silica gel column chromatography (0% to 20% EtOAc in hexanes on silica gel column). The pure fractions were evaporated to afford (E)-methyl 2-benzylidene-4-methoxybutanoate (7.00 g, 31.7 mmol) in 72% yield. LCMS (ESI+): 221.1 (M+H), 243.1 (M+Na).

Step 4: (E)-2-benzylidene-4-methoxybutan-1-ol (E)-methyl 2-benzylidene-4-methoxybutanoate (7 g, 31.7 mmol) dissolved in tetrahydrofuran (160 mL) and cooled to 0° C. Lithium aluminum hydride (1M in tetrahydrofuran, 31.7 mL, 31.7 mmol) was added dropwise at 0° C. The reaction mixture was stirred for 2 hours. The reaction mixture was quenched with ammonium chloride (aq., sat.) and 6N hydrochloric acid (aq.). The reaction mixture was extracted with EtOAc (2×). Organic layers were dried with Na₂SO₄, filtered and evaporated to afford (E)-2-benzylidene-4-methoxybutan-1-ol (5.20 g, 27.0 mmol) in 85% yield. LCMS (ESI+): 144.9 (M−OH−MeOH)⁺.

Step 5: (E)-2-benzylidene-4-methoxybutanal

Oxalyl chloride (3.21 mL, 37.8 mmol) was dissolved in methylene chloride (100 mL), cooled to 0° C., and dimethyl sulfoxide (3.82 mL, 54.0 mmol) was added dropwise. The reaction mixture was stirred for 15 minutes. At −78° C. a solution of (E)-2-benzylidene-4-methoxybutan-1-ol (5.2 g, 27.0 mmol) in methylene chloride (50 mL) was added to the reaction mixture and stirred for 30 minutes. Triethylamine (15.0 mL, 108 mmol) was added and stirred for 1.5 hour while increasing temperature to 25° C. The reaction mixture was quenched with ammonium chloride (aq.) and extracted with EtOAc. The organic layer was washed with brine, dried with sodium sulfate, filtered, and evaporated to afford (E)-2-benzylidene-4-methoxybutanal (4.66 g, 24.4 mmol) in 91% yield. LCMS (ESI+): 191 (M+H, weak), 159 (M−OMe+).

Step 6: (2E,4E)-ethyl 4-benzylidene-6-methoxyhex-2-enoate

Ethyl 2-(diethoxyphosphoryl)acetate (5.53 g, 24.7 mmol) was dissolved in THF (125 mL), 1M sodium tert-butoxide (26.4 mL, 26.4 mmol) was added in one portion the reaction mixture was stirred vigorously at 0° C. for 15 minutes. (E)-2-benzylidene-4-methoxybutanal (4.57 g, 24.0 mmol) in tetrahydrofuran (20 mL) was added by cannulation. The solvent was evaporated under reduced pressure and the residue was purified by column chromatography on silica gel (0% to 20% EtOAc in hexanes) to give (2E,4E)-ethyl 4-benzylidene-6-methoxyhex-2-enoate (3.35 g, 12.8 mmol) in 54% yield. LCMS (ESI+): 261.1 (M+H).

Step 7: (trans)-ethyl 2-(E)-4-methoxy-1-phenylbut-1-en-2-yl)cyclopropanecarboxylate Under nitrogen atmosphere, sodium hydride (383 mg, 60 wt %, 9.60 mmol) was dissolved in dimethyl sulfoxide (24 mL) and the mixture stirred for 15 minutes at 25° C. Trimethylsulfoxonium iodide (2.19 g, 9.98 mmol) was added, reaction mixture was stirred 45 minutes at 25° C. (2E,4E)-ethyl 4-benzylidene-6-methoxyhex-2-enoate (2 g, 7.68 mmol) dissolved in dimethyl sulfoxide (16 mL) was added. The reaction mixture was stirred at 40° C. for 16 hours. The reaction mixture was quenched with saturated aqueous ammonium chloride (250 mL) and brine (50 mL) with a water bath as a heat sink. The mixture was extracted with hexanes (300 mL, then 100 inL). Organic phase was evaporated under reduced pressure. The crude residue was taken up in MTBE (40 mL) and filtered on a 5 cm pad of silica, under suction. The filter cake was washed with MTBE. The filtrate was evaporated under reduced pressure and pumped under high vacuum for 15 minutes to afford (trans)-ethyl 2-((E)-4-methoxy-1-phenylbut-1-en-2-yl)cyclopropanecarboxylate (1.36 g, 4.95 mmol) in 71% yield. LCMS (ESI+): 275 (M+H).

Step 8: (trans)-2-(E)-4-methoxy-1-phenylbut-1-en-2-yl)cyclopropanecarboxylic Acid (trans)-ethyl 2-(E)-4-methoxy-1-phenylbut-1-en-2-yl)cyclopropanecarboxylate (1.34 g, 4.88 mmol) was dissolved in tetrahydrofuran (40 mL) and methanol (10 mL). Sodium hydroxide was added (6M aqueous, 6.5 mL, 39 mmol), and the reaction mixture was stirred for 3 hours at 50° C. Reaction mixture cooled to 0° C., acidified to pH 4 using hydrochloric acid (1M aqueous). Reaction mixture was partitioned between brine and EtOAc. Organic layer was washed with brine, dried with Na₂SO₄, filtered, and evaporated under reduced pressure to afford (trans)-2-((E)-4-methoxy-1-phenylbut-1-en-2-yl)cyclopropanecarboxylic acid (930 mg, 3.77 mmol) in 77% yield. LCMS (ESI+): 247 (M+H).

Step 9: (trans)-2-((E)-4-methoxy-1-phenylbut-1-en-2-yl)cyclopropanamine Hydrochloride (Racemic)

Racemic (trans)-2-((E)-4-methoxy-1-phenylbut-1-en-2-yl)cyclopropanecarboxylic acid (0.93 g, 3.77 mmol) was dissolved in tetrahydrofuran (19 mL) mixed with triethylamine (1.31 mL, 9.42 mmol), and the solution was then cooled to 0° C. The solution was mixed with ethyl chloroformate (374 µL, 551 mg, 5.08 mmol), and the reaction mixture was stirred at 0° C. for 0.5 hour. A solution of sodium azide (1.22 g, 18.8 mmol) in 40 ml of water was added and the reaction mixture was stirred at 0° C. for one hour. The reaction mixture was diluted with water and extracted with EtOAc. The combined extracts were washed with brine, dried with sodium sulphate and evaporated. The residue was taken up in 3 ml of benzene, and the solution was heated to reflux for 2 hours. Potassium trimethylsilanolate (724 mg, 5.65 mmol) was added to the mixture cooled at room temperature. Stirred for 1.5 hour. The reaction mixture was quenched with hydrochloric acid (2M aqueous, 40 mL, 80 mmol) and stirred. The volume of organics was increased to 250 mL with MTBE. Hydrochloric acid (2M aqueous) was added (250 mL), and the layers were separated. The organic layer was extracted twice with hydrochloric acid (2M aqueous) (2×300 mL), and the aqueous extracts were combined. The aqueous layer was basified to pH 10-11 using sodium hydroxide (6M), at which point the mixture becomes cloudy. The aqueous layer was extracted with methylene chloride (2×500 mL). The organic extracts were washed with brine, dried with Na₂SO₄, filtered and evaporated under reduced pressure. The compound was redissolved in MTBE, cooled to 0° C. and hydrochloric acid (2M in ethyl ether, 2.5 mL, 5 mmol) was added. The volatiles were evaporated under reduced pressure to afford racemic (trans)-2-((E)-4-methoxy-1-phenylbut-1-en-2-yl)cyclopropanamine hydrochloride (450 mg, 1.77 mmol) in 47% yield. LCMS (ESI+): 218.2 (M+H).

GENERAL PROCEDURE FOR THE ALKYLATION OF CYCLOPROPYLAMINES WITH ALDEHYDES AND KETONES

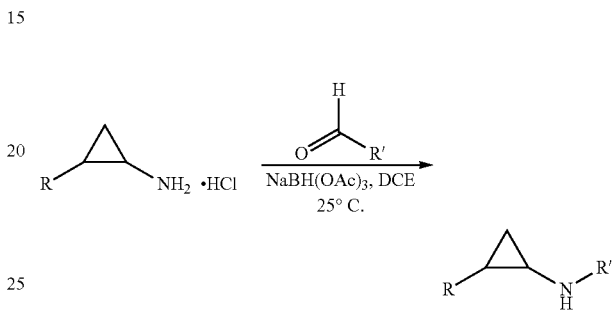

To a solution of the cyproylamine hydrochloride (1 eq.) and the aldehyde or ketone (0.95 eq.) in 1,2-dichloroethane (0.2 M) at 25° C. was added sodium (triacetoxy) borohydride (2 eq.). After 30 min., DCM and potassium carbonate (1M aqueous solution) were added to the reaction mixture. The organic phase was isolated and evaporated under reduced pressure.

The intermediates in the following table were synthesized according to the General Procedure for the alkylation of cyclopropylamines with aldehydes and ketones. Compounds were purified by silica gel column chromatography (0% to 10% Methanol in Ethyl acetate eluent mixture).

TABLE 1

| Intermediate | Aldehyde | Structure | ESI+ |
|---|---|---|---|
| D | Intermediate A | racemic tert-butyl 4-((4-(((2-((E)-styryl)cyclopropyl)amino)methyl)piperidin-1-yl)methyl)benzoate | 447 (M + H) |
| E | | tert-butyl (E)-3-(4-(((2-styrylcyclopropyl)amino)methyl)piperidin-1-yl)propanoate | 385 (M + H) |

TABLE 1-continued

| Intermediate | Aldehyde | Structure | ESI+ |
|---|---|---|---|
| F | Intermediate B | tert-butyl (E)-2-(4-((((2-styrylcyclopropyl)amino)methyl)piperidin-1-yl) acetate | 371 (M + H) |
| G | | tert-butyl (E)-4-fluoro-4-((((2-styrylcyclopropyl)amino)methyl)piperidine-1-carboxylate | 319 (M − tBu + H) |

The following intermediates in Table 1A were prepared according to the general procedure for the alkylation of cyclopropylamines using aldehdyes and ketones, using racemic 2-((E)-1-phenylbut-1-en-2-yl)cyclopropanamine hydrochloride as the amine.

TABLE 1A

| No. | Aldehyde or ketone | Structure | MS (ESI+) |
|---|---|---|---|
| 127 | | tert-butyl 4-((4-((((trans)-2-((E)-1-phenylbut-1-en-2-yl)cyclopropyl)amino)methyl)piperidin-1-yl)methyl)benzoate (racemic) | 475.0 (M + H) |
| 128a | | tert-butyl 4-((4-(((trans)-2-((E)-1-phenylbut-1-en-2-yl)cyclopropyl)amino)piperidin-1-yl)methyl)benzoate (racemic) | 461.3 (M + H) |

4-(((trans)-2-((E)-1-phenylbut-1-en-2-yl)cyclopropyl)amino)cyclohexanone Hydrochloride (Racemic)

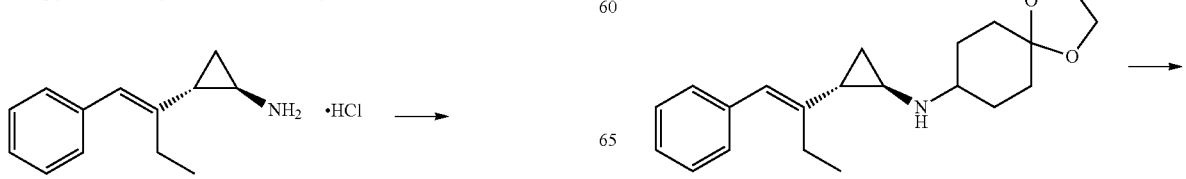

-continued

-continued

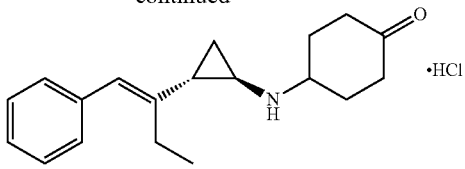

Step 1: N-((trans)-2-(E)-1-phenylbut-1-en-2-yl)cyclopropyl)-1,4-dioxaspiro[4.5]decan-8-amine To (trans)-2-((E)-1-phenylbut-1-en-2-yl)cyclopropanamine hydrochloride (0.284 g, 1.26 mmol) and 1,4-dioxaspiro[4.5]decan-8-one (199 mg, 1.28 mmol) in 6 mL of 1,2-dichloroethane was added sodium (triacetoxy)borohydride (534 mg, 2.52 mmol). After 30 min, methylene chloride and potassium carbonate (1M aqueous) were added. The organic phase was evaporated and the crude residue purified by column chromatography (silica, 0% to 10% methanol in EtOAc) to afford N-((trans)-2-((E)-1-phenylbut-1-en-2-yl)cyclopropyl)-1,4-dioxaspiro[4.5]decan-8-amine (354 mg, 1.08 mmol) (86% yield). LCMS (ESI+): 328.2 (M+H).

Step 2: 4-(((trans)-2-((E)-1-phenylbut-1-en-2-yl)cyclopropyl)amino)cyclohexan-1-one Hydrochloride (Racemic)

N-((trans)-2-((E)-1-phenylbut-1-en-2-yl)cyclopropyl)-1,4-dioxaspiro[4.5]decan-8-amine (353 mg, 1.07 mmol) was dissolved in tetrahydrofuran (5 mL) and hydrochloric acid (6M aqueous, 1.4 mL, 6 mmol) was added and the reaction mixture was stirred at 60° C. for 16 hours. The solution was partitioned between a potassium carbonate (aqueous) solution and ethyl acetate. The aqueous layer was extracted once with ethyl acetate. The combined organic layers were washed with brine, dried with sodium sulfate, filtered and evaporated. The crude residue was purified by silica gel column chromatography (methanol:ethyl acetate gradient). The fractions were evaporated and the compound was redissolved in MTBE, cooled to 0° C., and hydrogen chloride was added (2M in diethyl ether, 0.6 mL, 1.2 mmol) to afford 4-(((trans)-2-((E)-1-phenylbut-1-en-2-yl)cyclopropyl)amino)cyclohexan-1-one hydrochloride (301 mg, 941 µmol) (88% yield) LCMS (ESI+): 284.2 (M+H).

methyl 2-(4-oxo-1-piperidyl)acetate

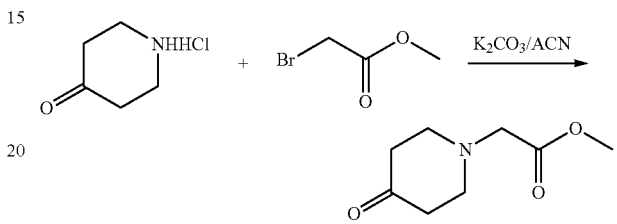

To a stirred solution of piperidin-4-one (1.00 g, 7.38 mmol, 1.00 eq, HCl) and methyl 2-bromoacetate (1.13 g, 7.38 mmol, 1.00 eq) in MeCN (20.00 mL) was added $K_2CO_3$ (3.06 g, 22.14 mmol, 3.00 eq). The mixture was stirred at 70° C. for 17 h. The reaction was quenched by water (20 mL) and extracted with DCM (50 mL×3). The combined organics layer was dried over anhydrous $Na_2SO_4$, filtered, and concentrated to afford methyl 2-(4-oxo-1-piperidyl)acetate (600.00 mg).

The following intermediates in Table 1B were synthesized following the procedure outlined above using the appropriate starting materials and modifications.

TABLE 1B

| Electrophile | Intermediate structure | Intermediate name | LCMS |
|---|---|---|---|
| Br~~~O~ | O=⟨piperidinone⟩N~~O~ | 1-(2-methoxyethyl)piperidin-4-one | |
| CH₂=CHC(O)OMe | O=⟨piperidinone⟩N~~C(O)OMe | methyl 3-(4-oxopiperidin-1-yl)propanoate | |
| Br~~~OTBS | O=⟨piperidinone⟩N~~OTBS | 1-(2-((tert-butyldimethylsilyl)oxy)ethyl)piperidin-4-one | |
| H₂N-SO₂-C₆H₄-CH₂Br | O=⟨piperidinone⟩N-CH₂-C₆H₄-SO₂NH₂ | 4-((4-oxopiperidin-1-yl)methyl)benzenesulfonamide | |

TABLE 1B-continued

| Electrophile | Intermediate structure | Intermediate name | LCMS |
|---|---|---|---|
| (Br-CH2-pyridine-CO2Me structure) | (piperidinone-CH2-pyridine-CO2Me structure) | methyl 6-((4-oxopiperidin-1-yl)methyl)nicotinate | | methyl 5-(bromomethyl)pyrimidine-2-carboxylate

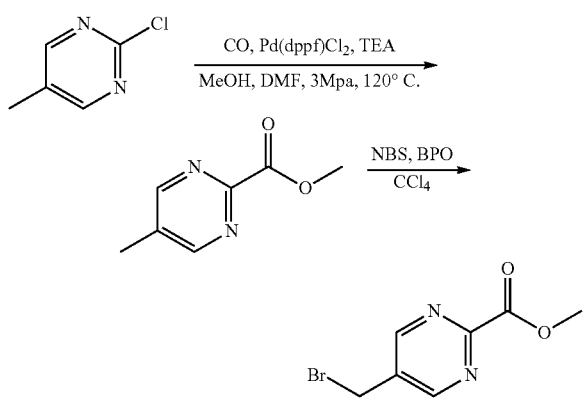

Step 1: methyl 5-methylpyrimidine-2-carboxylate

To a solution of 2-chloro-5-methyl-pyrimidine (500.00 mg, 3.89 mmol, 1.00 eq) in MeOH (10.00 mL) and DMF (2.00 mL) was added triethylamine (1.18 g, 11.67 mmol, 1.62 mL, 3.00 eq) and Pd(dppf)Cl2 (426.87 mg, 583.39 umol, 0.15 eq) under CO. The suspension was degassed and purged with CO several times. The mixture was stirred under CO (3 Mpa) at 120° C. for 16 h. The reaction mixture was filtered and the filtrate was concentrated. The crude residue was purified by column chromatography (Petroleum ether: Ethyl acetate=20:1 to 0:1) to afford methyl 5-methylpyrimidine-2-carboxylate (350.00 mg). LCMS (M+H$^+$) m/z: 153.

Step 2: Synthesis of methyl 5-(bromomethyl)pyrimidine-2-carboxylate

To a solution of methyl 5-methylpyrimidine-2-carboxylate (100.00 mg, 657.25 umol, 1.00 eq) in CCl$_4$ (3.00 mL) were added benzoyl peroxide (31.84 mg, 131.45 umol, 0.20 eq) and 1-bromopyrrolidine-2,5-dione (105.28 mg, 591.53 umol, 0.90 eq). The mixture was stirred at 70° C. for 16 h. The reaction mixture was quenched by addition H$_2$O (10 mL) and extracted with DCM (10 mL*3). The combined organic layers were dried over anhydrous Na$_2$SO$_4$ and concentrated. The crude residue was purified by column chromatography (Petroleum ether:Ethyl acetate=20:1 to 1:1) to afford methyl 5-(bromomethyl)pyrimidine-2-carboxylate (47.00 mg). LCMS (M+H$^+$) m/z: 231.

Synthesis of tert-butyl 5-formylpicolinate

Step 1: tert-butyl 5-vinylpicolinate (tert-butyl 5-vinylpicolinate structure)

To tert-butyl 5-bromopicolinate (568 mg, 2.20 mmol) dissolved in DMF (9 mL) in a sealable tube was added tributyl(vinyl)stannane (703 mg, 2.22 mmol). The reaction mixture was degassed under a stream of nitrogen before addition of copper(I) iodide (20.9 mg, 110 μmol) and Pd(PPh$_3$)4 (177 mg, 154 μmol).The tube was sealed and heated to 100° C. for 24 h. The reaction mixture was partitioned between brine and EtOAc. The organic layer was washed with brine, dried with sodium sulfate, filtered and evaporated under reduced pressure. The crude residue was purified by column chromatography (0% to 10% MeOH in EtOAc) to afford tert-butyl 5-vinylpicolinate (460 mg, 2.24 mmol). LCMS m/z: 228.1 (M+Na)

Step 2: tert-butyl 5-(1,2-dihydroxyethyl)picolinate

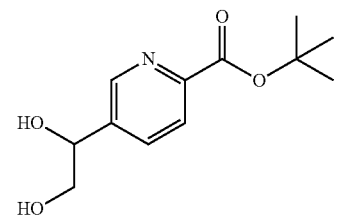 [SMILES: CC(C)(C)OC(=O)c1ccc(C(O)CO)cn1]

To tert-butyl 5-vinylpicolinate (467 mg, 2.27 mmol) dissolved in tBuOH (2.5 mL) and water (2.5 mL) was cooled to 0° C. To this solution was added AD-mix-beta (2.25 g) and the reaction mixture was stirred overnight. The reaction mixture was partitioned between brine and EtOAc. The organic layer was dried with Na$_2$SO$_4$, filtered and evaporated. The crude residue was used in the next step without further purification. LCMS m/z: 240.0 (M+H)/184.0 (M-tBu+H)

Step 3: tert-butyl 5-formylpicolinate

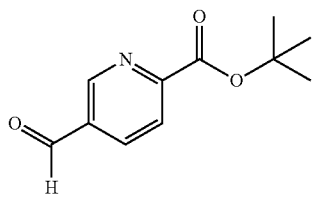

To tert-butyl 5-(1,2-dihydroxyethyl)picolinate (500 mg, 2.08 mmol) dissolved in THF (3 mL) and water (2 mL) at 0° C. was added sodium periodate (1.33 g, 6.24 mmol). The reaction mixture was stirred under a stream of nitrogen for 16 h. The reaction mixture was partitioned between brine and EtOAc. The organic layer was isolated, washed with brine, dried with sodium sulfate, filtered and evaporated under reduced pressure. The crude residue was purified by column chromatography (0% to 10% MeOH in EtOAc) to afford tert-butyl 5-formylpicolinate (228 mg, 1.10 mmol). LCMS m/z: 152.0 (M-tBu+H)

Using appropriate starting materials and modifications the following aldehyde intermediates were synthesized following the synthetic procedures described for tert-butyl 5-formylpicolinate.

| Structure/Name | LCMS m/z |
| --- | --- |
| methyl 4-formyl-2-methylbenzoate | 179 |
| methyl 4-formyl-3-methylbenzoate | 179 |

Synthesis of tert-butyl 4-((3-(2-oxoethyl)azetidin-1-yl)methyl)benzoate

Step 1: 2-(azetidin-3-yl)acetate

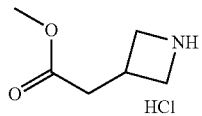

To a solution of tert-butyl 3-(2-methoxy-2-oxo-ethyl)azetidine-1-carboxylate (200 mg, 872.33 umol, 1.00 eq) in MeOH (2 mL) was added HCl (4 M in MeOH, 2 mL, 9.17 eq) at 0° C. The mixture was stirred at 25° C. for 2 h. The mixture was concentrated to afford crude methyl 2-(azetidin-3-yl)acetate (112 mg, 867.14 umol).

$^1$H NMR (400 MHz, CD$_3$OD) δ 4.16 (t, J=9.9 Hz, 2H), 3.95-3.87 (m, 2H), 3.73-3.65 (m, 3H), 3.28-3.19 (m, 1H), 2.78-2.69 (m, 2H).

Step 2: tert-butyl 4-((3-(2-methoxy-2-oxoethyl)azetidin-1-yl)methyl)benzoate

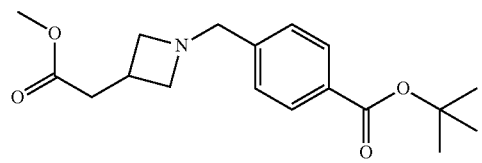 [SMILES: COC(=O)CC1CN(Cc2ccc(C(=O)OC(C)(C)C)cc2)C1]

To a mixture of methyl 2-(azetidin-3-yl)acetate; hydrochloride (112 mg, 676.25 umol, 1.00 eq), diisopropylethylamine (437 mg, 3.38 mmol, 590.53 uL, 5.00 eq) in acetonitrile (3 mL) was added tert-butyl 4-(bromomethyl)benzoate (183 mg, 676.25 umol, 1.00 eq). The mixture was stirred at 25° C. for 5 h. To the mixture was added H$_2$O (5 mL). The mixture was extracted with ethyl acetate (5 mL*2). The organic phase was dried with Na$_2$SO$_4$ and concentrated under vacuum. The crude residue was purified by column chromatography (SiO$_2$, Petroleum ether/Ethyl acetate=10/1 to 8:1) to afford tert-butyl 4-((3-(2-methoxy-2-oxoethyl)azetidin-1-yl)methyl)benzoate (120 mg, 360.69 umol). LCMS (M+H$^+$) m/z: calcd 320.18; found 319.9.

Step 3: tert-butyl 4-((3-(2-hydroxyethyl)azetidin-1-yl)methyl)benzoate

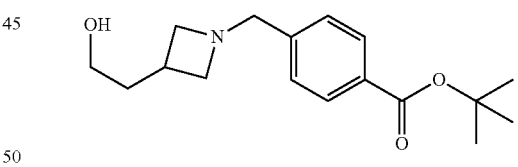

To a solution of tert-butyl 4-((3-(2-methoxy-2-oxoethyl)azetidin-1-yl)methyl)benzoate (120 mg, 375.72 umol, 1.00 eq) in THF (3 mL) was added DIBAL-H (1 M, 1.1 mL, 3.00 eq) (toluene) at −78° C. The mixture was stirred at 0° C. for 2 h. To the mixture was added H$_2$O (5 mL). The mixture was extracted with ethyl acetate (8 mL*3). The organic phase was dried with Na$_2$SO$_4$, and concentrated to afford crude tert-butyl 4-((3-(2-hydroxyethyl)azetidin-1-yl)methyl)benzoate (100 mg, 343.19 umol). LCMS (M+H$^+$) m/z: calcd 292.18; found 291.9. $^1$H NMR (400 MHz, CDCl$_3$) δ 7.94 (d, J=8.4 Hz, 2H), 7.35 (s, 2H), 4.31 (s, 1H), 3.92 (s, 1H), 3.75 (br. s., 2H), 3.67 (s, 2H), 3.48 (s, 1H), 3.12 (br. s., 1H), 2.30 (s, 1H), 1.83 (br. s., 2H), 1.64-1.56 (m, 11H).

Step 4: tert-butyl 4-((3-(2-oxoethyl)azetidin-1-yl)methyl)benzoate

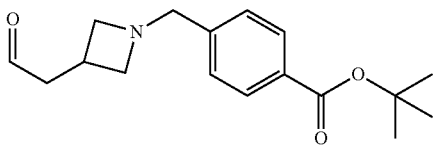 [SMILES: CC(C)(C)OC(=O)c1ccc(CN2CC(CC=O)C2)cc1]

To a solution of tert-butyl 4-((3-(2-hydroxyethyl)azetidin-1-yl)methyl)benzoate (100 mg, 343.19 umol, 1.00 eq) in DCM (5 mL) was added Dess-Martin periodinane (291 mg, 686.38 umol, 212.50 uL, 2.00 eq) at 0° C. The mixture was stirred at 25° C. for 2 h. To the mixture was added NaHCO$_3$ (5*9 mL). The organic phase was dried with Na$_2$SO$_4$ and concentrated to afford crude tert-butyl 4-((3-(2-oxoethyl)azetidin-1-yl)methyl)benzoate (180 mg, crude).

$^1$H NMR (400 MHz, CDCl$_3$) δ 9.76 (s, 1H), 8.26 (d, J=7.9 Hz, 1H), 8.06-7.97 (m, 1H), 7.97-7.83 (m, 3H), 7.76-7.67 (m, 1H), 7.30 (d, J=7.5 Hz, 2H), 3.64 (s, 2H), 3.49 (t, J=6.0 Hz, 2H), 2.91 (d, J=4.9 Hz, 2H), 2.83-2.73 (m, 2H), 2.26 (s, 3H), 1.81 (br. s., 3H), 1.58 (s, 9H), 0.88 (br. s., 2H)

Synthesis of ethyl 1-(2,2-dimethyl-3-oxo-propyl)piperidine-4-carboxylate

Step 1: 1-(3-hydroxy-2,2-dimethyl-propanoyl)piperidine-4-carboxylate

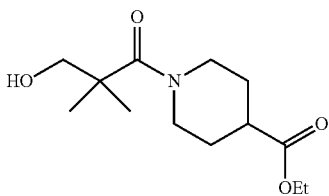 [SMILES: CCOC(=O)C1CCN(C(=O)C(C)(C)CO)CC1]

To a mixture of 3-hydroxy-2,2-dimethyl-propanoic acid (100 mg, 846.53 umol, 1.00 eq) in DCM (10 mL) were added HATU (400 mg, 1.05 mmol, 1.24 eq) diisopropylethylamine (350 mg, 2.71 mmol, 472.97 uL, 3.20 eq) and ethyl piperidine-4-carboxylate (135 mg, 858.72 umol, 132.35 uL, 1.01 eq).The reaction mixture was stirred at 15° C. for 16 h. Water was added and the mixture was extracted with DCM (20 mL*3). The combined organic phase was washed with brine (30 mL*2), dried with anhydrous Na$_2$SO$_4$, filtered and concentrated. The crude residue was purified by silica gel chromatography (Petroleum ether/Ethyl acetate=20/1-3/1) to afford ethyl 1-(3-hydroxy-2,2-dimethyl-propanoyl)piperidine-4-carboxylate (110 mg, 427.47 umol).

Step 2: ethyl 1-(3-hydroxy-2,2-dimethyl-propyl)piperidine-4-carboxylate

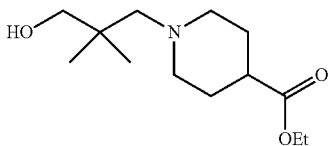 [SMILES: CCOC(=O)C1CCN(CC(C)(C)CO)CC1]

To a mixture of ethyl 1-(3-hydroxy-2,2-dimethyl-propanoyl)piperidine-4-carboxylate (100 mg, 388.61 umol, 1.00 eq) in THF (5 mL) was added dropwise BH$_3$—Me$_2$S (10 M, 300 uL, 7.72 eq) at 0° C. The reaction mixture was stirred at 15° C. for 17 h. The reaction mixture was added to ice-water (10 mL) and the mixture was extracted with EtOAc (10 mL*3).The combined organic phase was washed with brine (20 mL*2), dried with anhydrous Na$_2$SO$_4$, filtered and concentrated in to afford crude ethyl 1-(3-hydroxy-2,2-dimethyl-propyl)piperidine-4-carboxylate (40 mg, 164.38 umol).

Step 3: ethyl 1-(2,2-dimethyl-3-oxo-propyl)piperidine-4-carboxylate

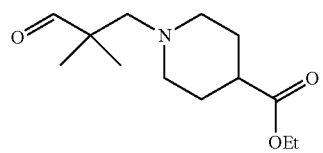 [SMILES: CCOC(=O)C1CCN(CC(C)(C)C=O)CC1]

To a solution of ethyl 1-(3-hydroxy-2,2-dimethyl-propyl)piperidine-4-carboxylate (40 mg, 164.38 umol, 1.00 eq) in DCM (2 mL) was added Dess-Martin periodinane (140 mg, 330.08 umol, 102.19 uL, 2.01 eq) at 0° C. The mixture was stirred at 15° C. for 4 h. The reaction mixture was quenched by addition of Na$_2$S$_2$O$_3$ (aq, 15 mL) at 0° C., and then diluted with NaHCO$_3$ (aq, 15 mL) and extracted with DCM (10 mL*3). The combined organic layers were washed with brine (30 mL*3), dried with anhydrous Na$_2$SO$_4$, filtered and concentrated to afford crude ethyl 1-(2,2-dimethyl-3-oxo-propyl)piperidine-4-carboxylate (40 mg, crude).

Synthesis of tert-butyl N-tert-butoxycarbonyl-N-[(4-formyloxazol-2-yl) methyl]carbamate Step 1: methyl 2[[bis(tert-butoxycarbonyl)amino]methyl]oxazole-4-carboxylate

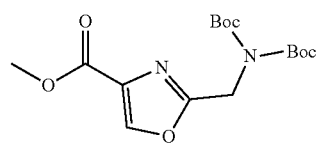 [SMILES: COC(=O)c1coc(CN(C(=O)OC(C)(C)C)C(=O)OC(C)(C)C)n1]

To a solution of methyl 2-(chloromethyl)oxazole-4-carboxylate (300 mg, 1.7 mmol, 1.00 eq) in CH$_3$CN (5 mL) were added K$_2$CO$_3$ (708.5 mg, 5.1 mmol, 3.00 eq) and tert-butyl N-tert-butoxycarbonylcarbamate (1.11 g, 5.13 mmol, 3.00 eq). The mixture was stirred at 60° C. for 40 min. The reaction mixture was filtered and concentrated under reduced pressure to give a residue. The residue was purified by prep-TLC (SiO$_2$, PE:EtOAc=3:1) to afford methyl 2[[bis(tert-butoxycarbonyl)amino]methyl]oxazole-4-carboxylate (200 mg, 561.2 umol).

Step 2: tert-butyl N-tert-butoxycarbonyl-N-[[4-(hydroxymethyl) oxazol-2-yl]methyl]carbamate

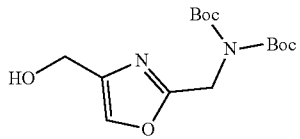

To a solution of methyl 2-[[bis(tert-butoxycarbonyl)amino]methyl]oxazole-4-carboxylate (220.0 mg, 617.3 umol, 1.00 eq) in DCM (6.0 mL) was added DIBAL-H (1 M, 1.85 mL, 3.00 eq) at −78° C. The mixture was stirred at 0° C. for 4 h. The reaction mixture was quenched by aqueous NH$_4$Cl 5 mL at 0° C. and extracted with DCM (10 mL*3). The combined organic layers were washed with brine 10 mL (5 mL*2), dried over Na$_2$SO$_4$, filtered and concentrated under reduced pressure to afford crude tert-butyl N-tert-butoxycarbonyl-N-[[4-(hydroxymethyl)oxazol-2-yl]methyl]carbamate (150 mg, 456.8 umol). LCMS (M+Na$^+$) m/z: calcd 351.16; found 350.9.

Step 3: tert-butyl N-tert-butoxycarbonyl-N-[(4-formyloxazol-2-yl) methyl]carbamate

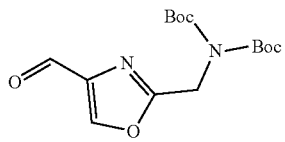 [SMILES: CC(C)(C)OC(=O)N(Cc1nc(C=O)co1)C(=O)OC(C)(C)C]

To a solution of tert-butyl N-tert-butoxycarbonyl-N-[[4-(hydroxymethyl)oxazol-2-yl]methyl]carbamate (100.0 mg, 304.5 umol, 1.00 eq) in DCM (6.0 mL) was added Dess-Martin periodinane (387.5 mg, 913.6 umol, 282.9 uL, 3.00 eq) at 0° C. The mixture was stirred at 25° C. for 16 h. The reaction mixture was diluted with EtOAc 20 mL, filtered and concentrated under reduced pressure to afford crude tert-butyl N-tert-butoxycarbonyl-N-[(4-formyloxazol-2-yl) methyl]carbamate (80.0 mg, 245.1 umol) LCMS (M-Boc-t-butyl +H$^+$) m/z: calcd 171.10; found 170.8. $^1$H NMR (400 MHz, CDCl$_3$) δ 9.92-9.79 (m, 1H), 7.69-7.64 (m, 1H), 4.45 (d, J=4.9 Hz, 2H), 1.57-1.20 (m, 18H).

Synthesis of tert-butyl 3-(4-formylpyrazol-1-yl)azetidine-1-carboxylate

Step 1: ethyl 1-(1-tert-butoxycarbonylazetidin-3-yl)pyrazole-4-carboxylate

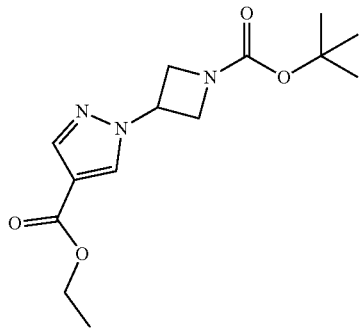 [SMILES: CCOC(=O)c1cnn(C2CN(C(=O)OC(C)(C)C)C2)c1]

The mixture of tert-butyl 3-iodoazetidine-1-carboxylate (500 mg, 1.77 mmol, 1.00 eq), ethyl 1H-pyrazole-4-carboxylate (248 mg, 1.77 mmol, 1.00 eq) and Cs$_2$CO$_3$ (1.15 g, 3.54 mmol, 2.00 eq) in DMF (4 mL) was stirred at 100° C. for 5 h. To the mixture was added water (10 mL) and the reaction was extracted with ethyl acetate (10 mL*2). The organic phases were combined, washed with water (10 mL), dried with Na$_2$SO$_4$, filtered and concentrated. The crude residue was purified by silica gel column chromatography (Petroleum ether:Ethyl acetate=20:1-1:1) to afford ethyl 1-(1-tert-butoxycarbonylazetidin-3-yl)pyrazole-4-carboxylate (430 mg, 1.46 mmol).

Step 2: tert-butyl 3-(4-(hydroxymethyl)-1H-pyrazol-1-yl)azetidine-1-carboxylate

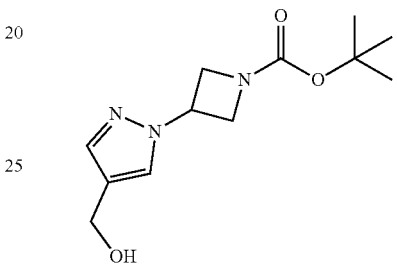

To the solution of ethyl 1-(1-tert-butoxycarbonylazetidin-3-yl)pyrazole-4-carboxylate (100 mg, 0.34 mmol, 1.00 eq) in THF (4 mL) was added DIBAL-H (0.75 mL, 0.75 mmol, 2.20 eq) (1 M in toluene) at −70° C. The mixture was stirred for 2 h at −70° C. To the mixture was added water (10 mL), ethyl acetate (10 mL) and potassium sodium tartrate (2 g). The mixture was stirred at 15° C. for 16 ho. The mixture was extracted with ethyl acetate (10 mL*2). The organic phases were combined, dried with Na$_2$SO$_4$, filtered and concentrated to afford crude tert-butyl 3-(4-(hydroxymethyl)-1H-pyrazol-1-yl)azetidine-1-carboxylate (120 mg).

Step 3: tert-butyl 3-(4-formylpyrazol-1-yl)azetidine-1-carboxylate

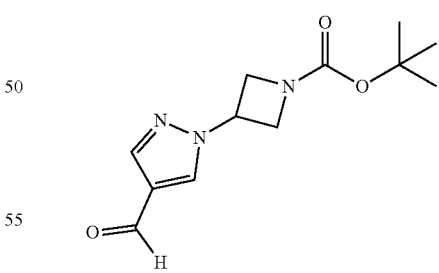

The mixture of tert-butyl 3-(4-(hydroxymethyl)-1H-pyrazol-1-yl)azetidine-1-carboxylate (180 mg, 0.71 mmol, 1.00 eq), Dess-Martin periodinane (600 mg, 1.42 mmol, 2.00 eq) in DCM (5 mL) was stirred at 15° C. for 16 h. The mixture was diluted with DCM (10 mL) and filtered. The filtrate was washed with aqueous NaHCO$_3$ (5 mL*3). The organic phases were combined, dried with Na$_2$SO$_4$, filtered and concentrated to afford crude tert-butyl 3-(4-formylpyrazol-1-yl)azetidine-1-carboxylate (110 mg).

Synthesis of tert-butyl ((4-formyltetrahydro-2H-pyran-4-yl)methyl)carbamate

Step 1: tert-butyl ((4-(hydroxymethyl)tetrahydro-2H-pyran-4-yl)methyl)carbamate

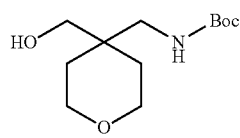

To a solution of [4-(aminomethyl)tetrahydropyran-4-yl] methanol (200 mg, 1.38 mmol, 1.00 eq) in DCM (2 mL) were added triethylamine (438 mg, 4.33 mmol, 600 uL, 3.14 eq) and (Boc)₂O (475 mg, 2.18 mmol, 500 uL, 1.58 eq) at 0° C. The mixture was stirred at 25° C. for 16 h. The reaction mixture was concentrated under reduced pressure to remove solvent. The residue was diluted with ethyl acetate 10 mL and washed with H₂O 15 mL (5 mL*3), dried over anhydrous Na₂SO₄, filtered and concentrated to afford crude tert-butyl N[[4-(hydroxymethyptetrahydropyran-4-yl]methyl]carbamate (251 mg, 1.02 mmol).

¹H NMR (400 MHz, CD₃OD) δ 3.65 (1, J=5.6 Hz, 4H), 3.54 (s, 2H), 2.69 (s, 2H), 1.55-1.37 (m, 4H)

Step 2: tert-butyl ((4-formyltetrahydro-2H-pyran-4-yl)methyl)carbamate

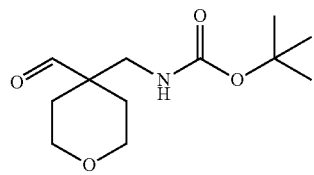 [SMILES: CC(C)(C)OC(=O)NCC1(C=O)CCOCC1]

To a solution of tert-butyl N-[[4-(hydroxymethyl)tetrahydropyran-4-yl]methyl]carbamate (100 mg, 407.7 umol, 1.00 eq) in DCM (3 mL) was added Dess-Martin periodinane (350 mg, 825.2 umol, 256 uL, 2.02 eq). The mixture was stirred at 25° C. for 2 h. The reaction mixture was concentrated under reduced pressure to remove solvent. The residue was diluted with saturated aqueous NaHCO₃(10 mL) and extracted with ethyl acetate 30 mL (10 mL*3). The combined organic layers were dried over anhydrous Na₂SO₄, filtered and concentrated. The crude residue was purified by prep-TLC (PE:EA=3:1) to afford tert-butyl ((4-formyltetrahydro-2H-pyran-4-yl)methyl)carbamate (30 mg,). ¹H NMR (400 MHz, CDCl₃) δ 9.48 (s, 1H), 5.29 (s, 1H), 3.85-3.75 (m, 3H), 3.74-3.66 (m, 2H), 3.54 (t, J=8.8 Hz, 3H), 3.32 (d, J=6.4 Hz, 2H), 1.40 (s, 9H)

Cyclopropane Containing Intermediates:

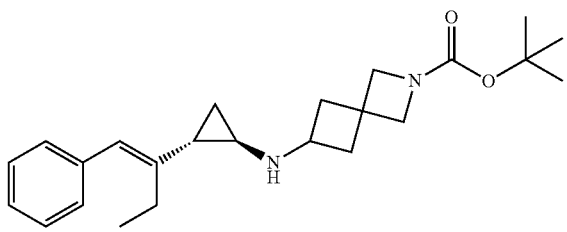 [SMILES: CC/C(=C\c1ccccc1)[C@@H]1C[C@H]1NC1CC2(C1)CN(C(=O)OC(C)(C)C)C2]

tert-butyl 6-(((trans)-2-(E)-1-phenylbut-1-en-2-yl)cyclopropyl)amino)-2-azaspiro[3.3]heptane-2-carboxylate (racemic)

To (trans)-2-((E)-1-phenylbut-1-en-2-yl)cyclopropanamine hydrochloride (177 mg, 794 μmol) and tert-butyl 6-oxo-2-azaspiro[3.3]heptane-2-carboxylate (167 mg, 794 μmol) in 1,2-DCE (8 mL) and sodium triacetoxyborohydride (350 mg, 1.66 mmol). After 30 min, the reaction was quenched with K₂CO₃, and extracted with DCM (2×50 mL). The organic phase was concentrated to afford crude tert-butyl 6-(((trans)-2-((E)-1-phenylbut-1-en-2-yl)cyclopropyl)amino)-2-azaspiro[3.3]heptane-2-carboxylate (303 mg, 792 μmol). LCMS m/z 383 [M+H⁺].

Using the appropriate starting materials and modifications the following intermediates were synthesized following the synthetic procedures described for tert-butyl 6-(((trans)-2-((E)-1-phenylbut-1-en-2-yl)cyclopropyl)amino)-2-azaspiro[3.3]heptane-2-carboxylate.

| Structure/name | Stereochemistry comment | LCMS m/z |
|---|---|---|
| tert-butyl ((trans)-3-((((trans)-2-((E)-1-phenylbut-1-en-2-yl)cyclopropyl)amino)methyl)cyclobutyl)carbamate | racemic | |

| Structure/name | Stereochemistry comment | LCMS m/z |
|---|---|---|
| 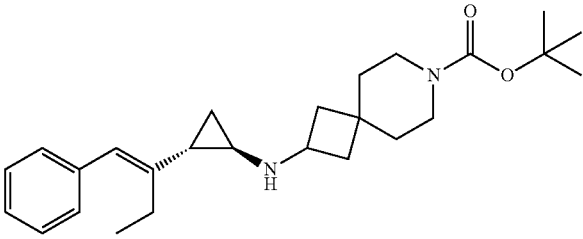<br>tert-butyl 2-(((trans)-2-((E)-1-phenylbut-1-en-2-yl)cyclopropyl)amino)-7-azaspiro[3.5]nonane-7-carboxylate | racemic | |
| 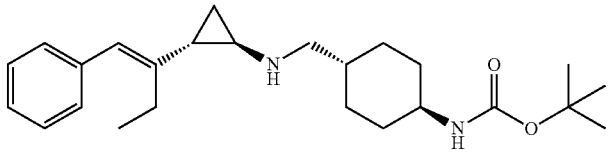<br>tert-butyl ((trans)-4-(((((trans)-2-((E)-1-phenylbut-1-en-2-yl)cyclopropyl)amino)methyl)cyclohexyl)carbamate | racemic | |
| 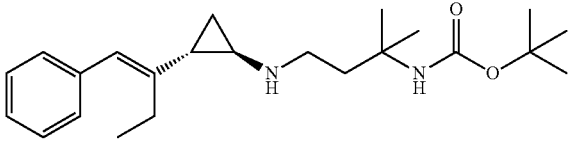<br>tert-butyl (2-methyl-4-(((trans)-2-((E)-1-phenylbut-1-en-2-yl)cyclopropyl)amino)butan-2-yl)carbamate | racemic | 373 |
| 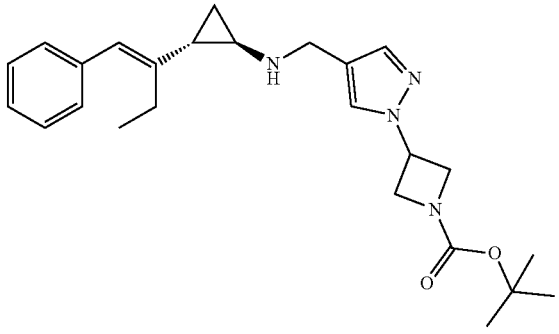<br>tert-butyl 3-(4-(((((trans)-2-((E)-1-phenylbut-1-en-2-yl)cyclopropyl)amino)methyl)-1H-pyrazol-1-yl)azetidine-1-carboxylate | racemic | 423 |
| 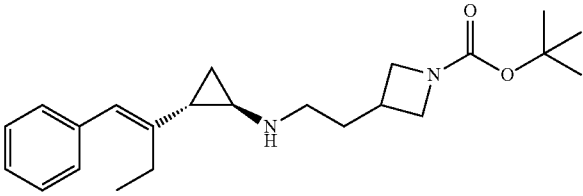<br>tert-butyl 3-(2-(((trans)-2-((E)-1-phenylbut-1-en-2-yl)cyclopropyl)amino)ethyl)azetidine-1-carboxylate | racemic | |

| Structure/name | Stereochemistry comment | LCMS m/z |
|---|---|---|
| ethyl 1-(2,2-dimethyl-3-(((trans)-2-((E)-1-phenylbut-1-en-2-yl)cyclopropyl)amino)propyl)piperidine-4-carboxylate | racemic | |
| tert-butyl 3-methyl-3-((((trans)-2-((E)-1-phenylbut-1-en-2-yl)cyclopropyl)amino)methyl)azetidine-1-carboxylate | racemic | 393 [M + Na] |
| tert-butyl 4-((3-(2-(((trans)-2-((E)-1-phenylbut-1-en-2-yl)cyclopropyl)amino)ethyl)azetidin-1-yl)methyl)benzoate | racemic | 461 |
| tert-butyl N-[[2-[[[(trans)-2-[(1E)-1-benzylidenepropyl]cyclopropyl]amino]methyl]oxazol-4-yl]methyl]-N-tert-butoxycarbonyl-carbamate | racemic | 398 [M − Boc + H]$^+$ |
| tert-butyl ((4-((((trans)-2-((E)-1-phenylbut-1-en-2-yl)cyclopropyl)amino)methyl)tetrahydro-2H-pyran-4-yl)methyl)carbamate | racemic | 415 |

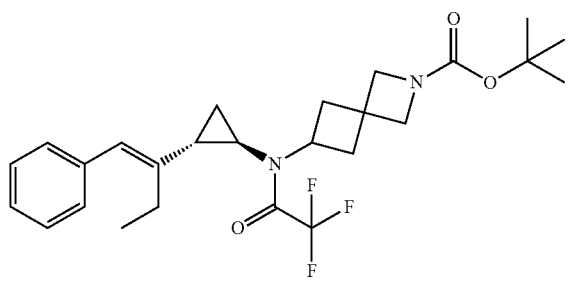 [SMILES: CC/C(=C\c1ccccc1)[C@@H]1C[C@H]1N(C(=O)C(F)(F)F)C1CC2(C1)CN(C(=O)OC(C)(C)C)C2]
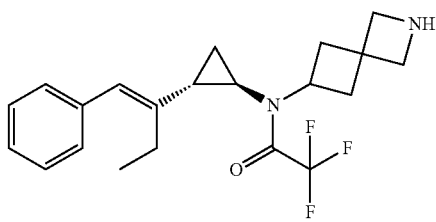 [SMILES: CC/C(=C\c1ccccc1)[C@@H]1C[C@H]1N(C(=O)C(F)(F)F)C1CC2(CNC2)C1]

tert-butyl 6-(2,2,2-trifluoro-N-((trans)-2-(E)-1-phenylbut-1-en-2-yl)cyclopropyl)acetamido)-2-azaspiro[3.3]heptane-2-carboxylate (Racemic)

tert-butyl 6-(((trans)-2-((E)-1-phenylbut-1-en-2-yl)cyclopropyl)amino)-2-azaspiro[3.3]heptane-2-carboxylate (304 mg, 794 µmol) was dissolved in DCM (9 mL) before addition of diisopropylethylamine (185 µL, 1.07 mmol). The solution was cooled to 0° C. and trifluoroacetic anhydride (137 µL, 992 µmol) was added. The reaction mixture was stirred for 24 h, while warming to room temperature. The volatiles were removed under reduced pressure. The crude residue was purified by column chromatography on silica gel (0% to 40% EtOAc in hexanes, 40 g). Pure fractions were evaporated to afford tert-butyl 6-(2,2,2-trifluoro-N-((trans)-2-((E)-1-phenylbut-1-en-2-yl)cyclopropyl)acetamido)-2-azaspiro[3.3]heptane-2-carboxylate (325 mg, 679 µmol). LCMS m/z 501 [M+Na⁺].

Using the appropriate starting materials and modifications the following intermediates were synthesized following the synthetic procedures described for tert-butyl 6-(2,2,2-trifluoro-N-((trans)-2-((E)-1-phenylbut-1-en-2-yl)cyclopropyl)acetamido)-2-azaspiro[3.3]heptane-2-carboxylate.

2,2,2-trifluoro-N-((trans)-2-(E)-1-phenylbut-1-en-2-yl)cyclopropyl)-N-(2-azaspiro[3.3]heptan-6-yl)acetamide (Racemic)

tert-butyl 6-(2,2,2-trifluoro-N-((trans)-2-((E)-1-phenylbut-1-en-2-yl)cyclopropyl)acetamido)-2-azaspiro[3.3]heptane-2-carboxylate (325 mg, 679 µmol) was dissolved in DCM (5 mL) and 2,6-lutidine (196 µL, 1.69 mmol) was added before the solution was cooled to 0° C. Trimethylsilyl trifluoromethanesulfonate (281 µL, 1.56 mmol) was added dropwise to this solution before being stirred for 72 h. The reaction mixture was partitioned between DCM and NaHCO₃ (aq. sat.). The organic phase was washed with brine, dried with Na₂SO₄, filtered and concentrated to afford crude 2,2,2-trifluoro-N-((trans)-2-((E)-1-phenylbut-1-en-2-yl)cyclopropyl)-N-(2-azaspiro[3.3]heptan-6-yl)acetamide (87.0 mg, 229 µmol). LCMS m/z 379 [M+H⁺]

Using the appropriate starting materials and modifications the following intermediates were synthesized using the experimental procedures described for the synthesis of 2,2,2-trifluoro-N-((trans)-2-(E)-1-phenylbut-1-en-2-yl)cyclopropyl)-N-(2-azaspiro[3.3]heptan-6-yl)acetamide.

| Structure/Name | Stereochemistry comment | LCMS m/z |
|---|---|---|
| tert-butyl 2-(2,2,2-trifluoro-N-((trans)-2-((E)-1-phenylbut-1-en-2-yl)cyclopropyl)acetamido)-7-azaspiro[3.5]nonane-7-carboxylate | racemic | 451 [M − tBu + H] |
| tert-butyl 3-methyl-3-((2,2,2-trifluoro-N-((trans)-2-((E)-1-phenylbut-1-en-2-yl)cyclopropyl)acetamido)methyl)azetidine-1-carboxylate | racemic | 489 [M + Na] |

| Structure/Name | Stereochemistry comment | LCMS m/z |
|---|---|---|
| 2,2,2-trifluoro-N-((trans)-2-((E)-1-phenylbut-1-en-2-yl)cyclopropyl)-N-(7-azaspiro[3.5]nonan-2-yl)acetamide hydrochloride | racemic | 407 |
| N-(((trans)-4-aminocyclohexyl)methyl)-2,2,2-trifluoro-N-((trans)-2-((E)-1-phenylbut-1-en-2-yl)cyclopropyl)acetamide | racemic | 395 |
| N-(((trans)-3-aminocyclobutyl)methyl)-2,2,2-trifluoro-N-((trans)-2-((E)-1-phenylbut-1-en-2-yl)cyclopropyl)acetamide | racemic | 367 |
| 2,2,2-trifluoro-N-((3-methylazetidin-3-yl)methyl)-N-((trans)-2-((E)-1-phenylbut-1-en-2-yl)cyclopropyl)acetamide 2,2,2-trifluoroacetate | racemic | 367 |

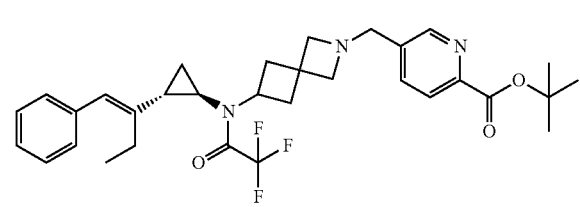 [SMILES: CC/C(=C\c1ccccc1)[C@@H]1C[C@H]1N(C(=O)C(F)(F)F)C1CC2(C1)CN(Cc1ccc(C(=O)OC(C)(C)C)nc1)C2]

tert-butyl 5-((6-(2,2,2-trifluoro-N-((trans)-2-(E)-1-phenylbut-1-en-2-yl)cyclopropyl)acetamido)-2-azaspiro[3.3]heptan-2-yl)methyl)picolinate (Racemic)

2,2,2-trifluoro-N-((trans)-2-(E)-1-phenylbut-1-en-2-yl)cyclopropyl)-N-(2-azaspiro[3.3]heptan-6-yl)acetamide (140 mg, 369 µmol) was dissolved in DCE (2 mL) and tert-butyl 5-formylpicolinate (114 mg, 553 µmol) was added. The reaction mixture was stirred at 25° C. for 30 min before addition of sodium triacetoxyborohydride (156 mg, 738 µmol) and the reaction mixture was stirred for 30 min. The reaction mixture was partitioned between potassium carbonate (aq.) and DCM. The organic layer was washed with brine, dried with $Na_2SO_4$, filtered, and concentrated. The crude product was purified by silica gel column chromatography to afford tert-butyl 5-((6-(2,2,2-trifluoro-N-((trans)-2-((E)-1-phenylbut-1-en-2-yl)cyclopropyl)acetamido)-2-azaspiro[3.3]heptan-2-yl)methyl)picolinate (76.0 mg, 133 µmol). LCMS m/z 570 [M+H$^+$]

Using the appropriate starting materials and modifications the following intermediates were synthesized following the synthetic procedures described for intermediate tert-butyl 5-((6-(2,2,2-trifluoro-N-((trans)-2-(E)-1-phenylbut-1-en-2-yl)cyclopropyl)acetamido)-2-azaspiro[3.3]heptan-2-yl)methyl)picolinate.

| Structure/Name | Stereochemical comment | LCMS m/z |
|---|---|---|
| benzyl 2,2-dimethyl-3-(((trans)-4-((2,2,2-trifluoro-N-((trans)-2-((E)-1-phenylbut-1-en-2-yl)cyclopropyl)acetamido)methyl)cyclohexyl)amino)propanoate | racemic | 585 |
| benzyl 2,2-dimethyl-3-(((trans)-4-((2,2,2-trifluoro-N-((trans)-2-((E)-1-phenylbut-1-en-2-yl)cyclopropyl)acetamido)methyl)cyclobutyl)amino)propanoate | racemic | 557 |
| ethyl 2-((6-(2,2,2-trifluoro-N-((trans)-2-((E)-1-phenylbut-1-en-2-yl)cyclopropyl)acetamido)-2-azaspiro[3.3]heptan-2-yl)methyl)thiazole-5-carboxylate | racemic | 543 |
| tert-butyl 4-((3-methyl-3-((2,2,2-trifluoro-N-((trans)-2-((E)-1-phenylbut-1-en-2-yl)cyclopropyl)acetamido)methyl)azetidin-1-yl)methyl)benzoate | racemic | 442 |

| Structure/Name | Stereochemical comment | LCMS m/z |
|---|---|---|
| methyl 4-((((trans)-3-((2,2,2-trifluoro-N-((trans)-2-((E)-1-phenylbut-1-en-2-yl)cyclopropyl)acetamido)methyl)cyclobutyl)amino)methyl)benzoate | racemic | 515 |
| methyl 5-((((trans)-3-((2,2,2-trifluoro-N-((trans)-2-((E)-1-phenylbut-1-en-2-yl)cyclopropyl)acetamido)methyl)cyclobutyl)amino)methyl)picolinate | racemic | | tert-butyl 4-((6-(2,2,2-trifluoro-N-((trans)-2-((E)-1-phenylbut-1-en-2-yl)cyclopropyl)acetamido)-2-azaspiro[3.3]heptan-2-yl)methyl)benzoate (Racemic)

2,2,2-trifluoro-N-((trans)-2-((E)-1-phenylbut-1-en-2-yl)cyclopropyl)-N-(2-azaspiro[3.3]heptan-6-yl)acetamide (67 mg, 177 µmol) was dissolved in DMF before addition of tert-butyl 4-(bromomethyl)benzoate (43.1 mg, 159 µmol) and potassium carbonate (61.0 mg, 442 µmol). The reaction mixture was stirred at room temperature for 24 h before being heated to 40° C. for 24 h. The reaction mixture was partitioned between NaHCO$_3$ (aq., sat.) and EtOAc, and the organic phase was washed successively with brine, dried with Na$_2$SO$_4$, filtered, and evaporated under reduced pressure. The crude residue was purified by column chromatography (5% to 100% EtOAc in hexanes) on silica gel to afford tert-butyl 4-((6-(2,2,2-trifluoro-N-((trans)-2-(E)-1-phenylbut-1-en-2-yl)cyclopropyl)acetamido)-2-azaspiro[3.3]heptan-2-yl)methyl)benzoate (30.0 mg, 52.7 µmol).

tert-butyl 3-(2-(2,2,2-trifluoro-N-((trans)-2-((E)-1-phenylbut-1-en-2-yl)cyclopropyl)acetamido)-7-azaspiro[3.5]nonan-7-yl)propanoate (Racemic)

2,2,2-trifluoro-N-((trans)-2-(E)-1-phenylbut-1-en-2-yl)cyclopropyl)-N-(7-azaspiro[3.5]nonan-2-yl)acetamide hydrochloride (70 mg, 158 µmol) was dissolved in THF (1.5 mL) and tert-butyl acrylate (24.2 mg, 189 µmol) was added, followed by diisopropylethylamine (54.9 µL, 316 µmol). The reaction mixture was stirred for 16 hours at room temperature. The reaction mixture was partitioned between water and EtOAc. The organics layer separated, washed with brine and concentrated to afford crude tert-butyl 3-(2-(2,2,2-trifluoro-N-((trans)-2-((E)-1-phenylbut-1-en-2-yl)cyclopropyl)acetamido)-7-azaspiro[3.5]nonan-7-yl)propanoate (90.0 mg, 168 µmol). LCMS m/z 535 [M+H$^+$]

Using the appropriate starting materials and modifications the following intermediates were synthesized following the synthetic procedures described for intermediate tert-butyl 3-(2-(2,2,2-trifluoro-N-((trans)-2-((E)-1-phenylbut-1-en-2-yl)cyclopropyl)acetamido)-7-azaspiro[3.5]nonan-7-yl)propanoate.

| Structure/Name | Stereochemical comment | LCMS m/z |
|---|---|---|
| 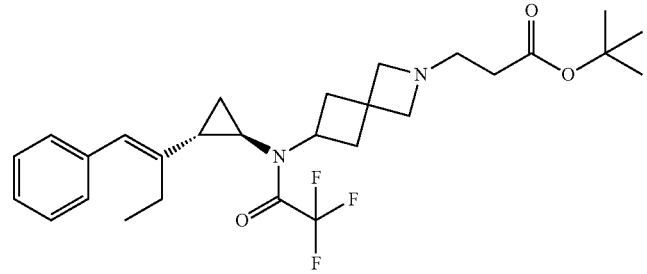<br>tert-butyl 3-(6-(2,2,2-trifluoro-N-((trans)-2-((E)-1-phenylbut-1-en-2-yl)cyclopropyl)acetamido)-2-azaspiro[3.3]heptan-2-yl)propanoate | racemic | 507 |

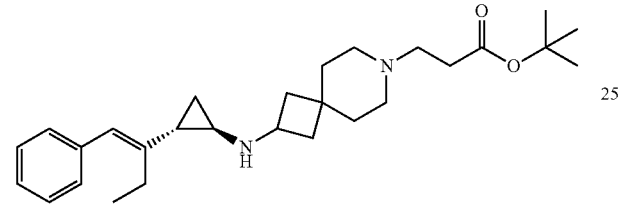

tert-butyl 3-(2-(((trans)-2-((E)-1-phenylbut-1-en-2-yl)cyclopropyl)amino)-7-azaspiro[3.5]nonan-7-yl)propanoate (Racemic)

tert-butyl 3-(2-(2,2,2-trifluoro-N-((trans)-2-((E)-1-phenylbut-1-en-2-yl)cyclopropyl)acetamido)-7-azaspiro[3.5]nonan-7-yl)propanoate (30 mg, 56.1 μmol) was dissolved in MeOH (1.5 mL) and NaOH (0.5 mL, 1M) was added. The reaction mixture was stirred for 45 min under a positive nitrogen atmosphere. The reaction mixture was partitioned between sodium bicarbonate (aq., sat.) and EtOAc. The organic layer was separated, washed with brine and evaporated under reduced pressure to afford crude tert-butyl 3-(2-(((trans)-2-((E)-1-phenylbut-1-en-2-yl)cyclopropyl)amino)-7-azaspiro[3.5]nonan-7-yl)propanoate (21.0 mg, 47.8 μmol). LCMS m/z 439 [M+H$^+$]

Using the appropriate starting materials and modifications the following intermediates were synthesized following the synthetic procedures described for intermediate tert-butyl 3-(2-(((trans)-2-((E)-1-phenylbut-1-en-2-yl)cyclopropyeamino)-7-azaspiro[3.5]nonan-7-yl)propanoate.

| Structure/Name | Stereochemical comment | LCMS m/z |
|---|---|---|
| 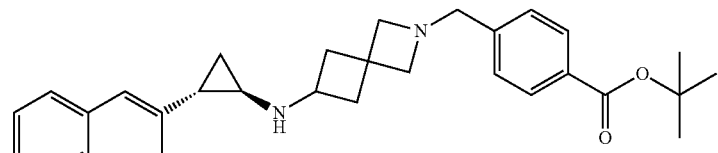<br>tert-butyl 4-((6-(((trans)-2-((E)-1-phenylbut-1-en-2-yl)cyclopropyl)amino)-2-azaspiro[3.3]heptan-2-yl)methyl)benzoate | racemic | 473 |

PREPARATIONS OF COMPOUNDS OF FORMULA 1

The compounds in the following table were synthesized from 2-((E)-styryl)cyclopropanamine hydrochloride using the General Procedure for the alkylation of cyclopropylamines with aldehydes and ketones, using the appropriate aldehyde. The compounds were purified using either preparative HPLC on a C18 column using a acetonitrile:water eluent mixture with 0.1% trifluoroacetic acid, or silica gel column chromatography, followed by salting with hydrochloric acid.

TABLE 2

| Example | Structure/Name | $^1$H-NMR | MS (M + H) |
|---|---|---|---|
| 106 | 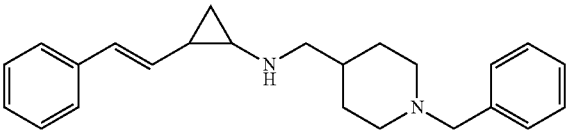<br>(E)-N-((1-benzylpiperidin-4-yl)methyl)-2-styrylcyclopropan-1-amine bis-trifluoroacetic acid salt | $^1$H NMR (400 MHz, DMSO-d6) δ 9.33-9.40 (m, 1H), 8.72-8.82 (m, 2H), 7.49 (s, 5H), 7.17-7.38 (m, 5H), 6.52-6.61 (m, 2H), 5.90-5.99 (m, 2H), 4.24-4.32 (m, 2H), 3.04-3.26 (m, 2H), 2.80-3.01 (m, 3H), 2.02-2.14 (m, 1H), 1.72-1.99 (m, 3H), 1.23-1.45 (m, 3H), 1.10-1.16 (m, 1H) | 347 |
| 113 | 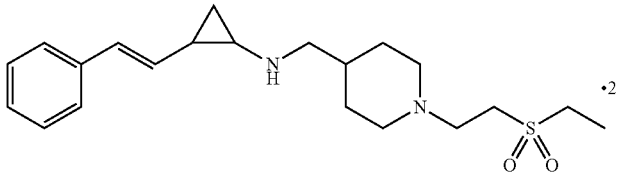<br>•2Hydrochloric acid<br>(E)-N-((1-(2-(ethylsulfonyl)ethyl)piperidin-4-yl)methyl)-2-styrylcyclopropan-1-amine dihydrochloride | $^1$H NMR (500 MHz, DMSO-d6) δ 10.97 (br. s, 1H), 9.44 (br. s, 2H), 7.25-7.39 (m, 4H), 7.17-7.23 (m, 1H), 6.56 (d, J = 16.11 Hz, 1H), 5.96 (dd, J = 8.54, 15.86 Hz, 1H), 3.66-3.99 (m, 4H), 3.54 (br. s., 2H), 3.44 (br. s., 2H), 3.21 (q, J = 7.40 Hz, 2H), 2.76-3.01 (m, 4H), 2.23 (s, 1H), 2.02 (d, J = 13.91 Hz, 2H), 1.36-1.62 (m, 3H), 1.25 (t, J = 7.44 Hz, 3H), 1.06 (s, 1H). | 377 |
| 116 | 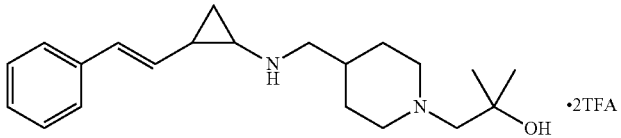<br>(E)-2-methyl-1-(4-(((2-styrylcyclopropyl)amino)methyl)piperidin-1-yl)propan-2-ol bis-trifluoroacetic acid salt | $^1$H NMR (400 MHz, DMSO-d6) δ 9.08 (br. s., 2H), 8.71-8.89 (m, 1H), 7.26-7.42 (m, 4H), 7.15-7.24 (m, 1H), 6.56 (d, J = 16.11 Hz, 1H), 5.96 (dd, J = 8.42, 15.75 Hz, 1H), 5.23 (br. s, 1H), 3.61 (d, J = 11.96 Hz, 2H), 2.72-3.34 (m, 8H), 2.04-2.15 (m, 1H), 1.89 (d, J = 12.94 Hz, 2H), 1.53-1.71 (m, 2H), 1.30-1.37 (m, 1H), 1.23 (s, 6H), 1.05-1.14 (m, 1H) | 329 |

(E)-4-((4-(((2-styrylcyclopropyl)amino)methyl)piperidin-1-yl)methyl)benzoic Acid Dihydrochloride, (101)

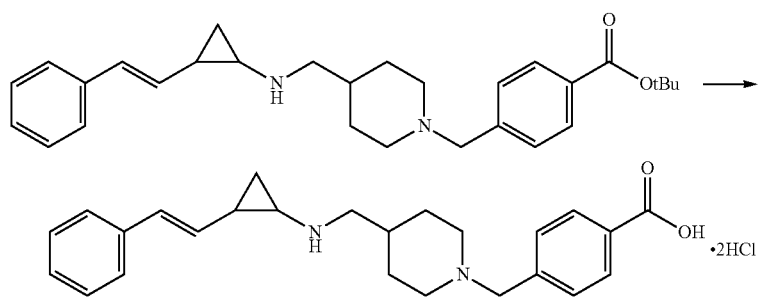

Racemic (E)-tert-butyl 4-((4-(((2-styrylcyclopropyl)amino)methyl)piperidin-1-yl)methyl)benzoate (Intermediate D) (109 mg, 244 µmol) was dissolved in 1,4-dioxane (1 mL), and 4M Hydrochloric acid in 1,4-dioxane (500 uL, 2 mmol) was added. The reaction mixture was heated to 40° C. and stirred for 15 hours. The volatiles were evaporated under reduced pressure. The material was re-dissolved in a 1:1 acetonitrile:water mixture (6 mL). The solution was frozen and lyophilized to afford (E)-4-((4-(((2-styrylcyclopropyl)amino)methyl)piperidin-1-yl)methyl)benzoic acid dihydrochloride (55.0 mg, 118 µmol) in 46% yield. $^1$H NMR (400 MHz, DMSO-d6) δ 12.98-13.24 (m, 1H), 10.46-10.74 (m, 1H), 9.11-9.52 (m, 2H), 7.99 (d, J=8.30 Hz, 2H), 7.71 (d, J=8.06 Hz, 2H), 7.25-7.39 (m, 4H), 7.14-7.25 (m, 1H), 6.55 (d, J=15.87 Hz, 1H), 5.95 (dd, J=8.55, 16.11 Hz, 1H), 4.32 (br. s., 2H), 3.34 (br. s., 2H), 3.03-3.20 (m, 1H), 2.76-2.99 (m, 4H), 2.08-2.28 (m, 1H), 1.97 (d, J=11.23 Hz, 3H), 1.48-1.66 (m, 2H), 1.35-1.45 (m, 1H), 0.98-1.10 (m, 1H). LCMS (ESI+): 391 (M+H).

The examples in the following table were prepared using the procedure described for compound 101, without purification or using preparative HPLC (acetonitrile:water+0.1% TFA) for purification.

TABLE 3

| Example | Structure/Name | 1H-NMR | Mass Spec. (M + H) |
|---|---|---|---|
| 105 | 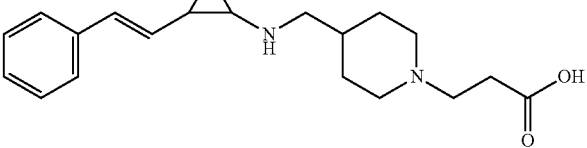<br>(E)-3-(4-(((2-styrylcyclopropyl)amino)methyl)piperidin-1-yl)propanoic acid | $^1$H NMR (400 MHz, DMSO-d6) δ 12.46-12.93 (m, 1H), 10.07-10.31 (m, 1H), 9.34 (br. s., 2H), 7.83-8.05 (m, 1H), 7.25-7.39 (m, 4H), 7.17-7.23 (m, 1H), 6.56 (d, J = 15.87 Hz, 1H), 5.96 (dd, J = 8.42, 15.75 Hz, 1H), 3.48 (d, J = 12.70 Hz, 2H), 3.23 (br. s., 3H), 2.76-3.00 (m, 5H), 2.15-2.27 (m, 1H), 1.77-2.06 (m, 3H), 1.29-1.63 (m, 3H), 0.99-1.11 (m, 1H) | 329 (M + H) |
| 111 | 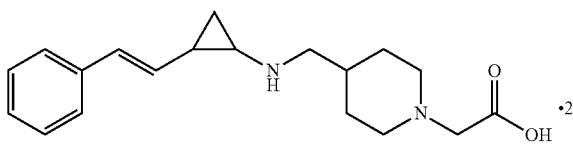<br>(E)-3-(4-(((2-styrylcyclopropyl)amino)methyl)piperidin-1-yl)acetic acid | $^1$H NMR (500 MHz, DMSO-d6) δ 13.05 (br. s, 1H), 8.99 (s, 2H), 7.26-7.44 (m, 4H), 7.15-7.24 (m, 1H), 6.56 (d, J = 15.87 Hz, 1H), 5.96 (dd, J = 8.42, 15.74 Hz, 1H), 3.93-4.03 (m, 2H), 3.36-3.51 (m, 3H), 2.92-3.04 (m, 4H), 2.81-2.90 (m, 1H), 2.02-2.13 (m, 1H), 1.82-1.97 (m, 3H), 1.43-1.61 (m, 2H), 1.24-1.36 (m, 1H), 1.04-1.13 (m, 1H) | 315 (M + H) |

TABLE 3-continued

| Example | Structure/Name | 1H-NMR | Mass Spec. (M + H) |
|---|---|---|---|
| 107 | 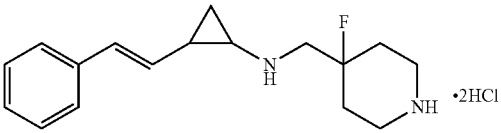 [SMILES: FC1(CNC2CC2/C=C/c2ccccc2)CCNCC1]<br>(E)-N-((4-fluoropiperidin-4-yl)methyl)-2-styrylcyclopropan-1-amine | ¹H NMR (400 MHz, DMSO-d6) δ 9.47-9.93 (m, 2H), 8.65-9.04 (m, 2H), 7.43 (d, J = 7.32 Hz, 2H), 7.34 (t, J = 7.69 Hz, 2H), 7.16-7.27 (m, 1H), 5.97 (d, J = 39.90 Hz, 1H), 3.25 (d, J = 12.70 Hz, 2H), 3.10 (br. s., 1H), 2.99 (br. s., 2H), 2.74-2.90 (m, 2H), 2.55 (d, J = 9.28 Hz, 1H), 2.06 (br. s., 1H), 1.95 (d, J = 12.94 Hz, 2H), 1.52-1.63 (m, 1H), 1.36-1.50 (m, 2H), 1.25-1.34 (m, 1H). | 275 (M + H) |

2-((E)-1-phenylprop-1-en-2-yl)cyclopropanamine Trifluoroacetic Acid Salt, (102)

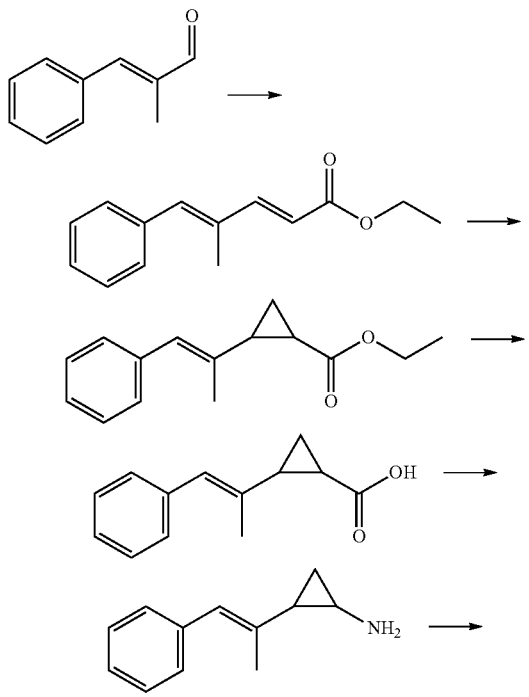

-continued

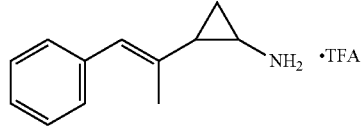

Step 1: (2E,4E)-ethyl 4-methyl-5-phenylpenta-2,4-dienoate

Under a nitrogen atmosphere, alpha-methyl-trans-cinnamaldehyde (5.23 g, 35.7 mmol) was dissolved in toluene (75 mL), ethyl 2-(triphenylphosphoranylidene)acetate (12.0 g, 34.6 mmol) was added in one portion the reaction mixture was stirred vigorously at 25° C. for 15 minutes. The reaction mixture was heated at 100° C. for 4 hours. The reaction mixture was concentrated under reduced pressure. The crude product was redissolved in MTBE (40 mL) and filtered under suction over a 5 cm pad of silica. The silica cake was washed with MTBE. The solvent was evaporated under reduced pressure. The crude material was purified by silica gel column chromatography (5% to 25% Ethyl acetate in hexanes). The pure fractions were evaporated to afford (2E,4E)-ethyl 4-methyl-5-phenylpenta-2,4-dienoate (5.50 g, 25.4 mmol) in 71% yield. LCMS (EST+):217 (M+H)

Step 2: (E)-ethyl 2-(1-phenylprop-1-en-2-yl)cyclopropanecarboxylate

Under a nitrogen atmosphere, sodium hydride, (60% in oil, 798 mg, 20.0 mmol) was dissolved with DMSO (72 mL)

(caution! Hydrogen gas evolution) and stirred 15 minutes at 25° C. Trimethylsulfoxonium iodide (4.57 g, 24.2 mmol) was added and stirred 45 minutes at 25° C. (2E,4E)-ethyl 4-methyl-5-phenylpenta-2,4-dienoate (5.24 g, 16.0 mmol) in 36 mL DMSO added. The reaction mixture was stirred at 40° C. for 16 hours. The reaction mixture was quenched with saturated aqueous ammonium chloride (250 mL) and brine (50 mL) with a water bath present to act as a heat sink. The mixture was extracted with hexanes (500 mL). The organic layer was isolated and evaporated under reduced pressure. The crude residue was taken up in MTBE and filtered under suction on a 5 cm pad of silica. The silica gel cake was washed with MTBE. The filtrate was evaporated under reduced pressure, and the residue was placed under high vacuum for 15 minutes to afford (E)-ethyl 2-(1-phenylprop-1-en-2-yl)cyclopropanecarboxylate (4.41 g, 19.1 mmol) in 79% yield. $^1$H NMR (400 MHz, DMSO-d6) δ 7.30-7.37 (m, 2H), 7.11-7.28 (m, 3H), 6.44 (s, 1H), 3.99-4.15 (m, 2H), 2.05-2.14 (m, 1H), 1.80-1.90 (m, 1H), 1.30 (ddd, J=4.39, 6.71, 8.42 Hz, 1H), 1.14-1.26 (m, 4H). LC-MS (ESI+):231 (M+H).

Step 3: 2-((E)-1-phenylprop-1-en-2-yl)cyclopropanecarboxylic Acid

Ethyl 2-((E)-1-phenylprop-1-en-2-yl)cyclopropanecarboxylate (4.41 g, 19.1 mmol) was dissolved in THF (40 mL) and methanol (10 mL). Sodium hydroxide (6M aqueous) was added (6 mL, 36 mmol) and the reaction mixture was stirred at 50° C. for 3 hours. The reaction mixture was cooled to 0° C. acidified to pH 2 using Hydrochloric acid (1M aqueous). Reaction mixture was partitioned between brine and Ethyl acetate. The organic layer was washed with brine, dried with $Na_2SO_4$, filtered, and evaporated under reduced pressure to afford 2-((E)-1-phenylprop-1-en-2-yl)cyclopropanecarboxylic acid (3.49 g, 17.2 mmol) in 90% yield. LCMS (ESI+): 203 (M+H).

Step 4:
2-(E)-1-phenylprop-1-en-2-yl)cyclopropanamine 2-((E)-1-phenylprop-1-en-2-yl)cyclopropanecarboxylic acid (3.49 g, 17.2 mmol) was dissolved in THF (85 mL), mixed with triethylamine (5.97 mL, 42.9 mmol), and the solution was then cooled to 0° C. The solution was mixed with ethyl chloroformate (2.51 g, 23.2 mmol) under vigorous stirring, and the reaction mixture was stirred at 0° C. for 0.5 hour. A solution of sodium azide (5.58 g, 85.9 mmol) dissolved in water (40 mL) was added and the reaction mixture was stirred at 0° C. for one hour. The reaction mixture was diluted with water and extracted with Ethyl acetate. The organic extracts were washed with brine, dried with sodium sulphate and evaporated under reduced pressure. The crude residue was placed under high vacuum for 15 minutes. The residue was taken up in 3 ml of toluene, and the solution is heated to reflux for 2 hours. The reaction mixture was cooled down to 25° C. Potassium trimethylsilanolate (4.41 g, 34.4 mmol) was added to the reaction mixture and stirred for 1.5 hour. The mixture was quenched with Hydrochloric acid (2M aqueous, 40 mL, 80 mmol), and stirred vigorsously for one hour. The volume of organics was increased to 250 mL with MTBE. Hydrochloric acid (2M aqueous) was added (250 mL), and the layers were separated. The organic layer was extracted twice with Hydrochloric acid (2M aqueous) (2×300 mL), and the aqueous extracts were combined. The aqueous layer was basified to pH 10-11 using sodium hydroxide (6M), at which point the mixture becomes cloudy. The Aqueous layer was extracted with DCM (2×500 mL).

The organic extracts were washed with brine, dried with $Na_2SO_4$, filtered and evaporated under reduced pressure. The crude residue was purified using silica gel chromatography, using a 1:10:90 $NH_4OH$ (30% aq.):methanol:DCM mixture as the eluent. The pure fractions were evaporated to afford racemic 2-((E)-1-phenylprop-1-en-2-yl)cyclopropanamine (1.88 g, 10.8 mmol) in 63% yield. LCMS (ESI+): 174 (M+H)/157 (M–NH2)+

Step 5: 2-((E)-1-phenylprop-1-en-2-yl)cyclopropanamine Trifluoroacetic Acid Salt Part of 2-((E)-1-phenylprop-1-en-2-yl)cyclopropanamine (15 mg) was re-purified using preparative HPLC using an acetonitrile:water+0.1% trifluoroacetic acid eluent mixture to afford 2-((E)-1-phenylprop-1-en-2-yl)cyclopropanamine trifluoroacetic acid salt (1.5 mg, 0.0052 mmol). LCMS (ESI+):174 (M+H)

Racemic-2-((E)-1-phenylprop-1-en-2-yl)-N-(piperidin-4-ylmethyl)cyclopropanamine Dihydrochloride (103)

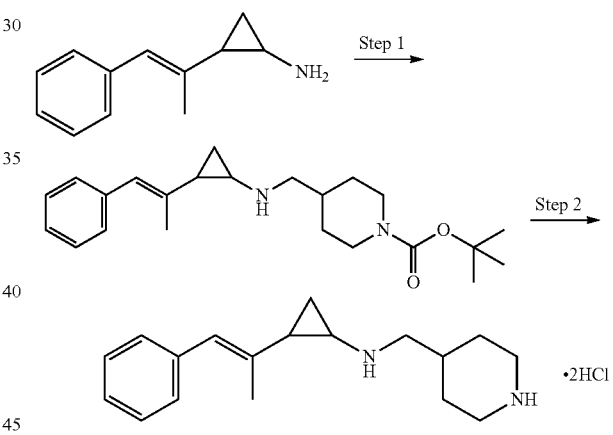

Step 1: racemic tert-butyl 4-(((2-((E)-1-phenylprop-1-en-2-yl)cyclopropyl)amino)methyl)piperidine-1-carboxylate (Z)-2-(1-phenylprop-1-en-2-yl)cyclopropanamine (419 mg, 2.41 mmol) and tert-butyl 4-formylpiperidine-1-carboxylate (486 mg, 2.28 mmol) were in 1,2-DCE (10 mL) at 25° C. To the stirred mixture was added Sodium (triacetoxy) borohydride (34 mg, 0.161 mmol). After 30 min stirring at 25° C., DCM (10 mL) and 1 M potassium carbonate (20 mL) were added to the reaction mixture. The mixture was stirred for 5 minutes, and the aqueous and organic layers were separated. The aqueous layer was extracted once with DCM (10 mL). The combined organic phases were washed with brine and evaporated under reduced pressure; and the crude residue was purified using silica gel column chromatography (0% to 10% Methanol in Ethyl acetate) to afford tert-butyl 4-(((2-((E)-1-phenylprop-1-en-2-yl)cyclopropyl)amino) methyl)piperidine-1-carboxylate (514 mg, 1.38 mmol) in 58% yield. LCMS (ESI+): 371 (M+H).

Step 2: racemic-2-(E)-1-phenylprop-1-en-2-yl)-N-(piperidin-4-ylmethyl)cyclopropanamine Dihydrochloride

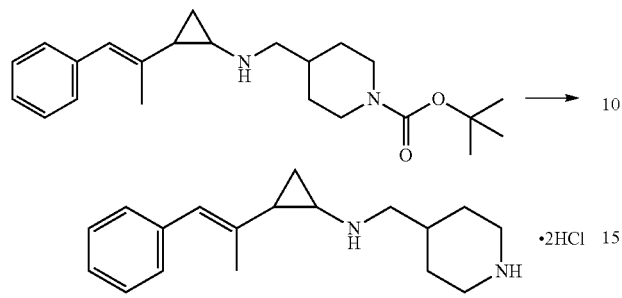

Racemic tert-butyl 4-((2-((E)-1-phenylprop-1-en-2-yl)cyclopropyl)amino)methyl)piperidine-1-carboxylate (24 mg, 0.065 µmol) was dissolved in 1,4-dioxane (2 mL) and Hydrochloric acid (4M in 1,4-dioxane, 130 uL, 0.520 mmol) was added. The reaction mixture was stirred for 2 hours at 50° C. After cooling to 25° C., MTBE (2 mL) was added, stirred for 5 minutes and the volatiles were evaporated under reduced pressure. The solid residue was triturated with MTBE (2×5 mL). The product was redissolved in a 1:1 Acetonitrile:water (1:1) mixture. The solution was frozen to −78° C. and lyophilized to afford racemic-2-((E)-1-phenylprop-1-en-2-yl)-N-(piperidin-4-ylmethyl)cyclopropanamine dihydrochloride (9.30 mg, 27.0 µmol) in 42% yield. $^1$H NMR (400 MHz, DMSO-d6) δ 9.54 (d, J=4.88 Hz, 2H), 8.98 (br. s., 1H), 8.85 (br. s., 1H), 7.28-7.41 (m, 2H), 7.10-7.26 (m, 3H), 6.36 (s, 1H), 3.16-3.30 (m, 2H), 2.91-3.02 (m, 2H), 2.72-2.89 (m, 3H), 2.16-2.28 (m, 1H), 2.02-2.09 (m, 1H), 1.96 (d, J=13.92 Hz, 2H), 1.79 (s, 3H), 1.30-1.52 (m, 3H), 1.12-1.20 (m, 1H). LCMS (ESI+):271 (M+H).

Procedure for the Separation of Enantiomers

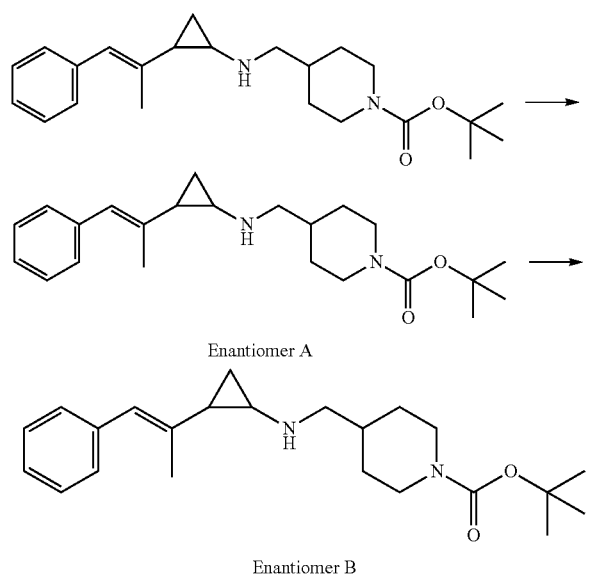

The enantiomers of tert-butyl 4-(((2-((E)-1-phenylprop-1-en-2-yl)cyclopropyl)amino)methyl)piperidine-1-carboxylate (490 mg) were separated using a chiral preparative SFC method with the following conditions.

Column: 2.1×25.0 cm Chiralpak AD-H from Chiral Technologies; CO$_2$ Co-solvent: Methanol with 0.25% Isopropylamine; Isocratic Method, 12% Co-solvent at 82 g/min; System Pressure: 120 bar Column Temperature 25° C.; Sample Diluent:Methanol. The first eluting fractions were evaporated to afford enantiomer A of tert-butyl 4-(((2-((E)-1-phenylprop-1-en-2-yl)cyclopropyl)amino)methyl)piperidine-1-carboxylate (143 mg).

The second eluting fractions were evaporated to afford enantiomer B of tert-butyl 4-(((2-((E)-1-phenylprop-1-en-2-yl)cyclopropyl)amino)methyl)piperidine-1-carboxylate (150 mg).

2-((E)-1-phenylprop-1-en-2-yl)-N-(piperidin-4-ylmethyl)cyclopropanamine Dihydrochloride, Enantiomer A

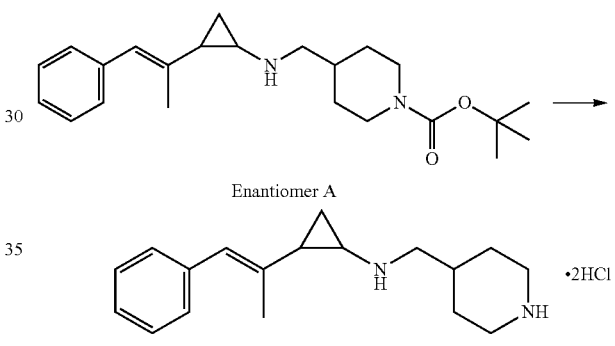

tert-butyl 4-(((2-((E)-1-phenylprop-1-en-2-yl)cyclopropyl)amino)methyl)piperidine-1-carboxylate, enantiomer A (143 mg, 0.385 mmol) was dissolved in 1,4-dioxane, Hydrochloric acid 4M in 1,4-dioxane (505 µL, 2.02 mmol) was added. Stirred at 50° C. for 16 hours. Reaction mixture dumped in MTBE 10 mL, stirred filtered on a fine fritted funnel. Washed with MTBE. Taken up in water (10 mL) and the solution was filtered on a hydrophilic 0.45 um filter. The solution was frozen and lyophilized for 24 hours. The solid was gently milled with a mortar and pestle to afford 2-((E)-1-phenylprop-1-en-2-yl)-N-(piperidin-4-ylmethyl)cyclopropanamine dihydrochloride, enantiomer A (65.0 mg, 189 µmol) in 47% yield. $^1$H NMR (400 MHz, DMSO-d6) δ 9.38 (br. s., 2H), 8.84 (br. s., 1H), 8.60-8.73 (m, 1H), 7.29-7.38 (m, 2H), 7.17-7.27 (m, 3H), 6.37 (s, 1H), 3.28 (d, J=12.94 Hz, 2H), 2.93-3.03 (m, 2H), 2.78-2.92 (m, 3H), 2.21 (br. s., 1H), 2.05 (br. s., 1H), 1.95 (d, J=15.38 Hz, 2H), 1.78 (s, 3H), 1.30-1.49 (m, 3H), 1.15-1.23 (m, 1H). LCMS (ESI+): 271 (M+H).

2-((E)-1-phenylprop-1-en-2-yl)-N-(piperidin-4-ylmethyl)cyclopropanamine Dihydrochloride, Enantiomer B

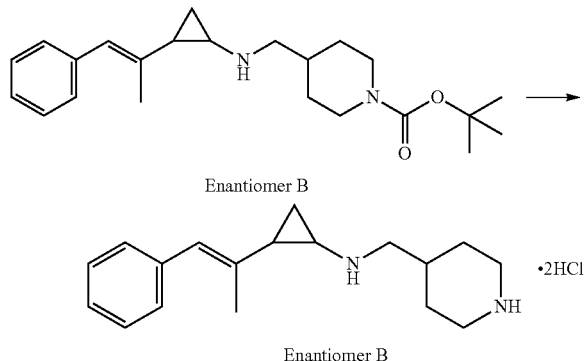

Enantiomer B

Enantiomer B

Tert-butyl 4-(((2-((E)-1-phenylprop-1-en-2-yl)cyclopropyl)amino)methyl)piperidine-1-carboxylate, enantiomer B (150 mg, 404 µmol) was dissolved in 1,4-dioxane, Hydrochloric acid 4M in 1,4-dioxane (505 µL, 2.02 mmol) was added. Stirred at 50° C. for 16 hours. Reaction mixture dumped in MTBE 10 mL, stirred filtered on a fine fritted funnel. Washed with MTBE. Taken up in water (10 mL) and the solution was filtered on a hydrophilic 0.45 um filter. The solution was frozen and lyophilized for 24 hours. The solid was gently milled with a mortar and pestle to afford 2-((E)-1-phenylprop-1-en-2-yl)-N-(piperidin-4-ylmethyl)cyclopropanamine dihydrochloride, enantiomer B (86 mg, 250 µmol) in 62% yield. $^1$H NMR (400 MHz, DMSO-d6) δ 9.38 (br. s., 2H), 8.84 (br. s., 1H), 8.60-8.73 (m, 1H), 7.29-7.38 (m, 2H), 7.17-7.27 (m, 3H), 6.37 (s, 1H), 3.28 (d, J=12.94 Hz, 2H), 2.93-3.03 (m, 2H), 2.78-2.92 (m, 3H), 2.21 (br. s., 1H), 2.05 (br. s., 1H), 1.95 (d, J=15.38 Hz, 2H), 1.78 (s, 3H), 1.30-1.49 (m, 3H), 1.15-1.23 (m, 1H). LCMS (ESI+): 271 (M+H).

N-((4-fluoropiperidin-4-yl)methyl)-2-((E)-1-phenylprop-1-en-2-yl)cyclopropanamine Dihydrochloride (107)

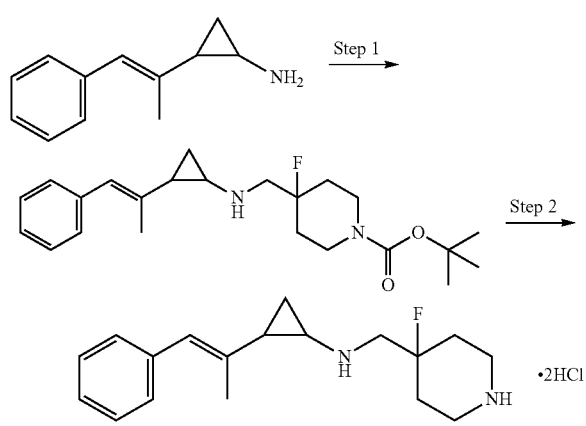

Step 1 tert-butyl (E)-4-fluoro-4-(((2-(1-phenylprop-1-en-2-yl)cyclopropyl)amino)methyl)piperidine-1-carboxylate was synthesized according to the General Procedure for the alkylation of cyclopropylamines with aldehydes and ketones, using tert-butyl 4-fluoro-4-formylpiperidine-1-carboxylate. Purification on silica gel (0% to 10% Methanol in EtOAc) was used. LCMS:389 (M+H)

Step 2

Racemic tert-butyl (E)-4-fluoro-4-(((2-(1-phenylprop-1-en-2-yl)cyclopropyl)amino)methyl)piperidine-1-carboxylate was dissolved in 1,4-dioxane (1 mL) and hydrochloric acid (4M in 1,4-dioxane, 1 mL, 4 mmol) was added. The reaction mixture was stirred at 40° C. for 16 hour. The volatiles were evaporated under reduced pressure, and the solid was triturated with MTBE (5 mL). The solid was re-dissolved in acetonitrile and water (1:1), frozen and lyophilized to afford (E)-N-((4-fluoropiperidin-4-yl)methyl)-2-(1-phenylprop-1-en-2-yl)cyclopropan-1-amine dihydrochloride in 34% yield over 2 steps. $^1$H NMR (400 MHz, DMSO-d6) δ 9.67 (br. s., 2H), 9.21 (br. s., 2H), 7.31-7.41 (m, 2H), 7.14-7.27 (m, 2H), 6.36 (s, 1H), 3.54-3.57 (m, 1H), 3.37-3.53 (m, 3H), 3.19-3.34 (m, 2H), 2.81-3.06 (m, 3H), 1.91-2.35 (m, 4H), 1.78 (s, 3H), 1.41 (dd, J=4.64, 9.52 Hz, 1H), 1.12-1.23 (m, 1H) LCMS (EST+):289 (M+H).

N-(2-((E)-1-phenylprop-1-en-2-yl)cyclopropyl)piperidin-4-amine Dihydrochloride (123)

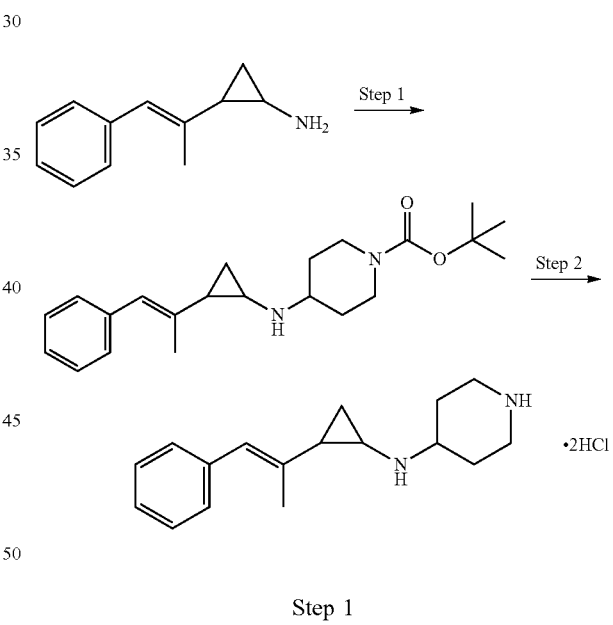

Step 1

Tert-butyl (E)-4-((2-(1-phenylprop-1-en-2-yl)cyclopropyl)amino)piperidine-1-carboxylate was obtained according to the General Procedure for the alkylation of cyclopropylamines with aldehydes and ketones, using tert-butyl 4-oxopiperidine-1-carboxylate. Purification on silica gel (0% to 10% Methanol in EtOAc) was used. LCMS: 357 (M+H)

Step 2

Tert-butyl (E)-4-((2-(1-phenylprop-1-en-2-yl)cyclopropyl)amino)piperidine-1-carboxylate was dissolved in 1,4-dioxane (1 mL) and hydrochloric acid (4M in 1,4-dioxane, 1 mL, 4 mmol) was added. The reaction mixture was stirred at 40° C. for 16 hour. The volatiles were evaporated under reduced pressure, and the solid was triturated with MTBE (5 mL). The solid was re-dissolved in acetonitrile and water (1:1), frozen and lyophilized to afford Racemic N-(2-(E)-1-phenylprop-1-en-2-yl)cyclopropyl)piperidin-4-amine dihydrochloride in 51% yield over 2 steps. ¹H NMR (400 MHz, DMSO-d6) δ 9.77 (br. s., 2H), 9.02 (br. s., 1H), 8.86 (br. s., 1H), 7.30-7.40 (m, 2H), 7.08-7.29 (m, 3H), 6.37 (s, 1H), 3.34-3.52 (m, 2H), 2.75-3.02 (m, 3H), 2.06-2.36 (m, 3H), 1.79-1.97 (m, 2H), 1.76 (s, 3H), 1.44-1.63 (m, 1H), 1.27-1.40 (m, 1H), 1.05-1.27 (m, 1H). LCMS (ESI+): 257 (M+H).

N-(cyclopropylmethyl)-2-((E)-1-phenylprop-1-en-2-yl)cyclopropanamine Hydrochloride (117)

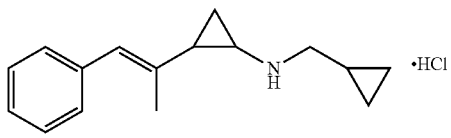 [SMILES: C/C(=C\c1ccccc1)C1CC1NCC1CC1 ; Cl]

To racemic 2-((E)-1-phenylprop-1-en-2-yl)cyclopropanamine (99 mg, 571 μmol) and cyclopropanecarbaldehyde (39.6 mg, 565 μmol) in DCE (4 mL) was added the sodium (triacetoxy)borohydride (241 mg, 1.14 mmol). After 30 min, DCM and 1 M potassium carbonate were added to the reaction mixture. The organic phase was evaporated and the crude residue purified by column chromatography (silica, 0% to 10% Methanol in Ethyl acetate). The isolated material was redissolved in acetonitrile:water and Hydrochloric acid (2M aq., 300 uL, 600 μmol)) was added. The solution was frozen and lyophilized to afford racemic N-(cyclopropylmethyl)-2-(E)-1-phenylprop-1-en-2-yl)cyclopropanamine hydrochloride (30.0 mg, 113 μmol) in 20% yield. ¹H NMR (400 MHz, DMSO-d6) δ 9.09-9.48 (m, 2H), 7.29-7.39 (m, 2H), 7.09-7.27 (m, 3H), 6.36 (s, 1H), 2.76-2.98 (m, 3H), 2.14 (br. s., 1H), 1.75 (s, 3H), 1.25-1.35 (m, 1H), 1.15-1.23 (m, 1H), 1.02-1.15 (m, 1H), 0.49-0.66 (m, 2H), 0.38 (q, J=4.48 Hz, 2H). LCMS (ESI+): 228.2 (M+H)

(E)-N1-(2-(1-phenylprop-1-en-2-yl)cyclopropyl)cyclohexane-1,4-diamine Dihydrochloride Diastereomer 1 (109) and Diastereomer 2 (110)

Step 1: racemic tert-butyl (E)-(4-((2-(1-phenylprop-1-en-2-yl)cyclopropyl)amino)cyclohexyl)carbamate (Diastereomer 1) and Racemic tert-butyl (E)-(4-((2-(1-phenylprop-1-en-2-yl)cyclopropyl)amino)cyclohexyl)carbamate (Diastereomer 2)

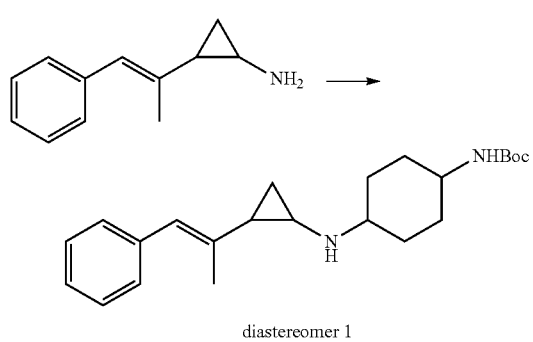

diastereomer 1

-continued

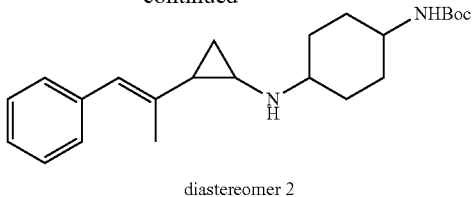

diastereomer 2

To the (E)-2-(1-phenylprop-1-en-2-yl)cyclopropanamine hydrochloride (135 mg, 643 μmol) and tert-butyl (4-oxocyclohexyl)carbamate (137 mg, 643 μmol) in 4 mL of DCE was added the Sodium (triacetoxy)borohydride (271 mg, 1.28 mmol). After 30 min stirring at 25° C., DCM (5 mL) and 1 M potassium carbonate (10 mL) were added to the reaction mixture. The mixture was stirred for 5 minutes, and the aqueous and organic layers were separated. The aqueous layer was extracted once with DCM (10 mL). The combined organic phase were washed with brine and evaporated under reduced pressure; and the crude residue was purified using silica gel column chromatography to afford two sets of fractions containing isomeric compounds. The early eluting fractions were evaporated under reduced pressure to afford racemic tert-butyl (E)-(4-((2-(1-phenylprop-1-en-2-yl)cyclopropyl)amino)cyclohexyl)carbamate (diastereomer 1) (45.0 mg, 121 μmol) (19% yield). The late eluting fractions were evaporated to afford racemic tert-butyl (E)-(4-((2-(1-phenylprop-1-en-2-yl)cyclopropyl)amino)cyclohexyl)carbamate (diastereomer 2) (95.0 mg, 256 μmol) (40% yield).

Step 2: (E)-N1-(2-(1-phenylprop-1-en-2-yl)cyclopropyl)cyclohexane-1,4-diamine Dihydrochloride (109)

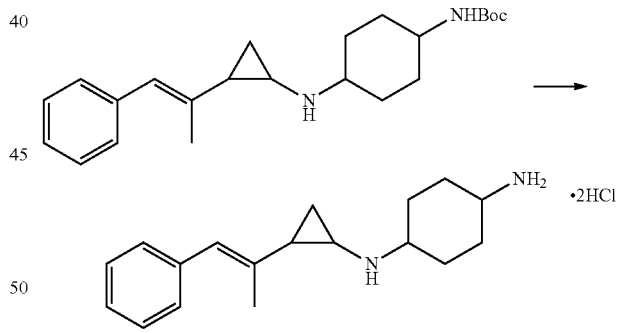

Racemic tert-butyl (E)-(4-((2-(1-phenylprop-1-en-2-yl)cyclopropyl)amino)cyclohexyl)carbamate (diastereomer 1) (45 mg, 121 μmol) was dissolved in 1,4-dioxane (2 mL). Hydrochloric acid 4M in 1,4-dioxane (121 uL, 0.484 mmol) was added, reaction vessel was sealed and heated at 40° C. for 12 hours. Evaporated, triturated with MTBE, filtered on a Fine Fritted funnel. The solid cake was redissolved in acetonitrile:water (1:1); solution filtered on a 0.45 uM PTFE filter, frozen, lyophilized to afford racemic (E)-N1-(2-(1-phenylprop-1-en-2-yl)cyclopropyl)cyclohexane-1,4-diamine dihydrochloride (36.0 mg, 104 μmol) in 87% yield. ¹H NMR (500 MHz, DMSO-d6) δ 9.47 (br. s., 2H), 8.18 (br. s., 3H), 7.29-7.37 (m, 2H), 7.15-7.26 (m, 3H), 6.36 (s, 1H), 3.18-3.32 (m, 2H), 2.85-2.94 (m, 1H), 2.19-2.27 (m, 1H), 1.94-2.05 (m, 2H), 1.83-1.94 (m, 4H), 1.76 (s, 3H), 1.64-1.76 (m, 2H), 1.31-1.41 (m, 1H), 1.12-1.27 (m, 1H). LCMS (ESI+): 271 (M+H).

(E)-N1-(2-(1-phenylprop-1-en-2-yl)cyclopropyl)cyclohexane-1,4-diamine (110)

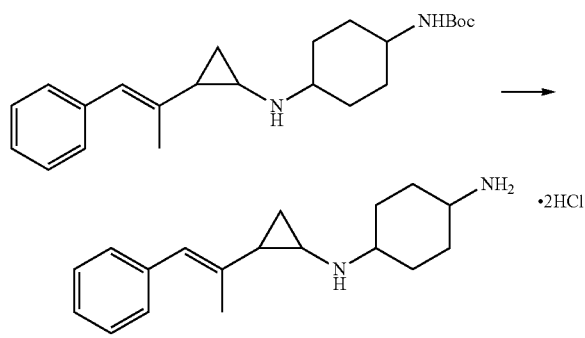

Racemic tert-butyl (E)-(4-((2-(1-phenylprop-1-en-2-yl)cyclopropyl)amino)cyclohexyl)carbamate (diastereomer 2) (95 mg, 256 µmol) was dissolved in 1,4-dioxane (2 mL). Hydrochloric acid (4M in 1,4-dioxane, 510 uL, 2.04 mmol) was added, reaction vessel sealed and the reaction mixture was heated at 50° C. for 24 hours. The volatiles were evaporated under reduced pressure, the crude residue was triturated with MTBE, filtered on a Fine Fritted funnel. The solid cake was redissolved in acetonitrile:water (1:1); solution filtered on a 0.45 uM PTFE filter, frozen, lyophilized to afford racemic (E)-N1-(2-(1-phenylprop-1-en-2-yl)cyclopropyl)cyclohexane-1,4-diamine (77.0 mg, 224 µmol) in 88% yield. $^1$H-NMR: (500 MHz, DMSO-d6) δ 9.45 (br. s., 2H), 8.06 (br. s., 3H), 7.30-7.36 (m, 2H), 7.19-7.25 (m, 3H), 6.36 (s, 1H), 3.06-3.17 (m, 1H), 2.91-3.04 (m, 1H), 2.79-2.88 (m, 1H), 2.11-2.24 (m, 3H), 1.98-2.09 (m, 2H), 1.75 (s, 3H), 1.07-1.58 (m, 6H). LCMS (ESI+): 271 (M+H)

((E)-1-phenylprop-1-en-2-yl)cyclopropanamine Trifluoroacetic Acid Salt (104)

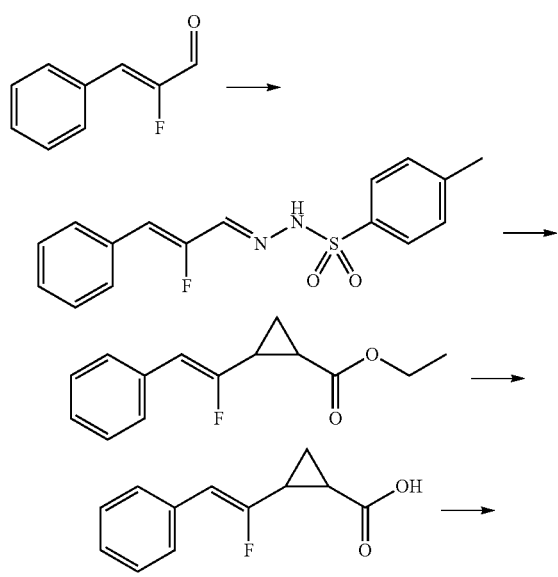

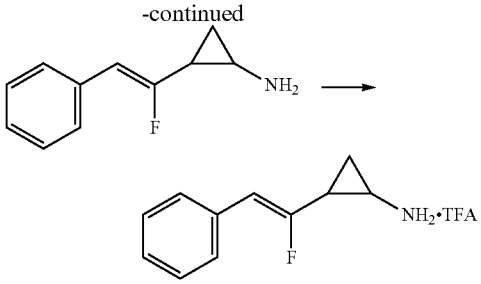

Step 1

A round bottom flask was charged with (Z)-2-fluoro-3-phenylacrylaldehyde (1.1 g, 7.32 mmol), a stirbar, and methanol (72 mL) before the addition of 4-methylbenzenesulfonohydrazide (1.36 g, 7.32 mmol). The reaction mixture was stirred at room temperature for 20 minutes. The white solid material was filtered on a paper filter under suction, washed with hexanes, dried under suction and collected to afford (E)-N'—((Z)-2-fluoro-3-phenylallylidene)-4-methylbenzenesulfonohydrazide (2.15 g, 6.75 mmol) in 96% yield. LCMS (ESI+): 319 (M+H).

Step 2

A round bottom flask was charged with (E)-N'—((Z)-2-fluoro-3-phenylallylidene)-4-methylbenzenesulfonohydrazide (2.15 g, 6.75 mmol), a stirbar, and 1,4-dioxane (60 mL, 0.11 M) before the addition of potassium carbonate (1.49 g, 10.8 mmol) and methyl acrylate (6.16 mL, 68.1 mmol). The reaction mixture was stirred at 110° C. for 16 hours. The mixture was cooled to 25° C., evaporated under reduced pressure, diluted with MTBE, and filtered on a pad of celite. The filter cake was washed with MTBE. The filtrate was evaporated under reduced pressure. The crude residue was purified by column chromatography (silica 24 g, 0% to 50% to Ethyl acetate in hexanes). Pure fractions were evaporated under reduced pressure to afford racemic-(Z)-methyl 2-(1-fluoro-2-phenylvinyl)cyclopropanecarboxylate (378 mg, 1.71 mmol) as a mixture of cis and trans isomers in 25% yield. LCMS (ESI+): 235 (M+H).

Step 3

(Z)-methyl 2-(1-fluoro-2-phenylvinyl)cyclopropanecarboxylate (378 mg, 1.71 mmol) dissolved in THF (3 mL) and methanol (1 mL). Sodium hydroxide 6M aqueous was added (1.7 mL, 10.2 mmol), and the reaction mixture was stirred for 1 hour at 50° C. The reaction mixture was acidified to pH 2 using Hydrochloric acid (1M aqueous). Reaction mixture was partitioned between brine and Ethyl acetate. Organic layer was washed with brine, dried with Na$_2$SO$_4$, filtered, evaporated under reduced pressure to afford racemic-(Z)-2-(1-fluoro-2-phenylvinyl)cyclopropanecarboxylic acid as a cis trans mixture (418 mg, 2.02 mmol). LCMS (ESI+): 207 (M+H).

Step 4

(Z)-2-(1-fluoro-2-phenylvinyl)cyclopropanecarboxylic acid (418 mg, 2.02 mmol) was dissolved in THF (20 mL), mixed with Triethylamine (703 uL, 5.05 mmol), and the solution was then cooled to 0° C. The solution was mixed with ethyl chloroformate (295 mg, 2.72 mmol) under vigorous stirring, and the reaction mixture was stirred at 0° C. for 0.5 hour. A solution of sodium azide (656 mg, 10.1 mmol) dissolved in 5 mL of water was added and the reaction mixture was stirred at 0° C. for one hour. The reaction mixture was diluted with water and extracted with Ethyl acetate. The organic extracts were washed with brine, dried with sodium sulphate and evaporated under reduced pressure. The crude residue was placed under high vacuum for 15 minutes. The residue was taken up in 3 nil of toluene, and the solution is heated to reflux for 2 hours. The reaction mixture was cooled down to 25° C. Potassium trimethylsilanolate (4.41 g, 34.4 mmol) was added to the reaction mixture and stirred for 1.5 hour. The mixture was quenched with Hydrochloric acid (2M aqueous, 10 mL, 20 mmol), and stirred vigorously for one hour. The volume of organics was increased to 50 mL with MTBE.

The organic and aqueous layers were separated. The aqueous layer was basified to pH 10-11 using sodium hydroxide (6M), at which point the mixture became cloudy. The Aqueous layer was extracted with DCM (2×50 mL). The organic extracts were washed with brine, dried with $Na_2SO_4$, filtered and evaporated under reduced pressure. The crude residue was purified using silica gel chromatography, using a 1:10:90 $NH_4OH$ (aq.):methanol:DCM mixture as the eluent. Pure fractions were evaporated to afford racemic 2-((Z)-1-fluoro-2-phenylvinyl)cyclopropanamine (116 mg, 542 μmol) in 27% yield. LCMS (ESI+): 178 (M+H).

Step 5

25 mg of 2-((E)-1-phenylprop-1-en-2-yl)cyclopropanamine was re-purified using preparative HPLC (acetonitrile:water+0.1% TFA) to afford 3.2 mg of ((E)-1-phenylprop-1-en-2-yl)cyclopropanamine trifluoroacetic acid salt. $^1$H NMR (400 MHz, DMSO-d6) δ 8.34 (br. s., 3H), 7.39-7.46 (m, 2H), 7.31-7.38 (m, 2H), 7.19-7.30 (m, 1H), 5.83-6.05 (m, 1H), 2.87-3.03 (m, 1H), 2.08-2.25 (m, 1H), 1.16-1.39 (m, 2H). LCMS (ESI+): 178 (M+H).

Racemic 2-((Z)-1-fluoro-2-phenylvinyl)-N-(piperidin-4-ylmethyl)cyclopropanamine Dihydrochloride (108)

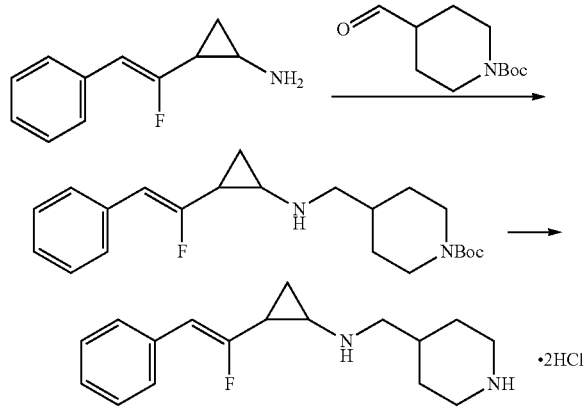

Step 1

To racemic (Z)-2-(1-fluoro-2-phenylvinyl)cyclopropanamine hydrochloride (56 mg, 262 μmol) and (Z)-2-(1-fluoro-2-phenylvinyl)cyclopropanamine hydrochloride (56 mg, 262 μmol) in DCE (4 mL) was added Sodium (triacetoxy)borohydride (279 mg). After 30 min, DCM and 1 M potassium carbonate (aqueous) were added. The organic phase was isolated, evaporated and the crude residue purified by column chromatography (silica, 0% to 10% Methanol in Ethyl acetate) to afford racemic tert-butyl 4-(((2-((Z)-1-fluoro-2-phenylvinyl)cyclopropyl)amino)methyl) piperidine-1-carboxylate (27.0 mg, 72.0 μmol), 27% yield. LCMS (ESI+): 375 (M+H)

Step 2

Tert-butyl 4-(((2-((Z)-1-fluoro-2-phenylvinyl)cyclopropyl)amino)methyl)piperidine-1-carboxylate (27.0 mg, 72.0 μmol) was dissolved in 1,4-dioxane (500 uL), and 4M Hydrochloric acid in 1,4-dioxane was added (250 uL, 1 mmol). The reaction mixture was heated at 50° C. for 16 hours. The volatiles were evaporated under reduced pressure. The residue was suspended in MTBE and stirred for 5 minutes. The solid was filtered, collected and redissolved in Acetonitrile:water (1:1). The solution was frozen and lyophilized to afford racemic 2-((Z)-1-fluoro-2-phenylvinyl)-N-(piperidin-4-ylmethyl)cyclopropanamine dihydrochloride (15.0 mg, 43.1 μmol) in 57% yield. $^1$H NMR (400 MHz, DMSO-d6) δ 9.47-9.93 (m, 2H), 8.65-9.04 (m, 2H), 7.43 (d, J=7.32 Hz, 2H), 7.34 (t, J=7.69 Hz, 2H), 7.16-7.27 (m, 1H), 5.97 (d, J=39.90 Hz, 1H), 3.25 (d, J=12.70 Hz, 2H), 3.10 (br. s., 1H), 2.99 (br. s., 2H), 2.74-2.90 (m, 2H), 2.55 (d, J=9.28 Hz, 1H), 2.06 (br. s., 1H), 1.95 (d, J=12.94 Hz, 2H), 1.52-1.63 (m, 1H), 1.36-1.50 (m, 2H), 1.25-1.34 (m, 1H). LCMS (ESI+): 275 (M+H).

Racemic 2-((E)-2-(pyridin-3-yl)vinyl)cyclopropanamine Trifluoroacetic Acid Salt (126)

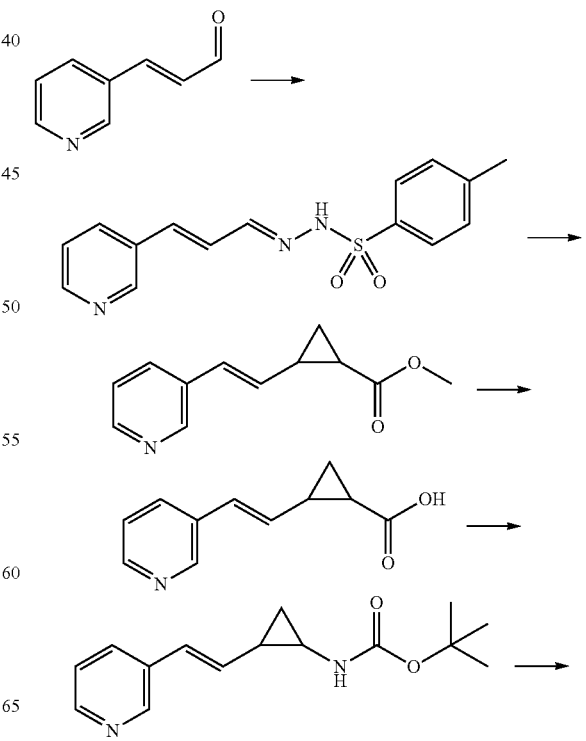

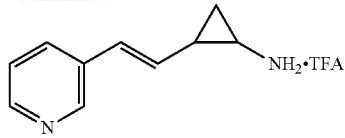

Step 1

A round bottom flask was charged with (E)-3-(pyridin-3-yl)acrylaldehyde (1.77 g, 13.2 mmol), a stirbar, and methanol (100 mL) before the addition of 4-methylbenzenesulfonohydrazide (2.45 g, 13.2 mmol). The reaction mixture was stirred at 25° C. for 15 minutes. The white solid material was filtered on a paper filter under suction, washed with hexanes, dried under suction and collected to afford (E)-4-methyl-N'-((E)-3-(pyridin-3-yl)allylidene)benzenesulfonohydrazide (3.67 g, 12.1 mmol), 92% yield. LCMS (ESI+): 302.5 (M+H)

Step 2

A round bottom flask was charged with (E)-4-methyl-N'-((E)-3-(pyridin-3-yl)allylidene)benzenesulfonohydrazide (2.67 g, 8.85 mmol), a stirbar, and 1,4-dioxane (75 mL) before the addition of potassium carbonate (1.82 g, 13.2 mmol) and methyl acrylate (8.01 mL, 88.5 mmol). The reaction mixture was stirred at 110° C. for 16 hours. The mixture was cooled, filtered on a pad of celite under suction, and the filtrate was concentrated under reduced pressure. The crude residue was purified by silica gel column chromatography (0% to 15% to Methanol in Ethyl acetate) to afford (E)-methyl 2-(2-(pyridin-3-yl)vinyl)cyclopropanecarboxylate (1.54 g, 7.57 mmol) in 86% yield. LCMS (ESI+): 204.1 (M+H)

Step 3

(E)-methyl 2-(2-(pyridin-3-yl)vinyl)cyclopropanecarboxylate (1.54 g, 7.57 mmol) was dissolved in THF (12 mL) and methanol (5 mL). Sodium hydroxide (6 M aqueous) was added (6 mL, 36 mmol) and the reaction mixture was stirred for 1 hour at 25° C. Reaction complete. The reaction mixture was acidified to pH 5 using Hydrochloric acid (1M aqueous). The reaction mixture was partitioned between brine and Ethyl acetate. The organic layer was separated, washed with brine, dried with Na$_2$SO$_4$, filtered, and evaporated under reduced pressure to afford racemic (E)-2-(2-(pyridin-3-yl)vinyl)cyclopropanecarboxylic acid (780 mg, 4.12 mmol), 54% yield.LCMS: Rt=1.926 min., 2.000 min., MS (ESI+): 190.2 (M+H)

Step 4

(E)-2-(2-(pyridin-3-yl)vinyl)cyclopropanecarboxylic acid (242 mg, 1.27 mmol) was dissolved in THF (25 mL) mixed with triethylamine (440 μL, 3.17 mmol), and the solution was then cooled to 0° C. The solution was mixed with ethyl chloroformate (185 mg, 1.71 mmol), and the reaction mixture was stirred at 0° C. for 0.5 hour. A solution of sodium azide (412 mg, 6.35 mmol) in 12 ml of water was added and the reaction mixture was stirred vigorously at 0° C. for one hour. The reaction mixture was diluted with water and extracted twice with Ethyl acetate. The combined organic extracts were washed with brine, dried with sodium sulphate and evaporated. The residue was taken up in 5 ml of toluene, and the solution was heated to reflux for 2 hours. tert-Butanol (2 mL) was added to the reaction mixture, and the mixture was heated at 100° C. for 16 hours. The volatiles were evaporated under reduced pressure and the crude residue was purified by column chromatography using an Ethyl acetate:Methanol mixture was eluent to afford racemic (E)-tert-butyl (2-(2-(pyridin-3-yl)vinyl)cyclopropyl)carbamate (114 mg, 437 μmol) in 34% yield. LCMS (ESI+): 261 (M+H)

Step 5

(E)-tert-butyl (2-(2-(pyridin-3-yl)vinyl)cyclopropyl)carbamate (57 mg, 218 μmol) was dissolved in 1,4-1,4-dioxane, and Hydrochloric acid (4M in 1,4-dioxane, 220 uL, 0.872 mmol) was added. The reaction mixture was stirred for 36 hours at 25° C. The volatiles were evaporated under reduced pressure. The crude residue was purified using preparative HPLC (water+0.1% TFA as eluent mixture). The pure fractions were pooled, concentrated, frozen and lyophilized to afford racemic 2-((E)-2-(pyridin-3-yl)vinyl)cyclopropanamine trifluoroacetic acid salt (21.0 mg, 76.5 μmol) in 35% yield. $^1$H NMR (400 MHz, DMSO-d6) δ 8.71 (br. s., 2H), 8.39 (br. s., 3H), 8.04-8.18 (m, 1H), 7.71-7.83 (m, 1H), 6.02 (dd, J=2.20, 5.86 Hz, 1H), 5.78 (dd, J=2.08, 5.74 Hz, 1H), 4.16 (hr. s., 1H), 3.68-3.79 (m, 1H), 2.97 (m, 1H), 2.39-2.48 (m, 1H). LCMS (ESI+): 161 (M+H).

1-methyl-2-((E)-styryl)cyclopropanamine (112)

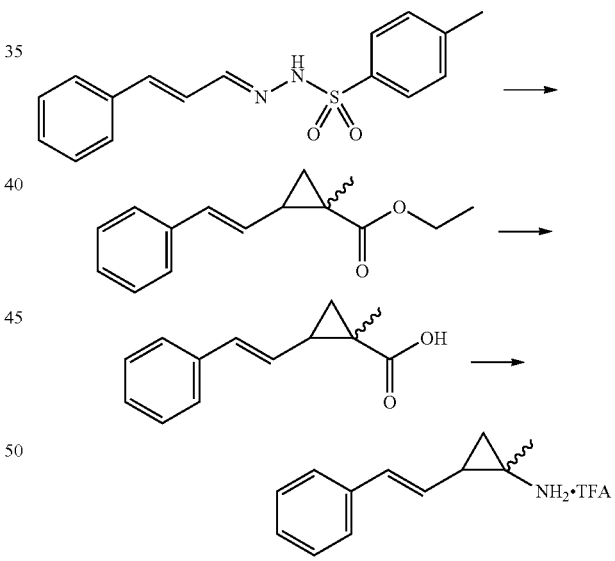

Step 1

A round bottom flask was charged with (E)-4-methyl-N'-((E)-3-phenylallylidene)benzenesulfonohydrazide (0.795 g, 2.64 mmol), a stirbar, and 1,4-dioxane (40 mL, 0.125 M) before the addition of potassium carbonate (547 mg, 3.96 mmol) and tert-butyl methacrylate (1.67 g, 13.2 mmol). The reaction mixture was heated to 110° C. in a microwave for 16 hours. The reaction mixture was cooled and the volatiles were evaporated under reduced pressure. The crude material was diluted with MTBE and filtered on a pad of celite. The filtrate was evaporated under reduced pressure. The crude residue was purified by column chromatography (silica 24 g, 5% to 50% to Ethyl acetate in hexanes) to afford racemic (E)-tert-butyl 1-methyl-2-styrylcyclopropanecarboxylate as a mixture of 1,2-cis and 1,2-trans isomers. LCMS (ESI+): 203 (M-tBu+H)

Step 2

Racemic (E)-cert-butyl 1-methyl-2-styrylcyclopropanecarboxylate was dissolved in 1,4-dioxane, and 4M Hydrochloric acid in1,4-dioxane (2 mL, 8 mmol) was added. 2 drops of water were added, and the reaction mixture was stirred at 40° C. for 16 hours. The reaction mixture was evaporated under reduced pressure and dried under high vacuum to afford racemic (E)-1-methyl-2-styrylcyclopropanecarboxylic acid (201 mg, 993 μmol) in 38% yield over 2 steps. LCMS (ESI+): 203 (M+H)

Step 3

Racemic (E)-1-methyl-2-styrylcyclopropanecarboxylic acid (200 mg, 988 μmol) is dissolved in THF (8 mL) mixed with Triethylamine (341 μL, 2.46 mmol), and the solution is then cooled to 0° C. The solution is mixed with ethyl carbonochloridate (ethyl chloroformate) (155 mg, 1.43 mmol), and the reaction mixture is stirred at 0° C. for 0.5 hour. A solution of sodium azide (320 mg, 4.93 mmol) in 2.5 ml of water was added and the reaction mixture is stirred at 0° C. for one hour. The reaction mixture was diluted with water and extracted with Ethyl acetate. The combined extracts were washed with brine, dried with sodium sulphate and evaporated under reduced pressure. The residue was taken up in toluene (3 mL), and the solution was heated to reflux for 2 hours. Potassium trimethylsilanolate (186 mg, 1.45 mmol) was added to the mixture cooled at 25° C. The volatiles were evaporated under reduced pressure and the crude residue was re-dissolved in acetic acid. The compound was purified by preparative HPLC (Acetonitrile:water+0.1% TFA) to afford racemic 1-methyl-2-((E)-styryl)cyclopropanamine trifluoroacetic acid (8.50 mg, 29.5 μmol) in 3% yield. LCMS: 157 (M−NH$_2$)+

Racemic (E)-3-((4-((2-(1-phenylprop-1-en-2-yl) cyclopropyl)amino)cyclohexyl)amino)propanoic acid (diastereomer 1) (124) and Racemic (E)-3-((4-((2-(1-phenylprop-1-en-2-yl)cyclopropyl)amino) cyclohexyl)amino)propanoic Acid (Diastereomer 2) (125)

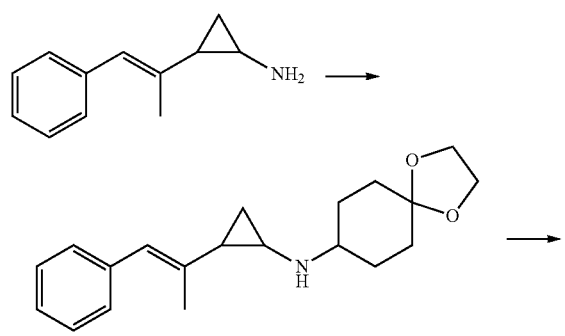

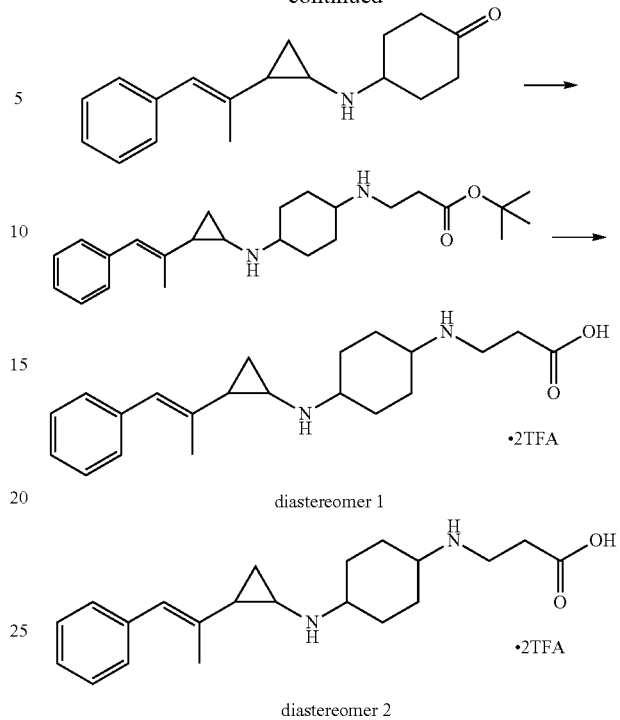

Step 1

To (E)-2-(1-phenylprop-1-en-2-yl)cyclopropanamine (210 mg, 1.21 mmol) and 1,4-dioxaspiro[4.5]decan-8-one (190 mg, 1.22 mmol) in DCE (6 mL) was added Sodium (triacetoxy)borohydride (512 mg, 2.42 mmol). After 30 min, DCM and 1 M aqueous potassium carbonate were added to the reaction mixture. The organic phase was isolated, evaporated under reduced pressure and the crude residue purified by column chromatography (silica, 0% to 10% Methanol in Ethyl acetate) to afford racemic N-(2-((E)-1-phenylprop-1-en-2-yl)cyclopropyl)-1,4-dioxaspiro[4.5]decan-8-amine (303 mg, 966 μmol) (80% yield). LCMS (ESI+): 314 (M+H).

Step 2

Racemic N-(2-((E)-1-phenylprop-1-en-2-yl)cyclopropyl)-1,4-dioxaspiro[4.5]decan-8-amine (151 mg, 481 μmol) was dissolved in acetic acid (3 ml) and water (1 ml), 2 drops of concentrated hydrochloric acid was added to the reaction mixture and the mixture was stirred at 60° C. for 5 hours. Water (30 ml) was added to the reaction mixture and the pH of the reaction mixture was adjusted to 8 using saturated potassium carbonate solution, followed by extraction with DCM (2 times). After drying with sodium sulfate and filtration, the solvent was removed under reduced pressure. The obtained oily substance was dried under high vacuum and used without further purification (4-((2-((E)-1-phenylprop-1-en-2-yl)cyclopropyl)amino)cyclohexanone (129 mg, 478 μmol), quantitative yield). LCMS (ESI+): 270 (M+H)

Step 3

To racemic 4-((2-((E)-1-phenylprop-1-en-2-yl)cyclopropyl)amino)cyclohexanone (129 mg, 0.478 mmol) and tert-butyl 3-aminopropanoate hydrochloride (86.8 mg, 0.478 mmol) in DCE (4 mL) was added the Sodium (triacetoxy) borohydride (279 mg). After 30 min, DCM and 1 M aqueous potassium carbonate were added to the reaction mixture. The organic phase was evaporated and the crude residue purified by column chromatography (silica, 0% to 10% Methanol in Ethyl acetate) to afford racemic tert-butyl 3-((4-((2-((E)-1-phenylprop-1-en-2-yl)cyclopropyl)amino)cyclohexyl)amino)propanoate (68.0 mg, 170 μmol) as a mixture of diastereomers, 36% yield. LCMS (ESI+): 399 (M+H).

Step 4

Racemic tert-butyl 3-((4-((2-((E)-1-phenylprop-1-en-2-yl)cyclopropyl)amino)cyclohexyl)amino)propanoate (68 mg, 170 μmol) was dissolved in 1,4-dioxane and Hydrochloric acid (4M in 1,4-dioxane, 0.2 mL, 0.850 mmol), and stirred at 40° C. for 16 hours. The reaction mixture was evaporated under reduced pressure, re-dissolved in THF, and purified directly by preparative HPLC (Acetonitrile:water+ 0.1% TFA, SunFire column) to afford two sets of fractions containing isomeric compounds. The first eluting fractions were pooled, frozen and lyophilized to afford racemic (E)-3-((4-((2-(1-phenylprop-1-en-2-yl)cyclopropyl)amino)cyclohexyl)amino)propanoic acid (diastereomer 1) bis-trifluoroacetic acid salt (15.0 mg, 26.2 μmol), 15% yield. $^1$H NMR (400 MHz, DMSO-d6) δ 12.72 (hr. s, 1H), 8.98 (hr. s., 2H), 8.56 (hr. s., 2H), 7.30-7.40 (m, 2H), 7.13-7.28 (m, 3H), 6.38 (s, 1H), 2.80-3.25 (m, 5H), 2.64 (t, J=7.08 Hz, 2H), 2.16 (d, J=14.65 Hz, 4H), 1.96-2.07 (m, 1H), 1.74 (d, J=1.22 Hz, 3H), 1.30-1.49 (m, 4H), 1.11-1.28 (m, 2H). LCMS (ESI+): 343 (M+H). The last eluting fractions were pooled, frozen, and lyophilized to afford racemic (E)-3-((4-((2-(1-phenylprop-1-en-2-yl)cyclopropyl)amino)cyclohexyl)amino)propanoic acid (diastereomer 2) bis-trifluoroacetic acid salt (5.00 mg, 8.76 μmol), 5% yield. $^1$H NMR (400 MHz, DMSO-d6) δ 12.49-12.96 (m, 1H), 9.01 (br. s., 2H), 8.55 (br. s., 2H), 7.28-7.38 (m, 2H), 7.15-7.27 (m, 3H), 6.38 (s, 1H), 3.41 (br. s., 1H), 3.27 (br. s., 1H), 3.02-3.22 (m, 3H), 2.96 (br. s., 1H), 2.60-2.71 (m, 2H), 2.04-2.12 (m, 1H), 1.90-2.02 (m, 2H), 1.78-1.89 (m, 3H), 1.75 (d, J=1.70 Hz, 3H), 1.35-1.46 (m, 2H), 1.21-1.28 (m, 1H), 1.10-1.20 (m, 1H) LCMS (ESI+): 343 (M+H).

(E)-3-(((2-styrylcyclopropyl)amino)methyl)pyridin-2-amine (114)

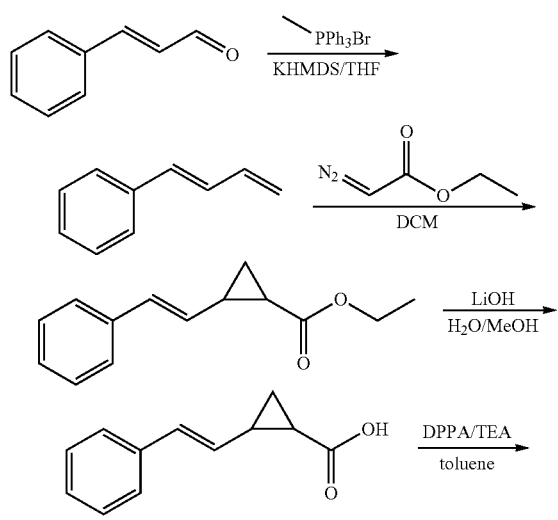

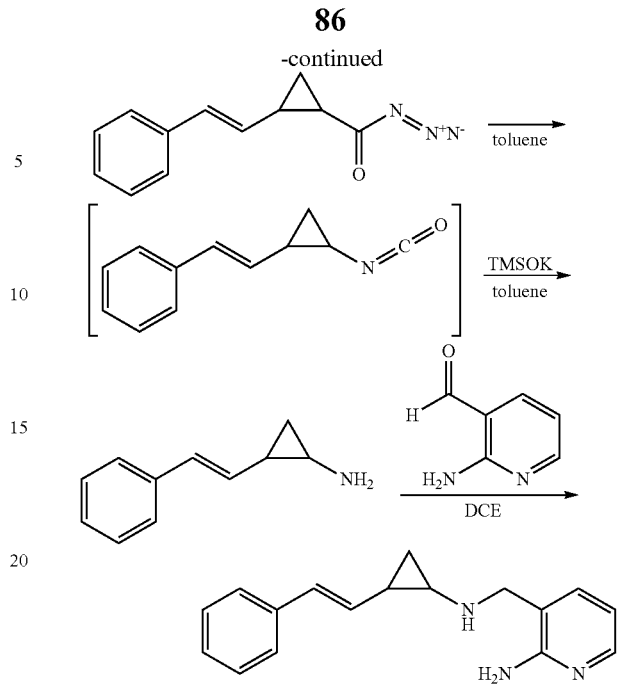

Step 1: Synthesis of (E)-buta-1,3-dien-1-ylbenzene

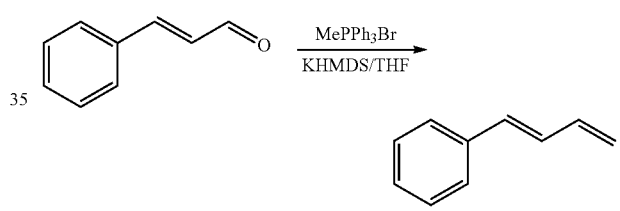

To a solution of bromo-methyl-triphenyl-phosphane (25.00 g, 69.99 mmol, 1.85 eq) in THF (50.00 mL) was added a solution of KHMDS in THF (70 mL, 70 mmol, 1 M) at 0° C. The mixture was allowed to stir at 15° C. for 0.5 h and (E)-3-phenylprop-2-enal (5.00 g, 37.83 mmol, 1.00 eq) was added. The mixture was allowed to stir at 15° C. for another 1.5 h. Water (20 mL) was added and the mixture was concentrated. The residue was extracted with ethyl acetate (50 mL*3). The combined organics layer was washed with brine, dried, and concentrated to afford the crude product. The crude was purified by column chromatography on silica gel (eluted, petroleum ether:ethyl acetate=100:1-50:1) to afford (E)-buta-1,3-dien-1-ylbenzene (4.50 g, 34.56 mmol, 91.37% yield) as a yellow oil.

Step 2: Synthesis of (E)-ethyl 2-styrylcyclopropanecarboxylate

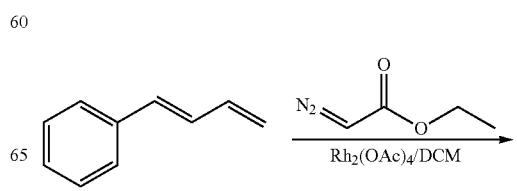

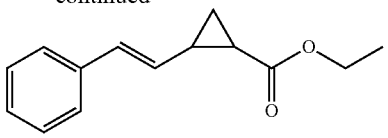

To a solution of Rh$_2$(OAc)$_4$ (50.00 mg, 226.25 umol, 0.06 eq) in DCM (10.00 mL) was added (E)-buta-1,3-dien-1-ylbenzene (500.00 mg, 3.84 mmol, 1.00 eq). The mixture was purged with Ar. Then (E)-buta-1,3-diene-1-ylbenzene (500.00 mg, 3.84 mmol, 1.00 eq) was added at 0° C. The mixture was warmed to 15 15° C. and stirred for 1 h. The mixture was filtered and concentrated under vacuum to afford the crude product. The crude residue was purified by column chromatography on silica gel (petroleum ether:ethyl acetate=100:1-40:1) to afford (E)-ethyl 2-styrylcyclopropanecarboxylate (600.00 mg, 2.77 mmol, 72.24% yield) as a colorless oil. LCMS (M+H$^+$) m/z: 217.

Step 3: Synthesis of
(E)-2-styrylcyclopropanecarboxylic Acid

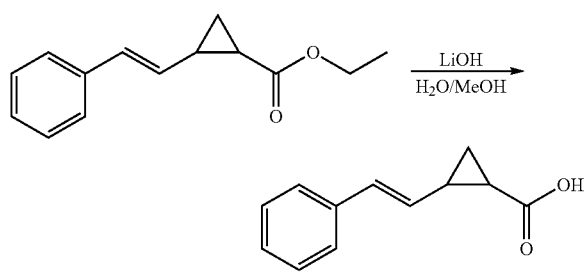

To a solution of (E)-ethyl 2-styrylcyclopropanecarboxylate (600.00 mg, 2.77 mmol, 1.00 eq) in MeOH (5.00 mL) were added LiOH (300.00 mg, 12.52 mmol, 4.52 eq) and H$_2$O (2.50 g, 138.50 mmol, 50.00 eq). The mixture was stirred at 70° C. for 1.5 h. The solution was then cooled to 0° C. and the pH was adjusted to 6 via addition of aq. HCl solution. The solution was extracted with EtOAc and the combined organics phase was washed with brine, dried, filtered, and concentrated to afford crude (E)-2-styrylcyclopropanecarboxylic acid (520.00 mg, crude) as a yellow solid. LCMS (M+H$^+$) m/z 189.

Step 4: Synthesis of
(E)-2-styrylcyclopropanecarbonyl Azide

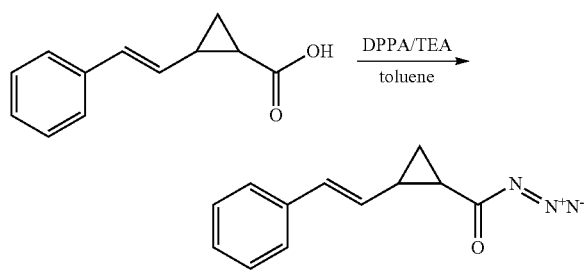

To a solution of (E)-2-styrylcyclopropanecarboxylic acid (520.00 mg, 2.76 mmol, 1.00 eq) in toluene (10.00 mL) were added triethylamine (900.00 mg, 8.89 mmol, 3.22 eq) and diphenylphosphorylazide (1.52 g, 5.52 mmol, 2.00 eq) at 0° C. The mixture was warmed to 15° C. and stirred for 1.5 h. The mixture was concentrated. The crude residue was purified by column chromatography on silica gel (eluted, petroleum ether:ethyl acetate=100:1) to afford (E)-2-styrylcyclopropanecarbonyl azide (530.00 mg, 2.49 mmol, 90.06% yield) as a yellow oil.

Step 5: Synthesis of (E)-2-styrylcyclopropanamine

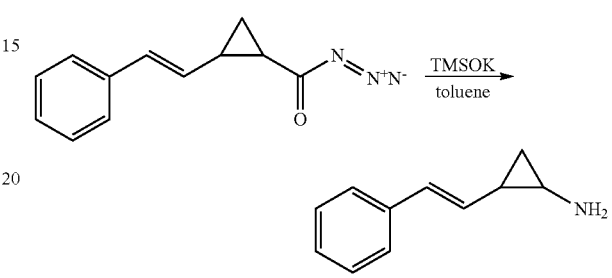

A solution of (E)-2-styrylcyclopropanecarbonyl azide (530.00 mg, 2.49 mmol, 1.00 eq) in toluene (10.00 mL) was refluxed for 3 h. The solution was cooled to room temperature and potassium trimethylsilanolate (501.52 mg, 3.91 mmol, 1.57 eq) was added. The mixture was stirred for 13 h before addition of water (5 mL). The volatiles were removed under vacuum. The aqueous solution was extracted with ethyl acetate (10 mL*3). The combined organic layers were concentrated under vacuum to afford the crude product. The crude residue was purified by column chromatography on silica gel (eluted, petroleum ether: ethyl acetate=5:1-1:1) to afford (E)-2-styrylcyclopropanamine (250.00 mg, 1.51 mmol, 60.53% yield) as a yellow solid. LCMS (M+H$^+$) m/z: 160.

Step 6: Synthesis of (E)-3-(((2-styrylcyclopropyl)amino)methyl)pyridin-2-amine

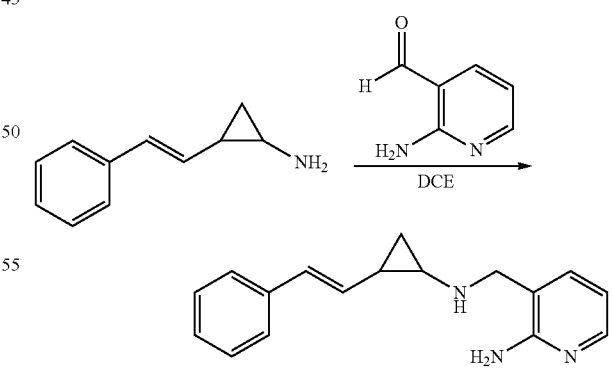

To a solution of (E)-2-styrylcyclopropanamine (30.00 mg, 188.41 umol, 1.00 eq) in Dichloroethane (3.00 mL) were added 2-aminopyridine-3-carbaldehyde (50.00 mg, 409.43 umol, 2.17 eq) and AcOH (10.00 mg, 166.53 umol, 0.88 eq). The mixture was stirred at room temperature for 5 h before addition of NaBH$_3$CN (30.00 mg, 477.40 umol, 2.53 eq). The mixture was stirred for 1 h before the reaction was filtered. The filtrate was concentrated under vacuum to afford the crude product. The crude residue was purified by Prep-HPLC (Mobile phase A: water with 0.05% HCl solution; Mobile phase B:ACN; column temperature: 30° C. Gradient: 5-35% B 10 min) to afford (E)-3-(((2-styrylcyclopropyl)amino)methyl)pyridin-2-amine (4 mg). LCMS (M+H⁺) m/z: 266. ¹H NMR (400 MHz, METHANOL-$d_4$) 8.24(d, J=7.2 Hz, 1H), 8.03(d, J=6 Hz, 1H), 7.38-7.22 (m, 5H), 7.07(t, J=7.2 Hz, 1H), 6.57(d, J=15.6, Hz, 1H), 5.92(d, J=15.6, 8.0 Hz, 1H), 4.49 (s, 2H), 3.0(m, 1H), 2.23-2.17(m, 1H), 0.93-0.89(m, 2H).

(E)-N1-(2-styrylcyclopropyl)cyclohexane-1,4-diamine Dihydrochloride (119)

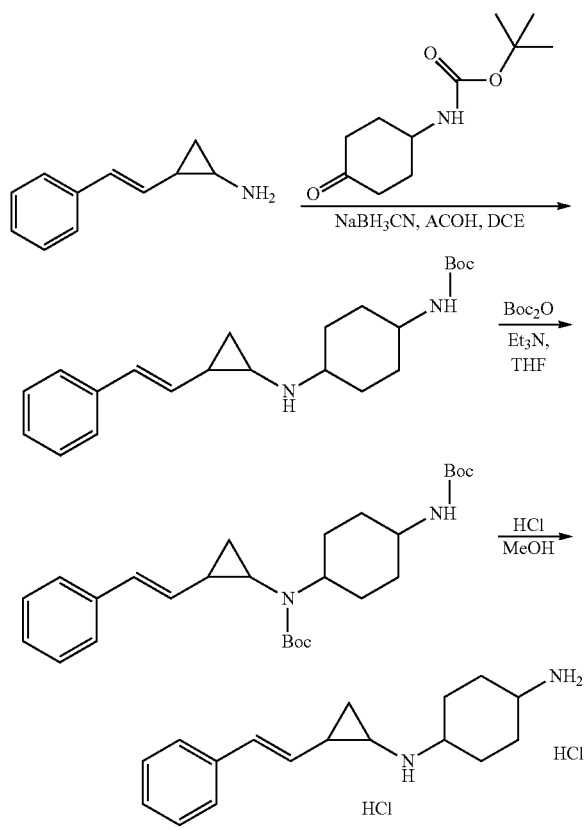

Step 1: Synthesis of (E)-tert-butyl (4-((2-styrylcyclopropyl)amino)cyclohexyl)carbamate

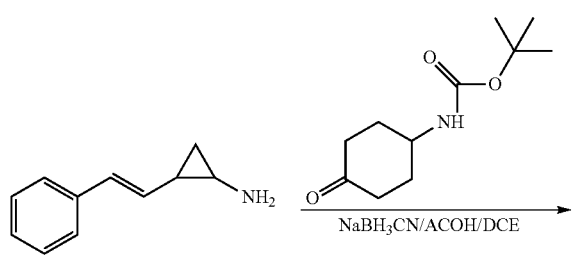

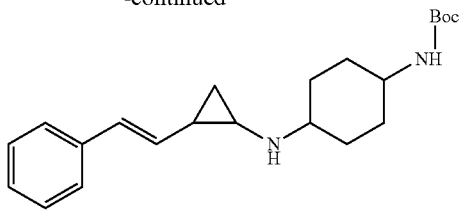

To a mixture of (E)-2-styrylcyclopropanamine (41.06 mg, 257.89 umol, 1.00 eq) and tert-butyl N-(4-oxocyclohexyl)carbamate (55.00 mg, 257.89 umol, 1.00 eq) in DICHLOROETHANE (5.00 mL) was added AcOH (46.46 mg, 773.67 umol, 3.00 eq). The mixture was stirred at room temperature for 15 h. Then NaBH₃CN (48.62 mg, 773.67 umol, 3.00 eq) was added. The reaction mixture was stirred at room temperature for 1 h. The reaction mixture was filtered and the filtrate was concentrated in vacuo to afford crude tert-hutyl (E)-(4-((2-styrylcyclopropyl)amino)cyclohexyl)carhamate (100.00 mg, crude) as yellow oil.

Step 2: Synthesis of (E)-tert-butyl (4-((tert-butoxycarbonyl)amino)cyclohexyl)(2-styrylcyclopropyl)carbamate

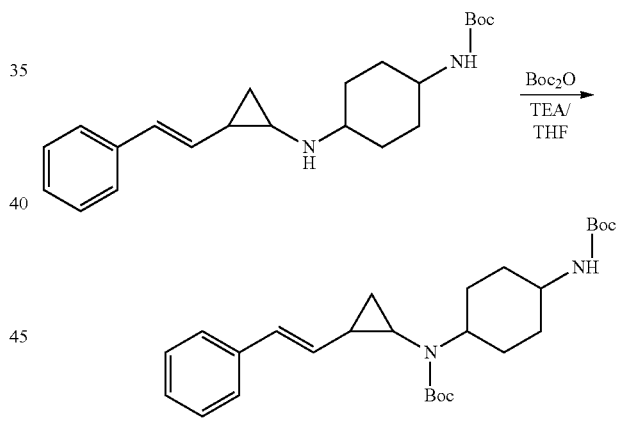

To a mixture of tert-butyl (E)-(4-((2-styrylcyclopropyl)amino)cyclohexyl)carbamate (100.00 mg, 280.50 umol, 1.00 eq) in THF (3.00 mL) was added triethylamine (141.92 mg, 1.40 mmol, 5.00 eq) and (Boc)₂O (61.22 mg, 280.50 umol, 1.00 eq). The reaction mixture was stirred at room temperature for 17 h. Water (20 mL) was added and the mixture was extracted with EtOAc (20 mL*3). The combined organics layer was concentrated in vacuo. The crude residue was purified by Prep-TLC (Petroleum ether: Ethyl acetate 5:1) to afford product tert-butyl (E)-(4-((tert-butoxycarbonyl)amino)cyclohexyl)(2-styrylcyclopropyl)carbamate (30.00 mg, 60.44 umol, 21.55% yield, 92% purity) as yellow oil. LCMS (M+Na⁺) m/z: 479.

Step 3: Synthesis of (E)-N1-(2-styrylcyclopropyl)cyclohexane-1,4-diamine Dihydrochloride

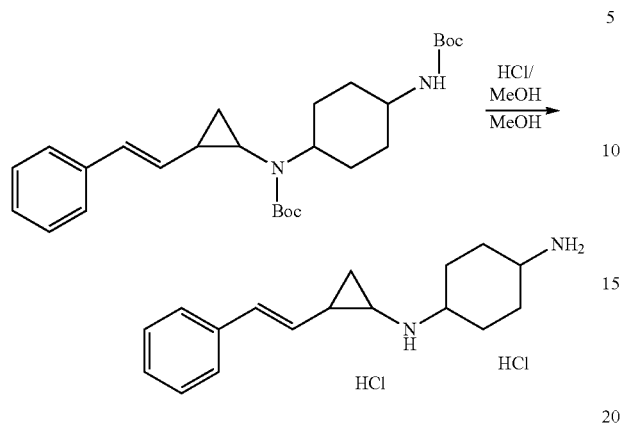

To a mixture of tert-butyl (E)-(4-((tert-butoxycarbonyl)amino)cyclohexyl)(2-styrylcyclopropyl)carbamate (30.00 mg, 65.70 umol, 1.00 eq) in MeOH (1.00 mL) was added HCl (4 M in MeOH, 1.00 mL, 60.88 eq). The reaction mixture was stirred at room temperature for 3 h. The reaction mixture was concentrated in vacuo to afford (E)-N1-(2-styrylcyclopropyl)cyclohexane-1,4-diamine dihydrochloride (9.30 mg, 29.53 umol, 44.95% yield) as a yellow solid. LCMS (M+H) m/z: 257. $^1$H NMR (400 MHz, CD$_3$OD): δ 7.26 (m, 5H), 6.63-6.60 (d, J=12.0 Hz, 1H), 5.91 (m, 1H), 3.16 (m, 1H), 2.89 (s, 1H), 2.05 (m, 7H), 1.56 (m, 3H) 1.23 (m, 2H).

(Z)-2-styrylcyclopropan-1-amine Hydrochloride (115)

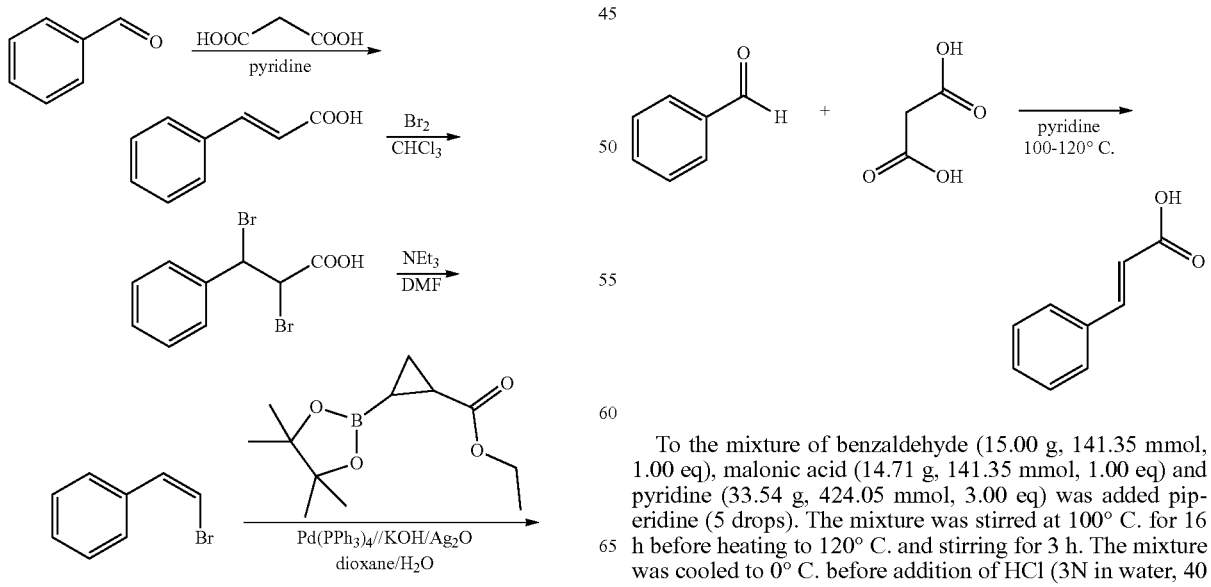

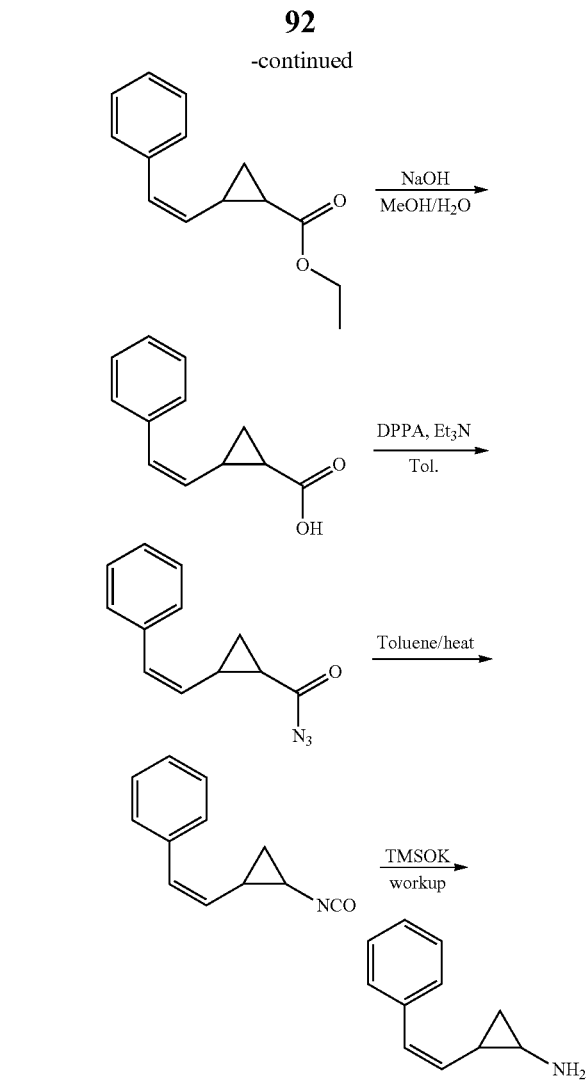

Step 1: Synthesis of (E)-3-phenylprop-2-enoic Acid

To the mixture of benzaldehyde (15.00 g, 141.35 mmol, 1.00 eq), malonic acid (14.71 g, 141.35 mmol, 1.00 eq) and pyridine (33.54 g, 424.05 mmol, 3.00 eq) was added piperidine (5 drops). The mixture was stirred at 100° C. for 16 h before heating to 120° C. and stirring for 3 h. The mixture was cooled to 0° C. before addition of HCl (3N in water, 40 mL). A precipitate formed and was collected by filtration.

The filter cake was dried under high vacuum to afford crude (E)-3-phenylprop-2-enoic acid (11.30 g, 76.27 mmol, 53.96% yield) as a yellow solid.

Step 2: Synthesis of
2,3-dibromo-3-phenyl-propanoic Acid

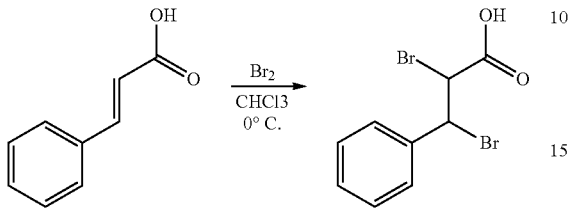

To the mixture of (E)-3-phenylprop-2-enoic acid (11.30 g, 76.27 mmol, 1.00 eq) dissolved in CHCl$_3$ (130.00 mL) was added molecular bromine (14.63 g, 91.52 mmol, 1.20 eq) dropwise at 0° C. The mixture was stirred at 0° C. for 2 h. A precipitate formed during the reaction and was collected via filtration. The filter cake was washed with cool CHCl$_3$ (15 mL*2). The solid was dried under high vacuum and collected to afford 2,3-dibromo-3-phenyl-propanoic acid (21.00 g, 68.19 mmol, 89.40% yield) as a white solid. $^1$H NMR (400 MHz, CD$_3$OD) δ 7.51-7.49 (d, J=6.8 Hz 2.0H), 7.42-7.36 (m, 3H), 5.41-5.39 (d, J=11.6 Hz, 1H), 5.05-5.02 (d, 1H).

Step 3: Synthesis of (Z)-(2-bromovinyl)benzene

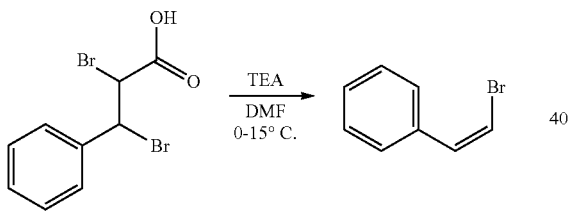

To the solution of 2,3-dibromo-3-phenyl-propanoic acid (21.00 g, 68.19 mmol, 1.00 eq) dissolved in DMF (30.00 mL) was added triethylamine (13.80 g, 136.38 mmol, 2.00 eq) dropwise at 0° C. The mixture was stirred at 0° C. for 0.5 h before warming the solution to room temperature and stirring for 5 h. Water (30 mL) was added and the mixture was extracted with MBTE (40 mL*3). The organic phases were combined and concentrated in vacuo to afford (Z)-(2-bromovinyl)benzene (10.00 g, 54.63 mmol, 80.12% yield) as brown oil. $^1$H NMR (400 MHz, CD$_3$OD) δ 7.68-7.66 (d, J=7.2 Hz, 2.0H), 7.37-7.30 (m, 3H), 7.13-7.11 (d, J=8.4 Hz, 1.0H), 6.52-6.50 (d, J=7.6 Hz, 1.0H).

Step 4: Synthesis of ethyl
(Z)-2-styrylcyclopropane-1-carboxylate

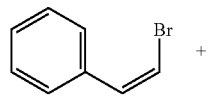

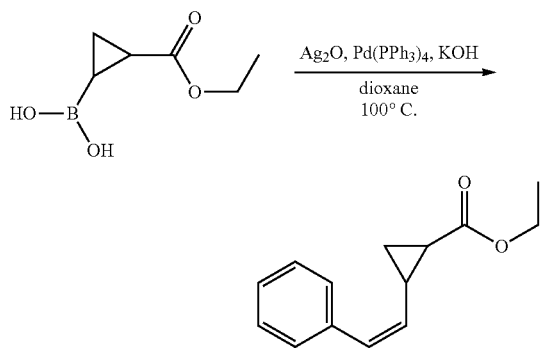

A mixture of (Z)-(2-bromovinyl)benzene (200.00 mg, 1.09 mmol, 1.00 eq), (2-ethoxycarbonylcyclopropyl)boronic acid (172.60 mg, 1.09 mmol, 1.00 eq), Pd(PPh$_3$)$_4$ (126.26 mg, 109.27 umol, 0.10 cq), KOH (183.93 mg, 3.28 mmol, 3.00 cq) and Ag$_2$O (379.82 mg, 1.64 mmol, 1.50 eq) in dioxane (10.00 mL) was stirred at 100° C. for 16 h under N$_2$ atmosphere. To the mixture was added water (5 mL). The mixture was filtered and extracted with ethyl acetate (20 mL*2). The organic phases were combined and concentrated in vacuo. The residue was purified by Prep-TLC (Petroleum ether: Ethyl acetate=7:1) to afford ethyl (Z)-2-styrylcyclopropane-1-carboxylate (30.00 mg, 138.71 umol, 12.73% yield) as a yellow oil. $^1$HNMR (400 MHz, CDCl$_3$) δ 7.32-7.25 (m, 4H), 7.18-7.14 (m, 1H), 6.47-6.37 (m, 1H), 5.82-5.00 (m, 1H), 4.12-4.04 (m, 2H), 2.40-2.25 (m, 1H), 1.97-1.92 (m, 1H), 1.67-1.63 (m, 1H), 1.52 (s, 1H), 1.44-1.41 (m, 1H), 0.98-0.93 (m, 1H).

Step 5: Synthesis of
(Z)-2-styrylcyclopropane-1-carboxylic Acid

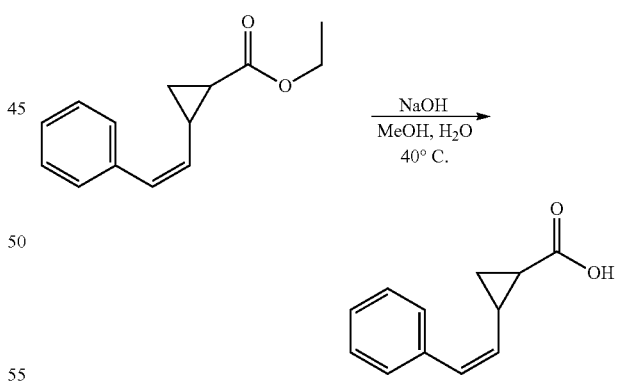

A mixture of ethyl (Z)-2-styrylcyclopropane-1-carboxylate (700.00 mg, 3.24 mmol, 1.00 eq) and NaOH (648.00 mg, 16.20 mmol, 5.00 eq) in MeOH (10.00 mL) and H$_2$O (3.00 mL) was stirred at 40° C. for 4 h. The mixture was concentrated in vacuo. The residue was dissolved in water (10 mL) and acidified to pH 5 with aqueous HCl (1N). The mixture was extracted with dichloromethane and methanol (30:1, 15 mL*3). The combined organics phase was concentrated to afford (Z)-2-styrylcyclopropane-1-carboxylic acid (440.00 mg, 2.34 mmol, 72.15% yield) as a yellow oil.

Step 6: Synthesis of (Z)-2-styrylcyclopropane-1-carbonyl Azide

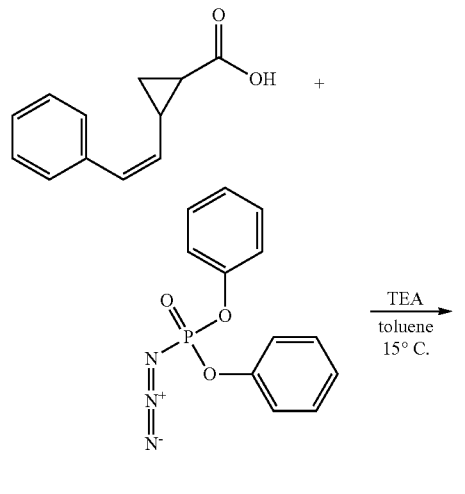

To the solution of (Z)-2-styrylcyclopropane-1-carboxylic acid (440.00 mg, 2.34 mmol, 1.00 eq) dissolved in toluene (10.00 mL) was added triethylamine (710.35 mg, 7.02 mmol, 3.00 eq) and diphenylphosphorylazide (643.33 mg, 2.34 mmol, 1.00 eq). The solution was stirred at room temperature for 4 h. To the solution was added water (5 mL). The mixture was concentrated in vacuo. The crude residue was purified by silica gel column chromatography (Petroleum ether to Petroleum ether: Ethyl acetate=100:1) to afford (Z)-2-styrylcyclopropane-1-carbonyl azide (420.00 mg, 1.71 mmol, 73.08% yield) as a yellow oil. LCMS (M-N$_2$) m/z: 185. $^1$H NMR (400 MHz, CD$_3$OD) δ 7.34-7.33 (m, 4H), 7.24-7.23 (m, 1H), 6.56-6.48 (m, 1H), 5.14 (m, 1H), 2.51-2.46 (m, 1H), 1.81-1.55 (m, 1H), 1.28-1.21 (m, 1H), 0.89-0.85 (m, 1H).

Synthesis of (Z)-2-styrylcyclopropan-1-amine Hydrochloride (115)

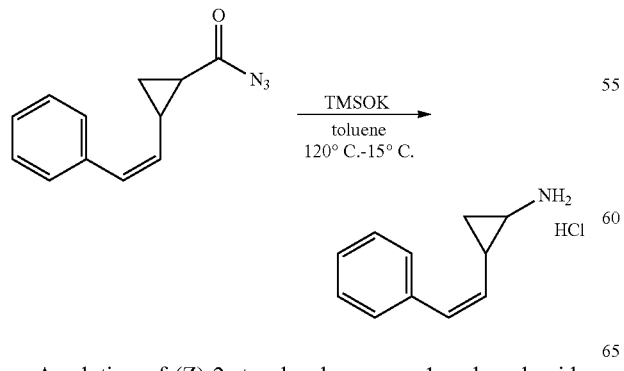

A solution of (Z)-2-styrylcyclopropane-1-carbonyl azide (420.00 mg, 1.97 mmol, 1.00 eq) dissolved in toluene (10.00 mL) was stirred at 120° C. for 4 h. The mixture was cooled to room temperature and potassium trimethylsilanolate (277.96 mg, 2.17 mmol, 1.10 eq) was added. The mixture was stirred at room temperature for 20 h. To the mixture was added water (5 mL). The mixture was concentrated in vacuo. The crude residue was dissolved in water (5 mL) and extracted with ethyl acetate (10 mL*2). The organic phases were combined and the pH adjusted to 4 with HCl (4 N in MeOH) and concentrated in vacuo to afford (Z)-2-styrylcyclopropan-1-amine hydrochloride (80.00 mg, 408.81 umol, 20.75% yield) as a brown solid. LCMS (M+H$^+$) m/z: 160. $^1$H NMR (400 MHz, CD$_3$OD) δ 7.41-7.36 (m, 4H), 7.34-7.25 (m, 1H), 6.57-6.54 (d, J=11.6 Hz, 1H), 5.18-5.13 (m, 1H), 2.76-2.72 (m, 1H), 2.31-2.24 (m, 1H), 1.08-1.06 (m, 1H), 1.03-0.88 (m, 1H).

(E)-2-(2-fluorostyryl)cyclopropan-1-amine Hydrochloride (120)

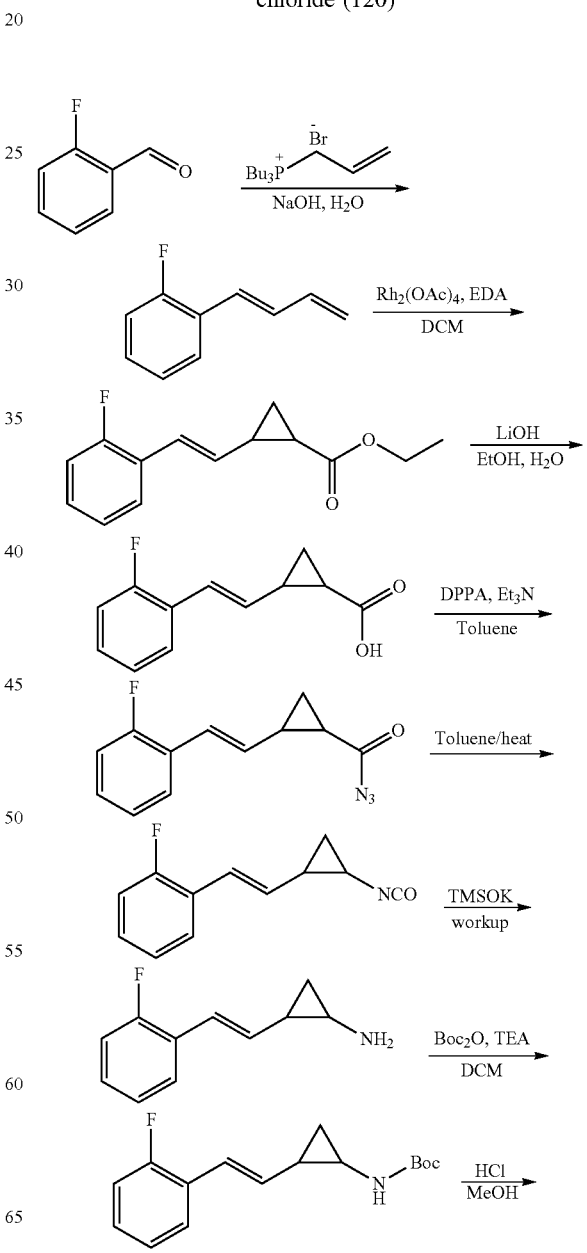

-continued

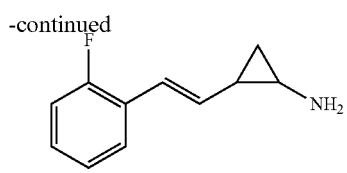

Step 1: Synthesis of Allyltributylphosphonium Bromide

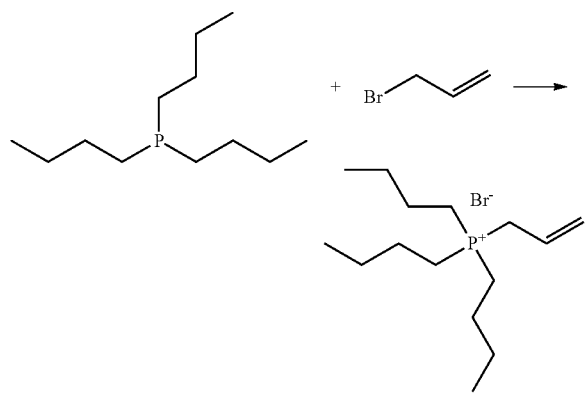

To a mixture of tributylphosphine (20.00 g, 98.85 mmol, 1.00 eq) in DCM (30.00 mL) was added 3-bromoprop-1-ene (13.16 g, 108.74 mmol, 1.10 eq) at 0° C. under $N_2$. The mixture was stirred at 0° C. for 0.5 h and then warmed to room temperature and stirred for 10 h. The mixture was concentrated to afford crude allyltributylphosphonium bromide (32.00 g, 98.98 mmol) as a white solid.

Step 2: Synthesis of (E)-1-(buta-1,3-dien-1-yl)-2-fluorobenzene

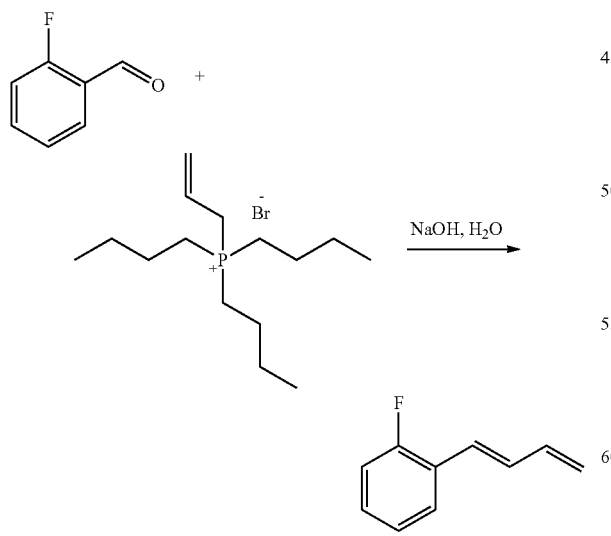

To a mixture of allyltributylphosphonium bromide (28.65 g, 88.63 mmol, 1.10 eq) in water (30.00 mL) was added NaOH (12.89 g, 322.28 mmol, 4.00 eq) at 0° C. The mixture was stirred at 0° C. for 0.5 h before addition of 2-fluorobenzaldehyde (10.00 g, 80.57 mmol, 1.00 eq). The mixture was warmed to room temperature and stirred for 0.5 h. This mixture was then heated to 70° C.-80° C. and stirred for 2 h. The reaction mixture was diluted with water (100 mL), extracted with DCM (20 mL*3), and the combined organics phase dried over $Na2SO_4$, filtered, and concentrated. The crude residue was purified by column chromatography (SiO$_2$, DCM:MeOH=1:0) to afford (E)-1-(buta-1,3-dien-1-yl)-2-fluorobenzene (10.00 g, 67.49 mmol, 83.77% yield) as a yellow oil.

Step 3: Synthesis of ethyl (E)-2-(2-fluorostyryl)cyclopropane-1-carboxylate

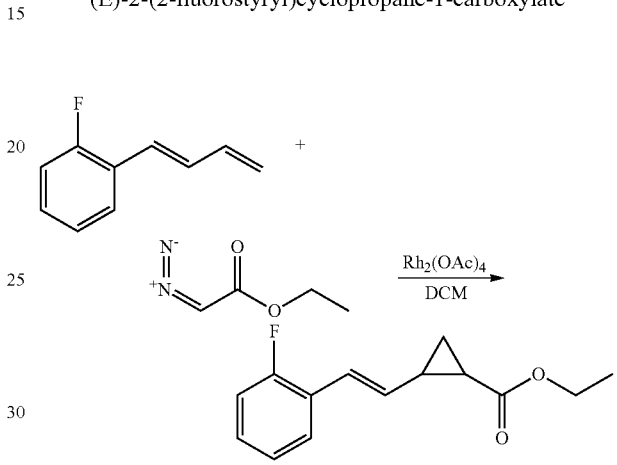

To a solution of (E)-1-(buta-1,3-dien-1-yl)-2-fluorobenzene (11.00 g, 74.23 mmol, 1.00 eq) and $Rh_2(OAc)_4$ (328.09 mg, 742.30 umol, 0.01 eq) in DCM (100.00 mL) was added ethyl 2-diazoacetate (16.94 g, 148.46 mmol, 2.00 eq) dropwise at 0° C. under $N_2$. The reaction mixture was warmed to room temperature and stirred for 20 h. The reaction mixture was concentrated. The crude residue was purified by column chromatography (SiO$_2$, petroleum ether/ethyl acetate=100:1 to 50:1) to afford ethyl (E)-2-(2-fluorostyryl)cyclopropane-1-carboxylate (10.00 g, 42.69 mmol, 57.51% yield) as a yellow oil.

Step 4: Synthesis of (E)-2-(2-fluorostyryl)cyclopropane-1-carboxylic Acid

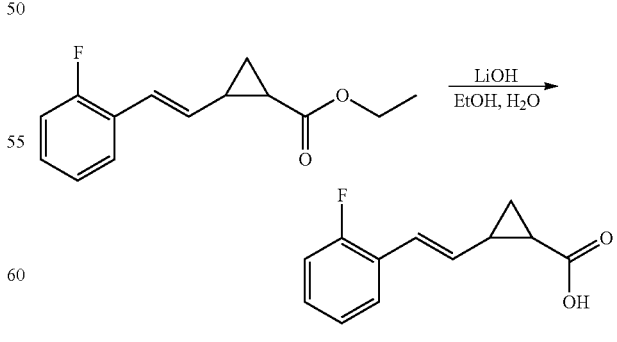

A mixture of ethyl (E)-2-(2-fluorostyryl)cyclopropane-1-carboxylate (10.00 g, 42.69 mmol, 1.00 eq), lithium hydroxide monohydrate (8.96 g, 213.45 mmol, 5.00 eq), MeOH (20.00 mL), and water (10.00 mL) was stirred at 60° C. for 8 h. The methanol was removed in vacuo and the residual aqueous layer was diluted with water (20 mL) before being acidified to pH=3-4 with aqueous HCl solution (4N, 40 mL). The acidified aqueous phase was extracted with ethyl acetate (30 mL*3). The combined organics layer was washed with saturated brine (20 mL), dried over anhydrous sodium sulfate, and concentrated to afford (E)-2-(2-fluorostyryl) cyclopropane-1-carboxylic acid (4.20 g, 20.37 mmol, 47.72% yield) as a yellow solid.

Step 5: Synthesis of (E)-2-(2-fluorostyryl)cyclopropane-1-carbonyl Azide

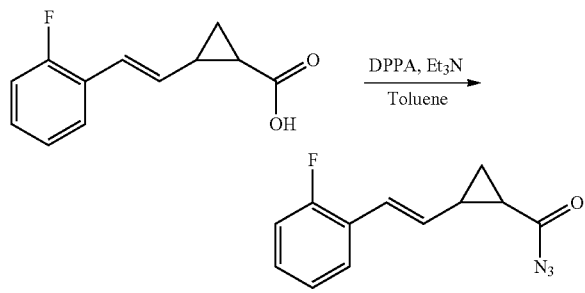

A mixture of the (E)-2-(2-fluorostyryl)cyclopropane-1-carboxylic acid (1.80 g, 8.73 mmol, 1.00 eq), triethylamine (1.32 g, 13.09 mmol, 1.50 eq) and diphenylphosphoryl azide (2.88 g, 10.47 mmol, 1.20 eq) in toluene (10.00 mL) was stirred at room temperature for 8 h. The mixture was concentrated. The crude residue was purified by column chromatography (SiO$_2$, petroleum ether/ethyl acetate=50:1 to 10:1) to afford (E)-2-(2-fluorostyryl)cyclopropane-1-carbonyl azide (1.20 g, 5.19 mmol, 59.46% yield) as a yellow oil.

Step 6: Synthesis of (E)-2-(2-fluorostyryl)cyclopropan-1-amine

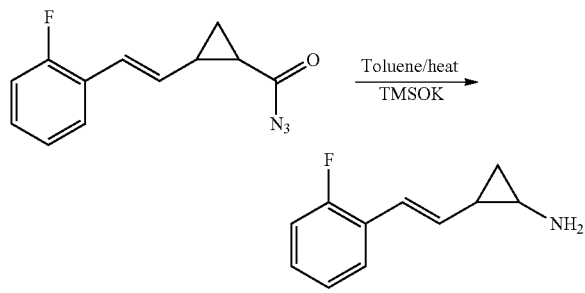

A solution (E)-2-(2-fluorostyryl)cyclopropane-1-carbonyl azide (1.20 g, 5.19 mmol, 1.00 eq) dissolved in toluene (10.00 mL) was stirred at 100° C. for 2 h. The solution was cooled to room temperature before addition of potassium triethylsilanolate (732.41 mg, 5.71 mmol, 1.10 eq). The mixture was stirred at room temperature for 2 h. The reaction mixture was diluted with water (30 mL), extracted with ethyl acetate (20 mL*2), and the combined organics layer dried over Na$_2$SO$_4$, filtered, and concentrated to afford crude (E)-2-(2-fluorostyryl)cyclopropan-1-amine (800.00 mg) as a yellow solid.

Step 7: Synthesis of tert-butyl (E)-(2-(2-fluorostyryl)cyclopropyl)carbamate

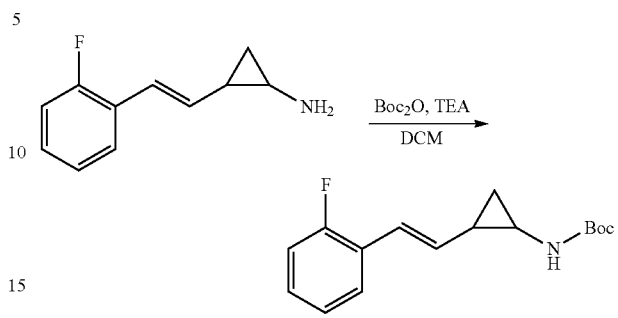

A mixture of (E)-2-(2-fluorostyryl)cyclopropan-1-amine (800.00 mg, 3.74 mmol, 1.00 eq), triethylamine (1.14 g, 11.23 mmol, 3.00 eq), and Boc$_2$O (1.63 g, 7.49 mmol, 2.00 eq) in DCM (30.00 mL) was stirred at room temperature for 8 h. The reaction mixture was concentrated to afford crude residue. The crude residue was purified by column chromatography (silica, petroleum ether/ethyl acetate=100:1 to 50:1) to afford tert-butyl (E)-(2-(2-fluorostyryl)cyclopropyl) carbamate (600.00 mg, 2.16 mmol, 57.69% yield) as a yellow oil.

Synthesis of (E)-2-(2-fluorostyryl)cyclopropan-1-amine Hydrochloride

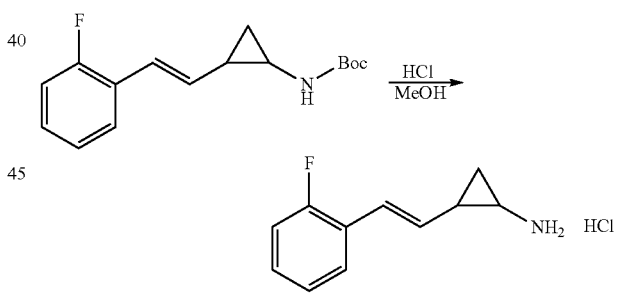

A mixture of tert-butyl (E)-(2-(2-fluorostyryl)cyclopropyl) carbamate (20.00 mg, 72.12 umol, 1.00 eq) dissolved in methanolic HCl (4 M, 10.00 mL, 554.63 eq) was stirred at room temperature for 2 h. The mixture was concentrated. The crude residue was purified by prep-HPLC to afford (E)-2-(2-fluorostyryl)cyclopropan-1-amine hydrochloride (1.80 mg) as a red oil. LCMS (M+H$^+$) m/z: 178. $^1$H NMR (400 MHz, METHANOL-d$_4$) δ=7.50 (q, J=7.9 Hz, 1H), 7.39-7.28 (m, 1H), 7.28-7.18 (m, 1H), 7.18-6.98 (m, 1H), 6.55 (d, J=11.5 Hz, 1H), 5.35-5.23 (m, 1H), 2.83-2.72 (m, 1H), 2.22-2.09 (m, 1H), 1.36-1.22 (m, 1H), 1.11 (q, J=6.5 Hz, 1H).

Compound 129: 4-(2-(2-aminocyclopropyl)prop-1-en-1-yl)benzonitrile Hydrochloride

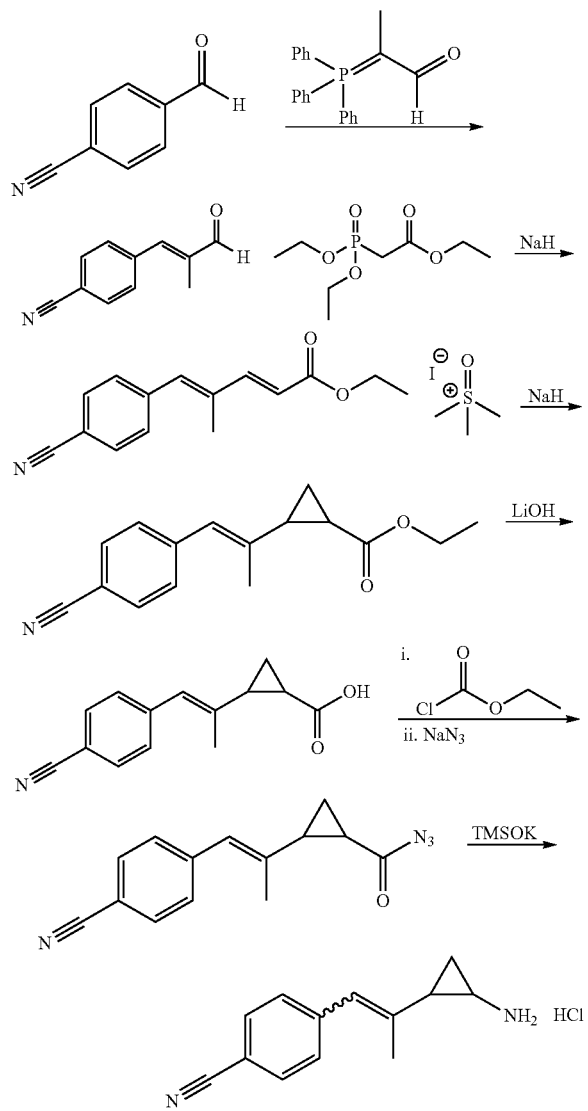

Step 1: (E)-4-(2-methyl-3-oxoprop-1-en-1-yl)benzonitrile

To a resealable vial was added 4-formylbenzonitrile (2.8 g, 21.3 mmol), 2-(triphenylphosphoranylidene)propanal (6.78 g, 21.3 mmol), and toluene (24 mL). The vial was sealed and the solution was heated to 100° C. overnight. The solution was cooled to room temperature and concentrated. The crude residue was purified via Biotage to afford (E)-4-(2-methyl-3-oxoprop-1-en-1-yl)benzonitrile (3.50 g, 20.4 mmol). LCMS 172.

Step 2: ethyl (2E,4E)-5-(4-cyanophenyl)-4-methylpenta-2,4-dienoate

To a round bottomed flask was added ethyl 2-(diethoxyphosphoryl)acetate (9.14 g, 40.8 mmol), THF, and sodium hydride (2.43 g, 61.1 mmol). The solution was stirred at room temperature for 30 min before addition of (E)-4-(2-methyl-3-oxoprop-1-en-1-yl)benzonitrile (3.5 g, 20.4 mmol). The reaction was stirred until complete as judged by LCMS. The solution was diluted with water and extracted with EtOAc. The combined organics phase was washed with water, brine, dried over $Na_2SO_4$, filtered, and concentrated. The crude material was purified via Biotage to afford (2E,4E)-ethyl 5-(4-cyanophenyl)-4-methylpenta-2,4-dienoate (2.15 g, 8.94 mmol). LCMS 242.

Step 3: ethyl (E)-2-(1-(4-cyanophenyl)prop-1-en-2-yl)cyclopropane-1-carboxylate To a round bottomed flask was added sodium hydride (373 mg, 9.36 mmol), DMSO, and trimethylsulfoxonium iodide (2.16 g, 9.86 mmol). The solution was stirred at room temperature for 30 min before addition of (2E,4E)-ethyl 5-(4-cyanophenyl)-4-methylpenta-2,4-dienoate (1.19 g, 4.93 mmol). The reaction was stirred at room temperature for 5 h before diluting with water and extracting with hexanes. The organics layer was washed with water, brine, dried over $Na_2SO_4$, filtered, and concentrated. The crude residue was purified via Biotage to afford (E)-ethyl 2-(1-(4-cyanophenyl)prop-1-en-2-yl)cyclopropanecarboxylate (540 mg, 2.11 mmol). LCMS 256.

Step 4: (E)-2-(1-(4-cyanophenyl)prop-1-en-2-yl)cyclopropane-1-carboxylic Acid To a round bottomed flask was added (E)-ethyl 2-(1-(4-cyanophenyl)prop-1-en-2-yl)cyclopropanecarboxylate (540 mg, 2.11 mmol), MeOH:THF:water (2:2:1), and lithium hydroxide (151 mg, 6.32 mmol). The solution was stirred at room temperature for 3 h before diluting with water and acidifying to pH=2-3 with HCl (1N). The solution was extracted with EtOAc and the combined organics layer was washed with water, brine, dried over $Na_2SO_4$, filtered, and concentrated to afford (E)-2-(1-(4-cyanophenyl)prop-1-en-2-yl)cyclopropanecarboxylic acid (456 mg, 2.00 mmol). LCMS 228.

Step 5: (E)-2-(1-(4-cyanophenyl)prop-1-en-2-yl)cyclopropane-1-carbonyl Azide To a round bottomed flask was added (E)-2-(1-(4-cyanophenyl)prop-1-en-2-yl)cyclopropanecarboxylic acid (499 mg, 2.19 mmol), acetone, triethylamine (664 mg, 6.57 mmol), and the solution cooled to 0° C. To this reaction was added ethyl carbonochloridate (260 mg, 2.40 mmol) and the solution stirred until complete conversion of the acid to the mixed anhydride was observed via LCMS (~1 h). To this solution was added sodium azide (427 mg, 6.57 mmol) dissolved in the minimal amount of water and the reaction stirred at room temperature until complete conversion to the acyl azide was observed. The solution was diluted with water and extracted with EtOAc. The combined organics layer was washed with water, brine, dried over $Na_2SO_4$, filtered, and concentrated to afford crude (E)-2-(1-(4-cyanophenyl)prop-1-en-2-yl)cyclopropanecarbonyl azide.

Step 6: 4-(2-(2-aminocyclopropyl)prop-1-en-1-yl)benzonitrile Hydrochloride

To a round bottomed flask was added (E)-2-(1-(4-cyanophenyl)prop-1-en-2-yl)cyclopropanecarbonyl azide (549 mg, 2.18 mmol) and toluene. The solution was heated to 105° C. for 2 h before cooling to room temperature and addition of potassium trimethylsilanolate (838 mg, 6.54 mmol) dissolved in THF. The solution was stirred at room temperature for 1 h before the solution was extracted with DCM. The combined organics phase was dried over Na₂SO₄, filtered, and concentrated. The crude residue was purified via Biotage to afford the freebased cyclopropylamine. This material was taken up in dioxane and treated with hydrogen chloride (545 µL, 2.18 mmol) and concentrated to afford 4-(2-(2-aminocyclopropyl)prop-1-en-1-yl)benzonitrile hydrochloride (88 mg). LCMS 199

The following examples were synthesized following the procedures outlined above using the appropriate starting materials and modifications.

Step 1: tert-butyl (4-((2-(1-(4-cyanophenyl)prop-1-en-2-yl)cyclopropyl)amino)cyclohexyl)carbamate To a round bottomed flask was added tert-butyl (4-oxo-cyclohexyl)carbamate (66 mg, 309 µmol), (E)-4-(2-(2-aminocyclopropyl)prop-1-en-1-yl)benzonitrile hydrochloride (65 mg, 276 µmol), and DCM. The solution was stirred at room temperature for 5 min before addition of sodium triacetoxyborohydride (87.5 mg, 413 µmol). The solution was stirred at room temperature for 1 h before diluting MeOH and letting stir at room tempertaure for 30 min. The solution was concentrated and the crude residue was purified via Biotage to afford two isomers. Isomer A: 25 mg, LCMS 395. Isomer B: 36 mg, LCMS 395.

Step 2: 4-(2-(2-(((cis)-4-aminocyclohexyl)amino)cyclopropyl)prop-1-en-1-yl)benzonitrile Dihydrochloride (Racemic)

To a round bottomed flask was added isomer A (25 mg, 63.2 µmol), dioxane, and hydrogen chloride (79.0 µL, 316

| Cmpd. | Structure/name | 1H NMR | LCMS |
|---|---|---|---|
| 130 | (trans)-2-((E)-1-(4-methoxyphenyl)prop-1-en-2-yl)cyclopropan-1-amine 2,2,2-trifluoroacetate (racemic) | ¹H NMR (400 MHz, DMSO-d₆) δ 8.16 (br. s., 2H), 7.13-7.19 (m, 2H), 6.86-6.92 (m, 2H), 6.28 (s, 1H), 3.70-3.76 (m, 3H), 2.66-2.75 (m, 1H), 1.84-1.91 (m, 1H), 1.72 (d, J = 1.22 Hz, 3H), 1.09-1.17 (m, 1H), 1.02-1.08 (m, 1H) | 187 |

Compound 131 and Compound 132: 4-(2-(2-(((cis)-4-aminocyclohexyl)amino)cyclopropyl)prop-1-en-1-yl)benzonitrile Dihydrochloride (Racemic) and 4-(2-(2-(((trans)-4-aminocyclohexyl)amino)cyclopropyl)prop-1-en-1-yl)benzonitrile Dihydrochloride (Racemic)

µmol). The solution was then heated to 40° C. overnight. The solution was concentrated and the crude residue was purified via trituration to afford 4-(2-(2-(((cis)-4-aminocyclohexyl)amino)cyclopropyl)prop-1-en-1-yl)benzonitrile dihydrochloride (2.5 mg). LCMS=296. Isomer B was processed following the procedure for Isomer A.

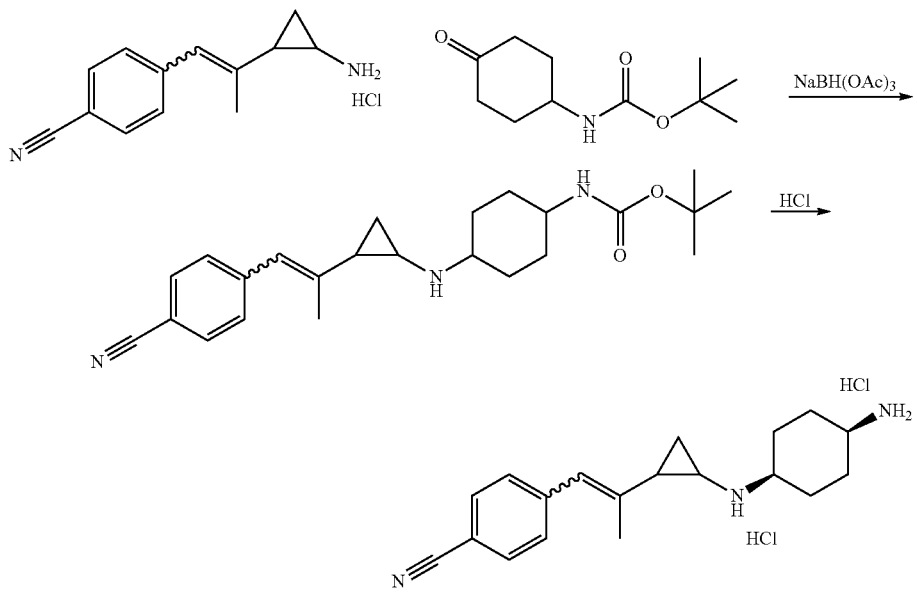

| Cmp. | Structure/Name | 1H NMR | LCMS |
|---|---|---|---|
| 132 | 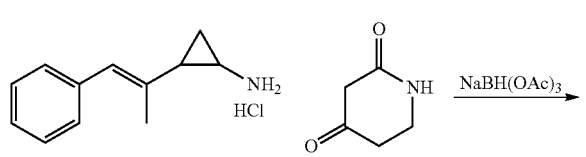<br>4-(2-(2-(((trans)-4-aminocyclohexyl)amino)cyclopropyl)prop-1-en-1-yl)benzonitrile dihydrochloride (racemic) | $^1$H NMR (400 MHz, DMSO-d$_6$) δ = 8.72 (br. s., 1 H), 8.51 (br. s., 1 H), 8.12 (br. s., 3 H), 7.86 (d, J = 8.5 Hz, 2 H), 7.54 (d, J = 8.1 Hz, 2 H), 5.71 (br. s., 1 H), 4.21-4.10 (m, 1 H), 4.05 (d, J = 8.3 Hz, 1 H), 2.89 (br. s., 1 H), 2.78 (br. s., 1 H), 2.73-2.63 (m, 1 H), 2.58-2.52 (m, 1 H), 2.17-2.06 (m, 1 H), 1.97 (br. s., 2H), 1.88-1.78 (m, 1 H), 1.51 (s, 3 H), 1.48-1.39 (m, 1 H), 1.38-1.20 (m, 1 H) | 296 |

Compound 133: (E)-4-((2-(1-phenylprop-1-en-2-yl)cyclopropyl)amino)piperidin-2-one 2,2,2-trifluoroacetate

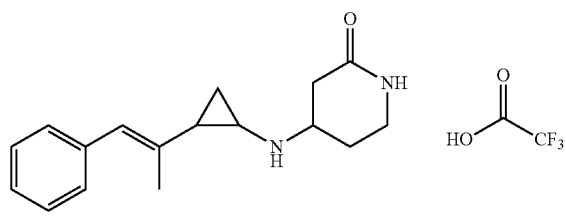

To a round bottomed flask was added (E)-2-(1-phenyl-prop-1-en-2-yl)cyclopropanamine hydrochloride (50 mg, 0.2384 mmol), piperidine-2,4-dione (32.3 mg, 0.2860 mmol), and DCM. To this solution was added sodium triacetoxyhydroborate (151 mg, 0.7152 mmol). The solution was stirred at room temperature for 30 min before concentrating. The crude residue was purified via HPLC to afford (E)-4-((2-(1-phenylprop-1-en-2-yl)cyclopropyl)amino)piperidin-2-one 2,2,2-trifluoroacetate (1.3 mg). LCMS 271.

Compound 134: 3-((4-(((trans)-2-((E)-1-phenylprop-1-en-2-yl)cyclopropyl)amino)piperidin-1-yl)methyl)pyridin-2(1H)-one bis(2,2,2-trifluoroacetate) (Racemic)

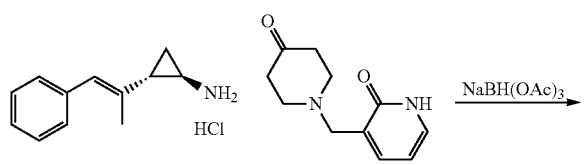

-continued

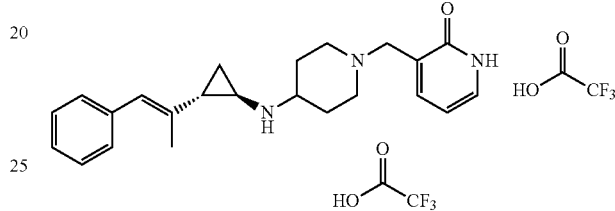

To a round bottomed flask was added (trans)-2-((E)-1-phenylprop-1-en-2-yl)cyclopropanamine hydrochloride (112 mg, 536 µmol), 3-((4-oxopiperidin-1-yl)methyl)pyridin-2(1H)-one (133 mg, 644 µmol), and DCM. The solution was stirred at room temperature for 5 min before addition of sodium triacetoxyborohydride (113 mg, 536 µmol). The solution was stirred at room temperature for 1 h before diluting with MeOH and concentrating. The crude residue was purified via reverse phase HPLC to afford 3-((4-(((trans)-2-((E)-1-phenylprop-1-en-2-yl)cyclopropyl)amino)piperidin-1-yl)methyl)pyridin-2(1H)-one bis(2,2,2-trifluoroacetate) (32.7 mg, 55.2 LCMS 364. $^1$H NMR (400 MHz, DMSO-d$_6$) δ=12.10 (br. s., 1H), 10.07-9.66 (m, 1H), 9.45 (br. s., 2H), 7.70 (d, J=5.9 Hz, 1H), 7.55 (d, J=5.4 Hz, 1H), 7.39-7.28 (m, 2H), 7.27-7.16 (m, 3H), 6.36 (s, 1H), 6.30 (t, J=6.6 Hz, 1H), 4.07 (br. s., 2H), 3.56-3.41 (m, 2H), 3.08 (t, J=11.7 Hz, 1H), 2.91 (br. s., 1H), 2.33-2.12 (m, 2H), 2.09-2.00 (m, 1H), 1.95-1.78 (m, 2H), 1.75 (s, 3H), 1.23 (t, J=6.7 Hz, 2H).

The following examples were prepared according to the General procedure for the alkylation of cyclopropylamines using aldehydes and ketones and purified using by silica gel chromatography (methanol:ethyl acetate gradient). The compounds were subsequently converted to bis-hydrochloric salts by the addition of hydrogen chloride (2M in diethyl ether, 2.5 equiv.).

| Cmp. | Structure and name | ¹H-NMR | MS (M + H) |
|---|---|---|---|
| 135 | 3-(4-((((trans)-2-((E)-1-phenylprop-1-en-2-yl)cyclopropyl)amino)methyl)piperidin-1-yl)propanenitrile dihydrochloride (racemic) •2HCl | ¹H NMR (400 MHz, DMSO-d6) δ 10.99 (br. s., 1H), 9.46 (br. s., 2H), 7.29-7.38 (m, 2H), 7.16-7.27 (m, 3H), 6.37 (s, 1H), 3.35-3.61 (m, 4H), 3.16 (br. s., 2H), 2.75-3.05 (m, 5H), 2.22 (br. s., 1H), 1.90-2.12 (m, 3H), 1.78 (s, 3H), 1.41-1.71 (m, 2H), 1.30-1.39 (m, 1H), 1.11-1.24 (m, 1H). | 324.3 |
| 136 | N-methyl-4-((4-(((trans)-2-((E)-1-phenylprop-1-en-2-yl)cyclopropyl)amino)piperidin-1-yl)methyl)benzamide dihydrochloride (racemic) •2HCl | ¹H NMR (400 MHz, DMSO-d6) δ 10.97 (br. s., 1H), 9.75 (br. s., 2H), 8.48-8.58 (m, 2H), 7.90 (d, J = 8.30 Hz, 2H), 7.67 (d, J = 8.06 Hz, 2H), 7.28-7.36 (m, 2H), 7.15-7.25 (m, 3H), 6.35 (s, 1H), 4.30 (br. s., 2H), 3.57-3.68 (m, 1H), 3.16-3.32 (m, 1H), 3.00 (d, J = 10.50 Hz, 2H), 2.86 (br. s., 1H), 2.79 (d, J = 4.39 Hz, 3H), 2.24-2.35 (m, 2H), 1.97-2.19 (m, 3H), 1.75 (d, J = 1.22 Hz, 3H), 1.25-1.33 (m, 1H), 1.16-1.24 (m, 1H) | 404.2 |
| 137 | 4-((4-(((trans)-2-((E)-1-phenylprop-1-en-2-yl)cyclopropyl)amino)piperidin-1-yl)methyl)benzamide dihydrochloride (racemic) •2HCl | ¹H NMR (400 MHz, DMSO-d6) δ 11.07 (br. s., 1H), 9.80 (br. s., 2H), 8.06 (br. s., 1H), 7.89-7.96 (m, 2H), 7.67 (d, J = 8.30 Hz, 2H), 7.47 (s, 1H), 7.29-7.36 (m, 2H), 7.13-7.27 (m, 3H), 6.35 (s, 1H), 4.31 (d, J = 4.39 Hz, 2H), 3.33-3.39 (m, 1H), 3.24 (br. s., 1H), 2.92-3.07 (m, 2H), 2.85 (br. s., 1H), 2.30 (br. s., 2H), 1.98-2.21 (m, 3H), 1.75 (d, J = 0.98 Hz, 3H), 1.26-1.33 (m, 1H), 1.16-1.25 (m, 1H) | 390.2 |

The following examples were prepared according to the General procedure for the alkylation of cyclopropylamines using aldehdyes and ketones, using racemic 2-((E)-1-phenylprop-1-en-2-yl)cyclopropanamine as the amine. The compounds were separated using preparative HPLC (SunFire C18 OBD column 5 μm (19×100 mm), 5% to 50% acetonitrile in water gradient over 9 minutes, 0.1% trifluoroacetic acid as phase modifier) to afford two sets of fractions, one early eluting (HPLC fraction A), one later eluting (HPLC fraction B)

| Cmpd. | HPLC fraction | Structure and name | $^1$H-NMR | MS (M + H) |
|---|---|---|---|---|
| 138 | A | 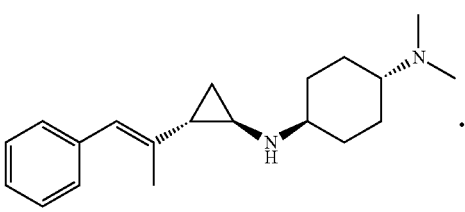<br>(trans)-N$^1$,N$^1$-dimethyl-N$^4$-((trans)-2-((E)-1-phenylprop-1-en-2-yl)cyclopropyl)cyclohexane-1,4-diamine<br>(racemic)<br>•2TFA | $^1$H NMR (400 MHz, METHANOL-d4) δ 7.28-7.35 (m, 2H), 7.14-7.24 (m, 3H), 6.43 (s, 1H), 4.88 (s, 6H), 3.33-3.40 (m, 1H), 3.30 (br. s., 1H), 2.90-2.96 (m, 1H), 2.36-2.45 (m, 2H), 2.20-2.29 (m, 2H), 2.05-2.12 (m, 1H), 1.83 (d, J = 1.70 Hz, 3H), 1.48-1.77 (m, 5H), 1.31-1.38 (m, 1H), 1.22-1.31 (m, 1H) | 299.2 |
| 139 | A | 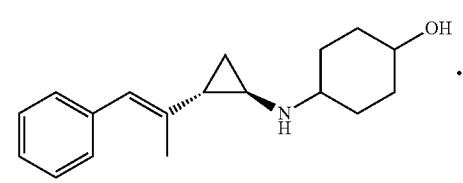<br>4-(((trans)-2-((E)-1-phenylprop-1-en-2-yl)cyclopropyl)amino)cyclohexanol-trifluoroacetic acid salt, diastereomer A<br>(racemic)<br>•TFA | 1H NMR (400 MHz, DMSO-d6) δ 8.47-9.07 (m, 2H), 7.29-7.40 (m, 2H), 7.12-7.27 (m, 3H), 6.38 (s, 1H), 4.72 (br. s, 1H), 3.35 (d, J = 6.35 Hz, 1H), 3.04-3.19 (m, 1H), 2.78-2.94 (m, 1H), 1.95-2.12 (m, 3H), 1.84-1.93 (m, 2H), 1.74 (d, J = 0.98 Hz, 3H), 1.29-1.44 (m, 2H), 1.08-1.28 (m, 4H) | 272.2 |
| 140 | B | 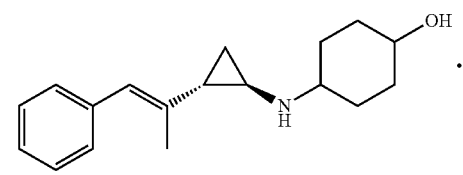<br>4-(((trans)-2-((E)-1-phenylprop-1-en-2-yl)cyclopropyl)amino)cyclohexanol trifluoroacetic acid salt, diastereomer B<br>(racemic)<br>•TFA | 1H NMR (400 MHz, DMSO-d6) δ 8.64 (d, J = 18.68 Hz, 2H), 7.31-7.40 (m, 2H), 7.13-7.29 (m, 3H), 6.39 (s, 1H), 4.53 (br. s, 1H), 3.82 (br. s., 1H), 3.12-3.22 (m, 2H), 2.92 (br. s., 1H), 1.92-2.07 (m, 2H), 1.63-1.86 (m, 7H), 1.41-1.52 (m, 2H), 1.11-1.29 (m, 2H). | 272.2 (M + H) |
| 141 | A | 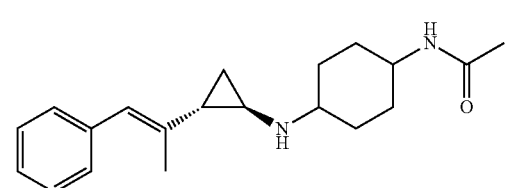<br>N-(4-(((trans)-2-((E)-1-phenylprop-1-en-2-yl)cyclopropyl)amino)cyclohexyl)acetamide trifluoroacetic acid salt, diastereomer A<br>(racemic)<br>•TFA | 1H NMR (400 MHz, DMSO-d6) δ 8.68-9.07 (m, 2H), 7.80 (d, J = 7.81 Hz, 1H), 7.29-7.38 (m, 2H), 7.15-7.27 (m, 3H), 6.39 (s, 1H), 3.38-3.53 (m, 2H), 3.10-3.24 (m, 1H), 2.80-2.97 (m, 1H), 2.07-2.17 (m, 2H), 2.02 (ddd, J = 3.66, 6.35, 9.77 Hz, 1H), 1.87 (d, J = 10.74 Hz, 2H), 1.77 (s, 3H), 1.75 (s, 3H), 1.41 (q, J = 12.61 Hz, 2H), 1.11-1.29 (m, 3H) | 313.2 (M + H)/ 335.2 (M + Na) |

| Cmpd. | HPLC fraction | Structure and name | $^1$H-NMR | MS (M + H) |
|---|---|---|---|---|
| 142 | B | N-(4-(((trans)-2-((E)-1-phenylprop-1-en-2-yl)cyclopropyl)amino)cyclohexyl)acetamide trifluoroacetic acid salt, diastereomer B (racemic) | $^1$H NMR (400 MHz, DMSO-d6) δ 8.72-8.96 (m, 2H), 7.72 (d, J = 5.86 Hz, 1H), 7.30-7.40 (m, 2H), 7.14-7.28 (m, 3H), 6.37 (s, 1H), 3.71 (br. s., 2H), 3.17-3.29 (m, 1H), 2.83-2.96 (m, 1H), 2.02 (m, 1H), 1.62-1.93 (m, 11H), 1.46-1.60 (m, 2H), 1.11-1.33 (m, 2H). | 313.2 (M + H)/ 335.2 (M + Na) |

The following examples were prepared according to the following procedure:

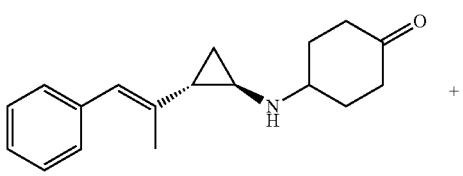

+

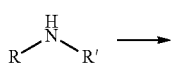

→

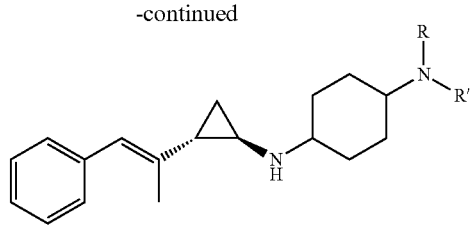

Mixture of diastereomers, separated by preparative HPLC 4-(((trans)-2-((E)-1-phenylprop-1-en-2-yl)cyclopropyl)amino)cyclohexan-1-one (1 equiv.) was dissolved in 1,2-DCE, amine added (1.2 equiv.) followed by sodium triacetoxyborohydride. The isomers were separated using preparative HPLC (SunFire C18 OBD column 5 μm (19× 100 mm), 5% to 50% acetonitrile in water gradient over 9 minutes, 0.1% trifluoroacetic acid as phase modifier) to afford to sets of fractions, one early eluting (HPLC fraction A), one later eluting (HPLC fraction B).

| Cmpd. | HPLC fraction | Structure and name | $^1$H-NMR | MS (ESI+) |
|---|---|---|---|---|
| 143 | A | (trans)-N1-(2-methoxyethyl)-N4-((trans)-2-((E)-1-phenylprop-1-en-2-yl)cyclopropyl)cyclohexane-1,4-diamine bis(trifluoroacetic acid salt) (racemic) | $^1$H NMR (400 MHz, DMSO-d6) δ 8.79-9.09 (m, 2H), 8.57 (br. s., 2H), 7.27-7.39 (m, 2H), 7.14-7.27 (m, 3H), 6.38 (s, 1H), 3.57 (t, J = 5.01 Hz, 2H), 3.31 (s, 3H), 2.79-3.20 (m, 5H), 2.09-2.26 (m, 4H), 1.95-2.04 (m, 1H), 1.74 (d, J = 0.98 Hz, 3H), 1.02-1.56 (m, 6H). | 329 (M + H) |
| 144 | B | (cis)-N1-(2-methoxyethyl)-N4-((trans)-2-((E)-1-phenylprop-1-en-2-yl)cyclopropyl)cyclohexane-1,4-diamine bis(trifluoroacetic acid) salt | $^1$H NMR (400 MHz, DMSO-d6) δ 8.79-9.09 (m, 2H), 8.49-8.61 (m, 2H), 7.29-7.37 (m, 2H), 7.15-7.25 (m, 3H), 6.37 (s, 1H), 3.55-3.62 (m, 2H), 3.31 (d, J = 0.73 Hz, 3H), 2.88-3.27 (m, 6H), 1.91-2.15 (m, 3H), 1.79-1.88 (m, 5H), 1.75 (s, | 329 (M + H) |

| Cmpd. | HPLC fraction | Structure and name | ¹H-NMR | MS (ESI+) |
|---|---|---|---|---|
| | | (racemic) | 3H), 1.15-1.33 (m, 2H). | |
| 276 | A | N-methyl-4-(((trans)-4-(((trans)-2-((E)-1-phenylprop-1-en-2-yl)cyclopropyl)amino)cyclohexyl)amino)butanamide bis(trifluoroacetic acid) salt (racemic) •2TFA | ¹H NMR (400 MHz, DMSO-d6) δ 8.78-9.03 (m, 2H), 8.54 (br. s., 2H), 7.85-7.94 (m, 1H), 7.31-7.39 (m, 2H), 7.24 (m, 3H), 6.39 (s, 1H), 3.99-4.16 (m, 1H), 3.57 (s, 2H), 3.18-3.27 (m, 2H), 3.00-3.11 (m, 1H), 2.93 (br. s., 3H), 2.58 (d, J = 4.64 Hz, 3H), 1.96-2.23 (m, 5H), 1.79-1.83 (m, 1H), 1.75 (s, 3H), 1.14-1.46 (m, 6H). | 370 (M + H) |
| 145 | B | N-methyl-4-(((cis)-4-(((trans)-2-((E)-1-phenylprop-1-en-2-yl)cyclopropyl)amino)cyclohexyl)amino)butanamide bis(trifluoroacetic acid) salt (racemic) •2TFA | ¹H NMR (400 MHz, DMSO-d6) δ 8.86-9.09 (m, 2H), 8.61 (br. s., 2H), 7.88-7.98 (m, 1H), 7.29-7.38 (m, 2H), 7.09-7.27 (m, 3H), 6.38 (s, 1H), 3.24 (br. s., 2H), 2.96 (br. s., 3H), 2.57 (d, J = 4.64 Hz, 3H), 2.16-2.26 (m, 2H), 2.06 (br. s., 1H), 1.93 (br. s., 2H), 1.78-1.87 (m, 6H), 1.76 (s, 3H), 1.16-1.34 (m, 2H) | 370 (M + H) |
| 146 | A | 3-(((trans)-4-(((trans)-2-((E)-1-phenylprop-1-en-2-yl)cyclopropyl)amino)cyclohexyl)amino)-1-(pyrrolidin-1-yl)propan-1-one bis(trifluoroacetic acid) salt (racemic) •2TFA | ¹H NMR (400 MHz, METHANOL-d4) δ 7.29-7.37 (m, 2H), 7.17-7.27 (m, 3H), 6.44 (s, 1H), 3.40-3.53 (m, 5H), 3.35 (t, J = 6.04 Hz, 2H), 3.15-3.29 (m, 2H), 2.91-2.98 (m, 1H), 2.77 (t, J = 6.00 Hz, 2H), 2.28-2.45 (m, 4H), 1.87-2.14 (m, 6H), 1.84 (d, J = 1.10 Hz, 3H), 1.50-1.67 (m, 4H), 1.33-1.41 (m, 1H), 1.21-1.30 (m, 1H) | 396 (M + H) |
| 147 | B | 3-(((cis)-4-(((trans)-2-((E)-1-phenylprop-1-en-2- •2TFA | ¹H NMR (400 MHz, METHANOL-d4) δ 7.28-7.35 (m, 2H), 7.14-7.27 (m, 3H), 6.44 (s, 1H), 3.40-3.59 (m, 7H), 3.36 (s, 2H), 2.92-3.00 (m, 1H), 2.82 (t, J = 6.00 Hz, 2H), 1.97-2.19 (m, 11H), 1.92 (s, 2H), 1.84 (d, J = 1.32 Hz, 3H), 1.23-1.43 (m, 3H) | 396 (M + H) |

| Cmpd. | HPLC fraction | Structure and name | ¹H-NMR | MS (ESI+) |
|---|---|---|---|---|
| | | yl)cyclopropyl)amino)cyclohexyl)amino)-1-(pyrrolidin-1-yl)propan-1-one bis(trifluoroacetic acid) salt (racemic) | | |
| 148 | A | 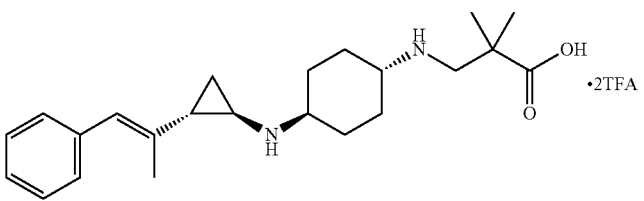 [SMILES: C/C(=C\c1ccccc1)[C@@H]1C[C@H]1N[C@H]1CC[C@H](NCC(C)(C)C(=O)O)CC1]<br>2,2-dimethyl-3-(((trans)-4-(((trans)-2-((E)-1-phenylprop-1-en-2-yl)cyclopropyl)amino)cyclohexyl)amino)propanoic acid bis(trifluoroacetic acid) salt (racemic) | ¹H NMR (400 MHz, DMSO-d6) δ 12.88 (br. s, 1H), 8.92 (br. s., 2H), 8.31 (br. s., 2H), 7.31-7.38 (m, 2H), 7.19-7.27 (m, 2H), 6.39 (s, 1H), 3.21 (br. s., 2H), 3.07 (br. s., 3H), 2.92 (br. s., 2H), 2.20 (d, J = 9.77 Hz, 3H), 1.97-2.08 (m, 2H), 1.76 (d, J = 1.22 Hz, 3H), 1.36-1.53 (m, 4H), 1.25-1.29 (m, 1H), 1.22 (s, 6H) 36/36 | 371.2 (M + H) |
| 149 | B | 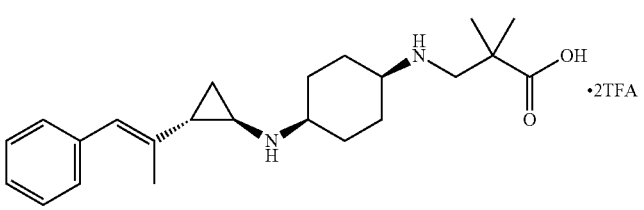 [SMILES: C/C(=C\c1ccccc1)[C@@H]1C[C@H]1N[C@H]1CC[C@@H](NCC(C)(C)C(=O)O)CC1]<br>2,2-dimethyl-3-(((cis)-4-(((trans)-2-((E)-1-phenylprop-1-en-2-yl)cyclopropyl)amino)cyclohexyl)amino)propanoic acid bis(trifluoroacetic acid) salt (racemic) | ¹H NMR (400 MHz, DMSO-d6) δ 13.04 (br. s, 1H), 8.95 (br. s, 2H), 8.33 (br. s., 2H), 7.28-7.41 (m, 2H), 7.17-7.28 (m, 3H), 6.39 (s, 1H), 3.43-3.56 (m, 2H), 3.16-3.30 (m, 2H), 3.04-3.11 (m, 2H), 2.93-3.02 (m, 1H), 2.00-2.15 (m, 3H), 1.79-1.93 (m, 5H), 1.76 (d, J = 1.22 Hz, 3H), 1.26-1.31 (m, 1H), 1.24 (s, 6H) | 371.2 (M + H) |
| 150 | A | 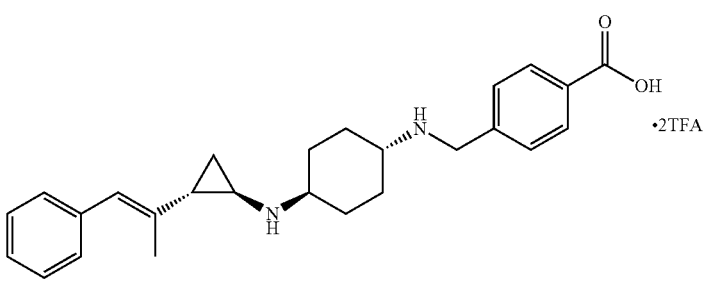 [SMILES: C/C(=C\c1ccccc1)[C@@H]1C[C@H]1N[C@H]1CC[C@H](NCc2ccc(C(=O)O)cc2)CC1]<br>4-((((trans)-4-(((trans)-2-((E)-1-phenylprop-1-en-2-yl)cyclopropyl)amino)cyclohexyl)amino)methyl)benzoic acid bis(trifluoroacetic acid) salt (racemic) | ¹H NMR (400 MHz, DMSO-d6) δ 12.93 (br. s, 1H), 8.92 (br. s., 3H), 8.02 (d, J = 8.30 Hz, 2H), 7.62 (d, J = 7.81 Hz, 2H), 7.31-7.42 (m, 2H), 7.09-7.29 (m, 3H), 6.41 (s, 1H), 4.17-4.33 (m, 2H), 2.82-3.27 (m, 5H), 2.12-2.31 (m, 3H), 1.97-2.10 (m, 1H), 1.78-1.95 (m, 1H), 1.73 (s, 3H), 1.32-1.53 (m, 3H), 1.11-1.31 (m, 2H) | 405.2 (M + H) |
| 151 | A | 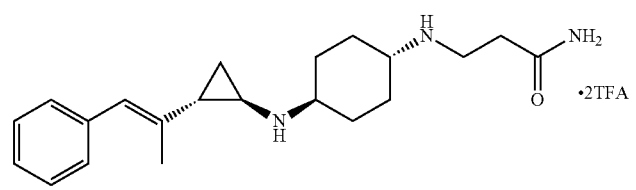 [SMILES: C/C(=C\c1ccccc1)[C@@H]1C[C@H]1N[C@H]1CC[C@H](NCCC(N)=O)CC1]<br>3-(((trans)-4-(((trans)-2-((E)-1-phenylprop-1-en-2-yl)cyclopropyl)amino)cyclohexyl)amino)propanamide bis(trifluoroacetic acid) salt (racemic) | ¹H NMR (400 MHz, DMSO-d6) δ 8.89-9.09 (m, 2H), 8.47 (br. s., 2H), 7.58 (br. s., 1H), 7.31-7.38 (m, 2H), 7.17-7.26 (m, 3H), 7.12 (br. s., 1H), 6.38 (s, 1H), 3.12 (m, 5H), 2.07-2.30 (m, 4H), 1.94-2.07 (m, 2H), 1.75 (d, J = 1.22 Hz, 3H), 1.40 (m, 4H), 1.23 (m, 3H). | 342.2 (M + H) |

-continued

| Cmpd. | HPLC fraction | Structure and name | ¹H-NMR | MS (ESI+) |
|---|---|---|---|---|
| 152 | B | 3-(((cis)-4-(((trans)-2-((E)-1-phenylprop-1-en-2-yl)cyclopropyl)amino)cyclohexyl)amino) propanamide bis(trifluoroacetic acid) salt (racemic) | ¹H NMR (400 MHz, DMSO-d6) δ 8.94-9.19 (m, 2H), 8.57 (br. s., 2H), 7.64 (br. s., 1H), 7.29-7.37 (m, 2H), 7.18-7.25 (m, 3H), 7.15 (br. s., 1H), 6.38 (s, 1H), 2.91-3.45 (m, 6H), 2.52 (t, J = 6.96 Hz, 2H), 2.04-2.13 (m, 1H), 1.78-2.02 (m, 8H), 1.75 (d, J = 1.22 Hz, 3H), 1.25 (t, J = 6.90 Hz, 1H) | 342.2 (M + H) |
| 153 | A | 2-(((trans)-4-(((trans)-2-((E)-1-phenylprop-1-en-2-yl)cyclopropyl)amino)cyclohexyl)amino) ethan-1-ol bis(trifluoroacetic acid) salt (racemic) | ¹H NMR (400 MHz, DMSO-d6) δ 8.93-9.11 (m, 2H), 8.54 (br. s., 2H), 7.28-7.39 (m, 2H), 7.15-7.26 (m, 3H), 6.38 (s, 1H), 5.29 (br. s., 1H), 3.65 (br. s., 2H), 3.01 (m, 5H), 2.15 (br. s., 4H), 1.95-2.10 (m, 2H), 1.75 (d, J = 1.22 Hz, 2H), 1.40 (t, J = 8.79 Hz, 4H), 1.16-1.27 (m, 2H) | 315.2 (M + H) |
| 154 | B | 2-(((cis)-4-(((trans)-2-((E)-1-phenylprop-1-en-2-yl)cyclopropyl)amino)cyclohexyl)amino) ethan-1-ol bis(trifluoroacetic acid) salt (racemic) | | 315.2 (M + H) |
| 155 | A | 3-(((trans)-4-(((trans)-2-((E)-1-phenylprop-1-en-2-yl)cyclopropyl)amino)cyclohexyl)amino) propanenitrile bis(trifluoroacetic acid) salt (racemic) | ¹H NMR (400 MHz, DMSO-d6) δ 8.88-9.06 (m, 2H), 8.84 (br. s., 2H), 7.30-7.40 (m, 2H), 7.12-7.28 (m, 3H), 6.39 (s, 1H), 3.35-3.40 (m, 1H), 3.12-3.28 (m, 2H), 3.01-3.11 (m, 1H), 2.83-2.97 (m, 3H), 2.07-2.23 (m, 4H), 1.97-2.05 (m, 1H), 1.75 (d, J = 1.22 Hz, 3H), 1.31-1.43 (m, 3H), 1.10-1.30 (m, 3H). | 324.2 (M + H) |
| 156 | B | 3-(((cis)-4-(((trans)-2-((E)-1-phenylprop-1-en-2-yl)cyclopropyl)amino)cyclohexyl)amino) propanenitrile bis(trifluoroacetic acid) salt (racemic) | ¹H NMR (400 MHz, DMSO-d6) δ 8.76-9.14 (m, 4H), 7.29-7.39 (m, 2H), 7.14-7.25 (m, 3H), 6.38 (s, 1H), 3.41 (br. s., 2H), 3.23-3.31 (m, 2H), 2.77-3.03 (m, 4H), 2.01-2.13 (m, 1H), 1.80-2.00 (m, 7H), 1.75 (d, J = 0.98 Hz, 3H), 1.14-1.33 (m, 2H). | 324.2 (M + H) |

The following examples were prepared using the following procedure:

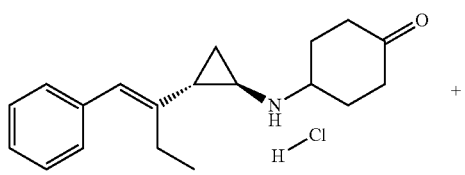

+

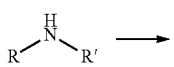

→

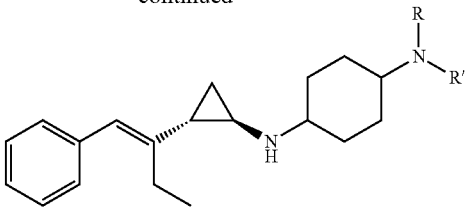

Mixture of diastereomers, separated by preparative HPLC 4-(((trans)-2-((E)-1-phenylbut-1-en-2-yl)cyclopropyl)amino)cyclohexanone hydrochloride (1 equiv.) was dissolved in 1,2-DCE, amine added (1.2 equiv.), followed by sodium triacetoxyborohydride (2.5 to 3 equiv.). The isomers were separated using preparative HPLC (SunFire C18 ODB column (19×100 mm), 5% to 50% acetonitrile in water gradient over 9 minutes, 0.1% trifluoroacetic acid as phase modifier) to afford to sets of fractions, one early eluting (HPLC fraction A), one later eluting (HPLC fraction B).

| Cmpd. | HPLC fraction | Structure and name | $^1$H-NMR | MS (M + H) |
|---|---|---|---|---|
| 157 | A | 2,2-dimethyl-3-(((trans)-4-(((trans)-2-((E)-1-phenylbut-1-en-2-yl)cyclopropyl)amino)cyclohexyl)amino)propanenitrile bis(trifluoroacetic acid salt) (racemic) •2TFA | $^1$H NMR (400 MHz, DMSO-d6) δ 9.11 (br. s., 1H), 8.93 (br. s., 1H), 8.84 (br. s., 2H), 7.29-7.38 (m, 2H), 7.10-7.27 (m, 3H), 6.22 (s, 1H), 3.03-3.30 (m, 5H), 2.88 (br. s., 1H), 2.11-2.30 (m, 5H), 1.99 (br. s., 1H), 1.34-1.55 (m, 9H), 1.15-1.31 (m, 3H), 1.02-1.13 (m, 3H). | 366.3 (M + H) |
| 158 | B | 2,2-dimethyl-3-(((cis)-4-(((trans)-2-((E)-1-phenylbut-1-en-2-yl)cyclopropyl)amino)cyclohexyl)amino)propanenitrile bis(trifluoroacetic acid salt) (racemic) •2TFA | $^1$H NMR (400 MHz, DMSO-d6) δ 8.85-9.00 (br. s., 4H), 7.28-7.40 (m, 2H), 7.13-7.26 (m, 3H), 6.23 (s, 1H), 3.49 (br. s., 1H), 3.27 (br. s., 4H), 2.84-3.04 (m, 1H), 2.25 (q, J = 7.32 Hz, 2H), 2.07 (m, 2H), 1.82 (br. s., 6H), 1.37-1.52 (m, 5H), 1.16-1.32 (m, 3H), 1.11 (t, J = 7.57 Hz, 3H) | 366.3 (M + H) |
| 159 | A | 2-(((trans)-4-(((trans)-2-((E)-1-phenylbut-1-en-2-yl)cyclopropyl)amino)cyclohexyl)amino)ethan-1-ol bis(trifluoroacetic acid salt) (racemic) •2TFA | $^1$H NMR (400 MHz, DMSO-d6) δ 9.02 (br. s., 1H), 8.85 (br. s., 1H), 8.49 (br. s., 2H), 7.30-7.40 (m, 2H), 7.07-7.26 (m, 3H), 6.22 (s, 1H), 5.23-5.34 (m, 1H), 3.57-3.71 (m, 2H), 3.10-3.27 (m, 2H), 2.93-3.10 (m, 3H), 2.80-2.93 (m, 1H), 2.04-2.30 (m, 5H), 1.89-2.01 (m, 1H), 1.31-1.47 (m, 4H), 1.14-1.28 (m, 2H), 1.11 (t, J = 7.45 Hz, 3H), 34/34 | 329.2 (M + H) |

| Cmpd. | HPLC fraction | Structure and name | ¹H-NMR | MS (M + H) |
|---|---|---|---|---|
| | | | LCMS: Rt = 3.121 min., MS (ESI+): 357.2 (M + H), | |
| 160 | A | 4-methoxy-6-methyl-3-((((trans)-4-(((trans)-2-((E)-1-phenylbut-1-en-2-yl)cyclopropyl)amino)cyclohexyl)amino)methyl)pyridin-2(1H)-one bis(trifluoroacetic acid salt) (racemic) •2TFA | ¹H NMR (400 MHz, DMSO-d6) δ 11.82 (s, 1H), 8.97-9.10 (m, 1H), 8.78-8.91 (m, 1H), 8.38 (br. s, 1H), 7.35 (s, 2H), 7.10-7.28 (m, 3H), 6.47-6.64 (m, 1H), 6.23 (s, 2H), 3.87-3.92 (m, 1H), 3.86 (s, 3H), 2.78-3.30 (m, 6H), 2.25-2.29 (m, 1H), 2.23 (s, 3H), 2.14-2.22 (m, 3H), 1.93-2.02 (m, 1H), 1.31-1.52 (m, 4H), 1.17-1.28 (m, 2H), 1.12 (t, J = 7.57 Hz, 3H). | 436.2 (M + H) |
| 161 | A | (3-((((trans)-4-(((trans)-2-((E)-1-phenylbut-1-en-2-yl)cyclopropyl)amino)cyclohexyl)amino)methyl)oxetan-3-yl)methanolbis(trifluoroacetic acid salt) (racemic) •2TFA | ¹H NMR (400 MHz, DMSO-d6) δ 9.08-9.18 (m, 1H), 8.88-9.00 (m, 1H), 8.25-8.47 (m, 2H), 7.28-7.37 (m, 2H), 7.09-7.28 (m, 3H), 6.18-6.26 (m, 1H), 5.27-5.36 (m, 1H), 4.34-4.38 (m, 2H), 4.29-4.33 (m, 2H), 3.66-3.74 (m, 2H), 3.27-3.32 (m, 2H), 2.99-3.25 (m, 3H), 2.82-2.92 (m, 1H), 2.11-2.28 (m, 6H), 1.95-2.02 (m, 1H), 1.35-1.50 (m, 4H), 1.22-1.29 (m, 1H), 1.15-1.21 (m, 1H), 1.11 (t, J = 7.45 Hz, 2H) 38H/38H | 385.3 (M + H) |
| 162 | A | 2-(2-(((trans)-4-(((trans)-2-((E)-1-phenylbut-1-en-2-yl)cyclopropyl)amino)cyclohexyl)amino)ethoxy)acetic acidbis(trifluoroacetic acid salt) (racemic) •2TFA | ¹H NMR (500 MHz, DMSO-d6) δ 12.59-13.11 (m, 1H), 8.86-9.01 (m, 1H), 8.72-8.83 (m, 1H), 8.40-8.62 (m, 2H), 7.28-7.39 (m, 2H), 7.12-7.27 (m, 3H), 6.22 (s, 1H), 4.11 (s, 2H), 3.69-3.76 (m, 2H), 3.03-3.23 (m, 5H), 2.85-2.93 (m, 1H), 2.11-2.29 (m, 5H), 1.93-1.99 (m, 1H), 1.33-1.45 (m, 4H), 1.16-1.26 (m, 2H), 1.11 (t, J = 7.48 Hz, 3H) | 387.3 (M + H) |

The following compounds were prepared according to the following procedure:

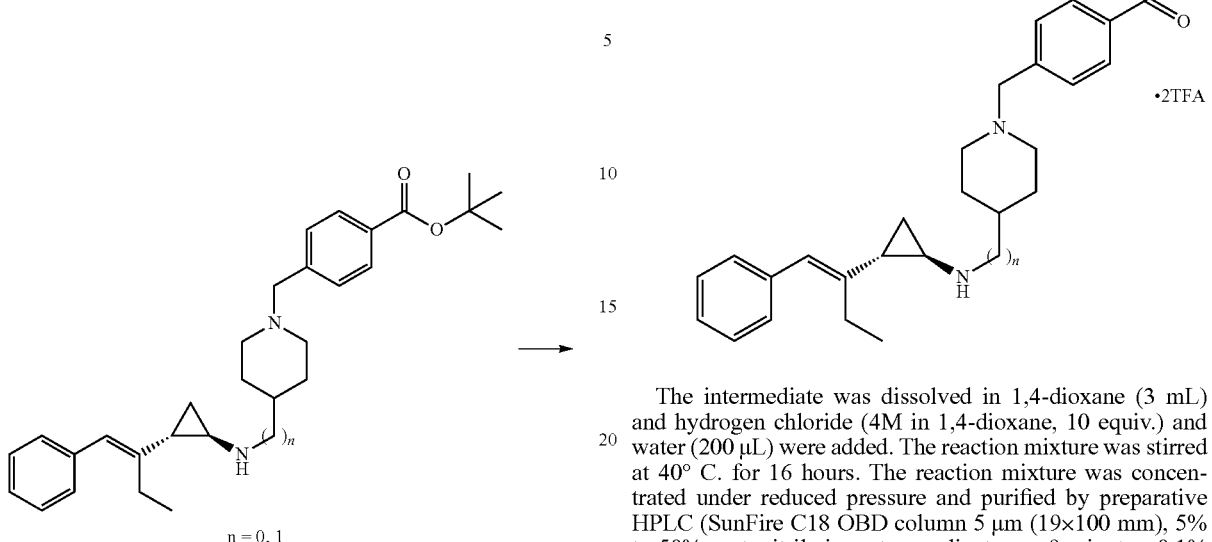

n = 0, 1

The intermediate was dissolved in 1,4-dioxane (3 mL) and hydrogen chloride (4M in 1,4-dioxane, 10 equiv.) and water (200 μL) were added. The reaction mixture was stirred at 40° C. for 16 hours. The reaction mixture was concentrated under reduced pressure and purified by preparative HPLC (SunFire C18 OBD column 5 μm (19×100 mm), 5% to 50% acetonitrile in water gradient over 9 minutes, 0.1% trifluoroacetic acid as phase modifier).

| Cmpd. | Intermediate | Example | | MS (ESI+) |
|---|---|---|---|---|
| 163 | tert-butyl 4-((4-((((trans)-2-((E)-1-phenylbut-1-en-2-yl)cyclopropyl)amino)methyl)piperidin-1-yl)methyl)benzoate | 4-((4-((((trans)-2-((E)-1-phenylbut-1-en-2-yl)cyclopropyl)amino)methyl)piperidin-1-yl)methyl)benzoic acid bis trifluoroacetic acid salt (racemic) | | 1H NMR (400 MHz, DMSO-d6) δ 13.19 (br.s, 1H), 9.74 (br. s., 1H), 9.03 (br. s., 1H), 8.90 (br. s., 1H), 8.03 (d, J = 8.30 Hz, 2H), 7.62 (d, J = 8.06 Hz, 2H), 7.31-7.38 (m, 2H), 7.14-7.27 (m, 3H), 6.22 (s, 1H), 4.37 (br. s., 2H), 2.82-3.27 (m, 5H), 2.21-2.29 (m, 2H), 1.76-2.11 (m, 4H), 1.32-1.49 (m, 2H), 1.21-1.29 (m, 1H), 1.15-1.20 (m, 1H), 1.12 (t, J = 7.57 Hz, 3H) | 419.3 (M + H) |
| 128 | tert-butyl 4-((4-(((trans)-2-((E)-1-phenylbut-1-en-2-yl)cyclopropyl)amino)piperidin-1-yl)methyl)benzoate | 4-((4-(((trans)-2-((E)-1-phenylbut-1-en-2-yl)cyclopropyl)amino)piperidin-1-yl)methyl)benzoic acid bis-trifluoroacetic acid salt (racemic) | | 1H NMR (400 MHz, DMSO-d6) δ 13.14 (br. s, 1H), 9.92 (br. s, 1H), 8.88-9.32 (m, 2H), 7.86-8.08 (m, 2H), 7.50-7.73 (m, 2H), 7.29-7.41 (m, 2H), 7.02-7.27 (m, 3H), 6.22 (s, 1H), 4.37 (br. s., 2H), 2.81-3.09 (m, 3H), 1.54-2.37 (m, 8H), 1.18 (d, J = 6.84 Hz, 2H), 0.92-1.14 (m, 4H), 34/34 | 405 (M + H) |

Compound 164 and Compound 165 Synthesis of 4-(((trans)-4-(((trans)-2-((E)-1-phenylprop-1-en-2-yl)cyclopropyl)amino)cyclohexyl)amino)butanoic Acid bis(trifluoroacetic Acid) Salt (Racemic) and 4-(((cis)-4-(((trans)-2-((E)-1-phenylprop-1-en-2-yl)cyclopropyl)amino)cyclohexyl)amino)butanoic Acid bis(trifluoroacetic Acid) Salt (Racemic)

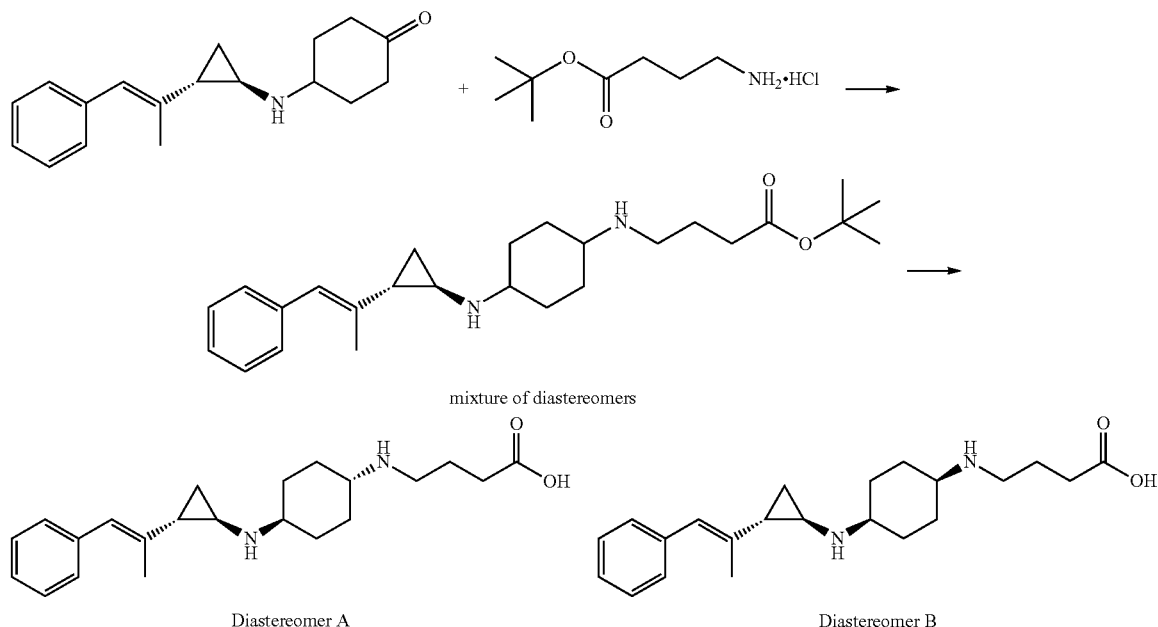

Step 1: tert-butyl 4-((4-(((trans)-2-(E)-1-phenyl-prop-1-en-2-yl)cyclopropyl)amino)cyclohexyl)amino)butanoate (Mixture of Diastereomers)

To 4-(((trans)-2-((E)-1-phenylprop-1-en-2-yl)cyclopropyl)amino)cyclohexanone (132 mg, 490 μmol) and tert-butyl 4-aminobutanoate hydrochloride (119 mg, 612 μmol) in 1,2-dichloroethane (4 mL) was added sodium (triacetoxy) borohydride (207 mg, 0.980 mmol). After 30 min, methylene chloride and potassium carbonate (1M aqueous) were added. The organic phase was isolated, evaporated and the crude residue purified by column chromatography (24 g silica, 0% to 10% methanol in EtOAc) to afford a mixture of two diastereomers of tert-butyl 4-((4-(((trans)-2-((E)-1-phenylprop-1-en-2-yl)cyclopropyl)amino)cyclohexyl)amino) butanoate (85.0 mg, 213 μmol) in 42% yield as a mixture of stereoisomers. LCMS (ESI+): 412.8 (M+H).

Step 2: 4-(((trans)-4-(((trans)-2-((E)-1-phenylprop-1-en-2-yl)cyclopropyl)amino)cyclohexyl)amino) butanoic Acid bis(trifluoroacetic Acid) Salt (Racemic) and 4-(((cis)-4-(((trans)-2-((E)-1-phenylprop-1-en-2-yl)cyclopropyl)amino)cyclohexyl)amino) butanoic Acid bis(trifluoroacetic Acid) Salt (Racemic)

To tert-butyl 4-((4-(((trans)-2-(E)-1-phenylprop-1-en-2-yl)cyclopropyl)amino)cyclohexyl)amino)butanoate (85 mg, 206 μmol) was dissolved in 1,4-dioxane (1 mL) and hydrogen chloride (4M in 1,4-dioxane, 200 μL, 800 μmol) was added, followed by addition of water (100 μL). The reaction mixture was stirred at 40° C. for 16 hours. The mixture was separated by preparative HPLC (SunFire C18 OBD column 5 μm (19×100 mm), 5% to 50% acetonitrile in water gradient over 9 minutes, 0.1% trifluoroacetic acid as phase modifier) to afford two sets of fractions containing isomeric products, one early eluting and one late eluting.

The first eluting fractions were frozen and lyophilized diastereomer A of racemic 4-(((trans)-4-(((trans)-2-((E)-1-phenylprop-1-en-2-yl)cyclopropyl)amino)cyclohexyl) amino)butanoic acid bis(trifluoroacetic acid) salt (18.0 mg, 30.7 μmol) in 28% yield. 1H NMR (400 MHz, DMSO-d6) δ 12.28 (br. s, 1H), 8.96 (br. s, 2H), 8.49 (br. s, 2H), 7.29-7.39 (m, 2H), 7.16-7.27 (m, 3H), 6.38 (s, 1H), 2.73-3.23 (m, 6H), 2.30-2.39 (m, 2H), 2.08-2.25 (m, 4H), 1.98-2.06 (m, 1H), 1.76-1.86 (m, 3H), 1.75 (d, J=0.98 Hz, 2H), 1.32-1.47 (m, 3H), 1.13-1.29 (m, 2H). LCMS (ESI+): 357.3 (M+H).

The second eluting set of fractions were frozen and lyophilized diastereomer A of racemic 4-(((cis)-4-(((trans)-2-((E)-1-phenylprop-1-en-2-yl)cyclopropyl)amino)cyclohexyl)amino)butanoic acid bis(trifluoroacetic acid) salt (34.0 mg, 58.1 μmol) in 15% yield. $^1$H NMR (400 MHz, DMSO-d6) δ 12.19-12.41 (m, 1H), 8.88 (br. s., 2H), 8.46 (br. s., 2H), 7.30-7.40 (m, 2H), 7.14-7.27 (m, 3H), 6.39 (s, 1H), 3.42 (br. s., 2H), 3.26 (br. s., 2H), 2.97 (br. s., 3H), 2.37 (t, J=7.20 Hz, 2H), 2.07 (s, 1H), 1.95 (d, J=5.37 Hz, 2H), 1.79-1.89 (m, 6H), 1.76 (d, J=1.22 Hz, 3H), 1.15-1.32 (m, 2H). LCMS (ESI+): 357.3 (M+H).

Compound 166: 4-((4-(((trans)-2-((E)-1-phenylprop-1-en-2-yl)cyclopropyl)amino)piperidin-1-yl)methyl) benzoic Acid bis(trifluoroacetic Acid) Salt (Racemic)

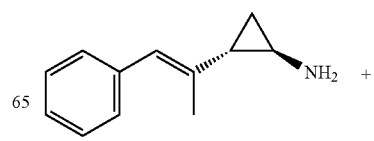

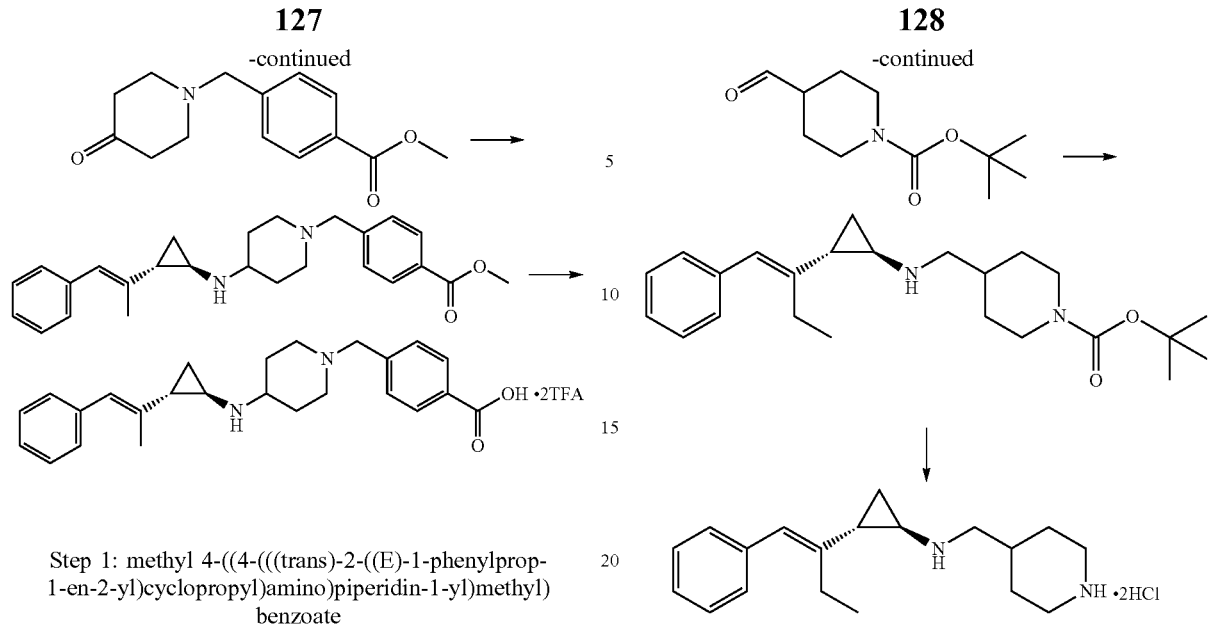

Step 1: methyl 4-((4-(((trans)-2-((E)-1-phenylprop-1-en-2-yl)cyclopropyl)amino)piperidin-1-yl)methyl)benzoate To racemic (trans)-2-((E)-1-phenylprop-1-en-2-yl)cyclopropan-1-amine (48 mg, 277 µmol) and methyl 4-((4-oxopiperidin-1-yl)methyl)benzoate (68.4 mg, 277 µmol) in 2 mL of 1,2-dichloroethane was added sodium (triacetoxy)borohydride (117 mg, 0.55 mmol). After 30 min, methylene chloride and potassium carbonate (1M aqueous) were added. The organic phase was isolated, evaporated and the crude residue purified by column chromatography (silica, 0% to 10% methanol in EtOAc) to afford methyl 4-((4-(((trans)-2-((E)-1-phenylprop-1-en-2-yl)cyclopropyl)amino)piperidin-1-yl)methyl)benzoate (45.0 mg, 111 µmol) in 40% yield. LCMS (ESI+): 405 (M+H)

Step 2: 4-((4-(((trans)-2-((E)-1-phenylprop-1-en-2-yl)cyclopropyl)amino)piperidin-1-yl)methyl)benzoic Acid bis(trifluoroacetic Acid) Salt (Racemic)

methyl 4-((4-(((trans)-2-((E)-1-phenylprop-1-en-2-yl)cyclopropyl)amino)piperidin-1-yl)methyl)benzoate (45 mg, 111 µmol) was dissolved in tetrahydrofuran:methanol (4:1) and sodium hydroxide (6M aq., 500 µL, 3 mmol) was added. The mixture was stirred for 16 hours. The product was purified by preparative HPLC (SunFire C18 OBD column 5 µm (19×100 mm), 5% to 50% acetonitrile in water gradient over 9 minutes, 0.1% trifluoroacetic acid as phase modifier). The pure fractions were frozen and lyophilized to afford 4-((4-(((trans)-2-((E)-1-phenylprop-1-en-2-yl)cyclopropyl)amino)piperidin-1-yl)methyl)benzoic acid bis(trifluoroacetic acid) salt (2 mg) in 3% yield. LCMS (ESI+): 491.3.

Compound 167: (trans)-2-(1-phenylbut-1-en-2-yl)-N-(piperidin-4-ylmethyl)cyclopropanamine Dihydrochloride (Racemic)

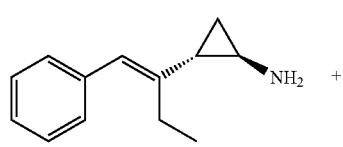

Step 1: tert-butyl 4-((((trans)-2-((E)-1-phenylbut-1-en-2-yl)cyclopropyl)amino)methyl)piperidine-1-carboxylate To the (trans)-2-((E)-1-phenylbut-1-en-2-yl)cyclopropan-1-amine (120 mg, 640 µmol) and tert-butyl 4-formylpiperidine-1-carboxylate (122 mg, 576 µmol) in 1,2-dichloroethane (4 mL) was added sodium (triacetoxy)borohydride (269 mg, 1.27 mmol). After 30 min, methylene chloride and potassium carbonate (1M aqueous) were added to the reaction mixture. The organic phase was evaporated and the crude residue purified by column chromatography (silica, 0% to 10% methanol in EtOAc) to afford tert-butyl 4-((((trans)-2-((E)-1-phenylbut-1-en-2-yl)cyclopropyl)amino)methyl)piperidine-1-carboxylate (75.0 mg, 195 µmol) in 30% yield. LCMS (ESI+): 385 (M+H)

Step 2: (trans)-2-(1-phenylbut-1-en-2-yl)-N-(piperidin-4-ylmethyl)cyclopropanamine Dihydrochloride (Racemic)

tert-butyl 4-((((trans)-2-((E)-1-phenylbut-1-en-2-yl)cyclopropyl)amino)methyl)piperidine-1-carboxylate (75 mg, 195 µmol) was dissolved in 1,4-dioxane, hydrogen chloride (4M in 1,4-dioxane) (42.6 mg, 1.17 mmol) was added, and stirred at 40° C. for 4 hours. MTBE was added to the cooled reaction mixture. The mixture was stirred then sonicated to afford a white suspension. The solid was filtered on a fine (F) fitted funnel and washed with MTBE. The compound was dried under suction and a stream of nitrogen for 15 minutes. The solid was collected, redissolved in Water:ACN mixture (2:1), frozen and lyophilized to afford (trans)-2-(1-phenylbut-1-en-2-yl)-N-(piperidin-4-ylmethyl)cyclopropanamine dihydrochloride (64.0 mg, 179 µmol) as an amorphous solid in 92% yield. $^1$H NMR (400 MHz, DMSO-d6) δ 9.52 (br. s., 2H), 8.73-9.06 (m, 2H), 7.30-7.40 (m, 2H), 7.13-7.28 (m, 3H), 6.21 (s, 1H), 3.13-3.35 (m, 2H), 2.97 (m, 2H), 2.70-2.91 (m, 4H), 2.18-2.29 (m, 2H), 1.78-2.15 (m, 4H), 1.32-1.51 (m, 3H), 1.13 (t, J=7.57 Hz, 3H). LCMS (ESI+): 285.3 (M+H).

Synthesis of tert-butyl ((cis)-4-(((trans)-2-((E)-1-phenylbut-1-en-2-yl)cyclopropyl)amino)cyclohexyl)carbamate (Racemic) and tert-butyl ((trans)-4-(((trans)-2-((E)-1-phenylbut-1-en-2-yl)cyclopropyl)amino)cyclohexyl)carbamate (Racemic)

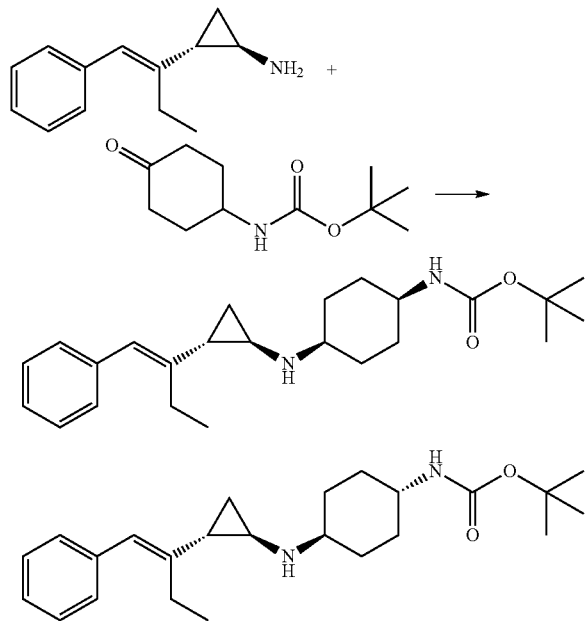

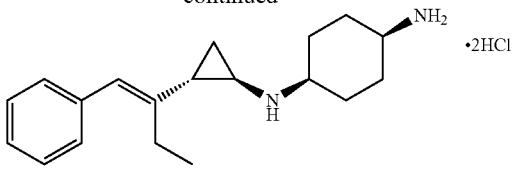

To (trans)-2-((E)-1-phenylbut-1-en-2-yl)cyclopropan-1-amine (120 mg, 640 μmol) and tert-butyl (4-oxocyclohexyl)carbamate (132 mg, 620 μmol) in 1,2-dichloroethane (4 mL) was added sodium (triacetoxy)borohydride (267 mg, 1.27 mmol). After 30 min, potassium carbonate (1M aqueous) and methylene chloride were added. The organic phase was isolated, washed with brine and dried with Na$_2$SO$_4$, filtered and evaporated. The crude residue purified by column chromatography (silica, 0% to 10% methanol in EtOAc) to afford two sets of fractions containing isomeric products, one early eluting and one late eluting.

The first eluting set of fractions was pooled and evaporated to afford tert-butyl ((cis)-4-(((trans)-2-((E)-1-phenyl-but-1-en-2-yl)cyclopropyl)amino)cyclohexyl)carbamate (65.0 mg, 169 μmol), 26% yield. LCMS (ESI+): 385.4 (M+H).

The second eluting set of fractions was pooled and evaporated to afford tert-butyl ((trans)-4-(((trans)-2-(E)-1-phenylbut-1-en-2-yl)cyclopropyl)amino)cyclohexyl)carbamate (43.0 mg, 111 μmol), 17% yield. LCMS (ESI+): 385.4 (M+H).

Compound 168: Synthesis of (cis)-N$^1$-((trans)-2-((E)-1-phenylbut-1-en-2-yl)cyclopropyl)cyclohexane-1,4-diamine Dihydrochloride (Racemic)

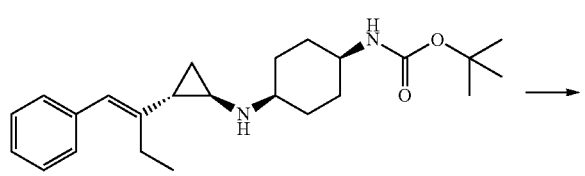

tert-butyl ((cis)-4-(((trans)-2-((E)-1-phenylbut-1-en-2-yl)cyclopropyl)amino)cyclohexyl)carbamate (65 mg, 169 μmol) was dissolved in 1,4-dioxane (1 mL), hydrogen chloride (4M in 1,4-dioxane, 250 μL, 1.01 mmol) was added, and reaction mixture was stirred at 40° C. for 3 hours. MTBE was added to the cooled reaction mixture which was stirred and sonicated to afford a white suspension. Filtered on a fine fitted funnel under suction and the solid cake was washed with MTBE. The compound was dried under vacuum and a stream of nitrogen for 15 minutes. Solid collected, redissolved in Water:ACN (2:1), frozen and lyophilized to afford (cis)-N1-((trans)-2-((E)-1-phenylbut-1-en-2-yl)cyclopropyl)cyclohexane-1,4-diaminedihydrochloride (55.0 mg, 153 μmol) as an amorphous solid, in 91% yield. $^1$H NMR (400 MHz, DMSO-d6) d 9.34-9.58 (m, 2H), 8.14 (br. s., 2H), 7.29-7.43 (m, 2H), 7.12-7.25 (m, 3H), 6.22 (s, 1H), 3.37-3.51 (m, 2H), 3.14-3.35 (m, 2H), 2.79-3.05 (m, 2H), 1.57-2.05 (m, 8H), 1.24-1.46 (m, 2H), 1.15-1.20 (m, 1H), 1.10-1.15 (t, J=7.45 Hz, 3H). LCMS (ESI+): 285.3 (M+H).

Compound 169: (trans)-N$^1$-((trans)-2-((E)-1-phenyl-but-1-en-2-yl)cyclopropyl)cyclohexane-1,4-diamine Dihydrochloride (Racemic)

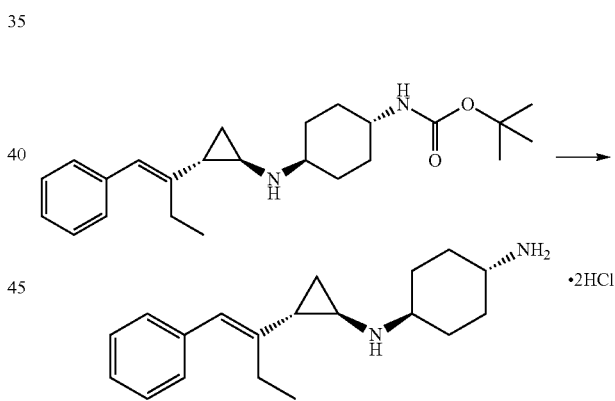

tert-butyl ((trans)-4-(((trans)-2-((E)-1-phenylbut-1-en-2-yl)cyclopropyl)amino)cyclohexyl)carbamate (43 mg, 111 μmol) was dissolved in 1,4-dioxane (1 mL), hydrogen chloride (4M in 1,4-dioxane) (166 μL, 666 μmol) was added, and the reaction mixture was stirred at 40° C. for 16 hours. MTBE was added to the cooled reaction mixture; stirred than sonicated to afford a white suspension. Filtered on a fine fritted funnel, washed with MTBE. The compound was dried under vacuum and a stream of nitrogen for 15 minutes. Solid collected, redissolved in Water:ACN (2:1), frozen and lyophilized to afford (trans)-N$^1$-((trans)-2-(E)-1-phenylbut-1-en-2-yl)cyclopropyl)cyclohexane-1,4-diaminedihydrochloride (32.0 mg, 89.5 μmol) as an amorphous solid, in 81% yield. $^1$H NMR (400 MHz, DMSO-d6) δ 9.33-9.67 (m, 2H), 8.09 (br. s., 3H), 7.30-7.40 (m, 2H), 7.12-7.28 (m, 3H), 6.21 (s, 1H), 3.07-3.22 (m, 1H), 2.90-3.04 (m, 1H), 2.73-

2.84 (m, 1H), 1.81-2.36 (m, 7H), 1.28-1.62 (m, 5H), 0.96-1.22 (m, 4H). LCMS (ESI+): 285 (M+H).

Synthesis of tert-butyl ((cis)-4-(((trans)-2-((E)-1-phenylprop-1-en-2-yl)cyclopropyl)amino)cyclohexyl)carbamate (Racemic) and tert-butyl ((trans)-4-(((trans)-2-((E)-1-phenylprop-1-en-2-yl)cyclopropyl)amino)cyclohexyl)carbamate (Racemic)

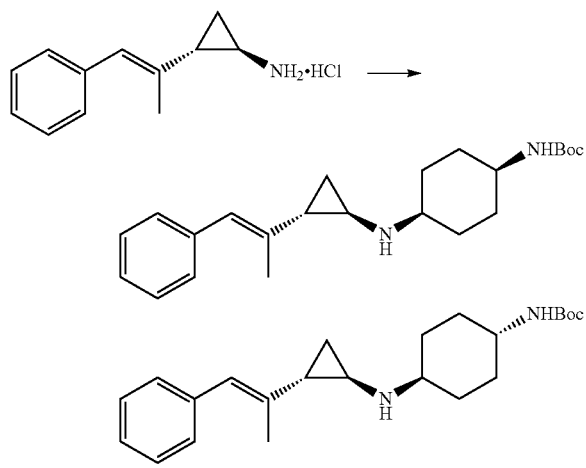

To (trans)-2-((E)-1-phenylprop-1-en-2-yl)cyclopropan-1-amine hydrochloride (1.23 g, 5.86 mmol) and tert-butyl (4-oxocyclohexyl)carbamate (1.24 g, 5.86 mmol) in 1,2-dichloroethane (4 mL) was added sodium (triacetoxy)borohydride (2.47 g, 11.7 mmol). After 30 min, methylene chloride and potassium carbonate (1M aqueous) were added. The organic phase was isolated and evaporated. The crude residue purified by column chromatography (silica, 0% to 10% methanol in EtOAc) to afford two sets of fractions.

The first eluting fractions were pooled and evaporated to afford tert-butyl ((cis)-4-(((trans)-2-((E)-1-phenylprop-1-en-2-yl)cyclopropyl)amino)cyclohexyl)carbamate (630 mg, 1.70 mmol) in 29% yield. LCMS (ESI): 371 (M+H).

The last eluting fractions were pooled and evaporated to afford tert-butyl ((trans)-4-(((trans)-2-((E)-1-phenylprop-1-en-2-yl)cyclopropyl)amino)cyclohexyl)carbamate (970 mg, 2.61 mmol) in 45% yield. LCMS (ESI): 371 (M+H).

Supercritical Fluid Chromatography Separation of tert-butyl ((trans)-4-(((trans)-2-((E)-1-phenylprop-1-en-2-yl)cyclopropyl)amino)cyclohexyl)carbamate The enantiomers of racemic tert-butyl ((trans)-4-(((trans)-2-((E)-1-phenylprop-1-en-2-yl)cyclopropyl)amino)cyclohexyl)carbamate (960 mg, 2.61 mmol) were separated using the following Supercritical Fluid chromatography conditions:

| Column | 2.1 × 25.0 cm Chiralcel OX-H from Chiral Technologies (West Chester, PA) |
|---|---|
| CO2 Co-solvent (Solvent B) | Methanol/Isopropanol (1:1) with 0.25% Isopropylamine |
| Isocratic Method | 12% Co-solvent at 82 g/min |
| System Pressure | 100 bar |
| Column Temperature | 25° C. |
| Sample Diluent | Methanol/Dichloromethane (3:1) |

| | Retention Time | Mass Recovered | % ee |
|---|---|---|---|
| Fraction 1 | 3.0 min | 205.0 mg | 95.5% |
| Fraction 2 | 3.4 min | 147.3 mg | 98.0% |

The collected fractions were dried using a rotary evaporator at 40° C., rinsed with acetonitrile and transferred into the final containers using methanol and methylene chloride. The residues were dissolved in MTBE, converted to hydrochloric salts using hydrogen chloride (4M in 1,4-dioxane, 1.2 equiv.) and evaporated under reduced pressure.

The first eluting fractions afforded tert-butyl ((trans)-4-(((1R,2S)-2-((E)-1-phenylprop-1-en-2-yl)cyclopropyl)amino)cyclohexyl)carbamate hydrochloride (enantiomer A) (205 mg, 0.503 mmol) in 95.5% enantiomeric excess.

The second eluting fractions afforded tort-butyl ((trans)-4-(((1S,2R)-2-((E)-1-phenylprop-1-en-2-yl)cyclopropyl)amino)cyclohexyl)carbamate hydrochloride (enantiomer B) (147 mg, 0.362 mmol) in 98% enantiomeric excess.

Compound 170: Synthesis of (1r,4R)—N1-((1R,2S)-2-((E)-1-phenylprop-1-en-2-yl)cyclopropyl)cyclohexane-1,4-diamine Dihydrochloride (Single Stereoisomer)

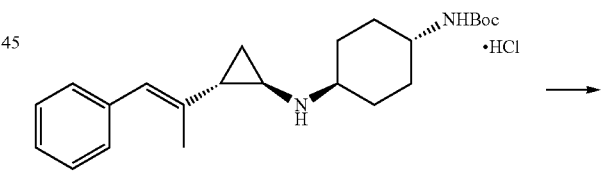

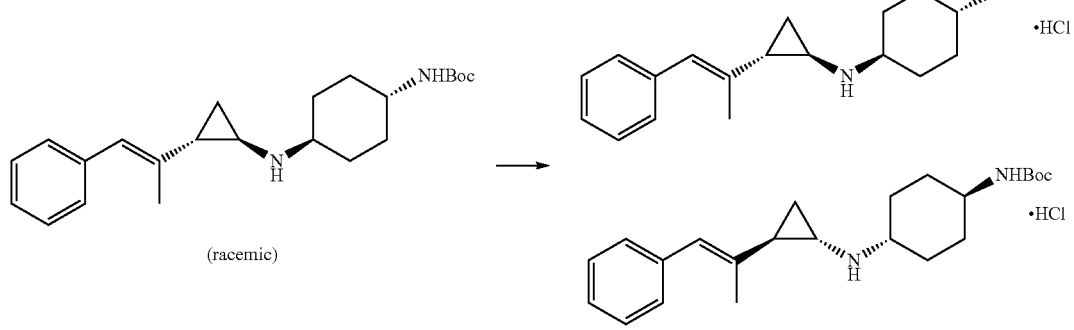

(racemic)

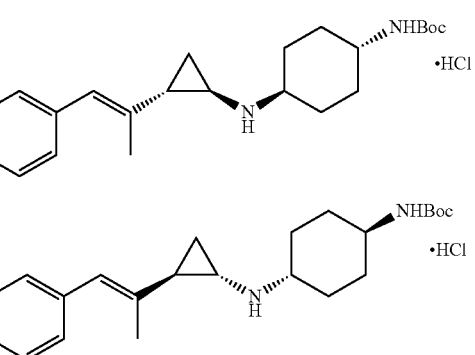

-continued

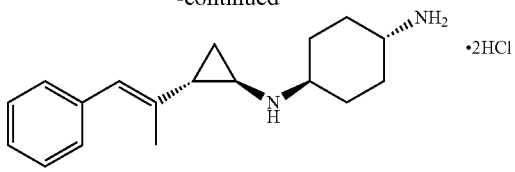

tert-butyl ((trans)-4-((((1R,2S)-2-((E)-1-phenylprop-1-en-2-yl)cyclopropyl)amino)cyclohexyl)carbamate hydrochloride (205 mg, 503 μmol) was dissolved in 1,4-dioxane, hydrogen chloride (4M in 1,4-dioxane, 2000 μL, 8.00 mmol) was added and the reaction mixture was stirred at 50° C. for 16 hours. The reaction mixture was diluted in MTBE (10 mL), stirred, and filtered on a fine fritted funnel. The cake was washed with MTBE. The solid was taken up in water:Acetonitrile (5 mL:5 mL) and filtered on a hydrophilic 0.45 um filter. The solution was frozen and lyophilized to give (1r,4R)—N1-((1R,2S)-2-((E)-1-phcnylprop-1-en-2-yl)cyclopropyl)cyclohexane-1,4-diaminc dihydrochloride (135 mg, 393 μmol) in 78% yield. 1H NMR (400 MHz, DMSO-d6) δ 9.51 (br. s., 2H), 8.11 (br. s., 3H), 7.30-7.37 (m, 2H), 7.14-7.27 (m, 3H), 6.36 (s, 1H), 3.08-3.18 (m, 1H), 2.91-3.02 (m, 1H), 2.79-2.89 (m, 1H), 2.12-2.27 (m, 3H), 2.04 (d, J=10.25 Hz, 2H), 1.75 (s, 3H), 1.15-1.57 (m, 6H). LCMS (ESI+): 271.2 (M+H)

Compound 171: Synthesis of (1r,4S)—N1-((1S,2R)-2-((E)-1-phenylprop-1-en-2-yl)cyclopropyl)cyclohexane-1,4-diamine Dihydrochloride (Single Stereoisomer)

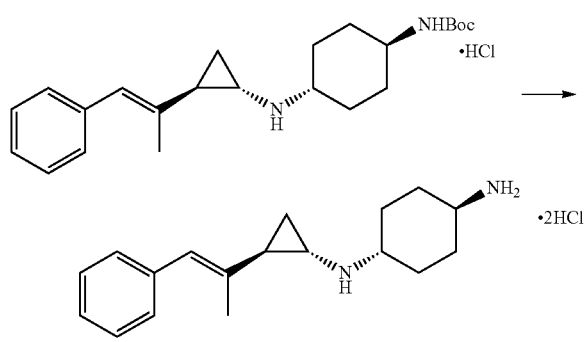

tert-butyl ((trans)-4-((((1S,2R)-2-((E)-1-phenylprop-1-en-2-yl)cyclopropyl)amino)cyclohexyl)carbamate hydrochloride (147 mg, 361 μmol) was dissolved in 1,4-dioxane, hydrogen chloride (4M in 1,4-dioxane, 2000 μL, 8.00 mmol) was added and the reaction mixture was stirred at 50° C. for 16 hours. Reaction mixture was diluted in MTBE (10 mL), stirred, and filtered on a fine fritted funnel. The cake was washed with MTBE. The solid was taken up in water:Acetonitrile (5 mL:5 mL) and filtered on a hydrophilic 0.45 um filter. The solution was frozen and lyophilized to give (1r,4S)—N1-((1S,2R)-2-((E)-1-phenylprop-1-en-2-yl)cyclopropyl)cyclohexane-1,4-diamine dihydrochloride (96.0 mg, 279 μmol), 78% yield. 1H NMR (400 MHz, DMSO-d6) δ 9.40 (br. s., 2H), 8.03 (br. s., 3H), 7.30-7.37 (m, 2H), 7.16-7.26 (m, 3H), 6.37 (s, 1H), 3.06-3.19 (m, 1H), 2.91-3.02 (m, 1H), 2.78-2.90 (m, 1H), 2.11-2.25 (m, 3H), 1.98-2.09 (m, 2H), 1.75 (s, 3H), 1.13-1.55 (m, 6H). LCMS (ESI+): 271 (M+H)

Compound 172: Synthesis of N,N-dimethyl-3-(4-((((trans)-2-((E)-1-phenylprop-1-en-2-yl)cyclopropyl)amino)methyl)piperidin-1-yl)propanamide bis (trifluoroacetic Acid) Salt (Racemic)

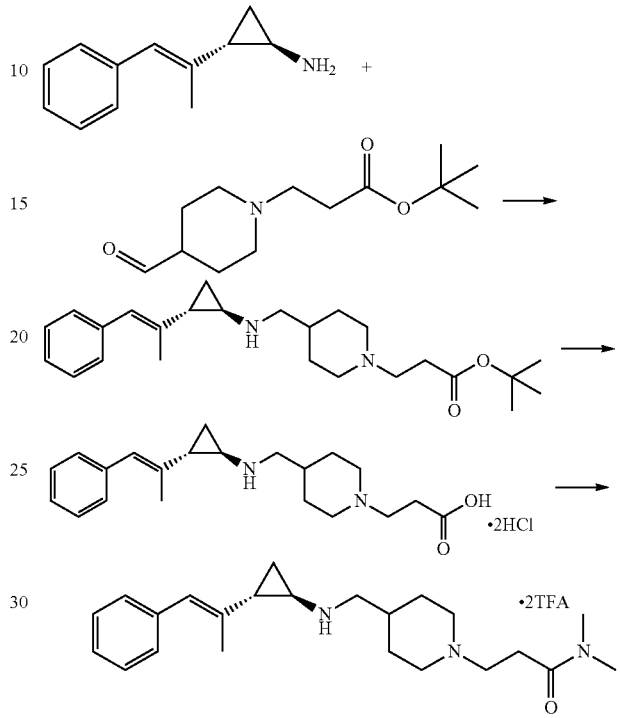

Step 1: tert-butyl 3-(4-((((trans)-2-((E)-1-phenylprop-1-en-2-yl)cyclopropyl)amino)methyl)piperidin-1-yl)propanoate To (E)-2-(1-phenylprop-1-en-2-yl)cyclopropanamine hydrochloride (108 mg, 517 μmol) and tert-butyl 3-(4-formylpiperidin-1-yl)propanoate (125 mg, 517 μmol) in 1,2-dichloroethane (2.5 mL) was added sodium (triacetoxy) borohydride (218 mg, 1.03 mmol). After 30 min, methylene chloride and potassium carbonate (1M aqueous) were added. The organic phase was isolated and evaporated under reduced pressure, and the crude residue was purified by column chromatography (silica, 0% to 10% methanol in EtOAc) to afford tert-butyl 3-(4-((((trans)-2-((E)-1-phenylprop-1-en-2-yl)cyclopropyl)amino)methyl)piperidin-1-yl)propanoate (163 mg, 408 μmol). LCMS: 399.3 (M+H).

Step 2: 3-(4-((((trans)-2-((E)-1-phenylprop-1-en-2-yl)cyclopropyl)amino)methyl)piperidin-1-yl)propanoic Acid tert-butyl 3-(4-((((trans)-2-((E)-1-phenylprop-1-en-2-yl)cyclopropyl)amino)methyl)piperidin-1-yl)propanoate (163 mg, 408 μmol) was dissolved in 1,4-dioxane (2 mL) and hydrogen chloride (4M in 1,4-dioxane, 500 μL, 2 mmol) and water (200 μL) were added. The mixture was heated to 45° C. under stirring for 16 hours. The reaction mixture was cooled down, frozen, and lyophilized to afford 3-(4-((((trans)-2-((E)-1-phenylprop-1-en-2-yl)cyclopropyl)

amino)methyl)piperidin-1-yl)propanoic acid dihydrochloride (125 mg, 300 µmol) in 58% yield over 2 steps. LCMS (ESI+): 343.2 (M+H).

Step 3: N,N-dimethyl-3-(4-(((((trans)-2-((E)-1-phenylprop-1-en-2-yl)cyclopropyl)amino)methyl)piperidin-1-yl)propanamide bis(trifluoroacetic Acid) Salt (Racemic)

3-(4-(((((trans)-2-((E)-1-phenylprop-1-en-2-yl)cyclopropyl)amino)methyl)piperidin-1-yl)propanoic acid dihydrochloride (40 mg, 96.2 µmol) was dissolved in DMF (1 mL), and methylamine in tetrahydrofuran (2M, 1 ml, 2 mmol) was added. Cooled to 0° C. Diisopropylethylamine (58.4 µL, 336 µmol) was added followed by O-(7-Azabenzotriazol-1-yl)-N,N,N',N'-tetramethyluronium hexafluorophosphate (38.4 mg, 101 µmol). Stirred for 1 hour. Concentrated under reduced pressure, purified directly by prep HPLC. Pure fractions concentrated under reduced pressure, frozen, lyophilized to afford N,N-dimethyl-3-(4-(((((trans)-2-(E)-1-phenylprop-1-en-2-yl)cyclopropyl)amino)methyl)piperidin-1-yl)propanamide bis(trifluoroacetic Acid) Salt (15.0 mg, 25.1 µmol) in 26% yield. $^1$H NMR (400 MHz, METHANOL-d4) δ 7.27-7.37 (m, 2H), 7.14-7.26 (m, 3H), 6.43 (s, 1H), 3.67-3.76 (m, 2H), 3.38-3.45 (m, 2H), 3.29-3.31 (m, 1H), 3.16-3.22 (m, 2H), 2.87-3.11 (m, 11H), 2.07-2.17 (m, 4H), 1.86 (d, J=1.32 Hz, 3H), 1.54-1.70 (m, 2H), 1.33 (s, 2H). LCMS (ESI+): 370.3 (M+H).

Compound 173: Synthesis of 1-ethyl-2-((E)-1-phenylprop-1-en-2-yl)-N-(piperidin-4-ylmethyl)cyclopropanamine Dihydrochloride

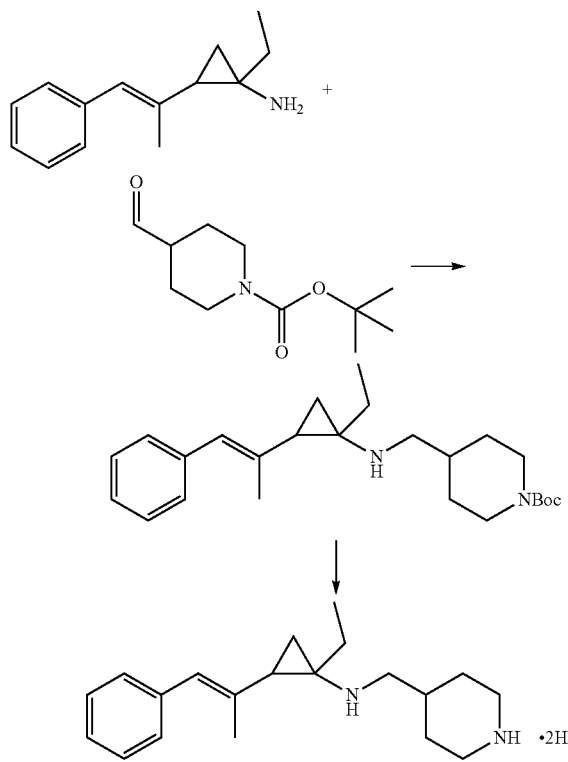

Step 1: (E)-tert-butyl 4-(((1-ethyl-2-(1-phenylprop-1-en-2-yl)cyclopropyl)amino)methyl)piperidine-1-carboxylate To the (E)-1-ethyl-2-(1-phenylprop-1-en-2-yl)cyclopropanamine (E)-1-ethyl-2-(1-phenylprop-1-en-2-yl)cyclopropan-1-amine hydrochloride (150 mg, 630 µmol) and tert-butyl 4-formylpiperidine-1-carboxylate (127 mg, 598 µmol) in 1,2-dichloroethane (3 mL) was added the sodium (triacetoxy)borohydride (264 mg, 1.25 mmol). After 30 min, added methylene chloride and potassium carbonate (1M aqueous). The organic phase was evaporated and the crude residue purified by column chromatography (silica, 0% to 10% methanol in EtOAc) to afford (E)-tert-butyl 4-(((1-ethyl-2-(1-phenylprop-1-en-2-yl)cyclopropyl)amino)methyl)piperidine-1-carboxylate (87.0 mg, 218 µmol) in 35% yield. LCMS (ESI+): 399.3 (M+H).

Step 2: 1-ethyl-2-((E)-1-phenylprop-1-en-2-yl)-N-(piperidin-4-ylmethyl)cyclopropanamine Dihydrochloride (E)-tert-butyl 4-(((1-ethyl-2-(1-phenylprop-1-en-2-yl)cyclopropyl)amino)methyl)piperidine-1-carboxylate (87 mg, 218 µmol) was dissolved in 1,4-dioxane, hydrogen chloride (4M in 1,4-dioxane) was added. The reaction mixture was stirred for 4 hours. The reaction mixture was frozen and lyophilized to afford 1-ethyl-2-((E)-1-phenylprop-1-en-2-yl)-N-(piperidin-4-ylmethyl)cyclopropanamine dihydrochloride (25.0 mg, 67.3 µmol) in 32% yield. $^1$H NMR (400 MHz, DMSO-d6) δ 9.38 (br. s., 1H), 9.22 (br. s., 1H), 8.95 (br. s., 1H), 8.75 (br. s., 1H), 7.30-7.43 (m, 2H), 7.12-7.28 (m, 3H), 6.27 (s, 1H), 3.27-3.70 (m, 3H), 2.93-3.09 (m, 2H), 2.24 (t, J=1.00 Hz, 2H), 2.08 (t, J=8.06 Hz, 1H), 1.98 (s, 3H), 1.64-1.86 (m, 3H), 1.49-1.61 (m, 1H), 1.15-1.30 (m, 2H), 0.99 (t, J=7.32 Hz, 3H). LCMS (ESI+): 299.2 (M+H).

Compound 174: Synthesis of (E)-1-ethyl-2-(1-phenylprop-1-en-2-yl)-N-(piperidin-4-ylmethyl)cyclopropanamine bis(trifluoroacetic Acid) Salt

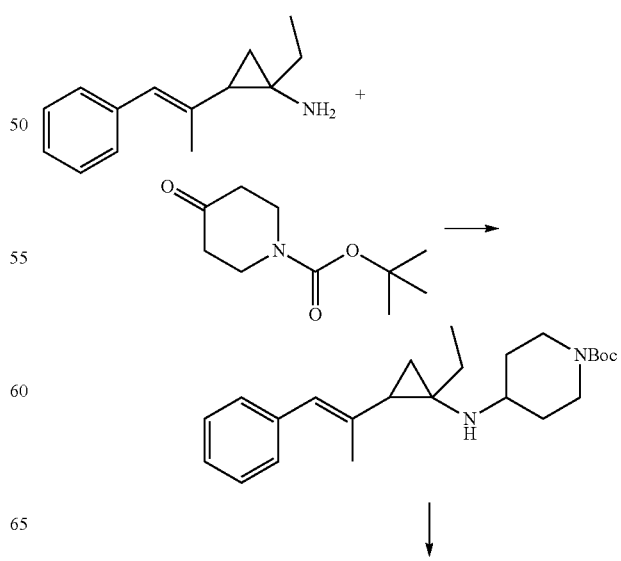

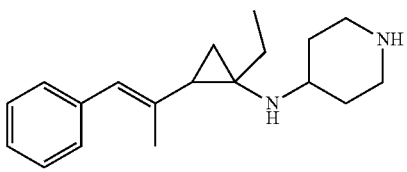

Step 1: (E)-tert-butyl 4-((1-ethyl-2-(1-phenylprop-1-en-2-yl)cyclopropyl)amino)piperidine-1-carboxylate To (E)-1-ethyl-2-(1-phenylprop-1-en-2-yl)cyclopropanamine hydrochloride (150 mg, 630 µmol) and tert-butyl 4-oxopiperidine-1-carboxylate (125 mg, 630 µmol) in 1,2-dichloroethane (3 mL) was added sodium (triacetoxy)borohydride (264 mg, 1.25 mmol). After 30 min, methylene chloride and potassium carbonate (1M aqueous) were added. The organic phase was evaporated and the crude residue was purified by column chromatography (silica, 0% to 10% methanol in EtOAc) to afford (E)-tert-butyl 4-((1-ethyl-2-(1-phenylprop-1-en-2-yl)cyclopropyl)amino)piperidine-1-carboxylate (85.0 mg, 221 µmol) in 35% yield. LCMS (ESI+): 385.3 (M+H).

Step 2: (E)-1-ethyl-2-(1-phenylprop-1-en-2-yl)-N-(piperidin-4-ylmethyl)cyclopropanamine bis(trifluoroacetic Acid) Salt (E)-tert-butyl 4-((1-ethyl-2-(1-phenylprop-1-en-2-yl)cyclopropyl)amino)piperidine-1-carboxylate (87 mg, 218 µmol) was dissolved in 1,4-dioxane (1 mL), hydrogen chloride (4M in 1,4-dioxane, 0.5 mL, 2 mmol) was added. The reaction mixture was stirred for 4 hours. The reaction mixture was purified by preparative HPLC to afford (E)-1-ethyl-2-(1-phenylprop-1-en-2-yl)-N-(piperidin-4-ylmethyl)cyclopropanamine bis(trifluoroacetic Acid) Salt (25.0 mg, 67.3 µmol) in 32% yield. LCMS (ESI+): 285 (M+H).

Compound 175: Synthesis of N-((trans)-2-(E)-1-(4-(1-methyl-1H-pyrazol-4-yl)phenyl)prop-1-en-2-yl)cyclopropyl)piperidin-4-amine bis(trifluoroacetic Acid) Salt (Racemic)

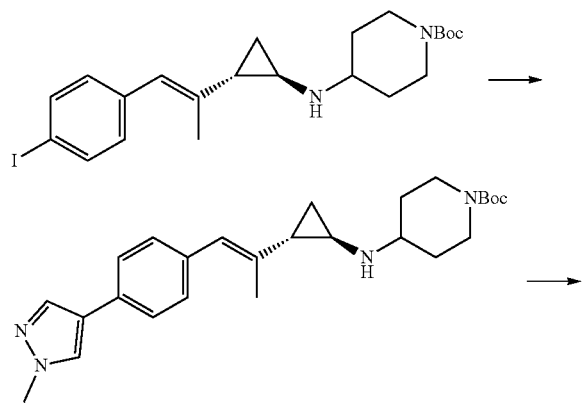

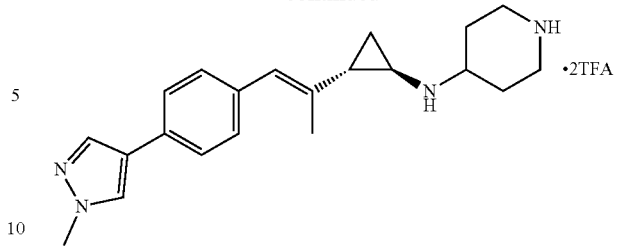

Step 1: tert-butyl 4-(((trans)-2-(E)-1-(4-(1-methyl-1H-pyrazol-4-yl)phenyl)prop-1-en-2-yl)cyclopropyl)amino)piperidine-1-carboxylate tert-butyl 4-(((trans)-2-((E)-1-(4-iodophenyl)prop-1-en-2-yl)cyclopropyl)amino)piperidine-1-carboxylate hydrochloride (110 mg, 212 µmol), 1-methyl-4-(4,4,5,5-tetramethyl-1,3,2-dioxaborolan-2-yl)-1H-pyrazole (44.1 mg, 212 µmol) and potassium carbonate (87.8 mg, 636 µmol)) were added together with 2 mL 1,4-dioxane and 0.5 mL water. The mixture was degassed with a stream of nitrogen. The reaction mixture was stirred at 95° C. for 16 hours. The cooled reaction mixture was diluted with ethyl acetate (10 mL) and brine was added. The aqueous layer was extracted with ethyl acetate (3×10 mL). The combined organic phase was dried over Na$_2$SO$_4$, filtered and concentrated. The residue was purified by a flash chromatography (20% to 100% EtOAc in hexanes, followed by 0% to 10% methanol in ethyl acetate) on silica gel to afford tert-butyl 4-(((trans)-2-((E)-1-(4-(1-methyl-1H-pyrazol-4-yl)phenyl)prop-1-en-2-yl)cyclopropyl)amino)piperidine-1-carboxylate (16.0 mg, 36.6 µmol) in 17% yield. LCMS (ESI+): 437.3 (M+H).

Step 2: N-((trans)-2-((E)-1-(4-(1-methyl-1H-pyrazol-4-yl)phenyl)prop-1-en-2-yl)cyclopropyl)piperidin-4-amine bis(trifluoroacetic Acid) Salt (Racemic)

tert-butyl 4-(((trans)-2-((E)-1-(4-(1-methyl-1H-pyrazol-4-yl)phenyl)prop-1-en-2-yl)cyclopropyl)amino)piperidine-1-carboxylate (15 mg, 34.3 µmol) was dissolved in 1,4-dioxane, and hydrogen chloride (4M in 1,4-dioxane) (500 µL, 2 mmol) was added. The reaction mixture was stirred at room temperature for 1 hour. Reaction complete. Diluted with MTBE, stirred for 15 minutes. Filtered on a fritted funnel (Fine) under suction. The solid was collected, dissolved in 1:1 water:acetonitrile, frozen, lyophilized and purified by preparative HPLC (SunFire C18 OBD column 5 µm (19×100 mm), 5% to 50% acetonitrile in water gradient over 9 minutes, 0.1% trifluoroacetic acid as phase modifier). Pure fractions were collected, pooled, frozen and lyophilized to afford N-((trans)-2-((E)-1-(4-(1-methyl-1H-pyrazol-4-yl)phenyl)prop-1-en-2-yl)cyclopropyl)piperidin-4-amine bis(trifluoroacetic acid) salt (9.00 mg, 15.9 µmol) in 47% yield. LCMS (ESI+): 337.2 (M+H).

Compound 176: Synthesis of 4-((((trans)-4-(((trans)-2-((E)-1-phenylbut-1-en-2-yl)cyclopropyl)amino)cyclohexyl)amino)methyl)benzoic Acid Dihydrochloride (Racemic)

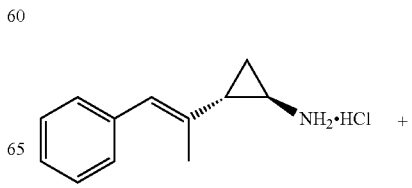

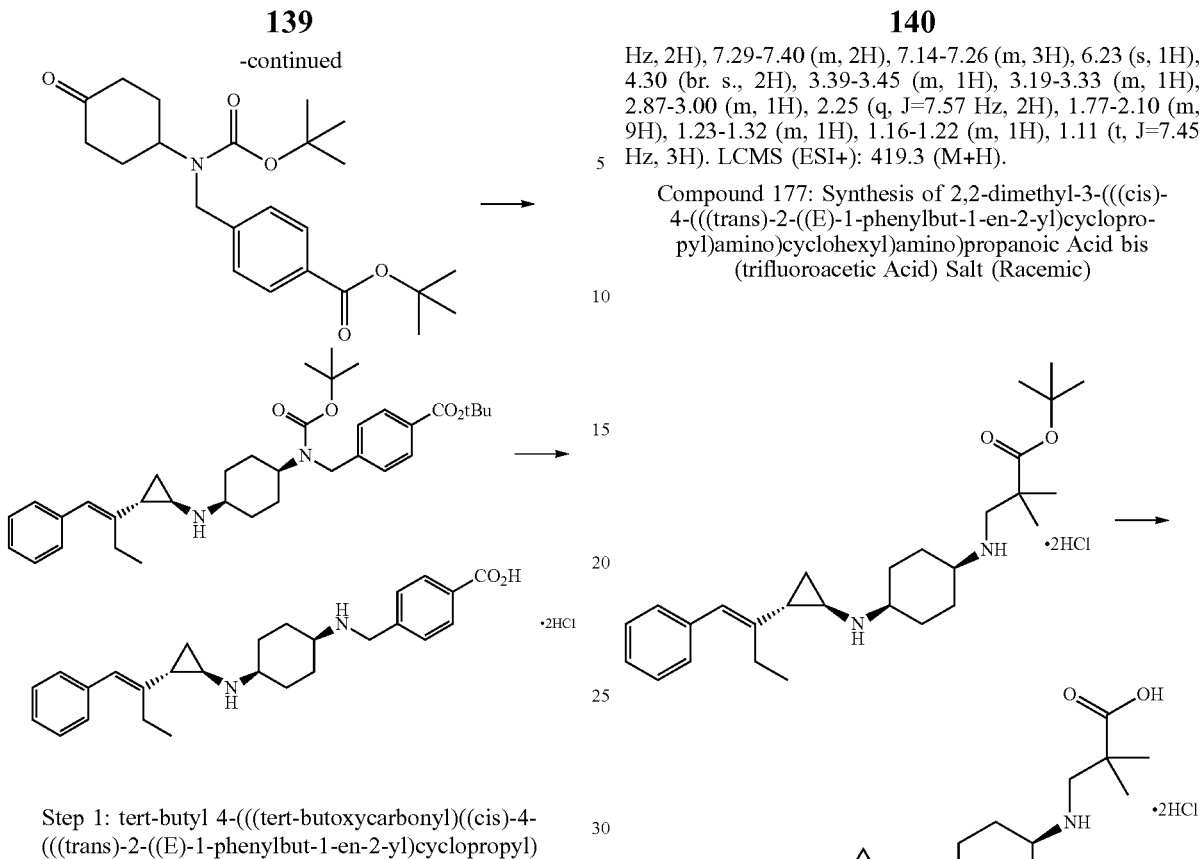

Step 1: tert-butyl 4-(((tert-butoxycarbonyl)((cis)-4-(((trans)-2-((E)-1-phenylbut-1-en-2-yl)cyclopropyl)amino)cyclohexyl)amino)methyl)benzoate To (trans)-2-((E)-1-phenylbut-1-en-2-yl)cyclopropanamine hydrochloride (668 mg, 2.99 mmol) and tert-butyl 4-(((tert-butoxycarbonyl)(4-oxocyclohexyl)amino)methyl)benzoate (1.19 g, 2.94 mmol) in 1,2-dichloroethane (15 mL) was added sodium (triacetoxy)borohydride (1.24 g, 5.88 mmol). After 30 min, potassium carbonate (1M aq.) was added followed by methylene chloride. The organic phase was isolated, evaporated and the crude residue purified by silica gel column chromatography (120 g column, 50:50 EtOAc:Hex to 100:0 in 7 column volumes) to afford two sets of fractions containing isomeric compounds. The first eluting set of fractions was pooled and evaporated to afford tert-butyl 4-(((tert-butoxycarbonyl)((cis)-4-(((trans)-2-(E)-1-phenylbut-1-en-2-yl)cyclopropyl)amino)cyclohexyl)amino)methyl)benzoate (625 mg, 1.08 mmol) in 37% yield. LCMS: Rt=3.756 min., MS (ESI+): 519.3 (M-tBu+H), 575.4 (M+H, weak).

Step 2: 4-(((((trans)-4-(((trans)-2-((E)-1-phenylbut-1-en-2-yl)cyclopropyl)amino)cyclohexyl)amino)methyl)benzoic Acid Dihydrochloride (Racemic)

tert-butyl 4-(((tert-butoxycarbonyl)((cis)-4-(((trans)-2-(E)-1-phenylbut-1-en-2-yl)cyclopropyl)amino)cyclohexyl)amino)methyl)benzoate (185 mg, 0.322 mmol) (first eluting fraction set from previous step) was dissolved in 1,4-dioxane (10 mL) and hydrochloric acid (6M aqueous, 5 mL, 30 mmol) was added. The reaction mixture was heated at 50° C. for 24 hours. The solution was frozen and lyophilized to afford 4-(((((trans)-4-(((trans)-2-((E)-1-phenylbut-1-en-2-yl)cyclopropyl)amino)cyclohexyl)amino)methyl)benzoic acid dihydrochloride (125 mg, 0.299 mmol) in 93% yield. $^1$H NMR (400 MHz, DMSO-d6) δ 12.95-13.29 (m, 1H), 8.74-9.26 (m, 4H), 7.99 (d, J=7.81 Hz, 2H), 7.66 (d, J=8.06 Hz, 2H), 7.29-7.40 (m, 2H), 7.14-7.26 (m, 3H), 6.23 (s, 1H), 4.30 (br. s., 2H), 3.39-3.45 (m, 1H), 3.19-3.33 (m, 1H), 2.87-3.00 (m, 1H), 2.25 (q, J=7.57 Hz, 2H), 1.77-2.10 (m, 9H), 1.23-1.32 (m, 1H), 1.16-1.22 (m, 1H), 1.11 (t, J=7.45 Hz, 3H). LCMS (ESI+): 419.3 (M+H).

Compound 177: Synthesis of 2,2-dimethyl-3-(((cis)-4-(((trans)-2-((E)-1-phenylbut-1-en-2-yl)cyclopropyl)amino)cyclohexyl)amino)propanoic Acid bis(trifluoroacetic Acid) Salt (Racemic)

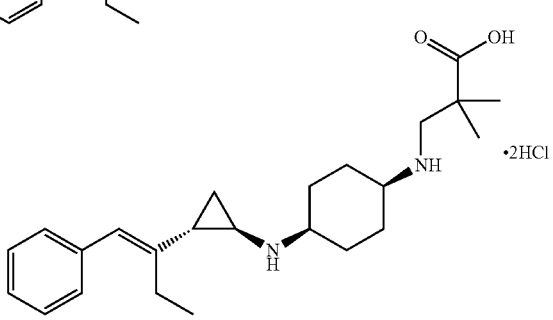

Step 1: tert-butyl 2,2-dimethyl-3-(((cis)-4-(((trans)-2-(E)-1-phenylbut-1-en-2-yl)cyclopropyl)amino)cyclohexyl)amino)propanoate Dihydrochloride To (trans)-2-((E)-1-phenylbut-1-en-2-yl)cyclopropanamine hydrochloride (2.93 g, 13.1 mmol) and tert-butyl 2,2-dimethyl-3-((4-oxocyclohexyl)amino)propanoate (3.45 g, 12.8 mmol) in 60 mL of DCE was added sodium (triacetoxy)borohydride (5.59 g, 26.4 mmol). After 30 min, 1M potassium carbonate (aq.) was added followed by methylene chloride. The organic phase was isolated and evaporated under reduced pressure. The crude residue was taken up in MTBE and evaporated under reduced pressure. The residue was redissolved in MTBE and hydrogen chloride (2M diethyl ether, 16 mL, 32 mmol) was added dropwise to the solution. The mixture was evaporated under reduced pressure. The solid was triturated with iPrOH:MTBE (1:5), and filtered on a nylon filter under suction. The filtrate was evaporated under reduced pressure to afford tert-butyl 2,2-dimethyl-3-(((cis)-4-(((trans)-2-((E)-1-phenylbut-1-en-2-yl)cyclopropyl)amino)cyclohexyl)amino)propanoate dihydrochloride (1.71 g, 3.33 mmol) in 25% yield. LCMS (ESI+): 441.3 (M+H).

Step 2: 2,2-dimethyl-3-(((cis)-4-(((trans)-2-((E)-1-phenylbut-1-en-2-yl)cyclopropyl)amino)cyclohexyl)amino)propanoic Acid bis(trifluoroacetic Acid) Salt (Racemic)

2,2-dimethyl-3-(((cis)-4-(((trans)-2-((E)-1-phenylbut-1-en-2-yl)cyclopropyl)amino)cyclohexyl)amino)propanoic acid dihydrochloride (105 mg, 229 μmol) was taken up in 1,4-dioxane (3 mL) and evaporated under reduced pressure to remove any residual iso-propanol. The reactant was dissolved in 1,4-dioxane (3 mL) and hydrochloric acid (6M aq., 0.5 mL, 3 mmol) was added. The reaction mixture was heated overnight at 45° C. The reaction mixture was concentrated under reduced pressure and the compound was purified by preparative HPLC. The pure fractions were lyophilized to afford 2,2-dimethyl-3-(((cis)-4-(((trans)-2-((E)-1-phenylbut-1-en-2-yl)cyclopropyl)amino)cyclohexyl) amino)propanoic acid bis(trifluoroacetic acid) salt (35.0 mg, 57.1 μmol), 25% yield. $^1$H NMR (400 MHz, DMSO-d6) δ 12.71-13.21 (m, 1H), 9.07 (br. s., 1H), 8.91 (br. s., 1H), 8.32 (br. s., 2H), 7.29-7.38 (m, 2H), 7.11-7.26 (m, 3H), 6.23 (s, 1H), 2.89-3.52 (m, 7H), 2.25 (q, J=7.57 Hz, 2H), 1.98-2.13 (m, 2H), 1.68-1.98 (m, 6H), 1.26-1.32 (m, 1H), 1.20-1.26 (m, 5H), 1.15-1.20 (m, 1H), 1.09-1.14 (m, 3H). LCMS (ESI+): 385.3 (M+H).

Compound 277: Synthesis of N-((trans)-2-((E)-3-methyl-1-phenylbut-1-en-2-yl)cyclopropyl)piperidin-4-amine Dihydrochloride (Racemic)

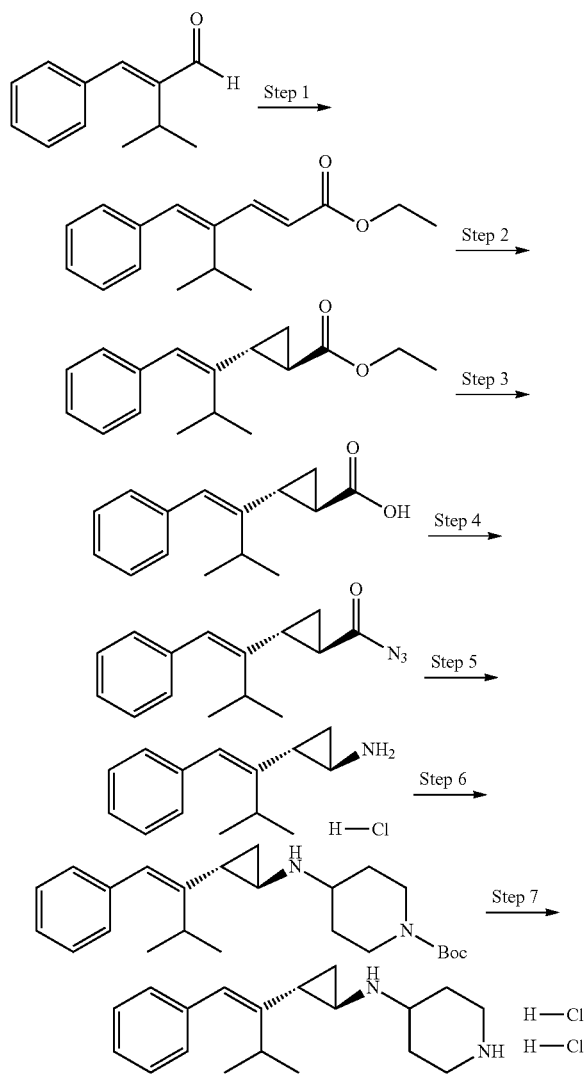

Starting material (E)-2-benzylidene-3-methylbutanal Was prepared according to the procedure described by Brenna, E.; Gatti, F. G.; Monti, D.; Parmeggiani, F.; Sacchetti, A. ChemCatChem 2012, 4, 653-659. LCMS (ESI+): 175.5 (M+H).

Step 1: Ethyl (E)-4-((E)-benzylidene)-5-methylhex-2-enoate

To a solution of triethylphosphonoacetate (8.78 g, 39.2 mmol) in anhydrous tetrahydrofuran (80 mL) was added sodium tert-butoxide (3.61 g, 37.6 mmol) at 0° C. After 15 min, (E)-2-benzylidene-3-methylbutanal (5.7 g, 32.7 mmol) (contaminated with benzaldehyde) was added and the reaction was stirred at 0° C. for After 1 h, extra triethylphosphonoacetate (2.2 g, 9.8 mmol) and sodium tert-butoxide (0.90 g, 9.4 mmol) were added at 0° C. After 1 h, the reaction was quenched with an aqueous solution of ammonium chloride. The desired product was extracted with methyl tert-butylether (three times) and the combined organic layers were dried over sodium sulfate, filtered and concentrated under vacuum. The residue was purified by flash chromatography (silical gel, 2% to 30% ethylacetate in hexane) to give a mixture of the title compound and ethyl cinnamate. LCMS (ESI+): 245.6 (M+H).

Step 2: ethyl (trans)-2-((E)-3-methyl-1-phenylbut-1-en-2-yl)cyclopropane-1-carboxylate Sodium hydride (60% in oil, 1.88 g, 47.2 mmol) was added to dimethylsulfoxide (100 mL) at room temperature (caution: gas evolution). After 15 min, trimethylsulfoxonium iodide (10.8 g, 49.1 mmol) was added at room temperature and the reaction was stirred for 1 h (caution: gas evolution). A solution of ethyl (E)-4-((E)-benzylidene)-5-methylhex-2-enoate (10.8 g, 37.8 mmol) (contaminated with ethyl cinnamate) in dimethylsulfoxide (100 mL) was added and the reaction was heated at 40° C. for 48 h. The reaction was quenched with an aqueous ammonium chloride solution. The desired product was extracted with methyl tert-butylether (three times), the combined organic layers were washed with water and brine, dried over sodium sulfate, filtered and concentrated under vacuum. The crude product was used without purification in the next step. LCMS (ESI+): 259.6 (M+H).

Step 3: (trans)-2-(E)-3-methyl-1-phenylbut-1-en-2-yl)cyclopropane-1-carboxylic Acid To a solution of ethyl (trans)-2-((E)-3-methyl-1-phenyl-but-1-en-2-yl)cyclopropane-1-carboxylate (8.2 g, 31.7 mmol) in a mixture of methanol (60 mL) and water (5 mL) was added sodium hydroxide (3.16 g, 79.2 mmol) at room temperature. After 1 h the reaction was heated to 60° C. Upon complete consumption of the starting material, the reaction was quenched with 1M hydrochloric acid. The desired product was extracted with MTBE (four times) and the combined organic layers were dried over sodium sulfate, filtered and concentrated under vacuum. The residue was purified by flash chromatography (silical gel, 0% to 80% ethylacetate in hexane) to give the title compound in 32% yield over four steps. LCMS (ESI+): 231.5 (M+H).

Step 4: (trans)-2-(E)-3-methyl-1-phenylbut-1-en-2-yl)cyclopropane-1-carbonyl Azide To a solution of (trans)-2-((E)-3-methyl-1-phenylbut-1-en-2-yl)cyclopropane-1-carboxylic acid (3.44 g, 14.9 mmol)

in tetrahydrofuran (75 mL) was added Hunig's base (3.88 mL, 22.3 mmol) and isobutyl chloroformate (2.41 mL, 18.6 mmol) at 0° C. After 3 h at 0° C., a solution of sodium azide (4.84 g, 74.5 mmol) in water (50 mL) was added. The reaction is stirred at 0° C. for 1 h before the desired product was extracted with methyl tert-butylether (three times). The combined organic layers were dried over sodium sulfate, filtered and concentrated under vacuum. The residue was purified by flash chromatography (silical gel, 2% to 20% ethylacetate in hexane) to give the titled compound. LCMS (ESI+): 228 (isocyanate+H).

Step 5: (trans)-2-((E)-3-methyl-1-phenylbut-1-en-2-yl)cyclopropan-1-amine Hydrochloride A solution of (trans)-2-((E)-3-methyl-1-phenylbut-1-en-2-yl)cyclopropane-1-carbonyl azide (3.8 g, 15 mmol) in toluene (140 mL) was heated at 100° C. for 1 h (caution: gas evolution). The solution was cooled to room temperature and potassium trimethylsilanolate (2.8 g, 22 mmol) was added. After 30 min, the reaction was quenched with 1M hydrochloric acid and the precipitate was collected by filtration and dried under vacuum (title compound). The aqueous layer from the filtrate was isolated and its pH was adjusted to >12 with a 2M solution of sodium hydroxide. The desired product was extracted with methyl tert-butylether (three times) and the combined organic layers were dried over sodium sulfate and filtered. A 4M hydrochloric acid solution in 1,4-dioxane (6 mL) was next added to extract containing the desired amine and the desired salt was concentrated to dryness. The precipitate and the extracted product were combined to give the title compound in 88% yield over two steps. LCMS (ESI+): 202.6 (M+H).

Step 6: tert-butyl 4-(((trans)-2-((E)-3-methyl-1-phenylbut-1-en-2-yl)cyclopropyl)amino)piperidine-1-carboxylate To a suspension of (trans)-2-((E)-3-methyl-1-phenylbut-1-en-2-yl)cyclopropan-1-amine hydrochloride (75 mg, 0.32 mmol) and tert-butyl 4-oxopiperidine-1-carboxylate (50 mg, 0.25 mmol) in 1,2-dichloroethane (3 mL) was added sodium triacetoxyborohydride (167 mg, 0.789 mmol) at room temperature. Extra tert-butyl 4-oxopiperidine-1-carboxylate (13 mg, 0.063 mmol) was added after 30 min and the reaction was stirred for an additional 30 min before being quenched with an aqueous sodium bicarbonate solution. The desired product was extracted with methyl tert-butylether (three times) and the combined organic layers were dried with sodium sulfate, filtered and concentrated to dryness. The residue was purified by flash chromatography (silical gel, 15% to 50% ethylacetate in hexane) to give the titled compound in 85% yield. LCMS (ESI+): 385.3 (M+H).

Step 7: N-((trans)-2-((E)-3-methyl-1-phenylbut-1-en-2-yl)cyclopropyl)piperidin-4-amine Dihydrochloride (Racemic)

To a solution of tert-butyl 4-(((trans)-2-((E)-3-methyl-1-phenylbut-1-en-2-yl)cyclopropyl)amino)piperidine-1-carboxylate (103 mg, 0.268 mmol) in methanol (12 mL) was added a 4M hydrogen chloride solution in 1,4 dioxane (12 mL, 48 mmol) at 0° C. The reaction was concentrated to dryness after 90 min to give the titled compound in 98% yield. $^1$H NMR (400 MHz, DMSO-$d_6$) δ 9.96 (br. d, J=19.80 Hz, 2H), 9.32 (br. s., 1H), 9.05 (d, J=8.30 Hz, 1H), 7.33 (t, J=6.84 Hz, 2H), 7.20 (t, J=7.30 Hz, 1H), 7.14 (d, J=7.32 Hz, 2H), 6.06 (s, 1H), 3.37-3.51 (m, 3H), 3.06 (spt, J=6.80 Hz, 1H), 2.80-2.98 (m, 3H), 2.24-2.33 (m, 3H), 1.94 (q, J=12.04 Hz, 2H), 1.36-1.43 (m, 1H), 1.13 (d, J=6.84 Hz, 3H), 1.04-1.09 (m, 4H). LCMS (ESI+): 285.2 (M+H).

Compound 178: Synthesis of (trans)-N$^1$-((trans)-2-(E)-3-methyl-1-phenylbut-1-en-2-yl)cyclopropyl)cyclohexane-1,4-diamine Dihydrochloride (Racemic)

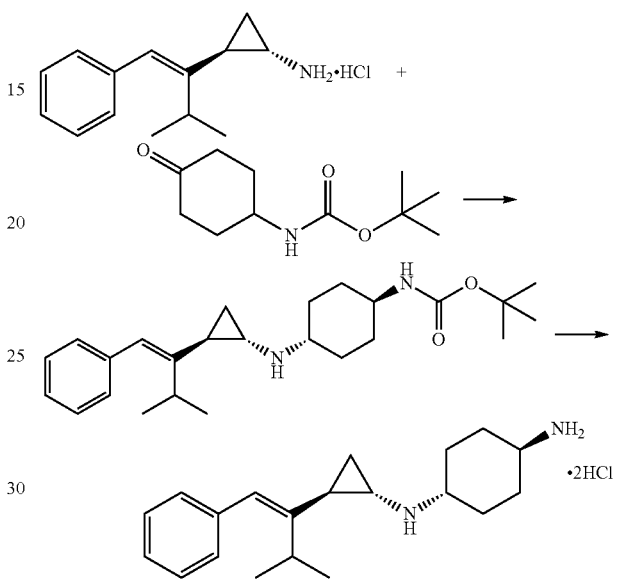

Step 1: tert-butyl ((cis)-4-(((trans)-2-((E)-3-methyl-1-phenylbut-1-en-2-yl)cyclopropyl)amino)cyclohexyl)carbamate and tert-butyl ((trans)-4-(((trans)-2-(E)-3-methyl-1-phenylbut-1-en-2-yl)cyclopropyl)amino)cyclohexyl)carbamate To (trans)-2-((E)-3-methyl-1-phenylbut-1-en-2-yl)cyclopropanamine hydrochloride (100 mg, 420 μmol) and tert-butyl (4-oxocyclohexyl)carbamate (89.5 mg, 420 μmol) in 1,2-dichloroethane (4 mL) was added sodium (triacetoxy) borohydride (178 mg, 0.84 mmol). After 30 min, were added methylene chloride and potassium carbonate (1M aqueous) were added. The organic phase was isolated, evaporated and the crude residue purified by column chromatography (silica, 0% to 10% methanol in EtOAc) to afford two sets of fractions.

The first eluting fractions were pooled and evaporated to afford tert-butyl ((cis)-4-(((trans)-2-((E)-3-methyl-1-phenylbut-1-en-2-yl)cyclopropyl)amino)cyclohexyl)carbamate (92.0 mg, 230 μmol) in 45% yield. LCMS (ESI+): 399.3 (M+H).

The second eluting fractions were pooled and evaporated to afford tert-butyl ((trans)-4-(((trans)-2-((E)-3-methyl-1-phenylbut-1-en-2-yl)cyclopropyl)amino)cyclohexyl)carbamate (95.0 mg, 238 μmol) in 47% yield in the second eluting fractions. LCMS (ESI+): 399.3 (M+H)

Step 2: (trans)-N1-((trans)-2-(E)-3-methyl-1-phenylbut-1-en-2-yl)cyclopropyl)cyclohexane-1,4-diamine (Racemic)

tert-butyl ((trans)-4-(((trans)-2-((E)-3-methyl-1-phenylbut-1-en-2-yl)cyclopropyl)amino)cyclohexyl)carbamate (95 mg, 238 μmol) was dissolved in 1,4-dioxane (2 mL), Hydrogen chloride (4M in 1,4-dioxane, 1 mL, 4.00 mmol) is added under stirring at 40° C. Reaction stopped after 16 hours. Compound crashes out of solution. The reaction mixture was diluted with MTBE, filtered on a fine fritted funnel. The solid was collected and dissolved in a 2:1 water:ACN mixture. Solution was filtered on a Milex filter, frozen and lyophilized to afford (trans)-N1-((trans)-2-((E)-3-methyl-1-phenylbut-1-en-2-yl)cyclopropyl)cyclohexane-1,4-diamine dihydrochloride (49.0 mg, 131 μmol) in 55% yield. ¹H NMR (400 MHz, DMSO-d 6) δ 9.43 (br. s., 2H), 8.06 (br. s., 3H), 7.28-7.40 (m, 2H), 7.19-7.26 (m, 1H), 7.15 (d, J=7.57 Hz, 2H), 6.06 (s, 1H), 3.03-3.20 (m, 2H), 2.94-3.02 (m, 1H), 2.86 (br. s., 1H), 2.11-2.27 (m, 3H), 2.05 (d, J=11.96 Hz, 2H), 1.29-1.62 (m, 5H), 1.14 (d, J=6.84 Hz, 3H), 1.08 (d, J=6.84 Hz, 3H), 1.03-1.07 (m, 1H). LCMS (ESI+): 399 (M+H).

Compound 179: Synthesis of 4-((4-(((trans)-2-((E)-3-methyl-1-phenylbut-1-en-2-yl)cyclopropyl)amino)piperidin-1-yl)methyl)benzoic Acid bis(trifluoroacetic Acid) Salt (Racemic)

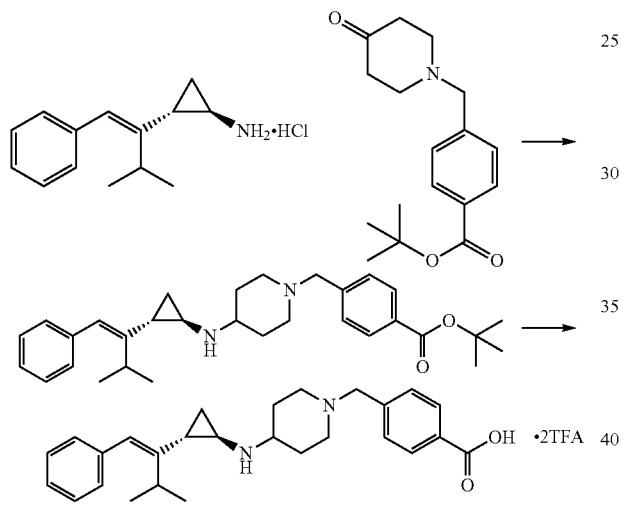

Step 1: tert-butyl 4-((4-(((trans)-2-((E)-3-methyl-1-phenylbut-1-en-2-yl)cyclopropyl)amino)piperidin-1-yl)methyl)benzoate To (trans)-2-((E)-3-methyl-1-phenylbut-1-en-2-yl)cyclopropanamine hydrochloride (80 mg, 336 μmol) and tert-butyl 4-((4-oxopiperidin-1-yl)methyl)benzoate (97.2 mg, 336 μmol) in 1,2-dichloroethane (4 mL) was added sodium (triacetoxy)borohydride (142 mg, 0.67 mmol). After 30 min, added methylene chloride and potassium carbonate (1M aqueous) were added. The organic phase was isolated, evaporated and the crude residue purified by column chromatography (silica, 0% to 10% methanol in EtOAc) to afford tert-butyl 4-((4-(((trans)-2-((E)-3-methyl-1-phenylbut-1-en-2-yl)cyclopropyl)amino)piperidin-1-yl)methyl)benzoate (94.0 mg, 198 μmol) in 59% yield. LCMS (ESI+): 475.3 (M+H).

Step 2: 4-((4-(((trans)-2-((E)-3-methyl-1-phenylbut-1-en-2-yl)cyclopropyl)amino)piperidin-1-yl)methyl)benzoic Acid (Racemic)

tert-butyl 4-((4-(((trans)-2-((E)-3-methyl-1-phenylbut-1-en-2-yl)cyclopropyl)amino)piperidin-1-yl)methyl)benzoate (92 mg, 193 μmol) was dissolved in 1,4-dioxane (2 mL), hydrogen chloride (4M in 1,4-dioxane, 2 mL, 8.00 mmol) was added followed by 5 drops of water, stirred at 40° C. for 4 hours. The reaction mixture was cooled, diluted with MTBE, and filtered on a fine fritted funnel. The solid was collected and purified by preparative HPLC (SunFire C18 OBD column 5 pm (19×100 mm), 5% to 50% acetonitrile in water gradient over 9 minutes, 0.1% trifluoroacetic acid as phase modifier). Pure fractions frozen and lyophilized to afford 4-((4-(((trans)-2-(E)-3-methyl-1-phenylbut-1-en-2-yl)cyclopropyl)amino)piperidin-1-yl)methyl)benzoic acid bis(trifluoroacetic acid) salt (40 mg, 62 umol) in 32% yield. ¹H NMR (400 MHz, DMSO-d6) δ 13.03-13.20 (m, 1H), 10.88 (br. s., 1H), 9.64 (br. s., 1H), 8.00 (d, J=8.06 Hz, 1H), 7.71 (d, J=7.81 Hz, 1H), 7.28-7.37 (m, 2H), 7.16-7.28 (m, 1H), 7.14 (d, J=7.57 Hz, 1H), 6.05 (s, 1H), 4.26-4.38 (m, 2H), 3.56 (s, 2H), 3.34-3.40 (m, 2H), 2.76-3.10 (m, 6H), 1.80-2.36 (m, 8H), 1.27-1.37 (m, 1H), 1.03-1.17 (m, 5H), 0.74-0.98 (m, 2H) 38/38 LCMS (ESI+): 419.2 (M+H).

Compound 180: Synthesis of 4-(((trans)-4-(((trans)-2-((E)-1-phenylbut-1-en-2-yl)cyclopropyl)amino)cyclohexyl)amino)butanoic Acid bis(trifluoroacetic Acid) Salt (Racemic)

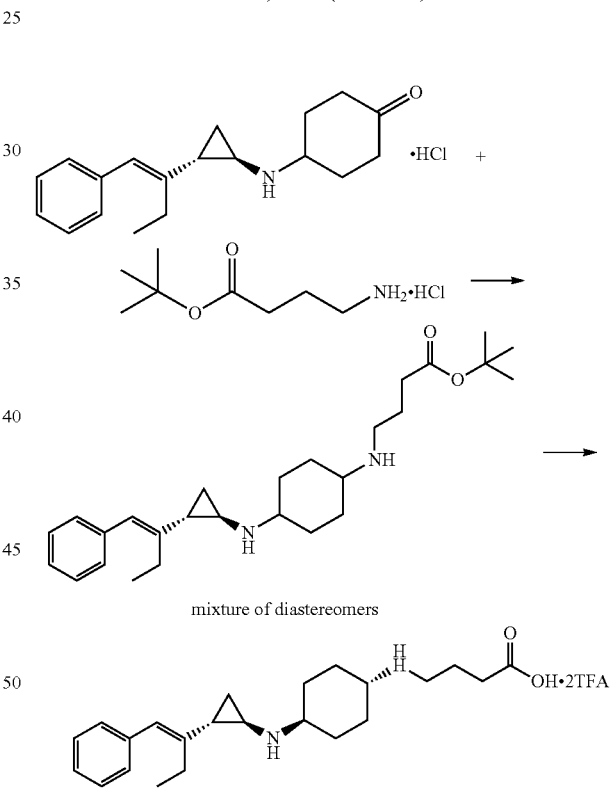

mixture of diastereomers

Step 1: tert-butyl 4-((4-(((trans)-2-(E)-1-phenylbut-1-en-2-yl)cyclopropyl)amino)cyclohexyl)amino)butanoate (Diastereomeric Mixture)

To 4-(((trans)-2-((E)-1-phenylbut-1-en-2-yl)cyclopropyl)amino)cyclohexanone hydrochloride (100 mg, 312 μmol) and tert-butyl 4-amino butanoate hydrochloride (63.9 mg, 327 μmol) in 1,2-dichloroethane (3 mL) was added sodium (triacetoxy)borohydride (247 mg, 1.17 mmol). After 30 min, added methylene chloride and potassium carbonate (1M aqueous) were added. The organic phase was isolated, evaporated and the crude residue purified by column chromatography (0% to 100% 1:10:90 ammonia (30% aqueous): methanol:methylene chloride in methylene chloride) to afford tert-butyl 4-((4-(((trans)-2-((E)-1-phenylbut-1-en-2-yl)cyclopropyl)amino)cyclohexyl)amino)butanoate as a cis, trans diastereomeric mixture (68.0 mg, 159 μmol) in 51% yield. LCMS (ESI+): 427.3 (M+H).

Step 2: 4-(((trans)-4-(((trans)-2-((E)-1-phenylbut-1-en-2-yl)cyclopropyl)amino)cyclohexyl)amino)butanoic Acid bis(trifluoroacetic Acid) Salt (Racemic)

The cis-, trans-mixture of tert-butyl 4-((4-(((trans)-2-(E)-1-phenylbut-1-en-2-yl)cyclopropyl)amino)cyclohexyl)amino)butanoate (68 mg, 170 μmol) was dissolved in 1,4-dioxane (500 μL) and hydrogen chloride (6M aqueous, 100 μL, 0.6 mmol) was added and the reaction mixture was heated at 45° C. for 16 hours. The compound was purified by preparative HPLC (SunFire C18 OBD column 5 μm (19×100 mm), 5% to 50% acetonitrile in water gradient over 9 minutes, 0.1% trifluoroacetic acid as phase modifier). The earlier eluting fractions were pooled, frozen and lyophilized to afford 4-(((trans)-4-(((trans)-2-((E)-1-phenylbut-1-en-2-yl)cyclopropyl)amino)cyclohexyl)amino)butanoic Acid bis(trifluoroacetic Acid) Salt (29.0 mg, 48.4 μmol) in 8.6% yield. LCMS (ESI+): 371.3 (M+H).

Compound 181: Synthesis of 4-(((((trans)-4-(((trans)-2-((E)-3-methyl-1-phenylbut-1-en-2-yl)cyclopropyl)amino)cyclohexyl)amino)methyl)benzoic Acid Dihydrochloride (Racemic)

Step 1: tert-butyl 4-(((tert-butoxycarbonyl)((trans)-4-(((trans)-2-((E)-3-methyl-1-phenylbut-1-en-2-yl)cyclopropyl)amino)cyclohexyl)amino)methyl)benzoate To racemic 2-((E)-3-methyl-1-phenylbut-1-en-2-yl)cyclopropanamine hydrochloride (72.9 mg, 307 μmol) and tert-butyl 4-(((tert-butoxycarbonyl)(4-oxocyclohexyl)amino)methyebenzoate (124 mg, 307 μmol) in 1,2-dichloroethane (3 mL) was added sodium (triacetoxy)borohydride (178 mg, 0.84 mmol). After 30 min methylene chloride and potassium carbonate (1M aqueous) were added. The organic phase was isolated, evaporated and the crude residue purified by column chromatography (silica, 0% to 10% methanol in EtOAc) to afford a tert-butyl 4-(((tert-butoxycarbonyl)((cis)-4-(((trans)-2-((E)-3-methyl-1-phenylbut-1-en-2-yl)cyclopropyl)amino)cyclohexyl)amino)methyl)benzoate (60.0 mg, 101 μmol) (33% yield) in the first eluting fractions, and tert-butyl 4-(((tert-butoxycarbonyl)((trans)-4-(((trans)-2-((E)-3-methyl-1-phenylbut-1-en-2-yl)cyclopropyl)amino)cyclohexyl)amino)methyl)benzoate (44.0 mg, 74.7 μmol) (24% yield) in the second eluting fractions. LCMS (ESI+): 533.1 (M-tBu+H)

Step 2: 4-(((((trans)-4-(((trans)-2-(E)-3-methyl-1-phenylbut-1-en-2-yl)cyclopropyl)amino)cyclohexyl)amino)methyl)benzoic Acid Dihydrochloride (Racemic)

tert-butyl 4-(((tert-butoxycarbonyl)((trans)-4-(((trans)-2-(E)-3-methyl-1-phenylbut-1-en-2-yl)cyclopropyl)amino)cy-

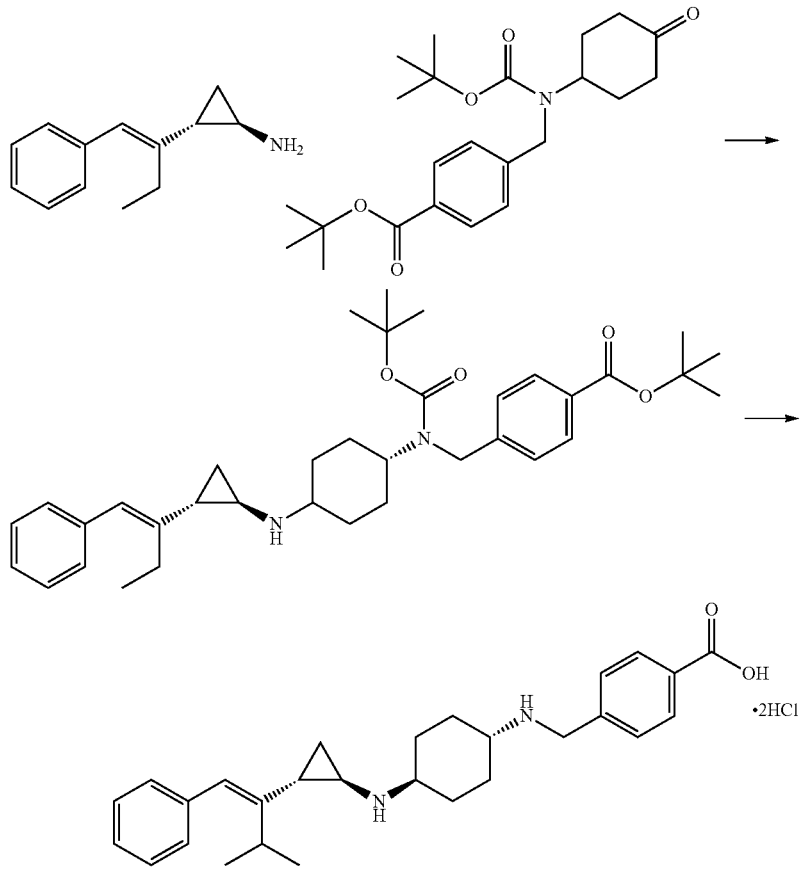

clohexyl)amino)methyl)benzoate (44 mg, 74.7 µmol) was dissolved in 1,4-dioxane (1 mL). Hydrogen chloride (4M in 1,4-dioxane, 500 µL, 2 mmol) and 6M aqueous HCl (200 µL, 1.2 mmol) were added and the reaction mixture was stirred at 45° C. for 16 hours. The solution was cooled down, frozen and lyophilized to afford (E)-4-(((4-((2-(1-phenylbut-1-en-2-yl)cyclopropyl)amino)cyclohexyl)amino)methyl)benzoic acid dihydrochloride (25.0 mg, 49.4 µmol) in 66% yield. $^1$H NMR (400 MHz, DMSO-d 6) δ 12.85-13.20 (m, 1H), 9.00-9.31 (m, 4H), 8.00 (d, J=8.55 Hz, 2H), 7.66 (d, J=8.30 Hz, 2H), 7.34 (s, 2H), 7.18-7.24 (m, 1H), 7.10-7.17 (m, 2H), 6.03-6.09 (m, 1H), 4.17-4.29 (m, 2H), 2.78-3.22 (m, 5H), 2.14-2.30 (m, 4H), 1.93-2.12 (m, 2H), 1.27-1.59 (m, 4H), 1.13 (d, J=6.84 Hz, 3H), 1.08 (d, J=6.84 Hz, 3H). LCMS (ESI+): 433.3 (M+H)

Compound 182 and Compound 183: 2-(((trans)-4-(((trans)-2-((E)-1-phenylbut-1-en-2-yl)cyclopropyl)amino)cyclohexyl)amino)acetic acid (racemic) and 2-(((cis)-4-(((trans)-2-((E)-1-phenylbut-1-en-2-yl)cyclopropyl)amino)cyclohexyl)amino)acetic Acid (Racemic)

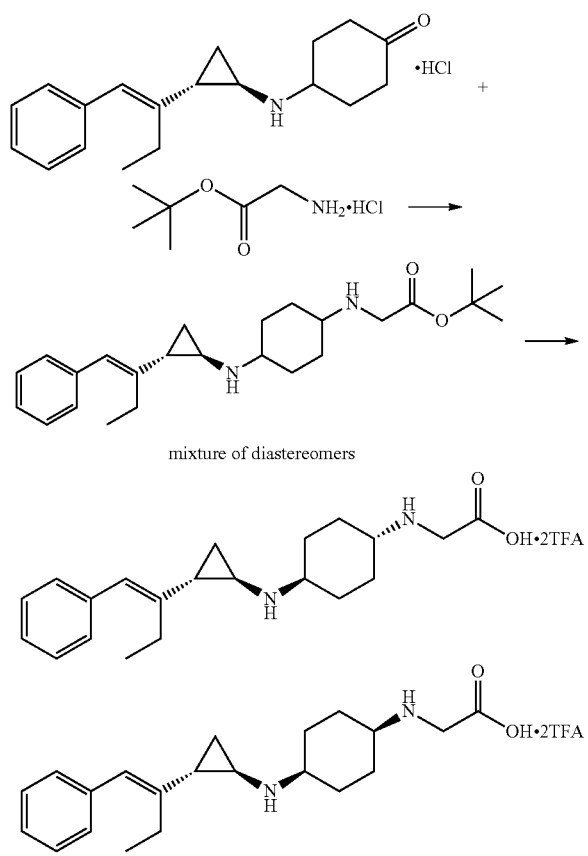

Step 1: tert-butyl (4-(((trans)-2-((E)-1-phenylbut-1-en-2-yl)cyclopropyl)amino)cyclohexyl)glycinate To 4-(((trans)-2-((E)-1-phenylbut-1-en-2-yl)cyclopropyl)amino)cyclohexan-1-one hydrochloride (150 mg, 468 µmol) and tert-butyl 2-aminoacetate hydrochloride (98.0 mg, 585 µmol) in 1,2-dichloroethane (4 mL) was added sodium (triacetoxy)borohydride (296 mg, 1.40 mmol). After 30 min, methylene chloride and potassium carbonate (1M aqueous) were added. The organic phase was isolated, evaporated and the crude residue purified by column chromatography (silica, 0% to 10% methanol in EtOAc) to afford a mixture of diastereomers of tert-butyl (4-(((trans)-2-((E)-1-phenylbut-1-en-2-yl)cyclopropyl)amino)cyclohexyl)glycinate (17.0 mg, 42.6 µmol) in 9% yield.

Step 2: 2-(((trans)-4-(((trans)-2-((E)-1-phenylbut-1-en-2-yl)cyclopropyl)amino)cyclohexyl)amino)acetic Acid bis(trifluoroacetic Acid) Salt (Racemic) and 2-(((cis)-4-(((trans)-2-((E)-1-phenylbut-1-en-2-yl)cyclopropyl)amino)cyclohexyl)amino)acetic Acid bis(trifluoroacetic Acid) Salt (Racemic)

tert-butyl (4-(((trans)-2-((E)-1-phenylbut-1-en-2-yl)cyclopropyl)amino)cyclohexyl)glycinate (17.0 mg, 42.6 µmol) was dissolved in 1,4-dioxane (2 ml), hydrogen chloride (4M in 1,4-dioxane, 1 ml, 4 mmol) and hydrochloric acid in water (6M aqueous, 200 µL, 1.2 mmol). The reaction mixture was stirred at 45° C. for 16 hours. Purified by preparative HPLC (SunFire C18 OBD column 5 µm (19×100 mm), 5% to 50% acetonitrile in water gradient over 9 minutes, 0.1% trifluoroacetic acid as phase modifier) to afford two sets of fractions containing isomeric compounds.

The earlier eluting set of fractions was pooled frozen and lyophilized to afford 2-(((trans)-4-(((trans)-2-((E)-1-phenylbut-1-en-2-yl)cyclopropyl)amino)cyclohexyl)amino)acetic acid bis(trifluoroacetic acid) salt (56.0 mg, 98.1 µmol) in 35% yield. $^1$H NMR (400 MHz, DMSO-d6) δ 9.03 (br. s., 3H), 8.17-8.51 (m, 1H), 7.48-7.83 (m, 1H), 7.29-7.40 (m, 2H), 7.13-7.26 (m, 3H), 6.21 (s, 1H), 3.87 (s, 2H), 2.71-3.22 (m, 4H), 2.54 (br. s., 2H), 2.08-2.30 (m, 4H), 1.92-2.04 (m, 1H), 1.40 (m, 3H), 1.20-1.26 (m, 1H), 1.14-1.19 (m, 1H), 1.11 (t, J=7.45 Hz, 3H). LCMS (ESI+): 343.3 (M+H).

The later eluting set of fractions was pooled frozen and lyophilized to afford 2-(((cis)-4-(((trans)-2-((E)-1-phenylbut-1-en-2-yl)cyclopropyl)amino)cyclohexyl)amino)acetic acid bis(trifluoroacetic acid) salt (21.0 mg, 36.8 µmol) in 13% yield. $^1$H NMR (400 MHz, DMSO-d6) δ 8.90 (br. s., 3H), 8.74-8.84 (m, 1H), 7.29-7.38 (m, 2H), 7.14-7.26 (m, 3H), 6.23 (s, 1H), 3.93 (br. s., 2H), 3.40 (br. s., 2H), 3.25 (br. s., 2H), 2.94 (br. s., 1H), 2.20-2.28 (m, 2H), 1.91-2.05 (m, 3H), 1.76-1.87 (m, 5H), 1.26 (d, J=4.15 Hz, 1H), 1.16-1.22 (m, 1H), 1.11 (t, J=7.57 Hz, 3H). LCMS (ESI+): 343.3 (M+H)

Synthesis of Compound 278: 3-(((trans)-4-(((trans)-2-(E)-1-phenylbut-1-en-2-yl)cyclopropyl)amino)cyclohexyl)amino)propanoic Acid bis(trifluoroacetic Acid) Salt (Racemic) and Compound 279: 3-(((cis)-4-(((trans)-2-(E)-1-phenylbut-1-en-2-yl)cyclopropyl)amino)cyclohexyl)amino)propanoic Acid bis(trifluoroacetic Acid) Salt (Racemic)

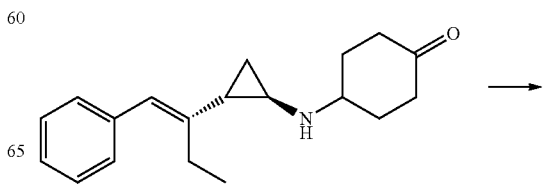

-continued

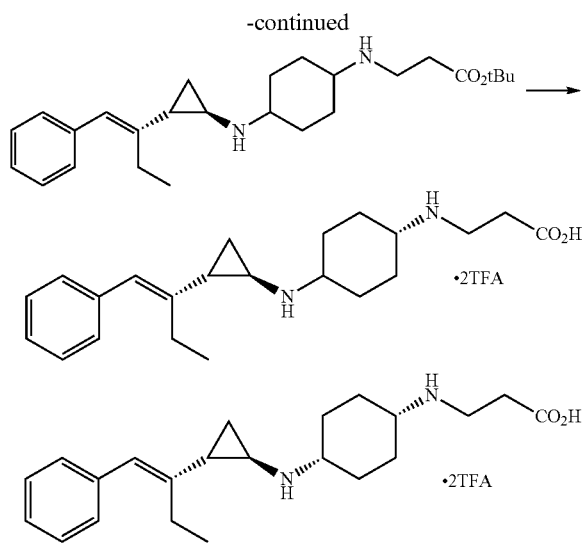

Step 1: tert-butyl 3-(((trans)-4-(((trans)-2-(E)-1-phenylbut-1-en-2-yl)cyclopropyl)amino)cyclohexyl)amino)propanoate and tert-butyl 3-(((cis)-4-(((trans)-2-((E)-1-phenylbut-1-en-2-yl)cyclopropyl)amino)cyclohexyl)amino)propanoate To a re-sealable vial containing 4-(((trans)-2-((E)-1-phenylbut-1-en-2-yl)cyclopropyl)amino)cyclohexan-1-one (201 mg, 0.630 mmol) and 3-(tert-butoxy)-3-oxopropan-1-aminium chloride (145 mg, 0.798 mmol) was added 1,2-dichloroethane (1.0 mL). The resulting suspension was stirred for 30 min at room temperature, followed by addition of Na(OAc)$_3$BH (169 mg, 0.798 mmol) in one portion. The reaction mixture turned homogeneous immediately. The mixture was stirred and monitored by LC-MS until complete conversion of SM was observed. After 2 h, the reaction mixture was partitioned between sat. NaHCO$_3$ and CH$_2$Cl$_2$. The aqueous layer was extracted with CH$_2$Cl$_2$ (3×). The combined organic layers were washed with water, dried over Na$_2$SO$_4$, and concentrated to give a mixture of tert-butyl 3-(((trans)-4-(((trans)-2-((E)-1-phenylbut-1-en-2-yl)cyclopropyl)amino)cyclohexyl)amino)propanoate and tert-butyl 3-(((cis)-4-(((trans)-2-((E)-1-phenylbut-1-en-2-yl)cyclopropyl)amino)cyclohexyl)amino)propanoate (256 mg, 0.620 mmol, 98.8% yield combined) as a clear oil. The mixture of products were subjected to the next transformation without further purification. LC/MS: m/z 413 [M−H]$^+$.

Step 2: 3-(((trans)-4-(((trans)-2-((E)-1-phenylbut-1-en-2-yl)cyclopropyl)amino)cyclohexyl)amino)propanoic Acid bis(trifluoroacetic Acid) Salt (Racemic) and 3-(((cis)-4-(((trans)-2-((E)-1-phenylbut-1-en-2-yl)cyclopropyl)amino)cyclohexyl)amino)propanoic Acid bis(trifluoroacetic Acid) Salt (Racemic)

To a solution of (E)-tert-butyl 3-((4-((2-(1-phenylbut-1-en-2-yl)cyclopropyl)amino)cyclohexyl)amino)propanoate (256 mg, 0.6204 mmol) in 1,4-dioxane (3 mL) was added an aqueous solution of 6N hydrogen chloride (1.03 mL, 6.20 mmol). The reaction mixture was heated to 40° C. overnight. After 24 h, the reaction mixture was cooled to room temperature and concentrated to dryness. The mixture of diastereomers were separated by reverse phase HPLC (gradient 5% CH$_3$CN: 95% Water with 0.1% TFA to 35% CH$_3$CN: 65% Water with 0.1% TFA over 11 min, then ramp to 95% CH$_3$CN: 5% Water over 1 min) to yield 3-(((trans)-4-(((trans)-2-((E)-1-phenylbut-1-en-2-yl)cyclopropyl)amino)cyclohexyl)amino)propanoic Acid bis(trifluoroacetic Acid) Salt (83.0 mg, 0.142 mmol) as white solids and 3-(((cis)-4-(((trans)-2-((E)-1-phenylbut-1-en-2-yl)cyclopropyl)amino)cyclohexyl)amino)propanoic Acid bis(trifluoroacetic Acid) Salt (76.3 mg, 0.131 mmol) as white solids after drying.

(trans)-N1-(2-carboxyethyl)-N4-((trans)-2-((E)-1-phenylbut-1-en-2-yl)cyclopropyl)cyclohexane-1,4-diaminium 2,2,2-trifluoroacetate: $^1$H NMR (400 MHz, DMSO-d6) δ 9.15-8.84 (m, 2H), 8.53 (br. s., 2H), 7.41-7.30 (m, 2H), 7.26-7.15 (m, 3H), 6.22 (s, 1H), 3.16 (br. s., 3H), 3.07 (br. s., 1H), 2.87 (br. s., 1H), 2.64 (t, J=7.08 Hz, 2H), 2.29-2.10 (m, 6H), 1.97 (br. s., 1H), 1.39 (br. s., 4H), 1.16-1.27 (m, 2H), 1.12 (t, J=7.57 Hz, 3H); LC/MS: m/z 357 [M+H]$^+$.

(cis)-N1-(2-carboxyethyl)-N4-((trans)-2-(E)-1-phenylbut-1-en-2-yl)cyclopropyl)cyclohexane-1,4-diaminium 2,2,2-trifluoroacetate: $^1$H NMR (400 MHz, DMSO-d6) δ 9.10 (br. s., 1H), 8.93 (br. s., 1H), 8.54 (br. s., 2H), 7.39-7.31 (m, 2H), 7.26-7.14 (m, 3H), 6.24 (s, 1H), 3.43 (br. s., 1H), 3.29 (br. s., 1H), 3.18 (br. s., 2H), 2.94 (br. s., 1H), 2.68 (t, J=7.08 Hz, 2H), 2.25 (q, J=7.57 Hz, 2H), 2.08-2.01 (m, 1H), 1.96 (hr. s., 2H), 1.90-1.78 (m, 6H), 1.31-1.25 (m, 1H), 1.20 (q, 1=6.84 Hz, 1H), 1.12 (t, =7.57 Hz, 3H); LC/MS: m/z 357 [M+H]$^+$.

Synthesis of Compound 280: (E)-N-((1H-imidazol-4-yl)methyl)-2-(1-phenylprop-1-en-2-yl)cyclopropan-1-amine Dihydrochloride

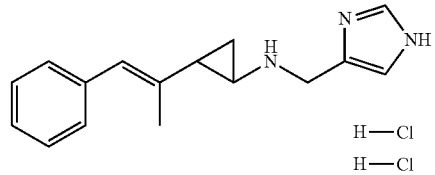

To a solution of (E)-2-(1-phenylprop-1-en-2-yl)cyclopropanamine hydrochloride (50 mg, 0.24 mmol) and 1H-imidazole-5-carbaldehyde (21 mg, 0.21 mmol) in 1,2-dichloroethane (1 mL) was added sodium triacetoxyborohydride (126 mg, 0.596 mmol) at room temperature. The reaction was stirred for 1 h before it was quenched with an aqueous sodium bicarbonate solution. The mixture was stirred vigorously for 5 min then the desired product was extracted with methyl tert-butylether (four times). The combined organic layers were dried over sodium sulfate, filtered and concentrated under vacuum. The residue was purified by flash chromatography (silica gel, 50% to 100% ethyl acetate in hexane followed by 0% to 20% methanol in ethyl acetate) and salted with 4M hydrochloric acid in 1,4-dioxane to give the titled compound in 31% yield. $^1$H NMR (400 MHz, DMSO-d$_6$) δ 14.73 (br. s, 2H), 10.42 (br. s, 2H), 9.12 (s, 1H), 7.83 (s, 1H), 7.34 (t, J=7.30 Hz, 2H), 7.15-7.27 (m, 3H), 6.28 (s, 1H), 4.43 (d, J=14.80 Hz, 1H), 4.38 (d, J=14.80 Hz, 1H), 2.94 (td, J=3.94, 7.51 Hz, 1H), 2.14-2.26 (m, 1H), 1.73 (s, 3H), 1.27-1.38 (m, 1H), 1.15-1.26 (m, 1H). LCMS (ESI+): 254 (M+H).

Synthesis of Compound 281: (E)-N-(2-(1-phenyl-prop-1-en-2-yl)cyclopropyl)azetidin-3-amine Dihydrochloride

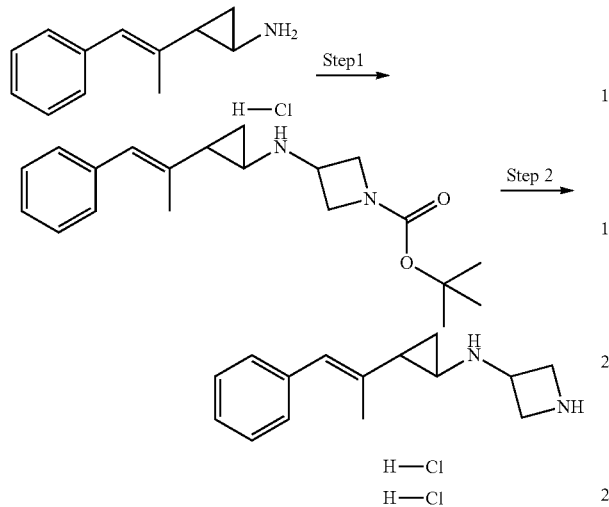

Step 1: tert-butyl (E)-3-((2-(1-phenylprop-1-en-2-yl)cyclopropyl)amino)azetidine-1-carboxylate To a solution of (E)-2-(1-phenylprop-1-en-2-yl)cyclopropanamine hydrochloride (50 mg, 0.24 mmol) and tert-butyl 3-oxoazetidine-1-carboxylate (37 mg, 0.21 mmol) in 1,2-dichloroethane (2.5 mL) was added sodium triacetoxyborohydride (126 mg, 0.596 μmol) at room temperature. The reaction was stirred for 1 h before it was quenched with an aqueous sodium bicarbonate solution. The mixture was stirred vigorously for 5 min then the desired product was extracted with methyl tert-butylether (four times). The combined organic layers were dried over sodium sulfate, filtered and concentrated under vacuum. The residue was purified by flash chromatography (silical gel, 50% to 100% ethylacetate in hexane) to give the title compound in 37% yield. LCMS (ESI+): 351 (M+Na).

Step 2: (E)-N-(2-(1-phenylprop-1-en-2-yl)cyclopropyl)azetidin-3-amine Dihydrochloride To a solution of tert-butyl (E)-3-((2-(1-phenylprop-1-en-2-yl)cyclopropyl)amino)azetidine-1-carboxylate (29 mg, 0.088 mmol) in 1,4-dioxane (1 mL) was added hydrogen chloride (4M in 1,4-dioxane) (550 μL, 2.2 mmol) at room temperature. The reaction was heated to 50° C. for 45 min before it was concentrated to dryness under vacuum to give the title compound in 83% yield. $^1$H NMR (400 MHz, DMSO-$d_6$) δ 10.81 (hr. s., 2H), 9.75 (br. s., 1H), 9.26 (br. s., 1H), 7.34 (t, J=7.80 Hz, 2H), 7.17-7.27 (m, 2H), 6.35 (s, 1H), 4.27-4.46 (m, 3H), 4.14 (br. s., 2H), 2.87-2.96 (m, 1H), 2.16-2.25 (m, 1H), 1.76 (d, J=0.73 Hz, 3H), 1.30-1.38 (m, 1H), 1.15-1.22 (m, 1H). LCMS (ESI+): 229 (M+H).

Synthesis of Compound 282: (E)-3,3-difluoro-N-(2-(1-phenylprop-1-en-2-yl)cyclopropyl)piperidin-4-amine Dihydrochloride

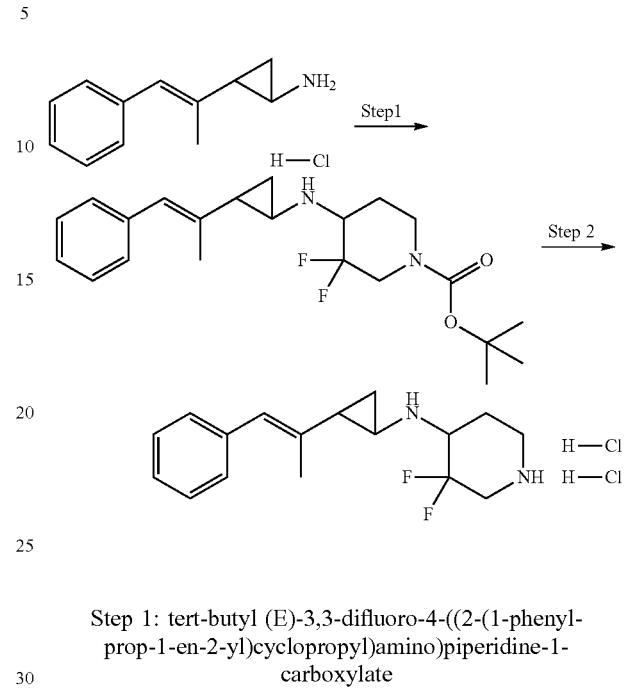

Step 1: tert-butyl (E)-3,3-difluoro-4-((2-(1-phenylprop-1-en-2-yl)cyclopropyl)amino)piperidine-1-carboxylate A solution of (E)-2-(1-phenylprop-1-en-2-yl)cyclopropanamine hydrochloride (100 mg, 0.48 mmol) and tert-butyl 3,3-difluoro-4,4-dihydroxypiperidine-1-carboxylate (120 mg, 0.48 mmol) in 1,2-dichloroethane (2 mL) was stirred at room temperature for 15 min before sodium triacetoxyborohydride (252 mg, 1.19 mmol) was added. After 2 h the reaction was quenched with an aqueous sodium bicarbonate solution. The mixture was stirred vigorously for 5 min then the desired product was extracted with methyl tert-butylether (four times). The combined organic layers were dried over sodium sulfate, filtered and concentrated under vacuum. The residue was purified by flash chromatography (silical gel, 20% to 100% ethylacetate in hexane) to give the title compound in 56% yield. LCMS (ESI+): 415.8 (M+Na).

Step 2: (E)-3,3-difluoro-N-(2-(1-phenylprop-1-en-2-yl)cyclopropyl)piperidin-4-amine Dihydrochloride To a solution of tert-butyl 3,3-difluoro-4-(((trans)-2-(E)-1-phenylprop-1-en-2-yl)cyclopropyl)amino)piperidine-1-carboxylate (105 mg, 0.268 mmol) in 1,4-dioxane (2 mL) was added hydrogen chloride (4M in 1,4-dioxane) (2.0 mL, 8.0 mmol) at room temperature. The reaction was heated to 50° C. for 45 min before it was concentrated to dryness under vacuum to give the title compound in 98% yield. $^1$H NMR (400 MHz, DMSO-$d_6$) δ 10.70 (br. s, 2H), 9.88 (br. s, 2H), 7.34 (t, J=7.30 Hz, 2H), 7.18-7.26 (m, 3H), 6.35 (s, 1H), 4.06-4.51 (m, 3H), 3.87-4.00 (m, 1H), 3.11 (t, J=13.31 Hz, 1H), 2.85-2.94 (m, 1H), 2.59 (d, J=12.70 Hz, 1H), 2.22-2.36 (m, 1H), 2.02-2.16 (m, 1H), 1.78 (s, 3H), 1.34-1.47 (m, 1H), 1.24 (quin, J=6.71 Hz, 1H). LCMS (ESI+): 293.6 (M+H).

Compound 184: Synthesis of 3-(((trans)-4-(((trans)-2-((E)-4-methoxy-1-phenylbut-1-en-2-yl)cyclopropyl)amino)cyclohexyl)amino)-2,2-dimethylpropanoic Acid bis(trifluoroacetic Acid) Salt (Racemic)

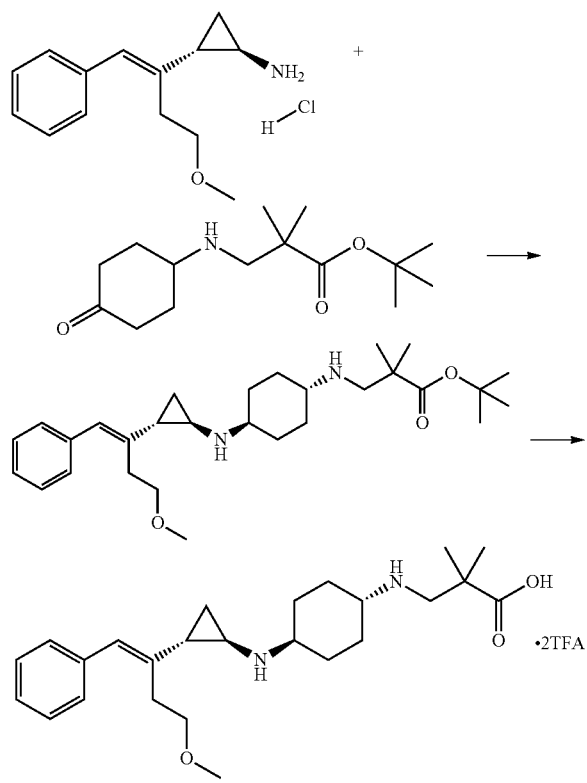

Step 1: tert-butyl 3-(((trans)-4-(((trans)-2-((E)-4-methoxy-1-phenylbut-1-en-2-yl)cyclopropyl)amino)cyclohexyl)amino)-2,2-dimethylpropanoate To (trans)-2-((E)-4-methoxy-1-phenylbut-1-en-2-yl)cyclopropanamine hydrochloride (0.166 g, 654 μmol) and tert-butyl 2,2-dimethyl-3-((4-oxocyclohexyl)amino)propanoate (176 mg, 654 μmol) in 1,2-dichloroethane (60 mL) was added sodium (triacetoxy)borohydride (5.59 g, 26.4 mmol). After 30 min, 1M potassium carbonate (aq.) was added followed by methylene chloride. The organic phase was isolated and evaporated under reduced pressure. The crude residue was purified by silica gel column chromatography (1:10:90 ammonia (30% aqueous):methanol:methylene chloride in methylene chloride (0% to 50% gradient), 40 g column) to afford two sets of fractions containing isomeric compounds. The last eluting fractions were evaporated to afford tert-butyl 3-(((trans)-4-(((trans)-2-((E)-4-methoxy-1-phenylbut-1-en-2-yl)cyclopropyl)amino)cyclohexyl)amino)-2,2-dimethylpropanoate (60.0 mg, 127 μmol) in 19% yield. LCMS (ESI+): 471.3 (M+H).

Step 2: 3-(((trans)-4-(((trans)-2-((E)-4-methoxy-1-phenylbut-1-en-2-yl)cyclopropyl)amino)cyclohexyl)amino)-2,2-dimethylpropanoic Acid bis(trifluoroacetic Acid) Salt tert-butyl 3-(((trans)-4-(((trans)-2-(E)-4-methoxy-1-phenylbut-1-en-2-yl)cyclopropyl)amino)cyclohexyl)amino)-2,2-dimethylpropanoate dihydrochloride (60 mg, 110 μmol) was taken in 1,4-dioxane (2 mL) and hydrochloric acid (1M aqueous, 0.6 ml, 0.6 mmol) was added. The reaction mixture was heated at 45° C. for 18 hours. The compound was purified by preparative HPLC (SunFire C18 OBD column 5 μm (19×100 mm), 5% to 50% acetonitrile in water gradient over 9 minutes, 0.1% trifluoroacetic acid as phase modifier) to afford 3-(((trans)-4-(((trans)-2-((E)-4-methoxy-1-phenylbut-1-en-2-yl)cyclopropyl)amino)cyclohexyl)amino)-2,2-dimethylpropanoic Acid bis(trifluoroacetic Acid) Salt (15.0 mg, 23.3 μmol) in 21% yield. (. $^1$H NMR (400 MHz, DMSO-d6) delta 12.98 (br. s, 1H), 8.81-9.11 (m, 2H), 8.37 (br. s., 2H), 7.29-7.40 (m, 2H), 7.14-7.29 (m, 3H), 6.32 (s, 1H), 3.53 (t, J=6.96 Hz, 2H), 3.35-3.45 (m, 1H), 3.24 (s, 3H), 3.18 (br. s., 1H), 2.77-3.10 (m, 4H), 2.51-2.57 (m, 1H), 2.07-2.28 (m, 4H), 2.02 (br. s., 1H), 1.33-1.54 (m, 4H), 1.20 (s, 6H), 1.08-1.29 (m, 2H). LCMS (ESI+): 415.2 (M+H).

Compound 185: Synthesis of 5-((((trans)-4-(((trans)-2-((E)-4-methoxy-1-phenylbut-1-en-2-yl)cyclopropyl)amino)cyclohexyl)amino)methyl)picolinic Acid bis(trifluoroacetic Acid) Salt (Racemic)

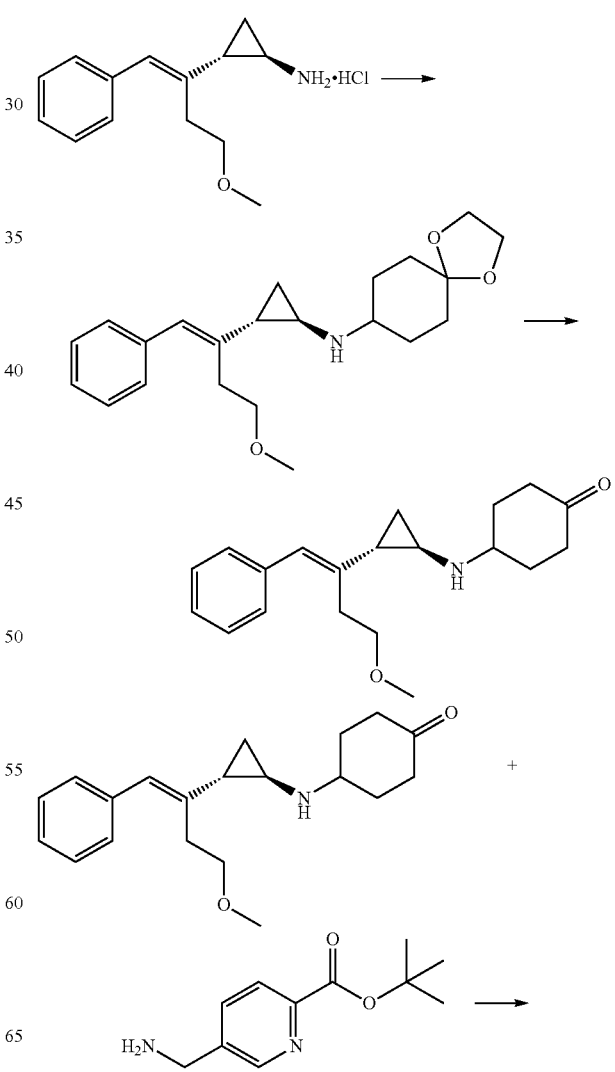

-continued

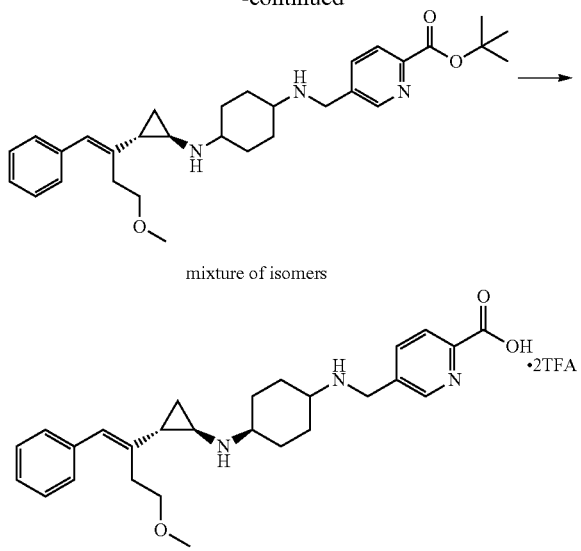

mixture of isomers

Step 1: N-((trans)-2-((E)-4-methoxy-1-phenylbut-1-en-2-yl)cyclopropyl)-1,4-dioxaspiro[4.5]decan-8-amine To (trans)-2-((E)-4-methoxy-1-phenylbut-1-en-2-yl)cyclopropanamine hydrochloride (0.166 g, 654 μmol) and 1,4-dioxaspiro[4.5]decan-8-one (102 mg, 654 μmol) in 60 mL of 1,2-dichloroethane (6 mL) was added sodium (triacetoxy)borohydride (275 mg, 1.3 mmol). After 30 min, 1M potassium carbonate (aq.) was added followed by methylene chloride. The organic phase was isolated, evaporated. Purified by silica gel column chromatography (10% to 100% EtOAc in hexanes, 25 g column) to afford N-((trans)-2-(E)-4-methoxy-1-phenylbut-1-en-2-yl)cyclopropyl)-1,4-dioxaspiro[4.5]decan-8-amine (211 mg, 590 μmol) LCMS (ESI+): 358.2 (M+H).

Step 2: 4-(((trans)-2-((E)-4-methoxy-1-phenylbut-1-en-2-yl)cyclopropyl)amino)cyclohexanone N-((trans)-2-((E)-4-methoxy-1-phenylbut-1-en-2-yl)cyclopropyl)-1,4-dioxaspiro[4.5]decan-8-amine (211 mg, 590 μmol) was dissolved in tetrahydrofuran (3 mL) and hydrochloric acid (6M aqueous, 1 mL, 6 mmol) was added. The reaction mixture was heated at 60° C. for 16 hours. The reaction mixture was partitioned between EtOAc and sodium bicarbonate (aq. Sat.). The organic layer was washed with brine, dried with Na2SO4, filtered and evaporated under reduced pressure. Purified by silica gel column chromatography (10% to 100% EtOAc in hexanes) to afford 4-(((trans)-2-((E)-4-methoxy-1-phenylbut-1-en-2-yl)cyclopropyl)amino)cyclohexanone (120 mg, 382 μmol) in 59% yield. LCMS (ESI+): 314.2 (M+H).

Step 3: tert-butyl 5-(((4-(((trans)-2-((E)-4-methoxy-1-phenylbut-1-en-2-yl)cyclopropyl)amino)cyclohexyl)amino)methyl)picolinate To 4-(((trans)-2-((E)-4-methoxy-1-phenylbut-1-en-2-yl)cyclopropyl)amino)cyclohexanone (120 mg, 382 μmol) and tert-butyl 5-(aminomethyl)picolinate (75.3 mg, 362 μmol) in 1,2-dichloroethane (4 mL) was added sodium (triacetoxy)borohydride (202 mg, 955 μmol). After 30 min, methylene chloride and potassium carbonate (1M aqueous) were added to the reaction mixture. The organic phase was isolated, evaporated and the crude residue purified by column chromatography (silica, 0% to 10% methanol in EtOAc) to afford tert-butyl 5-(((4-(((trans)-2-((E)-4-methoxy-1-phenylbut-1-en-2-yl)cyclopropyl)amino)cyclohexyl)amino)methyl)picolinate as a mixture of diastereomers (15.0 mg, 29.6 μmol) in 8% yield. LCMS (ESI+): 506.3 (M+H)

Step 4: 5-((((trans)-4-(((trans)-2-((E)-4-methoxy-1-phenylbut-1-en-2-yl)cyclopropyl)amino)cyclohexyl)amino)methyl)picolinic Acid bis(trifluoroacetic Acid) Salt (Racemic)

tert-butyl 5-(((4-(((trans)-2-((E)-4-methoxy-1-phenylbut-1-en-2-yl)cyclopropyl)amino)cyclohexyl)amino)methyl)picolinate (15.0 mg, 29.6 μmol) was dissolved in 1,4-dioxane (1 mL) and 6M aqueous hydrochloric acid (0.5 mL, 3 mmol) was added. The reaction mixture was heated for 9 hours at 45° C. The reaction mixture was concentrated under reduced pressure and purified by preparative HPLC. The pure fractions were frozen and lyophilized to afford 5-((((trans)-4-(((trans)-2-((E)-4-methoxy-1-phenylbut-1-en-2-yl)cyclopropyl)amino)cyclohexyl)amino)methyl)picolinic acid bis (trifluoroacetic Acid) Salt (5.00 mg, 7.37 μmol) in 25% yield. $^1$H NMR (400 MHz, DMSO-d6) δ 13.11-13.57 (br. s, 1H), 9.08 (br. s., 3H), 8.86-8.94 (m, 1H), 8.81 (s, 1H), 8.05-8.15 (m, 2H), 7.31-7.38 (m, 2H), 7.18-7.28 (m, 3H), 6.34 (s, 1H), 4.28-4.38 (m, 2H), 3.54 (t, J=6.84 Hz, 2H), 3.24 (s, 3H), 3.12 (s, 2H), 2.84-2.93 (m, 1H), 2.51-2.55 (m, 1H), 2.24 (br. s., 4H), 1.99-2.07 (m, 1H), 1.43 (m, 4H), 1.12-1.32 (m, 3H). LCMS (ESI+): 450.1 (M+H)

Compound 186: (E)-2-(2-fluorostyryl)-N-(piperidin-4-ylmethyl)cyclopropan-1-amine Dihydrochloride

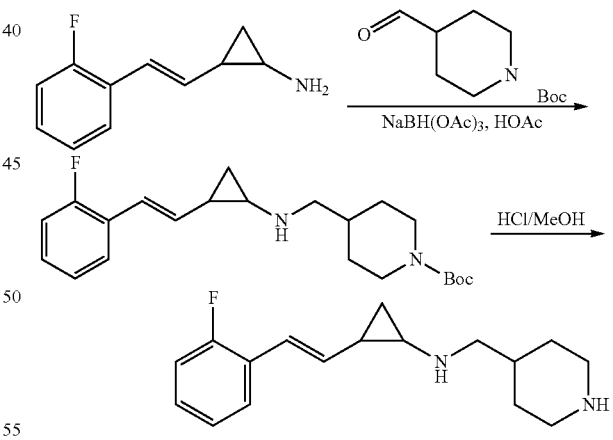

Step 1: tert-butyl (E)-4-(((2-(2-fluorostyryl)cyclopropyl)amino)methyl)piperidine-1-carboxylate A mixture of tert-butyl 4-formylpiperidine-1-carboxylate (50.00 mg, 234.44 umol, 1.00 eq), 2-[(E)-2-(2-fluorophenyl) vinyl]cyclopropanamine (62.32 mg, 351.66 umol, 1.50 eq), acetic acid (28.16 mg, 468.88 umol, 2.00 eq) and DCE (5.00 mL) was stirred at 20° C. for 0.5 h. To this solution was then added NaBH(OAc)$_3$ (99.37 mg, 468.88 umol, 2.00 eq) and the reaction stirred at 20° C. for 6 h. The reaction was then concentrated to afford crude tert-butyl (E)-4-(((2-(2-fluorostyryl)cyclopropyl)amino)methyl)piperidine-1-carboxylate (85.00 mg) as a yellow oil.

Step 2: (E)-2-(2-fluorostyryl)-N-(piperidin-4-ylmethyl)cyclopropan-1-amine Dihydrochloride A mixture of tert-butyl 4-[[[2-[(E)-2-(2-fluorophenyl)vinyl]cyclopropyl]amino]methyl]piperidine-1-carboxylate (85.00 mg, 226.98 umol, 1.00 eq) in HCl (4 M in MeOH, 10.00 mL, 176.23 eq) was stirred at 20° C. for 2 h. The mixture was purified by prep-HPLC (HCl) to afford (E)-2-(2-fluorostyryl)-N-(piperidin-4-ylmethyl)cyclopropan-1-amine Dihydrochloride (11.10 mg) as a yellow oil. LCMS (M+H$^+$) m/z: 275.

Compound 187: (E)-2-(2-phenylprop-1-en-1-yl)cyclopropan-1-amine Hydrochloride

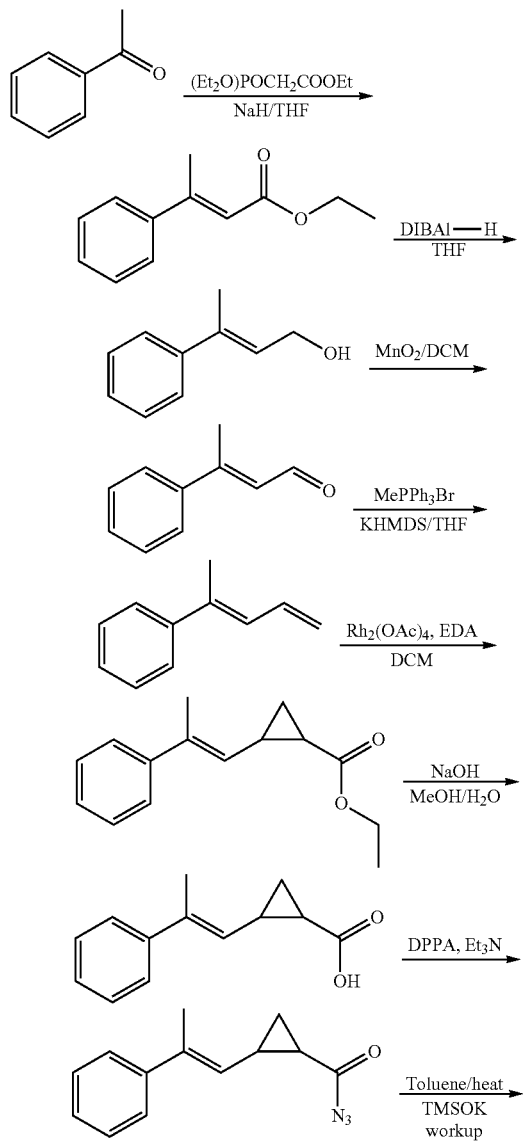

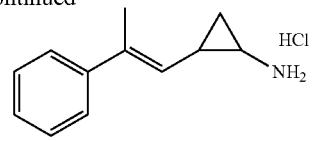

Step 1: ethyl (E)-3-phenylbut-2-enoate

To a stirred solution of ethyl 2-(diethoxyphosphoryl)acetate (9.33 g, 41.61 mmol, 1.00 eq) in THF (50.00 mL) was added NaH (4.00 g, 100.00 mmol, 2.40 eq) (60% purity) at 0° C. The mixture stirred at 0° C. for 0.5 h. Then 1-phenylethanone (5.00 g, 41.61 mmol, 1.00 eq) was added at 0° C. The mixture was stirred at 20° C. for 2 h. The reaction solution was quenched by addition of water (100 mL) and extracted with EtOAc (200 mL×3). The combined organics layer was dried over anhydrous Na$_2$SO$_4$, filtered and concentrated. The crude product was purified by silica gel chromatography (Petroleum ether/Ethyl acetate=1/0, 50/1) to afford ethyl (E)-3-phenylbut-2-enoate (3.60 g) as a light yellow oil.

Step 2: (E)-3-phenylbut-2-en-1-ol

To a stirred solution of ethyl (E)-3-phenylbut-2-enoate (3.60 g, 18.92 mmol, 1.00 eq) in THF (100.00 mL) was added DIBAL-H (1 M, 37.85 mL, 2.00 eq) at −75° C. under a nitrogen atmosphere. The reaction was stirred at −75° C. for 2 h. The reaction was quenched by addition of MeOH (5 mL) and water (100 mL) at 0° C. To this solution was added sodium potassium tartrate (30 g) and the mixture was stirred at 20° C. for 4 h and then extracted with EtOAc (50 mL, ×2). The combined organics layer was dried over anhydrous Na$_2$SO$_4$, filtered and concentrated. The crude product was purified via silica gel chromatography (Petroleum ether/Ethyl acetate=1/0, 10/1) to afford (E)-3-phenylbut-2-en-1-ol (1.20 g, 8.10 mmol, 42.80% yield) as a colorless oil.

Step 3: (E)-3-phenylbut-2-enal

To a stirred solution of (E)-3-phenylbut-2-en-1-ol (1.50 g, 10.12 mmol, 1.00 eq) in DCM (20.00 mL) was added MnO$_2$ (8.80 g, 101.20 mmol, 10.00 eq). The mixture was stirred at 20° C. for 17 h. The reaction was filtered and the filtrate was dried over anhydrous Na$_2$SO$_4$, filtered and concentrated. The crude product was purified by silica gel column chromatography (Petroleum ether/Ethyl acetate=1:0, 10:1) to afford (E)-3-phenylbut-2-enal (1.20 g, 8.21 mmol, 81.13% yield) as a light yellow oil. $^1$H NMR (400 MHz, CDCl$_3$) δ 10.19 (d, J=7.9 Hz, 1H), 7.55 (dd, J=6.4, 2.9 Hz, 2H), 7.47-7.38 (m, 3H), 6.40 (d, J=7.9 Hz, 1H), 2.58 (s, 3H).

Step 4: (E)-penta-2,4-dien-2-ylbenzene

To a stirred solution of bromo(methyl)triphenylphosphorane (8.80 g, 24.63 mmol, 3.00 eq) in THF (45 mL) was added KHMDS (1 M, 24.63 mL, 3.00 eq) at 0° C. under a nitrogen atmosphere. The mixture was stirred at 20° C. for 2 h. To this solution was then added (E)-3-phenylbut-2-enal (1.20 g, 8.21 mmol, 1.00 eq) dissolved in THF (5 mL). The reaction was stirred at 20° C. for 2 h before being quenched by water (100 mL). The aqueous solution was extracted with EtOAc (100 mL×3). The combined organic layers were dried over anhydrous Na$_2$SO$_4$, filtered and concentrated.

The crude product was purified by silica gel chromatography (Petroleum ether/Ethyl acetate=1/0) to afford (E)-penta-2,4-dien-2-ylbenzene (1.00 g) as a colorless oil. $^1$H NMR (400 MHz, CDCl$_3$) δ 7.52 (d, J=7.5 Hz, 2H), 7.39 (t, J=7.5 Hz, 2H), 7.35-7.28 (m, 1H), 6.84 (td, J=16.8, 10.6 Hz, 1H), 6.54 (d, J=10.6 Hz, 1H), 5.39 (d, J=16.8 Hz, 1H), 5.26 (d, J=10.1 Hz, 1H), 2.24 (s, 3H).

Step 5: ethyl (E)-2-(2-phenylprop-1-en-1-yl)cyclopropane-1-carboxylate

To a stirred solution of (E)-penta-2,4-dien-2-ylbenzene (1.00 g, 6.93 mmol, 1.00 eq) in DCM (20.00 mL) was added Rh$_2$(OAc)$_4$ (612.60 mg, 1.39 mmol, 0.20 eq). Then ethyldiazoacetate (2.37 g, 20.79 mmol, 3.00 eq) was added at 0° C. under an Ar atmosphere. The mixture was stirred at 20° C. for 4 h. The reaction was quenched by water (10 mL) and the aqueous solution was extracted with DCM (30 mL×3). The combined organic layers were dried over anhydrous Na$_2$SO$_4$, filtered and concentrated. The crude product was purified by silica gel chromatography (Petroleum ether/Ethyl acetate=1/0, 50/1) to afford ethyl (E)-2-(2-phenylprop-1-en-1-yl)cyclopropane-1-carboxylate (1.30 g, 5.64 mmol, 81.45% yield) as a colorless oil. LCMS (M+H$^+$) m/z: 231.

Step 6: (E)-2-(2-phenylprop-1-en-1-yl)cyclopropane-1-carboxylic Acid

To a stirred solution of ethyl (E)-2-(2-phenylprop-1-en-1-yl)cyclopropane-1-carboxylate (1.30 g, 5.64 mmol, 1.00 eq) in MeOH (50.00 mL) and H$_2$O (20.00 mL) was added NaOH (2.26 g, 56.40 mmol, 10.00 eq) at 0° C. The mixture was stirred at 80° C. for 2 h. The reaction was concentrated. The aqueous solution was adjusted to pH=4 by addition of HCl (4 N) and then extracted with EtOAc (50 mL×3). The combined organic layers were dried over anhydrous Na$_2$SO4, filtered and concentrated to afford crude (E)-2-(2-phenylprop-1-en-1-yl)cyclopropane-1-carboxylic acid (680.00 mg) as a yellow solid. LCMS (M+H$^+$) m/z: 203.

Step 7: (E)-2-(2-phenylprop-1-en-1-yl)cyclopropane-1-carbonyl Azide

To a stirred solution of (E)-2-(2-phenylprop-1-en-1-yl)cyclopropane-1-carboxylic acid (650.00 mg, 3.21 mmol, 1.00 eq) in toluene (10.00 mL) was added triethylamine (975.63 mg, 9.64 mmol, 3.00 eq) and diphenylphosphorylazide (1.06 g, 3.86 mmol, 1.20 eq). The mixture was stirred at 20° C. for 4 h. The reaction was concentrated and the crude product was purified by silica gel chromatography (Petroleum ether/Ethyl acetate=1/0, 50/1) to afford (E)-2-(2-phenylprop-1-en-1-yl)cyclopropane-1-carbonyl azide (560.00 mg) as a yellow oil.

Step 8: (E)-2-(2-phenylprop-1-en-1-yl)cyclopropan-1-amine Hydrochloride (E)-2-(2-phenylprop-1-en-1-yl)cyclopropane-1-carbonyl azide (420.00 mg, 1.85 mmol, 1.00 eq) was dissolved in toluene (20.00 mL) and the mixture was stirred at 120° C. for 4 h. The reaction was then cooled to 20° C. before addition of potassium trimethylsilanolate (355.64 mg, 2.77 mmol, 1.50 eq). The reaction was stirred at 20° C. for 17 h before being quenched by water (20 mL) and stirred for 0.5 h before being concentrated. The aqueous solution was extracted with EtOAc (20 mL×1) and DCM (20 mL×2). The combined organic layers were dried over anhydrous Na$_2$SO$_4$, filtered and then treated with HCl (4 N in MeOH). The mixture was concentrated under vacuum to afford (E)-2-(2-phenylprop-1-en-1-yl)cyclopropan-1-amine hydrochloride (200.00 mg) as a yellow solid. LCMS (M+H$^+$) m/z: 174.

Compound 188: (Z)—N-(piperidin-4-ylmethyl)-2-styrylcyclopropan-1-amine Dihydrochloride

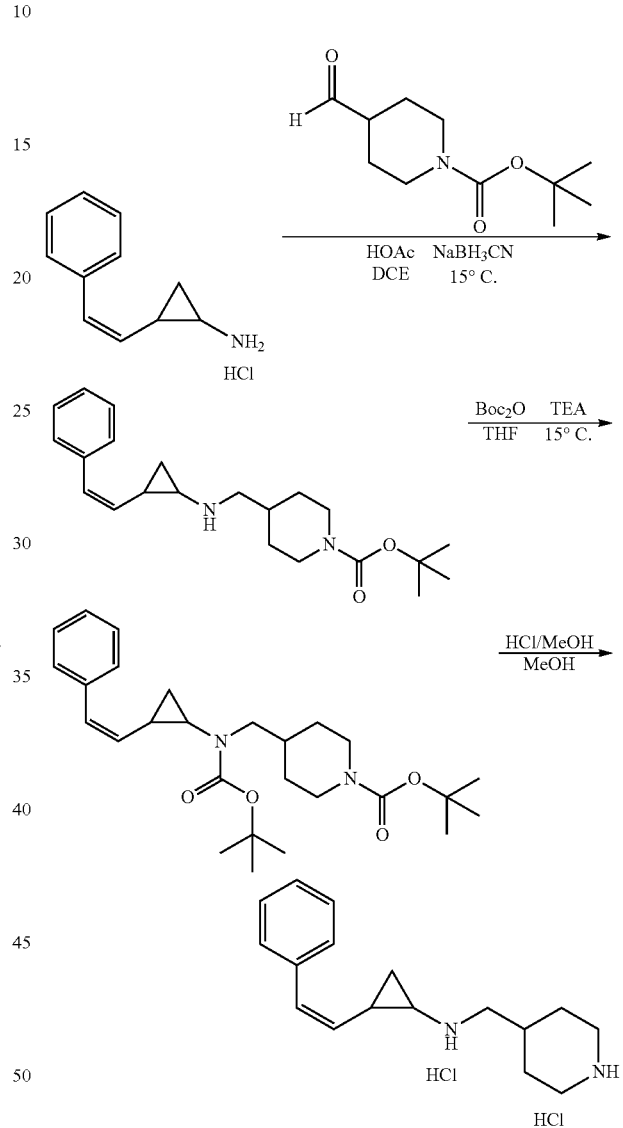

Step 1: tert-butyl (Z)-4-(((2-styrylcyclopropyl)amino)methyl)piperidine-1-carboxylate A solution of (Z)-2-styrylcyclopropan-1-amine hydrochloride (50.00 mg, 255.51 umol, 1.00 eq) dissolved in DCM (5 mL) was freebased by the addition of aqueous K$_2$CO$_3$. The phases were separated and the aqueous phase was extracted with DCM (5 mL*2). The combined organics phase was concentrated in vacuo. The resulting residue was dissolved in DCE (5.00 mL) and tert-butyl 4-formylpiperidine-1-carboxylate (54.49 mg, 255.51 umol, 1.00 eq) was added. The reaction was stirred at 15° C. for 16 h before addition of NaBH$_3$CN (48.17 mg, 766.53 umol, 3.00 eq).

The reaction was then stirred at 15° C. for 3 h before addition of water (5 mL). The mixture was extracted with DCM (5 mL*3) and the combined organics phase was concentrated in vacuo to afford crude tert-butyl (Z)-4-(((2-styrylcyclopropyl)amino)methyl)piperidine-1-carboxylate (160.00 mg) as a yellow oil.

Step 2: tert-butyl (Z)-4-(((tert-butoxycarbonyl)(2-styrylcyclopropyl)amino)methyl)piperidine-1-carboxylate To a solution of tert-butyl (Z)-4-(((2-styrylcyclopropyl)amino)methyl)piperidine-1-carboxylate (160.00 mg, 251.33 umol, 1.00 eq), triethylamine (76.30 mg, 754.00 umol, 3.00 eq), and THF (5.00 mL) was added Boc$_2$O (60.34 mg, 276.47 umol, 1.10 eq). The solution was stirred at 15° C. for 3 h before addition of water (5 mL). The reaction was extracted with ethyl acetate (10 mL*2) and the combined organics phase was concentrated in vacuo to afford crude tert-butyl (Z)-4-(((tert-butoxycarbonyl)(2-styrylcyclopropyl)amino)methyl)piperidine-1-carboxylate (20.00 mg, 41.61 umol, 16.56% yield, 95% purity) as a yellow solid.

Step 3: (Z)—N-(piperidin-4-ylmethyl)-2-styrylcyclopropan-1-amine Dihydrochloride To a solution of tert-butyl (Z)-4-(((tert-butoxycarbonyl)(2-styrylcyclopropyl)amino)methyl)piperidine-1-carboxylate (20.00 mg, 43.80 umol, 1.00 eq) in MeOH (500.00 uL) was added HCl (4M in MeOH, 1.00 mL) and the reaction was stirred at 15° C. for 1 h. The reaction was concentrated in vacuo to (Z)—N-(piperidin-4-ylmethyl)-2-styrylcyclopropan-1-amine Dihydrochloride (15.00 mg) as a brown solid. LCMS (M+H) m/z 257.

Compound 189: (E)-2-(2-phenylprop-1-en-1-yl)-N-(piperidin-4-ylmethyl)cyclopropan-1-amine Dihydrochloride and tert-butyl 4-formylpiperidine-1-carboxylate (184.65 mg, 865.80 umol, 1.00 eq) was added acetic acid (155.97 mg, 2.60 mmol, 3.00 eq). The mixture was stirred at 20° C. for 2 h before addition of NaBH(OAc)$_3$ (220.20 mg, 1.04 mmol, 1.20 eq). The mixture was stirred at 20° C. for 2 h. The reaction was quenched by addition of H$_2$O (20 mL) and extracted with DCM (20 mL×3). The combined organics layer was dried over anhydrous Na$_2$SO$_4$, filtered and concentrated. The crude product was purified via prep-TLC (PE/EtOAc=0:1) to afford tert-butyl (E)-4-(((2-(2-phenylprop-1-en-1-yl)cyclopropyl)amino)methyl)piperidine-1-carboxylate (50 mg). LCMS (M+H$^+$) m/z: 371.

Step 2: (E)-2-(2-phenylprop-1-en-1-yl)-N-(piperidin-4-ylmethyl)cyclopropan-1-amine Dihydrochloride To a stirred solution of tert-butyl (E)-4-(((2-(2-phenylprop-1-en-1-yl)cyclopropyl)amino)methyl)piperidine-1-carboxylate (50.00 mg, 134.94 umol, 1.00 eq) in EtOAc (5.00 mL) was added HCl (4 M in MeOH, 10.00 mL, 296.43 eq). The mixture was stirred at 20° C. for 4 h. The reaction was concentrated and the crude product was purified by prep-HPLC (Mobile phase A: water with 0.05% HCl solution; Mobile phase B: CH$_3$CN; column temperature: 30° C., Gradient: 2-32% 8 min) to afford (E)-2-(2-phenylprop-1-en-1-yl)-N-(piperidin-4-ylmethyl)cyclopropan-1-amine Dihydrochloride (4.20 mg) as a yellow solid. LCMS (M+H$^+$) m/z: 271

Compound 190 and Compound 191: (1R,2S)-2-((E)-1-phenylprop-1-en-2-yl)cyclopropan-1-amine hydrochloride (single stereoisomers) and (1S,2R)-2-((E)-1-phenylprop-1-en-2-yl)cyclopropan-1-amine Hydrochloride (Single Stereoisomers)

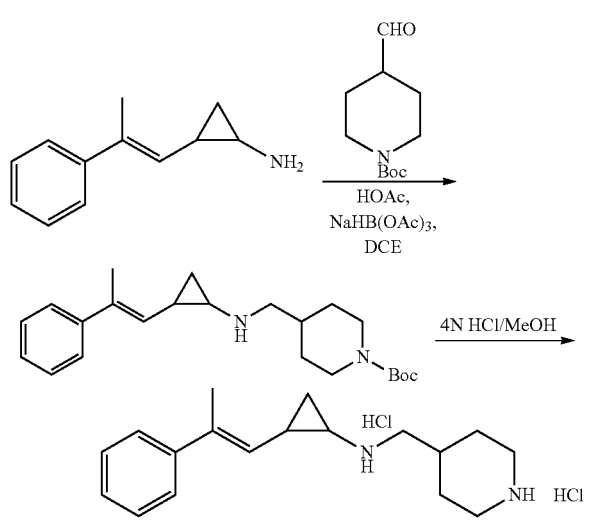

Step 1: tert-butyl (E)-4-(((2-(2-phenylprop-1-en-1-yl)cyclopropyl)amino)methyl)piperidine-1-carboxylate To a stirred solution of (E)-2-(2-phenylprop-1-en-1-yl)cyclopropan-1-amine (150.00 mg, 865.80 umol, 1.00 eq)

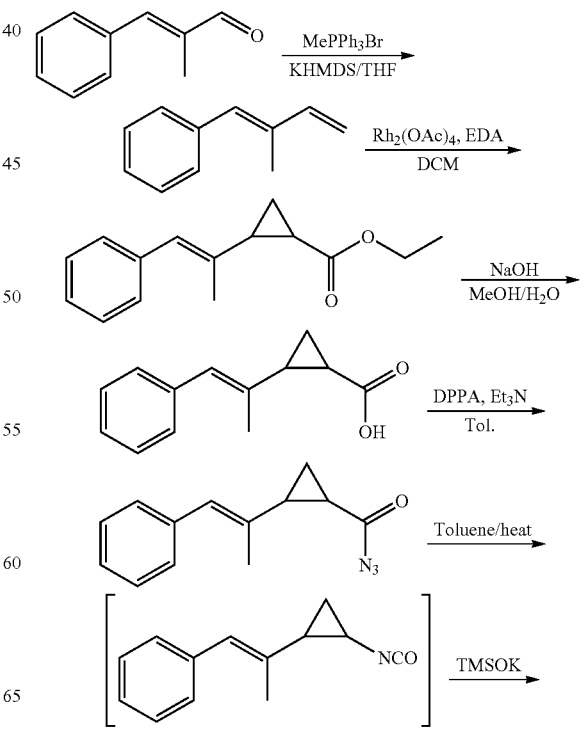

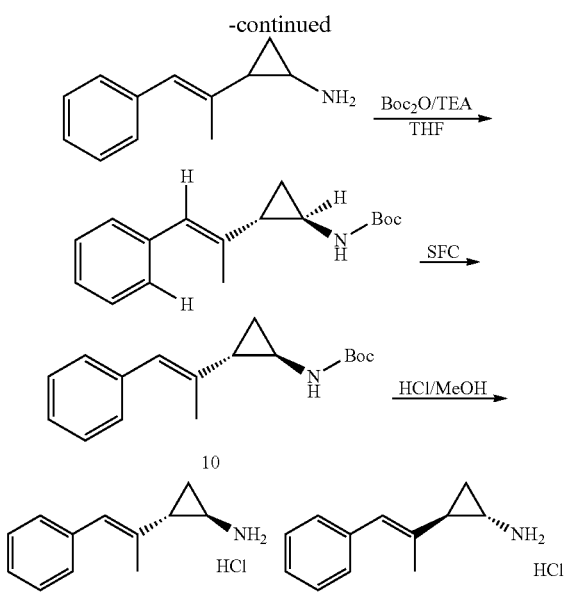

Step 1: (E)-(2-methylbuta-1,3-dien-1-yl)benzene

To a mixture of bromo-methyl-triphenyl-phosphane (20.04 g, 56.09 mmol, 1.64 eq) in THF (200.00 mL) was added KHMDS (1 M, 59.85 mL, 1.75 eq) at −78° C. The mixture was stirred at −78° C. for 0.5 h and 0° C. for 0.5 h. (E)-2-methyl-3-phenyl-prop-2-enal (5.00 g, 34.20 mmol, 1.00 eq) was added and the mixture was stirred at 16° C. for 6 h. Sat. NH$_4$Cl (10 mL) and water (30 mL) were added and the volatiles were removed in vacuo. The aqueous mixture was extracted with petroleum ether (50 mL*3). The combined organics layer was washed with brine, dried over anhydrous Na$_2$SO$_4$, filtered, and concentrated. The crude material was purified by column chromatography on silica gel (elute: petroleum ether) to afford (E)-(2-methylbuta-1,3-dien-1-yl)benzene (2.70 g, 18.72 mmol, 54.74% yield) as a colorless oil.

Step 2: (E)-2-(1-phenylprop-1-en-2-yl)cyclopropane-1-carboxylate

To a mixture of (E)-(2-methylbuta-1,3-dien-1-yl)benzene (500.00 mg, 3.47 mmol, 1.00 eq) and Rh$_2$(OAc)$_4$ (153.25 mg, 347.00 umol, 0.10 eq) in DCM (15.00 mL) was added ethyl 2-diazoacetate (1.58 g, 13.88 mmol, 4.00 eq) dropwise under Ar. The mixture was stirred at 16° C. for 3 h. The mixture was filtered and the filtrate was concentrated. The residue was purified by column chromatography on silica gel to afford ethyl (E)-2-(1-phenylprop-1-en-2-yl)cyclopropane-1-carboxylate (1.00 g, crude) as a colorless oil.

Step 3: (E)-2-(1-phenylprop-1-en-2-yl)cyclopropane-1-carboxylic Acid

To a solution of (E)-2-(1-phenylprop-1-en-2-yl)cyclopropane-1-carboxylate (1.00 g, 4.34 mmol, 1.00 eq) in H$_2$O (5.00 mL) and MeOH (3.00 mL) was added NaOH (1.74 g, 43.40 mmol, 10.00 eq). The mixture was stirred at 18° C. for 12 h and 60° C. for 3 h. The reaction mixture was cooled to room temperature and concentrated. The remaining aqueous phase was washed with petroleum ether:ethyl acetate (10 mL, 5:1). The aqueous layer was adjusted to pH=~6 and a brown solid appeared. The mixture was filtered and the filter cake was collected. The cake was dissolved in toluene and the mixture was concentrated to afford (E)-2-(1-phenylprop-1-en-2-yl)cyclopropane-1-carboxylic acid (500.00 mg, 2.27 mmol, 52.41% yield, 92% purity).

Step 4: (E)-2-(1-phenylprop-1-en-2-yl)cyclopropane-1-carbonyl Azide

To a solution of (E)-2-(1-phenylprop-1-en-2-yl)cyclopropane-1-carboxylate (500.00 mg, 2.47 mmol, 1.00 eq) in toluene (10.00 mL) was added diphenylphosphoryl azide (747.72 mg, 2.72 mmol, 1.10 eq) and triethylamine (749.82 mg, 7.41 mmol, 3.00 eq) The mixture was stirred at 18° C. for 2 h. The mixture was washed with brine (5 mL) and concentrated. The crude residue was purified by column chromatography on silica gel (elute: petroleum ether to petroleum ether:ethyl acetate=15:1) to afford (E)-2-(1-phenylprop-1-en-2-yl)cyclopropane-1-carbonyl azide (300.00 mg, 1.27 mmol, 51.31% yield, 96% purity) as a yellow oil.

Step 5: (trans)-2-((E)-1-phenylprop-1-en-2-yl)cyclopropan-1-amine

A solution of (E)-2-(1-phenylprop-1-en-2-yl)cyclopropane-1-carbonyl azide (300.00 mg, 1.32 mmol, 1.00 eq) in toluene (10.00 mL) was stirred at 120° C. for 2 h. potassium trimethylsilanolate (169.35 mg, 1.32 mmol, 1.00 eq) was added and the mixture was stirred at 18° C. for 12 h. Water (10 mL) was added and the mixture was stirred for 1 h. The mixture was extracted with ethyl acetate. The combined organics layer was concentrated to afford (trans)-2-((E)-1-phenylprop-1-en-2-yl)cyclopropan-1-amine (0.2 g, crude)

Step 6: tert-butyl ((trans)-2-((E)-1-phenylprop-1-en-2-yl)cyclopropyl)carbamate

To a solution of (trans)-2-((E)-1-phenylprop-1-en-2-yl)cyclopropan-1-amine (200.00 mg, 1.15 mmol, 1.00 eq) in THF (5.00 mL) were added Boc$_2$O (250.99 mg, 1.15 mmol, 1.00 eq) and triethylamine (116.37 mg, 1.15 mmol, 1.00 eq). The mixture was stirred at 20° C. for 12 h. The reaction was concentrated and the residue taken up in DCM (20 mL). The organic layer was washed with brine (5 mL) and then concentrated. The crude residue was purified by prep-TLC (PE:EA=3:1) to afford tert-butyl ((trans)-2-((E)-1-phenylprop-1-en-2-yl)cyclopropyl)carbamate (100.00 mg, 358.49 umol, 31.17% yield, 98% purity) as a white solid.

Step 7: tert-butyl ((1R,2S)-2-(E)-1-phenylprop-1-en-2-yl)cyclopropyl)carbamate and tert-butyl ((1S,2R)-2-((E)-1-phenylprop-1-en-2-yl)cyclopropyl)carbamate tert-butyl ((trans)-2-((E)-1-phenylprop-1-en-2-yl)cyclopropyl)carbamate (80.00 mg, 292.64 umol) was separated by chiral SFC (Instrument: SFC-14, Column: AD (250 mm*30 mm, 5 um), Condition: Base-MeOH, Begin B: 25%, FlowRate (ml/min): 60 ML/MIN) to afford tert-butyl ((1S,2R)-2-((E)-1-phenylprop-1-en-2-yl)cyclopropyl)carbamate (40.00 mg, 144.86 umol, 49.50% yield, 99% purity, 99% ee) and tert-butyl ((1R,2S)-2-((E)-1-phenylprop-1-en-2-yl)cyclopropyl)carbamate (20.00 mg, 72.43 umol, 24.75% yield, 99% purity, 99% ee) as white solids.

Step 8: (1S,2R)-2-((E)-1-phenylprop-1-en-2-yl)cyclopropan-1-amine Hydrochloride (Compound 190)

tert-butyl ((1S,2R)-2-((E)-1-phenylprop-1-en-2-yl)cyclopropyl)carbamate (40.00 mg, 146.32 umol, 1.00 eq) was added into methanolic HCl (4N, 3.00 mL). The mixture was stirred at 16° C. for 1 h. The mixture was concentrated to afford (1S,2R)-2-((E)-1-phenylprop-1-en-2-yl)cyclopropan-1-amine hydrochloride (15.00 mg) as brown solid. LCMS (M+H$^+$) m/z: 174. $^1$H NMR (400 MHz, METHANOL-d$_4$) δ 7.34-7.20 (m, 5H), 6.40 (s, 1H), 2.79-2.77 (m, 1H), 2.04-2.01 (m, 1H), 1.85 (s, 3H), 1.30-1.16 (m, 2H).

(1R,2S)-2-(E)-1-phenylprop-1-en-2-yl)cyclopropan-1-amine hydrochloride was synthesized following the above procedure for the boc deprotection with HCl LCMS (M+m/z: 174. $^1$H NMR (400 MHz, METHANOL-d$_4$) δ 7.34-7.21 (m, 5H), 6.41 (s, 1H), 2.82-2.76 (m, 1H), 2.04-2.01 (m, 1H), 1.85 (s, 3H), 1.30-1.18 (m, 2H).

Compound 273: 4-((4-(((1R,2S)-2-((E)-1-phenyl-prop-1-en-2-yl)cyclopropyl)amino)piperidin-1-yl)methyl)benzoic Acid Dihydrochloride (Single Stereoisomer)

stirred overnight. The solution was concentrated and the crude reside purified via Biotage to afford tert-butyl 4-((4-(((1R,2S)-2-((E)-1-phenylprop-1-en-2-yl)cyclopropyl)amino)piperidin-1-yl)methyl)benzoate (667 mg, 1.49 mmol). LCMS 447.

Step 2: 4-((4-(((1R,2S)-2-(E)-1-phenylprop-1-en-2-yl)cyclopropyl)amino)piperidin-1-yl)methyl)benzoic Acid Dihydrochloride (Single Stereoisomer)

To a round bottomed flask was added tert-butyl 4-((4-(((1R,2S)-2-((E)-1-phenylprop-1-en-2-yl)cyclopropyl)amino)piperidin-1-yl)methyl)benzoate (667 mg, 1.49 mmol), dioxane (3.5 mL), and hydrogen chloride (2.48 mL, 14.9 mmol). The solution was heated 50° C. for 1.5 h before cooling to room temperature. To this solution was added deionized water and the solution was frozen and lyophilized. The resulting solid was triturated with MTBE to afford 4-((4-(((1R,2S)-2-((E)-1-phenylprop-1-en-2-yl)cyclopropyl)amino)piperidin-1-yl)methyl)benzoic acid dihydrochlo-

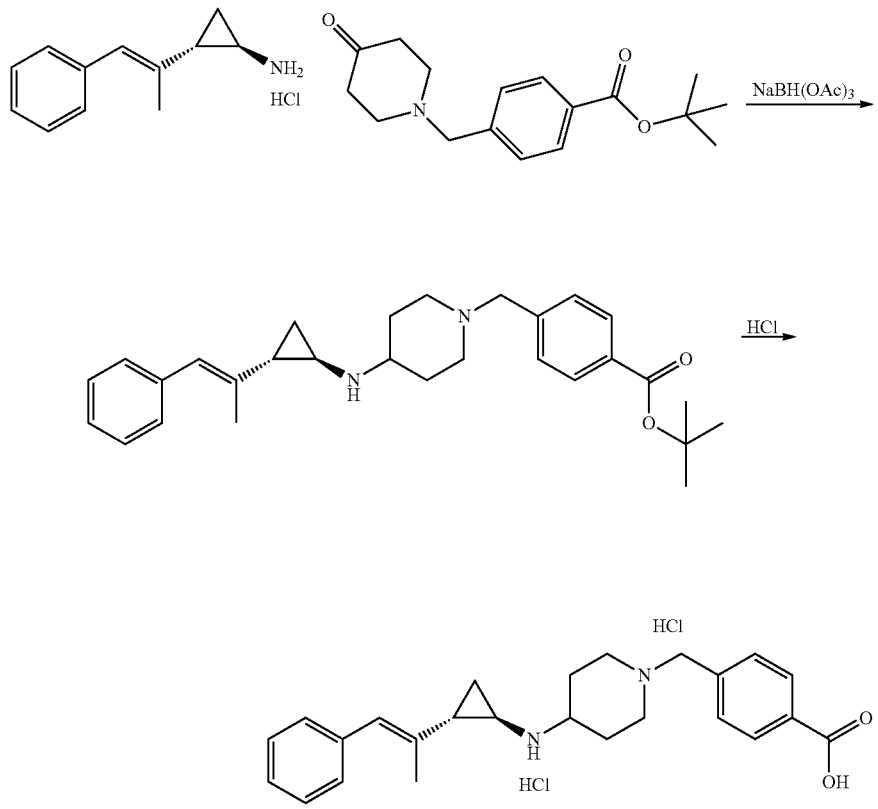

Step 1: tert-butyl 4-((4-(((1R,2S)-2-((E)-1-phenyl-prop-1-en-2-yl)cyclopropyl)amino)piperidin-1-yl)methyl)benzoate (Single Stereoisomer)

To a round bottomed flask was added (1R,2S)-2-((E)-1-phenylprop-1-en-2-yl)cyclopropanamine hydrochloride (501 mg, 2.38 mmol), tert-butyl 4-((4-oxopiperidin-1-yl)methyl)benzoate (1.03 g, 3.56 mmol), and DCM (12 mL). The solution was stirred at room temperature for 5 min before addition of sodium triacetoxyborohydride (754 mg, 3.56 mmol) and the reaction stirred for 1 h at room temperature. The solution was then diluted with MeOH and ride. LCMS 391. $^1$H NMR (400 MHz,DMSO-d$_6$) δ=11.03 (br. s., 1H), 9.78 (br. s., 2H), 8.00 (d, J=8.1 Hz, 2H), 7.79-7.67 (m, 2H), 7.38-7.29 (m, 2H), 7.27-7.16 (m, 3H), 6.36 (s, 1H), 4.34 (br. s., 2H), 3.52-3.33 (m, 3H), 3.00 (br. s., 2H), 2.87 (br. s., 1H), 2.36-2.25 (m, 2H), 2.21-2.13 (m, 1H), 2.13-2.00 (m, 2H), 1.76 (s, 3H), 1.35-1.27 (m, 1H), 1.25-1.17 (m, 1H).

The following examples were synthesized following the procedures outlined above using the appropriate starting materials and modifications.

| Cmpd. | Structure | 1H NMR | LCMS |
|---|---|---|---|
| 192 | 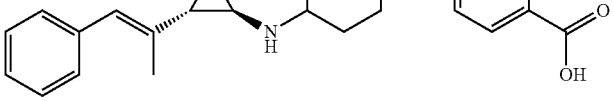<br>4-((4-(((1S,2R)-2-((E)-1-phenylprop-1-en-2-yl)cyclopropyl)amino)piperidin-1-yl)methyl)benzoic acid<br>(single stereoisomer) | $^1$H NMR (400 MHz, DMSO-$d_6$) δ 10.30-10.58 (m, 1 H), 9.46 (br. s., 2H), 8.01 (d, J = 7.81 Hz, 2H), 7.64 (br. s., 2H), 7.31-7.38 (m, 2H), 7.15-7.29 (m, 3H), 6.37 (s, 1H), 4.36 (br. s., 2H), 3.48 (br. s., 3H), 2.86-3.11 (m, 3H), 2.19-2.35 (m, 2H), 2.07 (br. s., 1H), 1.91 (br. s., 1H), 1.75 (s, 3H), 1.24 (t, J = 7.08 Hz, 2H) | 391 |

Compound 193: methyl 2-(4-(((trans)-2-((E)-1-phenylprop-1-en-2-yl)cyclopropyl)amino)piperidin-1-yl)acetate Dihydrochloride (Racemic)

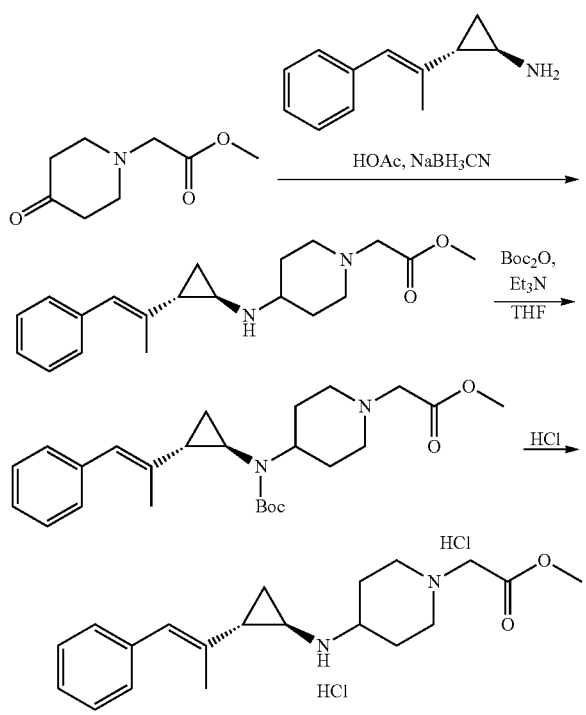

Step 1: methyl 2-(4-(((trans)-2-((E)-1-phenylprop-1-en-2-yl)cyclopropyl)amino)piperidin-1-yl)acetate To a stirred solution of (trans)-2-((E)-1-phenylprop-1-en-2-yl)cyclopropan-1-amine (150.00 mg, 865.80 umol, 1.00 eq) and methyl 2-(4-oxo-1-piperidyl)acetate (177.86 mg, 1.04 mmol, 1.20 eq) was added acetic acid (155.97 mg, 2.60 mmol, 3.00 eq). The mixture was stirred at 20° C. for 3 h before addition of NaBH$_3$CN (81.61 mg, 1.30 mmol, 1.50 eq). The mixture was stirred at 20° C. for 2 h before addition of water (20 mL). The reaction was extracted with DCM (30 mL×3) and the combined organic layers were dried over Na$_2$SO$_4$, filtered and concentrated to afford crude methyl 2-(4-(((trans)-2-((E)-1-phenylprop-1-en-2-yl)cyclopropyl)amino)piperidin-1-yl)acetate (400.00 mg) as a yellow oil. LCMS (M+H$^+$) m/z: 329.

Step 2: methyl 2-(4-((tert-butoxycarbonyl)((trans)-2-(E)-1-phenylprop-1-en-2-yl)cyclopropyl)amino) piperidin-1-yl)acetate To a stirred solution of methyl 2-(4-(((trans)-2-((E)-1-phenylprop-1-en-2-yl)cyclopropyl)amino)piperidin-1-yl)acetate (400.00 mg, 1.22 mmol, 1.00 eq) in THF (10.00 mL) was added triethylamine (370.36 mg, 3.66 mmol, 3.00 eq) and Boc$_2$O (319.52 mg, 1.46 mmol, 1.20 eq). The mixture was stirred at 20° C. for 17 h. The reaction was quenched by water (10 mL) and extracted with EtOAc (30 mL×3). The combined organic layers were dried over anhydrous Na$_2$SO$_4$, filtered and concentrated. The crude product was purified by prep-TLC (petroleum ether/ethyl acetate=0/1) to afford methyl 2-(4-((tert-butoxycarbonyl)((trans)-2-((E)-1-phenylprop-1-en-2-yl)cyclopropyl)amino)piperidin-1-yl)acetate (40.00 mg, 80.27 umol, 6.58% yield, 86% purity) as a light yellow oil. LCMS (M+H$^+$) m/z: 429.

Step 3: methyl 2-(4-(((trans)-2-((E)-1-phenylprop-1-en-2-yl)cyclopropyl)amino)piperidin-1-yl)acetate Dihydrochloride (Racemic)

To a stirred solution of methyl 2-(4-((tert-butoxycarbonyl)((trans)-2-(E)-1-phenylprop-1-en-2-yl)cyclopropyl)amino)piperidin-1-yl)acetate (20.00 mg, 46.67 umol, 1.00 eq) in MeOH (5.00 mL) was added HCl (4 M in MeOH, 10.00 mL, 857.08 eq). The mixture was stirred at 20° C. for 3 h. The reaction was concentrated to afford methyl 2-(4-(((trans)-2-((E)-1-phenylprop-1-en-2-yl)cyclopropyl)amino)piperidin-1-yl)acetate dihydrochloride (5.70 mg) as a yellow solid. LCMS (M+H$^+$) m/z: 329.

Compound 194: 2-(4-(((trans)-2-((E)-1-phenylprop-1-en-2-yl)cyclopropyl)amino)piperidin-1-yl)acetic Acid Dihydrochloride (Racemic)

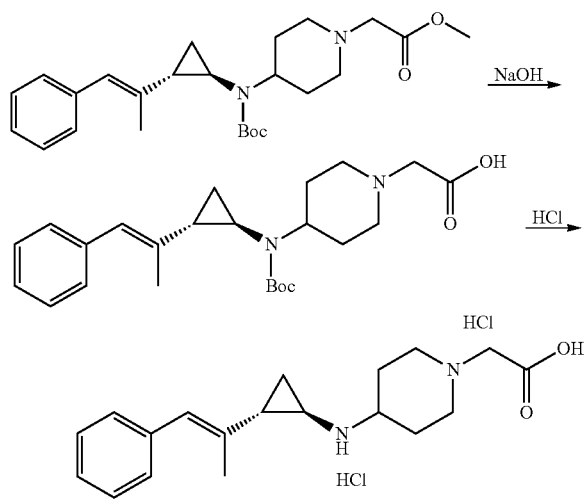

Step 1: 2-(4-((tert-butoxycarbonyl)((trans)-2-((E)-1-phenylprop-1-en-2-yl)cyclopropyl)amino)piperidin-1-yl)acetic Acid To a stirred solution of 2-(4-((tert-butoxycarbonyl)((trans)-2-((E)-1-phenylprop-1-en-2-yl)cyclopropyl)amino)piperidin-1-yl)acetate (60.00 mg, 140.00 umol, 1.00 eq) in MeOH (2.00 mL) and water (3.00 mL) was added NaOH (56.00 mg, 1.40 mmol, 10.00 eq). The mixture was stirred at 20° C. for 3 h. The reaction was concentrated and the remaining aqueous solution was adjusted to pH=6 by addition of HCl (4N) and then extracted with EtOAc (50 mL×3). The combined organic layers were dried over anhydrous $Na_2SO_4$, filtered, and concentrated to afford 2-(4-((tert-butoxycarbonyl)((trans)-2-(E)-1-phenylprop-1-en-2-yl)cyclopropyl)amino)piperidin-1-yl)acetic acid (50.00 mg, crude) as a yellow solid. LCMS (M+H$^+$) m/z: 415. $^1$H NMR (400 MHz, MeOD) δ 7.34-7.26 (m, 2H), 7.24-7.13 (m, 3H), 6.43 (s, 1H), 3.91 (s, 2H), 3.86-3.75 (m, 1H), 3.70 (d, J=11.8 Hz, 2H), 3.16 (t, J=12.8 Hz, 2H), 2.76 (dt, J=5.8, 3.8 Hz, 1H), 2.63-2.38 (m, 2H), 2.07-1.96 (m, 2H), 1.90-1.79 (m, 1H), 1.74 (d, J=1.0 Hz, 3H), 1.53-1.43 (m, 9H), 1.14 (dd, J=8.0, 6.3 Hz, 2H).

Step 2: 2-(4-(((trans)-2-((E)-1-phenylprop-1-en-2-yl)cyclopropyl)amino)piperidin-1-yl)acetic Acid Dihydrochloride (Racemic)

To a stirred solution of 2-(4-((tert-butoxycarbonyl)((trans)-2-((E)-1-phenylprop-1-en-2-yl)cyclopropyl)amino)piperidin-1-yl)acetic acid (20.00 mg, 48.25 umol, 1.00 eq) in dioxane (2.00 mL) was added HCl (4 M in dioxane, 5.00 mL, 414.51 eq). The mixture was stirred at 20° C. for 2 h. The reaction was concentrated and the crude product was purified by prep-HPLC (Mobile phase A: water with 0.05% HCl solution; Mobile phase B: CH3CN; column temperature: 30° C., Gradient: 5-35% 12 min) to afford 2-(4-(((trans)-2-((E)-1-phenylprop-1-en-2-yl)cyclopropyl)amino)piperidin-1-yl)acetic acid dihydrochloride (1.80 mg, 5.13 umol, 10.63% yield, HCl) as a yellow solid. LCMS (M+H$^+$) m/z: 315. $^1$H NMR (400 MHz, D$_2$O) δ7.39-7.32 (m, 2H), 7.30-7.20 (m, 3H), 6.40 (s, 1H), 3.86-3.61 (m, 6H), 3.18 (br. s., 2H), 2.91 (td, J=3.9, 7.6 Hz, 1H), 2.45 (d, J=13.2 Hz, 2H), 2.16-1.95 (m, 3H), 1.75 (s, 3H), 1.35 (q, J=7.1 Hz, 1H), 1.30-1.20 (m, 1H).

Compound 195: 1-(2-methoxyethyl)-N-((trans)-2-(E)-1-phenylprop-1-en-2-yl)cyclopropyl)piperidin-4-amine Dihydrochloride (Racemic)

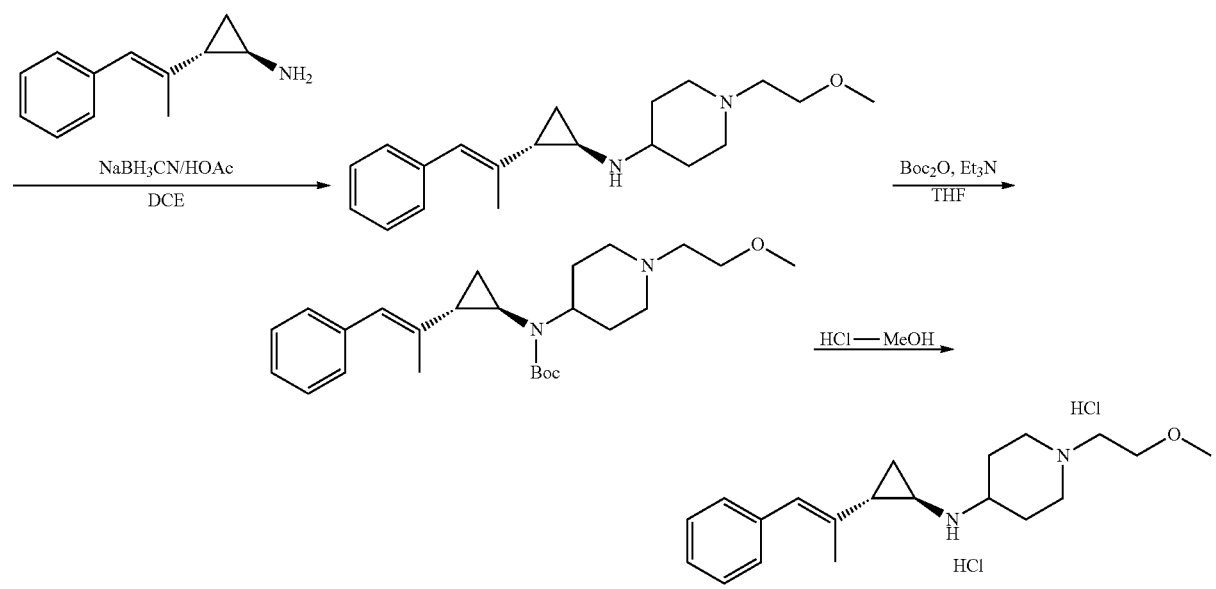

Step 1: 1-(2-methoxyethyl)-N-((trans)-2-(E)-1-phenylprop-1-en-2-yl)cyclopropyl)piperidin-4-amine To the mixture of 1-(2-methoxyethyl)piperidin-4-one (200.00 mg, 1.27 mmol, 1.00 eq) and (trans)-2-((E)-1- phenylprop-1-en-2-yl)cyclopropan-1-amine (242.45 mg, 1.40 mmol, 1.10 eq) in DCE (10.00 mL) was added acetic acid (152.53 mg, 2.54 mmol, 2.00 eq). The mixture was stirred at 15° C. for 1 h. To the mixture was added NaBH$_3$CN (239.83 mg, 3.82 mmol, 3.00 eq) and the reaction stirred at 15° C. for 16 h. To the mixture was added water (10 mL) and the reaction was extracted with dichloromethane (10 mL*2). The organic phases were combined and concentrated. The crude residue was purified by Prep-TLC (dichloromethane:methanol=20:1) to afford 1-(2-methoxyethyl)-N-((trans)-2-((E)-1-phenylprop-1-en-2-yl)cyclopropyl)piperidin-4-amine (190.00 mg) as a yellow solid. LCMS (M+H$^+$) m/z: 315.

Step 2: tert-butyl (1-(2-methoxyethyl)piperidin-4-yl) ((trans)-2-((E)-1-phenylprop-1-en-2-yl)cyclopropyl) carbamate Hydrochloride The solution of 1-(2-methoxyethyl)-N-((trans)-2-((E)-1-phenylprop-1-en-2-yl)cyclopropyl)piperidin-4-amine (190.00 mg, 368.57 umol, 1.00 eq), Boc$_2$O (80.44 mg, 368.57 umol, 1.00 eq) and triethylamine (74.59 mg, 737.14 umol, 2.00 eq) in THF (10.00 mL) was stirred at 15° C. for 16 h. The reaction was concentrated and the crude residue was purified by Prep-HPLC (Instrument: Phenomenex Synergi C18 150*30 mm*4 um Mobile phase A:water with 0.05% HCl Mobile phase B: acetonitrile, Gradient 18-48% B) to afford tert-butyl (1-(2-methoxyethyl)piperidin-4-yl) ((trans)-2-((E)-1-phenylprop-1-en-2-yl)cyclopropyl)carbamate hydrochloride (35.00 mg, 84.42 umol, 22.91% yield, 100% purity) as a white solid. LCMS (M+H$^+$) m/z: 415.

Step 3: 1-(2-methoxyethyl)-N-((trans)-2-(E)-1-phenylprop-1-en-2-yl)cyclopropyl)piperidin-4-amine Dihydrochloride (Racemic)

To the solution of tert-butyl (1-(2-methoxyethyl)piperidin-4-yl)((trans)-2-(E)-1-phenylprop-1-en-2-yl)cyclopropyl)carbamate hydrochloride (15.00 mg, 36.18 umol, 1.00 eq) in MeOH (2.00 mL) was added HCl (4 M in MeOH, 2.00 mL). The solution was stirred at 15° C. for 0.5 h. The solution was concentrated to afford 1-(2-methoxyethyl)-N-((trans)-2-((E)-1-phenylprop-1-en-2-yl)cyclopropyl)piperidin-4-amine Dihydrochloride (5.00 mg) as a yellow solid. LCMS (M+H$^+$) m/z: 315.

Compound 196: 2-(4-(((trans)-2-((E)-1-phenylprop-1-en-2-yl)cyclopropyl)amino)piperidin-1-yl)acetamide Dihydrochloride (Racemic)

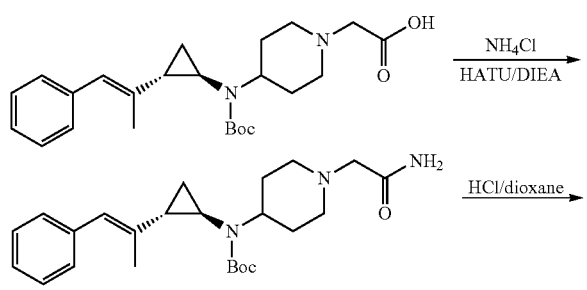

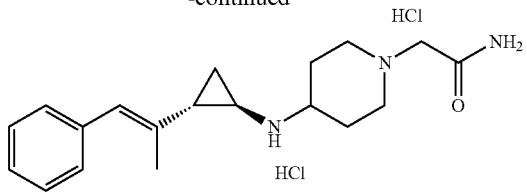

Step 1: tert-butyl (1-(2-amino-2-oxoethyppiperidin-4-yl)((trans)-2-((E)-1-phenylprop-1-en-2-yl)cyclopropyl)carbamate To a stirred solution of 2-(4-((tert-butoxycarbonyl) ((trans)-2-((E)-1-phenylprop-1-en-2-yl)cyclopropyl)amino) piperidin-1-yl)acetic acid (50.00 mg, 120.62 umol, 1.00 eq) in DCM (3.00 mL) were added HATU (55.03 mg, 144.74 umol, 1.20 eq) and diisopropylethylaniine (46.77 mg, 361.85 umol, 3.00 eq). The mixture was stirred at 20° C. for 0.5 h, then NH$_4$Cl (12.90 mg, 241.23 umol, 2.00 eq) was added to the reaction and the mixture was stirred at 20° C. for 2.5 h. The reaction was quenched by water (20 mL) and extracted with DCM (50 mLx3). The combined organic layers were dried over anhydrous Na$_2$SO$_4$, filtered, and concentrated. The crude residue was purified by prep-TLC (petroleum ether/ethyl acetate=0/1) to afford tert-butyl (1-(2-amino-2-oxoethyl)piperidin-4-yl)((trans)-2-((E)-1-phenylprop-1-en-2-yl)cyclopropyl)carbamate (35.00 mg, 81.25 umol, 67.36% yield) as a light yellow oil. LCMS (M+H$^+$) m/z: 414.

Step 2: 2-(4-(((trans)-2-((E)-1-phenylprop-1-en-2-yl)cyclopropyl)amino)piperidin-1-yl)acetamide Dihydrochloride To a stirred solution of tert-butyl (1-(2-amino-2-oxoethyl) piperidin-4-yl)((trans)-2-((E)-1-phenylprop-1-en-2-yl)cyclopropyl)carbamate (35.00 mg, 84.63 umol, 1.00 eq) in dioxane (3.00 mL) was added HCl (4 M in dioxane, 84.63 umol, 1.00 eq). The mixture was stirred at 20° C. for 2 h. The reaction was concentrated and the crude product was purified by prep-HPLC (Mobile phase A: water with 0.05% HCl solution; Mobile phase B: CH$_3$CN; column temperature: 30° C., Gradient: 5-35% 12 min) to afford 2-(4-(((trans)-2-((E)-1-phenylprop-1-en-2-yl)cyclopropyl)amino)piperidin-1-yl) acetamide dihydrochloride (1.80 mg) as a yellow solid. LCMS (M+H$^+$) m/z: 314. $^1$H NMR (400 MHz, D$_2$O) δ 7.41-7.34 (m, 2H), 7.32-7.23 (m, 3H), 6.41 (s, 1H), 4.03 (s, 2H), 3.80-3.65 (m, 4H), 3.26 (d, J=11.0 Hz, 3H), 2.93 (td, J=7.9, 4.0 Hz, 1H), 2.48 (d, J=13.2 Hz, 2H), 2.17-1.98 (m, 4H), 1.77 (s, 3H), 1.41-1.33 (m, 1H), 1.32-1.23 (m, 1H). (racemic)

Compound 283: N-((trans)-2-(E)-1-phenylprop-1-en-2-yl)cyclopropyl)-1-(pyrimidin-2-yl)piperidin-4-amine Hydrochloride (Racemic)

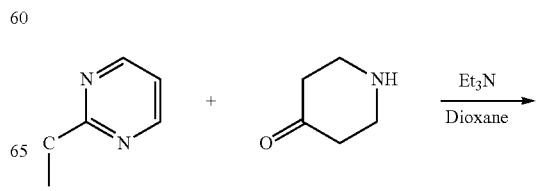

175
-continued

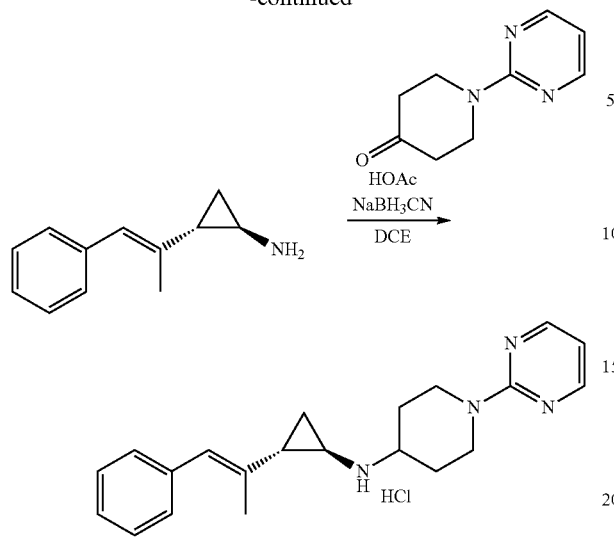

Step 1: 1-(pyrimidin-2-yl)piperidin-4-one

To a mixture of 2-chloropyrimidine (300.00 mg, 2.62 mmol, 1.00 eq) and piperidin-4-one (311.59 mg, 3.14 mmol, 1.20 eq) in dioxane (5.00 mL) was added triethylamine (795.35 mg, 7.86 mmol, 3.00 eq) and the mixture was stirred at 90° C. for 12 h. The mixture was concentrated under reduced pressure. The crude residue was purified by column chromatography (SiO2, PE/EA=10/1 to 1/1) to afford 1-pyrimidin-2-ylpiperidin-4-one (100.00 mg, 564.33 umol, 21.54% yield) as a yellow solid. $^1$H NMR (400 MHz, CHLOROFORM-d) δ=8.37 (d, J=4.9 Hz, 2H), 6.59 (t, J=4.6 Hz, 1H), 4.21-4.11 (m, 4H), 2.51 (t, J=6.2 Hz, 4H).

Step 2: N-((trans)-2-((E)-1-phenylprop-1-en-2-yl)cyclopropyl)-1-(pyrimidin-2-yl)piperidin-4-amine Hydrochloride (Racemic)

To a mixture of (trans)-2-((E)-1-phenylprop-1-en-2-yl)cyclopropan-1-amine (110.00 mg, 634.92 umol, 1.00 eq) and 1-(pyrimidin-2-yl)piperidin-4-one (112.51 mg, 634.92 umol, 1.00 eq) in DCE (2.00 mL) was added acetic acid (38.13 mg, 634.92 umol, 1.00 eq) and the mixture was stirred at 20° C. for 2 h. NaBH3CN (79.80 mg, 1.27 mmol, 2.00 eq) was added to the mixture and the reaction was stirred at 20° C. for 2 h. The mixture was concentrated and the crude residue was purified by prep-HPLC (HCl) to afford N-((trans)-2-((E)-1-phenylprop-1-en-2-yl)cyclopropyl)-1-(pyrimidin-2-yl)piperidin-4-amine hydrochloride (32.90 mg) as a yellow solid. LCMS (M+H+) m/z: 335. $^1$HNMR (400 MHz, METHANOL-d4) δ=8.51 (d, J=5.0 Hz, 2H), 7.37-7.29 (m, 2H), 7.26-7.18 (m, 3H), 6.86 (t, J=5.0 Hz, 1H), 6.45 (s, 1H), 4.83 (d, J=14.6 Hz, 2H), 3.76-3.67 (m, 1H), 3.21 (t, J=13.1 Hz, 2H), 3.00 (td, J=4.0, 7.7 Hz, 1H), 2.35 (d, J=12.0 Hz, 2H), 2.18-2.12 (m, 1H), 1.85 (s, 3H), 1.80-1.68 (m, 2H), 1.40-1.28 (m, 2H).

176

Compound 197: 1-(oxetan-3-yl)-N-((trans)-2-((E)-1-phenylprop-1-en-2-yl)cyclopropyl)piperidin-4-amine Dihydrochloride (Racemic)

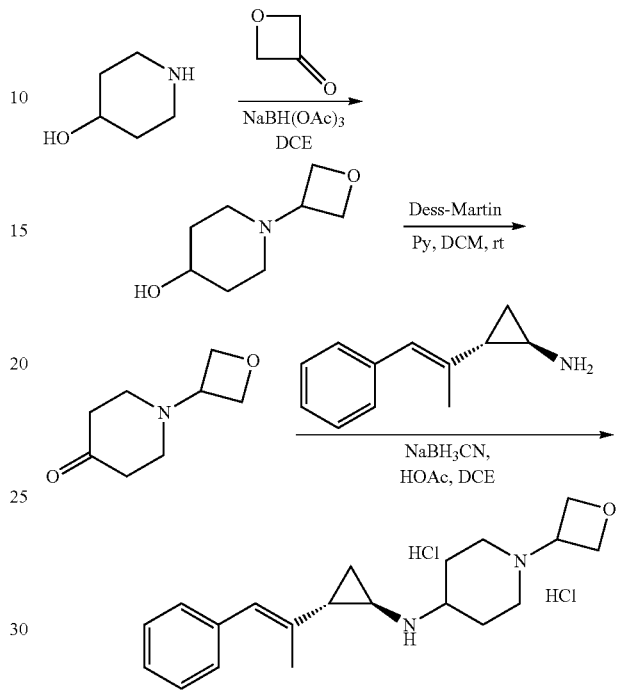

Step 1: 1-(oxetan-3-yl)piperidin-4-ol

To a mixture of oxetan-3-one (1.00 g, 13.88 mmol, 1.00 eq) in DCE (50.00 mL) was added piperidin-4-ol (1.68 g, 16.66 mmol, 1.20 eq) and the mixture was stirred at 20° C. for 2 hr. Then NaBH(OAc)3 (4.71 g, 22.21 mmol, 1.60 eq) was added and the mixture was stirred at 20° C. for 12 hr. The mixture was concentrated and the crude residue was diluted with a saturated solution of NaHCO3 (20 mL) and extracted with (DCM/MeOH=10/1) (20 mL*3). The combined organics phase was dried over anhydrous Na2SO4, filtered, and concentrated. The residue was purified by column chromatography (DCM/MeOH=10/1 to 5/1) to afford 1-(oxetan-3-yl)piperidin-4-ol (588.00 mg, 3.74 mmol, 26.95% yield) as a light yellow solid. $^1$H NMR (400 MHz, CHLOROFORM-d) δ=4.68-4.56 (m, 4H), 3.78-3.70 (m, 1H), 3.47 (quin, J=6.5 Hz, 1H), 2.64-2.53 (m, 2H), 2.08-1.98 (m, 2H), 1.92 (dd, J=3.5, 13.1 Hz, 2H), 1.67-1.53 (m, 3H).

Step 2: 1-(oxetan-3-yl)piperidin-4-one

To a mixture of 1-(oxetan-3-yl)piperidin-4-ol (100.00 mg, 636.09 umol, 1.00 eq) in DCM (4.00 mL) were added Dess-Martin periodinane (404.69 mg, 954.14 umol, 1.50 eq) and pyridine (980.00 mg, 12.39 mmol, 19.48 eq) at 0° C. and the mixture was warmed to room temperature and stirred for 2 h. The mixture was quenched by addition of a saturated solution (10 mL) of NaHCO3/Na2S2O3 (1:1) and extracted with (DCM/MeOH=10/1) (10 mL*3). The combined organic layers were dried over anhydrous Na2SO4, filtered and concentrated. The crude residue was purified by prep-TLC (DCM/MeOH=10/1) to afford 1-(oxetan-3-yl)piperidin-4-one (85.00 mg, 547.72 umol, 86.11% yield) as a light yellow solid. $^1$H NMR (400 MHz, CHLOROFORM-d) δ=4.75-4.63 (m, 4H), 3.61 (quin, J=6.3 Hz, 1H), 2.61 (t, J=5.9 Hz, 4H), 2.51 (t, J=5.9 Hz, 4H).

Step 3: 1-(oxetan-3-yl)-N-((trans)-2-(E)-1-phenyl-prop-1-en-2-yl)cyclopropyl)piperidin-4-amine Dihydrochloride (Racemic)

A mixture of (trans)-2-((E)-1-phenylprop-1-en-2-yl)cyclopropan-1-amine (50.00 mg, 288.60 umol, 1.00 eq), 1-(oxetan-3-yl)piperidin-4-one (44.79 mg, 288.60 umol, 1.00 eq) and acetic acid (17.33 mg, 288.60 umol, 1.00 eq) in DCE (2.00 mL) was stirred at 20° C. for 1.5 h. Then NaBH$_3$CN (36.27 mg, 577.20 umol, 2.00 eq) was added to the mixture and the mixture was stirred at 20° C. for 1.5 h. The mixture was concentrated and the crude residue was purified by prep-HPLC (HCl) to afford 1-(oxetan-3-yl)-N-((trans)-2-((E)-1-phenylprop-1-en-2-yl)cyclopropyl)piperidin-4-amine Dihydrochloride (5.80 mg) as a yellow solid. LCMS (M+H$^+$) m/z: 313. $^1$H NMR (400 MHz, METHANOL-d4) δ=7.35-7.29 (m, 2H), 7.25-7.18 (m, 3H), 6.46 (s, 1H), 4.91-4.87 (m, 4H), 4.44 (br. s., 1H), 3.75-3.65 (m, 3H), 3.18 (br. s., 1H), 3.08 (br. s., 1H), 3.05-2.99 (m, 2H), 2.51 (d, J=13.2 Hz, 2H), 2.22-2.17 (m, 2H), 1.85 (s, 3H), 1.41-1.34 (m, 2H).

Compound 198: N,N-dimethyl-3-(4-(((trans)-2-(E)-1-phenylprop-1-en-2-yl)cyclopropyl)amino)piperidin-1-yl)propanamide Dihydrochloride (Racemic)

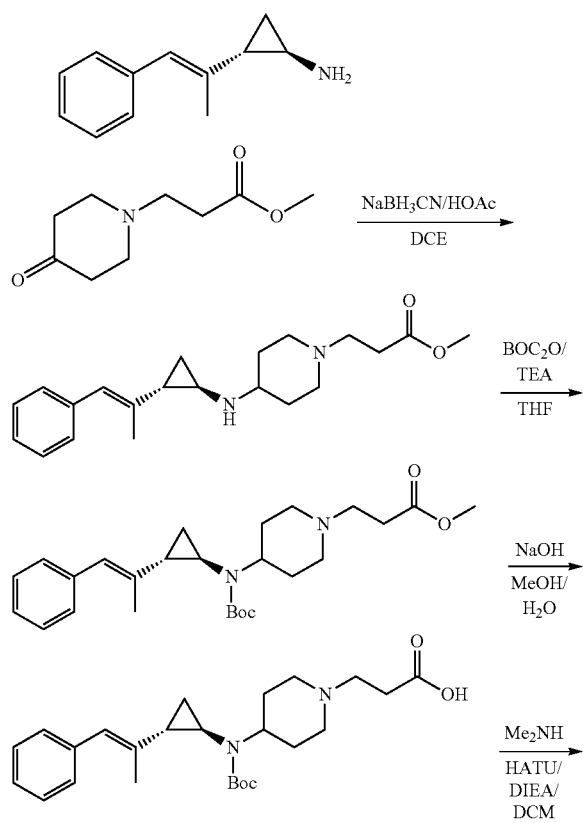

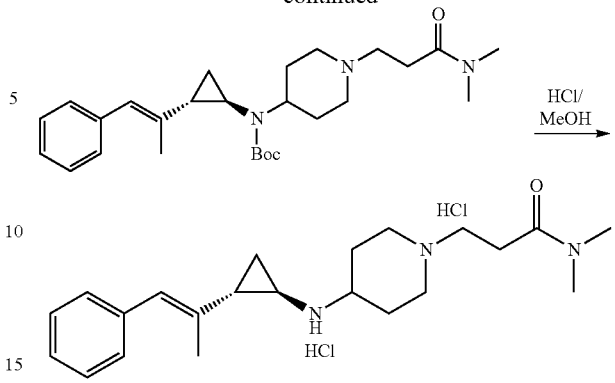

Step 1: methyl 3-(4-(((trans)-2-((E)-1-phenylprop-1-en-2-yl)cyclopropyl)amino)piperidin-1-yl)propanoate To a mixture of methyl 3-(4-oxo-1-piperidyl)propanoate (500.00 mg, 2.70 mmol, 1.00 eq) and (trans)-2-((E)-1-phenylprop-1-en-2-yl)cyclopropan-1-amine (467.69 mg, 2.70 mmol, 1.00 eq) in DCE (20.00 mL) was added acetic acid (486.31 mg, 8.10 mmol, 3.00 eq). The reaction mixture was stirred at 18° C. for 16 h before addition of NaBH$_3$CN (508.91 mg, 8.10 mmol, 3.00 eq) and the mixture was stirred at 18° C. for 1 h. The reaction was diluted with water (50 mL) and the mixture was extracted with DCM (50 mL*2). The combined organics phase was washed with brine (50 mL*2), dried with anhydrous Na$_2$SO$_4$, filtered and concentrated to afford methyl 3-(4-(((trans)-2-((E)-1-phenylprop-1-en-2-yl)cyclopropyl)amino)piperidin-1-yl)propanoate (600.00 mg, crude) as a yellow oil.

Step 2: methyl 3-(4-((tert-butoxycarbonyl)((trans)-2-(E)-1-phenylprop-1-en-2-yl)cyclopropyl)amino) piperidin-1-yl)propanoate To a mixture of 3-(4-(((trans)-2-((E)-1-phenylprop-1-en-2-yl)cyclopropyl)amino)piperidin-1-yl)propanoate (200.00 mg, 583.99 umol, 1.00 eq) in DCM (5.00 mL) were added triethylamine (177.28 mg, 1.75 mmol, 3.00 eq) and Boc$_2$O (152.95 mg, 700.79 umol, 1.20 eq). The reaction mixture was stirred at 18° C. for 16 h. The reaction was diluted with water (30 mL) and the mixture was extracted with DCM (20 mL*2). The organic layers were concentrated and the crude residue was purified by silica gel chromatography (Petroleum ether:Ethyl acetate 5:1 to 1:1) to afford methyl 3-(4-((tert-butoxycarbonyl)((trans)-2-(E)-1-phenylprop-1-en-2-yl)cyclopropyl)amino)piperidin-1-yl)propanoate (140.00 mg) as a yellow oil.

Step 3: 3-(4-((tert-butoxycarbonyl)((trans)-2-((E)-1-phenylprop-1-en-2-yl)cyclopropyl)amino)piperidin-1-yl)propanoic Acid To a mixture of methyl 3-(4-((tert-butoxycarbonyl) ((trans)-2-((E)-1-phenylprop-1-en-2-yl)cyclopropyl)amino) piperidin-1-yl)propanoate (140.00 mg, 316.32 umol, 1.00 eq) in MeOH (3.00 mL) and water (1.00 mL) was added NaOH (12.65 mg, 316.32 umol, 1.00 eq) at 0° C. The reaction mixture was stirred at 18° C. for 3 h. The volatiles were removed under vacuum and the mixture was adjusted to pH=7 with 4M HCl. The mixture was extracted with EtOAc (3 times) and the organic layers were concentrated to afford crude 3-(4-((tert-butoxycarbonyl)((trans)-2-((E)-1-phenylprop-1-en-2-yl)cyclopropyl)amino)piperidin-1-yl)propanoic acid (100.00 mg) as a yellow oil. LCMS (M+H⁺) m/z: 429.

Step 4: tert-butyl (1-(3-(dimethylamino)-3-oxopropyl)piperidin-4-yl)((trans)-2-((E)-1-phenylprop-1-en-2-yl)cyclopropyl)carbamate To a mixture of 3-(4-((tert-butoxycarbonyl)((trans)-2-((E)-1-phenylprop-1-en-2-yl)cyclopropyl)amino)piperidin-1-yl)propanoic acid (100.00 mg, 233.34 umol, 1.00 eq) in DCM (10.00 mL) were added HATU (133.08 mg, 350.01 umol, 1.50 eq) and diisopropylethylamine (90.47 mg, 700.02 umol, 3.00 eq). The reaction mixture was stirred at 18° C. for 30 min before addition of dimethylamine hydrochloride (28.54 mg, 350.01 umol, 1.50 eq). The reaction mixture was stirred at 18° C. for 5 h before mixture was concentrated. The crude residue was purified by Prep-TLC (Ethyl acetate:Methanol=5:1) to afford tert-butyl (1-(3-(dimethylamino)-3-oxopropyl)piperidin-4-yl)((trans)-2-((E)-1-phenylprop-1-en-2-yl)cyclopropyl)carbamate (50.00 mg) as an off-white solid.

Step 5: N,N-dimethyl-3-(4-(((trans)-2-((E)-1-phenylprop-1-en-2-yl)cyclopropyl)amino)piperidin-1-yl)propanamide Dihydrochloride (Racemic)

To a mixture of tert-butyl (1-(3-(dimethylamino)-3-oxopropyl)piperidin-4-yl)((trans)-2-((E)-1-phenylprop-1-en-2-yl)cyclopropyl)carbamate (40.00 mg, 87.79 umol, 1.00 eq) in MeOH (5.00 mL) was added HCl (4 M in MeOH, 4.00 mL, 182.23 eq). The reaction mixture was stirred at 17° C. for 3 h before the reaction mixture was concentrated. The crude residue was purified by Prep-HPLC (Mobile phase A: 0.05% HCl-ACN; Mobile phase B: Phenomenex Synergi C18 250*21.2 mm*4 um, Gradient: 10-40% B 10 min) to afford N,N-dimethyl-3-(4-(((trans)-2-((E)-1-phenylprop-1-en-2-yl)cyclopropyl)amino)piperidin-1-yl)propanamide dihydrochloride (4.60 mg) as a yellow solid. LCMS (M+H) m/z 356. ¹H NMR (400 MHz, MeOD): δ=7.31 (m, 2H), 7.21 (m, 3H), 6.45 (s, 1H), 3.83 (m, 2H), 3.66 (m, 2H), 3.43 (m, 2H), 3.19 (m, 2H), 3.08 (s, 3H), 2.96 (m, 5H), 2.51-2.47 (d, J=16 Hz, 2H), 2.15 (m, 3H), 1.84 (s, 3H), 1.35(m, 2H).

Compound 199: 3-(4-(((trans)-2-((E)-1-phenylprop-1-en-2-yl)cyclopropyl)amino)piperidin-1-yl)propanoic Acid Dihydrochloride (Racemic)

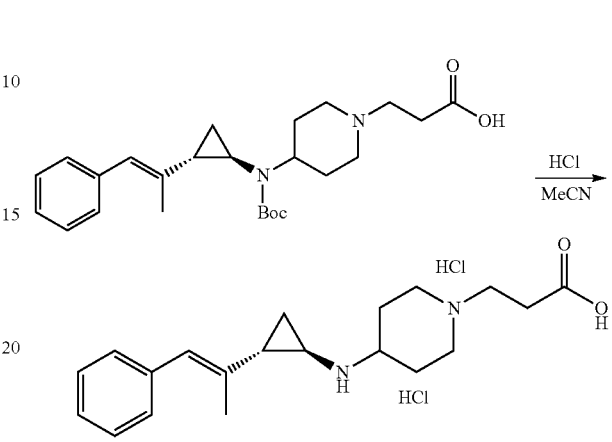

To a mxiture of 3-(4-((tert-butoxycarbonyl)((trans)-2-((E)-1-phenylprop-1-en-2-yl)cyclopropyl)amino)piperidin-1-yl)propanoic acid (100.00 mg, 233.34 umol, 1.00 eq) in MeCN (500.00 uL) was added HCl (4 M, 3.00 mL, 51.43 eq) at 0° C. The reaction mixture was stirred at 18° C. for 30 min. The reaction was concentrated and the crude product was purified by Prep-HPLC (Mobile phase A: 0.05% HCl-ACN; Mobile phase B: Phenomenex Synergi C18 250*21.2 mm*4 um, Gradient: 5-35% B 10 min) to 3-(4-(((trans)-2-(E)-1-phenylprop-1-en-2-yl)cyclopropyl)amino)piperidin-1-yl)propanoic acid dihydrochloride (14.40 mg, 43.84 umol, 18.79% yield, 100% purity) as an off-white solid. LCMS (M+H) m/z: 329. ¹H NMR (400 MHz, MeOD): δ 7.31 (m, 2H), 7.20 (m, 3H), 6.45 (s, 1H), 3.72 (m, 4H), 3.45 (m, 2H), 3.20 (m, 2H), 2.97 (m, 2H), 2.51-2.47 (d, J=16.0 Hz, 2H), 2.13 (m, 3H), 1.84 (s, 3H), 1.36(m, 2H).

Compound 200: 5-((4-(((trans)-2-((E)-1-phenylprop-1-en-2-yl)cyclopropyl)amino)piperidin-1-yl)methyl)picolinic Acid Dihydrochloride (Racemic)

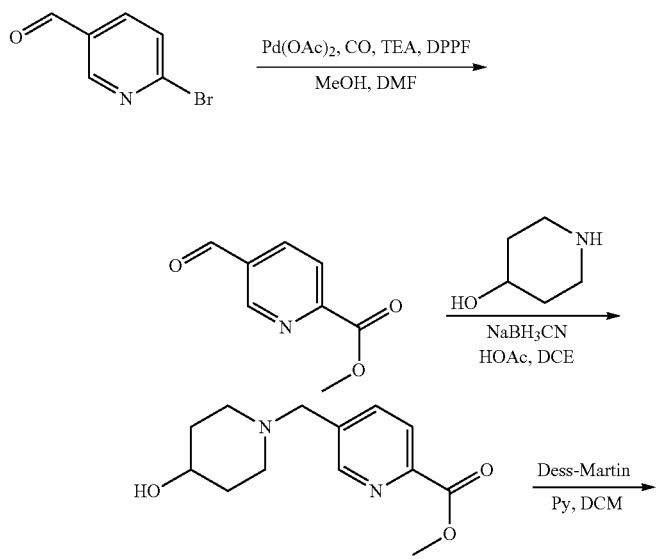

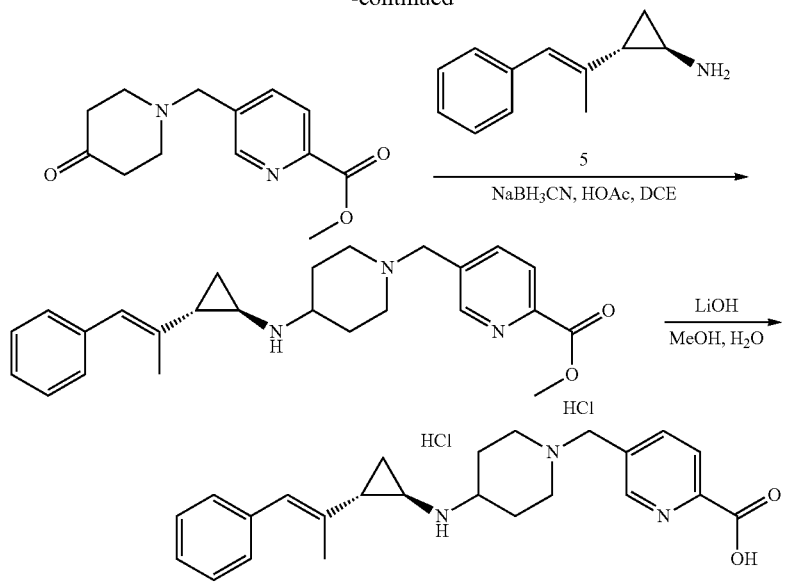

Step 1: methyl 5-formylpyridine-2-carboxylate

To a mixture of 6-bromopyridine-3-carbaldehyde (500.00 mg, 2.69 mmol, 1.00 eq) in MeOH (5.00 mL) and DMF (2.00 mL) were added Pd(OAc)$_2$ (60.39 mg, 269.00 umol, 0.10 eq), DPPF (596.08 mg, 1.08 mmol, 0.40 eq) and triethylamine (816.00 mg, 8.07 mmol, 3.00 eq) and the mixture was stirred under CO (50 psi) at 55° C. for 48 h. The mixture was filtered through celite and the filtrate was concentrated under reduced pressure. The residue was diluted with water (10 mL) and the mixture was extracted with ethyl acetate (10 mL*3). The organic layers were dried over anhydrous Na$_2$SO$_4$ and filtered. The filtrate was concentrated and the crude residue was purified by column chromatography (SiO2, petroleum ether/ethyl acetate=10/1 to 1/1) to afford methyl 5-formylpyridine-2-carboxylate (280.00 mg, 1.63 mmol, 60.51% yield, 96% purity) as a white solid. LCMS (M+H$^+$) m/z: 166. $^1$H NMR (400 MHz, CHLOROFORM-d) δ=10.23 (s, 1H), 9.21 (s, 1H), 8.37-8.28 (m, 2H), 4.07 (s, 3H).

Step 2: methyl 5-((4-hydroxypiperidin-1-yl)methyl)picolinate

To a mixture of methyl 5-formylpyridine-2-carboxylate (150.00 mg, 908.27 umol, 1.00 eq) and piperidin-4-ol (137.81 mg, 1.36 mmol, 1.50 eq) in DCE (4.00 mL) was added acetic acid (54.54 mg, 908.27 umol, 1.00 eq) and the mixture stirred at 20° C. 12 h. To this mixture was added NaBH$_3$CN (114.15 mg, 1.82 mmol, 2.00 eq) and the reaction stirred at 20° C. for 2 h. The reaction was concentrated under reduced pressure to afford a residue which was diluted with saturated NaHCO$_3$ solution (15 mL) and extracted with ethyl acetate (3 times). The organic layers were washed with brine (15 mL), dried over anhydrous Na$_2$SO$_4$, filtered and concentrated. The crude residue was purified by prep-TLC (petroleum ether/ethyl acetate=0/1) top afford methyl 5-((4-hydroxypiperidin-1-yl)methyl)picolinate (80.00 mg) as a yellow oil.

Step 3: methyl 5-((4-oxopiperidin-1-yl)methyl)picolinate

To a mixture of methyl 5-[(4-hydroxy-1-piperidyl)methyl]pyridine-2-carboxylate (40.00 mg, 159.81 umol, 1.00 eq) in DCM (3.00 mL) were added Dess-Martin periodinane (101.67 mg, 239.71 umol, 1.50 eq) and pyridine (12.64 mg, 159.81 umol, 1.00 eq) at 0° C. and the mixture was stirred at 20° C. for 12 h. The mixture was quenched by addition of a saturated solution (10 mL) of NaHCO$_3$ and Na$_2$S$_2$O$_3$ (1:1) and extracted with DCM (10 mL*3). The combined organic layers were dried over anhydrous Na$_2$SO$_4$, filtered and concentrated. The residue was purified by prep-TLC (PE/EA=0/1) to afford methyl 5-[(4-oxo-1-piperidyl)methyl]pyridine-2-carboxylate (34.00 mg, 136.94 umol, 85.69% yield) as a light yellow oil. $^1$H NMR (400 MHz, CHLOROFORM-d) δ=8.76-8.68 (m, 1H), 8.13 (d, J=8.4 Hz, 1H), 7.88 (dd, J=1.8, 7.9 Hz, 1H), 4.04-3.99 (m, 3H), 3.72 (s, 2H), 2.77 (t, J=6.0 Hz, 4H), 2.47 (t, J=6.0 Hz, 4H).

Step 4: methyl 5-((4-(((trans)-2-((E)-1-phenylprop-1-en-2-yl)cyclopropyl)amino)piperidin-1-yl)methyl) picolinate To a mixture of (trans)-2-((E)-1-phenylprop-1-en-2-yl) cyclopropan-1-amine (30.00 mg, 173.16 umol, 1.00 eq) and methyl 5-[(4-oxo-1-piperidyemethyl]pyridine-2-carboxylate (34 mg, 138.53 umol, 0.80 eq) in DCE (3.00 mL) was added acetic acid (10.40 mg, 173.16 umol, 1.00 eq) and the mixture was stirred at 20° C. for 12 h. To this mixture was added NaBH$_3$CN (21.76 mg, 346.32 umol, 2.00 eq) and the reaction was stirred at 20° C. for 2 h. The mixture was concentrated and the resulting residue was diluted with water (10 mL), saturated NaHCO$_3$ solution, and extracted with DCM (10 mL*3). The organic layers were dried over anhydrous Na$_2$SO$_4$, filtered, and concentrated. The crude residue was purified by prep-TLC (DCM/MeOH=10/1) to afford methyl 5-((4-(((trans)-2-(E)-1-phenylprop-1-en-2-yl) cyclopropyl)amino)piperidin-1-yl)methyl)picolinate (40.00 mg) as a yellow solid. LCMS (M+Na$^+$) m/z: 428.

Step 5: 5-((4-(((trans)-2-((E)-1-phenylprop-1-en-2-yl)cyclopropyl)amino)piperidin-1-yl)methyl)picolinic Acid Dihydrochloride (Racemic)

To a mixture of methyl 5-((4-(((trans)-2-((E)-1-phenylprop-1-en-2-yl)cyclopropyl)amino)piperidin-1-yl)methyl)

picolinate (40.00 mg, 98.64 umol, 1.00 eq) in MeOH (2.00 mL) and water (1.00 mL) was added LiOH.H₂O (20.69 mg, 493.20 umol, 5.00 eq) and the mixture was stirred at 50° C. for 2.5 h. The mixture was concentrated and the residue was purified by prep-HPLC (HCl) to afford 5-((4-(((trans)-2-((E)-1-phenylprop-1-en-2-yl)cyclopropyl)amino)piperidin-1-yl)methyl)picolinic acid dihydrochloride (4.80 mg) as a light yellow solid. LCMS (M+m/z: 392. ¹H NMR (400 MHz, METHANOL-d4) δ=8.95 (br. s., 1H), 8.40 (br. s., 1H), 8.33 (br. s., 1H), 7.31 (t, J=7.3 Hz, 2H), 7.25-7.16 (m, 3H), 6.44 (br. s., 1H), 4.58 (br. s., 3H), 3.71 (br. s., 3H), 2.98 (br. s., 1H), 2.48 (br. s., 2H), 2.16 (br. s., 3H), 1.83 (s, 3H), 1.35 (br. s., 2H).

Compound 201: 2-(4-(((trans)-2-((E)-1-phenylprop-1-en-2-yl)cyclopropyl)amino)piperidin-1-yl)ethan-1-ol Dihydrochloride (Racemic)

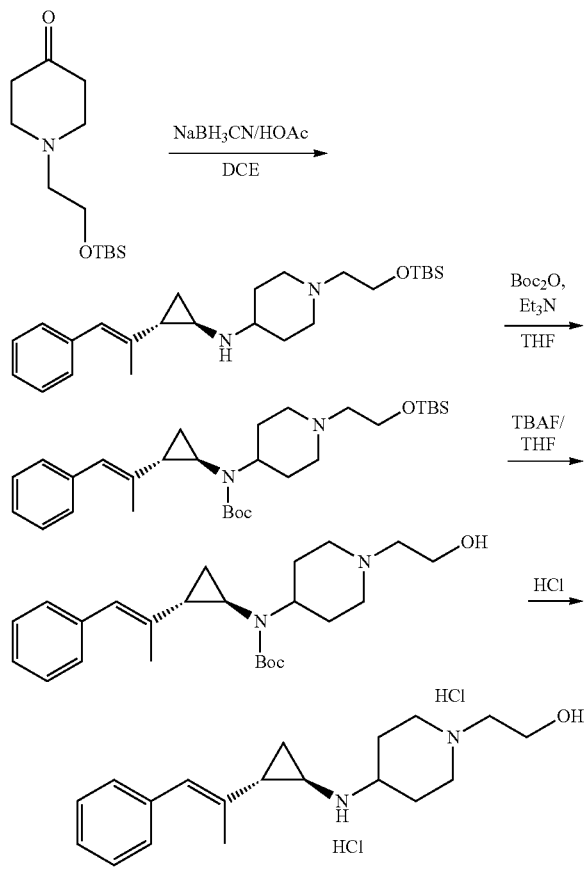

Step 1: 1-(2-((tert-butyldimethylsilyl)oxy)ethyl)-N-((trans)-2-(E)-1-phenylprop-1-en-2-ypcyclopropyl)piperidin-4-amine To a mixture of 1-(2-((tert-butyldimethylsilyl)oxy)ethyl) piperidin-4-one (700.00 mg, 2.72 mmol, 1.00 eq) and (trans)-2-((E)-1-phenylprop-1-en-2-yl)cyclopropan-1-amine (471.08 mg, 2.72 mmol, 1.00 eq) in DCE (15.00 mL) was added acetic acid (490.01 mg, 8.16 mmol, 3.00 eq). The reaction mixture was stirred at 18° C. for 16 h before addition of NaBH₃CN (512.77 mg, 8.16 mmol, 3.00 eq) at 0° C. The reaction mixture was warmed to room temperature and stirred for 1 h. Water (100 mL) was added and the mixture was extracted with EtOAc (50 mL*3). The combined organic layers were concentrated and the crude residue was purifed by silica gel chromatography (Dichloromethane:Methanol=100:1 to 10:1) to afford 1-(2-((tert-butyldimethylsilyl)oxy)ethyl)-N-((trans)-2-((E)-1-phenylprop-1-en-2-yl)cyclopropyl)piperidin-4-amine (700.00 mg) as a yellow oil. LCMS (M+H⁺) m/z: 415.

Step 2: tert-butyl (1-(2-((tert-butyldimethylsilyl)oxy)ethyl)piperidin-4-yl)((trans)-2-(E)-1-phenylprop-1-en-2-yl)cyclopropyl)carbamate To a mixture of 1-(2-((tert-butyldimethylsilyl)oxy)ethyl)-N-((trans)-2-((E)-1-phenylprop-1-en-2-yl)cyclopropyl)piperidin-4-amine (100.00 mg, 241.14 umol, 1.00 eq) in DCM (3.00 mL) were added triethylamine (73.20 mg, 723.42 umol, 3.00 eq) and (Boc)₂O (52.63 mg, 241.14 umol, 1.00 eq). The reaction mixture was stirred at 18° C. for 16 h. Water was added and the mixture was extracted with DCM (15 mL*3). The organic layers were concentrated and the crude residue was purified by silica gel column chromatography (Petroleum ether/Ethyl acetate=30:1, 10:1) to afford tert-butyl (1-(2-((tert-butyldimethylsilyl)oxy)ethyl)piperidin-4-yl)((trans)-2-(E)-1-phenylprop-1-en-2-yl)cyclopropyl)carbamate (110.00 mg) as a yellow oil. LCMS (M+H⁺) m/z: 515.

Step 3: tert-butyl (1-(2-hydroxyethyl)piperidin-4-yl)((trans)-2-((E)-1-phenylprop-1-en-2-yl)cyclopropyl)carbamate To a mixture of tert-butyl (1-(2-((tert-butyldimethylsilyl)oxy)ethyl)piperidin-4-yl)((trans)-2-(E)-1-phenylprop-1-en-2-yl)cyclopropyl)carbamate (90.00 mg, 174.82 umol, 1.00 eq) in THF (3.00 mL) was added TBAF (1 M, 524.46 uL, 3.00 eq). The reaction mixture was stirred at 18° C. for 16 h. Water (10 mL) was added and the mixture was extracted with EtOAc (5 mL*2). The combined organic phase was washed with brine (5 mL*2), dried over anhydrous Na₂SO₄, filtered and concentrated to afford tert-butyl (1-(2-hydroxyethyl)piperidin-4-yl)((trans)-2-((E)-1-phenylprop-1-en-2-yl)cyclopropyl)carbamate (70.00 mg) as a yellow oil.

Step 4: 2-(4-(((trans)-2-((E)-1-phenylprop-1-en-2-yl)cyclopropyl)amino)piperidin-1-yl)ethan-1-ol Dihydrochloride (Racemic)

To a mixture of tert-butyl (1-(2-hydroxyethyl)piperidin-4-yl)((trans)-2-((E)-1-phenylprop-1-en-2-yl)cyclopropyl)carbamate (70.00 mg, 174.76 umol, 1.00 eq) in MeOH (3.00 mL) was added HCl (4 M in MeOH, 1.00 mL, 22.89 eq) at 0° C. The reaction mixture was then stirred at 18° C. for 1 h. The reaction mixture was concentrated and the crude residue was purified by Prep-HPLC (Mobile phase A: 0.05% HCl-ACN; Mobile phase B: Boston Green ODS 150*30 5u, Gradient: 10-40% B 10 min) to afford 2-(4-(((trans)-2-((E)-1-phenylprop-1-en-2-yl)cyclopropyl)amino)piperidin-1-yl) ethan-1-oldihydrochloride (6.30 mg) as a yellow solid. LCMS [M+H]⁺=301. ¹H NMR (400 MHz, MeOD): δ 7.31 (m, 2H), 7.21 (m, 3H), 6.45 (s, 1H), 3.85 (m, 5H), 3.68 (m, 2H), 3.21 (m, 2H), 2.99 (m, 1H), 2.50-2.47 (d, J=12.0 Hz, 2H), 2.14 (m, 3H), 1.84 (s, 3H), 1.35 (m, 2H).

Compound 202: 4-((4-(((trans)-2-((E)-1-phenylprop-1-en-2-yl)cyclopropyl)amino)piperidin-1-yl)methyl)benzenesulfonamide Dihydrochloride (Racemic)

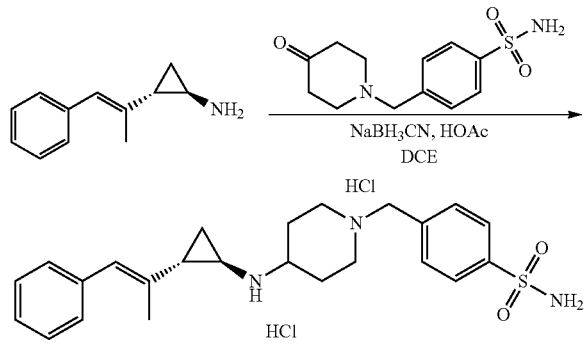

A mixture of 4-[(4-oxo-1-piperidyl)methyl]benzenesulfonamide (150.00 mg, 559.01 umol, 1.00 eq), (trans)-2-((E)-1-phenylprop-1-en-2-yl)cyclopropan-1-amine (106.53 mg, 614.91 umol, 1.10 eq) and acetic acid (67.14 mg, 1.12 mmol, 63.94 uL, 2.00 eq) in DCE (6.00 mL) was stirred at 20° C. for 16 h before addition of NaBH$_3$CN (175.64 mg, 2.80 mmol, 5.00 eq). The resulting mixture was stirred at 20° C. for 2 h. The reaction was poured into saturated Na$_2$CO$_3$ (20 mL). The resulting mixture was extracted with DCM (30 mL*2). The combined organic layers were concentrated and the crude residue was purified by prep TLC (Methanol:Dichloromethane=10:1) and prep-HPLC (HCl) to afford 4-((4-(((trans)-2-((E)-1-phenylprop-1-en-2-yl)cyclopropyl)amino)piperidin-1-yl)methyl)benzenesulfonamide dihydrochloride (9.70 mg) as a white solid. LCMS (M+H$^+$) m/z: 426. $^1$H NMR (400 MHz, METHANOL-d$_4$) δ 7.93-8.12 (d, J=8.4 Hz, 2H), 7.85-7.75 (d, J=8.4 Hz, 2H), 7.35-7.28 (m, 2H), 7.25-7.15 (m, 2H), 6.45 (s, 1H), 4.48 (s, 2H), 3.68-3.65 (m, 3H), 3.27 (s, 2H), 2.98 (s, 1H), 2.50-2.47 (m, 2H), 2.17 (s, 3H), 1.84 (s, 3H), 1.21-1.48 (m, 3H).

Compound 203: 6-((4-(((trans)-2-((E)-1-phenylprop-1-en-2-yl)cyclopropyl)amino)piperidin-1-yl)methyl)nicotinic Acid Dihydrochloride (Racemic)

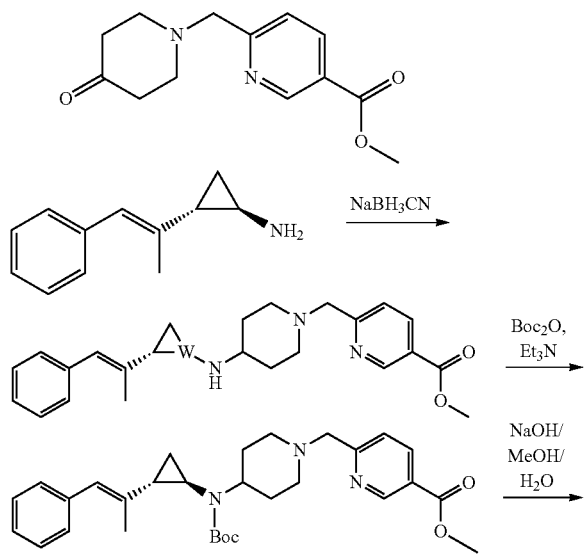

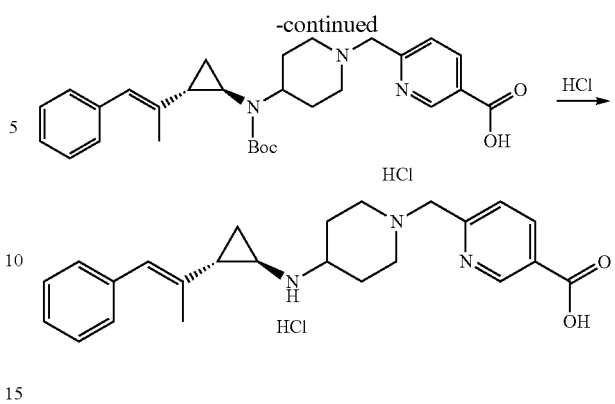

Step 1: methyl 6-((4-(((trans)-2-((E)-1-phenylprop-1-en-2-yl)cyclopropyl)amino)piperidin-1-yl)methyl)nicotinate To a stirred mixture of methyl 6-((4-oxopiperidin-1-yl)methyl)nicotinate (200.00 mg, 805.54 umol, 1.00 eq) in DCE (10.00 mL) were added (trans)-2-((E)-1-phenylprop-1-en-2-yl)cyclopropan-1-amine (140.00 mg, 808.08 umol, 1.00 eq) and acetic acid (96.75 mg, 1.61 mmol, 92.14 uL, 2.00 eq). The resulting mixture was stirred at 20° C. for 2 h before addition of NaBH$_3$CN (253.10 mg, 4.03 mmol, 5.00 eq). The reaction was stirred for 1 h before pouring into saturated Na$_2$CO$_3$ (30 mL). The mixture was extracted with DCM (50 mL*2) and the combined organic layers were concentrated and the crude residue was purified by prep-TLC (Dichloromethane:Methanol=10:1) to afford methyl 6-((4-(((trans)-2-((E)-1-phenylprop-1-en-2-yl)cyclopropyl)amino)piperidin-1-yl)methyl)nicotinate (60.00 mg) as a light yellow oil. LCMS (M+H$^+$) m/z: 406.

Step 2: methyl 6-((4-((tert-butoxycarbonyl)((trans)-2-((E)-1-phenylprop-1-en-2-yl)cyclopropyl)amino)piperidin-1-yl)methyl)nicotinate To a solution of methyl 6-((4-(((trans)-2-((E)-1-phenylprop-1-en-2-yl)cyclopropyl)amino)piperidin-1-yl)methyl)nicotinate (60.00 mg, 147.95 umol, 1.00 eq) in THF (6.00 mL) was added triethylamine (119.77 mg, 1.18 mmol, 164.07 uL, 8.00 eq) and Boc$_2$O (129.16 mg, 591.80 umol, 135.96 uL, 4.00 eq). The mixture was stirred at 20° C. for 4 h before the mixture was concentrated. The residue was diluted with water (10 mL) and then extracted with by EtOAc (20 mL*2). The combined organic layers were concentrated and the crude residue was purified by silica gel column chromatography (eluent: Petroleum ether:Ethyl acetate=10:1 to 1:1) to afford methyl 6-((4-((tert-butoxycarbonyl)((trans)-2-((E)-1-phenylprop-1-en-2-yl)cyclopropyl)amino)piperidin-1-yl)methyl)nicotinate (46.00 mg) as a colorless oil. LCMS (M+H$^+$) m/z: 506.

Step 3: 6-((4-((tert-butoxycarbonyl)((trans)-2-((E)-1-phenylprop-1-en-2-yl)cyclopropyl)amino)piperidin-1-yl)methyl)nicotinic Acid To a solution of methyl 6-((4-((tert-butoxycarbonyl)((trans)-2-((E)-1-phenylprop-1-en-2-yl)cyclopropyl)amino)piperidin-1-yl)methyl)nicotinate (46.00 mg, 90.97 umol, 1.00 eq) in MeOH (3.00 mL) was added NaOH (25.47 mg, 636.79 umol, 7.00 eq) dissolved in water (3.00 mL). The mixture was stirred at 20° C. for 2 h before the volatiles were removed to afford crude 6-((4-((tert-butoxycarbonyl)

((trans)-2-((E)-1-phenylprop-1-en-2-yl)cyclopropyl)amino)piperidin-1-yl)methyl)nicotinic acid. LCMS (M+H⁺) m/z: 492.

Step 4: 6-((4-(((trans)-2-((E)-1-phenylprop-1-en-2-yl)cyclopropyl)amino)piperidin-1-yl)methyl)nicotinic Acid Dihydrochloride (Racemic)

To a solution of 6-((4-((tert-butoxycarbonyl)((trans)-2-((E)-1-phenylprop-1-en-2-yl)cyclopropyl)amino)piperidin-1-yl)methyl)nicotinic acid (44.72 mg, 90.96 umol, 1.00 eq) in water (2.00 mL) was added HCl (12 M, 2.00 mL, 263.85 eq). The mixture was stirred at 20° C. for 1 h before the mixture was filtered. The filtrate was purified by prep-HPLC (Instrument: Phenomenex Synergi C18 250*21.2 mm*4 um. Mobile phase A: water with 0.05% HCl Mobile phase B: acetonitrile, Gradient 7-37% B) to afford 6-((4-(((trans)-2-((E)-1-phenylprop-1-en-2-yl)cyclopropyl)amino)piperidin-1-yl)methyl)nicotinic acid dihydrochloride (6.50 mg) as a light yellow solid. LCMS (M+H⁺) m/z: 392. ¹H NMR (400 MHz, METHANOL-d₄) δ 9.22 (s, 1H), 8.45-8.42 (dd, J=7.9, 2.2 Hz, 1H), 7.64-7.62 (d, J=8.4 Hz, 1H) 7.34-7.24 (m, 2H) 7.24-7.10 (m, 3H) 6.43 (s, 1H) 4.68-4.58 (m, 2H) 3.87-3.62 (m, 3H) 3.44-3.33 (m, 2H) 2.98 (s, 1H) 2.50-2.46 (d, J=13.2 Hz, 2H) 2.27-2.08 (m, 3H) 1.82 (s, 3H) 1.35 (t, J=7.3 Hz, 2H).

Compound 204: 2-(2-(4-(((trans)-2-((E)-1-phenylprop-1-en-2-yl)cyclopropyl)amino)piperidin-1-yl)ethoxy)acetic Acid Dihydrochloride (Racemic)

Step 1: methyl 2-(2-(4-((tert-butoxycarbonyl)((trans)-2-(E)-1-phenylprop-1-en-2-yl)cyclopropyl)amino)piperidin-1-yl)ethoxy)acetate To a mixture of tert-butyl (1-(2-hydroxyethyl)piperidin-4-yl)((trans)-2-((E)-1-phenylprop-1-en-2-yl)cyclopropyl)carbamate (100.00 mg, 249.66 umol, 1.00 eq) in THF (5.00 mL) was added NaH (29.96 mg, 748.98 umol, 60% purity, 3.00 eq) at 0° C. The reaction mixture was stirred at 18° C. for 30 min. Methyl 2-bromoacetate (38.19 mg, 249.66 umol, 23.57 uL, 1.00 eq) was added and the reaction mixture was stirred at 18° C. for 16 h. Water (10 mL) was added and the mixture was extracted with EtOAc (10 mL*3). The combined organic layers were concentrated and the crude product was purified by silica gel column chromatography (Dichloromethane: Methanol=1:0 to 50:1) to afford methyl 2-(2-(4-((tert-butoxycarbonyl)((trans)-2-((E)-1-phenylprop-1-en-2-yl)cyclopropyl)amino)piperidin-1-yl)ethoxy)acetate (28.00 mg) as a yellow oil.

Step 2: 2-(2-(4-((tert-butoxycarbonyl)((trans)-2-(E)-1-phenylprop-1-en-2-yl)cyclopropyl)amino)piperidin-1-yl)ethoxy)acetic Acid To a mixture of 2-(2-(4-((tert-butoxycarbonyl)((trans)-2-(E)-1-phenylprop-1-en-2-yl)cyclopropyl)amino)piperidin-1-yl)ethoxy)acetate (28.00 mg, 59.24 umol, 1.00 eq) in MeOH (2.00 mL) were added NaOH (7.11 mg, 177.72 umol, 3.00 eq) and water (1.00 mL). The reaction mixture was stirred at 18° C. for 2 h. The reaction was concentrated to afford crude 2-(2-(4-((tert-butoxycarbonyl)((trans)-2-((E)-1-

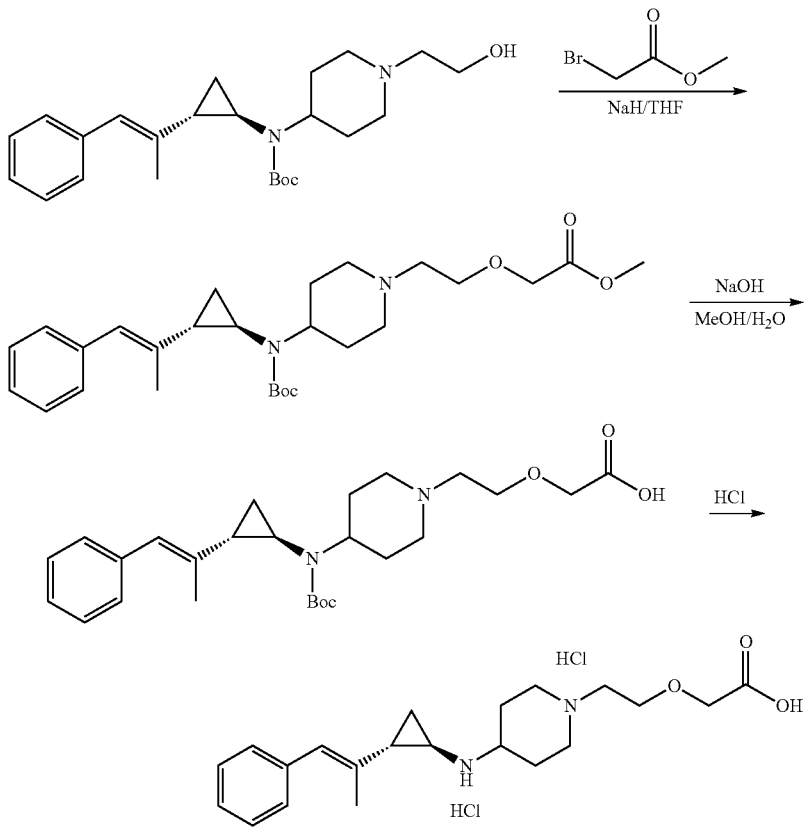

phenylprop-1-en-2-yl)cyclopropyl)amino)piperidin-1-yl) ethoxy)acetic acid (50.00 mg) as a yellow oil.

Step 3: 2-(2-(4-(((trans)-2-((E)-1-phenylprop-1-en-2-yl)cyclopropyl)amino)piperidin-1-yl)ethoxy)acetic Acid Dihydrochloride (Racemic)

To a mixture of 2-(2-(4-((tert-butoxycarbonyl)((trans)-2-((E)-1-phenylprop-1-en-2-yl)cyclopropyl)amino)piperidin-1-yl)ethoxy)acetic acid (50.00 mg, 109.03 umol, 1.00 eq) in MeCN (500.00 uL) was added HCl (4 M, 285.96 uL, 73.37 eq). The reaction mixture was stirred at 18° C. for 1 h before the reaction was concentrated. The crude residue was purified by Prep-HPLC (Mobile phase A:0.05% HCl-ACN; Column: Boston Green ODS 150*30 5u, Gradient: 5-35% B 10 min) to afford 2-(2-(4-(((trans)-2-((E)-1-phenylprop-1-en-2-yl)cyclopropyl)amino)piperidin-1-yl)ethoxy)acetic acid dihydrochloride (1.00 mg) as a yellow oil. LCMS [M+H] 359.

Compound 205: N-(2-(4-(((trans)-2-(E)-1-phenylprop-1-en-2-yl)cyclopropyl)amino)piperidin-1-yl) ethyl)methanesulfonamide Dihydrochloride (Racemic)

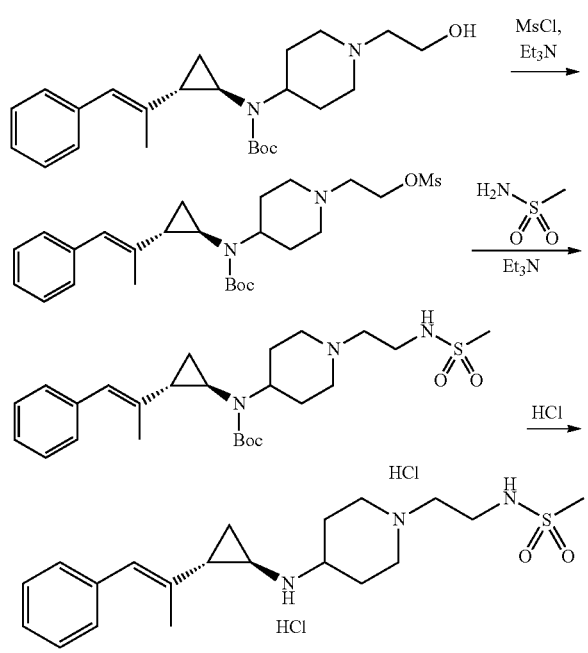

Step 1: 2-(4-((tert-butoxycarbonyl)((trans)-2-((E)-1-phenylprop-1-en-2-yl)cyclopropyl)amino)piperidin-1-yl)ethyl methanesulfonate To a mixture of tert-butyl (1-(2-hydroxyethyl)piperidin-4-yl)((trans)-2-((E)-1-phenylprop-1-en-2-yl)cyclopropyl)carbamate (100.00 mg, 249.66 umol, 1.00 eq) in THF (3.00 mL) were added triethylamine (75.79 mg, 748.98 umol, 103.82 uL, 3.00 eq) and MsCl (85.80 mg, 748.98 umol, 57.97 uL, 3.00 eq). The reaction mixture was stirred at 18° C. for 18 h. The reaction was poured into water (20 mL) and then extracted with EtOAc (10 mL*3). The combined organic phase was washed with brine (20 mL*2), dried over anhydrous $Na_2SO_4$, filtered and concentrated to afford crude 2-(4-((tert-butoxycarbonyl)((trans)-2-((E)-1-phenylprop-1-en-2-yl)cyclopropyl)amino)piperidin-1-yl)ethyl methanesulfonate (150.00 mg) as a yellow oil.

Step 2: tert-butyl (1-(2-(methylsulfonamido)ethyl) piperidin-4-yl)((trans)-2-((E)-1-phenylprop-1-en-2-yl)cyclopropyl)carbamate To a mixture of 2-(4-((tert-butoxycarbonyl)((trans)-2-((E)-1-phenylprop-1-en-2-yl)cyclopropyl)amino)piperidin-1-yl)ethyl methanesulfonate (60.00 mg, 125.36 umol, 1.00 eq) in DMF (2.00 mL) were added methanesulfonamide (14.31 mg, 150.43 umol, 1.20 eq) and $K_2CO_3$ (51.98 mg, 376.07 umol, 3.00 eq). The reaction mixture was stirred at 85° C. for 2 h before the reaction mixture was poured into water and extracted with EtOAc (30 mL*3). The organic layers were concentrated and the crude product was purified by Prep-HPLC (Mobile phase A: 0.05% HCl-ACN; Column: Phenomenex Synergi C18 250*21.2 mm*4 um, Gradient: 31-61% B 10 min) to afford tert-butyl (1-(2-(methylsulfonamido)ethyl)piperidin-4-yl)((trans)-2-(E)-1-phenylprop-1-en-2-yl)cyclopropyl)carbamate (10.00 mg) as a white solid. LCMS (M+H$^+$) m/z: 478.

Step 3: N-(2-(4-(((trans)-2-(E)-1-phenylprop-1-en-2-yl)cyclopropyl)amino)piperidin-1-yl)ethyl)methanesulfonamide Dihydrochloride (Racemic)

To a round bottomed flask containing tert-butyl (1-(2-(methylsulfonamido)ethyl)piperidin-4-yl)((trans)-2-(E)-1-phenylprop-1-en-2-yl)cyclopropyl)carbamate (10.00 mg, 20.94 umol, 1.00 eq) was added HCl (2 M, 3.00 mL, 286.53 eq) and the mixture was stirred at 23° C. for 1 h. The reaction mixture was lyophilized to afford N-(2-(4-(((trans)-2-((E)-1-phenylprop-1-en-2-yl)cyclopropyflamino)piperidin-1-yl) ethyl)methanesulfonamide dihydrochloride (6.90 mg) as a yellow solid. LCMS [M+H] 378.

Compound 206: 4-(2-(4-(((trans)-2-((E)-1-phenylprop-1-en-2-yl)cyclopropyl)amino)piperidin-1-yl) ethyl)benzoic Acid Dihydrochloride (Racemic)

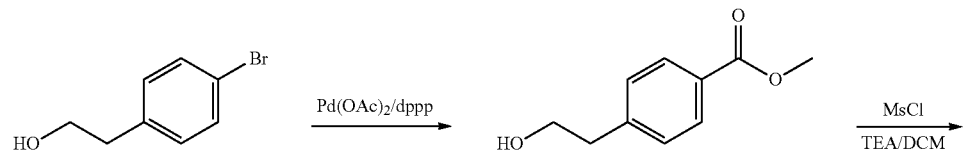

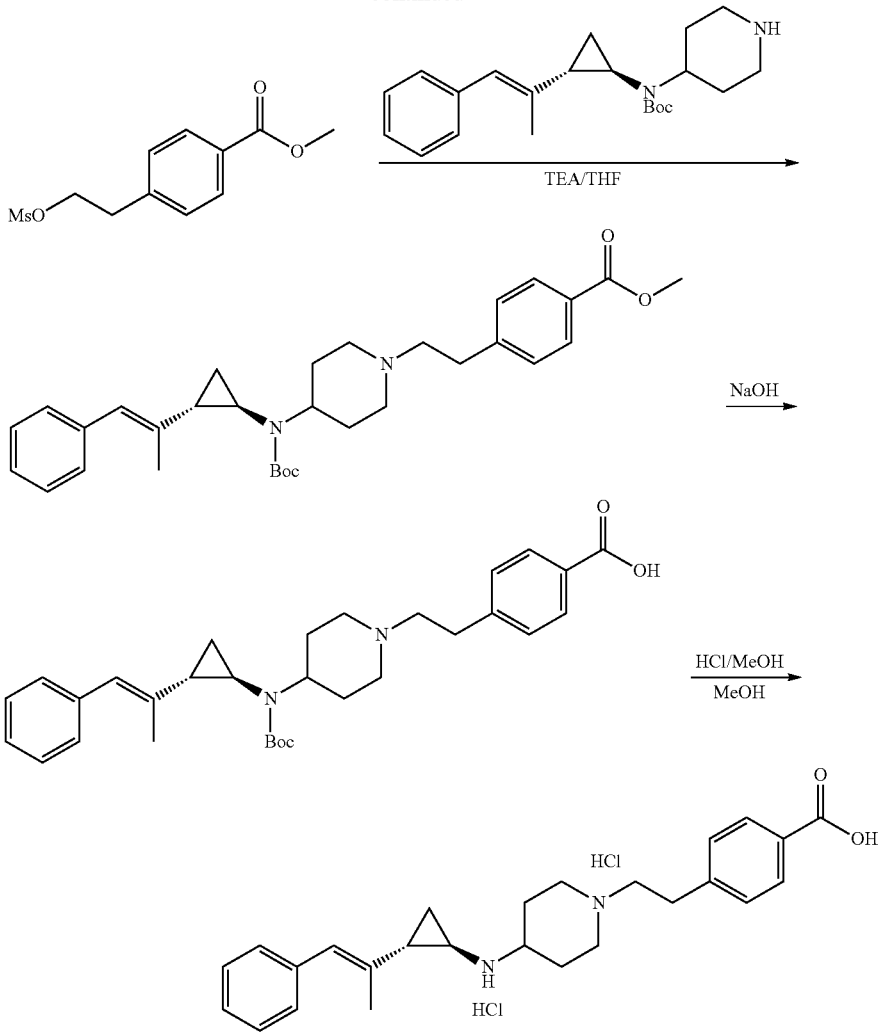

Step 1: methyl 4-(2-hydroxyethyl)benzoate

To a solution of 2-(4-bromophenyl)ethanol (500.00 mg, 2.49 mmol, 347.22 uL, 1.00 eq) in MeOH (20.00 mL) and THF (10.00 mL) were added KOAc (1.95 g, 19.92 mmol, 8.00 eq), Pd(OAc)$_2$ (55.90 mg, 249.00 umol, 0.10 eq), and 3-diphenylphosphanylpropyl(diphenyl)phosphane (154.05 mg, 373.50 umol, 0.15 eq). The suspension was degassed and purged with CO. The mixture was stirred under an atmosphere of CO (50 psi) at 80° C. for 16 h. The crude product was purified by silica gel column chromatography (Petroleum ether:Ethyl acetate 20:1 to 3:1) to afford methyl 4-(2-hydroxyethyl)benzoate (425.00 mg) as a yellow oil. LCMS (M+H$^+$) m/z: 181.

Step 2: methyl 4-(2-((methylsulfonyl)oxy)ethyl)benzoate

To a mixture of methyl 4-(2-hydroxyethyl)benzoate (100.00 mg, 554.94 umol, 1.00 eq) in THF (3.00 mL) were added triethylamine (56.15 mg, 554.94 umol, 76.92 uL, 1.00 eq) and MsCl (95.35 mg, 832.41 umol, 64.43 uL, 1.50 eq). The reaction mixture was stirred at 18° C. for 17 h. The reaction mixture was concentrated and the crude product was purified by Prep-TLC (Petroleum ether:Ethyl acetate=5:1) to afford methyl 4-(2-methylsulfonyloxyethyl)benzoate (130.00 mg) as a white solid.

Step 3: methyl 4-(2-(4-((tert-butoxycarbonyl) ((trans)-2-((E)-1-phenylprop-1-en-2-yl)cyclopropyl) amino)piperidin-1-yl)ethyl)benzoate To a mixture of tert-butyl ((trans)-2-((E)-1-phenylprop-1-en-2-yl)cyclopropyl)(piperidin-4-yl)carbamate (80.00 mg, 224.40 umol, 1.00 eq) in THF (10.00 mL) were added methyl 4-(2-methylsulfonyloxyethyl)benzoate (57.96 mg, 224.40 umol, 1.00 eq) and triethylamine (68.12 mg, 673.21 umol, 93.32 uL, 3.00 eq). The reaction mixture was stirred at 80° C. for 17 h. The reaction was concentrated and the crude product was purified by Prep-TLC (Petroleum ether:Ethyl acetate=1:1) to afford methyl 4-(2-(4-((tert-butoxycarbonyl)((trans)-2-((E)-1-phenylprop-1-en-2-yl)cyclopropyl) amino)piperidin-1-yl)ethyl)benzoate (27.00 mg) as a colorless oil. LCMS (M+H$^+$) m/z: 519.

Step 4: 4-(2-(4-((tert-butoxycarbonyl)((trans)-2-((E)-1-phenylprop-1-en-2-yl)cyclopropyl)amino) piperidin-1-yl)ethyl)benzoic Acid To a mixture of methyl 4-(2-(4-((tert-butoxycarbonyl) ((trans)-2-(E)-1-phenylprop-1-en-2-yl)cyclopropyl)amino)

piperidin-1-yl)ethyl)benzoate (27.00 mg, 52.05 umol, 1.00 eq) in MeOH (3.00 mL) and water (1.00 mL) was added NaOH (10.41 mg, 260.25 umol, 5.00 eq). The reaction mixture was stirred at 80° C. for 1 h. The reaction mixture was concentrated and the mixture was adjusted to pH=6 with 4M HCl. The mixture was extracted with DCM (10 mL*3) and the combined organic phase was washed with brine (20 mL*3), dried over anhydrous $Na_2SO_4$, filtered and concentrated to afford crude 4-(2-(4-((tert-butoxycarbonyl)((trans)-2-((E)-1-phenylprop-1-en-2-yl)cyclopropyl)amino)piperidin-1-yl)ethyl)benzoic acid (30.00 mg) as a yellow oil.

Step 5: 4-(2-(4-(((trans)-2-((E)-1-phenylprop-1-en-2-yl)cyclopropyl)amino)piperidin-1-yl)ethyl)benzoic Acid Dihydrochloride (Racemic)

To a solution of 4-(2-(4-((tert-butoxycarbonyl)((trans)-2-(E)-1-phenylprop-1-en-2-yl)cyclopropyl)amino)piperidin-1-yl)ethyl)benzoic acid (30.00 mg) in MeOH (3.00 mL) was added HCl (4 M in MeOH, 1.00 mL, 67.28 eq). The reaction mixture was stirred at 26° C. for 6 h before the reaction was concentrated. The crude residue was purified by Prep-HPLC (Mobile phase A: 0.05% HCl-ACN; Column: Phenomenex Synergi C18 250*21.2 mm*4 um, Gradient: 10-40% B 10 min) to afford 4-(2-(4-(((trans)-2-(E)-1-phenylprop-1-en-2-yl)cyclopropyl)amino)piperidin-1-yl)ethyl)benzoic acid dihydrochloride (5.30 mg) as a yellow solid. LCMS [M+H] m/z 405. $^1$H NMR (400 MHz, $CDCl_3$) δ 8.01-7.99 (d, J=8 Hz, 2H), 7.45-7.43 (d, J=8 Hz, 2H), 7.31 (m, 5H), 6.45 (s, 1H), 3.83 (s, 2H), 3.73 (s, 1H), 3.42 (s, 2H), 3.22 (m, 2H), 3.0 (s, 1H), 2.50 (s, 2H), 2.19-2.17 (d, J=8 Hz, 2H), 2.02-2.01 (d, J=4 Hz, 1H), 1.84 (s, 3H), 1.31 (s, 4H).

Compound 207: 2-(((4-(((trans)-2-((E)-1-phenylbut-1-en-2-yl)cyclopropyl)amino)cyclohexyl)amino) methyl)benzoic Acid Dihydrochloride (Racemic)

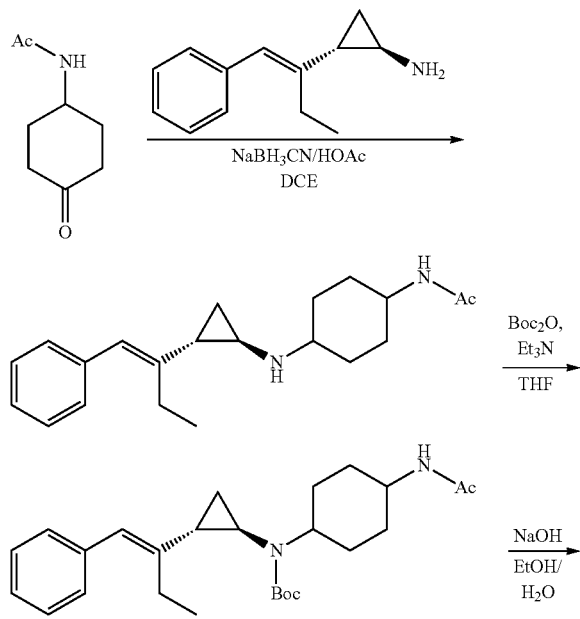

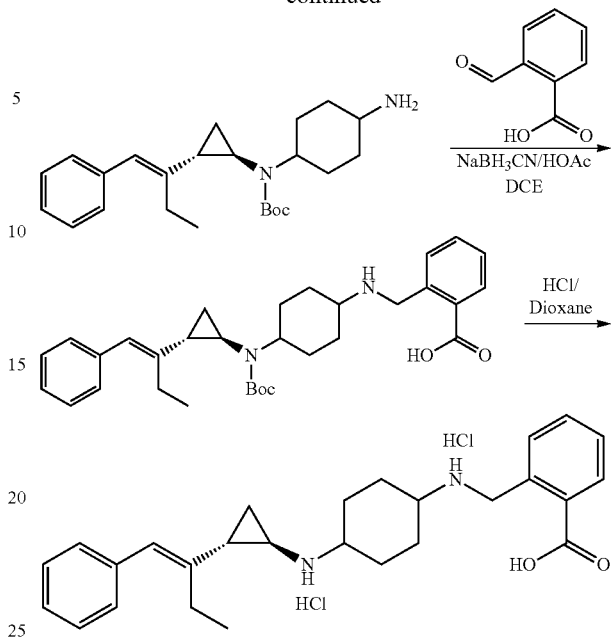

Step 1: N-(4-(((trans)-2-((E)-1-phenylbut-1-en-2-yl) cyclopropyl)amino)cyclohexyl)acetamide The mixture of (trans)-2-((E)-1-phenylbut-1-en-2-yl)cyclopropan-1-amine hydrochloride (720.44 mg, 3.22 mmol, 1.00 eq) in water (5 mL) was treated with saturated aqueous $Na_2CO_3$ and the mixture was extracted with a mixture of DCM and MeOH (10 mL, 20:1). The organic phases were combined and concentrated. The residue was dissolved in DCE (10.00 mL) and to this solution was added N-(4-oxocyclohexyl)acetamide (500.00 mg, 3.22 mmol, 1.00 eq) and acetic acid (386.72 mg, 6.44 mmol, 368.30 uL, 2.00 eq). The solution was stirred for 1.5 h at 25° C. before addition of $NaBH_3CN$ (809.38 mg, 12.88 mmol, 4.00 eq). The solution was stirred for 1.5 h at 25° C. before diluting with water (10 mL). The mixture was extracted with DCM (15 mL*2). The organic phases were combined and concentrated to afford crude N-(4-(((trans)-2-((E)-1-phenylbut-1-en-2-yl) cyclopropyl)amino)cyclohexyl)acetamide (1.05 g) as a yellow oil. LCMS (M+H) m/z: 327.

Step 2: tert-butyl (4-acetamidocyclohexyl)((trans)-2-((E)-1-phenylbut-1-en-2-yl)cyclopropyl)carbamate The solution of N-(4-(((trans)-2-(E)-1-phenylbut-1-en-2-yl)cyclopropyl)amino)cyclohexyl)acetamide (1.05 g, 3.22 mmol, 1.00 eq), $Boc_2O$ (702.77 mg, 3.22 mmol, 739.75 uL, 1.00 eq) and triethylamine (977.50 mg, 9.66 mmol, 1.34 mL, 3.00 eq) in THF (20.00 mL) was stirred for 16 h at 25° C. The solution was concentrated and the crude residue was purified by silica gel column chromatography (petroleum ether:ethyl acetate=10:1-3:1) to afford tert-butyl (4-acetamidocyclohexyl)((trans)-2-(E)-1-phenylbut-1-en-2-yl)cyclopropyl)carbamate (700.00 mg) as a yellow oil. LCMS (M+Na$^+$) m/z: 449.

Step 3: tert-butyl (4-aminocyclohexyl)((trans)-2-((E)-1-phenylbut-1-en-2-yl)cyclopropyl)carbamate The solution of tert-butyl (4-acetamidocyclohexyl) ((trans)-2-((E)-1-phenylbut-1-en-2-yl)cyclopropyl)carbamate (350.00 mg, 848.36 umol, 1.00 eq) and NaOH (2.04 g, 50.90 mmol, 60.00 eq) in EtOH (6.00 mL) and water (3.00 mL) was stirred at 100° C. for 26 h. The mixture was concentrated and the residue was suspended in water (10 mL) and acidified to pH 4 with aqueous HCl (0.12 N). The mixture was washed with ethyl acetate and petroleum ether (10 mL*2, 1:1) and the organics discarded. The aqueous phase was basified to pH 8 with saturated aqueous $Na_2CO_3$. The solution was extracted with DCM (15 mL*4). The combined organics phase was dried with $Na_2SO_4$ and concentrated to afford tert-butyl (4-aminocyclohexyl)((trans)-2-(E)-1-phenylbut-1-en-2-yl)cyclopropyl)carbamate (50.00 mg,) as a white solid. LCMS (M+H$^+$) m/z: 385.

Step 4: 2-(((4-((tert-butoxycarbonyl)((trans)-2-((E)-1-phenylbut-1-en-2-yl)cyclopropyl)amino)cyclohexyl)amino)methyl)benzoic Acid The solution of tert-butyl (4-aminocyclohexyl)((trans)-2-(E)-1-phenylbut-1-en-2-yl)cyclopropyl)carbamate (50.00 mg, 130.02 umol, 1.00 eq), 2-formylbenzoic acid (19.52 mg, 130.02 umol, 1.00 eq) and acetic acid (15.62 mg, 260.04 umol, 14.87 uL, 2.00 eq) in DCE (6.00 mL) was stirred for 16 h at 25° C. before addition of $NaBH_3CN$ (32.68 mg, 520.09 umol, 4.00 eq). The mixture was stirred for 2 hours at 25° C. and then diluted with water (10 mL). The mixture was extracted with DCM (15 mL*2). The combined organics phase was dried with $Na_2SO_4$ and concentrated to afford crude 2-(((4-((tert-butoxycarbonyl)((trans)-2-((E)-1-phenyl- but-1-en-2-yl)cyclopropyl)amino)cyclohexyl)amino) methyl)benzoic acid (160.00 mg, crude) as a yellow oil. LCMS (M+H$^+$) m/z: 519.

Step 5: 2-(((4-(((trans)-2-(E)-1-phenylbut-1-en-2-yl) cyclopropyl)amino)cyclohexyl)amino)methyl)benzoic Acid Dihydrochloride (Racemic)

To a solution of 2-(((4-((tert-butoxycarbonyl)((trans)-2-((E)-1-phenylbut-1-en-2-yl)cyclopropyl)amino)cyclohexyl) amino)methyl)benzoic acid (150.00 mg, 289.19 umol, 1.00 eq) in dioxane (2.00 mL) was added HCl (4 M in dioxane, 2.00 mL, 27.66 eq). The mixture was stirred at 25° C. for 6 h before being concentrated. The crude residue was purified by prep-HPLC (Instrument: DuraShell 150*25 mm*Sum Mobile phase A: water with 0.05% HCl Mobile phase B: acetonitrile, column temperature: 30° C., Gradient 18-48% B) to afford 2-(((4-(((trans)-2-((E)-1-phenylbut-1-en-2-yl) cyclopropyl)amino)cyclohexyl)amino)methyl)benzoic acid dihydrochloride (4.10 mg) as a white solid. LCMS (M+m/z: 419. $^1$H NMR (400 MHz, methanol-d$_4$) δ=8.21 (d, J=7.5 Hz, 1H), 7.63 (m, 3H), 7.33 (d, J=7.5 Hz, 2H), 7.23 (d, J=8.0 Hz, 3H), 6.33 (s, 1H), 4.53 (s, 2H), 3.41 (s, 2H), 2.98 (s, 1H), 2.68 (m, 3H), 2.45 (d, J=8.5 Hz, 3H), 2.36 (d, J=7.5 Hz, 2H), 1.72 (m, 3H), 1.32 (in., 2H), 1.21 (t, J=7.5 Hz, 3H).

Compound 208: 3-(((4-(((trans)-2-(E)-1-phenylbut-1-en-2-yl)cyclopropyl)amino)cyclohexyl)amino) methyl)benzoic Acid Dihydrochloride (Racemic)

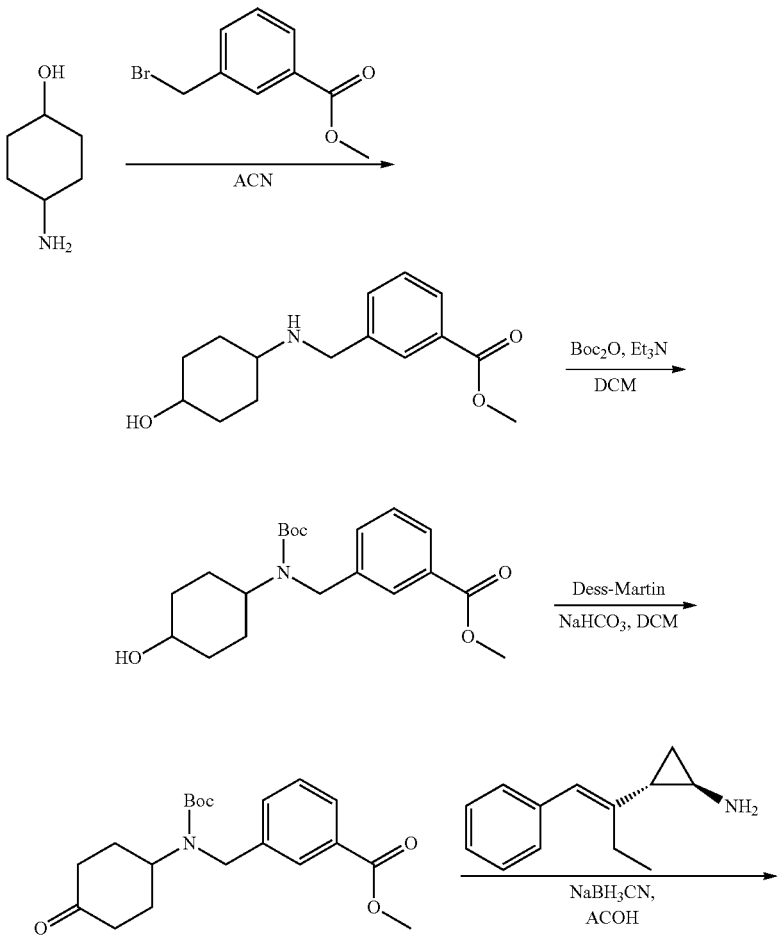

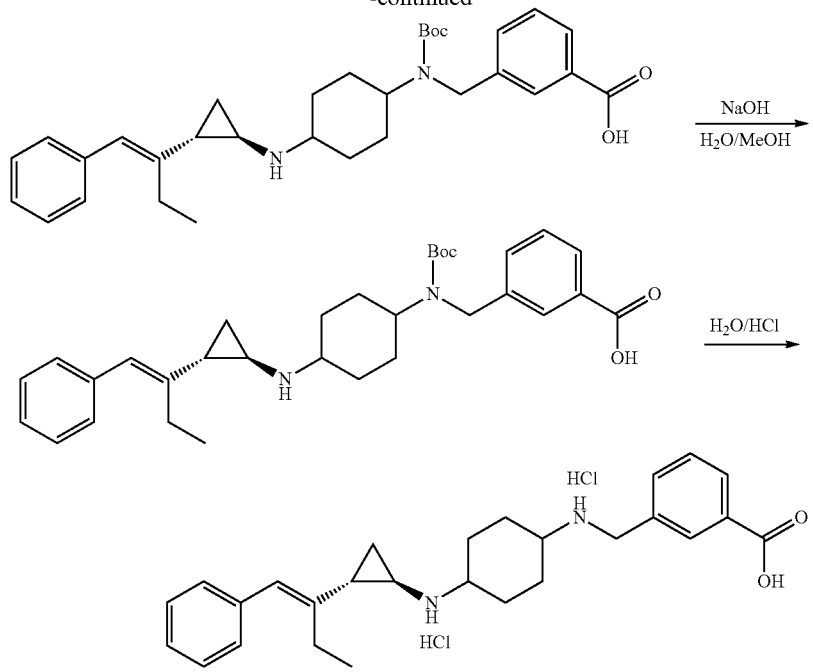

Step 1: methyl 3-(((4-hydroxycyclohexyl)amino)methyl)benzoate

Step 2: methyl 3-0(tert-butoxycarbonyl)(4-hydroxycyclohexyl)amino)methyl)benzoate

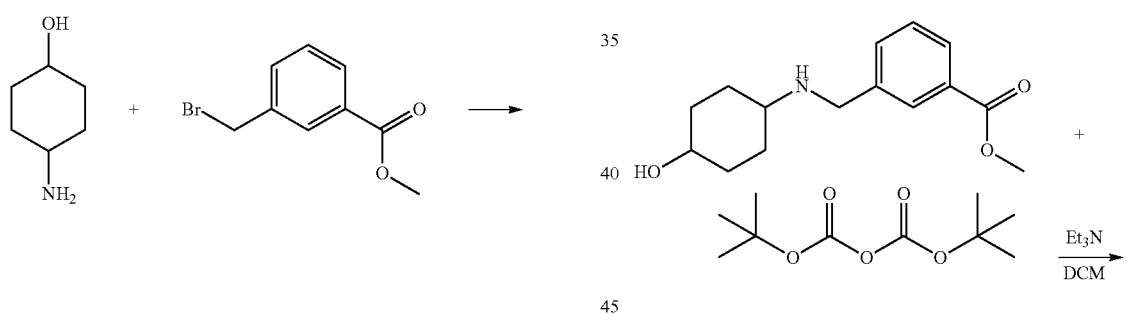

To a mixture of 4-aminocyclohexanol (780.00 mg, 6.77 mmol, 1.00 eq) in MeCN (35.00 mL) was added methyl 3-(bromomethyl)benzoate (1.55 g, 6.77 mmol, 1.00 eq). The reaction mixture was stirred at 26° C. for 17 h. The mixture was concentrated and the crude residue was purified by column chromatography (Ethyl acetate:Methanol=1:0 to 30:1) to afford methyl 3-(((4-hydroxycyclohexyl)amino) methyl)benzoate (980.00 mg) as an off-white solid.

To a solution of methyl 3-(((4-hydroxycyclohexyl)amino) methyl)benzoate (730.00 mg, 2.77 mmol, 1.00 eq) in DCM (15.00 mL) were added Boc$_2$O (786.54 mg, 3.60 mmol, 827.94 uL, 1.30 eq) and triethylamine (841.55 mg, 8.32 mmol, 1.15 mL, 3.00 eq). The reaction mixture was stirred at 26° C. for 16 h before the reaction was concentrated. The crude residue was purified by silica gel column chromatography (Petroleum ether/Ethyl acetate=20:1 to 3:1) to afford methyl 3-(((tert-butoxycarbonyl)(4-hydroxycyclohexyl) amino)methyl)benzoate (900.00 mg, 2.48 mmol, 89.46% yield) as a white solid.

Step 3: methyl 3-0(tert-butoxycarbonyl)(4-oxocyclohexyl)amino)methyl)benzoate

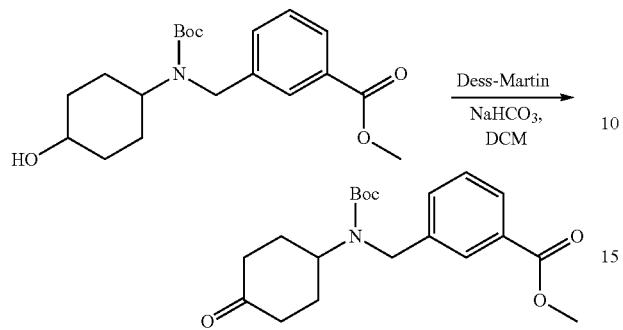

To a solution of methyl 3-(((tert-butoxycarbonyl)(4-hydroxycyclohexyeamino)methyl)benzoate (450.00 mg, 1.24 mmol, 1.00 eq) in DCM (10.00 mL) were added Dess-Martin periodinane (2.10 g, 4.96 mmol, 1.54 mL, 4.00 eq) and NaHCO₃ (208.34 mg, 2.48 mmol, 96.46 uL, 2.00 eq). The reaction mixture was stirred at 23° C. for 16 h. The mixture was quenched by the addition of saturated aqueous Na₂S₂O₃ (10 mL) and extracted with DCM (30 mL*3). The organic layers were concentrated. The crude product was purified by silica gel column chromatography (Petroleum ether/Ethyl acetate=20:1 to 1:1) to afford methyl 3-(((tert-butoxycarbonyl)(4-oxocyclohexyl)amino)methyl)benzoate (430.00 mg) as a white solid.

Step 4: methyl 3-(((tert-butoxycarbonyl)(4-(((trans)-2-((E)-1-phenylbut-1-en-2-yl)cyclopropyl)amino)cyclohexyl)amino)methyl)benzoate

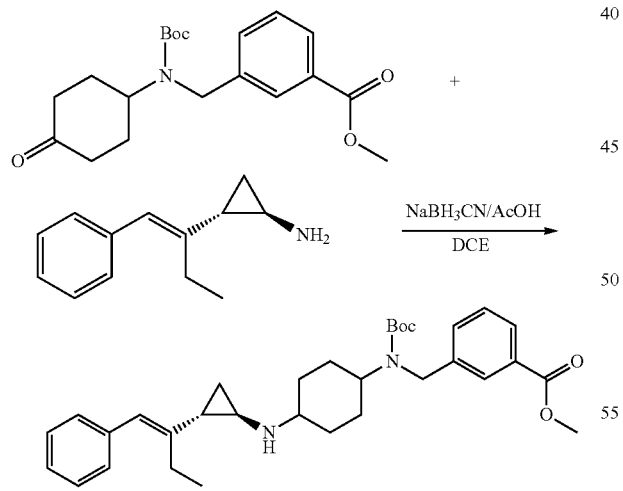

To a mixture of methyl 3-(((tert-butoxycarbonyl)(4-oxocyclohexyl)amino)methyl)benzoate (25.00 mg, 69.17 umol, 1.00 eq) and (trans)-2-((E)-1-phenylbut-1-en-2-yl)cyclopropan-1-amine (12.95 mg, 69.17 umol, 1.00 eq) in DCE (2.00 mL) was added acetic acid (12.46 mg, 207.51 umol, 11.87 uL, 3.00 eq). The reaction mixture was stirred at 27° C. for 17 h before addition of NaBH₃CN (21.73 mg, 345.85 umol, 5.00 eq) and stirring at 27° C. for 0.5 h. The reaction was diluted with water (10 mL) and the mixture was extracted with DCM (5 mL*3). The organic layers were concentrated and the crude residue was purified by Prep-TLC (Petroleum ether:Ethyl acetate=1:1) to afford methyl 3-(((tert-butoxycarbonyl)(4-(((trans)-2-((E)-1-phenylbut-1-en-2-yl)cyclopropyl)amino)cyclohexyl)amino)methyl)benzoate (17.00 mg) as a colorless oil. LCMS (M+H⁺) m/z: 533.

Step 5: 3-(((tert-butoxycarbonyl)((trans)-4-(((trans)-24(E)-1-phenylbut-1-en-2-yl)cyclopropyl)amino)cyclohexyl)amino)methyl)benzoic Acid

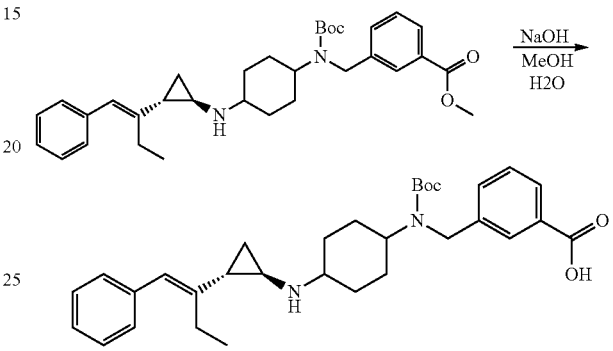

To a mixture of methyl 3-(((tert-butoxycarbonyl)(4-(((trans)-2-((E)-1-phenylbut-1-en-2-yl)cyclopropyl)amino)cyclohexyl)amino)methyl)benzoate (17.00 mg, 31.91 umol, 1.00 eq) in MeOH (1.00 mL) and water (500.00 uL) was added NaOH (12.76 mg, 319.10 umol, 10.00 eq). The reaction mixture was stirred at 60° C. for 3 h. The reaction mixture was adjusted to pH=5 with HCl (4M) and was extracted with DCM (5 mL*2). The organic layers were concentrated to afford crude 3-(((tert-butoxycarbonyl)(4-(((trans)-2-((E)-1-phenylbut-1-en-2-yl)cyclopropyl)amino)cyclohexyl)amino)methyl)benzoic acid (20.00 mg) as a yellow oil.

Step 6: 3-(((4-(((trans)-2-((E)-1-phenylbut-1-en-2-yl)cyclopropyl)amino)cyclohexyl)amino)methyl)benzoic Acid Dihydrochloride (Racemic)

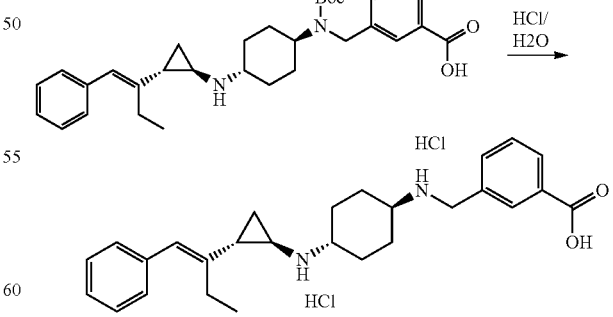

A mixture of 3-(((tert-butoxycarbonyl)(4-(((trans)-2-((E)-1-phenylbut-1-en-2-yl)cyclopropyl)amino)cyclohexyl)amino)methyl)benzoic acid (20.00 mg, 38.56 umol, 1.00 eq) and aqueous HCl (4 M, 3.00 mL, 2176.49 eq) was stirred at 26° C. for 10 h. The reaction mixture was concentrated and the crude product was purified by Prep-HPLC (HCl) to afford 3-(((4-(((trans)-2-((E)-1-phenylbut-1-en-2-yl)cyclopropyl)amino)cyclohexyl)amino)methyl)benzoic acid dihydrochloride (1.30 mg) as a white solid. LCMS (M+H$^+$) m/z: 419. $^1$HNMR (400 MHz, MeOD-d$_4$) δ=8.23 (s, 1H), 8.15-8.13 (d, J=8 Hz, 1H), 7.78-7.76 (d, J=8 Hz, 1H), 7.63 (m, 2H), 7.34 (m, 2H), 7.23-7.21 (d, J=8 Hz, 2H), 6.32 (s, 1H), 4.37 (s, 2H), 2.97 (s, 2H), 2.44 (m, 6H), 2.10 (s, 1H), 1.64 (s, 4H), 1.33 (m, 3H), 1.21 (m, 3H).

Compound 209: N-((trans)-2-((E)-1-phenylbut-1-en-2-yl)cyclopropyl)pyrrolidin-3-amine Dihydrochloride (Racemic)

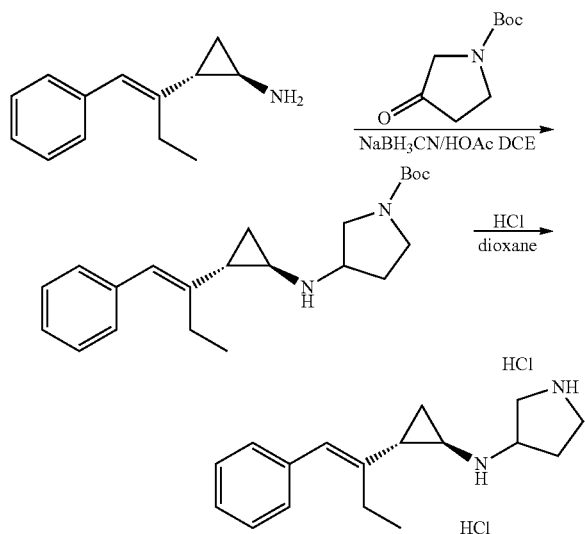

Step 1: tert-butyl 3-(((trans)-2-((E)-1-phenylbut-1-en-2-yl)cyclopropyl)amino)pyrrolidine-1-carboxylate

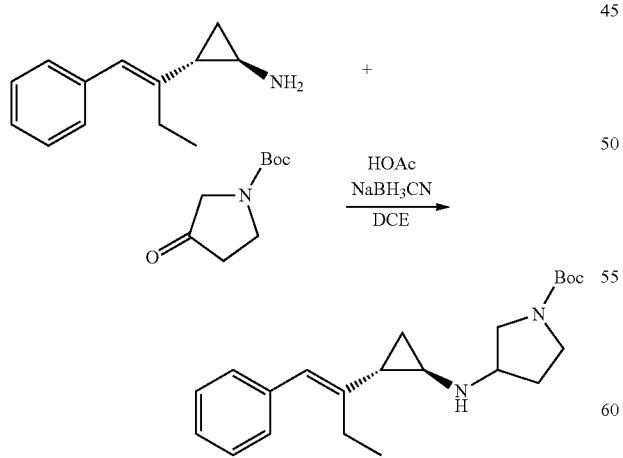

To a mixture of (trans)-2-((E)-1-phenylbut-1-en-2-yl)cyclopropan-1-amine (203.00 mg, 1.08 mmol, 1.00 eq) and tert-butyl 3-oxopyrrolidine-1-carboxylate (200.04 mg, 1.08 mmol, 1.00 eq) in DCE (4.00 mL) was added acetic acid (194.56 mg, 3.24 mmol, 185.30 uL, 3.00 eq). The reaction mixture was stirred at 0° C. for 1 h before addition of NaBH$_3$CN (339.34 mg, 5.40 mmol, 5.00 eq). The reaction mixture was stirred at 0° C. for 15 min before the reaction mixture was concentrated. The crude product was purified by column chromatography (Petroleum ether:Ethyl acetate=10:1 to 3:1) to afford tert-butyl 3-(((trans)-2-((E)-1-phenylbut-1-en-2-ypcyclopropyl)amino)pyrrolidine-1-carboxylate (500.00 mg, crude) as a yellow oil. LCMS (M+H$^+$) m/z: 257.

Step 2: N-((trans)-2-((E)-1-phenylbut-1-en-2-yl)cyclopropyl)pyrrolidin-3-amine Dihydrochloride (Racemic)

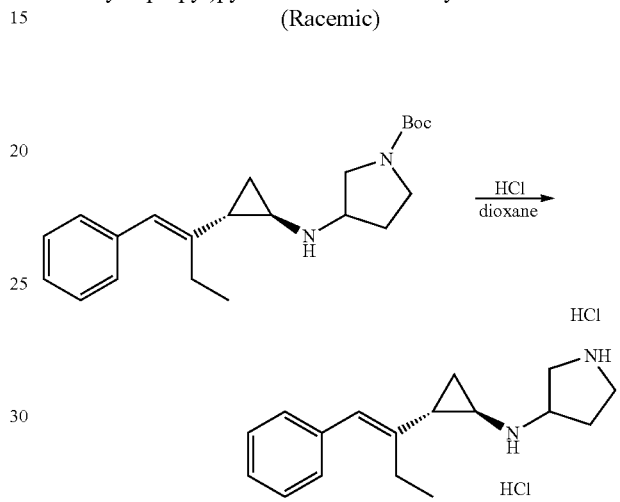

To a mixture of tert-butyl 3-(((trans)-2-((E)-1-phenylbut-1-en-2-yl)cyclopropyl)amino)pyrrolidine-1-carboxylate (250.00 mg, 701.26 umol, 1.00 eq) was added HCl (4 M, 428.89 uL, 17.11 eq). The reaction mixture was stirred at 26° C. for 16 h. The reaction mixture was extracted with ethyl acetate (10 mL*3) and concentrated. The crude product was purified by column chromatography (Petroleum ether: Ethyl acetate=5:1 to 1:2) to afford N-((trans)-2-(E)-1-phenylbut-1-en-2-yl)cyclopropyl)pyrrolidin-3-amine dihydrochloride (23.00 mg) as a yellow oil. LCMS (M+H$^+$) m/z: 257. $^1$H NMR (400 MHz, METHANOL-d$_4$) δ=7.33-7.17 (m, 5H), 6.31 (s, 1H), 4.32-4.21 (m, 1H), 3.82 (s, 1H), 3.65 (br. s., 2H), 3.49-3.42 (m, 1H), 3.05-2.94 (m, 1H), 2.67-2.57 (m, 1H), 2.34 (d, J=7.5 Hz, 4H), 1.52-1.43 (m, 1H), 1.34-1.26 (m, 1H), 1.18 (t, J=7.5 Hz, 3H).

Compound 210: 2-(4-(((4-(((trans)-2-((E)-1-phenylbut-1-en-2-yl)cyclopropyl)amino)cyclohexyl)amino)methyl)-1H-pyrazol-1-yl)acetic Acid Dihydrochloride (Racemic)

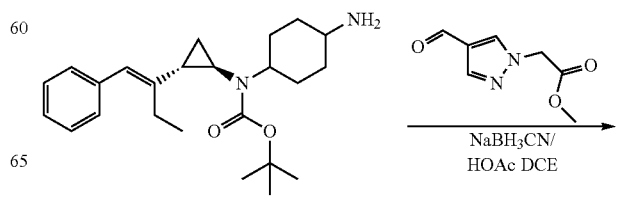

-continued

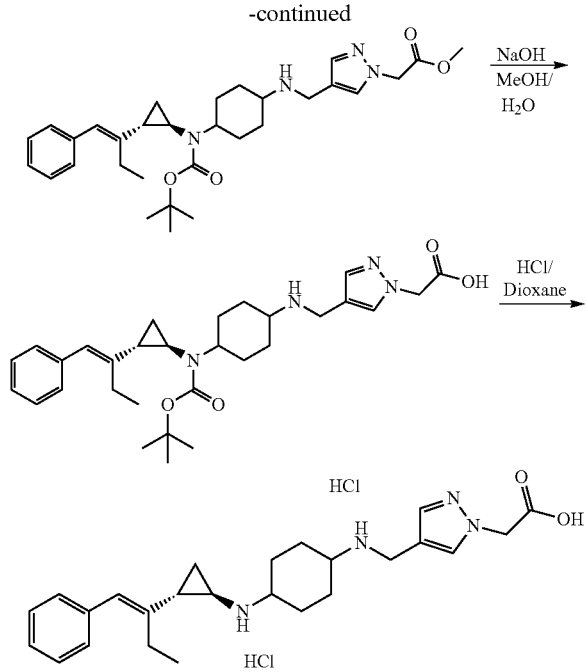

Step 1: methyl 2-(4-(((4-((tert-butoxycarbonyl)
((trans)-2-((E)-1-phenylbut-1-en-2-yl)cyclopropyl)
amino)cyclohexyl)amino)methyl)-1H-pyrazol-1-yl)
acetate

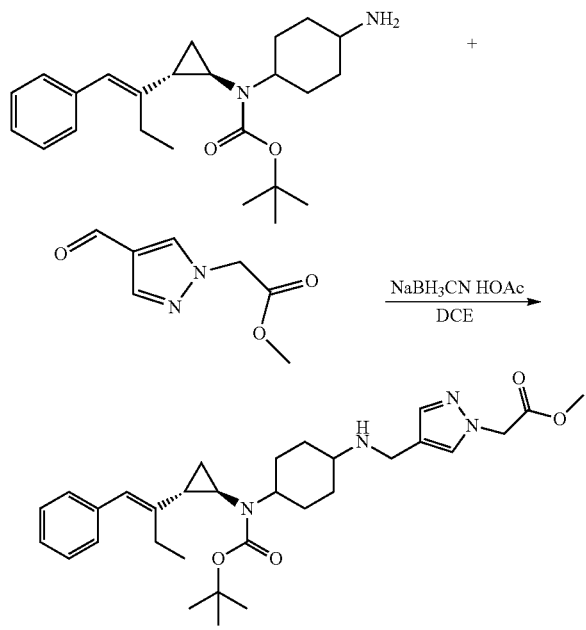

The solution of tert-butyl (4-aminocyclohexyl)((trans)-2-(E)-1-phenylbut-1-en-2-yl)cyclopropyl)carbamate (100.00 mg, 260.04 umol, 1.00 eq), methyl 2-(4-formylpyrazol-1-yl)acetate (43.73 mg, 260.04 umol, 1.00 eq) and acetic acid (62.46 mg, 1.04 mmol, 59.49 uL, 4.00 eq) in DCE (10.00 mL) was stirred for 2 h at 25° C. before addition of NaBH₃CN (98.05 mg, 1.56 mmol, 6.00 eq). The mixture was stirred for 16 h at 25° C. before addition of water (10 mL). This mixture was extracted with DCM (15 mL*2) and the combined organics phase was dried over Na₂SO₄ and concentrated. The crude residue was purified by Prep-HPLC (Instrument: Phenomenex Synergi C18 250*21.2 mm*4 um Mobile phase A: water with 0.05% HCl Mobile phase B: acetonitrile, column temperature: 30° C., Gradient 40-70% B) to afford methyl 2-(4-(((4-((tert-butoxycarbonyl)((trans)-2-((E)-1-phenylbut-1-en-2-yl)cyclopropyl)amino)cyclohexyl)amino)methyl)-1H-pyrazol-1-yl)acetate (15.00 mg) as a white solid. LCMS (M+H⁺) m/z: 537.

Step 2: 2-(4-(((4-((tert-butoxycarbonyl)((trans)-2-(E)-1-phenylbut-1-en-2-yl)cyclopropyl)amino)cyclohexyl)amino)methyl)-1H-pyrazol-1-yl)acetic Acid

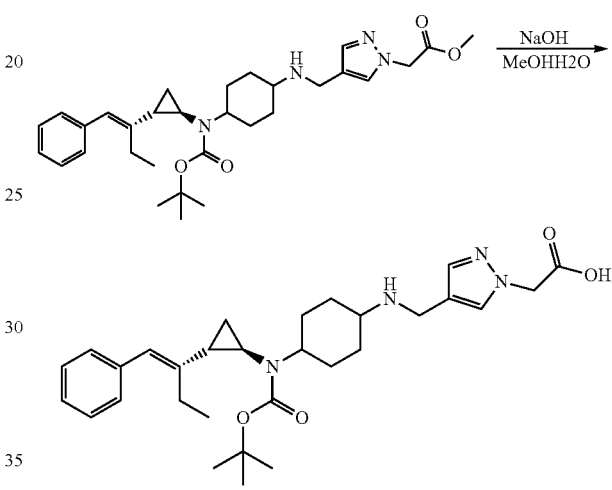

The solution of methyl 2-(4-(((4-((tert-butoxycarbonyl)((trans)-2-((E)-1-phenylbut-1-en-2-yl)cyclopropyl)amino)cyclohexyeamino)methyl)-1H-pyrazol-1-yl)acetate (15.00 mg, 27.95 umol, 1.00 eq) and NaOH (11.18 mg, 279.49 umol, 10.00 eq) in MeOH (5.00 mL) and water (1.00 mL) was stirred for 16 h at 80° C. The mixture was concentrated and the crude residue was suspended in water (5 mL) and extracted with DCM/MeOH (10 mL*2, 20:1). The combined organic phases were dried with Na₂SO₄ and concentrated to afford crude 2-(4-(((4-((tert-butoxycarbonyl)((trans)-2-((E)-1-phenylbut-1-en-2-yl)cyclopropyl)amino)cyclohexyl)amino)methyl)-1H-pyrazol-1-yl)acetic acid (18.00 mg) as a yellow oil. LCMS (M+H⁺) m/z: 523.

Step 3: 2-(4-(((4-(((trans)-2-(E)-1-phenylbut-1-en-2-yl)cyclopropyl)amino)cyclohexyl)amino)methyl)-1H-pyrazol-1-yl)acetic Acid Dihydrochloride Dihydrochloride (Racemic)

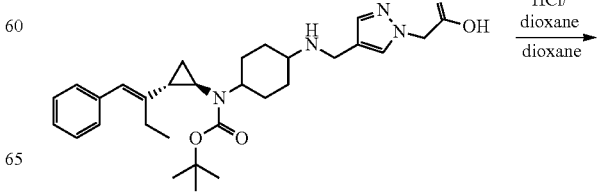

-continued

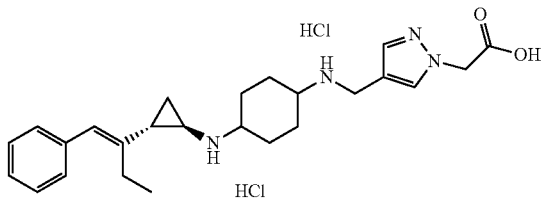

To the solution of 2-(4-(((4-((tert-butoxycarbonyl)((trans)-2-((E)-1-phenylbut-1-en-2-yl)cyclopropyl)amino)cyclohexyl)amino)methyl)-1H-pyrazol-1-yl)acetic acid (15.00 mg, 28.70 umol, 1.00 eq) in dioxane (500.00 uL) was added HCl (4 M in dioxane, 500.00 uL, 69.69 eq) at 0° C. The mixture was stirred for 3 hours at 25° C. before being concentrated. The crude residue was purified by Prep-HPLC (Instrument: Phenomenex Synergi C18 250*21.2 mm*4 um Mobile phase A: water with 0.05% HCl Mobile phase B: acetonitrile, column temperature: 30° C., Gradient 12-42% B) to 2-(4-(((4-(((trans)-2-((E)-1-phenylbut-1-en-2-yl)cyclopropyl)amino)cyclohexyl)amino)methyl)-1H-pyrazol-1-yl)acetic acid dihydrochloride (2.00 mg, 3.01 umol, 10.48% yield, 69% purity) as a white solid. LCMS (M+H$^+$) m/z: 423. $^1$H NMR (400 MHz, methanol-d$_4$) δ=7.94 (s, 1H), 7.70 (s, 1H), 7.35-7.31 (m, 2H), 7.23-7.21 (m, 3H), 6.32 (s, 1H), 5.04 (s, 2H), 4.23 (s, 2H), 3.49-3.45 (m, 2H), 3.41 (m, 1H), 3.26 (m, 1H), 2.96 (s, 1H), 2.40-2.35 (m, 2H), 2.23-2.2 (m, 1H), 2.14-2.04 (m, 4H), 1.64 (m, 4H), 1.22-1.18 (t, 3H).

Compound 211: 1-amino-4-(((trans)-2-((E)-1-phenylbut-1-en-2-yl)cyclopropyl)amino)cyclohexane-1-carboxylic Acid Dihydrochloride (Racemic)

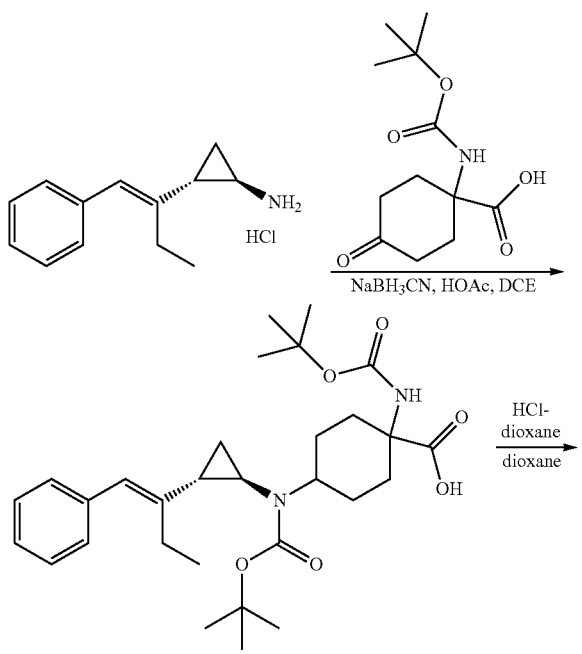

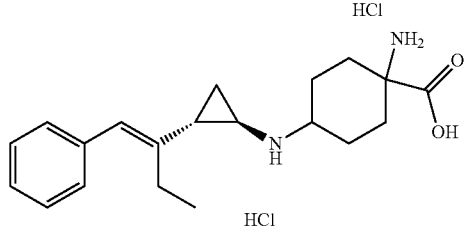

Step 1: 4-((tert-butoxycarbonyl)((trans)-2-((E)-1-phenylbut-1-en-2-yl)cyclopropyl)amino)-1-((tert-butoxycarbonyl)amino)cyclohexane-1-carboxylic Acid The mixture of (trans)-2-((E)-1-phenylbut-1-en-2-yl)cyclopropan-1-amine hydrochloride (40.00 mg, 178.78 umol, 1.00 eq) in water (2 mL) was treated with saturated aqueous Na$_2$CO$_3$. The mixture was extracted with dichloromethane and methanol (5 mL*2, 20:1). The organic phases were combined, dried with Na$_2$SO$_4$, and concentrated. The residue was dissolved in DCE (5.00 mL) and 1-(tert-butoxycarbonylamino)-4-oxo-cyclohexanecarboxylic acid (46.00 mg, 178.78 umol, 1.00 eq) and HOAc (21.47 mg, 357.56 umol, 20.45 uL, 2.00 eq) were added to the solution. The mixture was stirred for 1 h at 25° C. To the mixture was added NaBH$_3$CN (33.70 mg, 536.34 umol, 3.00 eq). The mixture was stirred for 1 h at 25° C. The solution was diluted with water (4 mL) and extracted with DCM (5 mL*2). The organic phases were combined, dried with Na$_2$SO$_4$, filtered and concentrated to afford crude 4-((tert-butoxycarbonyl)((trans)-2-((E)-1-phenylbut-1-en-2-yl)cyclopropyl)amino)-1-((tert-butoxycarbonyl)amino)cyclohexane-1-carboxylic acid (60.00 mg). LCMS (M-Boc+H$^+$) m/z: 429.

Step 2: 1-amino-4-(((trans)-2-((E)-1-phenylbut-1-en-2-yl)cyclopropyl)amino)cyclohexane-1-carboxylic Acid Dihydrochloride (Racemic)

To the solution of crude 4-((tert-butoxycarbonyl)((trans)-2-((E)-1-phenylbut-1-en-2-yl)cyclopropyl)amino)-1-((tert-butoxycarbonyl)amino)cyclohexane-1-carboxylic acid (60.00 mg, 140.00 umol, 1.00 eq) in dioxane (2.00 mL) was added HCl (4 M in dioxane, 1.50 mL, 42.86 eq) at 0° C. The solution was stirred for 1 hour at 0° C. The solution was concentrated and the crude residue was purified by Prep-HPLC (Instrument: Phenomenex Synergi C18 150*30 mm*4 um Mobile phase A: water with 0.05% HCl Mobile phase B: acetonitrile, column temperature: 30° C., Gradient 10-40% B) to 1-amino-4-(((trans)-2-((E)-1-phenylbut-1-en-2-yl)cyclopropyl)amino)cyclohexane-1-carboxylic acid dihydrochloride (20.50 mg). LCMS (M+H$^+$) m/z: 329. $^1$H NMR (400 MHz, D2O) δ=7.27-7.24 (m, 2H), 7.16-7.15 (m, 3H), 6.13 (s, 1H), 3.41-3.31 (m, 1H), 2.82-2.78 (m, 1H), 2.28-1.84 (m, 9H), 1.52 (m, 2H), 1.21-1.17 (m, 2H), 1.01-0.97 (m, 3H).

Compound 212 and Compound 213: 3-(methyl ((trans)-4-(((trans)-2-((E)-1-phenylbut-1-en-2-yl) cyclopropyl)amino)cyclohexyl)amino)propanoic Acid Dihydrochloride (Racemic) and 3-(methyl ((cis)-4-(((trans)-2-((E)-1-phenylbut-1-en-2-yl)cyclopropyl)amino)cyclohexyl)amino)propanoic Acid Dihydrochloride (Racemic)

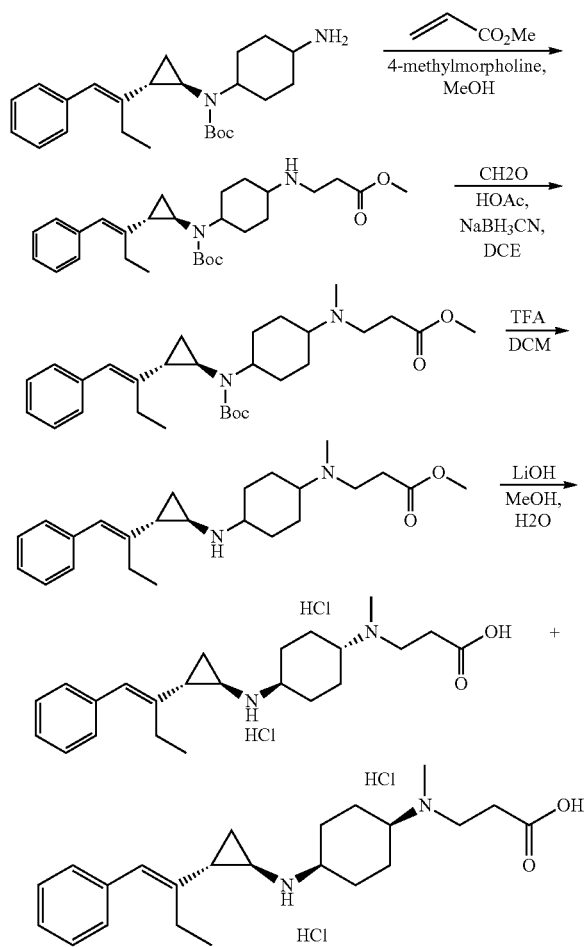

Step 1: methyl 3-((4-((tert-butoxycarbonyl)((trans)-2-(E)-1-phenylbut-1-en-2-yl)cyclopropyl)amino) cyclohexyl)amino)propanoate To a solution of tert-butyl (4-aminocyclohexyl)((trans)-2-(E)-1-phenylbut-1-en-2-yl)cyclopropyl)carbamate (50.00 mg, 130.02 umol, 1.00 eq) in MeOH (2.00 mL) was added 4-methylmorpholine (39.45 mg, 390.06 umol, 42.88 uL, 3.00 eq) and methyl prop-2-enoate (22.39 mg, 260.04 umol, 23.32 uL, 2.00 eq). The mixture was stirred at 70° C. for 1 h before the mixture was concentrated. To the crude residue was added water (10 mL) and the mixture was extracted with DCM (20 mL*3). The combined organics phase was dried with Na$_2$SO$_4$ and concentrated to afford crude methyl 3-((4-((tert-butoxycarbonyl)((trans)-2-(E)-1-phenylbut-1-en-2-yl) cyclopropyl)amino)cyclohexyl)amino)propanoate (77.00 mg) as a yellow oil. LCMS (M+H$^+$) m/z: 471.

Step 2: methyl 3-((4-((tert-butoxycarbonyl)((trans)-2-((E)-1-phenylbut-1-en-2-Acyclopropyl)amino) cyclohexyl)(methyl)amino)propanoate To a solution of methyl 3-((4-((tert-butoxycarbonyl) ((trans)-2-(E)-1-phenylbut-1-en-2-yl)cyclopropyl)amino) cyclohexyl)amino)propanoate (77.00 mg, 163.61 umol, 1.00 eq) in DCE (2.50 mL) were added acetic acid (9.82 mg, 163.61 umol, 9.35 uL, 1.00 eq) and formaldehyde (20.00 mg, 665.89 umol, 18.35 uL, 4.07 eq). The mixture was stirred at 25° C. for 1 h before addition of NaBH$_3$CN (30.00 mg, 477.74 umol, 2.92 eq). The mixture was stirred at 25° C. for 1 h before it was diluted with water (15 mL). The mixture was extracted with DCM (20 mL) and the combined organics phase was dried with Na$_2$SO$_4$ and concentrated to afford crude methyl 3-((4-((tert-butoxycarbonyl)((trans)-2-(E)-1-phenylbut-1-en-2-yl)cyclopropyl)amino)cyclohexyl) (methyl)amino)propanoate (100.00 mg) as a yellow oil. LCMS (M+H$^+$) m/z: 485.

Step 3: methyl 3-(methyl(4-(((trans)-2-((E)-1-phenylbut-1-en-2-yl)cyclopropyl)amino)cyclohexyl) amino)propanoate A mixture of methyl 3-((4-((tert-butoxycarbonyl)((trans)-2-(E)-1-phenylbut-1-en-2-yl)cyclopropyl)amino)cyclohexyl)(methyl)amino)propanoate (50.00 mg, 103.16 umol, 1.00 eq) and TFA (1.54 g, 13.51 mmol, 1.00 mL, 130.93 eq) in DCM (4.00 mL) was stirred at 0° C. for 1 h. The mixture was neutralized by saturated aqueous NaHCO$_3$ to pH=7 before extracting with DCM (20 mL*3). The combined organics phase was dried with Na$_2$SO$_4$ and concentrated to afford crude methyl 3-(methyl(4-(((trans)-2-((E)-1-phenylbut-1-en-2-yl)cyclopropyl)amino)cyclohexyl)amino)propanoate (30.00 mg) as a yellow solid. LCMS (M+H$^+$) m/z: 385.

Step 4: 3-(methyl((trans)-4-(((trans)-2-((E)-1-phenylbut-1-en-2-yl)cyclopropyl)amino)cyclohexyl) amino)propanoic Acid Dihydrochloride (Racemic) and 3-(methyl((cis)-4-(((trans)-2-((E)-1-phenylbut-1-en-2-yl)cyclopropyl)amino)cyclohexyl)amino)propanoic Acid Dihydrochloride (Racemic)

To a solution of methyl 3-(methyl(4-(((trans)-2-((E)-1-phenylbut-1-en-2-yl)cyclopropyl)amino)cyclohexyl)amino) propanoate (30.00 mg, 78.01 umol, 1.00 eq) in MeOH (5.00 mL) and water (2.00 mL) was added LiOH (9.34 mg, 390.07 umol, 5.00 eq). The mixture was stirred at 50° C. for 30 min before the reaction was concentrated. The residue was diluted with water (5 mL) and acidified with HCl (1M) to pH=6. The mixture was extracted with DCM (5 mL*3) and the combined organics phase was dried with Na$_2$SO$_4$ and concentrated. The crude residue was purified by prep-HPLC (HCl) to afford two compounds: 3-(methyl((trans)-4-(((trans)-2-((E)-1-phenylbut-1-en-2-yl)cyclopropyl)amino) cyclohexyl)amino)propanoic acid dihydrochloride (2.20 mg). LCMS (M+H$^+$) m/z: 371. $^1$H NMR (400 MHz, DEUTERIUM OXIDE) d=7.36-7.21 (m, 2H), 7.21-7.11 (m, 3H), 6.13 (s, 1H), 3.56-3.36 (m, 1H), 3.31 (br. s., 1H), 3.26-3.10 (m, 2H), 2.78 (t, J=7.7 Hz, 1H), 2.75-2.68 (m, 5H), 2.29 (d, J=10.6 Hz, 2H), 2.21-2.06 (m, 4H), 1.94 (d, J=19.8 Hz, 1H), 1.62 (br. s., 2H), 1.57-1.40 (m, 2H), 1.23-1.11 (m, 2H), 0.99 (t, J=7.5 Hz, 3H). 3-(methyl((cis)-4-(((trans)-2-((E)-1-phenylbut-1-en-2-yl)cyclopropyl)amino)cyclohexyl)amino) propanoic acid dihydrochloride (900.00 ug). LCMS (M+m/z: 371.

Compound 214: N1-((trans)-2-((E)-1-phenylbut-1-en-2-yl)cyclopropyl)cyclobutane-1,3-diamine Dihydrochloride

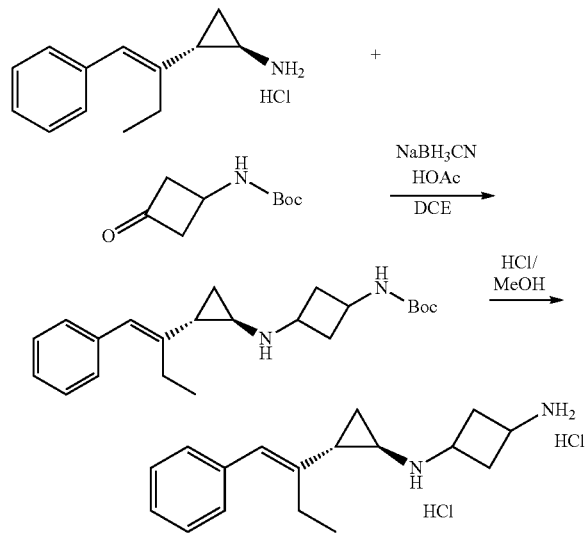

Step 1: tert-butyl (3-(((trans)-2-((E)-1-phenylbut-1-en-2-yl)cyclopropyl)amino)cyclobutyl)carbamate To a mixture of (trans)-2-(E)-1-phenylbut-1-en-2-yl)cyclopropan-1-amine hydrochlorideine (30.00 mg, 160.19 umol, 1.00 eq) and tert-butyl N-(3-oxocyclobutyl)carbamate (29.67 mg, 160.19 umol, 1.00 eq) in DCE (3.00 mL) was added acetic acid (31.50 mg, 524.56 umol, 30.00 uL, 3.27 eq). The reaction mixture was stirred at 0° C. for 1 h before addition of NaBH$_3$CN (50.33 mg, 800.95 umol, 5.00 eq) at 0° C. The reaction mixture was stirred at 0° C. for 0.5 hand then concentrated to afford crude tert-butyl (3-(((trans)-2-((E)-1-phenylbut-1-en-2-yl)cyclopropyl)amino)cyclobutyl) carbamate (40.00 mg). LCMS (M+H$^+$) m/z: 357.

Step 2: N1-((trans)-2-((E)-1-phenylbut-1-en-2-yl)cyclopropyl)cyclobutane-1,3-diamine Dihydrochloride To a mixture of tert-butyl (3-(((trans)-2-((E)-1-phenylbut-1-en-2-yl)cyclopropyl)amino)cyclobutyl)carbamate (40.00 mg, 112.20 umol, 1.00 eq) in DCM (500.00 uL) was added TFA (462.00 mg, 4.05 mmol, 300.00 uL, 36.11 eq). The reaction mixture was stirred at 26° C. for 45 min before the reaction mixture was concentrated under reduced pressure. The crude residue was purified by prep-HPLC (HCl) to afford N1-((trans)-2-((E)-1-phenylbut-1-en-2-yl)cyclopropyl)cyclobutane-1,3-diamine dihydrochloride (3.30 mg). LCMS (M+H$^+$) m/z: 257. $^1$HNMR (400 MHz, METHANOL-d$_4$)=7.33-7.27 (t, 2H), 7.20 (s, 3H), 6.27 (s, 1H), 4.28-4.03 (m, 1H), 3.92-3.64 (m, 1H), 2.95-2.80 (m, 3H), 2.69-2.52 (m, 2H), 2.40-2.30 (m, 2H), 2.20-2.12 (m, 1H), 1.44-1.33 (m, 1H), 1.27-1.23 (m, 1H), 1.18 (1, J=7.5 Hz, 3H)

Compound 215: (trans)-4-((((trans)-2-(E)-1-phenylbut-1-en-2-yl)cyclopropyl)amino)methyl)cyclohexan-1-amine Dihydrochloride (Racemic)

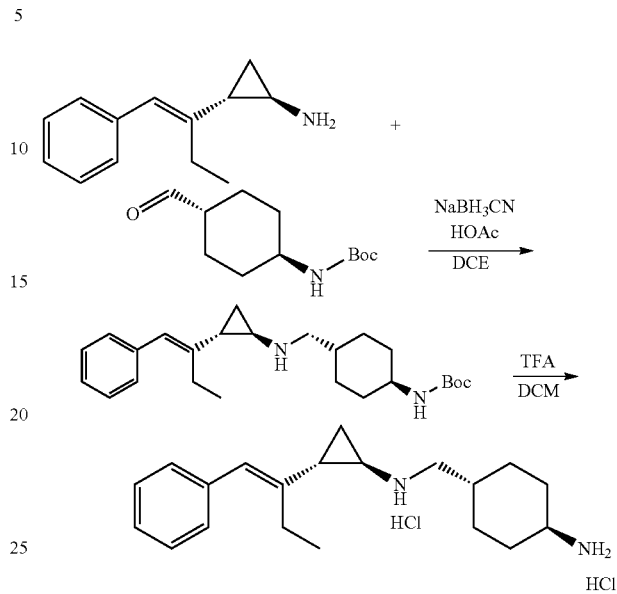

Step 1: tert-butyl ((trans)-4-((((trans)-2-((E)-1-phenylbut-1-en-2-yl)cyclopropyl)amino)methyl)cyclohexyl)carbamate To a mixture of (trans)-2-((E)-1-phenylbut-1-en-2-yl)cyclopropan-1-amine (100.00 mg, 446.95 umol, 1.00 eq, HCl) and tert-butyl N-(4-formylcyclohexyl)carbamate (101.59 mg, 446.95 umol, 1.00 eq) in DCE (3.00 mL) was added acetic acid (105.00 mg, 1.75 mmol, 100.00 uL, 3.91 eq). The reaction mixture was stirred at 0° C. for 1 hr before addition of NaBH$_3$CN (140.43 mg, 2.23 mmol, 5.00 eq) at 0° C. The reaction mixture was stirred at 0° C. for 0.5 hr. The reaction mixture was quenched by addition saturated solution NaHCO$_3$ (3 mL). Water (30 mL) was added and extracted the mixture was extracted with ethyl acetate (10 mL*3). The combined organic layers were dried over anhydrous Na$_2$SO$_4$, filtered and concentrated to afford crude tert-butyl ((trans)-4-((((trans)-2-((E)-1-phenylbut-1-en-2-yl)cyclopropyl)amino)methyl)cyclohexyl)carbamate (200.00 mg). LCMS (M+H) m/z: 399.

Step 2: (trans)-4-((((trans)-2-((E)-1-phenylbut-1-en-2-yl)cyclopropyl)amino)methyl)cyclohexan-1-amine Dihydrochloride (Racemic)

To a mixture of tert-butyl ((trans)-4-((((trans)-2-((E)-1-phenylbut-1-en-2-yl)cyclopropyl)amino)methyl)cyclohexyl)carbamate (200.00 mg, 501.78 umol, 1.00 eq) in DCM (1.00 mL) was added TFA (1.54 g, 13.51 mmol, 1.00 mL, 26.92 eq). The reaction mixture was stirred at 26° C. for 1 h before being concentrated. The crude residue was purified by prep-HPLC (HCl) to afford (trans)-4-((((trans)-2-((E)-1-phenylbut-1-en-2-yl)cyclopropyl)amino)methyl) cyclohexan-1-amine dihydrochloride (33.70 mg). LCMS (M+H$^+$) m/z: 299. $^1$HNMR (400 MHz, METHANOL-d$_4$) δ=7.34-7.27 (t, 2H), 7.23-7.16 (t, 3H), 6.32-6.26 (s, 1H), 3.17-3.04 (d, 3H), 2.95-2.87 (t, 1H), 2.41-2.28 (m, 2H), 2.24-2.16 (s, 1H), 2.15-2.07 (m, 2H), 2.05-1.96 (d, 2H), 1.92-1.74 (d, 2H), 1.53-1.35 (d, 3H), 1.19 (q, J=7.6 Hz, 5H).

Compound 275: 5-(((((trans)-4-(((trans)-2-((E)-1-phenylbut-1-en-2-yl)cyclopropyl)amino)cyclohexyl)amino)methyl)pyrimidine-2-carboxylic Acid Dihydrochloride (Racemic)

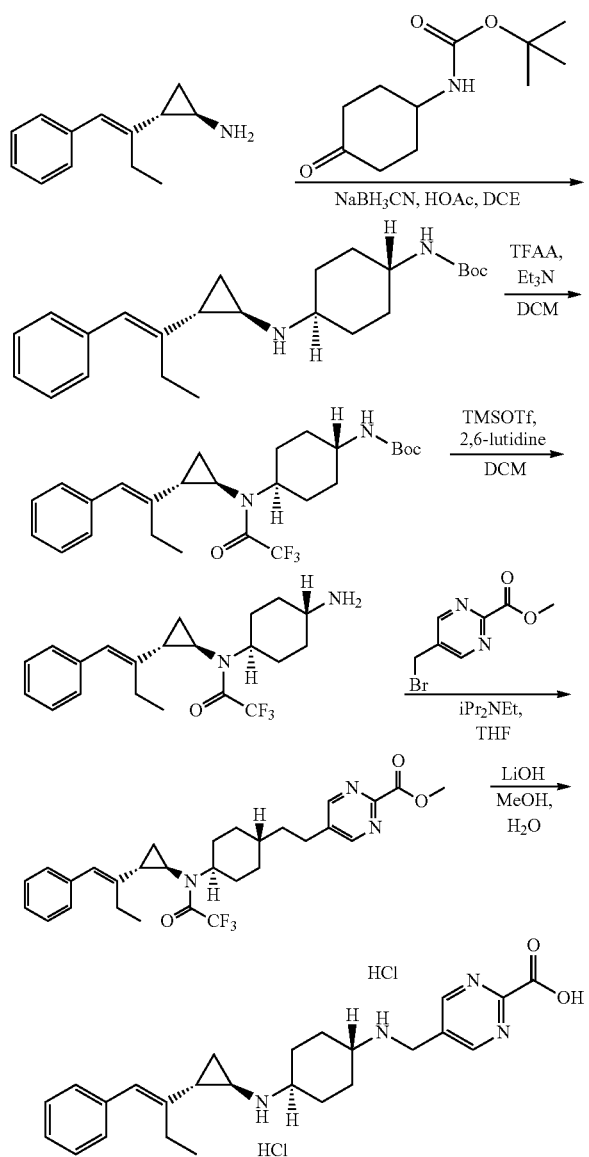

Step 1: tert-butyl ((trans)-4-(((trans)-2-((E)-1-phenylbut-1-en-2-yl)cyclopropyl)amino)cyclohexyl)carbamate Hydrochloride (trans)-2-(E)-1-phenylbut-1-en-2-yl)cyclopropan-1-amine hydrochloride (1.00 g, 4.47 mmol, 1.00 eq) was added to saturated aqueous NaHCO$_3$ and the mixture was extracted with DCM (20 mL*3). The combined organic phase was washed with brine (20 mL*2), dried over anhydrous Na$_2$SO$_4$, filtered and concentrated to afford (trans)-2-((E)-1-phenylbut-1-en-2-yl)cyclopropan-1-amine (0.8 g). To the freebased cyclopropylamine was added tert-butyl (4-oxocyclohexyl)carbamate (1.14 g, 5.36 mmol, 1.14 mL, 1.20 eq), DCE (15.00 mL), and acetic acid (805.18 mg, 13.41 mmol, 766.84 uL, 3.00 eq). The reaction mixture was stirred at 0° C. for 2 h before addition of NaBH$_3$CN (842.59 mg, 13.41 mmol, 3.00 eq) and stirring at 0° C. for 1 h. Water was added and the mixture was extracted with DCM (30 mL*3). The combined organics phase was washed with brine (50 mL*2), dried over anhydrous Na$_2$SO$_4$, filtered, and concentrated. The crude residue was purified by column chromatography (Petroleum ether:Ethyl acetate=20:1 to 5:1) to afford two diastereomers. The two products were separately treated with HCl (4N in MeOH to pH=5) and concentrated to afford tert-butyl ((cis)-4-(((trans)-2-((E)-1-phenylbut-1-en-2-yl)cyclopropyl)amino)cyclohexyl)carbamate hydrochloride (700.00 mg, 1.66 mmol, 37.14% yield) and tert-butyl ((trans)-4-(((trans)-2-(E)-1-phenylbut-1-en-2-yl)cyclopropyl)amino)cyclohexyl)carbamate hydrochloride (600.00 mg, 1.43 mmol, 31.99% yield) as a white solid.

Step 2: tert-butyl ((trans)-4-(2,2,2-trifluoro-N-Otrans)-2-((E)-1-phenylbut-1-en-2-yl)cyclopropyl) acetamido)cyclohexyl)carbamate To a mixture of tert-butyl ((trans)-4-(((trans)-2-((E)-1-phenylbut-1-en-2-yl)cyclopropyl)amino)cyclohexyl)carbamate hydrochloride (600.00 mg, 1.56 mmol, 1.00 eq) in DCM (10.00 mL) were added TFAA (655.41 mg, 3.12 mmol, 434.05 uL, 2.00 eq) and triethylamine (789.42 mg, 7.80 mmol, 1.08 mL, 5.00 eq) at 0° C. The reaction mixture was stirred at 23° C. for 16 h before being concentrated. The crude residue was purified by column chromatography (Petroleum ether/Ethyl acetate=20:1 to 10:1) to afford tert-butyl ((trans)-4-(2,2,2-trifluoro-N-((trans)-2-((E)-1-phenylbut-1-en-2-yl)cyclopropyl)acetamido)cyclohexyl)carbamate (310.00 mg, 645.08 umol, 41.35% yield).

Step 3: N-((trans)-4-aminocyclohexyl)-2,2,2-trifluoro-N-Otrans)-2-((E)-1-phenylbut-1-en-2-yl)cyclopropyl)acetamide To a solution of tert-butyl ((trans)-4-(2,2,2-trifluoro-N-((trans)-2-((E)-1-phenylbut-1-en-2-yl)cyclopropyl)acetamido)cyclohexyl)carbamate (100.00 mg, 208.09 umol, 1.00 eq) in DCM (3.00 mL) were added 2,6-lutidine (26.76 mg, 249.71 umol, 29.09 uL, 1.20 eq) and TMSOTf (60.13 mg, 270.52 umol, 48.89 uL, 1.30 eq). The mixture was stirred at 25° C. for 3 h. The reaction mixture was concentrated to afford crude N-((trans)-4-aminocyclohexyl)-2,2,2-trifluoro-N-((trans)-2-((E)-1-phenylbut-1-en-2-yl)cyclopropyl)acetamide (170.00 mg).

Step 4: methyl 5-(((((trans)-4-(2,2,2-trifluoro-N-((trans)-2-((E)-1-phenylbut-1-en-2-yl)cyclopropyl) acetamido)cyclohexyl)amino)methyl)pyrimidine-2-carboxylate To a solution of methyl 5-(bromomethyl)pyrimidine-2-carboxylate (35.00 mg, 151.48 umol, 1.00 eq) in THF (2.00 mL) were added iPr$_2$NEt (58.73 mg, 454.44 umol, 79.36 uL, 3.00 eq) and N-((trans)-4-aminocyclohexyl)-2,2,2-trifluoro-N-((trans)-2-((E)-1-phenylbut-1-en-2-yl)cyclopropyl)acetamide (57.63 mg, 151.48 umol, 1.00 eq). The mixture was stirred at 25° C. for 8 h. The reaction mixture was concentrated and the crude residue was purified by prep-TLC (Ethyl Acetate:MeOH=20:1) to afford methyl 5-((atrans)-4-(2,2,2-trifluoro-N-((trans)-2-((E)-1-phenylbut-1-en-2-yl)cyclopropyl)acetamido)cyclohexyeamino)methyl)pyrimidine-2-carboxylate (30.00 mg). LCMS (M+H⁺) m/z: 531.

Step 5: 5-((((trans)-4-(((trans)-2-((E)-1-phenylbut-1-en-2-yl)cyclopropyl)amino)cyclohexyl)amino)methyl)pyrimidine-2-carboxylic Acid Dihydrochloride (Racemic)

To a solution of methyl 5-(((((trans)-4-(2,2,2-trifluoro-N-((trans)-2-((E)-1-phenylbut-1-en-2-yl)cyclopropyl)acetamido)cyclohexyl)amino)methyl)pyrimidine-2-carboxylate (30.00 mg, 56.54 umol, 1.00 eq) in MeOH (3.00 mL) and H$_2$O (1.00 mL) was added LiOH (6.77 mg, 282.70 umol, 5.00 eq). The mixture was stirred at 25° C. for 2 h. The reaction mixture was concentrated and the crude residue was purified by prep-HPLC (HCl condition) to afford 5-((((trans)-4-(((trans)-2-((E)-1-phenylbut-1-en-2-yl)cyclopropyl)amino)cyclohexyl)amino)methyl)pyrimidine-2-carboxylic acid dihydrochloride (2.20 mg) as a white solid. LCMS (M+H⁺) m/z: 421. $^1$H NMR (400 MHz, METHANOL-d$_4$) δ 9.12 (br s., 2H), 7.36-7.27 (m, 2H), 7.26-7.14 (m, 3H), 6.30 (s, 1H), 4.48 (br. s., 2H), 3.41 (br. s 2H), 2.96 (br. s., 1H), 2.45 (br. s., 3H), 2.38-2.31 (m, 2H), 2.09 (br. s., 1H), 1.68 (br. s., 4H), 1.39-1.26 (m, 3H), 1.18 (t, J=7.5 Hz, 3H).

Compound 216: (trans)-N-(2-(azetidin-3-yl)ethyl)-2-(E)-1-phenylbut-1-en-2-yl)cyclopropan-1-amine Dihydrochloride (Racemic)

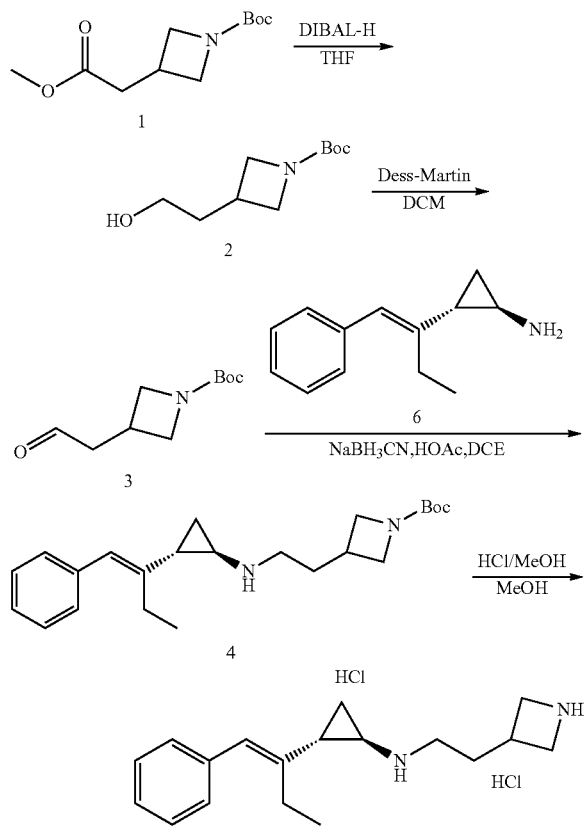

Step 1: tert-butyl 3-(2-hydroxyethyl)azetidine-1-carboxylate

To a mixture of tert-butyl 3-(2-methoxy-2-oxo-ethyl)azetidine-1-carboxylate (200.00 mg, 872.33 umol, 1.00 eq) in THF (10.00 mL) was added DIBAL-H (1 M, 2.62 mL, 3.00 eq) dropwise at −78° C. The reaction mixture was stirred at 0° C. for 2 h. Water (20 mL) was added and the mixture was extracted with EtOAc (15 mL*3). The organic layers were concentrated and the crude residue was purified by silica gel chromatography (Petroleum ether:Ethyl acetate=20:1 to 1:1) to afford tert-butyl 3-(2-hydroxyethyl)azetidine-1-carboxylate (103.00 mg).

Step 2: tert-butyl 3-(2-oxoethyl)azetidine-1-carboxylate

To a mixture of tert-butyl 3-(2-hydroxyethyl)azetidine-1-carboxylate (103.00 mg, 511.78 umol, 1.00 eq) in DCM (6.00 mL) was added Dess-Martin periodinane (434.13 mg, 1.02 mmol, 316.88 uL, 2.00 eq). The reaction mixture was stirred at 18° C. for 3 h. Water (5 mL) was added and the mixture was extracted with DCM (3 mL*3). The combined organics layer was concentrated to afford crude tert-butyl 3-(2-oxoethyl)azetidine-1-carboxylate (40.00 mg).

Step 3: tert-butyl 3-(2-(((trans)-2-((E)-1-phenylbut-1-en-2-yl)cyclopropyl)amino)ethyl)azetidine-1-carboxylate (trans)-2-((E)-1-phenylbut-1-en-2-yl)cyclopropan-1-amine hydrochloride (50.00 mg, 223.47 umol, 1.00 eq) was added to saturated aqueous NaHCO$_3$ and the mixture was extracted with DCM (50 mL*3,). The combined organic phase was washed with brine (20 mL*2), dried over anhydrous Na$_2$SO$_4$, filtered, and concentrated. To the freebased cyclopropylamine was added tert-butyl 3-(2-oxoethyl)azetidine-1-carboxylate (40.00 mg, 200.75 umol, 0.90 eq), DCE (5.00 mL), and acetic acid (40.26 mg, 670.41 umol, 38.34 uL, 3.00 eq). The reaction mixture was stirred at 0° C. for 2 h before addition of NaBH$_3$CN (42.13 mg, 670.41 umol, 3.00 eq) and stirring at 0° C. for 1 h. Water (15 mL) was added and the mixture was extracted with DCM (8 mL*3). The combined organic phase was washed with brine (20 mL*2), dried over anhydrous Na$_2$SO$_4$, filtered, and concentrated to afford tert-butyl 3-(2-(((trans)-2-((E)-1-phenylbut-1-en-2-yl)cyclopropyl)amino)ethyl)azetidine-1-carboxylate (80.00 mg).

Step 4: (trans)-N-(2-(azetidin-3-yl)ethyl)-24(E)-1-phenylbut-1-en-2-yl)cyclopropan-1-amine Dihydrochloride (Racemic)

To a mixture of tert-butyl 3-(2-(((trans)-2-((E)-1-phenylbut-1-en-2-yl)cyclopropyl)amino)ethyl)azetidine-1-carboxylate (80.00 mg, 215.91 umol, 1.00 eq) in MeOH (3.00 mL) was added HCl (4 M in MeOH, 2.00 mL, 37.05 eq). The reaction mixture was stirred at 17° C. for 1 h before being concentrated. The reaction mixture was concentrated and the crude residue purified by Prep-HPLC (HCl) to afford (trans)-N-(2-(azetidin-3-yl)ethyl)-2-(E)-1-phenylbut-1-en-2-yl)cyclopropan-1-amine dihydrochloride (13.00 mg). LCMS (M+H⁺) m/z: calcd. 271.2, found 271. $^1$HNMR (400 MHz, MeOD-d$_4$) δ=7.30 (m, 3H), 7.19-7.17 (d, J=8 Hz, 2H), 6.28 (s, 1H), 4.19 (s, 2H), 3.90 (s, 2H), 3.12 (br. s, 3H), 2.89 (s, 1H), 2.32 (m, 1H), 2.09 (br. s, 3H), 1.70 (m, 1H), 1.38 (s, 1H), 1.19 (m, 4H).

Compound 217: 2,2-dimethyl-N1-((trans)-2-((E)-1-phenylbut-1-en-2-yl)cyclopropyl)propane-1,3-diamine Dihydrochloride (Racemic)

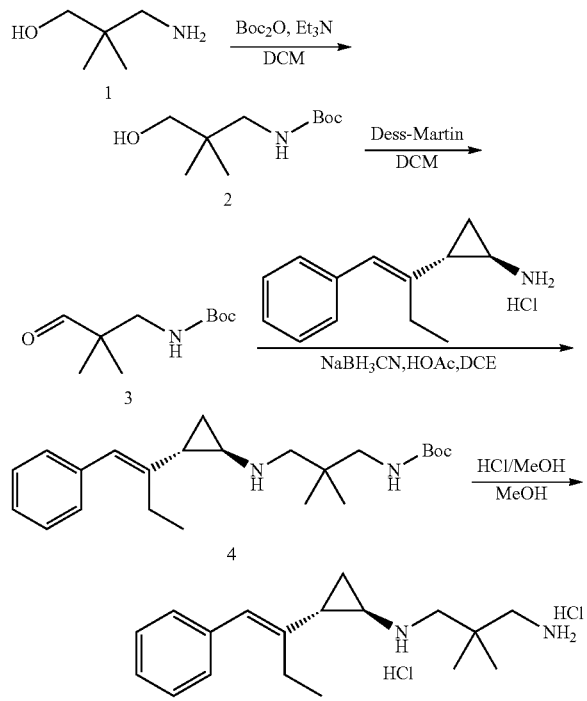

Step 1: tert-butyl N-(3-hydroxy-2,2-dimethyl-propyl)carbamate

To a solution of 3-amino-2,2-dimethyl-propan-1-ol (400.00 mg, 3.88 mmol, 1.00 eq) in DCM (3.00 mL) were added triethylamine (1.18 g, 11.63 mmol, 1.61 mL, 3.00 eq) and Boc$_2$O (1.27 g, 5.82 mmol, 1.34 mL, 1.50 eq) at 0° C. The mixture was stirred at 25° C. for 16 h. The reaction mixture was concentrated and the residue was diluted with ethyl acetate (10 mL) and washed with H$_2$O (10 mL*3), dried over anhydrous Na$_2$SO$_4$ and concentrated. The crude residue was purified by column chromatography (SiO2, Petroleum ether/Ethyl acetate=20:1 to 5:1) to afford tert-butyl N-(3-hydroxy-2,2-dimethyl-propyl)carbamate (254.00 mg). $^1$H NMR (400 MHz, CHLOROFORM-d) δ=3.69 (t, J=7.3 Hz, 1H), 3.18 (d, J=7.1 Hz, 2H), 2.95 (d, J=6.6 Hz, 2H), 1.44 (s, 9H), 0.84 (s, 6H)

Step 2: tert-butyl N-(2,2-dimethyl-3-oxo-propyl)carbamate

To a solution of tert-butyl N-(3-hydroxy-2,2-dimethyl-propyl)carbamate (250.00 mg, 1.23 mmol, 1.00 eq) in DCM (3.00 mL) was added Dess-Martin periodinane (1.04 g, 2.46 mmol, 761.59 uL, 2.00 eq). The mixture was stirred at 25° C. for 2 h. The reaction mixture was concentrated and the residue was diluted with saturated aqueous NaHCO$_3$ (10 mL) and extracted with ethyl acetate 30 mL (10 mL*3). The combined organic layers were dried over anhydrous Na$_2$SO$_4$ and concentrated. The crude residue was purified by column chromatography (Petroleum ether:Ethyl acetate=20:1 to 5:1) to afford tert-butyl N-(2,2-dimethyl-3-oxo-propyl)carbamate (130.00 mg). $^1$H NMR (400 MHz, CHLOROFORM-d) δ=9.44 (d, J=4.9 Hz, 1H), 3.23 (br. s., 2H), 1.42 (br. s., 9H), 1.08 (d, J=4.4 Hz, 6H)

Step 3: tert-butyl (2,2-dimethyl-3-(((trans)-2-((E)-1-phenylbut-1-en-2-yl)cyclopropyl)amino)propyl)carbamate ((trans)-2-(E)-1-phenylbut-1-en-2-yl)cyclopropan-1-amine hydrochloride (144.52 mg, 645.93 umol, 1.00 eq) was added to of saturated aqueous NaHCO$_3$, and the mixture was extracted with DCM (2 mL*2). The combined organic layers were dried over anhydrous Na$_2$SO$_4$ and concentrated. To the freebased cyclopropylamine was added tert-butyl N-(2,2-dimethyl-3-oxo-propyl)carbamate (130.00 mg, 645.93 umol, 1.00 eq), DCE (1.00 mL), and acetic acid (116.36 mg, 1.94 mmol, 110.82 uL, 3.00 eq). The mixture was stirred at 0° C. for 2 h before addition of NaBH$_3$CN (121.77 mg, 1.94 mmol, 3.00 eq) and stirring at 0° C. for 1 hour. The reaction mixture was quenched by addition H$_2$O (5 mL) and extracted with DCM (15 mL*3). The combined organic layers were dried over anhydrous Na$_2$SO$_4$ and concentrated under reduced pressure to afford crude tert-butyl (2,2-dimethyl-3-(((trans)-2-((E)-1-phenylbut-1-en-2-yl)cyclopropyl)amino)propyl)carbamate (230.00 mg). LCMS (M+H) m/z: 373.

Step 4: 2,2-dimethyl-N1-((trans)-2-((E)-1-phenylbut-1-en-2-yl)cyclopropyl)propane-1,3-diamine Dihydrochloride (Racemic)

To a solution of tert-butyl (2,2-dimethyl-3-(((trans)-2-(E)-1-phenylbut-1-en-2-yl)cyclopropyl)amino)propyl)carbamate (230.00 mg, 617.38 umol, 1.00 eq) in MeOH (4.00 mL) was added HCl (617.38 umol, 2.00 mL, 1.00 eq). The mixture was stirred at 25° C. for 2 h. The reaction mixture was concentrated and the crude residue was purified by prep-HPLC (HCl condition) to afford 2,2-dimethyl-N1-((trans)-2-((E)-1-phenylbut-1-en-2-yl)cyclopropyl)propane-1,3-diamine dihydrochloride (14.50 mg). LCMS (M+H$^+$) m/z: 273. $^1$H NMR (400 MHz, METHANOL-d$_4$) δ=7.33-7.28 (m, 2H), 7.24-7.16 (m, 3H), 6.32 (s, 1H), 3.28 (d, J=3.5 Hz, 1H), 3.06 (s, 2H), 3.03-2.99 (m, 1H), 2.48-2.22 (m, 4H), 1.52-1.45 (m, 1H), 1.26-1.16 (m, 9H), 1.10 (br. s., 1H).

(trans)-2-((E)-1-phenylbut-1-en-2-yl)cyclopropan-1-amine Hydrochloride (Racemic)

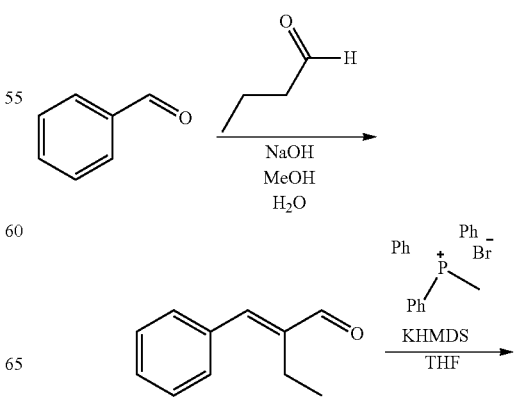

217

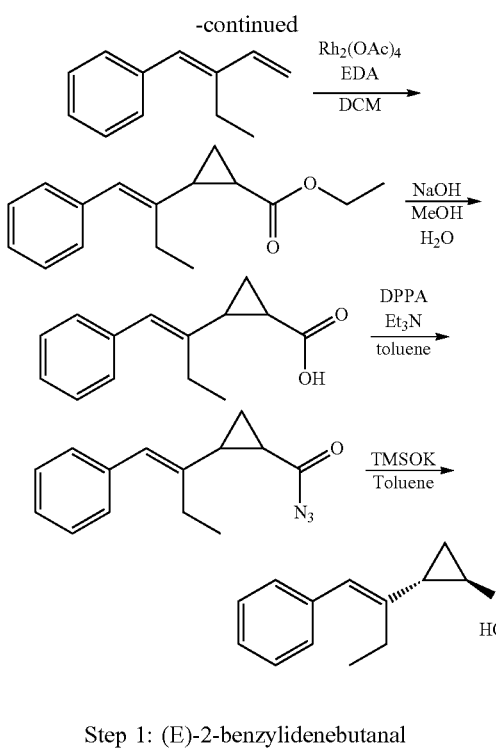

Step 1: (E)-2-benzylidenebutanal

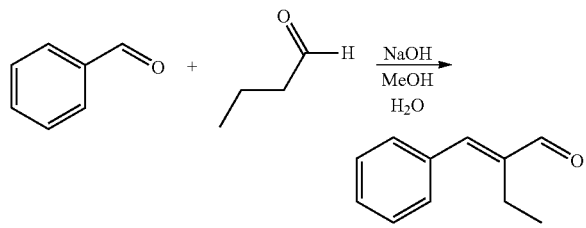

To the solution of benzaldehyde (50.00 g, 471.16 mmol) in MeOH (500.00 mL) was added a solution of NaOH (18.85 g, 471.16 mmol) in H$_2$O (180.00 mL) at 20° C. The solution was stirred at 20° C. for 15 min. To the solution was added butanal (50.96 g) dropwise at 0° C. The solution was stirred at 20° C. for 2 h before the solvent was removed and the residue was acidified by HCl (aq. 4N) to pH=5. The mixture was extracted with EtOAc (500 mL*3). The organic layers were combined, dried with Na$_2$SO$_4$, filtered and concentrated. The crude residue was purified by silica gel chromatography (Petroleum ether: Ethyl acetate=150: 1-60:1) to afford (E)-2-benzylidenebutanal (67.00 g, 418.20 mmol) in 88.8% yield as a yellow oil. LCMS (M+H$^+$) 161.

Step 2: (E)-(2-ethylbuta-1,3-dien-1-yl)benzene

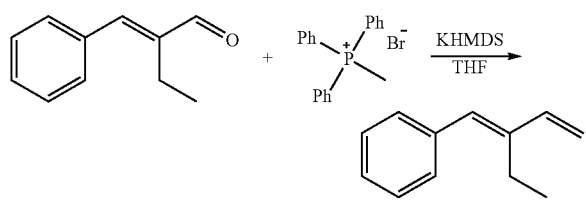

218

To the mixture of methyltriphenylphosphonium bromide (298.78 g, 836.40 mmol) in THF (500.00 mL) was added KHMDS (1 M, 878.22 mL) dropwise at 0° C. The mixture was stirred for 2 h at 20° C. To the mixture was added (E)-2-benzylidenebutanal (67.00 g, 418.20 mmol) dropwise at 10° C. The mixture was stirred at 20° C. for 2 h. To the mixture was added aqueous NH$_4$Cl (400 mL) at 0° C. The mixture was concentrated and the remaining aqueous layer was extracted with EtOAc (300 mL*2). The organic phases were combined, dried with Na$_2$SO$_4$, filtered and concentrated. The crude residue was purified by silica gel column chromatography (petroleum ether) to afford (E)-(2-ethylbuta-1,3-dien-1-yl)benzene (84.00 g) as a light yellow oil.

Step 3: ethyl (E)-2-(1-phenylbut-1-en-2-yl)cyclopropane-1-carboxylate

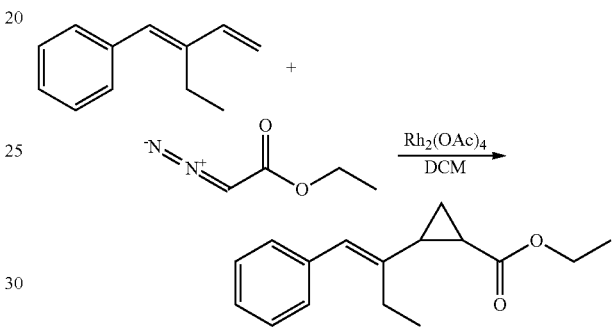

To the mixture of (E)-(2-ethylbuta-1,3-dien-1-yl)benzene (25.00 g, 157.99 mmol) and Rh$_2$(OAc)$_4$ (698.30 mg, 1.58 mmol) in DCM (200.00 mL) was added ethyl 2-diazoacetate (54.08 g, 473.97 mmol) dropwise at 25° C. The mixture was stirred for 16 h at 25° C. The mixture was washed with water (50 mL) and the organic phase was dried with Na$_2$SO$_4$ and concentrated. The crude residue was purified by silica gel column chromatography (petroleum ether to petroleum ether:ethyl acetate=200:1) to afford ethyl (E)-2-(1-phenylbut-1-en-2-yl)cyclopropane-1-carboxylate (30.00 g, 122.78 mmol, 77.71% yield) as a yellow oil. LCMS (M+H$^+$) m/z: 245.

Step 4: (E)-2-(1-phenylbut-1-en-2-yl)cyclopropane-1-carboxylic acid

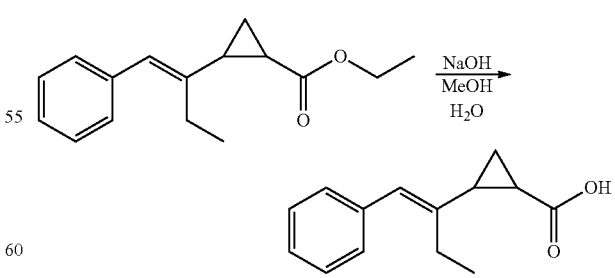

To the solution of ethyl (E)-2-(1-phenylbut-1-en-2-yl)cyclopropane-1-carboxylate (40.00 g, 163.71 mmol) in MeOH (160.00 mL) and H$_2$O (35.00 mL) was added NaOH (22 g, 550.0 mmol) at 25° C. The mixture was stirred at 60° C. for 3 h before the reaction was cooled to room temperature and the mixture was concentrated. The residue was suspended in water (100 mL) and the mixture was washed with a mixture of petroleum ether and EtOAc (10:1, 100 mL). The aqueous phase was acidified to pH=4 with aqueous HCl (4 N) and extracted with EtOAc (200 mL*3). The organic phases were combined, dried with $Na_2SO_4$, filtered and concentrated to afford crude (E)-2-(1-phenylbut-1-en-2-yl)cyclopropane-1-carboxylic acid (22.00 g) a yellow oil. Multiple batches were processed at the same time.

Step 5: (E)-2-(1-phenylbut-1-en-2-yl)cyclopropane-1-carbonyl azide

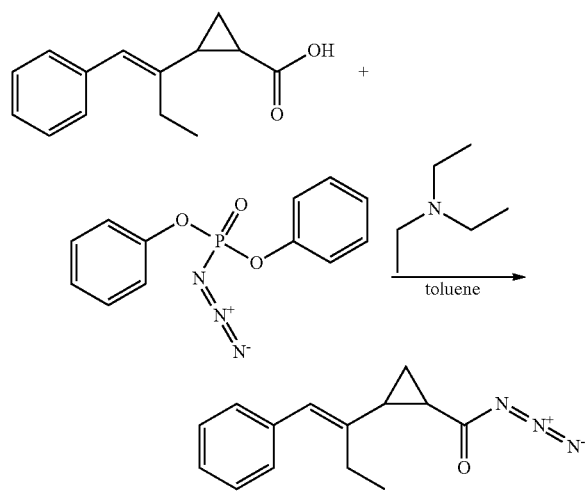

To a solution of (E)-2-(1-phenylbut-1-en-2-yl)cyclopropane-1-carboxylic acid (34.00 g, 157.20 mmol), triethylamine (47.72 g, 471.61 mmol, 65.37 mL), and toluene (250.00 mL) was added DPPA (51.91 g, 188.64 mmol, 40.88 mL). The solution was stirred for 16 h at 25° C. before the solution was concentrated. The crude residue was purified by silica gel column chromatography (PE to PE:EA=400:1) to afford (E)-2-(1-phenylbut-1-en-2-yl)cyclopropane-1-carbonyl azide (16 g) as a yellow oil. Multiple batches were processed at the same time.

Step 6: (trans)-2-((E)-1-phenylbut-1-en-2-yl)cyclopropan-1-amine hydrochloride (racemic)

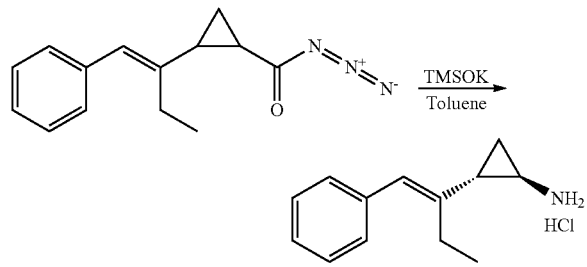

A solution of (E)-2-(1-phenylbut-1-en-2-yl)cyclopropane-1-carbonyl azide (33.00 g, 136.76 mmol) in toluene (240.00 mL) was stirred at 110° C. for 3 h. The reaction was cooled to room temperature before addition of TMSOK (20.00 g, 155.90 mmol). The mixture was stirred for 16 h at 25° C. before the reaction was diluted with water (250 mL). The mixture was stirred for 1 h at 25° C. and the mixture was extracted with ethyl acetate (300 mL*4). The organic phases were combined, dried with $Na_2SO_4$, filtered and concentrated. The crude residue was suspended in water (200 mL) and acidified to pH=4 with aqueous HCl (4 N). The aqueous solution was washed with petroleum ether and EtOAc (1:1, 200 mL*3). The aqueous phase was basified to pH=9 with aqueous $NaHCO_3$ and the mixture was extracted with dichloromethane (300 mL*4). The dichloromethane extracts were combined, dried with $Na_2SO_4$, filtered, and concentrated. The residue was dissolved in MeOH and treated with HCl (4N) before being concentrated to afford (trans)-2-(E)-1-phenylbut-1-en-2-yl)cyclopropan-1-amine hydrochloride (13.70 g, 59.88 mmol, 43.79% yield, 97.8% purity) as a yellow solid. LCMS (M+H$^+$) m/z: 188. $^1$HNMR (400 MHz, METHANOL-d$_4$) 7.33-7.29 (m, 2H), 7.22-7.18 (m, 3H), 6.25 (s, 1H), 2.74-2.70 (m, 1H), 2.37-2.32 (m, 2H), 1.99-1.93 (m, 1H), 1.24-1.17 (m, 5H).

tert-butyl ((1R,2S or 1S,2R)-2-((E)-1-phenylbut-1-en-2-yl)cyclopropyl)carbamate (Enantiomer A) and tert-butyl ((1R,2S or 1S,2R)-2-((E)-1-phenylbut-1-en-2-yl)cyclopropyl)carbamate (Enantiomer B)

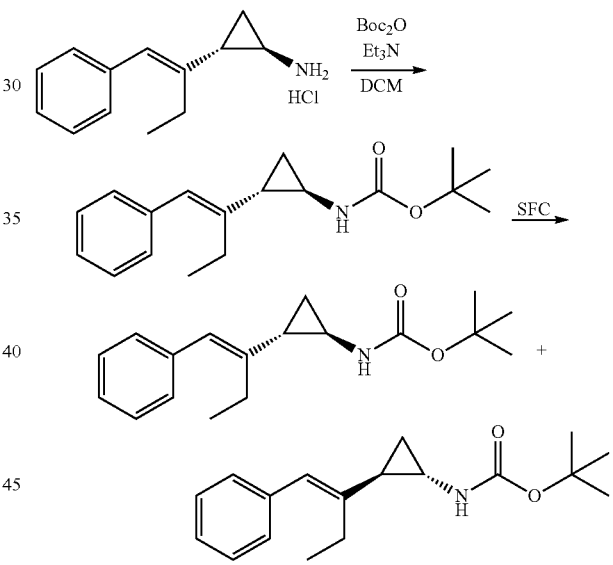

Step 1: tert-butyl ((trans)-2-((E)-1-phenylbut-1-en-2-yl)cyclopropyl)carbamate

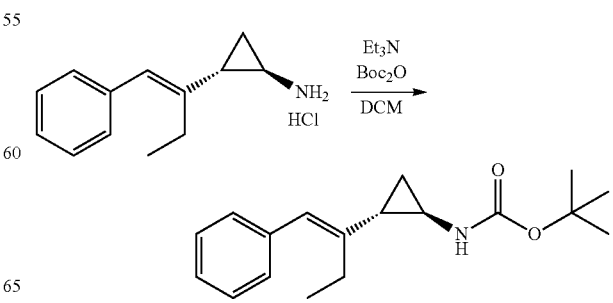

221

To a solution of (trans)-2-((E)-1-phenylbut-1-en-2-yl)cyclopropan-1-amine hydrochloride (21.00 g, 93.86 mmol) in DCM (250.00 mL) were added triethylamine (39.03 mL, 281.58 mmol) and Boc anhydride (26.63 g, 122.02 mmol, 28.03 mL) at 0° C. The mixture was warmed to room temperature and stirred for 3 h. The mixture was diluted with water (200 mL) and the mixture was extracted with DCM (200 mL*2). The combined organic layer was dried with $Na_2SO_4$, filtered, and concentrated. The crude residue was purified by column chromatography (EA/PE=0:1-1:10) to afford tert-butyl ((trans)-2-((E)-1-phenylbut-1-en-2-yl)cyclopropyl)carbamate (25.00 g, 85.86 mmol, 91.47% yield, 98.7% purity) as yellow oil. $^1$H NMR (400 MHz, CHLOROFORM-d) δ=7.33-7.26 (m, 2H), 7.21-7.13 (m, 3H), 6.13 (s, 1H), 4.76 (br. s., 1H), 2.68-2.58 (m, 1H), 2.43-2.23 (m, 2H), 1.63-1.54 (m, 1H), 1.46 (s, 9H), 1.16 (t, J=7.5 Hz, 3H), 1.11-1.02 (m, 1H), 0.95-0.84 (m, 1H). LCMS 188 (M-Boc+H).

Step 2: tert-butyl ((1R,2S or 1S,2R)-2-((E)-1-phenylbut-1-en-2-yl)cyclopropyl)carbamate (Enantiomer A) and tert-butyl ((1R,2S or 1S,2R)-2-((E)-1-phenylbut-1-en-2-yl)cyclopropyl)carbamate (Enantiomer B)

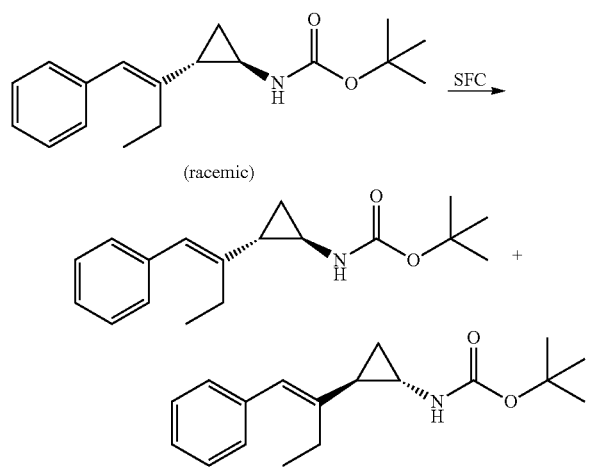

tert-butyl ((trans)-2-(E)-1-phenylbut-1-en-2-yl)cyclopropyl)carbamate (52 g) was separated by SFC (conditions: Column: AD (250 mm*50 mm,l0 um), Condition:Base-MeOH, FlowRate: 200 ml/min) to afford both enantiomers. tert-butyl ((1R,2S or 1S,2R)-2-((E)-1-phenylbut-1-en-2-yl) cyclopropyl)carbamate (enantiomer A) (25.00 g, 81.77 mmol, 45.19% yield, 94% purity) (99% ee) LCMS (M+H$^+$-Boc) m/z: 188. $^1$H NMR (400 MHz, METHANOL-d$_4$) δ=7.31-7.21 (m, 2H), 7.14 (d, J=7.5 Hz, 3H) 6.17-6.08 (m, 1H), 2.57-2.46 (m, 1H), 2.40-2.20 (m, 2H), 1.55-1.50 (m, 1H), 1.43 (s, 9H), 1.14 (s, 3H), 1.05-0.97 (m, 1H), 0.89-0.82 (m, 1H).

tert-butyl ((1R,2S or 1S,2R)-2-((E)-1-phenylbut-1-en-2-yl)cyclopropyl)carbamate (enantiomer B) (23.00 g, 79.23 mmol, 43.79% yield, 99% purity) (99% ee). LCMS (M+H$^+$-Boc) m/z:188. $^1$H NMR (400 MHz, METHANOL-d$_4$) δ=7.32-7.21 (m, 2H), 7.15 (d, J=7.5 Hz, 3H), 6.12 (br. s., 1H), 2.65-2.48 (m, 1H), 0.90-0.82 (m, 1H), 1.05-0.97 (m, 1H), 1.14 (t, J=7.5 Hz, 3H), 1.44 (s, 9H), 1.05-0.97 (m, 1H), 0.90-0.82 (m, 1H).

222

Compound 218: 4-((((trans)-4-(((trans)-2-((E)-1-phenylbut-1-en-2-yl)cyclopropyl)amino)cyclohexyl)amino)methyl)benzoic Acid Dihydrochloride (Racemic)

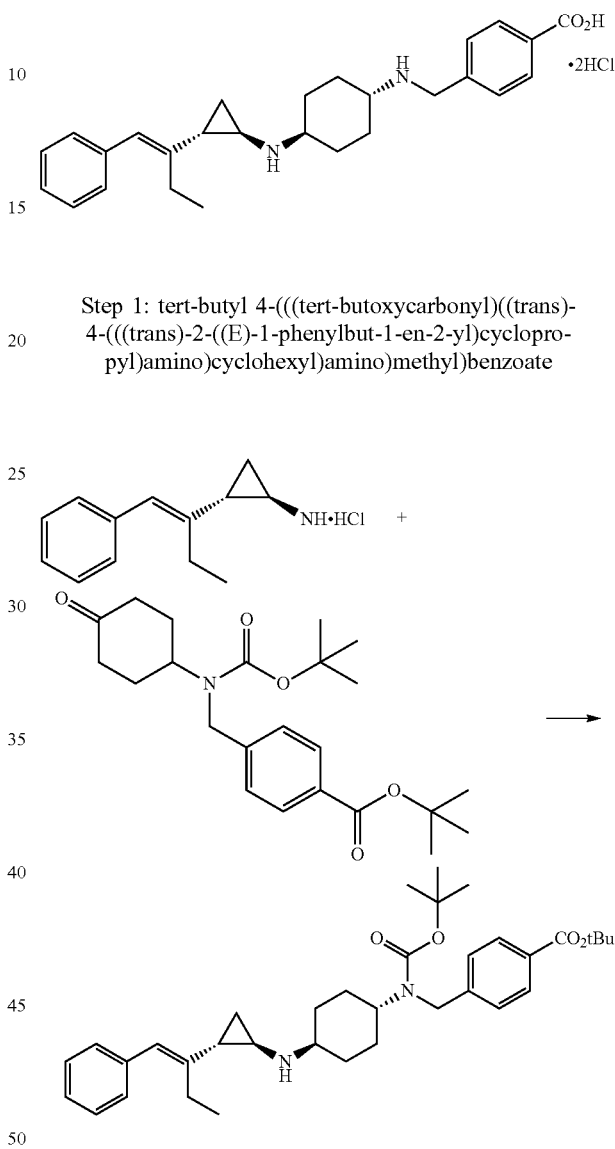

Step 1: tert-butyl 4-(((tert-butoxycarbonyl)((trans)-4-(((trans)-2-((E)-1-phenylbut-1-en-2-yl)cyclopropyl)amino)cyclohexyl)amino)methyl)benzoate To (trans)-2-((E)-1-phenylbut-1-en-2-yl)cyclopropanamine hydrochloride (668 mg, 2.99 mmol) and tert-butyl 4-(((tert-butoxycarbonyl)(4-oxocyclohexyl)amino)methyl) benzoate (1.19 g, 2.94 mmol) in DCE (15 mL) was added sodium triacetoxyborohydride (1.24 g, 5.88 mmol). After 30 min, potassium carbonate (1M aq.) was added followed by DCM. The organic phase was isolated, evaporated and the crude residue purified by silica gel column chromatography (120 g column, 50:50 EtOAc:Hex to 100:0 over 7 column volumes) to afford two sets of fractions containing isomeric compounds. The last eluting fractions were pooled and evaporated under reduced pressure to afford tert-butyl 4-(((tert-butoxycarbonyl)((trans)-4-(((trans)-2-((E)-1-phenylbut-1-en-2-yl)cyclopropyl)amino)cyclohexyl)amino) methyl)benzoate (551 mg, 958 μmol) in 33% yield. LCMS (ESI+): 519.3 (M-tBu+H), 575.4 (M+H, weak)

Step 2: 4-((((trans)-4-(((trans)-2-(E)-1-phenylbut-1-en-2-yl)cyclopropyl)amino)cyclohexyl)amino)methyl)benzoic Acid Dihydrochloride (Racemic)

Step 1: tert-butyl 2,2-dimethyl-3-(((trans)-4-(((trans)-2-((E)-1-phenylbut-1-en-2-yl)cyclopropyl)amino)cyclohexyl)amino)propanoate dihydrochloride

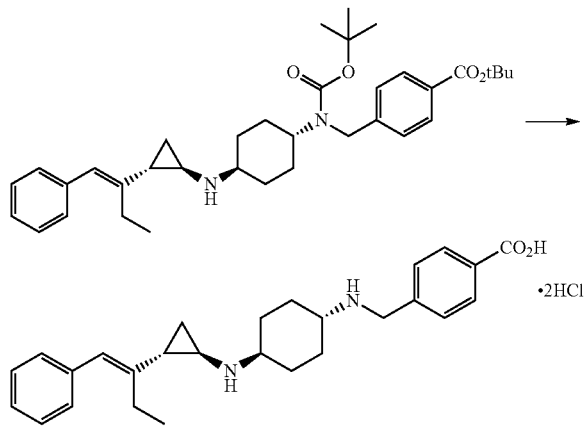

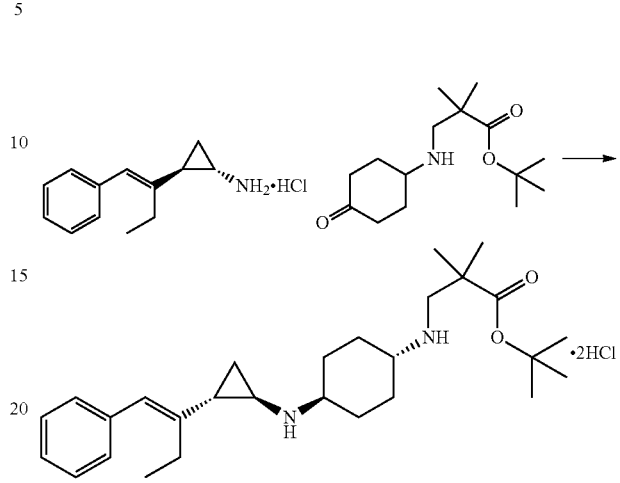

tert-butyl 4-(((tert-butoxycarbonyl)((trans)-4-(((trans)-2-((E)-1-phenylbut-1-en-2-yl)cyclopropyl)amino)cyclohexyl)amino)methyl)benzoate (551 mg, 958 μmol) (second eluting fractions set from the previous step) was dissolved in dioxane (10 ml) and HCl in water (6M aq., 5 mL, 30 mmol) was added. The reaction mixture was heated at 50° C. for 24 hours. The solvent volume was reduced by 70% under reduced pressure. The mixture was diluted with MTBE (50 mL) and filtered on a Fine fritted funnel under suction. The solid was collected and suspended in 2:1 ACN:water. The mixture was frozen and lyophilized to afford 4-((((trans)-4-(((trans)-2-((E)-1-phenylbut-1-en-2-yl)cyclopropyl)amino)cyclohexyl)amino)methyebenzoic acid dihydrochloride (425 mg, 864 μmol) in 90% yield. $^1$H NMR (400 MHz, DMSO-d6) δ 12.88-13.26 (m, 1H), 9.28-9.69 (m, 4H), 7.97 (d, J=8.30 Hz, 2H), 7.70 (d, J=8.30 Hz, 2H), 7.29-7.38 (m, 2H), 7.14-7.24 (m, 3H), 6.21 (s, 1H), 4.23 (br. s., 2H), 3.11-3.22 (m, 1H), 2.98-3.07 (m, 1H), 2.77-2.86 (m, 1H), 2.25 (m, 6H), 2.09-2.18 (m, 1H), 1.44-1.63 (m, 4H), 1.32-1.40 (m, 1H), 1.14-1.17 (m, 1H), 1.12 (t, J=7.57 Hz, 3H). LCMS (ESI+): 419.3 (M+H)

To (trans)-2-((E)-1-phenylbut-1-en-2-yl)cyclopropanamine hydrochloride (391 mg, 1.75 mmol) and tert-butyl 2,2-dimethyl-3-((4-oxocyclohexyl)amino)propanoate (472 mg, 1.75 mmol) in 1,2-methanol (7 mL) was added AcOH (1 mL) and Sodium cyanoborohydride (230 mg, 3.67 mmol). After 30 mins, potassium carbonate (aq.) was added. The reaction mixture was stirred for 15 minutes and extracted with DCM (2×50 mL). The organic phase was evaporated under reduced pressure. The crude residue was purified by silica gel column chromatography (1:10:90 anunonia (30% aqueous):methanol:DCM mixture in DCM (0% to 50%), 40 g column) to afford two sets of fractions containing isomeric products. The last fractions were collected and evaporated under reduced pressure. The solid was dissolved in MTBE and Hydrogen chloride (2M in Et$_2$O, 2 mL, 4 mmol) was added. The volatiles were evaporated and the solid was triturated with a 1:2 iPrOH:MTBE mixture to afford tert-butyl 2,2-dimethyl-3-(((trans)-4-(((trans)-2-((E)-1-phenylbut-1-en-2-yl)cyclopropyl)amino)cyclohexyl)amino)propanoate dihydrochloride (355 mg, 691 μmol) in 39% yield. LCMS (ESI+): 441.3 (M+H).

Compound 219: 2,2-dimethyl-3-(((trans)-4-(((trans)-2-((E)-1-phenylbut-1-en-2-yl)cyclopropyl)amino)cyclohexyl)amino)propanoic Acid Dihydrochloride (Racemic)

Step 2: 2,2-dimethyl-3-(((trans)-4-(((trans)-2-((E)-1-phenylbut-1-en-2-yl)cyclopropyl)amino)cyclohexyl)amino)propanoic Acid Dihydrochloride (Racemic)

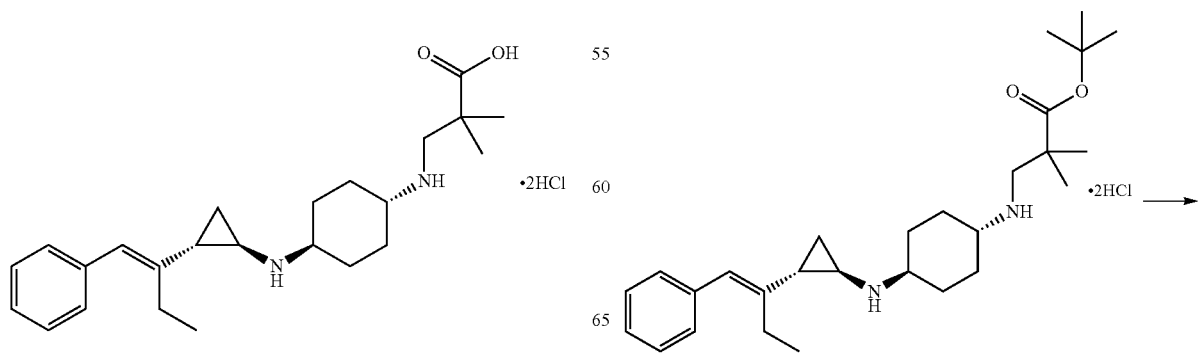

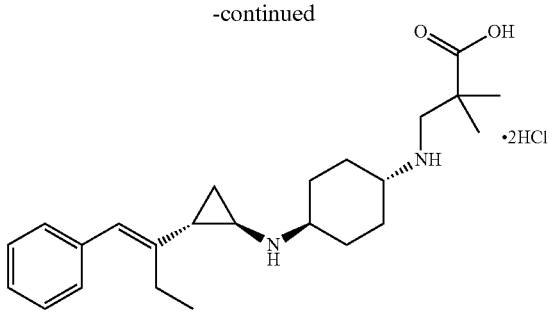

tert-butyl 2,2-dimethyl-3-(((trans)-4-(((trans)-2-((E)-1-phenylbut-1-en-2-yl)cyclopropyl)amino)cyclohexyl)amino)propanoate dihydrochloride was dissolved in dioxane (6 mL) and 1.2 mL of 6M HCl (aq.) was added. The reaction mixture was heated at 45° C. for 16 hours. Water was added until most of the material was solubilized, up to a volume of 15 mL total, and the mixture was filtered on a 0.45 micron PTFE acrodisc filter. The solution was frozen to −78° C. and lyophilized to afford 2,2-dimethyl-3-(((trans)-4-(((trans)-2-((E)-1-phenylbut-1-en-2-yl)cyclopropyl)amino)cyclohexyl)amino)propanoic acid dihydrochloride (420 mg, 918 µmol) in 94% yield. $^1$H NMR (400 MHz, DMSO-d6) δ 12.74-13.02 (m, 1H), 9.43-9.68 (m, 2H), 8.56 (br. s., 2H), 7.31-7.39 (m, 2H), 7.16-7.26 (m, 3H), 6.21 (s, 1H), 2.93-3.20 (m, 4H), 2.82 (br. s., 1H), 2.06-2.36 (m, 7H), 1.44-1.60 (m, 4H), 1.34-1.41 (m, 1H), 1.23 (s, 6H), 1.15-1.19 (m, 1H), 1.13 (t, J=7.45 Hz, 3H). LCMS (ESI+): 385.3 (M+H).

Using the appropriate starting material and modifications the following examples were synthesized using the synthetic procedures described for 2,2-dimethyl-3-(((trans)-4-(((trans)-2-((E)-1-phenylbut-1-en-2-yl)cyclopropyl)amino)cyclohexyl)amino)propanoic acid dihydrochloride.

| Structure/Name | Stereochemical Comment | LCMS m/z; $^1$H NMR |
|---|---|---|
| 1-((((trans)-4-(((trans)-2-((E)-1-phenylbut-1-en-2-yl)cyclopropyl)amino)cyclohexyl)amino)methyl)cyclobutane-1-carboxylic acid dihydrochloride (Compound 282) | racemic | 397 |

Compound 220: 2,2-dimethyl-3-(((trans)-4-(((1R,2S or 1S,2R)-2-((E)-1-phenylbut-1-en-2-yl)cyclopropyl)amino)cyclohexyl)amino)propanoic Acid Dihydrochloride (Single Stereoisomer)

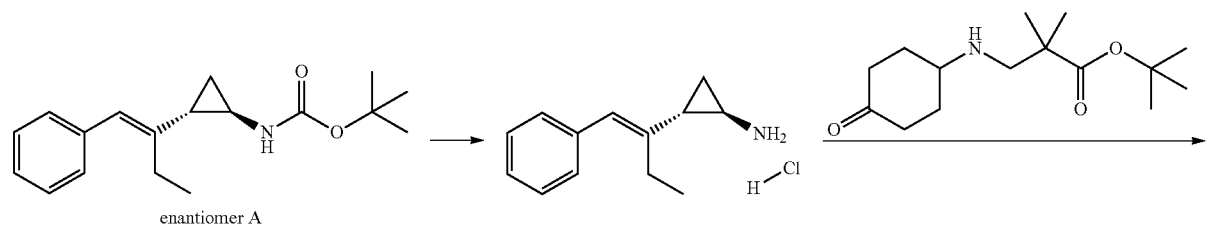

enantiomer A

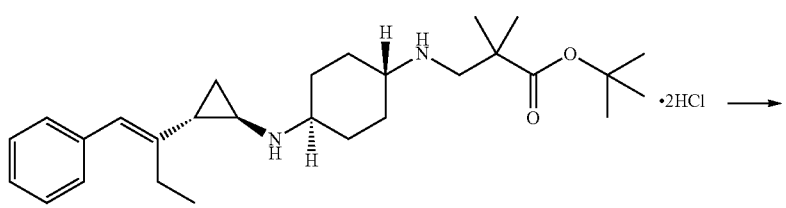

-continued

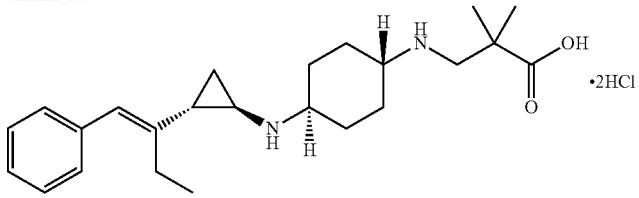

Step 1: (1R,2S or 1S,2R)-2-(E)-1-phenylbut-1-en-2-yl)cyclopropan-1-amine Hydrochloride (Single Stereoisomer)

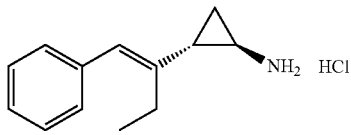

tert-butyl ((1R,2S or 1S,2R)-2-(E)-1-phenylbut-1-en-2-yl)cyclopropyl)carbamate (enantiomer A) (1.65 g, 5.74 mmol) was dissolved in DCM (30 mL) and 2,6-lutidine (1.74 mL, 14.92 mmol) was added. The mixture was cooled to 0° C. and trimethylsilyl trifluoromethanesulfonate (2.6 mL, 14.35 mmol) was added dropwise. The resulting mixture was stirred at 0° C. for 1 hour and then warmed up to RT and stirred overnight. It was diluted with water (30 mL) and the layers were thoroughly mixed and separated. The aqueous layer was extracted with DCM (2×15 mL) and the combined organic extracts were washed with brine (1×30 mL), dried with anhydrous $Na_2SO_4$, filtered, and evaporated under reduced pressure. The product was further dried under high vacuum overnight and the oil was re-dissolved in MTBE (10 mL), cooled to 0° C., and HCl (2M in diethyl ether, 5.74 mL, 11.5 mmol) was added. The solvents were removed under reduced pressure and the solid was triturated with MTBE, and used as is after drying overnight under high vac. The same reaction was repeated with 33.28 g of the Boc-protected starting material. A total of 27 g of (1R,2S or 1S,2R)-2-((E)-1-phenylbut-1-en-2-yl)cyclopropan-1-amine hydrochloride containing small amount of 2,6-lutidine—HCl salt was obtained. The desired amine-HCl salt was 80 wt % and was used for the next step without further purification.

Step 2: tert-butyl 2,2-dimethyl-3-(((trans)-4-(((1R, 2S or 1S,2R)-2-((E)-1-phenylbut-1-en-2-yl)cyclopropyl)amino)cyclohexyl)amino)propanoate Dihydrochloride (Single Stereoisomer)

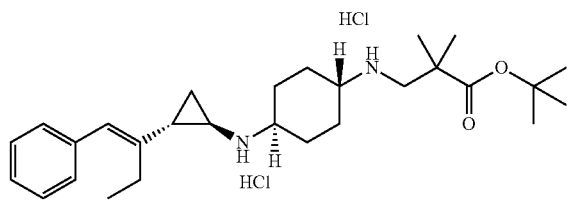 [SMILES: Cl ; CC/C(=C\c1ccccc1)[C@@H]1C[C@H]1N[C@H]1CC[C@H](NCC(C)(C)C(=O)OC(C)(C)C)CC1 ; Cl]

(1R,2S or 1S,2R)-2-((E)-1-phenylbut-1-en-2-yl)cyclopropan-1-amine hydrochloride (11 g, 80 wt %, 39.35 mmol) and tert-butyl 2,2-dimethyl-3-((4-oxocyclohexyl)amino)propanoate (10.6 g, 39.35 mmol) were dissolved in a solvent mixture of methanol (160 mL) and acetic acid (22 mL) and the mixture was cooled to 0° C. Sodium cyanoborohydride (5.2 g, 82.63 mmol) was then added and the cooling bath was removed and the reaction mixture was stirred at room temperature for 30 min. Aqueous potassium carbonate (600 mL, 1M) was added and the mixture was stirred for 15 min. The product was extracted with DCM (1×500 mL, 1×150 mL) and the combined organic extracts were dried over anhydrous sodium sulfate and concentrated under reduced pressure. The crude product was dissolved in MTBE (500 mL) and treated with hydrogen chloride (2.0 M in ether, 100 mL, 5.0 eq) at 0° C. The solvents were removed under reduced pressure and the solid was suspended in acetonitrile (200 ml). It was sonicated for 20 min and then filtered through a nylon membrane (0.45 um, 47 mm diameter) overnight. This process was repeated twice and the solid was collected and dried under high vacuum overnight to afford tert-butyl 2,2-dimethyl-3-(((trans)-4-(((1R,2S or 1S,2R)-2-((E)-1-phenylbut-1-en-2-yl)cyclopropyl)amino)cyclohexyl)amino)propanoate dihydrochloride (9.1 g). $^1$H NMR (400 MHz, DMSO-$d_6$) δ (ppm) 9.63-9.71 (m, 2H), 8.73 (br. s, 2H), 7.33-7.36 (m, 2H), 7.20-7.24 (m, 3H), 6.21 (s, 1H), 2.99-3.14 (m, 4H), 2.79-2.84 (m, 1H), 2.17-2.30 (m, 7H), 1.52-1.63 (m, 4H), 1.43 (s, 9H), 1.37-1.41 (m, 1H), 1.22 (s, 6H), 1.10-1.17 (m, 1H), 1.13 (t, J=7.7 Hz, 3H); LC/MS, 441.2 [M+H]$^+$.

Step 3: 2,2-dimethyl-3-(((trans)-4-(((1R,2S or 1S,2R)-2-((E)-1-phenylbut-1-en-2-yl)cyclopropyl)amino)cyclohexyl)amino)propanoic Acid Dihydrochloride (Single Stereoisomer)

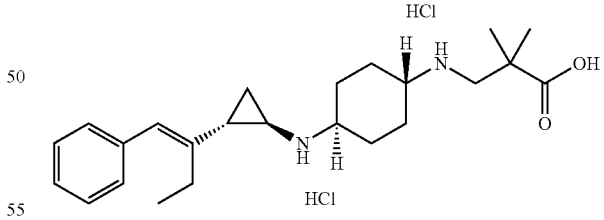

tert-butyl 2,2-dimethyl-3-(((trans)-4-(((1R,2S or 1S,2R)-2-((E)-1-phenylbut-1-en-2-yl)cyclopropyl)amino)cyclohexyl)amino)propanoate dihydrochloride (9.0 g, 17.52 mmol) was taken up in 1,4-dioxane (108 mL) and 6 M aqueous HCl (22 ml, 132 mmol) was added. The mixture was heated to 45° C. and stirred at this temperature for 9 h. The reaction mixture was cooled to room temperature and diluted with water to a volume of 270 mL. The solution was frozen and lyophilized to afford 2,2-dimethyl-3-(((trans)-4-(((1R,2S or 1S,2R)-2-((E)-1-phenylbut-1-en-2-yl)cyclopropyl)amino)cyclohexyl)amino)propanoic acid dihydrochloride (derived from enantiomer A) (8.0 g). ¹H NMR (400 MHz, DMSO-d₆) δ (ppm) 12.87 (br. s, 1H), 9.71 (m, 2H), 8.67 (br. s, 2H), 7.34-7.36 (m, 2H), 7.20-7.24 (m, 3H), 6.21 (s, 1H), 2.99-3.14 (m, 4H), 2.80 (bs, 1H), 2.20-2.28 (m, 7H), 1.52-1.60 (m, 4H), 1.37-1.43 (m, 1H), 1.23 (s, 6H), 1.11-1.17 (m, 1H), 1.13 (t, 3H, J=7.5 Hz); LC/MS, 385.2 [M+H]⁺.

Compound 221: 2,2-dimethyl-3-(((trans)-4-(((1R,2S or 1S,2R)-2-((E)-1-phenylbut-1-en-2-yl)cyclopropyl)amino)cyclohexyl)amino)propanoic Acid (Single Stereoisomer)

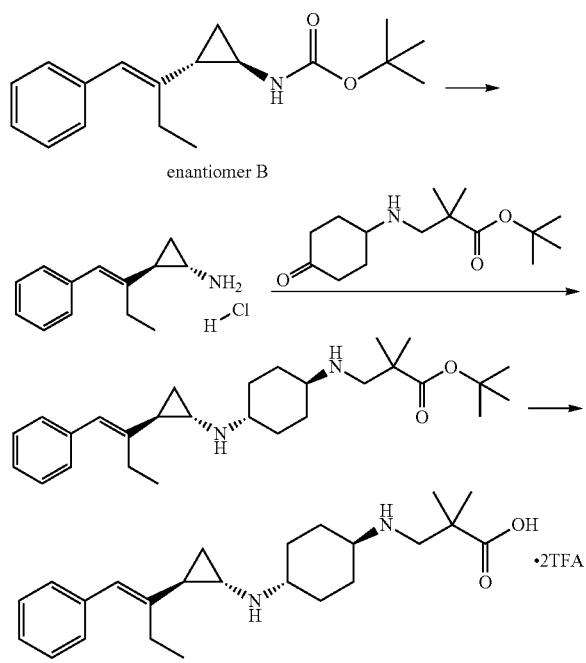

Step 1: (1S,2R)-2-((E)-1-phenylbut-1-en-2-yl)cyclopropanamine hydrochloride (single stereoisomer)

tert-butyl ((1R,2S or 1S,2R)-2-((E)-1-phenylbut-1-en-2-yl)cyclopropyl)carbamate (enantiomer B) (155 mg, 539 µmol) was dissolved in DCM (5 mL) and 2,6-lutidine (0.17 mL, 1.45 mmol) was added. The mixture was cooled to 0° C. and trimethylsilyl trifluoromethanesulfonate (0.24 mL, 1.34 mmol) was added dropwise. The resulting mixture was stirred at 0° C. for 1 hour and then warmed up to 25° C. and stirred overnight. The reaction mixture was diluted with water (30 mL) and the layers were thoroughly mixed and separated. The aqueous layer was extracted with DCM (2×15 mL) and the combined organic extracts were washed with brine (1×30 mL), dried with anhydrous Na₂SO₄, filtered, and evaporated under reduced pressure. The product was further dried under high vacuum overnight and the oil was re-dissolved in MTBE (5 mL), cooled to 0° C., and hydrogen chloride (2M in diethyl ether, 0.65 mL, 1.3 mmol) was added. The solvents were removed under reduced pressure and the solid was triturated with MTBE, and used as is after drying overnight under high vacuum to afford (1R,2S or 1S,2R)-2-(E)-1-phenylbut-1-en-2-yl)cyclopropanamine hydrochloride (66 mg, 0.29 mmol) in 55% yield. LCMS (ESI+): 188.2 (M+H)

Step 2: tert-butyl 2,2-dimethyl-3-(((trans)-4-(((1R, 2S or 1S,2R)-2-((E)-1-phenylbut-1-en-2-yl)cyclopropyl)amino)cyclohexyl)amino)propanoate Dihydrochloride (Single Stereoisomer)

To (1R,2S or 1S,2R)-2-((E)-1-phenylbut-1-en-2-yl)cyclopropanamine hydrochloride (60 mg, 268 µmol) and (72.1 mg, 268 µmol) in 1,2-methanol (2 mL) was added AcOH (0.3 mL) and sodium cyanoborohydride (35.3 mg, 562 µmol). After 15 min, 1.0 M aqueous potassium carbonate (600 mL) was added and the mixture was stirred for 15 min. The product was extracted with DCM (2×50 mL) and the combined organic extracts were dried over anhydrous sodium sulfate and concentrated under reduced pressure. The crude residue was purified by silica gel column chromatography (1:10:90 ammonia (30% aqueous):methanol:DCM in DCM (0% to 50%), 40 g column) to afford two sets of fractions containing isomeric compounds. The last eluting fractions were collected and evaporated under reduced pressure. The residue was redissolved in MTBE and hydrogen chloride HCl (2M in Et₂O, 2 mL) was added. The volatiles were evaporated under reduced pressure and the solid was triturated with acetonitrile. This process was repeated twice and the solid was collected and dried under high vacuum overnight to give tert-butyl 2,2-dimethyl-3-(((trans)-4-(((1R,2S or 1S,2R)-2-((E)-1-phenylbut-1-en-2-yl)cyclopropyl)amino)cyclohexyl)amino)propanoate dihydrochloride (36.0 mg, 70.0 µmol). LCMS (ESI+): 441.2 (M+H).

Step 3: 2,2-dimethyl-3-(((trans)-4-(((1R,2S or 1S,2R)-2-((E)-1-phenylbut-1-en-2-yl)cyclopropyl)amino)cyclohexyl)amino)propanoic Acid bis(trifluoroacetic Acid) Salt (Single Stereoisomer)

tert-butyl 2,2-dimethyl-3-(((trans)-4-(((1R,2S or 1S,2R)-2-((E)-1-phenylbut-1-en-2-yl)cyclopropyl)amino)cyclohexyl)amino)propanoate dihydrochloride (36.0 mg, 70.0 µmol) was dissolved in dioxane (1 mL) and hydrochloric acid (6M aq., 250 µL, 1.5 mmol). The mixture was heated to 45° C. and stirred at this temperature for 9 h. The product was purified by preparative HPLC (SunFire C18 OBD 5 µM column, 5% to 50% Acetonitrile (with 0.1% trifluoroacetic acid) in water (with 0.1% trifluoroacetic acid) gradient over 9 minutes). The pure fractions were frozen and lyophilized to yield 2,2-dimethyl-3-(((trans)-4-(((1R,2S or 1S,2R)-2-(E)-1-phenylbut-1-en-2-yl)cyclopropyl)amino)cyclohexyl)amino)propanoic acid bis-trifluoroacetic acid salt (derived from enantiomer B) (30.0 mg, 48.9 µmol) in 70% yield. ¹H NMR (500 MHz, DMSO-d6) δ 12.80-13.12 (m, 1H), 8.85-9.23 (m, 2H), 8.34 (br. s., 2H), 7.31-7.37 (m, 2H), 7.17-7.25 (m, 3H), 6.21 (s, 1H), 3.14-3.24 (m, 1H), 2.95-3.10 (m, 3H), 2.82-2.89 (m, 1H), 2.11-2.30 (m, 6H), 1.96-2.02 (m, 1H), 1.36-1.51 (m, 4H), 1.23-1.28 (m, 1H), 1.21 (s, 6H), 1.15-1.19 (m, 1H), 1.11 (t, J=7.55 Hz, 3H). LC/MS, 385.2 (M+H).

Compound 223: Synthesis of 1-((((trans)-4-(((trans)-2-((E)-1-phenylbut-1-en-2-yl)cyclopropyl)amino)cyclohexyl)amino)methyl)cyclopropane-1-carboxylic Acid (Racemic)

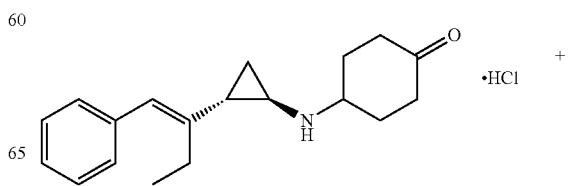

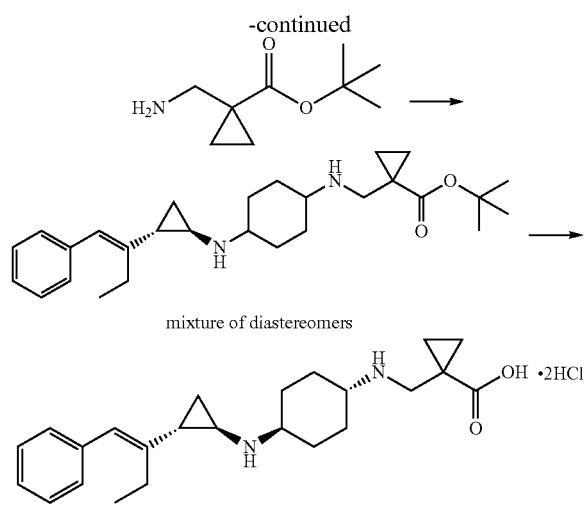

Step 1: tert-butyl 1-(((4-(((trans)-2-((E)-1-phenyl-but-1-en-2-yl)cyclopropyl)amino)cyclohexyl)amino)methyl)cyclopropane-1-carboxylate To 4-(((trans)-2-((E)-1-phenylbut-1-en-2-yl)cyclopropyeamino)cyclohexan-1-one hydrochloride (98 mg, 306 μmol) and tert-butyl 1-(aminomethyl)cyclopropanecarboxylate (54.9 mg, 321 μmol) in DCE (4 mL) was added sodium triacetoxyborohydride (185 mg, 0.87 mmol). After 30 min, added DCM and potassium carbonate (1M aqueous) were added. The organic phase was isolated, evaporated and the crude residue purified by column chromatography (silica, 0% to 10% methanol in EtOAc) to afford tert-butyl (E)-1-(((4-((2-(1-phenylbut-1-en-2-yl)cyclopropyl)amino)cyclohexyl)amino)methyl)cyclopropane-1-carboxylate (45.0 mg, 102 μmol) in 34% yield as a mixture of isomers. LCMS (ESI+): 439 (M+H)

Step 2: 1-((((trans)-4-(((trans)-2-((E)-1-phenylbut-1-en-2-yl)cyclopropyl)amino)cyclohexyl)amino)methyl)cyclopropane-1-carboxylic Acid Dihydrochloride (Racemic)

The isomeric mixture mixture of tert-butyl (E)-1-(((4-((2-(1-phenylbut-1-en-2-yl)cyclopropyl)amino)cyclohexyl)amino)methyl)cyclopropane-1-carboxylate (45 mg, 102 μmol) was dissolved in dioxane (500 μL) and 6M HCl (aq., 100 pL, 0.6 mmol) was added and the reaction mixture was heated overnight at 45° C. The reaction mixture was cooled down and MTBE (5 mL) was added to the reaction mixture. The resulting solid was filtered on fritted funnel, triturated with ACN:MTBE mixture (1:1) and filtered once more. The solid was collected redissolved in acetonitrile:water and frozen to afford a single diastereomer of 1-((((trans)-4-(((trans)-2-((E)-1-phenylbut-1-en-2-yl)cyclopropyl)amino)cyclohexyl)amino)methyl)cyclopropane-1-carboxylic acid dihydrochloride (14.0 mg, 30.7 μmol) in 30% yield. ¹H NMR (400 MHz, DMSO-d6) δ 12.75-12.95 (m, 1H), 9.08-9.43 (m, 2H), 8.44-8.77 (m, 2H), 7.26-7.45 (m, 2H), 7.13-7.25 (m, 3H), 6.20 (s, 1H), 2.76-3.17 (m, 6H), 2.12-2.28 (m, 6H), 2.01-2.07 (m, 1H), 1.36-1.51 (m, 4H), 1.26-1.33 (m, 1H), 1.18-1.23 (m, 2H), 1.14 (s, 2H), 1.12 (t, J=7.45 Hz, 3H). LCMS (ESI+): 383.3 (M+H).

Compound 224: 5-((((trans)-4-(((trans)-2-((E)-1-phenylbut-1-en-2-yl)cyclopropyl)amino)cyclohexyl)amino)methyl)picolinic acid (racemic)

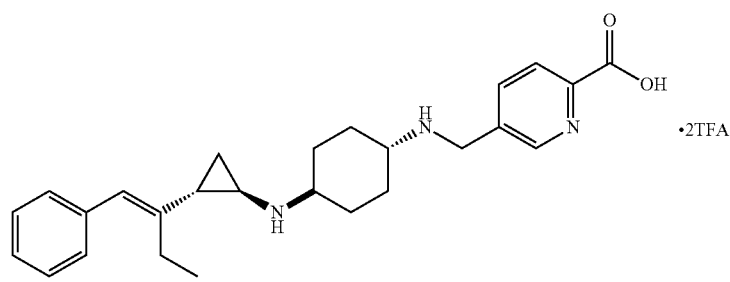

Step 1: tert-butyl 5-(((4-(((trans)-2-((E)-1-phenyl-but-1-en-2-yl)cyclopropyl)amino)cyclohexyl)amino)methyl)picolinate To 4-(((trans)-2-((E)-1-phenylbut-1-en-2-yl)cyclopropyl)amino)cyclohexanone hydrochloride (94 mg, 293 μmol) and tert-butyl 5-(aminomethyl)picolinate (73.0 mg, 351 μmol) in DCE (3 mL) was added sodium triacetoxyborohydride (136 mg, 0.64 mmol). After 30 min, DCM and potassium carbonate (1M aqueous) were added. The organic phase was isolated, evaporated and the crude residue purified by column chromatography (silica, 0% to 100% 1:10:90 ammonia (30% aqueous):methanol 0% to 10% methanol in EtOAc) to afford tert-butyl 5-(((4-(((trans)-2-((E)-1-phenylbut-1-en-2-yl)cyclopropyl)amino)cyclohexyl)amino)methyl)picolinate as a mixture of diastereomers (43.0 mg, 90.3 μmol) in 31% yield in the last eluting fractions. LCMS (ESI+): 476.3 (M+H)

Step 2: 5-((((trans)-4-(((trans)-2-((E)-1-phenylbut-1-en-2-yl)cyclopropyl)amino)cyclohexyl)amino)methyl)picolinic Acid (Racemic)

tert-butyl 5-(((4-(((trans)-2-((E)-1-phenylbut-1-en-2-yl)cyclopropyl)amino)cyclohexyl)amino)methyl)picolinate (mixture of isomers) (43 mg, 90.3 μmol) was dissolved in dioxane (500 μL) and hydrochloric acid (6M aq. 100 μL, 0.6 mmol) was added. The reaction mixture was heated for 15 hours at 45° C. The reaction mixture was concentrated under reduced pressure and the compound was purified by preparative HPLC (SunFire C18 OBD 5 μM column, 5% to 50% Acetonitrile (with 0.1% trifluoroacetic acid) in water (with 0.1% trifluoroacetic acid) gradient over 9 minutes). The first eluting fractions were pooled, frozen and lyophilized to afford 5-((((trans)-4-(((trans)-2-((E)-1-phenylbut-1-en-2-yl)cyclopropyl)amino)cyclohexyl)amino)methyl)picolinic Acid bis(trifluoroacetic Acid) salt (12.0 mg, 18.5 μmol) in 21% yield. $^1$H NMR (400 MHz, DMSO-d6) δ 8.90-9.06 (m, 2H), 8.81-8.85 (m, 1H), 8.78-8.80 (m, 1H), 8.03-8.16 (m, 2H), 7.30-7.38 (m, 2H), 7.13-7.25 (m, 3H), 6.22 (s, 1H), 4.26-4.36 (m, 2H), 3.22-3.25 (m, 1H), 3.04-3.14 (m, 2H), 2.78-2.98 (m, 2H), 2.14-2.29 (m, 5H), 1.92-2.00 (m, 1H), 1.34-1.47 (m, 4H), 1.15-1.28 (m, 3H), 1.12 (t, J=7.45 Hz, 3H). LCMS (ESI+): 420.3 (M+H).

Compound 225: 3-(2-(((trans)-2-((E)-1-phenylbut-1-en-2-yl)cyclopropyl)amino)-7-azaspiro[3.5]nonan-7-yl)propanoic Acid Bis Trifluoroacetate (Racemic)

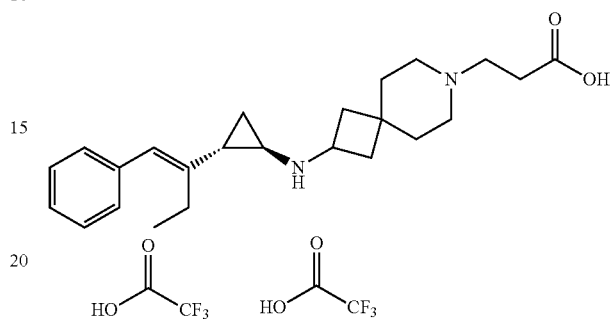

tert-butyl 3-(2-(((trans)-2-((E)-1-phenylbut-1-en-2-yl)cyclopropyl)amino)-7-azaspiro[3.5]nonan-7-yl)propanoate (21 mg, 47.8 μmol) was dissolved in HCl in 1,4-Dioxane (4M, 0.5 ml, 2 mmol) and water (0.25 mL). The solution was stirred overnight at 40° C. before cooling to room temperature and concentrating. The crude residue was purified by preparative HPLC (ACN:water+0.1% TFA, SunFire column) and the pure fractions lyophilized to afford 3-(2-(((trans)-2-(E)-1-phenylbut-1-en-2-yl)cyclopropyl)amino)-7-azaspiro[3.5]nonan-7-yl)propanoic Acid bis trifluoroacetate (4.7 mg). LCMS m/z 383 [M+H$^+$]1H NMR Using the appropriate starting materials and modifications the following intermediates were synthesized following the synthetic procedures described for intermediate 3-(2-(((trans)-2-((E)-1-phenylbut-1-en-2-yl)cyclopropyl)amino)-7-azaspiro[3.5]nonan-7-yl)propanoic acid bis trifluoroacetate.

| Cmpd. | Structure/Name | Stereochem comment | LCMS m/z; $^1$H NMR |
|---|---|---|---|
| 226 | ![structure] <br> 4-((6-(((trans)-2-((E)-1-phenylbut-en-2-yl)cyclopropyl)amino)-2-azaspiro[3.3]heptan-2-yl)methyl)benzoic acid bis trifluoroacetate | racemic | 417 [M + H$^+$]; $^1$H NMR (400 MHz, DMSO-d6) δ 13.05-13.28 (m, 1H), 10.45 (br. s., 1H), 9.29 (br. s., 2H), 7.99 (d, J = 8.30 Hz, 2H), 7.55 (d, J = 8.30 Hz, 2H), 7.29-7.38 (m, 2H), 7.08-7.25 (m, 3H), 6.19 (s, 1H), 4.40 (br. s., 2H), 4.17 (d, J = 15.14 Hz, 3H), 3.65-4.05 (m, 3H), 2.51-2.77 (m, 3H), 2.45 (br. s., 1H), 2.11-2.30 (m, 2H), 1.96 (br. s., 1H), 0.96-1.25 (m, 5H) |

| Cmpd. | Structure/Name | Stereochem comment | LCMS m/z; ¹H NMR |
|---|---|---|---|
| 227 | 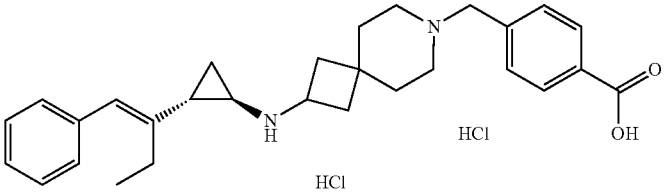 [SMILES: CC/C(=C\c1ccccc1)[C@@H]1C[C@H]1NC1CC2(CCN(Cc3ccc(C(=O)O)cc3)CC2)C1 ; Cl ; Cl]<br>4-((2-(((trans)-2-((E)-1-phenylbut-1-en-2-yl)cyclopropyl)amino)-7-azaspiro[3.5]nonan-7-yl)methyl)benzoic acid dihydrochloride | racemic | 445 [M + H⁺]; ¹H NMR (400 MHz, DMSO-d6) δ 12.98-13.35 (m, 1H), 10.53 (br. s., 1H), 9.75 (br. s., 2H), 8.00 (d, J = 8.30 Hz, 2H), 7.72 (d, J = 8.30 Hz, 2H), 7.29-7.39 (m, 2H), 7.13-7.28 (m, 3H), 6.20 (s, 1H), 4.33 (br. s., 2H), 3.84 (br. s., 1H), 3.69 (dd, J = 5.13, 14.16 Hz, 1H), 3.48 (dd, J = 4.27, 11.35 Hz, 1H), 3.12-3.26 (m, 2H), 2.74-3.06 (m, 3H), 2.67 (br. s., 1H), 2.16-2.39 (m, 3H), 2.11 (br. s., 2H), 1.75-2.01 (m, 4H), 1.29 (br. s., 1H), 1.13 (dt, J = 1.59, 7.51 Hz, 3H), |

Compound 228: 2,2-dimethyl-3-(2-(((trans)-2-(E)-1-phenylbut-1-en-2-yl)cyclopropyl)amino)-7-azaspiro[3.5]nonan-7-yl)propanoic Acid Bis Trifluoroacetate (Racemic)

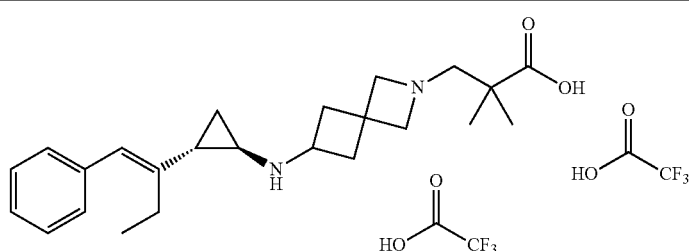

Benzyl 2,2-dimethyl-3-(2-(2,2,2-trifluoro-N-((trans)-2-((E)-1-phenylbut-1-en-2-yl)cyclopropyl)acetamido)-7-azaspiro[3.5]nonan-7-yl)propanoate (25 mg, 41.8 µmol) was dissolved in MeOH (1.5 mL) and NaOH (0.8 mL, 1M) was added. The reaction mixture was stirred at room temperature under a stream of nitrogen for 24 h. The reaction mixture was acidified with AcOH, and purified by prep HPLC (ACN:water+0.1% TFA, SunFire col.). Pure fractions were frozen and lyophilized to afford 2,2-dimethyl-3-(2-(((trans)-2-((E)-1-phenylbut-1-en-2-yl)cyclopropyl)amino)-7-azaspiro[3.5] nonan-7-yl)propanoic Acid bis trifluoroacetate (10.0 mg, 15.6 µmol). LCMS m/z 411 [M+H⁺] ¹H NMR (400 MHz, DMSO-d6) δ 12.93-13.21 (m, 1H), 9.24 (br. s., 2H), 8.71-8.94 (m, 1H), 7.27-7.39 (m, 2H), 7.10-7.26 (m, 3H), 6.44-6.60 (m, 1H), 6.21 (s, 1H), 3.88 (br. s., 1H), 3.18 (br. s., 2H), 2.79-3.14 (m, 4H), 2.72 (br. s., 1H), 1.69-2.37 (m, 11H), 1.23 (s, 6H), 1.18 (br. s., 1H), 1.10-1.15 (m, 3H).

Using the appropriate starting materials and modifications the following examples were synthesized using the procedure described for 2,2-dimethyl-3-(2-(((trans)-2-(E)-1-phenylbut-1-en-2-yl)cyclopropyeamino)-7-azaspiro[3.5] nonan-7-yl)propanoic acid.

| Cmpd. | Structure/Name | Stereochem comment | LCMS m/z; ¹H NMR |
|---|---|---|---|
| 229 | 2,2-dimethyl-3-(6-(((Itrans)-2-((E)-1-phenylbut-1-en-2-yl)cyclopropyl)amino)-2-azaspiro[3.3]heptan-2-yl)propanoic acid bis trifluoroacetate | racemic | 383 [M + H⁺]; ¹H NMR (400 MHz, DMSO-d6) δ 12.68-13.33 (m, 1H), 9.67-9.83 (m, 1H), 9.23-9.55 (m, 2H), 7.29-7.38 (m, 2H), 7.10-7.27 (m, 3H), 6.20 (s, 1H), 4.27 (br, s., 2H), 4.18 (s, 2H), 3.71-3.81 (m, 1H), 3.35 (s, 2H), 2.53-2.77 (m, 3H), 2.48 (br. s., 2H), 2.24 (dq, J = 3.66, 7.41 Hz, 2H), 1.95-2.03 (m, 1H), 1.16-1.24 (m, 2H), 1.15 (s, 6H), 1.12 (t, J = 7.57 Hz, 3H). |

-continued

| Cmpd. | Structure/Name | Stereochem comment | LCMS m/z; $^1$H NMR |
|---|---|---|---|
| 230 | 3-(6-(((trans)-2-((E)-1-phenylbut-1-en-2-yl)cyclopropyl)amino)-2-azaspiro[3.3]heptan-2-yl)propanoic acid bis trifluoroacetate | racemic | 355 [M + H$^+$]; 1H NMR (400 MHz, DMSO-d6) delta 12.75 (br. s., 1H), 9.80 (br. s., 1H), 9.19 (br. s., 2H), 7.31-7.39 (m, 2H), 7.10-7.27 (m, 3H), 6.21 (s, 1H), 4.18-4.27 (m, 1H), 4.02-4.16 (m, 3H), 3.72-3.83 (m, 1H), 3.24-3.36 (m, 2H), 2.70-2.80 (m, 1H), 2.57-2.70 (m, 2H), 2.55 (t, J = 7.08 Hz, 2H), 2.36-2.48 (m, 2H), 2.18-2.28 (m, 2H), 1.91-2.02 (m, 1H), 1.14-1.20 (m, 2H), 1.12 (t, J = 7.57 Hz, 3H). |
| 231 | 5-((6-(((trans)-2-((E)-1-phenylbut-1-en-2-yl)cyclopropyl)amino)-2-azaspiro[3.3]heptan-2-yl)methyl)picolinic acid bis trifluoroacetate | racemic | 418 [M + H$^+$]; 1H NMR (400 MHz, DMSO-d6) δ 13.28-13.46 (m, 1H), 10.61 (br. s., 2H), 9.30 (br. s., 2H), 8.75 (d, J = 1.95 Hz, 1H), 8.09-8.13 (m, 1H), 7.93-8.08 (m, 1H), 7.29-7.41 (m, 2H), 6.99-7.28 (m, 3H), 6.19 (s, 1H), 4.47 (br. s., 1H), 3.94-4.34 (m, 3H), 3.77 (br. s., 1H), 2.48-2.82 (m, 4H), 2.12-2.31 (m, 2H), 1.96 (t, J = 9.89 Hz, 1H), 0.90-1.30 (m, 5H) |
| 232 | 2,2-dimethyl-3-(((trans)-4-((((trans)-2-((E)-1-phenylbut-1-en-2-yl)cyclopropyl)amino)methyl)cyclohexyl)amino)propanoic acid dihydrochloride | racemic | 399 [M + H$^+$]; $^1$H NMR (400 MHz, CD$_3$OD) δ 7.29-7.24 (m, 2H), 7.17-7.12 (m, 3H), 6.09-6.05 (s, 1H), 3.04-2.97 (m, 1H), 2.95-2.93 (s, 2H), 2.58 (d, J = 6.4 Hz, 2H), 2.34-2.25 (m, 2H), 2.19-2.12 (m, 3H), 2.01-1.93 (m, 2H), 1.50-1.39 (m, 2H), 1.22-1.13 (m, 11H), 1.12-1.01 (m, 2H), 0.94-0.79 (m, 2H). |
| 233 | 2,2-dimethyl-3-(((trans)-3-((((trans)-2-((E)-1-phenylbut-1-en-2-yl)cyclopropyl)amino)methyl)cyclobutyl)amino)propanoic acid dihydrochloride | racemic | 371 [M + H$^+$]; $^1$H NMR (400 MHz, D$_2$O) δ 7.44-7.34 (m, 2H), 7.29 (d, J = 5.3 Hz, 3H), 6.26 (s, 1H), 3.93 (quin, J= 7.2 Hz, 1H), 3.41 (d, J = 7.9 Hz, 2H), 3.06 (s, 2H), 2.92-2.76 (m, 2H), 2.63-2.46 (m, 2H), 2.31 (td, J = 6.9, 13.5 Hz, 4H), 2.14-2.02 (m, 1H), 1.34-1.21 (m, 9H), 1.12 (t, J = 7.5 Hz, 3H) |
| 234 | 2,2,2-trifluoroacetic acid compound with 2-((6-(((trans)-2-((E)-1-phenylbut-1-en-2-yl)cyclopropyl)amino)-2-azaspiro[3.3]heptan-2-yl)methyl)thiazole-5-carboxylic acid (2:1) | racemic | 371 [M + H$^+$]; 1H-NMR: 1H NMR (400 MHz, DMSO-d6) delta 13.81 (br. s, 1H), 10.90 (br. s, 1H), 9.26 (br. s., 2H), 8.41 (s, 1H), 7.30-7.40 (m, 2H), 7.08-7.27 (m, 3H), 6.20 (s, 1H), 4.79 (br. s., 2H), 4.0- 4.32 (m, 4H), 3.66-3.86 (m, 2H), 2.70-2.78 (m, 1H), 2.56-2.68 (m, 2H), 2.40-2.48 (m. 1H), 2.16-2.30 (m, 2H), 1.92-2.01 (m, 1H), 1.15-1.21 (m, 2H), 1.12 (t, J = 7.57 Hz, 3H) |

| Cmpd. | Structure/Name | Stereochem comment | LCMS m/z; $^1$H NMR |
|---|---|---|---|
| 235 | 2,2,2-trifluoroacetic acid compound with 4-((3-methyl-3-(((trans)-2-((E)-1-phenylbut-1-en-2-yl)cyclopropyl)amino)methyl)azetidin-1-yl)methyl)benzoic acid (2:1) | racemic | 405 [M + H$^+$]; |
| 236 | 4-((((trans)-3-((((trans)-2-((E)-1-phenylbut-1-en-2-yl)cyclopropyl)amino)methyl)cyclobutyl)amino)methyl)benzoic acid dihydrochloride | racemic | 405 [M + H$^+$]; $^1$H NMR (400 MHz, D$_2$O) δ 8.06-7.96 (m, 2H), 7.52 (d, J = 8.4 Hz, 2H), 7.41-7.32 (m, 2H), 7.32-7.18 (m, 3H), 6.23 (s, 1H), 4.20 (s, 2H), 3.93 (td, J = 7.6, 15.3 Hz, 1H), 3.36 (d, J = 7.9 Hz, 1H), 2.87-2.77 (m, 2H), 2.58-2.42 (m, 3H), 2.36-2.18 (m, 4H), 2.09-2.01 (m, 1H), 1.30-1.22 (m, 2H), 1.10 (t, J = 7.7 Hz, 3H). |
| 237 | 5-((((trans)-3-((((trans)-2-((E)-1-phenylbut-1-en-2-yl)cyclopropyl)amino)methyl)cyclobutyl)amino)methyl)picolinic acid dihydrochloride | racemic | 406 [M + H$^+$]; $^1$H NMR (400 MHz, D$_2$O) δ 8.82 (s, 1H), 8.48 (s, 1H), 8.35-8.33 (d, J = 8.0 Hz, 1H), 7.40-7.37 (m, 2H), 7.29-7.27 (m, 2H), 6.25 (s, 1H), 4.41 (s, 2H), 4.03 (m, 1H), 3.39 (d, J = 7.9 Hz, 1H), 2.86 (m, 2H), 2.54-2.51 (m, 2H), 2.37-2.25 (m, 4H), 2.08 (m, 1H), 1.30-1.27 (m, 2H), 1.12 (m, 3H). |
| 238 | 1-(2,2-dimethyl-3-(((trans)-2-((E)-1-phenylbut-1-en-2-yl)cyclopropyl)amino)propyl)piperidine-4-carboxylic acid dihydrochloride | racemic | 385 [M + H$^+$]; $^1$H NMR (400 MHz, D$_2$O) δ 7.41-7.36 (m, 2H), 7.29-7.27 (m, 3H), 6.27 (s, 1H), 3.68 (br. s., 1H), 3.30-3.26 (m, 6H), 2.94-2.92 (m, 1H), 2.7 (br. s., 1H), 2.37-2.28 (m, 2H), 2.19-2.17 (m, 3H), 2.03 (br. s., 2H), 1.37-1.30 (m, 2H), 1.29 (s, 6H), 1.25-1.21 (m, 2H), 1.14-1.10 (t, J = 7.8 Hz, 3H). |

Compound 273: N-((trans)-2-(E)-1-phenylbut-1-en-2-yl)cyclopropyl)-2-azaspiro[3.3]heptan-6-amine bis(2,2,2-trifluoroacetate) (Racemic)

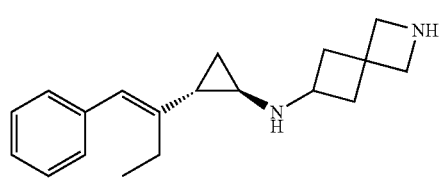

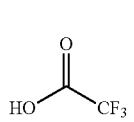 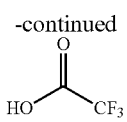

tert-butyl 6-(((trans)-2-((E)-1-phenylbut-1-en-2-yl)cyclopropyl)amino)-2-azaspiro[3.3]heptane-2-carboxylate (115 mg, 300 μmol) was dissolved in dioxane (6 mL) and HCl (1 mL, 6M aq.) was added. The solution was heated for 16 h at 45° C. The compound was purified by Prep HPLC. (ACN: water+0.1% TFA, SunFire column). Pure fractions were frozen and lyophilized to afford N-((trans)-2-((E)-1-phenylbut-1-en-2-yl)cyclopropyl)-2-azaspiro[3.3]heptan-6-amine bis(2,2,2-trifluoroacetate) (45.0 mg, 88.1 µmol). LCMS m/z 283 [M+H⁺]. 1H NMR (400 MHz, DMSO-d6) d 9.24 (hr. s., 2H), 8.63 (hr. s., 2H), 7.30-7.37 (m, 2H), 7.14-7.25 (m, 3H), 6.19 (s, 1H), 4.02 (t, J=5.62 Hz, 2H), 3.92 (t, J=5.74 Hz, 2H), 3.73 (br. s., 1H), 2.71 (br. s., 1H), 2.61 (d, J=7.57 Hz, 2H), 2.43 (d, J=6.35 Hz, 2H), 2.16-2.27 (m, 2H), 1.96 (br. s., 1H), 1.14-1.21 (m, 2H), 1.11 (t, J=7.57 Hz, 3H).

Using the appropriate starting materials and modifications the following examples were synthesized using the procedure described for N-((trans)-2-((E)-1-phenylbut-1-en-2-yl)cyclopropyl)-2-azaspiro[3.3]heptan-6-amine.

| Cmpd. | Structure/Name | Stereochem comment | LCMS m/z; ¹H NMR |
|---|---|---|---|
| 239 | 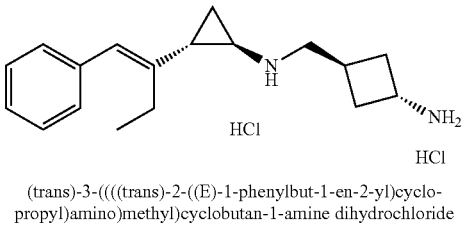 [SMILES: CC/C(=C\c1ccccc1)[C@@H]1C[C@H]1NC[C@H]1C[C@H](N)C1 ; Cl ; Cl]<br>(trans)-3-((((trans)-2-((E)-1-phenylbut-1-en-2-yl)cyclopropyl)amino)methyl)cyclobutan-1-amine dihydrochloride | racemic | 271 [M + H⁺]; ¹H NMR (400 MHz, CD₃OD) δ 7.36-7.28 (m, 2H), 7.24-7.15 (m, 3H), 6.29 (s, 1H), 3.94 (quin, J = 7.1 Hz, 1H), 3.43-3.36 (m, 2H), 2.96-2.85 (m, 2H), 2.49-2.39 (m, 3H), 2.38-2.30 (m, 2H), 2.23-2.08 (m, 1H), 2.03 (d, J = 5.7 Hz, 1H), 1.40-1.33 (m, 2H), 1.30 (br. s., 2H), 1.28-1.22 (m, 1H), 1.19 (t, J = 7.5 Hz, 3H). |
| 240 | 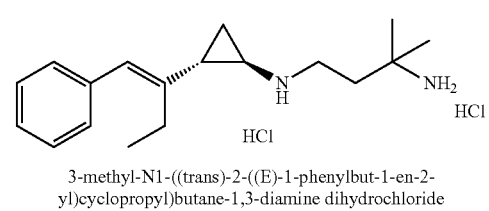 [SMILES: CC/C(=C\c1ccccc1)[C@@H]1C[C@H]1NCCC(C)(C)N ; Cl ; Cl]<br>3-methyl-N1-((trans)-2-((E)-1-phenylbut-1-en-2-yl)cyclopropyl)butane-1,3-diamine dihydrochloride | racemic | 273 [M + H⁺]; ¹H NMR (400 MHz, CD₃OD) δ 7.33-7.30 (m, 2H), 7.23-7.19 (m,3H), 6.30 (s, 1H), 2.96-2.93 (m, 1H), 2.38-2.33 (m, 2H), 2.21-2.12 (m, 3H), 1.43 (s, 6H), 1.41-1.39 (m, 2H), 1.29-1.26 (m, 2H), 1.22-1.18 (m, 3H). |
| 241 | 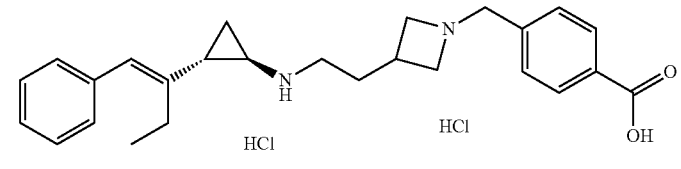<br>4-((3-(2-(((trans)-2-((E)-1-phenylbut-1-en-2-yl)cyclopropyl)amino)ethyl)azetidin-1-yl)methyl)benzoic acid dihydrochloride | racemic | 405 [M + H⁺]; ¹H NMR (400 MHz, DMSO-d₆) δ 7.98 (d, J = 6.6 Hz, 2H), 7.72 (d, J = 6.6 Hz, 2H), 7.39-7.28 (m, 2H), 7.20 (br. s., 3H), 6.20 (br. s., 1H), 4.21 (br. s., 2H), 3.06 (br. s., 5H), 2.25 (br. s., 5H), 1.98 (br. s., 1H), 1.75 (br. s., 1H), 1.42 (br. s., 1H), 1.23 (br. s., 1H), 1.13 (br. s., 4H) |
| 242 | 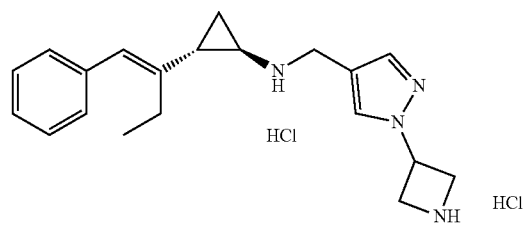<br>(trans)-N-((1-(azetidin-3-yl)-1H-pyrazol-4-yl)methyl)-2-((E)-1-phenylbut-1-en-2-yl)cyclopropan-1-amine dihydrochloride | racemic | 323 [M + H⁺]; ¹H NMR (400 MHz, CD₃OD) δ 8.0 (s, 1H), 7.86 (s, 1H), 7.33-7.30 (m, 2H), 7.23-7.19 (m, 3H), 6.24 (s, 1H), 5.52-5.45 (m, 1H), 4.55-4.51 (m, 4H), 4.35-4.27 (m, 2H), 2.91-2.89 (m, 1H), 2.36-2.32 (m, 2H), 2.16-2.12 (m, 1H), 1.25-1.14 (m, 5H). |
| 243 | 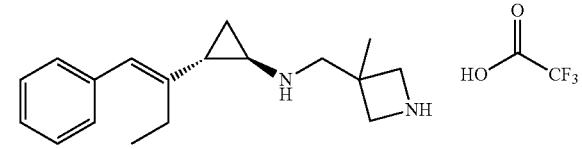<br>(trans)-N-((3-methylazetidin-3-yl)methyl)-2-((E)-1-phenylbut-1-en-2-yl)cyclopropanamine bis(2,2,2-trifluoroacetate) | racemic | 271 [M + H⁺]; 1H NMR (400 MHz, DMSO-d6) delta 9.03-9.15 (br. s., 1H), 8.94 (br. s., 2H), 8.72 (br. s., 1H), 7.30-7.39 (m, 2H), 7.13-7.27 (m, 3H), 6.24 (br. s., 1H), 3.98 (br. s., 2H), 3.62 (br. s., 2H), 3.39 (br. s., 2H), 2.91 (br. s., 1H), 2.27 (q, J = 7.24 Hz, 2H), 2.11 (br. s., 1H), 1.39 (s, 3H), 1.32 (s, 1H), 1.23 (br. s., 1H), 1.14 (t, J = 7.57 Hz, 3H). |
| 283 | 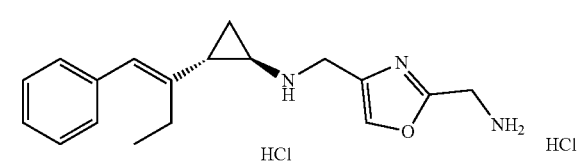<br>(trans)-N-((2-(aminomethyl)oxazol-4-yl)methyl)-2-((E)-1-phenylbut-1-en-2-yl)cyclopropan-1-amine dihydrochloride | racemic | 298 [M + H⁺]; ¹H NMR (400 MHz, CD₃OD) δ 8.25-8.14 (m, 1H), 7.34-7.26 (m, 2H), 7.24-7.15 (m, 3H), 6.27 (s, 1H), 4.37 (s, 4H), 3.01-2.93 (m, 1H), 2.38-2.26 (m, 2H), 2.16 (br. s., 1H), 1.41-1.33 (m, 1H), 1.30-1.22 (m, 1H), 1.17 (t, J = 7.5 Hz, 3H). |

| Cmpd. | Structure/Name | Stereochem comment | LCMS m/z; $^1$H NMR |
|---|---|---|---|
| 244 | 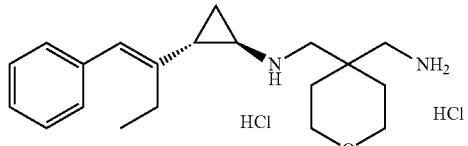<br>(trans)-N-((4-(aminomethyl)tetrahydro-2H-pyran-4-yl)methyl)-2-((E)-1-phenylbut-1-en-2-yl)cyclopropan-1-amine dihydrochloride | racemic | 315 [M + H$^+$]; $^1$H NMR (400 MHz, CD$_3$OD) δ 7.34-7.27 (m, 2H), 7.21 (d, J = 6.8 Hz, 3H), 6.33 (s, 1H), 3.80-3.71 (m, 4H), 3.48 (s, 2H), 3.32 (br. s., 2H), 3.11-3.07 (m, 1H), 2.43 (br. s., 1H), 2.36 (q, J = 7.6 Hz, 2H), 1.78-1.66 (m, 4H), 1.62-1.51 (m, 2H), 1.23-1.16 (m, 3H) |

Compound 245: Synthesis of 4-(((((trans)-4-((((trans)-2-(E)-1-phenylbut-1-en-2-Acyclopropyl)amino)methyl)cyclohexyl)amino)methyl)benzoic Acid Bis Trifluoroacetate (Racemic)

Step 1

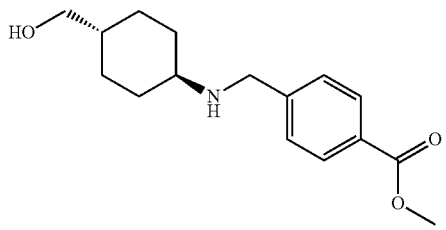 [SMILES: COC(=O)c1ccc(CN[C@H]2CC[C@H](CO)CC2)cc1]

methyl 4-((((trans)-4-(hydroxymethyl)cyclohexyl)amino)methyl)benzoate

To a solution of ((trans)-4-aminocyclohexyl)methanol hydrochloride (275 mg, 1.66 mmol) and methyl 4-formylbenzoate (272 mg, 1.66 mmol) dissolved in 1,2-DCE (8 mL) was added sodium triacetoxyborohydride (703 mg, 3.32 mmol). The solution was stirred for 30 min, quenched with K$_2$CO$_3$ (aq sat), and extracted with DCM (2×50 mL). The combined organics phase was concentrated to afford crude methyl 4-((((trans)-4-(hydroxymethyl)cyclohexyl)amino)methyl)benzoate (460 mg, 1.65 mmol). LCMS m/z 278

Step 2

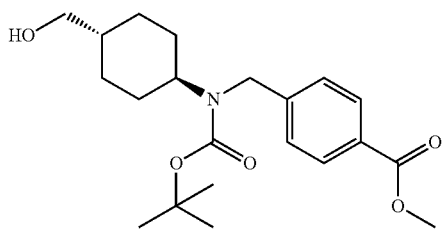 [SMILES: COC(=O)c1ccc(CN(C(=O)OC(C)(C)C)[C@H]2CC[C@H](CO)CC2)cc1]

methyl 4-(((tert-butoxycarbonyl)((trans)-4-(hydroxymethyl)cyclohexyl)amino)methyl)benzoate To a solution of methyl 4-((((trans)-4-(hydroxymethyl)cyclohexyl)amino)methyl)benzoate (460 mg, 1.65 mmol) dissolved in THF (16 mL) was added di-tert-butyl dicarbonate (395 mg, 1.81 mmol) and DMAP (5 mg). The reaction mixture was stirred at 25° C. for 16 h. The reaction mixture was partitioned between ammonium chloride (aq. sat.) and EtOAc. The organic layer was washed with brine, dried with sodium sulfate, filtered, and evaporated under reduced pressure. The crude residue was purified by column chromatography (24 g silica, 0% EtOAc to 50% in hexanes) to afford methyl 4-(((tert-butoxycarbonyl)((trans)-4-(hydroxymethyl)cyclohexyeamino)methyebenzoate (285 mg, 0.755 mmol). LCMS m/z: 399.8 (M+Na)/321.8 (M-tBu+H)

Step 3

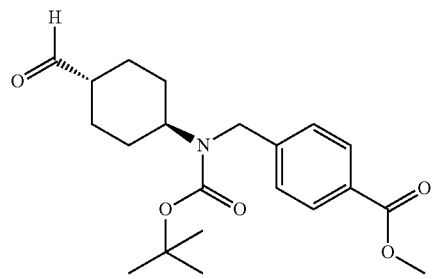 [SMILES: COC(=O)c1ccc(CN(C(=O)OC(C)(C)C)[C@H]2CC[C@H](C=O)CC2)cc1]

methyl 4-(((tert-butoxycarbonyl)((trans)-4-formylcyclohexyl)amino)methyl)benzoate Methyl 4-(((tert-butoxycarbonyl)((trans)-4-(hydroxymethyl)cyclohexyeamino)methyl)benzoate (142 mg, 376 μmol) was dissolved in DCM (5 mL) and cooled to 0° C. before addition of Dess-Martin periodinane (175 mg, 413 μmol). The reaction mixture was stirred for 16 hours before addition of iPrOH. The mixture was stirred for 5 min, diluted with DCM and sodium thio sulfate (aq. sat.). The layers were separates and the organics layer was washed with brine, dried with Na$_2$SO$_4$, filtered and concentrated to afford methyl 4-(((tert-butoxycarbonyl)((trans)-4-formylcyclohexyl)amino)methyl)benzoate (105 mg, 279 μmol). LCMS M/Z: 319.9 (M-tBu+H).

Step 4

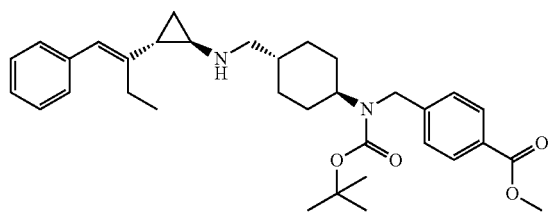 [SMILES: CC/C(=C\c1ccccc1)[C@@H]1C[C@H]1NC[C@H]1CC[C@H](N(Cc2ccc(C(=O)OC)cc2)C(=O)OC(C)(C)C)CC1]

methyl 4-(((tert-butoxycarbonyl)((trans)-4-((((trans)-2-((E)-1-phenylbut-1-en-2-yl)cyclopropyl)amino)methyl)cyclohexyl)amino)methyl)benzoate (Racemic)

To (trans)-2-((E)-1-phenylbut-1-en-2-yl)cyclopropanamine hydrochloride (47.6 mg, 213 μmol) and methyl 4-(((tert-butoxycarbonyl)((trans)-4-formylcyclohexyl)amino)methyl)benzoate (80 mg, 213 μmol) in 1,2-DCE (7 mL) was added 1 mL AcOH and sodium triacetoxyborohydride (94.3 mg, 447 μmol). The solution was stirred for 30 min. before being quenched with $K_2CO_3$ (aq.) and extracted with DCM (2×50 mL). The organic phase was concentrated and the crude residue was purified by column chromatography (40:60 to 100:0 EtOAc, followed by 0% to 10% MeOH in EtOAc, 25 g column) to afford methyl 4-(((tert-butoxycarbonyl)((1S,4r)-4-((((trans)-2-((E)-1-phenylbut-1-en-2-yl)cyclopropyl)amino)methypcyclohexyl)amino)methyebenzoate (116 mg, 212 μmol). LCMS m/z 491 [M-tBu+H$^+$]

Step 5

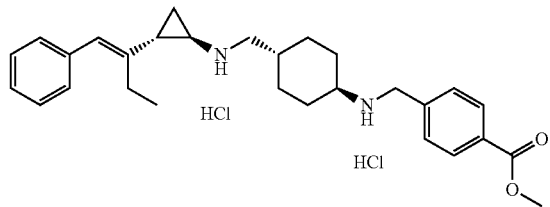 [SMILES: CC/C(=C\c1ccccc1)[C@@H]1C[C@H]1NC[C@H]1CC[C@H](NCc2ccc(C(=O)OC)cc2)CC1 ; Cl ; Cl]

methyl 4-((((trans)-4-((((trans)-2-((E)-1-phenylbut-1-en-2-yl)cyclopropyl)amino)methyl)cyclohexyl)amino)methyl)benzoate Dihydrochloride (Racemic)

Methyl 4-(((tert-butoxycarbonyl)((trans)-4-((((trans)-2-((E)-1-phenylbut-1-en-2-yl)cyclopropyl)amino)methyl)cyclohexyl)amino)methyl)benzoate (116 mg, 212 μmol) was dissolved in dioxane (1 mL) and HCl (4M in dioxane, 1 mL, 4 mmol) was added. The reaction mixture was stirred at 50° C. for 16 h before concentrating to afford crude methyl 4-((((trans)-4-((((trans)-2-((E)-1-phenylbut-1-en-2-yl)cyclopropyl)amino)methyl)cyclohexyl)amino)methyl)benzoate dihydrochloride. LCMS m/z 447 [M+H$^+$]

Step 6

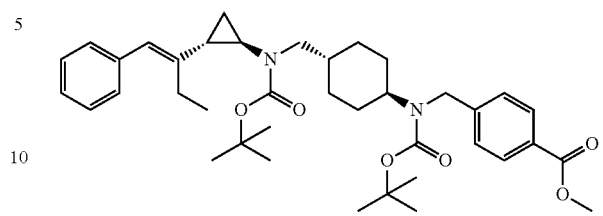

methyl 4-(((tert-butoxycarbonyl)((trans)-4-(((tert-butoxycarbonyl)((trans)-2-((E)-1-phenylbut-1-en-2-yl)cyclopropyl)amino)methypcyclohexyl)amino)methyl)benzoate (Racemic)

methyl 4-((((trans)-4-((((trans)-2-((E)-1-phenylbut-1-en-2-yl)cyclopropyl)amino)methyl)cyclohexyl)amino)methyl)benzoate dihydrochloride (50 mg, 96.2 μmol) was dissolved in THF, di-tert-butyl dicarbonate (52.3 mg, 240 μmol) was added, followed by diisopropylethylamine (55.1 μL, 317 μmol) and DMAP (5 mg). The reaction mixture was stirred at room temperature for 16 h. The reaction mixture was partitioned between ammonium chloride (aq. sat.) and EtOAc. The organic layer was washed with brine, dried with sodium sulfate, filtered, and concentrated to afford methyl 4-(((tert-butoxycarbonyl)((trans)-4-(((tert-butoxycarbonyl)((trans)-2-((E)-1-phenylbut-1-en-2-yl)cyclopropyl)amino)methypcyclohexyl)amino)methyl)benzoate (62.0 mg, 95.8 μmol).

Step 7

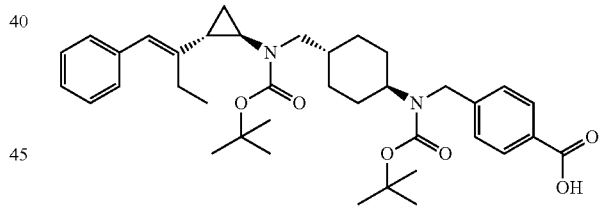

4-(((tert-butoxycarbonyl)((trans)-4-(((tert-butoxycarbonyl)((trans)-2-((E)-1-phenylbut-1-en-2-yl)cyclopropyl)amino)methyl)cyclohexyl)amino)methyl)benzoic Acid (Racemic)

To a round bottomed flask was added methyl 4-(((tert-butoxycarbonyl)((trans)-4-(((tert-butoxycarbonyl)((trans)-2-((E)-1-phenylbut-1-en-2-yl)cyclopropyl)amino)methypcyclohexyl)amino)methyl)benzoate (60 mg, 92.7 μmol), MeOH (1 mL), THF (1 mL), DMSO (0.5 mL), and NaOH (0.6 mL, 1M). The reaction was stirred overnight at 60° C. before cooling to room temperature and partitioning between EtOAc and NaHCO$_3$ (aq.). The organic layer was washed with brine, dried with $Na_2SO_4$, filtered and concentrated to afford 4-(((tert-butoxycarbonyl)((trans)-4-(((tert-butoxycarbonyl)((trans)-2-((E)-1-phenylbut-1-en-2-yl)cyclopropyl)amino)methyl)cyclohexyl)amino)methyl)benzoic acid (50.0 mg, 79.0 μmol).

Step 8

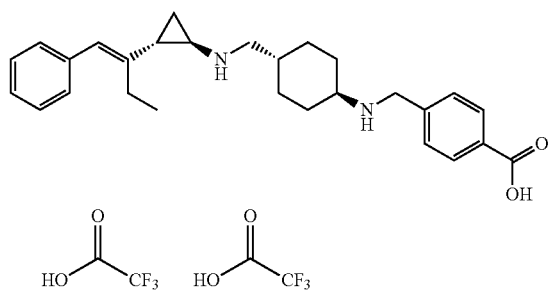

4-((((trans)-4-((((trans)-2-((E)-1-phenylbut-1-en-2-yl)cyclopropyl)amino)methyl)cyclohexyl)amino)methyl)benzoic Acid Bis Trifluoroacetate (Racemic)

To a solution 4-(((tert-butoxycarbonyl)((trans)-4-((((tert-butoxycarbonyl)((trans)-2-((E)-1-phenylbut-1-en-2-yl)cyclopropyl)amino)methyl)cyclohexyl)amino)methyl)benzoic acid (25 mg, 39.5 µmol) dissolved in DCM (5 mL), was added 2,6-lutidine (22.9 µL, 197 µmol) before being cooled to 0° C. To this solution was added TMSOTf (28.5 µL, 158 µmol) and the reaction was stirred until complete. The reaction mixture was partitioned between DCM and NaHCO3 (aq. sat.). The organic phase was washed with brine, dried with Na$_2$SO$_4$, filtered and concentrated. The crude residue was purified via preparative HPLC (ACN: Water+0.1% TFA, SunFire column). Pure fractions were frozen and lyophilized to afford 4-((((trans)-4-((((trans)-2-((E)-1-phenylbut-1-en-2-yl)cyclopropyl)amino)methyl)cyclohexyl)amino)methyl)benzoic acid bis trifluoroacetate (15.0 mg, 22.7 µmol). LCMS m/z 433 [M+H$^+$]1H NMR Compound 246: 5-((((trans)-2-((E)-1-phenylbut-1-en-2-yl)cyclopropyl)amino)methyl)pyrimidin-2-amine Hydrochloride (Racemic)

Step 1

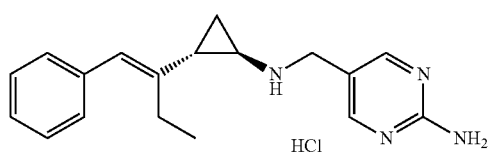 [SMILES: CC/C(=C\c1ccccc1)[C@@H]1C[C@H]1NCc1cnc(N)nc1 ; Cl]

5-((((trans)-2-((E)-1-phenylbut-1-en-2-yl)cyclopropyl)amino)methyl)pyrimidin-2-amine Hydrochloride (Racemic)

To a solution of (trans)-2-[(1E)-1-benzylidenepropyl]cyclopropanamine; hydrochloride (91 mg, 406.14 umol, 1.00 eq) in H$_2$O (2 mL) was added NaHCO$_3$ to pH=9. The mixture was extracted with DCM (5 mL*3). The organic phase was dried with Na$_2$SO$_4$, concentrated under vacuum. To a mixture of 2-aminopyrimidine-5-carbaldehyde (50 mg, 406.14 umol, 1.00 eq) and (trans)-2-((E)-1-phenylbut-1-en-2-yl)cyclopropanamine in DCE (3 mL) was added HOAc (49 mg, 812.28 umol, 46.46 uL, 2.00 eq). The mixture was stirred at 0° C. for 1 h. To the mixture was added NaBH$_3$CN (51 mg, 812.28 umol, 2.00 eq) and the mixture was stirred at 0° C. for 1 h. To the mixture was diluted with H$_2$O (5 mL) and extracted with DCM (8 mL*3). The organic phase was dried with Na$_2$SO$_4$, filtered, and concentrated. The crude residue was purified by prep-HPLC (Instrument: Boston Green ODS 150*30 5u Mobile phase A: water with 0.05% HCl Mobile phase B:ACN Gradient 15-45% B) to afford 5-[[[(trans)-2-[(1E)-1 benzylidenepropyl]cyclopropyl]amino]methyl]pyrimidin-2-amine; dihydrochloride (9.0 mg, 24.50 umol, 6.03% yield, 100% purity) was obtained as yellow solid. LCMS (M+H$^+$) m/z: calcd 295.18; found 295.0. $^1$H NMR (400 MHz, CD$_3$OD) δ 8.79 (s, 2H), 7.37-7.27 (m, 3H), 7.20 (d, J=7.5 Hz, 4H), 6.28 (s, 1H), 4.40 (d, J=5.3 Hz, 2H), 3.01 (td, J=3.9, 7.6 Hz, 1H), 2.33 (q, J=7.5 Hz, 2H), 2.22 (br. s., 1H), 1.34-1.23 (m, 3H), 1.17 (t, J=7.5 Hz, 3H)

Compound 247: (trans)-N-(2-(aminomethyl)benzyl)-2-((E)-1-phenylbut-1-en-2-yl)cyclopropan-1-amine (Racemic)

Step 1

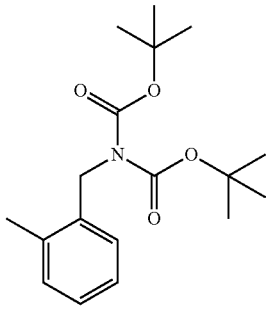 [SMILES: Cc1ccccc1CN(C(=O)OC(C)(C)C)C(=O)OC(C)(C)C]

tert-butyl N-tert-butoxycarbonyl-N-(o-tolylmethyl)carbamate

To a solution of o-tolylmethanamine (500 mg, 4.13 mmol, 0.51 mL, 1.00 eq) in DCM (10.0 mL) was added Boc$_2$O (901 mg, 4.13 mmol, 1.00 eq) and the mixture was stirred at 15° C. for 1 h. Then the mixture was concentrated to afford a residue. To this residue was added with DMAP (101 mg, 0.83 mmol, 0.20 eq) and Boc$_2$O (1.35 g, 6.20 mmol, 1.42 mL, 1.50 eq) before the mixture was heated to 80° C. for 4 h. The reaction mixture was concentratedand the crude residue was purified by column chromatography (SiO$_2$, Petroleum ether/Ethyl acetate=100/1 to 40/1) to afford tert-butyl N-tert-butoxycarbonyl-N-(o-tolylmethyl)carbamate (700 mg, 2.18 mmol). $^1$H NMR (400 MHz, CDCl$_3$) δ 7.12 (br. s., 4H), 4.77 (s, 2H), 2.29 (s, 3H), 1.42 (s, 18H).

Step 2

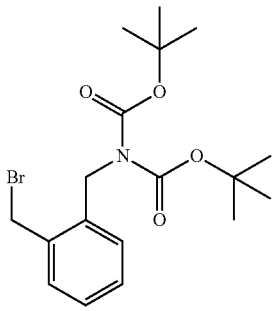 [SMILES: CC(C)(C)OC(=O)N(Cc1ccccc1CBr)C(=O)OC(C)(C)C]

tert-butyl N-[[2-(bromomethyl)phenyl]methyl]-N-tert-butoxycarbonylcarbamate

To a solution of tert-butyl N-tert-butoxycarbonyl-N-(o-tolylmethyl)carbamate (100 mg, 0.31 mmol, 1.00 eq) in CCl$_4$ (2.0 mL) were added AIBN (5.1 mg, 31 umol, 0.10 eq) and NBS (66 mg, 0.37 mmol, 1.20 eq). The mixture was stirred at 75° C. for 16 h under N$_2$ atmosphere. The reaction mixture was concentrated and the crude residue was purified by prep-TLC (SiO$_2$, Petroleum ether/Ethyl acetate=10/1) to afford tert-butyl N-[[2-(bromomethyl)phenyl]methyl]-N-tert-butoxycarbonyl-carbamate (70 mg, 0.18 mmol). $^1$H NMR (400 MHz, CDCl$_3$) δ 7.34-7.25 (m, 2H), 7.25-7.17 (m, 2H), 4.95 (s, 2H), 4.58 (s, 2H), 1.44 (s, 18H).

Step 3

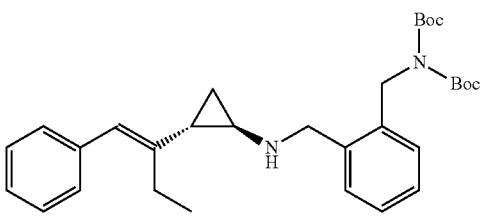 [SMILES: CC/C(=C\c1ccccc1)[C@@H]1C[C@H]1NCc1ccccc1CN(C(=O)OC(C)(C)C)C(=O)OC(C)(C)C]

tert-butyl N-[[2-[[[(trans)-2-[(1)-1-benzylidenepropyl]cyclopropyl]amino]methyl]phenyl]methyl]-N-tert-butoxycarbonylcarbamate (racemic)

(trans)-2-[(1E)-1-Benzylidenepropyl]cyclopropanamine (35 mg, 0.16 mmol, 1.00 eq, HCl) was dissolved in methanol/water (10 mL, 1:20). The mixture was basified to pH=9 with saturated aqueous NaHCO$_3$ and extracted with DCM (10 mL*3). The organic layer was dried over anhydrous Na$_2$SO$_4$ and filtered. The filtrate was concentrated under vacuum. To a solution of the amine in MeCN (2.0 mL) was added a mixture of tert-butyl N-[[2-(bromomethyl)phenyl]methyl]-N-tert-butoxycarbonylcarbamate (69 mg, 0.17 mmol, 1.10 eq) and DIEA (40 mg, 0.31 mmol, 55 uL, 2.00 eq) in MeCN (1.0 mL) dropwise and the mixture was stirred at 15° C. for 2 h under N$_2$ atmosphere. The reaction mixture was concentrated under vacuum to give the residue. Then EtOAc (10 mL) was added and the mixture was washed with water (5 mL*3). The organic layer was dried over anhydrous Na$_2$SO$_4$ and filtered. The filtrate was concentrated under vacuum to give crude product tert-butyl N-[[2-[[[(trans)-2-[(1E)-1-benzylidenepropyl]cyclopropyl]amino]methyl]phenyl]methyl]-N-tert-butoxycarbonylcarbamate (80 mg, crude) as yellow oil. LCMS (M+H$^+$) m/z: calcd 507.31; found 507.2.

Step 4

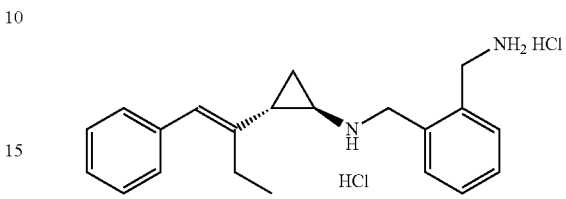

(trans)-N-[[2-(aminomethyl)phenyl]methyl]-2-[(1E)-1-benzylidenepropyl]cyclopropanamine dihydrochloride (racemic)

To a solution of tert-butyl N-[[2-[[[(trans)-2-[(1E)-1-benzylidenepropyl]cyclopropyl]amino]methyl]phenyl]methyl]-N-tert-butoxycarbonyl-carbamate (70 mg, 0.14 mmol, 1.00 eq) in MeOH (1.0 mL) was added HCl/MeOH (4 M, 1.0 mL, 28.9 eq). The mixture was stirred at 15° C. for 3 h under N$_2$ atmosphere. The reaction mixture was concentrated under vacuum to give the residue. The residue was purified by prep-HPLC (HCl) to give (trans)-N-[[2-(amino methyl)phenyl]methyl]-2-[(1E)-1-benzylidenepropyl]cyclopropanamine dihydrochloride (2.5 mg, 6.3 umol, 4.6% yield, 95.3% purity) as a black solid. $^1$H NMR (400 MHz, CD$_3$OD) δ 7.66 (hr. s., 1H), 7.61-7.53 (m, 3H), 7.34-7.27 (m, 2H), 7.20 (d, J=7.1 Hz, 3H), 6.28 (s, 1H), 4.61-4.50 (m, 2H), 4.38 (s, 2H), 3.08 (br. s., 1H), 2.33 (dd, J=4.0, 6.6 Hz, 2H), 2.22 (br. s., 1H), 1.47-1.40 (m, 1H), 1.26 (q, J=6.8 Hz, 1H), 1.17 (t, J=7.5 Hz, 3H). LCMS (M+H$^+$) m/z: calcd 307.21; found 307.0.

Compound 248: (trans)-N-[[2-(aminomethyl)oxazol-4-yl]methyl]-2-[(1E)-1-benzylidenepropyl]cyclopropanamine Dihydrochloride (Racemic)

Step 1

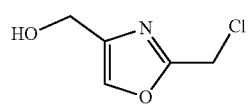

(2-(chloromethyl)oxazol-4-yl)methanol

To a solution of methyl 2-(chloromethyl)oxazole-4-carboxylate (200 mg, 1.1 mmol, 1.00 eq) in DCM (6 mL) was added DIBAL-H (1 M, 3.4 mL, 3.00 eq) at −78° C. The mixture was stirred at 0° C. for 1 hour. The reaction mixture was quenched by addition aqueous NH$_4$Cl (5 mL) at 0° C., filtrated, and extracted with DCM 10 mL (5 mL*2). The combined organic layers were washed with brine 10 mL (5 mL*2), dried over Na$_2$SO$_4$, filtered and concentrated under reduced pressure to afford (2-(chloromethyl)oxazol-4-yl)

methanol (100 mg, 678 umol). LCMS (M+H⁺) m/z: 148. ¹H NMR (400 MHz, CDCl₃) δ 7.55 (s, 1H), 4.69-4.45 (m, 4H).

Step 2

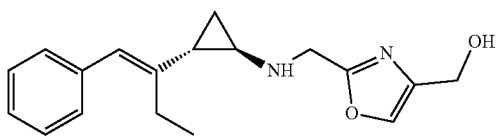 [SMILES: CC/C(=C\c1ccccc1)[C@@H]1C[C@H]1NCc1nc(CO)co1]

(2-((((trans)-2-(E)-1-phenylbut-1-en-2-yl)cyclopropyl)amino)methyl)oxazol-4-yl)methanol (Racemic)

To a solution of (trans)-2-[(1E)-1-benzylidenepropyl]cyclopropanamine hydrochloride (159.2 mg, 711.6 umol, 1.50 eq) and (2-(chloromethyl)oxazol-4-yl)methanol (70 mg, 474.4 umol, 1.00 eq) in CH₃CN (5 mL) was added K₂CO₃ (196.7 mg, 1.42 mmol, 3.00 eq). The mixture was stirred at 25° C. for 16 hour. The reaction mixture was diluted with EtOAc (10 mL), filtered, and concentrated under reduced pressure to give a residue. The residue was purified by prep-TLC (SiO₂, EtOAc) to afford (2-((((trans)-2-((E)-1-phenylbut-1-en-2-yl)cyclopropyeamino)methyl)oxazol-4-yl)methanol (100.0 mg, 335.1 umol).

LCMS (M+H⁺) m/z:299. ¹H NMR (400 MHz, CD₃OD) δ 7.82-7.72 (m, 1H), 7.21-7.05 (m, 5H), 6.04 (d, J=5.7 Hz, 1H), 4.59-4.39 (m, 2H), 4.05-3.88 (m, 2H), 2.33-2.18 (m, 4H), 1.18-1.05 (m, 5H).

Step 3

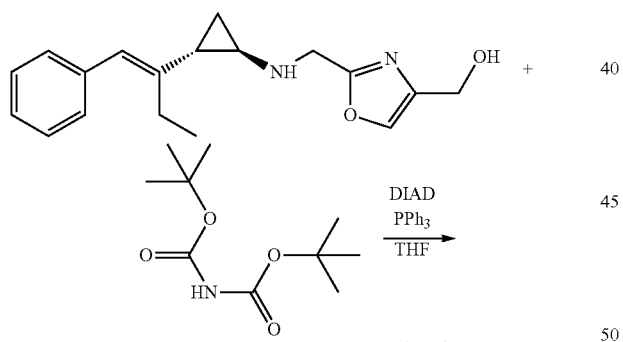

tert-butyl N-[[2-[[[(trans)-2-[(1E)-1-benzylidenepropyl]cyclopropyl]amino]methyl]oxazol-4-yl)methyl]-N-tert-butoxycarbonyl-carbamate (Racemic)

To a solution of (2-((((trans)-2-(E)-1-phenylbut-1-en-2-yl)cyclopropyl)amino)methyl)oxazol-4-yl)methanol (50.0 mg, 167.6 umol, 1.00 eq) and tert-butyl N-tert-butoxycarbonylcarbamate (36.4 mg, 167.6 umol, 1.00 eq) in THF (2 mL) were added PPh₃ (65.9 mg, 251.36 umol, 1.50 eq) and DIAD (67.8 mg, 335.14 umol, 65.16 uL, 2.00 eq) at 0° C. The mixture was stirred at 25° C. for 16 hours. The reaction mixture was quenched by addition water (5 mL) at 0° C., and extracted with EtOAc (20 mL). The combined organic layers were washed with brine (5 mL*2), dried over Na₂SO₄, filtered and concentrated under reduced pressure to give a residue. The residue was purified by prep-TLC (SiO₂, EtOAc:PE=2:1) to afford tert-butyl N-[[2-[[[(trans)-2-[(1E)-1-benzylidenepropyl]cyclopropyl]amino]methyl]oxazol-4-yl]methyl]-N-tert-butoxycarbonyl-carbamate (20 mg, 40.2 umol). LCMS (M+H⁺) m/z 498 ¹H NMR (400 MHz, CD₃OD) δ 7.69 (s, 1H), 7.20-7.08 (m, 5H), 6.02 (s, 1H), 4.68 (s, 2H), 3.94 (s, 2H), 2.30-2.18 (m, 4H), 1.49 (d, J=3.5 Hz, 18H), 1.11 (t, J=7.5 Hz, 5H).

Step 4

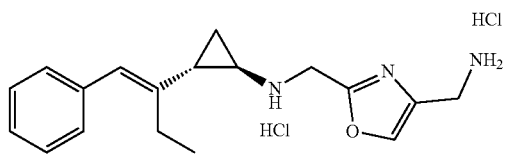 [SMILES: Cl ; CC/C(=C\c1ccccc1)[C@@H]1C[C@H]1NCc1nc(CN)co1 ; Cl]

(trans)-N-[[2-(aminomethyl)oxazol-4-yl]methyl]-2-[(1E)-1-benzylidenepropyl]cyclopropanamine; Dihydrochloride (Racemic)

To a solution of tert-butyl N-[[4-[[[(trans)-2-[(1E)-1-benzylidenepropyl]cyclopropyl]amino]methyl]oxazol-2-yl]methyl]-N-tert- butoxycarbonyl-carbamate (20.0 mg, 40.2 umol, 1.00 eq) in MeOH (1 mL) was added HCl (4 M in MeOH, 10 uL, 1.00 eq). The mixture was stirred at 25° C. for 2 hour. The residue was purified by prep-HPLC (HCl) to afford (trans)-N-[[2-(aminomethyl)oxazol-4-yl]methyl]-2-[(1E)-1-benzylidenepropyl]cyclopropanamine; dihydrochloride (2.4 mg, 6.5 umol). LCMS (M+H⁺) m/z 298. ¹H NMR (400 MHz, CD₃OD) δ 8.16 (s, 1H), 7.35-7.27 (m, 2H), 7.25-7.15 (m, 3H), 6.28 (s, 1H), 4.65 (s, 2H), 4.12 (s, 2H), 3.07 (td, J=3.9, 7.6 Hz, 1H), 2.40-2.27 (m, 2H), 2.24-2.14 (m, 1H), 1.42-1.34 (m, 1H), 1.30-1.25 (m, 1H), 1.18 (t, J=7.5 Hz, 3H).

Synthesis of (trans)-2-((E)-1-phenylbut-1-en-2-yl)cyclopropan-1-amine (S)-2-hydroxy-2-phenylacetate (1R,2S or 1S,2R)

Step 1

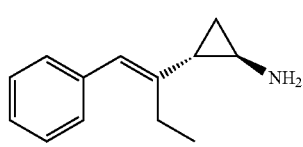

(trans)-2-((E)-1-phenylbut-1-en-2-yl)cyclopropan-1-amine (racemic)

Racemic compound (trans)-2-((E)-1-phenylbut-1-en-2-yl)cyclopropan-1-amine hydrochloride (1.8 kg, 8.04 mol)

was charged to a separatory funnel. 37% K₃PO₄(5.0 L, 2.8 vol) was added followed by EtOAc (18.0 L, 10 vol). The layers were separated and the organic layer was concentrated under reduced pressure to a low volume (~200 mL EtOAc). EtOH (200 proof, 1 L) was added to the flask and concentrated to a low volume (approximately 130 mL of solvent was remaining). GC analysis showed <1% EtOAc. The solution was polished filtered. *Absolute stereochemistry not determined.

Step 2

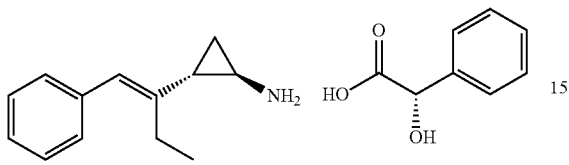

(1R,2S or 1S,2R)-2-((E)-1-phenylbut-1-en-2-yl) cyclopropan-1-amine (S)-2-hydroxy-2-phenylacetate (Single Stereoisomer)

A 50 L reactor equipped with mechanical stirrer, internal temperature probe, and nitrogen inlet was charged with (S)-Mandelic Acid (918 g, 6.03 mol). 95% EtOH (15 L) was charged and stirred until all solid dissolved. The freebase solution was added followed by 95% EtOH to obtain a total volume of 22.5 L (15 vol based on freebase). The reaction stirred over three days at 25° C. and was filtered. The solid was washed with 15% EtOH in water (4.0 L) and dried under vacuum at 45° C. to provide the chiral (S)-Mandelic acid salt (819 g, 2.41 mol, 30.0% yield, 98.9% er) as a single stereoisomer* as a white/off-white solid.
*Absolute stereochemistry not determined.

Reductive amination with mandelate salt

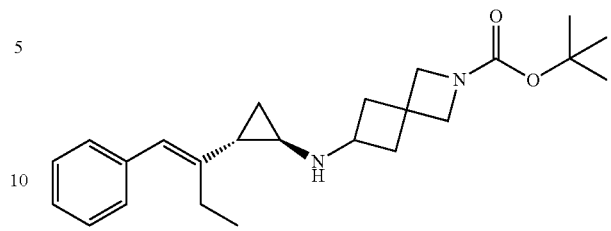

tert-butyl 6-(((1R,2S or 1S,2R)-2-(E)-1-phenylbut-1-en-2-yl)cyclopropyl)amino)-2-azaspiro[3.3]heptane-2-carboxylate (Single Stereoisomer)

To (1R,2S or 1S,2R)-2-((E)-1-phenylbut-1-en-2-yl)cyclopropanamine (S)-2-hydroxy-2-phenylacetate (6.82 g, 20.1 mmol) (single stereoisomer) and tert-butyl 6-oxo-2-azaspiro [3.3]heptane-2-carboxylate (4.25 g, 20.1 mmol) in 1,2-DCE (100 mL) was added sodium triacetoxyborohydride (8.98 g, 42.4 mmol). After 30 min. the reaction was quenched with K₂CO₃ (aq.) and extracted with DCM (2×150 mL). The organic phase was concentrated and the crude residue was purified via column chromatography (40 g column, 5% to 100% EtOAc:hexanes) to afford tert-butyl 6-(((1R,2S or 1S,2R)-2-((E)-1-phenylbut-1-en-2-yl)cyclopropyl)amino)-2-azaspiro[3.3]heptane-2-carboxylate (single stereoisomer) (1.35 g, 3.52 mmol). LCMS M/Z: 383.7 (M+H).

Using the appropriate starting materials and modifications the following intermediates were synthesized using the procedure described for tert-butyl 6-(((1R,2S or 1S, 2R)-2-((E)-1-phenylbut-1-en-2-yl)cyclopropyl)amino)-2-azaspiro [3.3]heptane-2-carboxylate.

| Structure/Name | Stereochemical comment | LCMS m/z |
|---|---|---|
| N-((1R,2S or 1S,2R)-2-((E)-1-phenylbut-1-en-2-yl)cyclopropyl)-1,4-dioxaspiro[4.5]decan-8-amine | single stereoisomer | |
| tert-butyl N-[[3-[[[(1R,2S or 1S,2R)-2-[(1E)-1-benzylidenepropyl]cyclopropyl]amino]methyl]-2-pyridyl]methyl]-N-tert-butoxycarbonyl-carbamate | single stereoisomer | 408 |

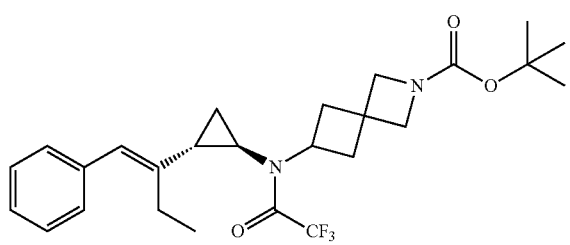 [SMILES: CC/C(=C\c1ccccc1)[C@@H]1C[C@H]1N(C(=O)C(F)(F)F)C1CC2(C1)CN(C(=O)OC(C)(C)C)C2]

tert-butyl 6-(2,2,2-trifluoro-N-((1R,2S or 1S,2R)-2-(E)-1-phenylbut-1-en-2-yl)cyclopropyl)acetamido)-2-azaspiro[3.3]heptane-2-carboxylate (Single Stereoisomer)

To tert-butyl 6-(((1R,2S or 1S,2R)-2-((E)-1-phenylbut-1-en-2-yl)cyclopropyl)amino)-2-azaspiro[3.3]heptane-2-carboxylate (1.35 g, 3.52 mmol) dissolved in DCM (9 mL) was added diisopropylethylamine (826 μL, 4.75 mmol). The solution was cooled to 0° C. before addition of trifluoroacetic anhydride (561 μL, 4.04 mmol). The reaction mixture was stirred for 24 h, while warming to room temperature. The volatiles were evaporated under reduced pressure and the crude residue purified by column chromatography on silica gel (0% to 40% EtOAc in hexanes, 40 g) to afford tert-butyl 6-(2,2,2-trifluoro-N-((1R,2S or 1S,2R)-2-((E)-1-phenylbut-1-en-2-yl)cyclopropyl)acetamido)-2-azaspiro[3.3]heptane-2-carboxylate (single stereoisomer) (1.34 g, 2.80 mmol). LCMS m/z: 501.1 (M+Na)/423.7 (M-tBu+H).

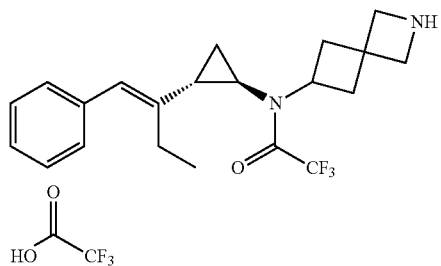

2,2,2-trifluoro-N-((1R,2S or 1S,2R)-2-(E)-1-phenylbut-1-en-2-yl)cyclopropyl)-N-(2-azaspiro[3.3]heptan-6-yl)acetamide 2,2,2-trifluoroacetate (Single Stereoisomer)

To tert-butyl 6-(2,2,2-trifluoro-N-((1R,2S or 1S,2R)-2-((E)-1-phenylbut-1-en-2-yl)cyclopropyl)acetamido)-2-azaspiro[3.3]heptane-2-carboxylate (1.36 g, 2.84 mmol) dissolved in DCM (10 mL) was added trifluoroacetic acid (2.16 mL, 28.4 mmol) and the solution stirred for 5 h. The reaction was concentrated to afford 2,2,2-trifluoro-N-((1R,2S or 1S,2R)-2-((E)-1-phenylbut-1-en-2-yl)cyclopropyl)-N-(2-azaspiro[3.3]heptan-6-yl)acetamide 2,2,2-trifluoroacetate (single stereoisomer)(1.39 mg, 2.82 μmol). LCMS m/z 379 [M+H$^+$].

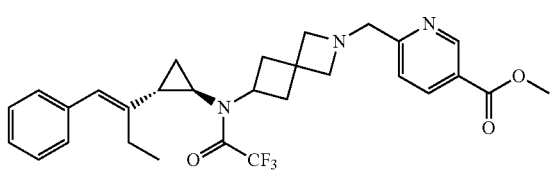 [SMILES: CC/C(=C\c1ccccc1)[C@@H]1C[C@H]1N(C(=O)C(F)(F)F)C1CC2(C1)CN(Cc1ccc(C(=O)OC)cn1)C2]

methyl 6-((6-(2,2,2-trifluoro-N-((1R,2S or 1S,2R)-2-((E)-1-phenylbut-1-en-2-yl)cyclopropyl)acetamido)-2-azaspiro[3.3]heptan-2-yl)methyl)nicotinate (Single Stereoisomer)

To 2,2,2-trifluoro-N-((1R,2S or 1S,2R)-2-(E)-1-phenylbut-1-en-2-yl)cyclopropyl)-N-(2-azaspiro[3.3]heptan-6-yl)acetamide 2,2,2-trifluoroacetate (196 mg, 400 μmol) dissolved in DCE (2 mL) was added methyl 6-formylnicotinate (72.6 mg, 440 μmol). The reaction mixture was stirred at room temperature for 30 min before addition of sodium triacetoxyborohydride (211 mg, 1 mmol). The reaction mixture was stirred for 30 min before being partitioned between potassium carbonate (aq.) and DCM. The organic layer was washed with brine, dried with Na$_2$SO$_4$, filtered, and concentrated. The crude product was purified by silica gel column chromatography to afford methyl 6-((6-(2,2,2-trifluoro-N-((1R,2S or 1S,2R)-2-(E)-1-phenylbut-1-en-2-yl)cyclopropyl)acetamido)-2-azaspiro[3.3]heptan-2-yl)methyl)nicotinate (single stereoisomer)(150 mg, 263 μmol); LCMS M/Z: 528 (M+H).

Using the appropriate starting materials and modifications the following intermediates were synthesized using the procedure described for methyl 6-((6(2,2,2-trifluoro-N-((1R,2S or 1S,2R)-2-((E)-1-phenylbut-1-en-2-yl)cyclopropyl)acetamido)-2-azaspiro[3.3]heptan-2-yl)methyl)nicotinate.

| Structure/Name | Stereochemical comment | LCMS m/z |
|---|---|---|
| methyl 4-((6-(2,2,2-trifluoro-N-((1R,2S or 1S,2R)-2-((E)-1-phenylbut-1-en-2-yl)cyclopropyl)acetamido)-2-azaspiro[3.3]heptan-2-yl)methyl)benzoate | single stereoisomer | |

| Structure/Name | Stereochemical comment | LCMS m/z |
|---|---|---|
| tert-butyl 5-((6-(2,2,2-trifluoro-N-((1R,2S or 1S,2R)-2-((E)-1-phenylbut-1-en-2-yl)cyclopropyl)acetamido)-2-azaspiro[3.3]heptan-2-yl)methyl)picolinate | single stereoisomer | |
| N-(2-(4-(1H-tetrazol-5-yl)benzyl)-2-azaspiro[3.3]heptan-6-yl)-2,2,2-trifluoro-N-((1R,2S or 1S,2R)-2-((E)-1-phenylbut-1-en-2-yl)cyclopropyl)acetamide | single stereoisomer | |
| methyl 3-methyl-4-((6-(2,2,2-trifluoro-N-((1R,2S or 1S,2R)-2-((E)-1-phenylbut-1-en-2-yl)cyclopropyl)acetamido)-2-azaspiro[3.3]heptan-2-yl)methyl)benzoate | single stereoisomer | 541 |
| methyl 2-methyl-4-((6-(2,2,2-trifluoro-N-((1R,2S or 1S,2R)-2-((E)-1-phenylbut-1-en-2-yl)cyclopropyl)acetamido)-2-azaspiro[3.3]heptan-2-yl)methyl)benzoate | single stereoisomer | 541 |
| methyl 5-((6-(2,2,2-trifluoro-N-((1R,2S or 1S,2R)-2-((E)-1-phenylbut-1-en-2-yl)cyclopropyl)acetamido)-2-azaspiro[3.3]heptan-2-yl)methyl)pyrazine-2-carboxylate | single stereoisomer | 529 |

| Structure/Name | Stereochemical comment | LCMS m/z |
|---|---|---|
| 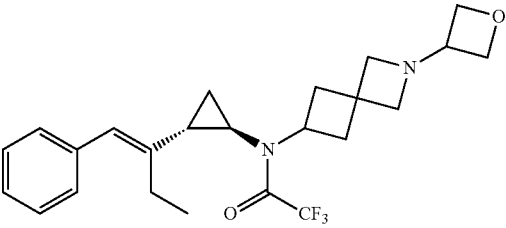   2,2,2-trifluoro-N-(2-(oxetan-3-yl)-2-azaspiro[3.3]heptan-6-yl)-N-((1R,2S or 1S,2R)-2-((E)-1-phenylbut-1-en-2-yl)cyclopropyl)acetamide | single stereoisomer | 435 |

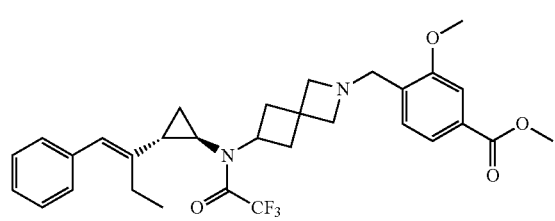 [SMILES: CC/C(=C\c1ccccc1)[C@@H]1C[C@H]1N(C(=O)C(F)(F)F)C1CC2(C1)CN(Cc1ccc(C(=O)OC)cc1OC)C2]

methyl 3-methoxy-4-((6-(2,2,2-trifluoro-N-((1R,2S or 1S,2R)-2-(E)-1-phenylbut-1-en-2-yl)cyclopropyl)acetamido)-2-azaspiro[3.3]heptan-2-yl)methyl)benzoate (Single Stereoisomer)

To 2,2,2-trifluoro-N-((1R,2S or 1S,2R)-2-(E)-1-phenylbut-1-en-2-yl)cyclopropyl)-N-(2-azaspiro[3.3]heptan-6-yl)acetamide 2,2,2-trifluoroacetate (270 mg, 548 µmol) dissolved in DMF was added methyl 4-(bromomethyl)-3-methoxybenzoate (134 mg, 520 µmol) followed by potassium carbonate (187 mg, 1.36 mmol). The reaction mixture was stirred at room temperature for 24 hours before being partitioned between NaHCO₃ (aq., sat.) and EtOAc. The organic phase was washed successively with brine, dried with Na2SO₄, filtered, and concentrated. The crude residue was purified by silica gel chromatography (5% to 100% EtOAc in hexanes, then 0% to 10% MeOH in EtOAc) to afford methyl 3-methoxy-4-((6-(2,2,2-trifluoro-N-((1R,2S or 1S,2R)-2-((E)-1-phenylbut-1-en-2-yl)cyclopropyl)acetamido)-2-azaspiro[3.3]heptan-2-yl)methyl)benzoate (single stereoisomer)(125 mg, 224 µmol). LCMS M/Z: 557.3 (M+H).

Using the appropriate starting materials and modifications the following intermediates were synthesized using the procedure described for methyl 3-methoxy-4-((6-(2,2,2-trifluoro-N-((1R,2S or 1S,2R)-2-((E)-1-phenylbut-1-en-2-yl)cyclopropyl)acetamido)-2-azaspiro[3.3]heptan-2-yl)methyl)benzoate.

| Structure/Name | Stereochemical comment | LCMS m/z |
|---|---|---|
| 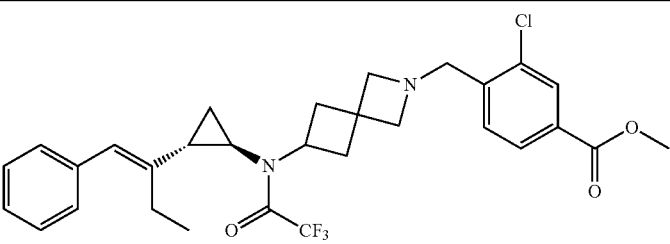   methyl 3-chloro-4-((6-(2,2,2-trifluoro-N-((1R,2S or 1S,2R)-2-((E)-1-phenylbut-1-en-2-yl)cyclopropyl)acetamido)-2-azaspiro[3.3]heptan-2-yl)methyl)benzoate | single stereoisomer | |
| 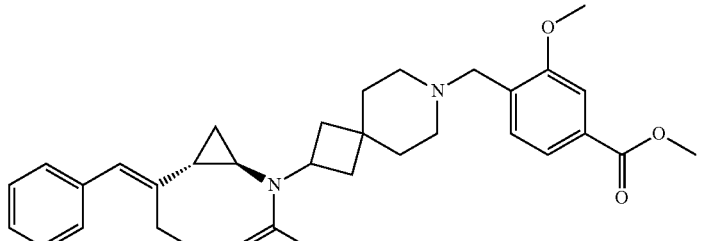   methyl 3-methoxy-4-((2-(2,2,2-trifluoro-N-((1R,2S or 1S,2R)-2-((E)-1-phenylbut-1-en-2-yl)cyclopropyl)acetamido)-7-azaspiro[3.5]nonan-7-yl)methyl)benzoate | single stereoisomer | 585 |

Compound 249: 6-((6-(((1R,2S or 1S,2R)-2-(E)-1-phenylbut-1-en-2-yl)cyclopropyl)amino)-2-azaspiro[3.3]heptan-2-yl)methyl)nicotinic Acid Bis Trifluoroacetate (Single Stereoisomer)

Step 1

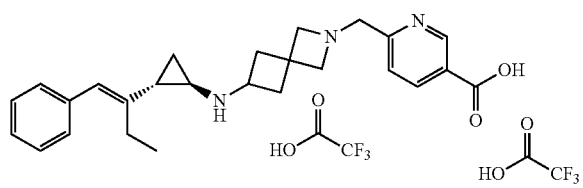

6-((6-(((1R,2S or 1S,2R)-2-((E)-1-phenylbut-1-en-2-yl)cyclopropyl)amino)-2-azaspiro[3.3]heptan-2-yl)methyl)nicotinic Acid Bis Trifluoroacetate (Single Stereoisomer)

To tert-butyl 6-((6-(2,2,2-trifluoro-N-((1R,2S or 1S,2R)-2-((E)-1-phenylbut-1-en-2-yl)cyclopropyl)acetamido)-2-azaspiro[3.3]heptan-2-yl)methyl)nicotinate (227 mg, 400 µmol) dissolved in MeOH (5 mL) at 0° C. was added NaOH (2 mL, 2 mL mmol). The reaction mixture was warmed to 40° C. for 24 h. The reaction was cooled to room temperature and acidified with acetic acid. The solution was concentrated to a volume of 4 ml and purified by preparative HPLC (ACN:water+0.1% TFA on Sunfire column). Pure fractions were frozen and lyophilized to afford 6-((6-(((1R,2S or 1S,2R)-2-(E)-1-phenylbut-1-en-2-yl)cyclopropyl)amino)-2-azaspiro[3.3]heptan-2-yl)methyl)nicotinic acid bis trifluoroacetate (single stereoisomer) (131 mg, 202 µmol). 1H NMR (400 MHz, DMSO-d6) δ 13.68 (br. s, 1H), 10.62 (br. s., 1H), 9.30 (br. s., 2H), 9.05 (d, J=2.20 Hz, 1H), 8.34 (dd, J=2.20, 8.06 Hz, 1H), 7.57 (d, J=8.30 Hz, 1H), 7.30-7.37 (m, 2H), 7.12-7.27 (m, 3H), 6.20 (s, 1H), 4.66 (br. s., 2H), 4.22-4.36 (m, 2H), 4.18 (br. s., 2H), 3.78 (br. s., 1H), 2.53-2.79 (m, 3H), 2.51-2.56 (m, 1H), 2.39-2.48 (m, 1H), 2.14-2.28 (m, 2H), 1.90-2.01 (m, 1H), 1.14-1.22 (m, 2H), 1.11 (t, J=7.45 Hz, 3H). LCMS M/Z: 418 (M+H).

Using the appropriate starting materials and modifications the following examples were synthesized using the procedure described for 6-((6-(((trans)-2-((E)-1-phenylbut-1-en-2-yl)cyclopropyl)amino)-2-azaspiro[3.3]heptan-2-yl)methyl)nicotinic acid.

| Example | Structure/Name | Stereochemical comment | LCMS m/z; 1H NMR |
|---|---|---|---|
| 250 | 4-((6-(((1R,2S or 1S,2R)-2-((E)-1-phenylbut-1-en-2-yl)cyclopropyl)amino)-2-azaspiro[3.3]heptan-2-yl)methyl)benzoic acid bis trifluoroacetate | single stereoisomer | 417; 1H NMR (400 MHz, DMSO-d6) δ 13.09-13.23 (br. s., 1H), 10.27 (br. s., 1H), 9.14 (br. s., 2H), 8.00 (d, J = 8.30 Hz, 2H), 7.55 (d, J = 8.30 Hz, 2H), 7.30-7.38 (m, 2H), 7.11-7.26 (m, 3H), 6.19 (s, 1H), 4.39 (m, 2H), 4.17 (m, 3H), 4.01 (m, 1H), 3.75 (m, 1H), 2.73 (br. s., 1H), 2.53-2.69 (m, 2H), 2.43 (br. s., 2H), 2.12-2.28 (m, 2H), 1.94 (br. s., 1H), 1.13-1.22 (m, 2H), 1.11 (t, J = 7.57 Hz, 3H). |
| 251 | 5-((6-(((1R,2S or 1S,2R)-2-((E)-1-phenylbut-1-en-2-yl)cyclopropyl)amino)-2-azaspiro[3.3]heptan-2-yl)methyl)picolinic acid bis trifluoroacetate | single stereoisomer | 418; 1H NMR (400 MHz, DMSO-d6) δ 13.18-13.50 (m, 1H), 10.43-10.79 (m, 1H), 9.31 (br. s., 2H), 8.74 (d, J = 1.71 Hz, 1H), 8.07-8.13 (m, 1H), 7.96-8.06 (m, 1H), 7.29-7.39 (m, 2H), 7.09-7.27 (m, 3H), 6.19 (s, 1H), 4.45 (br. s., 2H), 3.98-4.26 (m, 4H), 3.76 (quin, J = 7.93 Hz, 1H), 2.51-2.79 (m, 4H), 2.12-2.45 (m, 3H), 1.86-2.05 (m, 1H), 0.82-1.28 (m, 5H) |
| 252 | 2-(4-(1H-tetrazol-5-yl)benzyl)-N-((1R,2S or 1S,2R)-2-((E)-1-phenylbut-1-en-2-yl)cyclopropyl)-2-azaspiro[3.3]heptan-6-amine bis(2,2,2-trifluoroacetate) | single stereoisomer | 441; 1H NMR |

| Example | Structure/Name | Stereochemical comment | LCMS m/z; 1H NMR |
|---|---|---|---|
| 253 | 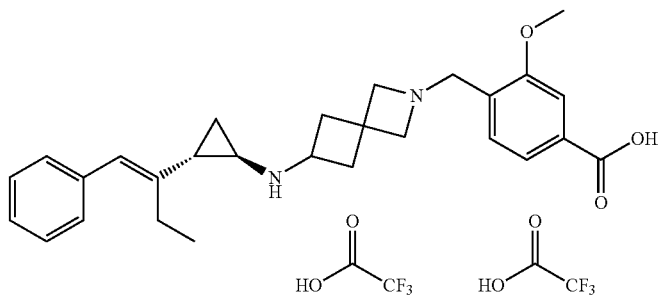<br>3-methoxy-4-((6-(((1R,2S or 1S,2R)-2-((E)-1-phenylbut-1-en-2-yl)cyclopropyl)amino)-2-azaspiro[3.3]heptan-2-yl)methyl)benzoic acid bis trifluoroacetate | single stereoisomer | 447; 1H NMR (400 MHz, DMSO-d6) δ 13.25 (br. s, 1H), 10.04 (br. s., 1H), 9.24 (br. s., 2H), 7.51-7.64 (m, 2H), 7.49 (d, J = 7.81 Hz, 1H), 7.28-7.39 (m, 2H), 7.11-7.27 (m, 3H), 6.19 (s, 1H), 4.36 (d, J = 4.39 Hz, 2H), 4.19 (d, J = 5.13 Hz, 2H), 4.00-4.16 (m, 2H), 3.90 (s, 3H), 3.75 (br. s., 2H), 2.73 (br. s., 1H), 2.53-2.69 (m, 2H), 2.38-2.47 (m, 2H), 2.15-2.29 (m, 2H), 1.90-2.01 (m, 1H), 1.13-1.20 (m, 1H), 1.11 (t, J = 7.45 Hz, 3H) |
| 254 | 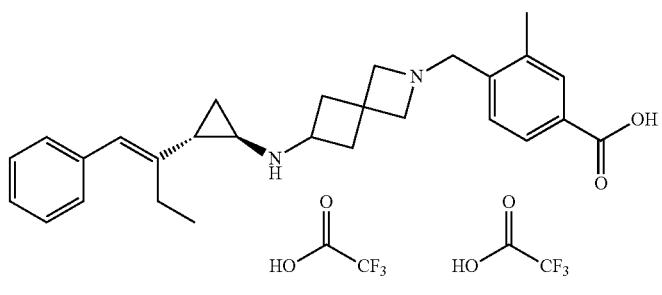<br>3-methyl-4-((6-(((1R,2S or 1S,2R)-2-((E)-1-phenylbut-1-en-2-yl)cyclopropyl)amino)-2-azaspiro[3.3]heptan-2-yl)methyl)benzoic acid bis trifluoroacetate | single stereoisomer | 431; 1H NMR |
| 255 | 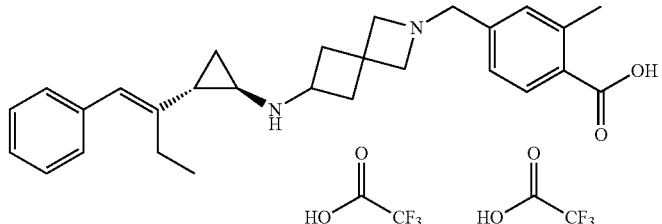<br>2-methyl-4-((6-(((1R,2S or 1S,2R)-2-((E)-1-phenylbut-1-en-2-yl)cyclopropyl)amino)-2-azaspiro[3.3]heptan-2-yl)methyl)benzoic acid bis trifluoroacetate | single stereoisomer | 431; 1H NMR (400 MHz, DMSO-d6) δ 13.05 (br. s, 1H), 10.40 (br. s., 1H), 9.29 (br. s., 2H), 7.86 (d, J = 8.06 Hz, 1H), 7.29-7.39 (m, 4H), 7.16-7.26 (m, 3H), 6.20 (s, 1H), 4.34 (d, J = 4.64 Hz, 2H), 4.08-4.24 (m, 3H), 4.01 (br. s., 1H), 3.68-3.83 (m, 1H), 2.56-2.79 (m, 3H), 2.52 (s, 3H), 2.40-2.48 (m, 2H), 2.15-2.31 (m, 2H), 1.92-2.01 (m, 1H), 1.14-1.20 (m, 2H), 1.11 (t, J = 7.45 Hz, 3H). |
| 256 | 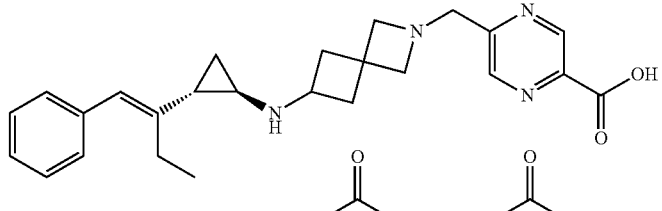<br>5-((6-(((1R,2S or 1S,2R)-2-((E)-1-phenylbut-1-en-2-yl)cyclopropyl)amino)-2-azaspiro[3.3]heptan-2-yl)methyl)pyrazine-2-carboxylic acid bis trifluoroacetate | single stereoisomer | 419; 1H NMR |

| Example | Structure/Name | Stereochemical comment | LCMS m/z; 1H NMR |
|---|---|---|---|
| 257 | 3-fluoro-4-((6-(((1R,2S or 1S,2R)-2-((E)-1-phenylbut-1-en-2-yl)cyclopropyl)amino)-2-azaspiro[3.3]heptan-2-yl)methyl)benzoic acid bis trifluoroacetate | single stereoisomer | 435; 1H NMR (400 MHz, DMSO-d6) δ 13.44 (br. s, 1 H), 10.79 (br. s., 1 H), 9.48 (br. s., 2 H), 7.83 (dd, J = 1.6, 7.9 Hz, 1 H), 7.75 (dd, J = 1.5, 10.3 Hz, 1 H), 7.65 (t, J = 7.6 Hz, 1 H), 7.37-7.29 (m, 2 H), 7.25-7.10 (m, 3 H), 6.19 (s, 1 H), 4.48 (s, 2 H), 4.30-3.93 (m, 4 H), 3.77 (br. s., 1 H), 2.81-2.51 (m, 5 H), 2.27-2.17 (m, 2 H), 2.00 (t, J = 9.9 Hz, 1 H), 1.25-1.14 (m, 2 H), 1.10 (t, J = 7.6 Hz, 3 H) |
| 258 | 3-chloro-4-((6-(((1R,2S or 1S,2R)-2-((E)-1-phenylbut-1-en-2-yl)cyclopropyl)amino)-2-azaspiro[3.3]heptan-2-yl)methyl)benzoic acid bis trifluoroacetate | single stereoisomer | 451; 1H NMR |
| 259 | 3-methoxy-4-((2-(((1R,2S or 1S,2R)-2-((E)-1-phenylbut-1-en-2-yl)cyclopropyl)amino)-7-azaspiro[3.5]nonan-7-yl)methyl)benzoic acid bis trifluoroacetate | single stereoisomer | 475; $^1$H NMR (400 MHz, DMSO-d$_6$) δ 13.30 (br s, 1H), 9.32 (br s, 2H), 7.64-7.55 (m, 3H), 7.38-7.32 (m, 2H), 7.26-7.17 (m, 3H), 6.21 (s, 1H), 4.35-4.26 (m, 2H), 3.92 (s, 3H), 3.90-3.80 (m, 1H), 3.35-3.20 (m, 3H), 3.12-2.99 (m, 1H), 2.98-2.87 (m, 1H), 2.72 (br s, 1H), 2.42-2.33 (m, 1H), 2.29-2.20 (m, 2H), 2.17-2.06 (m, 2H), 2.04-1.92 (m, 3H), 1.82-1.69 (m, 3H), 1.24-1.17 (m, 1H), 1.16-1.09 (m, 4H). |

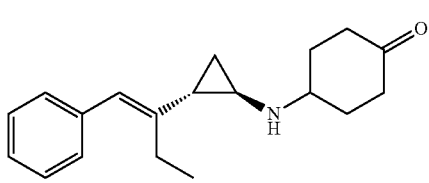 [SMILES: CC/C(=C\c1ccccc1)[C@@H]1C[C@H]1NC1CCC(=O)CC1]

4-(((1R,2S or 1S,2R)-2-((E)-1-phenylbut-1-en-2-yl)cyclopropyl)amino)cyclohexan-1-one (Single Stereoisomer)

To N-((1R,2S or 1S,2R)-2-((E)-1-phenylbut-1-en-2-yl)cyclopropyl)-1,4-dioxaspiro[4.5]decan-8-amine (2.89 g, 8.82 mmol) dissolved in THF (60 mL) was added hydrochloric acid (6M aqueous, 13.2 mL, 52.9 mmol) and the reaction mixture was stirred at 60° C. for 16 h. The solution was cooled, partitioned between potassium carbonate (aqueous) solution and ethyl acetate. The aqueous layer was extracted once with ethyl acetate. The combined organic layers were washed with brine, dried with sodium sulfate, filtered and concentrated. The crude residue was purified by silica gel column chromatography (methanol:ethyl acetate gradient) to afford 4-(((1R,2S or 1S,2R)-2-((E)-1-phenylbut-1-en-2-yl)cyclopropyl)amino)cyclohexanone (single stereoisomer)(2.50 g, 8.82 mmol). LCMS M/Z: 284.2 (M+H).

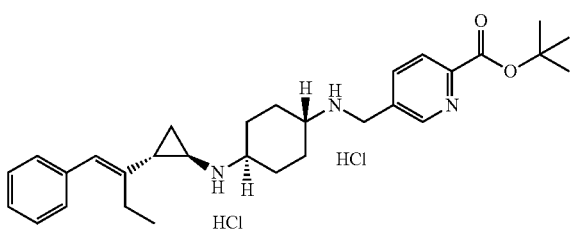 [SMILES: CC/C(=C\c1ccccc1)[C@@H]1C[C@H]1N[C@H]1CC[C@H](NCc2ccc(C(=O)OC(C)(C)C)nc2)CC1 ; Cl ; Cl]

tert-butyl 5-((((trans)-4-(((1R,2S or 1S,2R)-2-((E)-1-phenylbut-1-en-2-yl)cyclopropyl)amino)cyclohexyl)amino)methyl)picolinate Dihydrochloride (Single Stereoisomer)

To 4-(((1R,2S or 1S,2R)-2-((E)-1-phenylbut-1-en-2-yl)cyclopropyl)amino)cyclohexanone (306 mg, 1.08 mmol) and tert-butyl 5-(aminomethyl)picolinate (272 mg, 1.30 mmol) in DCE (3 mL) was added sodium triacetoxyborohydride (130 mg, 0.61 mmol). The reaction was stirred for 30 min before diluting with DCM and potassium carbonate solution (1 M). The organic phase was isolated, evaporated and the crude residue purified by column chromatography (silica, 0% to 100% 1:10:90 NH4OH:MeOH 0% to 10% MeOH in EtOAc). The last eluting fractions were collected. The residue was dissolved in MTBE and treated with HCl (2M in Et2O, 4 equiv.) before being evaporated under reduced pressure. The resulting solid was triturated with an acetonitrile:MTBE mixture (1:2) and collected via filtration to afford tert-butyl 5-((((trans)-4-(((1R,2S or 1S,2R)-2-(E)-1-phenylbut-1-en-2-yl)cyclopropyl)amino)cyclohexyl)amino)methyl)picolinate dihydrochloride (single stereoisomer). LCMS M/Z: 476.3 (M+H)/498.3 (M+Na)/420.3 (M-tBu+H).

Using the appropriate starting materials and modifications the following intermediates were synthesized using the procedure described for tert-butyl 5-((((trans)-4-(((trans)-2-((E)-1-phenylbut-1-en-2-yl)cyclopropyl)amino)cyclohexyl)amino)methyl)picolinate.

Compound 260: 5-((((trans)-4-(((1R,2S or 1S,2R)-2-((E)-1-phenylbut-1-en-2-yl)cyclopropyl)amino)cyclohexyl)amino)methyl)picolinic acid bis trifluoroacetate (single stereoisomer)

Step 1

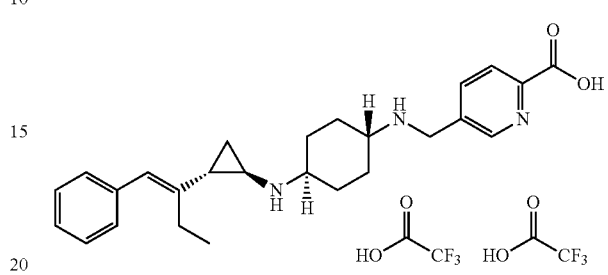

To tert-butyl 5-((((trans)-4-(((1R,2S or 1S,2R)-2-(E)-1-phenylbut-1-en-2-yl)cyclopropyl)amino)cyclohexyl)amino)methyl)picolinate trihydrochloride (135 mg, 230 µmol) dissolved in dioxane (500 uL) was added HCl (0.1 mL, 6 M). The solution was heated for 48 h at 45° C. The reaction was cooled to room temperature and concentrated. The crude residue was purified via preparative HPLC to afford 5-((((trans)-4-(((1R,2S or 1S,2R)-2-((E)-1-phenylbut-1-en-2-yl)cyclopropyl)amino)cyclohexyl)amino)methyl)picolinic acid bis trifluoroacetate (single stereoisomer) (4.7 mg). LCMS M/Z: 420.2 (M+H).

Using the appropriate starting materials and modifications the following intermediates were synthesized using the procedure described for 5-((((trans)-4-(((1R,2S or 1S,2R)-2-(E)-1-phenylbut-1-en-2-yl)cyclopropyl)amino)cyclohexyl)amino)methyl)picolinic acid.

| Structure/Name | Stereochemical comment | LCMS m/z |
|---|---|---|
| ![structure] methyl 3-methoxy-4-((((trans)-4-(((1R,2S or 1S,2R)-2-((E)-1-phenylbut-1-en-2-yl)cyclopropyl)amino)cyclohexyl)amino)methyl)benzoate | single stereoisomer | 463 |

| Cmpd. | Name/Structure | Stereochemical comment | LCMS m/z; 1H NMR |
|---|---|---|---|
| 261 | 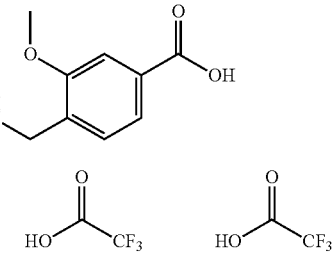<br>3-methoxy-4-(((((trans)-4-((((1R,2S or 1S,2R)-2-((E)-1-phenylbut-1-en-2-yl)cyclopropyl)amino)cyclohexyl)amino)methyl)benzoic acid bis trifluoroacetate | Single stereoisomer | 449; 1H NMR |

Compound 262: 2-(oxetan-3-yl)-N-((1R,2S or 1S,2R)-2-(E)-1-phenylbut-1-en-2-yl)cyclopropyl)-2-azaspiro[3.3]heptan-6-amine bis(2,2,2-trifluoroacetate) (Single Stereoisomer)

Step 1

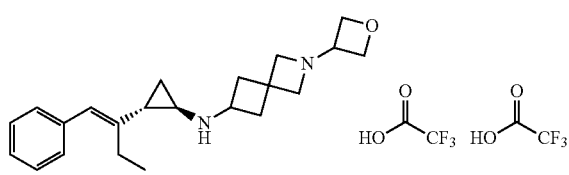 [SMILES: CC/C(=C\c1ccccc1)[C@@H]1C[C@H]1NC1CC2(C1)CN(C1COC1)C2 ; O=C(O)C(F)(F)F ; O=C(O)C(F)(F)F]

To 2,2,2-trifluoro-N-(2-(oxetan-3-yl)-2-azaspiro[3.3]heptan-6-yl)-N-((1R,2S or 1S,2R)-2-((E)-1-phenylbut-1-en-2-yl)cyclopropyl)acetamide (173 mg, 400 μmol) dissolved in MeOH was added NaOH (328 uL, 0.328 mmol) at 0° C. and the reaction was warmed to room temperature. The solution was acidified with AcOH and purified via prep HPLC (ACN:water+0.1 TFA, SunFire column) to afford 2-(oxetan-3-yl)-N-((1R,2S or 1S,2R)-2-(E)-1-phenylbut-1-en-2-yl)cyclopropyl)-2-azaspiro[3.3]heptan-6-amine bis(2,2,2-trifluoroacetate) (single stereoisomer) (15.0 mg, 26.4 μmol) after lyophilization. LCMS m/z: 339. 1H NMR (400 MHz, DMSO-d6) δ 11.17 (br. s, 1H), 9.25 (br. s., 2H), 7.28-7.42 (m, 2H), 7.07-7.27 (m, 3H), 6.20 (s, 1H), 4.67-4.79 (m, 2H), 4.35-4.52 (m, 3H), 3.95-4.30 (m, 5H), 3.73-3.85 (m, 1H), 2.56-2.80 (m, 3H), 2.18-2.28 (m, 2H), 1.88-2.02 (m, 1H), 1.15-1.22 (m, 2H), 1.11 (t, J=7.57 Hz, 3H).

Compound 263: tert-butyl 4-hydroxy-4-(((((1R,2S or 1S,2R)-2-((E)-1-phenylbut-1-en-2-yl)cyclopropyl)amino)methyl)piperidine-1-carboxylate (Single Stereoisomer)

Step 1

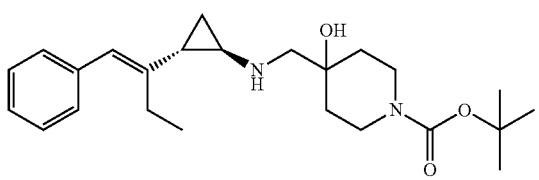 [SMILES: CC/C(=C\c1ccccc1)[C@@H]1C[C@H]1NCC1(O)CCN(C(=O)OC(C)(C)C)CC1]

To a round bottomed flask was added tert-butyl 1-oxa-6-azaspiro[2.5]octane-6-carboxylate (950 mg, 4.45 mmol), (1R,2S or 1S,2R)-2-(E)-1-phenylprop-1-en-2-yl)cyclopropanamine(S)-2-hydroxy-2-phenylacetate (1.44 g, 4.45 mmol), EtOH (25 mL), and N-ethyl-N-isopropylpropan-2-amine (1.71 g, 13.3 mmol). The solution was stirred at room temperature for 2 h. This reaction was then heated to 50° C. for 2 days before cooling to room temperature and concentrating. The crude residue was purified via Biotage to afford tert-butyl 4-hydroxy-4-(((((1R,2S or 1S,2R)-2-((E)-1-phenylbut-1-en-2-yl)cyclopropyl)amino)methyl)piperidine-1-carboxylate (single stereoisomer) (491 mg, 1.22 mmol). LCMS m/z 423 [M+Na⁺].

Step 2

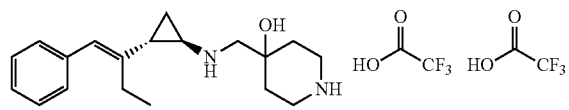 [SMILES: CC/C(=C\c1ccccc1)[C@@H]1C[C@H]1NCC1(O)CCNCC1 ; O=C(O)C(F)(F)F ; O=C(O)C(F)(F)F]

4-(((((1R,2S or 1S,2R)-2-((E)-1-phenylbut-1-en-2-yl)cyclopropyl)amino)methyl)piperidin-4-ol bis(2,2,2-trifluoroacetate) (Single Stereoisomer)

To a round bottomed flask was added tert-butyl 4-hydroxy-4-(((((1R,2S or 1S,2R)-2-((E)-1-phenylbut-1-en-2-yl)cyclopropyeamino)methyl)piperidine-1-carboxylate (50.2 mg, 0.1253 mmol), dioxane (5 mL), and hydrogen chloride (1.04 mL, 6.26 mmol). The vial was heated to 45° C. overnight before cooling to room temperature and concentrating. The crude residue was purified via preparative HPLC to afford 4-(((((1R,2S or 1S,2R)-2-((E)-1-phenylbut-1-en-2-yl)cyclopropyl)amino)methyl)piperidin-4-ol bis(2,2,2-trifluoroacetate) (single stereoisomer)(17.3 mg, 0.03273 mmol). LCMS m/z 301 [M+H⁺]

Compound 264: 2,2-dimethyl-3-(methyl((1R,2S or 1S,2R)-4-(((trans)-2-((E)-1-phenylbut-1-en-2-yl)cyclopropyl)amino)cyclohexyl)amino)propanoic Acid Dihydrochloride (Single Stereoisomer)

Step 1

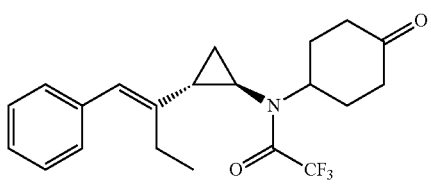 [SMILES: CC/C(=C\c1ccccc1)[C@@H]1C[C@H]1N(C(=O)C(F)(F)F)C1CCC(=O)CC1]

2,2,2-trifluoro-N-(4-oxocyclohexyl)-N-((1R,2S or 1S,2R)-2-((E)-1-phenylbut-1-en-2-yl)cyclopropyl)acetamide (Single Stereoisomer)

To 4-(((1R,2S or 1S,2R)-2-((E)-1-phenylbut-1-en-2-yl)cyclopropyl)amino)cyclohexanone (1.1 g, 3.88 mmol) dissolved in DCM (9 mL) was added diisopropylethylamine (877 μL, 5.04 mmol). The reaction was cooled to 0° C. before addition of trifluoroacetic anhydride (619 μL, 4.46 mmol). The reaction mixture was stirred for 24 h while warming to room temperature. The reaction was concentrated and the crude residue was purified by column chromatography on silica gel (0% to 40% EtOAc in hexanes, 40 g) to afford 2,2,2-trifluoro-N-(4-oxocyclohexyl)-N-((1R,2S or 1S,2R)-2-((E)-1-phenylbut-1-en-2-yl)cyclopropyl)acetamide (single stereoisomer)(1.45 g, 3.82 mmol). LCMS M/Z: 380.2 (M+H)/402.2 (M+Na).

Step 2

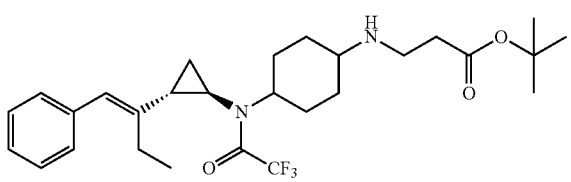 [SMILES: CC/C(=C\c1ccccc1)[C@@H]1C[C@H]1N(C(=O)C(F)(F)F)C1CCC(NCCC(=O)OC(C)(C)C)CC1]

tert-butyl 3-((4-(2,2,2-trifluoro-N-((1R,2S or 1S,2R)-2-(E)-1-phenylbut-1-en-2-yl)cyclopropyl)acetamido)cyclohexyl)amino)propanoate (mixture of diastereomers)

To 2,2,2-trifluoro-N-(4-oxocyclohexyl)-N-((1R,2S or 1S,2R)-2-((E)-1-phenylbut-1-en-2-yl)cyclopropyl)acetamide (450 mg, 1.18 mmol) and tert-butyl 3-aminopropanoate (223 mg, 1.29 mmol) in methanol (10 mL) was added AcOH (1.2 mL). The solution was cooled to 0° C. before addition of sodium cyanoborohydride (162 mg, 2.59 mmol). After stirring 45 min the reaction was quenched with K₂CO₃ (aq. sat.) and extracted with EtOAc (2×100 mL). The combined organics phase was concentrated and the crude residue purified by silica gel chromatography (25 g column, EtOAc:Hexanes, then MeOH:EtOAc) to afford tert-butyl 3-((4-(2,2,2-trifluoro-N-((1R,2S or 1S,2R)-2-((E)-1-phenylbut-1-en-2-yl)cyclopropyl)acetamido)cyclohexyl)amino)propanoate (300 mg, 559 μmol) as a mixture of isomers at the cyclohexane ring. This material was used without further purification in the next step. LCMS M/Z: 537.3 (M+H)

Step 3

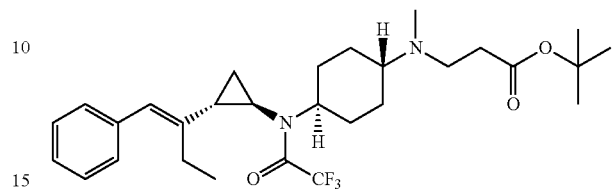

tert-butyl 3-(methyl((trans)-4-(2,2,2-trifluoro-N-((1R,2S or 1S,2R)-2-(E)-1-phenylbut-1-en-2-yl)cyclopropyl)acetamido)cyclohexyl)amino)propanoate (Single Stereoisomer)

To tert-butyl 3-((4-(2,2,2-trifluoro-N-((1R,2S or 1S,2R)-2-((E)-1-phenylbut-1-en-2-yl)cyclopropyl)acetamido)cyclohexyl)amino)propanoate (600 mg, 1.11 mmol) in methanol (10 mL) and AcOH (1.2 mL) was added formaldehyde (134 mg, 1.66 mmol). The reaction was cooled to 0° C. before addition of sodium cyanoborohydride (162 mg, 2.59 mmol). The solution was stirred for 16 h before being quenched with K₂CO₃ (aq. sat.) and extracted with EtOAc (2×100 mL). The combined organic phase as concentrated and the crude residue purified by silica gel chromatography (25 g column, EtOAc:Hexanes, then MeOH:EtOAc) to afford two diastereomers. The first eluting set of fractions contained tert-butyl 2,2-dimethyl-3-(methyl((cis)-4-(2,2,2-trifluoro-N-((1R,2S or 1S,2R)-2-((E)-1-phenylbut-1-en-2-yl)cyclopropyl)acetamido)cyclohexyl)amino)propanoate (single stereoisomer)(195 mg, 354 μmol). The second eluting set of fractions contained tert-butyl 2,2-dimethyl-3-(methyl((trans)-4-(2,2,2-trifluoro-N-((1R,2S or 1S,2R)-2-((E)-1-phenylbut-1-en-2-yl)cyclopropyl)acetamido)cyclohexyl)amino)propanoate (single stereoisomer) (320 mg, 581 μmol). cis cyclohexane: LCMS M/Z: 551.3 (M+H) trans cyclohexane: LCMS M/Z: 551.3 (M+H).

Step 4

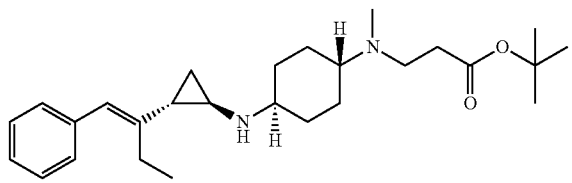 [SMILES: CC/C(=C\c1ccccc1)[C@@H]1C[C@H]1N[C@H]1CC[C@H](N(C)CCC(=O)OC(C)(C)C)CC1]

tert-butyl 3-(methyl((trans)-4-(((1R,2S or 1S,2R)-2-(E)-1-phenylbut-1-en-2-yl)cyclopropyl)amino)cyclohexyl)amino)propanoate (Single Stereoisomer)

To tert-butyl 2,2-dimethyl-3-(methyl((trans)-4-(2,2,2-trifluoro-N-((1R,2S or 1S,2R)-2-((E)-1-phenylbut-1-en-2-yl)cyclopropyl)acetamido)cyclohexyl)amino)propanoate (320 mg, 581 μmol) dissolved in MeOH was added sodium hydroxide (1.16 mL, 1.16 mmol) and the reaction was stirred at 0° C. When complete, the reaction was diluted with NaHCO₃ (sat. aq.) and EtOAc. The layers were separated and the organics were washed with brine, dried over Na₂SO₄, filtered, and concentrated. The crude residue was urified by column chromatography (0% to 15% MeOH in EtOAc, silica gel) to afford tert-butyl 2,2-dimethyl-3-(methyl((trans)-4-(MR,2S or 1S,2R)-2-((E)-1-phenylbut-1-en-2-yl)cyclopropyl)amino)cyclohexyl)amino)propanoate (single stereoisomer)(155 mg, 340 μmol) in 59% yield. LCMS M/Z: 455.4 (M+H).

Step 5

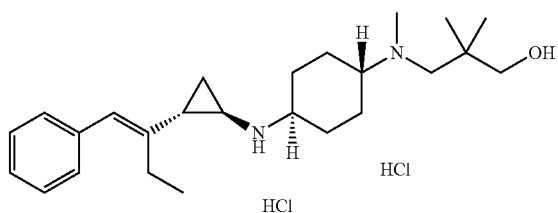 [SMILES: CC/C(=C\c1ccccc1)[C@@H]1C[C@H]1N[C@H]1CC[C@H](N(C)CC(C)(C)CO)CC1 ; Cl ; Cl]

2,2-dimethyl-3-(methyl((trans)-4-(((1R,2S or 1S,2R)-2-(E)-1-phenylbut-1-en-2-yl)cyclopropyl) amino)cyclohexyl)amino)propanoic Acid Dihydrochloride (Single Stereoisomer)

To tert-butyl 2,2-dimethyl-3-(methyl((trans)-4-(((1R,2S or 1S,2R)-2-((E)-1-phenylbut-1-en-2-yl)cyclopropyl) amino)cyclohexyl)amino)propanoate (155 mg, 340 μmol) dissolved in dioxane (6 mL) was added HCl (2.5 mL, 2.5 mmol.). The reaction was heated for 9 h at 45° C. To this solution was added additional HCl (1.0 mL, 4.0 mmol4M in dioxane) and the solution stirred for 7 h at 50° C. The solution was concentrated to afford 2,2-dimethyl-3-(methyl ((trans)-4-(((1R,2S or is,2R)-2-((E)-1-phenylbut-1-en-2-yl) cyclopropyl)amino)cyclohexyl)amino)propanoic acid dihydrochloride (single stereoisomer) (87.0 mg, 184 μmol). LCMS M/Z: 399.3 (M+H). 1H NMR (400 MHz, DMSO-d6) δ 13.04 (br. s, 1H), 9.77 (s, 1H), 9.44 (br. s, 1H), 8.24 (br. s., 1H), 7.28-7.42 (m, 2H), 7.14-7.26 (m, 3H), 6.22 (s, 1H), 3.39-3.78 (m, 5H), 2.94-3.26 (m, 3H), 2.64-2.86 (m, 4H), 1.98-2.39 (m, 5H), 1.50-1.77 (m, 3H), 1.35-1.50 (m, 1H), 1.28 (br. d, J=14.40 Hz, 6H), 1.13 (t, J=7.45 Hz, 3H). 40 protons found, 40 expected.

Compound 265: (1R,2S or 1S,2R)—N-((2-(aminomethyl)pyridin-3-yl)methyl)-2-((E)-1-phenylbut-1-en-2-yl)cyclopropan-1-amine Dihydrochloride (Single Stereoisomer)

Step 1

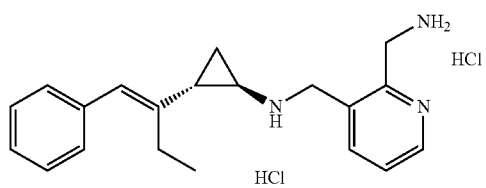 [SMILES: CC/C(=C\c1ccccc1)[C@@H]1C[C@H]1NCc1cccnc1CN ; Cl ; Cl]

To a solution of tert-butyl N-[[3-[[[(1R,2S or 1S,2R)-2-[(1E)-1-benzylidenepropyl]cyclopropyl]amino]methyl]-2-pyridyl]methyl]-N-tert-butoxycarbonyl-carbamate (20.0 mg, 39.4 umol, 1.00 eq) dissolved in MeOH (2.0 mL) was added HCl (4 M in MeOH, 1.0 mL, 101.52 eq) at 0° C. The mixture was stirred at 25° C. for 30 min. The reaction mixture was concentrated and the crude residue was purified by prep-HPLC to afford (1R,2S or 1S,2R)—N-((2-(aminomethyl)pyridin-3-yl)methyl)-2-((E)-1-phenylbut-1-en-2-yl)cyclopropan-1-amine dihydrochloride (single stereoisomer)(1.5 mg, 4.88 umol) as a yellow solid. ¹H NMR (400 MHz, CD₃OD) δ 8.71 (d, J=4.9 Hz, 1H), 8.05 (dd, J=0.9, 7.9 Hz, 1H), 7.52 (dd, J=4.6, 7.7 Hz, 1H), 7.36-7.24 (m, 1H), 7.24-7.11 (m, 1H), 6.30 (s, 1H), 4.60 (s, 2H), 4.51 (d, J=4.5 Hz, 1H), 3.18-3.01 (m, 1H), 2.34 (dd, J=3.7, 7.6 Hz, 2H), 2.26 (d, J=1.0 Hz, 1H), 1.46 (d, J=4.1 Hz, 1H), 1.33-1.29 (m, 1H), 1.18 (t, J=7.5 Hz, 3H). LCMS m/z 308.

Compound 266: 3-(6-(((1R,2S or 1S,2R)-2-(E)-1-phenylbut-1-en-2-yl)cyclopropyl)amino)-2-azaspiro [3.3]heptan-2-yl)propanoic Acid (Single Stereoisomer)

Step 1

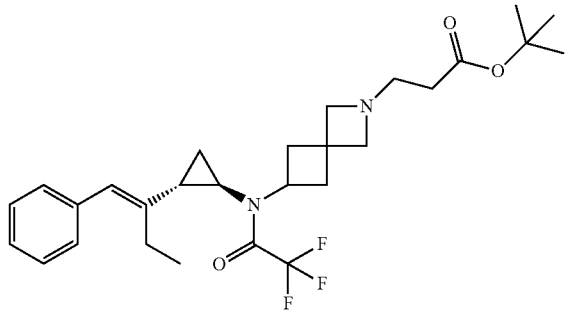 [SMILES: CC/C(=C\c1ccccc1)[C@@H]1C[C@H]1N(C(=O)C(F)(F)F)C1CC2(C1)CN(CCC(=O)OC(C)(C)C)C2]

tert-Butyl 3-(6-(2,2,2-trifluoro-N-((trans)-2-(E)-1-phenylbut-1-en-2-yl)cyclopropyl)acetamido)-2-azaspiro[3.3]heptan-2-yl)propanoate (Single Stereoisomer)

2,2,2-trifluoro-N-((1R,2S or 1S,2R)-2-((E)-1-phenylbut-1-en-2-yl)cyclopropyl)-N-(2-azaspiro[3.3]heptan-6-yl)acetamide 2,2,2-trifluoroacetate (150 mg, 305 μmol) was dissolved in methanol (2.0 mL). Diisopropylethylamine (106 μL, 610 μmol) was then added followed by tert-butyl acrylate (66.8 μL, 457 μmol) and the reaction mixture was stirred at room temperature for 23 hours. After 23 hours, the reaction mixture was concentrated under reduced pressure and the crude product was purified by silica gel column chromatography (dichloromethane/methanol) to afford the desired product as a light brown oil (single stereoisomer) (47.8 mg). LCMS (EST) m/z: 507.2 [M+H]⁺.

Step 2

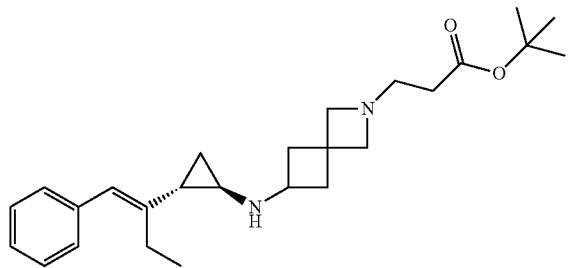 [SMILES: CC/C(=C\c1ccccc1)[C@@H]1C[C@H]1NC1CC2(C1)CN(CCC(=O)OC(C)(C)C)C2]

tert-Butyl 3-(6-(((1R,2S or 1S,2R)-2-((E)-1-phertyl-but-1-en-2-yl)cyclopropyl)amino)-2-azaspiro[3.3]heptan-2-yl)propanoate (Single Stereoisomer)

tert-Butyl 3-(6-(2,2,2-trifluoro-N-((1R,2S or 1S,2R)-2-((E)-1-phenylbut-1-en-2-yl)cyclopropyl)acetamido-2-azaspiro[3.3]heptan-2-yl)propanoate (47.8 mg, 94.3 μmol) was dissolved in methanol (942 μL). 1M NaOH solution (471 μL, 471 μmol) was then added and the reaction mixture was stirred at room temperature for 2 hours. After 2 hours, the reaction mixture was acidified with acetic acid to pH 2 then concentrated under reduced pressure. The crude product was purified by reverse phase column chromatography ($CH_3CN$/0.1% aqueous 2,2,2-trifluoroacetic acid). The pure fractions were combined, frozen and lyophilized overnight to afford the desired product as a beige amorphous solid (single stereoisomer) (44.1 mg). LCMS (ESI) m/z: 411.3 $[M+H]^+$.

Step 3

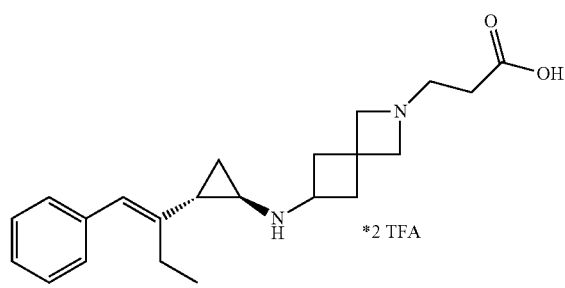 [SMILES: CC/C(=C\c1ccccc1)[C@@H]1C[C@H]1NC1CC2(C1)CN(CCC(=O)O)C2]

3-(6-(((1R,2S or 1S,2R)-2-((E)-1-phenylbut-1-en-2-yl)cyclopropyl)amino)-2-azaspiro[3.3]heptan-2-yl)propanoic Acid (Single Stereoisomer)

To a round bottom flask, tert-butyl 3-(6-(((1R,2S or 1S,2R)-2-((E)-1-phenylbut-1-en-2-yl)cyclopropyl)amino)-2-azaspiro[3.3]heptan-2-yl)propanoate (44.1 mg, 84.0 μmol) was dissolved in DCM (842 μL). Trifluoroacetic acid (64.2 μL, 840 μmol) was then added and the reaction mixture was stirred at room temperature for 3 hours. Following this, the reaction mixture was concentrated under reduced pressure and the crude product was purified by reverse phase column chromatography ($CH_3CN$/0.1% aqueous 2,2,2-trifluoroacetic acid). The pure fractions were combined, frozen and lyophilized overnight to afford the desired product as a beige amorphous solid (single stereoisomer)(37.5 mg,). LCMS (ESI) m/z: 355.2 $[M+H]^{+1}$H NMR (400 MHz, DMSO-$d_6$) δ 12.79 (br s, 1H), 9.87 (br s, 1H), 9.25 (s, 2H), 7.49-7.29 (m, 2H), 7.29-7.10 (m, 3H), 6.20 (s, 1H), 4.33-4.18 (m, 1H), 4.18-3.93 (m, 3H), 3.91-3.72 (m, 1H), 3.37-3.15 (m, 2H), 2.84-2.70 (m, 1H), 2.57 (t, J=27.5 Hz, 3H), 2.48-2.34 (m, 1H), 2.34-2.13 (m, 2H), 2.06-1.85 (m, 1H), 1.26-1.15 (m, 2H), 1.12 (t, J=7.4 Hz, 3H).

Compound 267: 2-((6-(((1R,2S or 1S,2R)-2-(E)-1-phenylbut-1-en-2-yl)cyclopropyl)amino)-2-azaspiro[3.3]heptan-2-yl)methyl)benzoic Acid (Single Stereoisomer)

Step 1

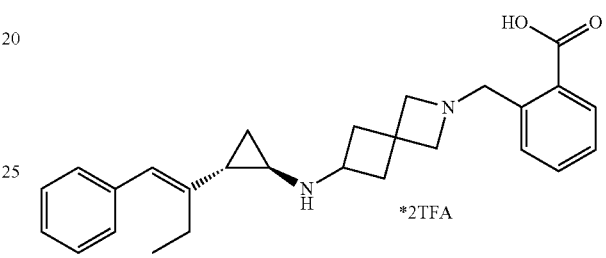

2-((6-(((trans)-2-((E)-1-phenylbut-1-en-2-yl)cyclopropyl)amino)-2-azaspiro[3.3]heptan-2-yl)methyl)benzoic-acid (1R,2S or 1S,2R)

To a round bottom flask, a solution of 2,2,2-trifluoro-N-((1R,2S or 1S,2R)-2-((E)-1-phenylbut-1-en-2-yl)cyclopropyl)-N-(2-azaspiro[3.3]heptan-6-yl)acetamide (119.4 mg, 241 μmol) and 2-formylbenzoic acid (36.1 mg, 241 μmol) were dissolved in of 1,2-dichloroethane (5.35 mL) and treated with a drop of acetic acid and sodium triacetoxyborohydride (102 mg, 482 μmol). The reaction was stirred for 2 hours and then quenched with 1.0 mL of 10% NaOH aqueous Volatiles were removed under reduced pressure and the crude mixture was dissolved in 1.0 mL of methanol and treated with NaOH (0.03 g, 750 umol). The reaction was left to stir at room temperature and followed by LCMS. Once completed, volatiles were removed under reduced pressure. The residue was purified by reverse phase column chromatography ($CH_3CN$/0.1% aqueous 2,2,2-trifluoroacetic acid). The pure fractions were combined, frozen and lyophilized overnight to afford the desired product as a yellow amorphous solid (single stereoisomer)(14 mg). LCMS (EST) m/z: 417.1 $[M+H]^{+1}$H NMR (400 MHz, DMSO-$d_6$) a mixture of minor isomers δ 10.8 (s br, 1H), 10.0 (s, br, 1H), 8.2 (s, 1H), 7.74-7.04 (m, 9H), 6.14 (s, 1H) 4.96-4.78 (m, 1H), 4.66-3.90 (m, 6H), 3.03-2.60 (m, 4H), 2.40-2.00 (m, 3H), 1.66-1.03 (m, 7H).

Compound 268: 2-(6-(((1R,2S or 1S,2R)-2-(E)-1-phenylbut-1-en-2-yl)cyclopropyl)amino)-2-azaspiro[3.3]heptan-2-yl)acetamide Bis Trifluoroacetate (Single Stereoisomer)

Step 1

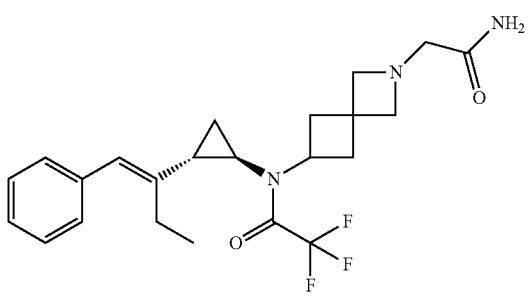 [SMILES: CC/C(=C\c1ccccc1)[C@@H]1C[C@H]1N(C(=O)C(F)(F)F)C1CC2(C1)CN(CC(N)=O)C2]

N-(2-(2-amino-2-oxoethyl)-2-azaspiro[3.3]heptan-6-yl)-2,2,2-trifluoro-N-((1R,2S or 1S,2R)-2-((E)-1-phenylbut-1-en-2-yl)cyclopropyl)acetamide (Single Stereoisomer)

2,2,2-trifluoro-N-((1R,2S or 1S,2R)-2-((E)-1-phenylbut-1-en-2-yl)cyclopropyl)-N-(2-azaspiro[3.3]heptan-6-yl)acetamide 2,2,2-trifluoroacetate (150 mg, 304 μmol) was dissolved in N,N-dimethylformamide (3.05 mL). Cesium carbonate (248 mg, 762 μmol) was then added followed by 2-chloroacetamide (28.4 mg, 304 μmol) and the reaction mixtuwas stirred at room temperature for 24 h to afford the crude desired product that was used directly in the subsequent step without further purification (single stereoisomer). LCMS (ESI) m/z: 436.1 [M+H]⁺.

Step 2

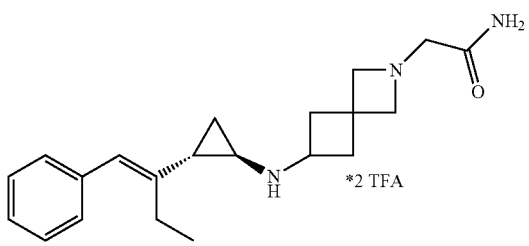 [SMILES: CC/C(=C\c1ccccc1)[C@@H]1C[C@H]1NC1CC2(C1)CN(CC(N)=O)C2]

2-(6-(((1R,2S or 1S,2R)-2-(E)-1-phenylbut-1-en-2-yl)cyclopropyl)amino)-2-azaspiro[3.3]heptan-2-yl)acetamide Bis Trifluoroacetate (Single Stereoisomer)

To a crude solution of N-(2-(2-amino-2-oxoethyl)-2-azaspiro[3.3]heptan-6-yl)-2,2,2-trifluoro-N-((1R,2S or 1S,2R)-2-((E)-1-phenylbut-1-en-2-yl)cyclopropyl)acetamide in N,N-dimethylformamide from previous step was added NaOH 1M aqueous (0.5 mL) and the reaction mixture was stirred at room temperature for 1 hour. Then the reaction mixture was cooled to 5° C. and acidified to pH 2 with concentrated acetic acid. The resulting mixture was partitioned between water (5 mL) and ethyl acetate (5 mL). The organic layer was extracted once with water (5 mL) and the aqueous layer was concentrated under reduced pressure. The crude mixture was purified by reverse phase column chromatography (CH₃CN/0.1% aqueous 2,2,2-trifluoroacetic acid). The pure fractions were combined, frozen and lyophilized overnight to afford 2-(6-(((1R,2S or 1S,2R)-2-((E)-1-phenylbut-1-en-2-yl)cyclopropyl)amino)-2-azaspiro[3.3]heptan-2-yl)acetamide (single stereoisomer) as a light beige amorphous solid after lyophilization (38.7 mg). LCMS (ESI) m/z: 340.1 [M+H]⁺. ¹H NMR (400 MHz, DMSO-d₆) δ 10.14 (s, 1H), 9.19 (s, 2H), 8.62 (s, 1H), 7.84 (s, 1H), 7.54 (s, 1H), 7.40-7.31 (m, 2H), 7.27-7.16 (m, 2H), 7.10 (s, 1H), 6.97 (s, 1H), 6.21 (s, 1H), 4.33-4.17 (m, 1H), 4.17-4.06 (m, 1H), 4.03 (t, J=6.0 Hz, 1H), 3.99-3.89 (m, 2H), 3.84-3.71 (m, 2H), 2.88-2.54 (m, 2H), 2.48-2.34 (m, 1H), 2.32-2.16 (m, 3H), 2.05-1.86 (m, 1H), 1.22-1.15 (m, 2H), 1.12 (t, J=7.5 Hz, 3H).

Compound 269: 2-(2,2-difluoroethyl)-N-((1R,2S or 1S,2R)-2-((E)-1-phenylbut-1-en-2-yl)cyclopropyl)-2-azaspiro[3.3]heptan-6-amine (Single Stereoisomer)

Step 1: 2,2-difluoroacetaldehyde

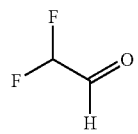

To a round bottom flask, a solution of oxalyl chloride (1.70 mL, 20.0 mmol) in dichloromethane (45 mL) at −78° C. was added dimethyl sulfoxide (2.83 mL, 40.0 mmol) dropwise over 5 minutes. After stirring for 2 minutes, a solution of 2,2-difluoroethanol (1.15 mL, 18.2 mmol) in dichloromethane (46 mL) was slowly added over 10 minutes. After the addition was completed, the mixture was stirred at −78° C. for 1 hour. The reaction mixture was quenched with triethylamine (7.60 mL, 54.6 mmol) and was allowed to warm to room temperature over 90 minutes which afforded the desired compound as a solution which was used directly in the subsequent step without further purification.

Step 2: N-(2-(2,2-difluoroethyl)-2-azaspiro[3.3]heptan-6-yl)-2,2,2-trifluoro-N-((1R,2S or 1S,2R)-2-((E)-1-phenylbut-1-en-2-yl)cyclopropyl)acetamide (Single Stereoisomer)

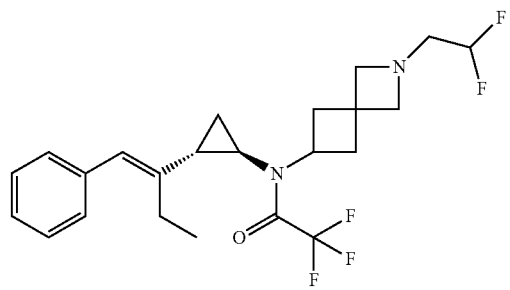 [SMILES: CC/C(=C\c1ccccc1)[C@@H]1C[C@H]1N(C(=O)C(F)(F)F)C1CC2(C1)CN(CC(F)F)C2]

To a round bottom flask, a solution of 2,2,2-trifluoro-N-((1R,2S or 1S,2R)-2-((E)-1-phenylbut-1-en-2-yl)cyclopropyl)-N-(2-azaspiro[3.3]heptan-6-yl)acetamide, difluoroacetaldehyde (6.67 mL, 1.21 mmol) solution in dichloromethane and 5 drops of acetic acid was treated with sodium triacetoxyborohydride (214 mg, 1.01 mmol). The reaction mixture was stirred at room temperature for 90 minutes. The mixture was quenched with sat. NaHCO$_3$ (10 mL), the phases were separated and the aqueous layer extracted once with dichloromethane (10 mL). The combined organic layers was dried with anhydrous Na$_2$SO$_4$ and evaporated under reduced pressure to afford the crude desired product as dark yellow oil (147.8 mg). The desired product (single stereoisomer) was used directly in the subsequent step without further purification. LCMS (ESI) m/z: 443.2 [M+H]$^+$.

Step 3: 2-(2,2-difluoroethyl)-N-((1R,2S or 1S,2R)-2-((E)-1-phenylbut-1-en-2-yl)cyclopropyl)-2-azaspiro[3.3]heptan-6-amine (Single Stereoisomer)

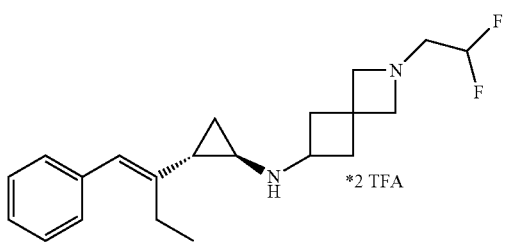 [SMILES: CC/C(=C\c1ccccc1)[C@@H]1C[C@H]1NC1CC2(C1)CN(CC(F)F)C2]

To a round bottom flask, a solution of N-(2-(2,2-difluoroethyl)-2-azaspiro[3.3]heptan-6-yl)-2,2,2-trifluoro-N-((1R,2S or 1S,2R)-2-((E)-1-phenylbut-1-en-2-yl)cyclopropyl)acetamide (147.8 mg, 332 µmol) in methanol (1.65 mL) was treated with aqueous NaOH (1.66 mL, 1.66 mmol). The reaction mixture was stirred at room temperature for 3 hours then concentrated under reduced pressure. The crude product was purified by reverse phase column chromatography (CH$_3$CN/0.1% aqueous 2,2,2-trifluoroacetic acid). The pure fractions were combined, frozen and lyophilized overnight to afford 2-(2,2-difluoroethyl)-N-((1R,2S or 1S,2R)-2-((E)-1-phenylbut-1-en-2-yl)cyclopropyl)-2-azaspiro[3.3]heptan-6-amine (single stereoisomer) as a beige amorphous solid (76.9 mg). LCMS (EST) m/z: 347.1 [M+H]$^+$. $^1$H NMR (400 MHz, DMSO-d$_6$) δ 10.83 (hr s, 1H), 9.20 (s, 2H), 7.41-7.31 (m, 2H), 7.30-7.16 (m, 3H), 6.21 (s, 1H), 4.34-4.08 (m, 3H), 3.87-3.72 (m, 3H), 2.83-2.71 (m, 1H), 2.71-2.57 (m, 1H), 2.55 (t, J=5.6 Hz, 1H), 2.48-2.37 (m, 2H), 2.29-2.18 (m, 2H), 2.03-1.88 (m, 1H), 1.21-1.15 (m, 2H), 1.12 (t, J=7.5 Hz, 3H).

Compound 270: 2-(2-(((1R,2S or 1S,2R)-2-(E)-1-phenylbut-1-en-2-yl)cyclopropyl)amino)-7-azaspiro[3.5]nonan-7-yl)acetamide bis(2,2,2-trifluoroacetate) (Single Stereoisomer)

Step 1: tert-butyl 2-(((1R,2S or 1S,2R)-2-((E)-1-phenylbut-1-en-2-yl)cyclopropyl)amino)-7-azaspiro[3.5]nonane-7-carboxylate (Single Stereoisomer)

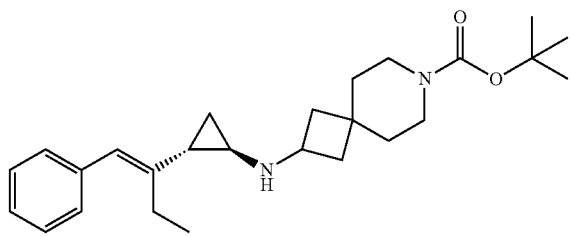 [SMILES: CC/C(=C\c1ccccc1)[C@@H]1C[C@H]1NC1CC2(CCN(C(=O)OC(C)(C)C)CC2)C1]

To a suspension of (1R,2S or 1S,2R)-2-(E)-1-phenylbut-1-en-2-yl)cyclopropanamine (S)-2-hydroxy-2-phenylacetate (1.5 g, 4.41 mmol) in 1,2-dichloroethane (33 mL) at 0° C. was added tert-butyl 2-oxo-7-azaspiro[3.5]nonane-7-carboxylate (1.10 g, 4.63 mmol) followed by sodium triacetoxyborohydride (2.05 g, 9.70 mmol). The reaction mixture was allowed to warm to 23° C. and stirred for 3 hours. Additionnal tert-butyl 2-oxo-7-azaspiro[3.5]nonane-7-carboxylate (106 mg, 0.44 mmol) and sodium triacetoxyborohydride (279 mg, 1.31 mmol) were then added and the reaction mixture was stirred at 23° C. for 16 hours. The reaction mixture was then diluted with a saturated aqueous K$_2$CO$_3$ solution (20 mL) and extracted with DCM (3×15 mL). The combined organic layers were washed with brine (15 mL), dried over Na$_2$SO$_4$, filtered, and concentrated under reduced pressure. The crude residue was purified via Biotage (gradient 0 to 100% EtOAc in hexanes) to afford the desired product (single stereoisomer) as a yellowish oil (1.287 g, 71% yield). LCMS (ESI) m/z: 411 [M+H]$^+$.

Step 2

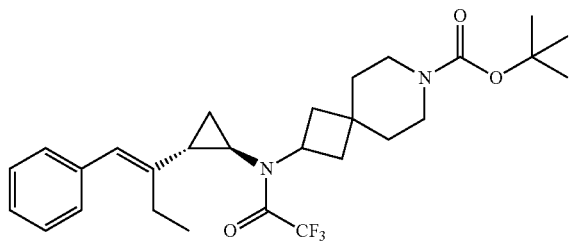 [SMILES: CC/C(=C\c1ccccc1)[C@@H]1C[C@H]1N(C(=O)C(F)(F)F)C1CC2(CCN(C(=O)OC(C)(C)C)CC2)C1]

tert-butyl 2-(2,2,2-trifluoro-N-((1R,2S or 1S,2R)-2-(E)-1-phenylbut-1-en-2-yl)cyclopropyl)acetamido)-7-azaspiro[3.5]nonane-7-carboxylate (Single Stereoisomer)

To a solution of tert-butyl 2-(((1R,2S or 1S,2R)-2-(E)-1-phenylbut-1-en-2-yl)cyclopropyl)amino)-7-azaspiro[3.5]nonane-7-carboxylate (1.287 g, 3.11 mmol) in DCM (20 mL) at 0° C. was added N,N-diisopropylethylamine (811 µL, 4.66 mmol) followed by trifluoroacetic anhydride (561 µL, 4.04 mmol). The reaction mixture was allowed to warm to 23° C. and stirred for 3 hours. The reaction mixture was then diluted with a saturated aqueous NaHCO₃ solution (20 mL) and the two layers were separated. The organic layer was washed with a saturated aqueous NH₄Cl solution (2×10 mL), dried over Na₂SO₄, filtered, and concentrated under reduced pressure. The crude residue was purified via Biotage (gradient 0 to 50% EtOAc in hexanes) to afford the desired product (single stereoisomer) as a yellow oil (1.324 g, 84% yield). LCMS (ESI) m/z: 529.4 [M+Na]⁺.

Step 3

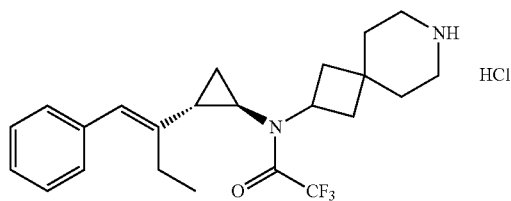 [SMILES: CC/C(=C\c1ccccc1)[C@@H]1C[C@H]1N(C(=O)C(F)(F)F)C1CC2(CCNCC2)C1 ; Cl]

2,2,2-trifluoro-N-((1R,2S or 1S,2R)-2-(E)-1-phenyl-but-1-en-2-yl)cyclopropyl)-N-(7-azaspiro[3.5] nonan-2-yl)acetamide hydrochloride (Single Stereoisomer)

To a solution of tert-butyl 2-(2,2,2-trifluoro-N-((1R,2S or 1S,2R)-2-((E)-1-phenylbut-1-en-2-yl)cyclopropyl)acetamido)-7-azaspiro[3.5]nonane-7-carboxylate (400 mg, 789 μmol) in dioxane (4 mL) at 23° C. was added a 4.0 M solution of HCl in dioxane (1.57 mL, 6.31 mmol) dropwise. The reaction mixture was stirred at 23° C. for 2 hours. Additional HCl (1.57 mL, 6.31 mmol, 4.0 M solution in dioxane) was then added and the reaction mixture was stirred at 23° C. for 1.5 hours. The reaction mixture was then concentrated under reduced pressure to afford the desired product (single stereoisomer) as a crude yellowish oil (390 mg, quantitative yield). LCMS (ESI) m/z: 407 [M+H]⁺.

Step 4: N-(7-(2-amino-2-oxoethyl)-7-azaspiro[3.5] nonan-2-yl)-2,2,2-trifluoro-N-((1R,2S or 1S,2R)-2-(E)-1-phenylbut-1-en-2-yl)cyclopropyl)acetamide (Single Stereoisomer)

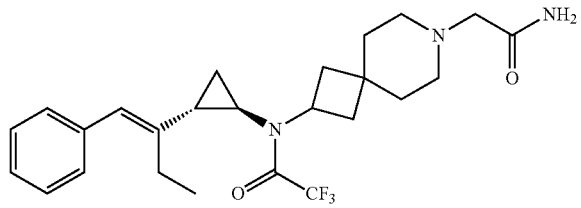 [SMILES: CC/C(=C\c1ccccc1)[C@@H]1C[C@H]1N(C(=O)C(F)(F)F)C1CC2(CCN(CC(N)=O)CC2)C1]

To a solution of 2,2,2-trifluoro-N-((1R,2S or 1S,2R)-2-((E)-1-phenylbut-1-en-2-yl)cyclopropyl)-N-(7-azaspiro [3.5]nonan-2-yl)acetamide hydrochloride (100 mg, 225 μmol) in DMF (1.5 mL) at 23° C. was added potassium carbonate (93.2 mg, 675 μmol) followed by 2-iodoacetamide (41.6 mg, 225 μmol). The reaction mixture was stirred at 23° C. for 4 hours protected from light (wrapped in aluminum foil). Additional 2-iodoacetamide (4.2 mg, 23 μmol) was then added and the reaction mixture was stirred at 23° C. for 2 hours. Additional 2-iodoacetamide (4.2 mg, 23 μmol) was added again and the reaction mixture was stirred at 23° C. for 16 hours. The reaction mixture was then diluted with water (1 mL) and extracted with EtOAc (3×1 mL). The combined organic layers were dried over Na₂SO₄, filtered, and concentrated under reduced pressure. The crude residue was purified via Biotage (gradient 0 to 100% EtOAc in hexanes then 0 to 10% MeOH in EtOAc) to afford the desired product (single stereoisomer) as a colorless oil (63 mg, 61% yield). LCMS (ESI) m/z: 464.3 [M+H]⁺.

Step 5: 2-(2-(((1R,2S or 1S,2R)-2-(E)-1-phenylbut-1-en-2-yl)cyclopropyl)amino)-7-azaspiro[3.5]nonan-7-yl)acetamide bis(2,2,2-trifluoroacetate) (Single Stereoisomer)

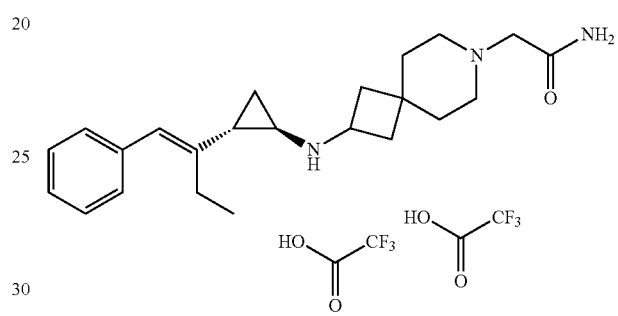

To a solution of N-(7-(2-amino-2-oxoethyl)-7-azaspiro [3.5]nonan-2-yl)-2,2,2-trifluoro-N-((1R,2S or 1S,2R)-2-(E)-1-phenylbut-1-en-2-yl)cyclopropyl)acetamide (63 mg, 135 μmol) in MeOH (1.3 mL) at 23° C. under a nitrogen atmosphere was added a 1.0 M sodium hydroxide aqueous solution (810 μL, 810 μmol) dropwise. The reaction mixture was stirred at 23° C. for 1 hour. The reaction mixture was then diluted with a saturated aqueous NaHCO₃ solution (1.5 mL) and extracted with EtOAc (3×1 mL). The combined organic layers were dried over Na₂SO₄, filtered, and concentrated under reduced pressure. The crude residue was purified via Biotage (gradient 0 to 50% DCM/MeOH/NH₄OH (90:10:1) in DCM) to afford the desired product not completely pure. The product was then dissolved in AcOH (2 mL) and purified by preparative HPLC (gradient 15 to 95% CH₃CN in water with 0.1% TFA). After concentration of the pure fractions under reduced pressure, the obtained residue was dissolved in dioxane (3 mL), frozen, and lyophilized to afford the desired product (single stereoisomer) as a white powder (23 mg, 29% yield).

LCMS (ESI) m/z: 368.4 [M+H]⁺. ¹H NMR (400 MHz, DMSO-d₆) δ 9.48 (br s, 1H), 9.34 (br s, 1H), 8.02-7.93 (br s, 1H), 7.68 (br s, 1H), 7.38-7.31 (m, 2H), 7.26-7.18 (m, 3H), 6.21 (s, 1H), 3.93-3.79 (br s, 3H), 3.10-2.88 (m, 3H), 2.77-2.67 (m, 1H), 2.40-2.31 (m, 1H), 2.29-2.21 (m, 2H), 2.18-2.06 (m, 2H), 2.05-1.95 (m, 2H), 1.93-1.75 (m, 6H), 1.25-1.18 (m, 1H), 1.18-1.10 (m, 4H). LCMS (ESI) m/z: 368.4 [M+H]⁺.

Compound 271: 2-(4-(((1R,2S or 1S,2R)-2-(E)-1-phenylbut-1-en-2-yl)cyclopropyl)amino)piperidin-1-yl)acetamide bis(2,2,2-trifluoroacetate) (Single Stereoisomer)

Step 1: 2-(4-oxopiperidin-1-yl)acetamide

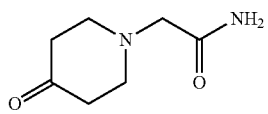

To a round bottomed flask was added piperidin-4-one hydrochloride (512 mg, 3.77 mmol), potassium carbonate (1.30 g, 9.42 mmol), 2-bromoacetamide (520 mg, 3.77 mmol), and acetonitrile. The solution was stirred at room temperature overnight before diluting with water and extracting with EtOAc. The combined organics layer was dried over $Na_2SO_4$, filtered, and concentrated to afford crude 2-(4-oxopiperidin-1-yl)acetamide. This material was used in subsequent steps without further purification. LCMS m/z 157 [M+H]$^+$.

Step 2: 2-(4-(((1R,2S or 1S,2R)-2-((E)-1-phenylbut-1-en-2-yl)cyclopropyl)amino)piperidin-1-yl)acetamide bis(2,2,2-trifluoroacetate) (Single Stereoisomer)

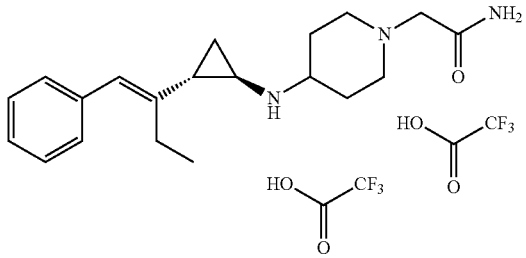

To a round bottomed flask was added (1R,2S or 1S,2R)-2-((E)-1-phenylbut-1-en-2-yl)cyclopropanamine (S)-2-hydroxy-2-phenylacetate (200 mg, 0.5892 mmol), 2-(4-oxopiperidin-1-yl)acetamide (138 mg, 0.8838 mmol), and DCM. The solution was stirred at room temperature for 5 min before addition of sodium triacetoxyborohydride (187 mg, 0.8838 mmol). The solution was stirred at room temperature for 1 h before diluting with $NaHCO_3$ (sat. aq.). The layers were separated and the organics were dried over $Na_2SO_4$, filtered, and concentrated. The crude residue was purified via HPLC to afford 2-(4-(((1R,2S or 1S,2R)-2-((E)-1-phenylbut-1-en-2-yl)cyclopropyl)amino)piperidin-1-yl)acetamide bis(2,2,2-trifluoroacetate) (single stereoisomer) (220 mg, 0.3960 mmol). LCMS m/z 328 [M+H]$^+$. $^1$H NMR (400 MHz,DMSO-d$_6$) δ=7.95 (br. s., 1H), 7.69 (br. s., 1H), 7.40-7.30 (m, 2H), 7.27-7.16 (m, 3H), 6.23 (s, 1H), 3.85 (br. s., 2H), 3.64-3.36 (m, 4H), 3.09 (br. s., 2H), 2.90 (br. s., 1H), 2.25 (q, J=7.4 Hz, 4H), 2.08-1.84 (m, 3H), 1.31-1.23 (m, 1H), 1.19 (q, J=6.7 Hz, 1H), 1.12 (t, J=7.6 Hz, 3H).

Compound 272

Step 1: 2,2,2-trifluoro-N-(2-(2-(methylsulfonyl)ethyl)-2-azaspiro[3.3]heptan-6-yl)-N-((1R,2S or 1S,2R)-2-((E)-1-phenylbut-1-en-2-yl)cyclopropyl)acetamide (Single Stereoisomer)

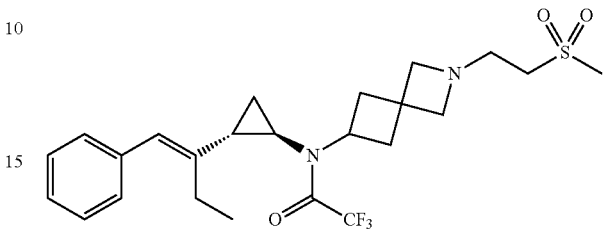

To 2,2,2-trifluoro-N-((1R,2S or 1S,2R)-2-((E)-1-phenylbut-1-en-2-yl)cyclopropyl)-N-(2-azaspiro[3.3]heptan-6-yl)acetamide 2,2,2-trifluoroacetate (271 mg, 550 μmol) dissolved in THF (4 mL) was added (methylsulfonyl)ethene (78.7 mg, 742 μmol), followed by diisopropylethylamine (188 μL, 1.09 mmol). The reaction mixture was stirred for 16 h at room temperature. The reaction mixture was partitioned between water and EtOAc. The organics layer was concentrated to afford 2,2,2-trifluoro-N-(2-(2-(methylsulfonyl)ethyl)-2-azaspiro[3.3]heptan-6-yl)-N-((1R,2S or 1S,2R)-2-((E)-1-phenylbut-1-en-2-yl)cyclopropyl)acetamide (single stereoisomer) (266 mg, 548 μmol); LCMS M/Z: 535 (M+H).

Step 2: 2-(2-(methylsulfonyl)ethyl)-N-((1R,2S or 1S,2R)-2-((E)-1-phenylbut-1-en-2-yl)cyclopropyl)-2-azaspiro[3.3]heptan-6-amine Dimethanesulfonate (Single Stereoisomer)

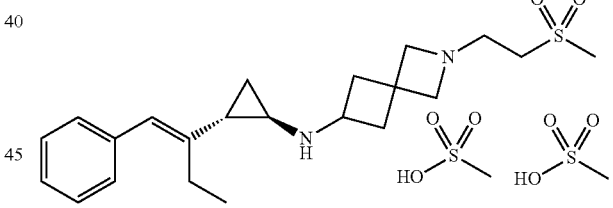

To 2,2,2-trifluoro-N-(2-(2-(methylsulfonyl)ethyl)-2-azaspiro[3.3]heptan-6-yl)-N-((1R,2S or1S,2R)-2-(E)-1-phenylbut-1-en-2-yl)cyclopropyl)acetamide (260 mg, 536 μmol) dissolved in MeOH was added sodium hydroxide (1.07 mL, 1.07 mmol) and the reaction stirred at 45° C. for 16 h. The solution was then partitioned between water and EtOAc. The organics layer was dried over $Na_2SO_4$, filtered, and concentrated. The crude residue was purified by column chromatography (MeOH:EtOAc on silica column) to afford the free-based compound. This material was then taken up in water, treated with methanesulfonic acid (1M aq. solution) and lyophilized to afford 2-(2-(methylsulfonyl)ethyl)-N-((1R,2S or 1S,2R)-2-((E)-1-phenylbut-1-en-2-yl)cyclopropyl)-2-azaspiro[3.3]heptan-6-amine dimethanesulfonate (single stereoisomer)(4.6 mg). LCMS M/Z: 389.2 (M+H), 1H NMR (400 MHz,DMSO-d6) δ=1H NMR (400 MHz, DMSO-d6) δ 9.81-9.94 (m, 1H), 9.12-9.12 (m, 1H), 8.89-9.18 (m, 2H), 7.34 (d, J=7.57 Hz, 2H), 7.04-7.29 (m, 3H), 6.21 (s, 1H), 4.04-4.28 (m, 4H), 3.74-3.86 (m, 1H), 3.57-

3.65 (m, 2H), 3.39-3.52 (m, 2H), 3.11 (s, 3H), 2.53-2.81 (m, 4H), 2.42-2.47 (m, 1H), 2.33 (s, 6H), 1.94-2.04 (m, 2H), 1.17-1.23 (m, 2H), 1.13 (t, J=7.45 Hz, 3H).
Other compounds include those described below in Table 4. These compounds can be made according to the general procedures described herein.
TABLE 4
| Cmpd. | Structure |
|---|---|
| 284 | 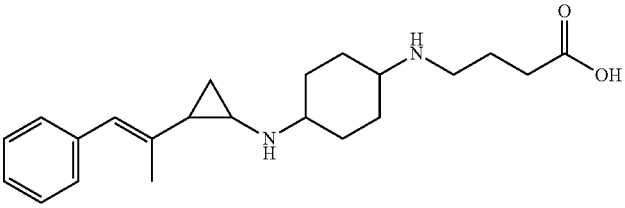 [SMILES: C/C(=C\c1ccccc1)C1CC1NC1CCC(NCCCC(=O)O)CC1] |
| 285 | 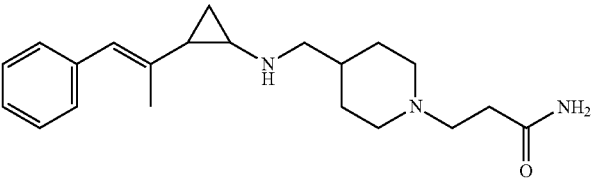 [SMILES: C/C(=C\c1ccccc1)C1CC1NCC1CCN(CCC(N)=O)CC1] |
| 286 | 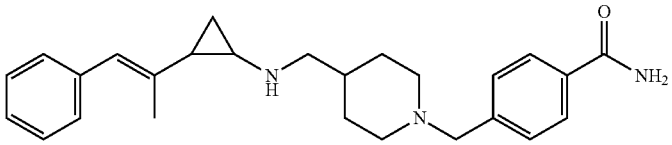 [SMILES: C/C(=C\c1ccccc1)C1CC1NCC1CCN(Cc2ccc(C(N)=O)cc2)CC1] |
| 287 | 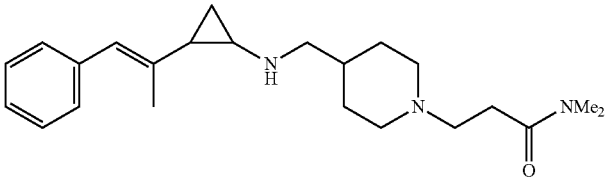 [SMILES: C/C(=C\c1ccccc1)C1CC1NCC1CCN(CCC(=O)N(C)C)CC1] |
| 288 | 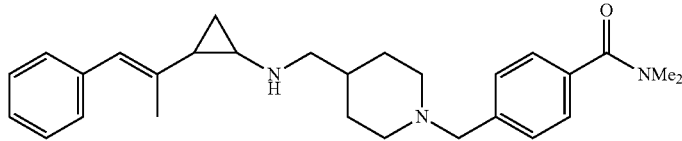 [SMILES: C/C(=C\c1ccccc1)C1CC1NCC1CCN(Cc2ccc(C(=O)N(C)C)cc2)CC1] |
| 289 | 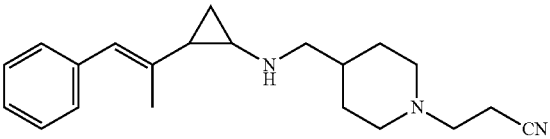 [SMILES: C/C(=C\c1ccccc1)C1CC1NCC1CCN(CCC#N)CC1] |
| 290 | 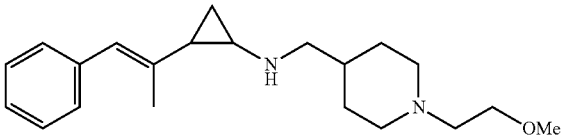 [SMILES: COCCN1CCC(CNC2CC2/C(C)=C/c2ccccc2)CC1] |
| 291 | 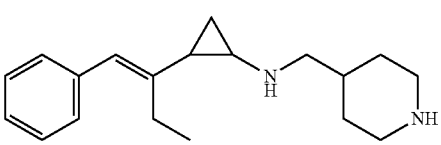 [SMILES: CC/C(=C\c1ccccc1)C1CC1NCC1CCNCC1] |

TABLE 4-continued

| Cmpd. | Structure |
|---|---|
| 292 | 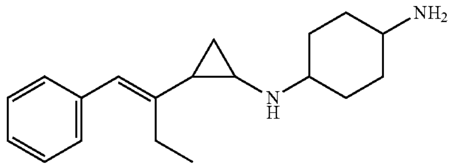 [SMILES: CC/C(=C\c1ccccc1)C1CC1NC1CCC(N)CC1] |
| 293 | 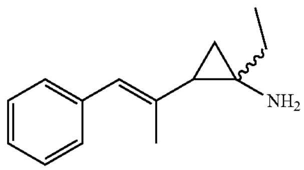 |
| 294 | 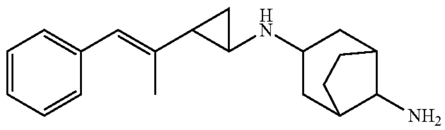 [SMILES: C/C(=C\c1ccccc1)C1CC1NC1CC2CCC(C1)C2N] |
| 295 | 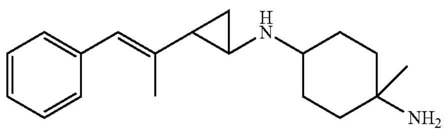 [SMILES: C/C(=C\c1ccccc1)C1CC1NC1CCC(C)(N)CC1] |
| 296 | 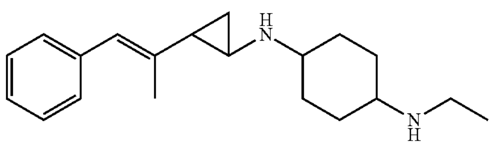 [SMILES: CCNC1CCC(NC2CC2/C(C)=C/c2ccccc2)CC1] |
| 297 | 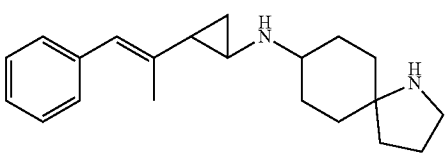 [SMILES: C/C(=C\c1ccccc1)C1CC1NC1CCC2(CCCN2)CC1] |
| 298 | 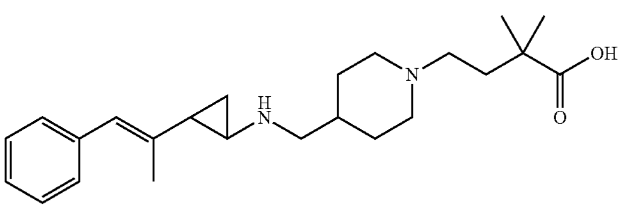 [SMILES: C/C(=C\c1ccccc1)C1CC1NCC1CCN(CCC(C)(C)C(=O)O)CC1] |
| 299 | 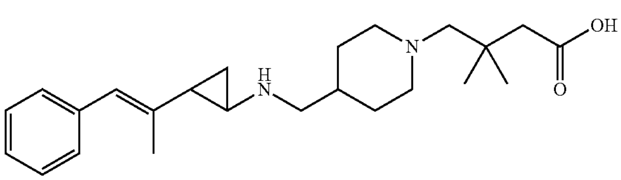 [SMILES: C/C(=C\c1ccccc1)C1CC1NCC1CCN(CC(C)(C)CC(=O)O)CC1] |
| 300 | 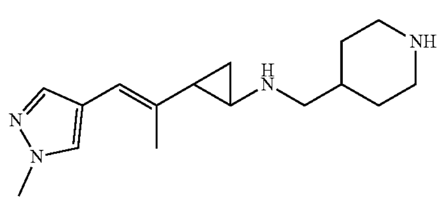 [SMILES: C/C(=C\c1cnn(C)c1)C1CC1NCC1CCNCC1] |

TABLE 4-continued

| Cmpd. | Structure |
|---|---|
| 301 | 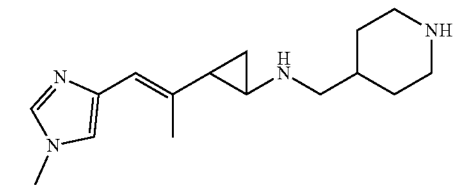 [SMILES: C/C(=C\c1cn(C)cn1)C1CC1NCC1CCNCC1] |
| 302 | 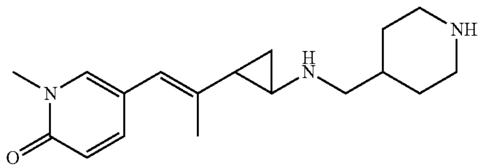 [SMILES: C/C(=C\c1ccc(=O)n(C)c1)C1CC1NCC1CCNCC1] |
| 303 | 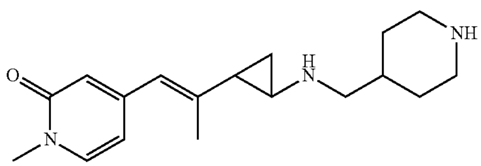 [SMILES: C/C(=C\c1ccn(C)c(=O)c1)C1CC1NCC1CCNCC1] |
| 304 | 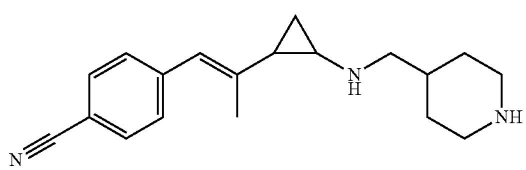 [SMILES: C/C(=C\c1ccc(C#N)cc1)C1CC1NCC1CCNCC1] |
| 305 | 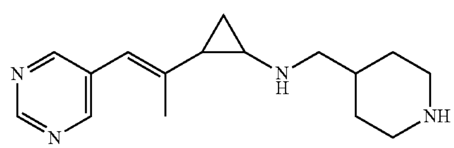 [SMILES: C/C(=C\c1cncnc1)C1CC1NCC1CCNCC1] |
| 306 | 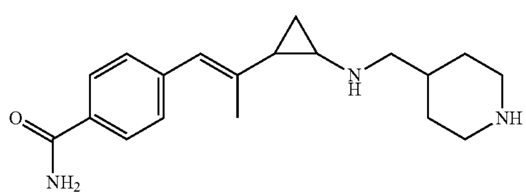 [SMILES: C/C(=C\c1ccc(C(N)=O)cc1)C1CC1NCC1CCNCC1] |
| 307 | 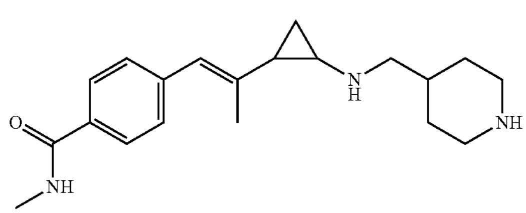 [SMILES: CNC(=O)c1ccc(/C=C(\C)C2CC2NCC2CCNCC2)cc1] |

LSD1 Assays

Biochemical assay for LSD1 activity

LSD1 demethylase reactions were carried out in 50 mM HEPES pH 7.4, 100 mM NaCl, 1 mM DTT, 0.01% Tween-20, and 0.1 mg/mL BSA. All enzymatic reactions were performed for 50 minutes at room temperature in a 10-μL volume. Five microliters of 800 nM biotinylated H3K4me1 peptide solution was added to each well of a black 384 well Proxiplate containing 80 nL compound (final concentration of 0.8% DMSO). Reactions were initiated by the addition of a mixture containing 20 nM LSD1 and 20 nM FAD (5 μL). Enzyme activity was stopped by the addition of 5 μL of high salt buffer consisting of 50 mM HEPES pH 7.4, 1.5 M NaCl, 1 mM DTT, 0.01% Tween-20, and 0.1 mg/mL BSA. Capture of the product peptide by the anti—H3K4me0 antibody and Streptavidin APC was allowed to proceed for 60 min at room temperature before measuring the TR-FRET signal. Europium-labeled antibody and Streptavidin APC were used at final concentrations of 0.003 nM and 100 nM, respectively (total assay volume of 20 μL). Plates were read on a Perkin Elmer EnVision. Percent inhibition was calculated using Max (no inhibitor) and Min (quenched with stop buffer) controls and inhibition curves plotted to determine IC$_{50}$ values.

Tables 5-7 show the activity of selected compounds of this invention in the LSD1 activity inhibition assay. LSD1_Pep_TR-FRET_1.0 (IC50 T50) IC$_{50}$ values are reported as follows: "A" indicates an IC$_{50}$ value of less than 100 nM; "B" indicates an IC$_{50}$ value of 100 nM to 1 μM; "C" indicates an IC$_{50}$ value of greater than 1 μM and less than 10 μM for each enzyme; "D" indicates an IC$_{50}$ value of greater than 10 μM for each enzyme; "*(X μM)" indicates that no inhibition was observed at the highest concentration (i.e., X μM) of compound tested; and "ND" is not determined.

TABLE 5

IC$_{50}$ values for selected compounds.

| Cmp. | LSD1_Pep_TR-FRET_1.0 (IC$_{50}$ T50) |
|---|---|
| 101 | B |
| 102 | B |
| 103 | A |
| 104 | B |
| 105 | B |
| 106 | B |
| 107 | B |
| 108 | B |
| 109 | A |
| 110 | A |
| 111 | A |
| 112 | B |
| 113 | A |
| 114 | ND |
| 115 | ND |
| 116 | ND |
| 117 | ND |
| 118 | ND |
| 119 | ND |
| 120 | ND |
| 121 | ND |
| 122 | ND |
| 123 | ND |
| 124 | ND |
| 125 | ND |
| 126 | ND |

TABLE 6

IC$_{50}$ values for selected compounds.

| Cmp. | LSD1_Pep_TR-FRET_1.0 (IC$_{50}$ T50) |
|---|---|
| 127 | B |
| 128 | A |
| 129 | D |
| 130 | C |
| 131 | D |
| 132 | D |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | ND |
| 148 | A |
| 149 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | A |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | A |
| 181 | A |
| 182 | A |
| 183 | A |
| 184 | A |
| 185 | A |
| 186 | A |
| 187 | C |
| 188 | A |
| 189 | A |
| 190 | B |
| 191 | B |
| 192 | B |
| 193 | A |
| 194 | A |
| 195 | A |
| 196 | A |
| 197 | A |
| 198 | A |
| 199 | A |
| 200 | A |
| 201 | A |
| 202 | A |
| 203 | A |
| 204 | D |
| 205 | A |
| 206 | B |
| 207 | A |
| 208 | B |
| 209 | B |
| 210 | B |
| 211 | A |
| 212 | A |
| 213 | B |
| 214 | A |
| 215 | A |
| 216 | A |
| 217 | A |
| 218 | A |
| 219 | A |

TABLE 6-continued

IC$_{50}$ values for selected compounds.

| Cmp. | LSD1_Pep_T R-FRET_1.0 (IC$_{50}$ T50) |
|---|---|
| 220 | A |
| 221 | B |
| 223 | A |
| 224 | A |
| 273 | A |
| 275 | A |
| 276 | ND |
| 277 | A |
| 278 | A |
| 279 | A |
| 280 | A |
| 281 | A |

TABLE 7

IC$_{50}$ values for selected compounds.

| Cmp. | LSD1_Pep_T R-FRET_1.0 (IC$_{50}$ T50) |
|---|---|
| 225 | A |
| 226 | A |
| 227 | A |
| 228 | A |
| 229 | A |
| 230 | A |
| 231 | A |
| 232 | B |
| 233 | A |
| 234 | A |
| 235 | A |
| 236 | A |
| 237 | ND |
| 238 | ND |
| 239 | A |
| 240 | A |
| 241 | A |
| 242 | A |
| 243 | A |
| 244 | ND |
| 245 | A |
| 246 | A |
| 247 | A |
| 248 | A |
| 249 | A |
| 250 | A |
| 251 | A |
| 252 | A |
| 253 | ND |
| 254 | A |
| 255 | A |
| 256 | A |
| 257 | ND |
| 258 | ND |
| 259 | ND |
| 260 | A |
| 261 | ND |
| 262 | A |
| 263 | ND |
| 264 | ND |
| 265 | ND |
| 266 | A |
| 267 | ND |
| 268 | A |
| 269 | ND |
| 270 | ND |
| 271 | ND |
| 272 | ND |

TABLE 7-continued

IC$_{50}$ values for selected compounds.

| Cmp. | LSD1_Pep_T R-FRET_1.0 (IC$_{50}$ T50) |
|---|---|
| 282 | A |
| 283 | A |

The invention claimed is:
1. A compound represented by structural Formula I:

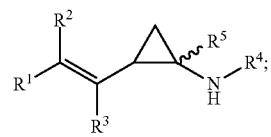

or a pharmaceutically acceptable salt thereof, wherein:
$R^1$ is selected from $C_3$-$C_{10}$carbocyclyl, heterocyclyl, aryl and heteroaryl, each of which being optionally substituted with up to 4 independently selected substituents;
each of $R^2$ and $R^3$ is independently selected from hydrogen, halo, —CN and optionally substituted $C_1$-$C_8$ alkyl;
$R^4$ is selected from hydrogen, optionally substituted $C_3$-$C_{10}$carbocyclyl, optionally substituted heterocyclyl, and —C($R^6$)($R^7$)($R^8$);
each $R^5$ is independently selected from hydrogen and $C_1$-$C_4$ alkyl;
$R^6$ is selected from hydrogen and —$C_1$-$C_4$ alkyl,
$R^7$ is selected from hydrogen, halo, —CN, and optionally substituted $C_1$-$C_8$ alkyl; and
$R^8$ is selected from hydrogen, halo, —$C_1$-$C_4$ alkyl, —($C_0$-$C_4$ alkylene)-$C_3$-$C_{10}$carbocyclyl, —($C_0$-$C_4$ alkylene)-heterocyclyl, —($C_0$-$C_4$ alkylene)-aryl, and —($C_0$-$C_4$ alkylene)-heteroaryl, wherein any $C_3$-$C_{10}$carbocyclyl, heterocyclyl, aryl, heteroaryl, or alkyl portion of $R^8$ is optionally substituted;
wherein the substituents for an optionally substituted alkyl, carbocyclyl, heterocyclyl, aryl group and heteroaryl group as defined above are selected from halogen, =O, —CN, —OR$^c$, —NR$^a$R$^b$, —S(O)$_i$R$^c$, —NR$^d$S(O)$_2$R$^c$, —S(O)$_2$NR$^e$R$^f$, —C(=O)OR$^c$, —OC(=O)OR$^c$, —OC(=O)R$^c$, —OC(=S)OR$^c$, —C(=S)OR$^c$, —O(C=S)R$^c$, —C(=O)NR$^e$R$^f$, —NR$^d$C(=O)R$^c$, —C(=S)NR$^e$R$^f$, —NR$^d$C(=S)R$^c$, —NR$^d$(C=O)OR$^c$, —O(C=O)NR$^e$R$^f$, —NR$^d$(C=S)OR$^c$, —O(C=S)NR$^e$R$^f$, —NR$^d$(C=O)NR$^e$R$^f$, —NR$^d$(C=S)NR$^e$R$^f$, —C(=S)R$^c$, —C(=O)R$^c$, ($C_1$-$C_6$) alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl and —(CH$_2$)$_{1-4}$-heteroaryl, wherein each of the ($C_1$-$C_6$)alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl and —(CH$_2$)$_{1-4}$-heteroaryl are optionally substituted with halogen, OR$^c$, —NO$_2$, —CN, —NR$^d$C(=O)R$^c$, —NR$^g$R$^h$, —S(O)$_i$R$^c$, —C(=O)OR$^c$, —C(=O)NR$^e$R$^f$, —C(=O)R$^c$, ($C_1$-$C_3$)alkyl, halo($C_1$-$C_3$)alkyl, ($C_1$-$C_3$)alkoxy($C_1$-$C_3$)alkyl, ($C_1$-$C_3$) alkoxy, and halo($C_1$-$C_3$)alkoxy;
$R^a$ and $R^b$ are each independently selected from —H and ($C_1$-$C_6$)alkyl optionally substituted with 1 to 3 substituents independently selected from halogen, hydroxy, COOH, —NR$^g$R$^h$, and ($C_1$-$C_3$)alkoxy;

R$^c$ is —H or (C$_1$-C$_6$)alkyl optionally substituted with 1 to 3 substituents independently selected from halogen, —NR$^g$R$^h$, hydroxyl, and (C$_1$-C$_3$)alkoxy;

R$^d$ is —H or (C$_1$-C$_6$)alkyl optionally substituted with 1 to 3 substituents independently selected from halogen, —NR$^g$R$^h$, hydroxyl, and (C$_1$-C$_3$)alkoxy;

R$^e$ and R$^f$ are each independently selected from —H and (C$_1$-C$_6$)alkyl optionally substituted with 1 to 3 substituents independently selected from halogen, —NR$^g$R$^h$, hydroxyl, and (C$_1$-C$_3$)alkoxy; or R$^e$ and R$^f$, together with the nitrogen to which they are attached, form a 3-8 membered ring optionally substituted with 1 to 3 substituents independently selected from halogen, —NR$^g$R$^h$, —CN, (C$_1$-C$_6$)alkyl, halo(C$_1$-C$_6$)alkyl, (C$_1$-C$_3$)alkoxy, halo(C$_1$-C$_3$)alkoxy, and (C$_1$-C$_3$)alkoxy(C$_1$-C$_6$)alkyl;

R$^g$ and R$^h$ are each independently selected from —H, (C$_1$-C$_6$)alkyl, halo(C$_1$-C$_6$)alkyl, hydroxy(C$_1$-C$_6$)alkyl, and (C$_1$-C$_3$)alkoxy(C$_1$-C$_6$)alkyl; and i is 0, 1 or 2;

provided that the compound is other than

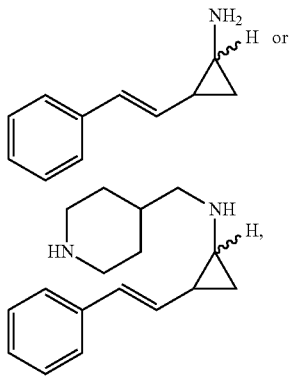

or a pharmaceutically acceptable salt thereof.

2. The compound of claim 1, wherein R$^7$ is hydrogen.

3. The compound of claim 1, wherein

R$^1$ is selected from C$_3$-C$_{10}$carbocyclyl, heterocyclyl, aryl and heteroaryl, each of which being optionally substituted with up to 3 substituents independently selected from R$^X$;

each of R$^2$ and R$^3$ is independently selected from hydrogen, halo, and C$_1$-C$_4$ alkyl;

each R$^5$ is independently selected from hydrogen and C$_1$-C$_4$ alkyl;

R$^6$ is hydrogen;

R$^8$ is selected from —(C$_0$-C$_4$ alkylene)-C$_3$-C$_{10}$carbocyclyl, —(C$_0$-C$_4$ alkylene)-heterocyclyl, —(C$_0$-C$_4$ alkylene)-aryl, and —(C$_0$-C$_4$ alkylene)-heteroaryl, wherein said C$_3$-C$_{10}$carbocyclyl, heterocyclyl, aryl, and heteroaryl are each optionally substituted with up to 3 substituents independently selected from R$^Y$; and R$^X$ and R$^Y$ are each independently selected from halogen, —CN, —OR$^c$, —NR$^a$R$^b$, —S(O)$_i$R$^c$, —NR$^d$S(O)$_2$R$^c$, —S(O)$_2$NR$^e$R$^f$, —C(=O)OR$^c$, —OC(=O)OR$^c$, —OC(=O)R$^c$, —OC(=S)OR$^c$, —C(=S)OR$^c$, —O(C=S)R$^c$, —C(=O)NR$^e$R$^f$, —NR$^d$C(=O)R$^c$, —C(=S)NR$^e$R$^f$, —NR$^d$C(=S)R$^c$, —NR$^d$C(=O)OR$^c$, —O(C=O)NR$^e$R$^f$, —NR$^d$(C=S)OR$^c$, —O(C=S)NR$^e$R$^f$, —NR$^d$(C=O)NR$^e$R$^f$, —NR$^d$(C=S)NR$^e$R$^f$, —C(=S)R$^c$, —C(=O)R$^c$, (C$_1$-C$_6$)alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl and —(CH$_2$)$_{1-4}$-heteroaryl, wherein each of the (C$_1$-C$_6$)alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl and —(CH$_2$)$_{1-4}$-heteroaryl are optionally substituted with halogen, OR$^c$, —NO$_2$, —CN, —NR$^d$C(=O)R$^c$, —NR$^g$R$^h$, —S(O)$_i$R$^c$, —C(=O)OR$^c$, —C(=O)NR$^e$R$^f$, —C(=O)R$^c$, (C$_1$-C$_3$)alkyl, halo(C$_1$-C$_3$)alkyl, (C$_1$-C$_3$)alkoxy(C$_1$-C$_3$)alkyl, (C$_1$-C$_3$)alkoxy, and halo(C$_1$-C$_3$)alkoxy; or two R$^X$ bonded to the same carbon atom or two R$^Y$ bonded to the same carbon atom are taken together to form =O.

4. The compound of claim 3, wherein R$^1$ is aryl, heteroaryl, or heterocyclyl, each being optionally substituted with up to 3 substituents independently selected from R$^X$.

5. The compound of claim 4, wherein R$^1$ is phenyl, pyridinyl, pyrazolyl, pyridinonyl, imidazolyl, or pyrimidinyl, each being optionally substituted with up to 3 substituents independently selected from R$^X$.

6. The compound of claim 3, wherein R$^X$ and R$^Y$ are each independently selected from halogen, halo(C$_1$-C$_4$)alkyl, (C$_1$-C$_4$)alkoxy, halo(C$_1$-C$_4$)alkoxy, hydroxy(C$_1$-C$_4$)alkyl, cyano(C$_1$-C$_4$)alkyl, hydroxy(C$_1$-C$_4$)alkoxy, (C$_1$-C$_4$)alkoxy(C$_1$-C$_4$)alkyl, halo(C$_1$-C$_4$)alkoxy(C$_1$-C$_4$)alkyl, —(CH$_2$)$_{1-4}$-aryl, —(CH$_2$)$_{1-4}$-aryl-COOH, —(CH$_2$)$_{1-4}$-aryl-C(=O)NR$^e$R$^f$, —NR$^d$(C=O)OR$^c$, —CN, —C(=O)NR$^e$R$^f$, —NR$^a$R$^b$, and (C$_1$-C$_4$)alkyl optionally substituted with —C(=O)NR$^e$R$^f$, —C(=O)OR$^c$, or —S(O)$_i$R$^c$; or two R$^X$ bonded to the same carbon atom or two R$^Y$ bonded to the same carbon atom are taken together to form =O.

7. The compound of claim 3, wherein R$^X$ is selected from halogen, halo(C$_1$-C$_4$)alkyl, (C$_1$-C$_4$)alkoxy, halo(C$_1$-C$_4$)alkoxy, hydroxy(C$_1$-C$_4$)alkyl, —CN, —C(=O)NR$^e$R$^f$, —NR$^a$R$^b$, and (C$_1$-C$_4$)alkyl optionally substituted with —C(=O)NR$^e$R$^f$; or two R$^X$ bonded to the same carbon atom are taken together to form =O.

8. The compound of claim 3, wherein R$^X$ is halogen, —CN, —C(=O)NR$^e$R$^f$, or (C$_1$-C$_4$)alkyl; or two R$^X$ on the same carbon atom are taken together to form =O.

9. The compound of claim 3, wherein R$^X$ is halogen, —CN, (C$_1$-C$_4$)alkyl, —C(=O)NH$_2$, or —C(=O)NH(C$_1$-C$_3$)alkyl; or two R$^X$ on the same carbon atom are taken together to form =O.

10. The compound of claim 1, wherein R$^1$ is selected from unsubstituted phenyl, 2-fluorophenyl, pyridin-3-yl, 1-methyl-1H-pyrazol-4-yl, 1-methyl-1H-imidazol-4-yl, 1-methyl-6-oxopyridin-3-yl, 1-methyl-6-oxopyridin-4-yl, 4-cyanophenyl, pyrimidin-5-yl, 4-aminocarbonylphenyl, and 4-methylaminocarbonylphenyl.

11. The compound of claim 1, wherein R$^1$ is selected from unsubstituted phenyl, 2-fluorophenyl and pyridin-3-yl.

12. The compound of claim 1, wherein R$^2$ is hydrogen.

13. The compound of claim 1, wherein R$^3$ is selected from hydrogen, halogen and C$_1$-C$_4$ alkyl.

14. The compound of claim 1, wherein R$^3$ is selected from hydrogen, fluoro, —CH$_3$ and —CH$_2$CH$_3$.

15. The compound of claim 1, wherein R$^3$ is selected from hydrogen and —CH$_3$.

16. The compound of claim 3, wherein R$^4$ is hydrogen, —CH$_2$— piperidinyl, —CH$_2$-pyridinyl, —CH$_2$-cyclopropyl, piperidinyl, 1-azaspiro[4.5]decane-8-yl, bicyclo[3.2.1]octan-8-amine-3-yl, or cyclohexyl, wherein each of said piperidinyl, pyridinyl, cyclopropyl, and cyclohexyl, is optionally substituted with up to 3 substituents independently selected from R$^Y$.

17. The compound of claim 3, wherein $R^Y$ is selected from halogen, halo($C_1$-$C_4$)alkyl, ($C_1$-$C_4$)alkoxy, halo($C_1$-$C_4$) alkoxy, cyano($C_1$-$C_4$)alkyl, hydroxy($C_1$-$C_4$)alkyl, hydroxy ($C_1$-$C_4$)alkoxy, ($C_1$-$C_4$)alkoxy($C_1$-$C_4$)alkyl, halo($C_1$-$C_4$) alkoxy($C_1$-$C_4$)alkyl, —$(CH_2)_{1-4}$-aryl, —$(CH_2)_{1-4}$-aryl-COOH, —$(CH_2)_{1-4}$-aryl-C(=O)$NR^eR^f$, —$NR^aR^b$, —$NR^d$ (C=O)$OR^c$, —C(=O)$NR^eR^f$, and ($C_1$-$C_6$)alkyl optionally substituted with —C(=O)$OR^c$, —C(=O)$NR^eR^f$, or —S(O)$_t$ $R^c$; or two $R^Y$ on the same carbon atom are taken together to form =O.

18. The compound of claim 3, wherein $R^Y$ is selected from —$NH_2$, —NH($C_1$-$C_4$)alkyl, ($C_1$-$C_4$)alkoxy($C_1$-$C_4$)alkyl, cyano($C_1$-$C_4$)alkyl, —$(CH_2)_{1-4}$-aryl, —$NR^a$(C=O)$OR^c$, —$(CH_2)_{1-4}$-arylCOOH, —$(CH_2)_{1-4}$-aryl-C(=O)$NR^eR^f$, hydroxy($C_1$-$C_6$)alkyl, —C(=O)$NR^eR^f$, —$NR^aR^b$ and ($C_1$-$C_6$)alkyl optionally substituted with —S(O)$_2R^c$, —C(=O) $OR^c$, or —C(=O)$NR^eR^f$, where $R^a$ is ($C_1$-$C_6$)alkyl optionally substituted with COOH; $R^b$ is —H; $R^e$ is —H or ($C_1$-$C_6$)alkyl; $R^f$ is —H or ($C_1$-$C_6$)alkyl; and $R^c$ is —H or ($C_1$-$C_6$)alkyl optionally substituted with COOH.

19. The compound of claim 1, wherein $R^4$ is selected from hydrogen, 1-((2-ethylsulfonyl)ethyl)piperidin-4-ylmethyl, 1-(2-cyanoethyl)piperidin-4-ylmethyl, 1-(2-hydroxy-2,2-dimethylethyl)piperidin-4-ylmethyl, 1-(3-carboxy-2,2-dimethylpropyl)piperidin-4-ylmethyl, 1-(3-carboxy-3,3-dimethylpropyl)piperidin-4-ylmethyl, 1-(4-aminocarbonylbenzyl) piperidin-4-ylmethyl, 1-(4-carboxybenzyl)piperidin-4-ylmethyl, 1-(4-dimethylaminocarbonylbenzyl)piperidin-4-ylmethyl, 1-(aminocarbonylethyl)piperidin-4-ylmethyl, 1-(carboxyethyl)piperidin-4-ylmethyl, 1-(carboxymethyl) piperidin-4-ylmethyl, 1-(dimethylaminoethyl)piperidin-4-ylmethyl, 1-(methoxyethyl)piperidin-4-ylmethyl, 1-benzylpiperidin-4-ylmethyl, 2-aminopyridin-3-ylmethyl, 4-amino-4-methylcyclohexyl, 4-aminocyclohexyl, 4-carboxypropylaminocyclhexyl, 4-carboxyethylaminocyclohexyl, 4-ethylaminocyclohexyl, 4-fluoropiperidin-4-ylmethyl, 8-aminobicyclo[3.2.1]octan-3-yl, azaspiro[4.5]decan-8-yl, cyclopropylmethyl, piperidin-4-yl, and piperidin-4-ylmethyl.

20. The compound of claim 1, wherein $R^4$ is selected from hydrogen 1-(4-carboxybenzyl)piperidin-4-ylmethyl, piperidin-4-ylmethyl, 1-(carboxyethyl)piperidin-4-ylmethyl, 1-benzylpiperidin-4-ylmethyl, 4-fluoropiperidin-4-ylmethyl, 4-aminocyclohexyl, 1-(carboxymethyl)piperidin-4-ylmethyl, 1-((2-ethylsulfonyl)ethyl)piperidin-4-ylmethyl, 2-aminopyridin-3-ylmethyl, 1-(2-hydroxy-2,2-dimethylethyl)piperidin-4-ylmethyl, cyclopropylmethyl, piperidin-4-ylmethyl, piperidin-4-yl, and 4-carboxyethylaminocyclohexyl.

21. The compound of claim 1, wherein the compound is of the formula

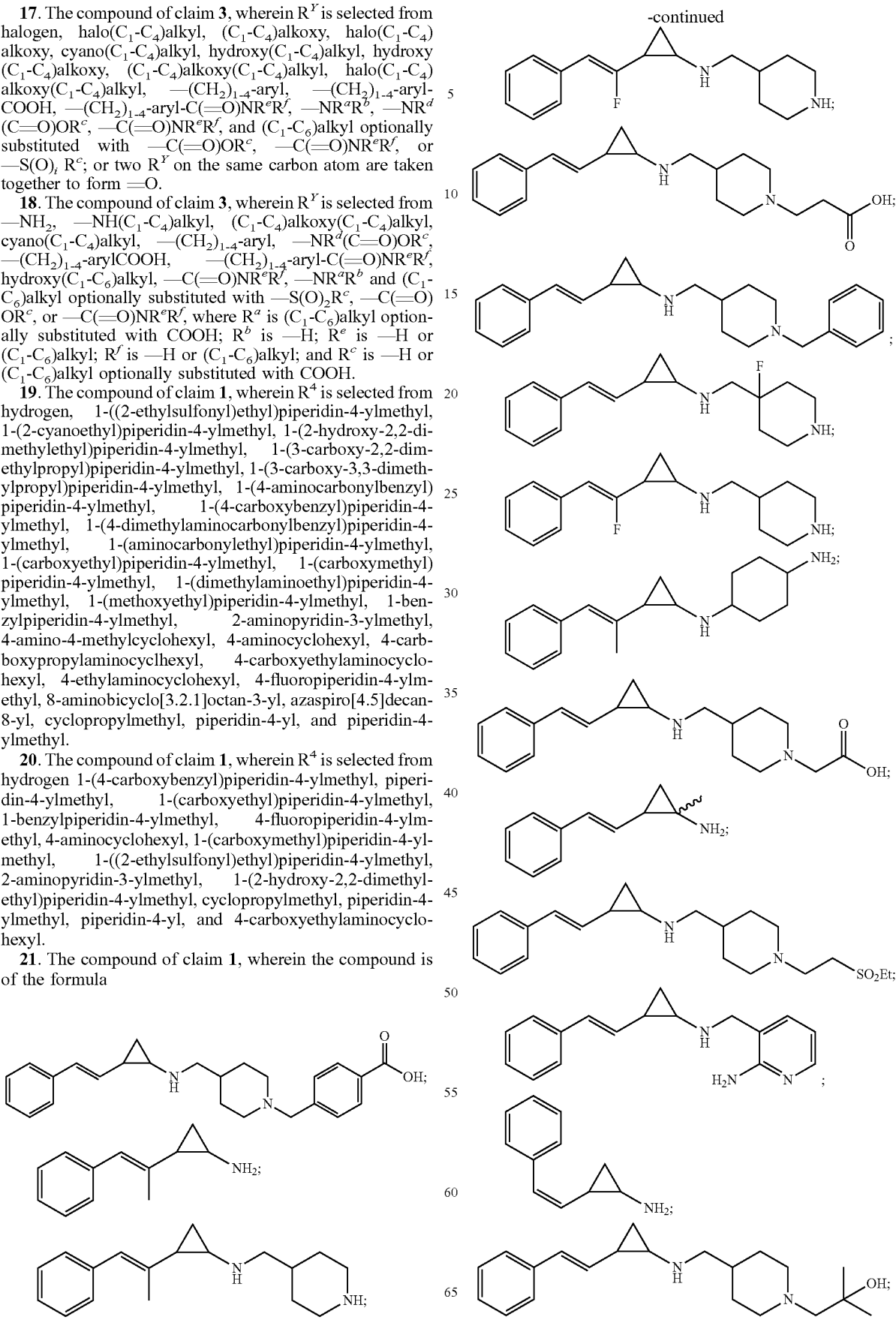

299
-continued
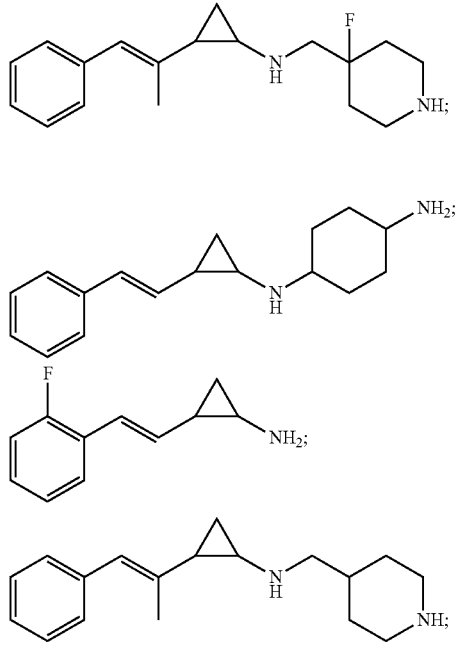
300
-continued
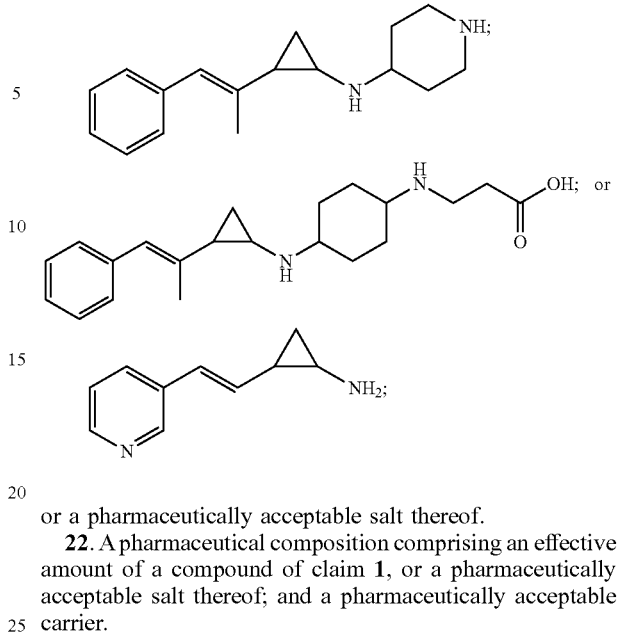
or a pharmaceutically acceptable salt thereof.
22. A pharmaceutical composition comprising an effective amount of a compound of claim 1, or a pharmaceutically acceptable salt thereof; and a pharmaceutically acceptable carrier.
* * * * *